(12) United States Patent
Plummer et al.

(10) Patent No.: US 7,897,744 B2
(45) Date of Patent: Mar. 1, 2011

(54) SARS VIRUS NUCLEOTIDE AND AMINO ACID SEQUENCES AND USES THEREOF

(75) Inventors: Frank Plummer, Winnipeg (CA); Heinz Feldmann, Winnipeg (CA); Steven Jones, Winnipeg (CA); Yan Li, Winnipeg (CA); Nathalie Bastien, Winnipeg (CA); Robert Conrad Brunham, Vancouver (CA); Angela Brooks-Wilson, Richmond (CA); Robert Holt, North Vancouver (CA); Christopher Upton, Victoria (CA); Rachel Roper, Winterville, NC (US); Caroline Astell, Vancouver (CA); Steven Jones, Burnaby (CA)

(73) Assignee: The Public Health Agency of Canada (CA)

( * ) Notice: Subject to any disclaimer, the term of this patent is extended or adjusted under 35 U.S.C. 154(b) by 906 days.

(21) Appl. No.: 10/555,073

(22) PCT Filed: Apr. 28, 2004

(86) PCT No.: PCT/CA2004/000626

§ 371 (c)(1),
(2), (4) Date: Dec. 19, 2006

(87) PCT Pub. No.: WO2004/096842

PCT Pub. Date: Nov. 11, 2004

(65) Prior Publication Data

US 2007/0258999 A1 Nov. 8, 2007

Related U.S. Application Data

(60) Provisional application No. 60/465,783, filed on Apr. 28, 2003, provisional application No. 60/466,733, filed on May 1, 2003.

(51) Int. Cl.
*C12N 15/50* (2006.01)
*C12N 7/00* (2006.01)
(52) U.S. Cl. .............. 536/23.72; 435/235.1; 435/320.1; 514/44
(58) Field of Classification Search ........................ None
See application file for complete search history.

(56) References Cited

U.S. PATENT DOCUMENTS

| | | | |
|---|---|---|---|
| 4,554,101 A | 11/1985 | Hopp | |
| 4,683,202 A | 7/1987 | Mullis | |
| 4,708,871 A | 11/1987 | Geysen | |
| 6,004,744 A | 12/1999 | Goelet et al. | |
| 6,188,783 B1 | 2/2001 | Balaban | |
| 6,484,183 B1 | 11/2002 | Balaban | |
| 7,220,852 B1 * | 5/2007 | Rota et al. | 536/23.72 |
| 2002/0132788 A1 | 9/2002 | Lewis et al. | |
| 2002/0173478 A1 | 11/2002 | Gewirtz | |

OTHER PUBLICATIONS

Marra, Marco A. et al. The Genome Sequence of the SARS-Associated Coronavirus *Science*. (2003) 300: 1399-404.
Rota, Paul A. et al. Characteriazation of a Novel Coronavirus Associated with Severe Acute Respiratory Syndrome. *Science*. (2003) 300: 1394-9.
Anand, Kanchan et. al. Coronavirus Main Proteinase (3CLpro) Structure: Basis for Design of anti-SARS Drugs. *Science*. (Jun. 2003) 300: 1763-7.
Altschul. S. F. et al., *Nucleic Acids Res* 25: 3389-3402 (Sep. 1, 1997).
Apweiler, R. et al., *Nucleic Acids Res* 29: 37-40 (Jan. 1, 2001).
Barry, M. A. et al., "Protection against mycoplasma infection using expression-library immunization", *Nature* 377: 632-635 (1995).
Bateman, A. et al., *Nucleic Acids Res* 30: 276-280 (Jan. 1, 2002).
Borrebaeck, C. A. et al., "Protein chips based on recombinant antibody fragments: a highly sensitive approach as detected by mass spectrometry", *Biotechniques* 30: 1126-1132 (2001).
Bowtell, D. D. L., *Nature Genetics Supplement* 21: 25-32 (1999).
Chen, J. et al., "MMDB: Entrez's 3D-structure database", *Nucleic Acids Research* 31(1): 474-477 (2003).
Cheung. V. G. et al., *Nature Genetics Supplement* 21:15-19 (1999).
Chiang, A. et al., "The Structure Superposition Database", *Nucleic Acids Research* 31(1): 505-510 (2003).
Eckert et al., *PCR Methods and Applications* 1: 17 (1991).
Eisenberg et al., *J. Mol. Bio.* 179:125-142 (1984).
Emili, A. Q. and Cagney, G., "Large-scale functional analysis using peptide or protein arrays", *Nature Biotechnol* 18: 393-397 (2000).
Evan et al., *Mol. Cell Biol.* 5: 3610-3616 (1985).
Ewing, B. and Green, P., *Genome Res* 8:186-194 (Mar. 1998).
Fynan, E. F. et al., "DNA vaccines: protective immunizations by parental, mucosal, and genegun inoculations", *Proc Natl Acad Sci USA* 90: 11478-11482 (1993).
Gibson, U. E. et al., "A novel method for real time quantitative RT-PCR", *Genome Research* 6(10): 995-1001 (Oct. 1996).
Gordon, D. et al., *Genome Res* 8: 195-202 (Mar. 1998).
Guatelli et al., *Proc. Nat. Acad. Sci. USA* 87: 1874 (1990).
Heid et al., "Real Time Quantitative PCT", *Genome Research*, pp. 986-994 (1996).
Higuchi, R. et al., "Kinetic PCR Analysis: Real-time Monitoring of DNA Amplification Reactions", *Bio/Technology* 11: 1026-1030 (1993).
Hofman, K. and Stoffel, W., *Biol. Chem. Hoope-Seyler* 374: 166 (1993).
Holland et al., *Proc. Natl. Acad. Sci.* 88: 7276-7280 (1991).
Holloway, A. J. et al., *Nature Genetics Supplement* 32: 481-489 (2002).

(Continued)

*Primary Examiner*—Bo Peng
(74) *Attorney, Agent, or Firm*—Nixon Peabody LLP

(57) ABSTRACT

The invention provides, in part, the genomic sequence of a putative coronavirus, the SARS virus, and provides novel nucleic acid and amino acid sequences that may be used, for example, for the diagnosis, prophylaxis, or therapy of a variety of SARS virus related disorders.

14 Claims, 55 Drawing Sheets

OTHER PUBLICATIONS

Huang, R. P., "Detection of multiple proteins in an antibody-based protein microarray system", *J Immunol Methods* 255:1-13 (2001).
Hung, L. H. and Samudrala, R., "PROTINFO: secondary and tertiary protein structure prediction", *Nucleic Acids Research* 31(13): 3296-3299 (2003).
Jonassen, C.M. et al., *J. Gen Virol* 79 (Pt. 4): 715-718 (Apr. 1998).
Kohler, et al., *Eur. J. Immunol.* 6:292 (1976).
Kohler, et al., *Eur. J. Immunol.* 6:511 (1976).
Kohler, et al., *Nature* 256: 495 (1975).
Kukar, T. et al., "Protein microarrays to detect protein-protein interactions using red and green fluorescent proteins", *Anal Biochem* 306:50-54 (2002).
Kwoh et al., *Proc. Natl. Acad. Sci. USA* 86: 1173 (1989).
Lai, M.M.C. and Cavanagh, D., *Adv Virus Res.* 48: 1-100 (1997).
Landegren et al., *Science* 241: 1077 (1988).
Levit-Binnun, N. et al., "Quantitative detection of protein arrays", *Anal Chem* 75:1436-1441 (2003).
Lipshutz, R. J. et al., *Nature Genetics Supplement* 21:20-24 (1999).
Lueking, A. et al., "Protein Microarrays for Gene Expression and Antibody Screening", *Anal. Biochem.* 270: 103-111 (1999).
MacBeath, G. and Schreiber, S. L., *Science* 289: 1760-1763 (2000).
Martzen, M. R. et al., *Science* 286:1153 (1999).
Mattila et al., *Nucleic Acids Res.* 19: 4967 (1991).
Munch, R., *Microbes Infect* 5 69-74 (Jan. 2003).
Nielsen, H. et al., *Prot Engineer* 10:1-6 (1997).
Parsons, J. D., *Comput Appl Biosci* 11: 615-619 (Dec. 1995).
Pearson, W. R. and Lipman, D. J., *Proc Natl Acad Sci USA* 85: 2444-2448 (Apr. 1988).
Sawicki, D.L. et al., *J. Gen Virol* 82, 386 (2001).
Sawicki, S.G. and Sawicki, D.L., *Adv. Exp. Med Biol.* 440: 215-9 (1998).
Sawicki, S.G. and Sawicki, D.L., *J. Virol.* 64: 1050 (1990).
Schaad, M. and Baric, R.S.J., *J. Virol.* 68: 8169 (1994).
Schweitzer, B. et al., *Nature Biotechnol.* 20: 359-365 (2002).
Sethna, P.B. et al., *Proc. Natl. Acad. Sci. U.S.A.* 86: 5626 (1989).
Singh-Gasson, S. et al., *Nature Biotechnol.* 17: 974-978 (1999).
Smith et al., *Gene* 67: 31-40 (1988).
Sonnhammer, E.L. et al., *Proc Int Conf Intell Syst Mol Biol* 6: 175-182 (1998).
Templin, M. F. et al., "Protein microarray technology", *Drug Discov Today* 7: 815-822 (2002).
Thompson, J.E. et al., *Nucleic Acids Res* 22: 4673-80 (Nov. 11, 1994).
Whalen, R. G. et al., "DNA-mediated immunization and the energetic immune response to hepatitis B surface antigen", *Clin Immunol Immunopathol* 75: 1-12 (1995).
Wolff, J. A. et al., "Direct gene transfer into mouse muscle in vivo", *Science* 247: 1465-1468 (1990).
Wu and Wallace, *Genomics* 4: 560 (1989).
Yamaguchi, A. et al., "Enlarged FAMSBASE: protein 3D structure models of genome sequences for 41 species", *Nucleic Acids Research* 31(1): 463-468 (2003).
Zdobnov, E. M. and Apweiler, R., *Bioinformatics* 17: 847-848 (Sep. 2001).
Zhu, H. et al., "Analysis of yeast protein kinases using protein chips", *Nature Genet* 26: 283-289 (2000).
Ziebuhr, J. et al., *J. Gen Virol* 81: 853-79 (Apr. 2000).

* cited by examiner

```
CTACCCAGGAAAAGCCAACCAACCTCGATCTCTTGTAGATCTGTTCTCTAAACGAACTTTAAAATCTGTGT
AGCTGTCGCTCGGCTGCATGCCTAGTGCACCTACGCAGTATAAACAATAATAAATTTTACTGTCGTTGACA
AGAAACGAGTAACTCGTCCCTCTTCTGCAGACTGCTTACGGTTTCGTCCGTGTTGCAGTCGATCATCAGCA
TACCTAGGTTTCGTCCGGGTGTGACCGAAAGGTAAGATGGAGAGCCTTGTTCTTGGTGTCAACGAGAAAAC
ACACGTCCAACTCAGTTTGCCTGTCCTTCAGGTTAGAGACGTGCTAGTGCGTGGCTTCGGGGACTCTGTGG
AAGAGGCCCTATCGGAGGCACGTGAACACCTCAAAAATGGCACTTGTGGTCTAGTAGAGCTGGAAAAAGGC
GTACTGCCCCAGCTTGAACAGCCCTATGTGTTCATTAAACGTTCTGATGCCTTAAGCACCAATCACGGCCA
CAAGGTCGTTGAGCTGGTTGCAGAAATGGACGGCATTCAGTACGGTCGTAGCGGTATAACACTGGGAGTAC
TCGTGCCACATGTGGGCGAAACCCCAATTGCATACCGCAATGTTCTTCTTCGTAAGAACGGTAATAAGGGA
GCCGGTGGTCATAGCTATGGCATCGATCTAAAGTCTTATGACTTAGGTGACGAGCTTGGCACTGATCCCAT
TGAAGATTATGAACAAAACTGGAACACTAAGCATGGCAGTGGTGCACTCCGTGAACTCACTCGTGAGCTCA
ATGGAGGTGCAGTCACTCGCTATGTCGACAACAATTTCTGTGGCCCAGATGGGTACCCTCTTGATTGCATC
AAAGATTTTCTCGCACGCGCGGGCAAGTCAATGTGCACTCTTTCCGAACAACTTGATTACATCGAGTCGAA
GAGAGGTGTCTACTGCTGCCGTGACCATGAGCATGAAATTGCCTGGTTCACTGAGCGCTCTGATAAGAGCT
ACGAGCACCAGACACCCTTCGAAATTAAGAGTGCCAAGAAATTTGACACTTTCAAAGGGGAATGCCCAAAG
TTTGTGTTTCCTCTTAACTCAAAAGTCAAAGTCATTCAACCACGTGTTGAAAAGAAAAAGACTGAGGGTTT
CATGGGGCGTATACGCTCTGTGTACCCTGTTGCATCTCCACAGGAGTGTAACAATATGCACTTGTCTACCT
TGATGAAATGTAATCATTGCGATGAAGTTTCATGGCAGACGTGCGACTTTCTGAAAGCCACTTGTGAACAT
TGTGGCACTGAAAATTTAGTTATTGAAGGACCTACTACATGTGGGTACCTACCTACTAATGCTGTAGTGAA
AATGCCATGTCCTGCCTGTCAAGACCCAGAGATTGGACCTGAGCATAGTGTTGCAGATTATCACAACCACT
CAAACATTGAAACTCGACTCCGCAAGGGAGGTAGGACTAGATGTTTTGGAGGCTGTGTGTTTGCCTATGTT
GGCTGCTATAATAAGCGTGCCTACTGGGTTCCTCGTGCTAGTGCTGATATTGGCTCAGGCCATACTGGCAT
TACTGGTGACAATGTGGAGACCTTGAATGAGGATCTCCTTGAGATACTGAGTCGTGAACGTGTTAACATTA
ACATTGTTGGCGATTTTCATTTGAATGAAGAGGTTGCCATCATTTTGGCATCTTTCTCTGCTTCTACAAGT
GCCTTTATTGACACTATAAAGAGTCTTGATTACAAGTCTTTCAAAACCATTGTTGAGTCCTGCGGTAACTA
TAAAGTTACCAAGGGAAAGCCCGTAAAAGGTGCTTGGAACATTGGACAACAGAGATCAGTTTTAACACCAC
TGTGTGGTTTTCCCTCACAGGCTGCTGGTGTTATCAGATCAATTTTTGCGCGCACACTTGATGCAGCAAAC
CACTCAATTCCTGATTTGCAAAGAGCAGCTGTCACCATACTTGATGGTATTTCTGAACAGTCATTACGTCT
TGTCGACGCCATGGTTTATACTTCAGACCTGCTCACCAACAGTGTCATTATTATGGCATATGTAACTGGTG
GTCTTGTACAACAGACTTCTCAGTGGTTGTCTAATCTTTTGGGCACTACTGTTGAAAAACTCAGGCCTATC
TTTGAATGGATTGAGGCGAAACTTAGTGCAGGAGTTGAATTTCTCAAGGATGCTTGGGAGATTCTCAAATT
TCTCATTACAGGTGTTTTTGACATCGTCAAGGGTCAAATACAGGTTGCTTCAGATAACATCAAGGATTGTG
TAAAATGCTTCATTGATGTTGTTAACAAGGCACTCGAAATGTGCATTGATCAAGTCACTATCGCTGGCGCA
AAGTTGCGATCACTCAACTTAGGTGAAGTCTTCATCGCTCAAAGCAAGGGACTTTACCGTCAGTGTATACG
TGGCAAGGAGCAGCTGCAACTACTCATGCCTCTTAAGGCACCAAAAGAAGTAACCTTTCTTGAAGGTGATT
CACATGACACAGTACTTACCTCTGAGGAGGTTGTTCTCAAGAACGGTGAACTCGAAGCACTCGAGACGCCC
GTTGATAGCTTCACAAATGGAGCTATCGTCGGCACACCAGTCTGTGTAAATGGCCTCATGCTCTTAGAGAT
TAAGGACAAAGAACAATACTGCGCATTGTCTCCTGGTTTACTGGCTACAAACAATGTCTTTCGCTTAAAAG
GGGGTGCACCAATTAAAGGTGTAACCTTTGGAGAAGATACTGTTTGGGAAGTTCAAGGTTACAAGAATGTG
AGAATCACATTTGAGCTTGATGAACGTGTTGACAAAGTGCTTAATGAAAGTGCTCTGTCTACACTGTTGA
ATCCGGTACCGAAGTTACTGAGTTTGCATGTGTTGTAGCAGAGGCTGTTGTGAAGACTTTACAACCAGTTT
CTGATCTCCTTACCAACATGGGTATTGATCTTGATGAGTGGAGTGTAGCTACATTCTACTTATTTGATGAT
GCTGGTGAAGAAACTTTTCATCACGTATGTATTGTTCCTTTTACCCTCCAGATGAGGAAGAAGAGGACGA
TGCAGAGTGTGAGGAAGAAGAAATTGATGAAACCTGTGAACATGAGTACGGTACAGAGGATGATTATCAAG
GTCTCCCTCTGGAATTTGGTGCCTCAGCTGAAACAGTTCGAGTTGAGGAAGAAGAAGAGGAAGACTGGCTG
GATGATACTACTGAGCAATCAGAGATTGAGCCAGAACCAGAACCTACACCTGAAGAACCAGTTAATCAGTT
TACTGGTTATTTAAAACTTACTGACAATGTTGCCATTAAATGTGTTGACATCGTTAAGGAGGCACAAAGTG
CTAATCCTATGGTGATTGTAAATGCTGCTAACATACACCTGAAACATGGTGGTGGTGTAGCAGGTGCACTC
AACAAGGCAACCAATGGTGCCATGCAAAAGGAGAGTGATGATTACATTAAGCTAAATGGCCCTCTTACAGT
AGGAGGGTCTTGTTTGCTTTCTGGACATAATCTTGCTAAGAAGTGTCTGCATGTTGTTGGACCTAACCTAA
ATGCAGGTGAGGACATCCAGCTTCTTAAGGCAGCATATGAAAATTTCAATTCACAGGACATCTTACTTGCA
CCATTGTTGTCAGCAGGCATATTTGGTGCTAAACCACTTCAGTCTTTACAAGTGTGCGTGCAGACGGTTCG
TACACAGGTTTATATTGCAGTCAATGACAAAGCTCTTTATGAGCAGGTTGTCATGGATTATCTTGATAACC
TGAAGCCTAGAGTGGAAGCACCTAAACAAGAGGAGCCACCAAACACAGAAGATTCCAAAACTGAGGAGAAA
TCTGTCGTACAGAAGCCTGTCGATGTGAAGCCAAAAATTAAGGCCTGCATTGATGAGGTTACCACAACACT
GGAAGAAACTAAGTTTCTTACCAATAAGTTACTCTTGTTTGCTGATATCAATGGTAAGCTTTACCATGATT
CTCAGAACATGCTTAGAGGTGAAGATATGTCTTTCCTTGAGAAGGATGCACCTTACATGGTAGGTGATGTT
```

FIGURE 3A

```
ATCACTAGTGGTGATATCACTTGTGTTGTAATACCCTCCAAAAAGGCTGGTGGCACTACTGAGATGCTCTC
AAGAGCTTTGAAGAAAGTGCCAGTTGATGAGTATATAACCACGTACCCTGGACAAGGATGTGCTGGTTATA
CACTTGAGGAAGCTAAGACTGCTCTTAAGAAATGCAAATCTGCATTTTATGTACTACCTTCAGAAGCACCT
AATGCTAAGGAAGAGATTCTAGGAACTGTATCCTGGAATTTGAGAGAAATGCTTGCTCATGCTGAAGAGAC
AAGAAAATTAATGCCTATATGCATGGATGTTAGAGCCATAATGGCAACCATCCAACGTAAGTATAAAGGAA
TTAAAATTCAAGAGGGCATCGTTGACTATGGTGTCCGATTCTTCTTTTATACTAGTAAAGAGCCTGTAGCT
TCTATTATTACGAAGCTGAACTCTCTAAATGAGCCGCTTGTCACAATGCCAATTGGTTATGTGACACATGG
TTTTAATCTTGAAGAGGCTGCGCGCTGTATGCGTTCTTCTTAAAGCTCCTGCCGTAGTGTCAGTATCATCAC
CAGATGCTGTTACTACATATAATGGATACCTCACTTCGTCATCAAAGACATCTGAGGAGCACTTTGTAGAA
ACAGTTTCTTTGGCTGGCTCTTACAGAGATTGGTCCTATTCAGGACAGCGTACAGAGTTAGGTGTTGAATT
TCTTAAGCGTGGTGACAAAATTGTGTACCACACTCTGGAGAGCCCCGTCGAGTTTCATCTTGACGGTGAGG
TTCTTTCACTTGACAAACTAAAGAGTCTCTTATCCCTGCGGGAGGTTAAGACTATAAAAGTGTTCACAACT
GTGGACAACACTAATCTCCACACACAGCTTGTGGATATGTCTATGACATATGGACAGCAGTTTGGTCCAAC
ATACTTGGATGGTGCTGATGTTACAAAAATTAAACCTCATGTAAATCATGAGGGTAAGACTTTCTTTGTAC
TACCTAGTGATGACACACTACGTAGTGAAGCTTTCGAGTACTACCATACTCTTGATGAGAGTTTTCTTGGT
AGGTACATGTCTGCTTTAAACCACACAAAGAAATGGAAATTTCCTCAAGTTGGTGGTTTAACTTCAATTAA
ATGGGCTGATAACAATTGTTATTTGTCTAGTGTTTTATTAGCACTTCAACAGCTTGAAGTCAAATTCAATG
CACCAGCACTTCAAGAGGCTTATTATAGAGCCCGTGCTGGTGATGCTGCTAACTTTTGTGCACTCATACTC
GCTTACAGTAATAAAACTGTTGGCGAGCTTGGTGATGTCAGAGAAACTATGACCCATCTTCTACAGCATGC
TAATTTGGAATCTGCAAAGCGAGTTCTTAATGTGGTGTGTAAACATTGTGGTCAGAAAACTACTACCTTAA
CGGGTGTAGAAGCTGTGATGTATATGGGTACTCTATCTTATGATAATCTTAAGACAGGTGTTTCCATTCCA
TGTGTGTGTGGTCGTGATGCTACACAATATCTAGTACAACAAGAGTCTTCTTTTGTTATGATGTCTGCACC
ACCTGCTGAGTATAAATTACAGCAAGGTACATTCTTATGTGCGAATGAGTACACTGGTAACTATCAGTGTG
GTCATTACACTCATATAACTGCTAAGGAGACCCTCATCGTATTGACGGAGCTCACCTTACAAAGATGTCA
GAGTACAAAGGACCAGTGACTGATGTTTTCTACAAGGAAACATCTTACACTACAACCATCAAGCCTGTGTC
GTATAAACTCGATGGAGTTACTTACACAGAGATTGAACCAAAATTGGATGGGTATTATAAAAGGATAATG
CTTACTATACAGAGCAGCCTATAGACCTTGTACCAACTCAACCATTACCAAATGCGAGTTTTGATAATTTC
AAACTCACATGTTCTAACACAAAATTTGCTGATGATTTAAATCAAATGACAGGCTTCACAAAGCCAGCTTC
ACGAGAGCTATCTGTCACATTCTTCCCAGACTTGAATGGCGATGTAGTGGCTATTGACTATAGACACTATT
CAGCGAGTTTCAAGAAAGGTGCTAAATTACTGCATAAGCCAATTGTTTGGCACATTAACCAGGCTACAACC
AAGACAACGTTCAAACCAAACACTTGGTGTTTACGTTGTCTTTGGAGTACAAAGCCAGTAGATACTTCAAA
TTCATTTGAAGTTCTGGCAGTAGAAGACACACAAGGAATGGACAATCTTGCTTGTGAAAGTCAACAACCCA
CCTCTGAAGAAGTAGTGGAAAATCCTACCATACAGAAGGAAGTCATAGAGTGTGACGTGAAAACTACCGAA
GTTGTAGGCAATGTCATACTTAAACCATCAGATGAAGGTGTTAAAGTAACACAAGAGTTAGGTCATGAGGA
TCTTATGGCTGCTTATGTGGAAAACACAAGCATTACCATTAAGAAACCTAATGAGCTTTCACTAGCCTTAG
GTTTAAAAACAATTGCCACTCATGGTATTGCTGCAATTAATAGTGTTCCTTGGAGTAAAATTTTGGCTTAT
GTCAAACCATTCTTAGGACAAGCAGCAATTACAACATCAAATTGCGCTAAGAGATTAGCACAACGTGTGTT
TAACAATTATATGCCTTATGTGTTTACATTATTGTTCCAATTGTGTACTTTTACTAAAAGTACCAATTCTA
GAATTAGAGCTTCACTACCTACAACTATTGCTAAAAATAGTGTTAAGAGTGTTGCTAAATTATGTTTGGAT
GCCGGCATTAATTATGTGAAGTCACCCAAATTTTCTAAATTGTTCACAATCGCTATGTGGCTATTGTTGTT
AAGTATTTGCTTAGGTTCTCTAATCTGTGTAACTGCTGCTTTTGGTGTACTCTTATCTAATTTTGGTGCTC
CTTCTTATTGTAATGGCGTTAGAGAATTGTATCTTAATTCGTCTAACGTTACTACTATGGATTTCTGTGAA
GGTTCTTTTCCTTGCAGCATTTGTTTAAGTGGATTAGACTCCCTTGATTCTTATCCAGCTCTTGAAACCAT
TCAGGTGACGATTTCATCGTACAAGCTAGACTTGACAATTTTAGGTCTGGCCGCTGAGTGGGTTTTGGCAT
ATATGTTGTTCACAAAATTCTTTTATTTATTAGGTCTTTCAGCTATAATGCAGGTGTTCTTTGGCTATTTT
GCTAGTCATTTCATCAGCAATTCTTGGCTCATGTGGTTTATCATTAGTATTGTACAAATGGCACCCGTTTC
TGCAATGGTTAGGATGTACATCTTCTTTGCTTCTTTCTACTACATATGGAAGAGCTATGTTCATATCATGG
ATGGTTGCACCTCTTCGACTTGCATGATGTGCTATAAGCGCAATCGTGCCACACGCGTTGAGTGTACAACT
ATTGTTAATGGCATGAAGAGATCTTTCTATGTCTATGCAAATGGAGGCCGTGGCTTCTGCAAGACTCACAA
TTGGAATTGTCTCAATTGTGACACATTTTGCACTGGTAGTACATTCATTAGTGATGAAGTTGCTCGTGATT
TGTCACTCCAGTTTAAAAGACCAATCAACCCTACTGACCAGTCATCGTATATTGTTGATAGTGTTGCTGTG
AAAAATGGCGCGCTTCACCTCTACTTTGACAAGGCTGGTCAAAAGACCTATGAGAGACATCCGCTCTCCCA
TTTTGTCAATTTAGACAATTTGAGAGCTAACAACACTAAAGGTTCACTGCCTATTAATGTCATAGTTTTTG
ATGGCAAGTCCAAATGCGACGAGTCTGCTTCTAAGTCTGCTTCTGTGTACTACAGTCAGCTGATGTGCCAA
CCTATTCTGTTGCTTGACCAAGCTCTTGTATCAGACGTTGGAGATAGTACTGAAGTTTCCGTTAAGATGTT
TGATGCTTATGTCGACACCTTTTCAGCAACTTTTAGTGTTCCTATGGAAAAACTTAAGGCACTTGTTGCTA
CAGCTCACAGCGAGTTAGCAAAGGGTGTAGCTTTAGATGGTGTCCTTTCTACATTCGTGTCAGCTGCCCGA
```

FIGURE 3B

```
CAAGGTGTTGTTGATACCGATGTTGACACAAAGGATGTTATTGAATGTCTCAAACTTTCACATCACTCTGA
CTTAGAAGTGACAGGTGACAGTTGTAACAATTTCATGCTCACCTATAATAAGGTTGAAAACATGACGCCCA
GAGATCTTGGCGCATGTATTGACTGTAATGCAAGGCATATCAATGCCCAAGTAGCAAAAAGTCACAATGTT
TCACTCATCTGGAATGTAAAAGACTACATGTCTTTATCTGAACAGCTGCGTAAACAAATTCGTAGTGCTGC
CAAGAAGAACAACATACCTTTTAGACTAACTTGTGCTACAACTAGACAGGTTGTCAATGTCATAACTACTA
AAATCTCACTCAAGGGTGGTAAGATTGTTAGTACTTGTTTTAAACTTATGCTTAAGGCCACATTATTGTGC
GTTCTTGCTGCATTGGTTTGTTATATCGTTATGCCAGTACATACATTGTCAATCCATGATGGTTACACAAA
TGAAATCATTGGTTACAAAGCCATTCAGGATGGTGTCACTCGTGACATCATTTCTACTGATGATTGTTTTG
CAAATAAACATGCTGGTTTTGACGCATGGTTTAGCCAGCGTGGTGGTTCATACAAAAATGACAAAAGCTGC
CCTGTAGTAGCTGCTATCATTACAAGAGAGATTGGTTTCATAGTGCCTGGCTTACCGGGTACTGTGCTGAG
AGCAATCAATGGTGACTTCTTGCATTTTCTACCTCGTGTTTTTAGTGCTGTTGGCAACATTTGCTACACAC
CTTCCAAACTCATTGAGTATAGTGATTTTGCTACCTCTGCTTGCGTTCTTGCTGCTGAGTGTACAATTTTT
AAGGATGCTATGGGCAAACCTGTGCCATATTGTTATGACACTAATTTGCTAGAGGGTTCTATTTCTTATAG
TGAGCTTCGTCCAGACACTCGTTATGTGCTTATGGATGGTTCCATCATACAGTTTCCTAACACTTACCTGG
AGGGTTCTGTTAGAGTAGTAACAACTTTTGATGCTGAGTACTGTAGACATGGTACATGCGAAAGGTCAGAA
GTAGGTATTTGCCTATCTACCAGTGGTAGATGGGTTCTTAATAATGAGCATTACAGAGCTCTATCAGGAGT
TTTCTGTGGTGTTGATGCGATGAATCTCATAGCTAACATCTTTACTCCTCTTGTGCCAACCTGTGGGTGCTT
TAGATGTGTCTGCTTCAGTAGTGGCTGGTGGTATTATTGCCATATTGGTGACTTGTGCTGCCTACTACTTT
ATGAAATTCAGACGTGTTTTTGGTGAGTACAACCATGTTGTTGCTGCTAATGCACTTTTGTTTTTGATGTC
TTTCACTATACTCTGTCTGGTACCAGCTTACAGCTTTCTGCCGGGAGTCTACTCAGTCTTTTACTTGTACT
TGACATTCTATTTCACCAATGATGTTTCATTCTTGGCTCACCTTCAATGGTTTGCCATGTTTTCTCCTATT
GTGCCTTTTTGGATAACAGCAATCTATGTATTCTGTATTTCTCTGAAGCACTGCCATTGGTTCTTTAACAA
CTATCTTAGGAAAAGAGTCATGTTTAATGGAGTTACATTTAGTACCTTCGAGGAGGCTGCTTTGTGTACCT
TTTTGCTCAACAAGGAAATGTACCTAAAATTGCGTAGCGAGACACTGTTGCCACTTACACAGTATAACAGG
TATCTTGCTCTATATAACAAGTACAAGTATTTCAGTGGAGCCTTAGATACTACCAGCTATCGTGAAGCAGC
TTGCTGCCACTTAGCAAAGGCTCTAAATGACTTTAGCAACTCAGGTGCTGATGTTCTCTACCAACCACCAC
AGACATCAATCACTTCTGCTGTTCTGCAGAGTGGTTTTAGGAAAATGGCATTCCCGTCAGGCAAAGTTGAA
GGGTGCATGGTACAAGTAACCTGTGGAACTACAACTCTTAATGGATTGTGGTTGGATGACACAGTATACTG
TCCAAGACATGTCATTTGCACAGCAGAAGACATGCTTAATCCTAACTATGAAGATCTGCTCATTCGCAAAT
CCAACCATAGCTTTCTTGTTCAGGCTGGCAATGTTCAACTTCGTGTTATTGGCCATTCTATGCAAAATTGT
CTGCTTAGGCTTAAAGTTGATACTTCTAACCCTAAGCACACCCAAGTATAAATTTGTCCGTATCCAACCTGG
TCAAACATTTTCAGTTCTAGCATGCTACAATGGTTCACCATCTGGTGTTTATCAGTGTGCCATGAGACCTA
ATCATACCATTAAAGGTTCTTTCCTTAATGGATCATGTGGTAGTGTTGGTTTTAACATTGATTATGATTGC
GTGTCTTTCTGCTATATGCATCATATGGAGCTTCCAACAGGAGTACACGCTGGTACTGACTTAGAAGGTAA
ATTCTATGGTCCATTTGTTGACAGACAAACTGCACAGGCTGCAGGTACAGACACAACCATAACATTAAATG
TTTTGGCATGGCTGTATGCTGCTGTTATCAATGGTGATAGGTGGTTTCTTAATAGATTCACCACTACTTTG
AATGACTTTAACCTTGTGGCAATGAAGTACAACTATGAACCTTTGACACAAGATCATGTTGACATATTGGG
ACCTCTTTCTGCTCAAACAGGAATTGCCGTCTTAGATATGTGTGCTGCTTTGAAAGAGCTGCTGCAGAATG
GTATGAATGGTCGTACTATCCTTGGTAGCACTATTTTAGAAGATGAGTTTACACCATTTGATGTTGTTAGA
CAATGCTCTGGTGTTACCTTCCAAGGTAAGTTCAAGAAAATTGTTAAGGGCACTCATCATTGGATGCTTTT
AACTTTCTTGACATCACTATTGATTCTTGTTCAAAGTACACAGTGGTCACTGTTTTCTTTGTTTACGAGA
ATGCTTCTTGCCATTTACTCTTGGTATTATGGCAATTGCTGCATGTGCTATGCTGCTTGTTAAGCATAAG
CACGCATTCTTGTGCTTGTTTCTGTTACCTTCTCTTGCAACAGTTGCTTACTTTAATATGGTCTACATGCC
TGCTAGCTGGGTGATGCGTATCATGACATGGCTTGAATTGGCTGACACTAGCTTGTCTGGTTATAGGCTTA
AGGATTGTGTTATGTATGCTTCAGCTTTAGTTTTGCTTATTCTCATGACAGCTCGCACTGTTTATGATGAT
GCTGCTAGACGTGTTTGGACACTGATGAATGTCATTACACTTGTTTACAAAGTCTACTATGGTAATGCTTT
AGATCAAGCTATTTCCATGTGGGCCTTAGTTATTTCTGTAACCTCTAACTATTCTGGTGTCGTTACGACTA
TCATGTTTTAGCTAGAGCTATAGTGTTTGTGTGTGTTGAGTATTACCCATTGTATTTATTACTGGCAAC
ACCTTACAGTGTATCATGCTTGTTTATTGTTTCTTAGGCTATTGTTGCTGCTGCTACTTTGGCCTTTTCTG
TTTACTCAACCGTTACTTCAGGCTTACTCTTGGTGTTTATGACTACTTGGTCTCTACACAAGAATTTAGGT
ATATGAACTCCCAGGGGCTTTTGCCTCCTAAGAGTAGTATTGATGCTTTCAAGCTTAACATTAAGTTGTTG
GGTATTGGAGGTAAACCATGTATCAAGGTTGCTACTGTACAGTCTAAAATGTCTGACGTAAAGTGCACATC
TGTGGTACTGCTCTCGGTTCTTCAACAACTAGAGTAGAGTCATCTTCTAAATTGTGGGCACAATGTGTAC
AACTCCACAATGATATTCTTCTTGCAAAAGACACAACTGAAGCTTTCGAGAAGATGGTTTCTCTTTTGTCT
GTTTTGCTATCCATGCAGGGTGCTGTAGACATTAATAGGTTGTGCGAGGAAATGCTCGATAACCGTGCTAC
TCTTCAGGCTATTGCTTCAGAATTTAGTTCTTTACCATCATATGCCGCTTATGCCACTGCCCAGGAGGCCT
ATGAGCAGGCTGTAGCTAATGGTGATTCTGAAGTCGTTCTCAAAAAGTTAAAGAAATCTTTGAATGTGGCT
```

FIGURE 3C

```
AAATCTGAGTTTGACCGTGATGCTGCCATGCAACGCAAGTTGGAAAAGATGGCAGATCAGGCTATGACCCA
AATGTACAAACAGGCAAGATCTGAGGACAAGAGGGCAAAAGTAACTAGTGCTATGCAAACAATGCTCTTCA
CTATGCTTAGGAAGCTTGATAATGATGCACTTAACAACATTATCAACAATGCGCGTGATGGTTGTGTTCCA
CTCAACATCATACCATTGACTACAGCAGCCAAACTCATGGTTGTTGTCCCTGATTATGGTACCTACAAGAA
CACTTGTGATGGTAACACCTTTACATATGCATCTGCACTCTGGGAAATCCAGCAAGTTGTTGATGCGGATA
GCAAGATTGTTCAACTTAGTGAAATTAACATGGACAATTCACCAAATTTGGCTTGGCCTCTTATTGTTACA
GCTCTAAGAGCCAACTCAGCTGTTAAACTACAGAATAATGAACTGAGTCCAGTAGCACTACGACAGATGTC
CTGTGCGGCTGGTACCACACAAACAGCTTGTACTGATGACAATGCACTTGCCTACTATAACAATTCGAAGG
GAGGTAGGTTTGTGCTGGCATTACTATCAGACCACCAAGATCTCAAATGGGCTAGATTCCCTAAGAGTGAT
GGTACAGGTACAATTTACACAGAACTGGAACCACCTTGTAGGTTTGTTACAGACACACCAAAAGGGCCTAA
AGTGAAATACTTGTACTTCATCAAAGGCTTAAACAACCTAAATAGAGGTATGGTGCTGGGCAGTTTAGCTG
CTACAGTACGTCTTCAGGCTGGAAATGCTACAGAAGTACCTGCCAATTCAACTGTGCTTTCCTTCTGTGCT
TTTGCAGTAGACCCTGCTAAAGCATATAAGGATTACCTAGCAAGTGGAGGACAACCAATCACCAACTGTGT
GAAGATGTTGTGTACACACTGGTACAGGACAGGCAATTACTGTAACACCAGAAGCTAACATGGACCAAG
AGTCCTTTGGTGGTGCTTCATGTTGTCTGTATTGTAGATGCCACATTGACCATCCAAATCCTAAAGGATTC
TGTGACTTGAAAGGTAAGTACGTCCAAATACCTACCACTTGTGCTAATGACCCAGTGGGTTTTACACTTAG
AAACACAGTCTGTACCGTCTGCGGAATGTGGAAAGGTTATGGCTGTAGTTGTGACCAACTCCGCGAACCCT
TGATGCAGTCTGCGGATGCATCAACGTTTTTAAACGGGTTTGCGGTGTAAGTGCAGCCCGTCTTACACCGT
GCGGCACAGGCACTAGTACTGATGTCGTCTACAGGGCTTTTGATATTTACAACGAAAAGTTGCTGGTTTT
GCAAAGTTCCTAAAAACTAATTGCTGTCGCTTCCAGGAGAAGGATGAGGAAGGCAATTTATTAGACTCTTA
CTTTGTAGTTAAGAGGCATACTATGTCTAACTACCAACATGAAGAGACTATTTATAACTTGGTTAAAGATT
GTCCAGCGGTTGCTGTCCATGACTTTTTCAAGTTTAGAGTAGATGGTGACATGGTACCACATATATCACGT
CAGCGTCTAACTAAATACACAATGGCTGATTTAGTCTATGCTCTACGTCATTTTGATGAGGGTAATTGTGA
TACATTAAAAGAAATACTCGTCACATACAATTGCTGTGATGATGATTATTTCAATAAGAAGGATTGGTATG
ACTTCGTAGAGAATCCTGACATCTTACGCGTATATGCTAACTTAGGTGAGCGTGCGTACGCCAATCATTATA
AAGACTGTACAATTCTGCGATGCTATGCGTGATGCAGGCATTGTAGGCGTACTGACATTAGATAATCAGGA
TCTTAATGGGAACTGGTACGATTTCGGTGATTTCGTACAAGTAGCACCAGGCTGCGGAGTTCCTATTGTGG
ATTCATATTACTCATTGCTGATGCCCATCCTCACTTTGACTAGGGCATTGGCTGCTGAGTCCCATATGGAT
GCTGATCTCGCAAAACCACTTATTAAGTGGGATTTGCTGAAATATGATTTTACGGAAGAGAGACTTTGTCT
CTTCGACCGTTATTTTAAATATTGGGACCAGACATACCATCCCAATTGTATTAACTGTTTGGATGATAGGT
GTATCCTTCATTGTGCAAACTTTAATGTGTTATTTTCTACTGTGTTTCCACCTACAAGTTTTGGACCACTA
GTAAGAAAAATATTTGTAGATGGTGTTCCTTTTGTTGTTTCAACTGGATACCATTTTCGTGAGTTAGGAGT
CGTACATAATCAGGATGTAAACTTACATAGCTCGCGTCTCAGTTTCAAGGAACTTTTAGTGTATGCTGCTG
ATCCAGCTATGCATGCAGCTTCTGGCAATTTATTGCTAGATAAACGCACTACATGCTTTTCAGTAGCTGCA
CTAACAAACAATGTTGCTTTTCAAACTGTCAAACCCGGTAATTTTAATAAAGACTTTTATGACTTTGCTGT
GTCTAAAGGTTTCTTTAAGGAAGGAAGTTCTGTTGAACTAAAACACTTCTTCTTTGCTCAGGATGGCAACG
CTGCTATCAGTGATTATGACTATTATCGTTATAATCTGCCAACAATGTGTGATATCAGACAACTCCTATTC
GTAGTTGAAGTTGTTGATAAATACTTTGATTGTTACGATGGTGGCTGTATTAATGCCAACCAAGTAATCGT
TAACAATCTGGATAAATCAGCTGGTTTCCCATTTAATAAATGGGGTAAGGCTAGACTTTATTATGACTCAA
TGAGTTATGAGGATCAAGATGCACTTTTCGCGTATACTAAGCGTAATGTCATCCCTACTATAACTCAAATG
AATCTTAAGTATGCCATTAGTGCAAAGAATAGAGCTCGCACCGTAGCTGGTGTCTCTATCTGTAGTACTAT
GACAAATAGACAGTTTCATCAGAAATTATTGAAGTCAATAGCCGCCACTAGAGGAGCTACTGTGGTAATTG
GAACAAGCAAGTTTTACGGTGGCTGGCATAATATGTTAAAAACTGTTTACAGTGATGTAGAAACTCCACAC
CTTATGGGTTGGGATTATCCAAAATGTGACAGAGCCATGCCTAACATGCTTAGGATAATGGCCTCTCTTGT
TCTTGCTCGCAAACATAACACTTGCTGTAACTTATCACACCGTTTCTACAGGTTAGCTAACGAGTGTGCGC
AAGTATTAAGTGAGATGGTCATGTGTGGCGGCTCACTATATGTTAAACCAGGTGGAACATCATCCGGTGAT
GCTACAACTGCTTATGCTAATAGTGTCTTTAACATTTGTCAAGCTGTTACAGCCAATGTAAATGCACTTCT
TTCAACTGATGGTAATAAGATAGCTGACAAGTATGTCCGCAATCTACAACACAGGCTCTATGAGTGTCTCT
ATAGAAATAGGGATGTTGATCATGAATTCGTGGATGAGTTTTACGCTTACCTGCGTAAACATTTCTCCATG
ATGATTCTTTCTGATGATGCCGTTGTGTGCTATAACAGTAACTATGCGGCTCAAGGTTTAGTAGCTAGCAT
TAAGAACTTTAAGGCAGTTCTTTATTATCAAAATAATGTGTTCATGTCTGAGGCAAAATGTTGGACTGAGA
CTGACCTTACTAAAGGACCTCACGAATTTTGCTCACAGCATACAATGCTAGTTAAACAAGGAGATGATTAC
GTGTACCTGCCTTACCCAGATCCATCAAGAATATTAGGCGCAGGCTGTTTTGTCGATGATATTGTCAAAAC
AGATGGTACACTTATGATTGAAAGGTTCGTGTCACTGGCTATTGATGCTTACCCACTTACAAAACATCCTA
ATCAGGAGTATGCTGATGTCTTTCACTTGTATTTACAATACATTAGAAAGTTACATGATGAGCTTACTGGC
CACATGTTGGACATGTATTCCGTAATGCTAACTAATGATAACACCTCACGGTACTGGGAACCTGAGTTTTA
TGAGGCTATGTACACACCACATACAGTCTTGCAGGCTGTAGGTGCTTGTGTATTGTGCAATTCACAGACTT
```

FIGURE 3D

```
CACTTCGTTGCGGTGCCTGTATTAGGAGACCATTCCTATGTTGCAAGTGCTGCTATGACCATGTCATTTCA
ACATCACACAAATTAGTGTTGTCTGTTAATCCCTATGTTTGCAATGCCCCAGGTTGTGATGTCACTGATGT
GACACAACTGTATCTAGGAGGTATGAGCTATTATTGCAAGTCACATAAGCCTCCCATTAGTTTTCCATTAT
GTGCTAATGGTCAGGTTTTTGGTTTATACAAAAACACATGTGTAGGCAGTGACAATGTCACTGACTTCAAT
GCGATAGCAACATGTGATTGGACTAATGCTGGCGATTACATACTTGCCAACACTTGTACTGAGAGACTCAA
GCTTTTCGCAGCAGAAACGCTCAAAGCCACTGAGGAAACATTTAAGCTGTCATATGGTATTGCCACTGTAC
GCGAAGTACTCTCTGACAGAGAATTGCATCTTTCATGGGAGGTTGGAAAACCTAGACCACCATTGAACAGA
AACTATGTCTTTACTGGTTACCGTGTAACTAAAAATAGTAAAGTACAGATTGGAGAGTACACCCTTTGAAAA
AGGTGACTATGGTGATGCTGTTGTGTACAGAGGTACTACGACATACAAGTTGAATGTTGGTGATTACTTTG
TGTTGACATCTCACACTGTAATGCCACTTAGTGCACCTACTCTAGTGCCACAAGAGCACTATGTGAGAATT
ACTGGCTTGTACCCAACACTCAACATCTCAGATGAGTTTTCTAGCAATGTTGCAAATTATCAAAAGGTCGG
CATGCAAAAGTACTCTACACTCCAAGGACCACCTGGTACTGGTAAGAGTCATTTTGCCATCGGACTTGCTC
TCTATTACCCATCTGCTCGCATAGTGTATACGGCATGCTCTCATGCAGCTGTTGATGCCCTATGTGAAAAG
GCATTAAATATTTGCCCATAGATAAATGTAGTAGAATCATACCTGCGCGTGCGCGCGTAGAGTGTTTTGA
TAAATTCAAAGTGAATTCAACACTAGAACAGTATGTTTTCTGCACTGTAAATGCATTGCCAGAAACAACTG
CTGACATTGTAGTCTTTGATGAAATCTCTATGGCTACTAATTATGACTTGAGTGTTGTCAATGCTAGACTT
CGTGCAAAACACTACGTCTATATTGGCGATCCTGCTCAATTACCAGCCCCCGCACATTGCTGACTAAAGG
CACACTAGAACCAGAATATTTTAATTCAGTGTGCAGACTTATGAAAACAATAGGTCCAGACATGTTCCTTG
GAACTTGTCGCCGTTGTCCTGCTGAAATTGTTGACACTGTGAGTGCTTTAGTTTATGACAATAAGCTAAAA
GCACACAAGGATAAGTCAGCTCAATGCTTCAAAATGTTCTACAAAGGTGTTATTACACATGATGTTTCATC
TGCAATCAACAGACCTCAAATAGGCGTTGTAAGAGAATTTCTTACACGCAATCCTGCTTGGAGAAAAGCTG
TTTTTATCTCACCTTATAATTCACAGAACGCTGTAGCTTCAAAAATCTTAGGATTGCCTACGCAGACTGTT
GATTCATCACAGGGTTCTGAATATGACTATGTCATATTCACACAAACTACTGAAACAGCACACTCTTGTAA
TGTCAACCGCTTCAATGTGGCTATCACAAGGGCAAAAATTGGCATTTTGTGCATAATGTCTGATAGAGATC
TTTATGACAAACTGCAATTTACAAGTCTAGAAATACCACGTCGCAATGTGGCTACATTACAAGCAGAAAAT
GTAACTGGACTTTTTAAGGACTGTAGTAAGATCATTACTGGTCTTCATCCTACACAGGCACCTACACACCT
CAGCGTTGATATAAAGTTCAAGACTGAAGGATTATGTGTTGACATACCAGGCATACCAAAGGACATGACCT
ACCGTAGACTCATCTCTATGATGGGTTTCAAAATGAATTACCAAGTCAATGGTTACCCTAATATGTTTATC
ACCCGCGAAGAAGCTATTCGTCACGTTCGTGCGTGGATTGGCTTTGATGTAGAGGGCTGTCATGCAACTAG
AGATGCTGTGGGTACTAACCTACCTCTCCAGCTAGGATTTTCTACAGGTGTTAACTTAGTAGCTGTACCGA
CTGGTTATGTTGACACTGAAAATAACACAGAATTCACCGAGTTAATGCAAAACCTCCACCAGGTGACCAG
TTTAAACATCTTATACCACTCATGTATAAAGGCTTGCCCTGGAATGTAGTGCGTATTAAGATAGTACAAAT
GCTCAGTGATACACTGAAAGGATTGTCAGACAGAGTCGTGTTCGTCCTTTGGGCGCATGGCTTTGAGCTTA
CATCAATGAAGTACTTTGTCAAGATTGGACCTGAAAGAACGTGTTGTCTGTGTGACAAACGTGCAACTTGC
TTTTCTACTTCATCAGATACTTATGCCTGCTGGAATCATTCTGTGGGTTTTGACTATGTCTATAACCCATT
TATGATTGATGTTCAGCAGTGGGCTTTACGGGTAACCTTCAGAGTAACCATGACCAACATTGCCAGGTAC
ATGGAAATGCACATGTGGCTAGTTGTGATGCTATCATGACTAGATGTTTAGCAGTCCATGAGTGCTTTGTT
AAGCGCGTTGATTGGTCTGTTGAATACCCTATTATAGGAGATGAACTGAGGGTTAATTCTGCTTGCAGAAA
AGTACAACACATGGTTGTGAAGTCTGCATTGCTTGCTGATAAGTTTCCAGTTCTTCATGACATTGGAAATC
CAAAGGCTATCAAGTGTGTGCCTCAGGCTGAAGTAGAATGGAAGTTCTACGATGCTCAGCCATGTAGTGAC
AAAGCTTACAAAATAGAGGAACTCTTCTATTCTTATGCTACACATCACGATAAATTCACTGATGGTGTTTG
TTTGTTTTGGAATTGTAACGTTGATCGTTACCCAGCCAATGCAATTGTGTGTAGGTTTGACACAAGAGTCT
TGTCAAACTTGAACTTACCAGGCTGTGATGGTGGTAGTTTGTATGTGAATAAGCATGCATTCCACACTCCA
GCTTTCGATAAAAGTGCATTTACTAATTTAAAGCAATTGCCTTTCTTTTACTATTCTGATAGTCCTTGTGA
GTCTCATGGCAAACAAGTAGTGTCGGATATTGATTATGTTCCACTCAAATCTGCTACGTGTATTACACGAT
GCAATTTAGGTGGTGCTGTTTGCAGACACCATGCAAATGAGTACCGACAGTACTTGGATGCATATAATATG
ATGATTTCTGCTGGATTTAGCCTATGGATTTACAAACAATTTGATACTTATAACCTGTGGAATACATTTAC
CAGGTTACAGAGTTTAGAAAATGTGGCTTATAATGTTGTTAATAAAGGACACTTTGATGGACACGCCGGCG
AAGCACCTGTTTCCATCATTAATAATGCTGTTTACACAAAGGTAGATGGTATTGATGTGGAGATCTTTGAA
AATAAGACAACACTTCCTGTTAATGTTGCATTTGAGCTTTGGGCTAAGCGTAACATTAAACCAGTGCCAGA
GATTAAGATACTCAATAATTTGGGTGTTGATATCGCTGCTAATACTGTAATCTGGGACTACAAAAGAGAAG
CCCCAGCACATGTATCTACAATAGGTGTCTGCACAATGACTGACATTGCCAAGAAACCTACTGAGAGTGCT
TGTTCTTCACTTACTGTCTTGTTTGATGGTAGAGTGGAAGGACAGGTAGACCTTTTTAGAAACGCCCGTAA
TGGTGTTTTAATAACAGAAGGTTCAGTCAAAGGTCTAACACCTTCAAAGGGACCAGCACAAGCTAGCGTCA
ATGGAGTCACATTAATTGGAGAATCAGTAAAAACACAGTTTAACTACTTTAAGAAAGTAGACGGCATTATT
CAACAGTTGCCTGAAACCTACTTTACTCAGAGCAGAGACTTAGAGGATTTTAAGCCCAGATCACAAATGGA
AACTGACTTTCTCGAGCTCGCTATGGATGAATTCATACAGCGATATAAGCTCGAGGGCTATGCCTTCGAAC
```

FIGURE 3E

```
ACATCGTTTATGGAGATTTCAGTCATGGACAACTTGGCGGTCTTCATTTAATGATAGGCTTAGCCAAGCGC
TCACAAGATTCACCACTTAAATTAGAGGATTTTATCCCTATGGACAGCACAGTGAAAAATTACTTCATAAC
AGATGCGCAAACAGGTTCATCAAAATGTGTGTGTTCTGTGATTGATCTTTTACTTGATGACTTTGTCGAGA
TAATAAAGTCACAAGATTTGTCAGTGATTTCAAAAGTGGTCAAGGTTACAATTGACTATGCTGAAATTTCA
TTCATGCTTTGGTGTAAGGATGGACATGTTGAAACCTTCTACCCAAAACTACAAGCAAGTCGAGCGTGGCA
ACCAGGTGTTGCGATGCCTAACTTGTACAAGATGCAAAGAATGCTTCTTGAAAAGTGTGACCTTCAGAATT
ATGGTGAAAATGCTGTTATACCAAAAGGAATAATGATGAATGTCGCAAAGTATACTCAACTGTGTCAATAC
TTAAATACACTTACTTTAGCTGTACCCTACAACATGAGAGTTATTCACTTTGGTGCTGGCTCTGATAAAGG
AGTTGCACCAGGTACAGCTGTGCTCAGACAATGGTTGCCAACTGGCACACTACTTGTCGATTCAGATCTTA
ATGACTTCGTCTCCGACGCATATTCTACTTTAATTGGAGACTGTGCAACAGTACATACGGCTAATAAATGG
GACCTTATTATTAGCGATATGTATGACCCTAGGACCAAACATGTGACAAAAGAGAATGACTCTAAAGAAGG
GTTTTTCACTTATCTGTGTGGATTTATAAAGCAAAAACTAGCCCTGGGTGGTTCTATAGCTGTAAAGATAA
CAGAGCATTCTTGGAATGCTGACCTTTACAAGCTTATGGGCCATTTCTCATGGTGGACAGCTTTTGTTACA
AATGTAAATGCATCATCATCGGAAGCATTTTTAATTGGGGCTAACTATCTTGGCAAGCCGAAGGAACAAAT
TGATGGCTATACCATGCATGCTAACTACATTTTCTGGAGGAACACAAATCCTATCCAGTTGTCTTCCTATT
CACTCTTTGACATGAGCAAATTTCCTCTTAAATTAAGAGGAACTGCTGTAATGTCTCTTAAGGAGAATCAA
ATCAATGATATGATTTATTCTCTTCTGGAAAAAGGTAGGCTTATCATTAGAGAAAACAACAGAGTTGTGGT
TTCAAGTGATATTCTTGTTAACAACTAAACGAACATGTTTATTTTCTTATTATTTCTTACTCTCACTAGTG
GTAGTGACCTTGACCGGTGCACCACTTTTGATGATGTTCAAGCTCCTAATTACACTCAACATACTTCATCT
ATGAGGGGGGTTTACTATCCTGATGAAATTTTTAGATCAGACACTCTTTATTTAACTCAGGATTTATTTCT
TCCATTTTATTCTAATGTTACAGGGTTTCATACTATTAATCATACGTTTGGCAACCCTGTCATACCTTTTA
AGGATGGTATTTATTTTGCTGCCACAGAGAAATCAAATGTTGTCCGTGGTTGGGTTTTTGGTTCTACCATG
AACAACAAGTCACAGTCGGTGATTATTATTAACAATTCTACTAATGTTGTTATACGAGCATGTAACTTTGA
ATTGTGTGACAACCCTTTCTTTGCTGTTTCTAAACCCATGGGTACACAGACACATACTATGATATTCGATA
ATGCATTTAATTGCACTTTCGAGTACATATCTGATGCCTTTTCGCTTGATGTTTCAGAAAAGTCAGGTAAT
TTTAAACACTTACGAGAGTTTGTGTTTAAAAATAAAGATGGGTTTCTCTATGTTTATAAGGGCTATCAACC
TATAGATGTAGTTCGTGATCTACCTTCTGGTTTTAACACTTTGAAACCTATTTTTAAGTTGCCTCTTGGTA
TTAACATTACAAATTTTAGAGCCATTCTTACAGCCTTTTCACCTGCTCAAGACATTTGGGGCACGTCAGCT
GCAGCCTATTTTGTTGGCTATTTAAAGCCAACTACATTTATGCTCAAGTATGATGAAAATGGTACAATCAC
AGATGCTGTTGATTGTTCTCAAAATCCACTTGCTGAACTCAAATGCTCTGTTAAGAGCTTTGAGATTGACA
AAGGAATTTACCAGACCTCTAATTTCAGGGTTGTTCCCTCAGGAGATGTTGTGAGATTCCCTAATATTACA
AACTTGTGTCCTTTTGGAGAGGTTTTTAATGCTACTAAATTCCCTTCTGTCTATGCATGGGAGAGAAAAAA
AATTTCTAATTGTGTTGCTGATTACTCTGTGCTCTACAACTCAACATTTTTTTCAACCTTTAAGTGCTATG
GCGTTTCTGCCACTAAGTTGAATGATCTTTGCTTCTCCAATGTCTATGCAGATTCTTTTGTAGTCAAGGGA
GATGATGTAAGACAAATAGCGCCAGGACAAACTGGTGTTATTGCTGATTATAATTATAAATTGCCAGATGA
TTTCATGGGTTGTGTCCTTGCTTGGAATACTAGGAACATTGATGCTACTTCAACTGGTAATTATAATTATA
AATATAGGTATCTTAGACATGGCAAGCTTAGGCCCTTTGAGAGAGACATATCTAATGTGCCTTTCTCCCCT
GATGGCAAACCTTGCACCCCACCTGCTCTTAATTGTTATTGGCCATTAAATGATTATGGTTTTTACACCAC
TACTGGCATTGGCTACCAACCTTACAGAGTTGTAGTACTTTCTTTTGAACTTTTAAATGCACCGGCCACGG
TTTGTGGACCAAAATTATCCACTGACCTTATTAAGAACCAGTGTGTCAATTTTAATTTTAATGGACTCACT
GGTACTGGTGTGTTAACTCCTTCTTCAAAGAGATTTCAACCATTTCAACAATTTGGCCGTGATGTTTCTGA
TTTCACTGATTCCGTTCGAGATCCTAAAACATCTGAAATATTAGACATTTCACCTTGCGCTTTTGGGGGTG
TAAGTGTAATTACACCTGGAACAAATGCTTCATCTGAAGTTGCTGTTCTATATCAAGATGTTAACTGCACT
GATGTTTCTACAGCAATTCATGCAGATCAACTCACACCACTTGGCGCATATATTCTACTGGAAACAATGT
ATTCCAGACTCAAGCAGGCTGTCTTATAGGAGCTGAGCATGTCGACACTTCTTATGAGTGCGACATTCCTA
TTGGAGCTGGCATTTGTGCTAGTTACCATACAGTTTCTTTATTACGTAGTACTAGCCAAAAATCTATTGTG
GCTTATACTATGTCTTTAGGTGCTGATAGTTCAATTGCTTACTCTAATAACACCATTGCTATACCTACTAA
CTTTTCAATTAGCATTACTACAGAAGTAATGCCTGTTTCTATGGCTAAAACCTCCGTAGATTGTAATATGT
ACATCTGCGGAGATTCTACTGAATGTGCTAATTTGCTTCTCCAATATGGTAGCTTTTGCACACAACTAAAT
CGTGCACTCTCAGGTATTGCTGCTGAACAGGATCGCAACACACGTGAAGTGTTCGCTCAAGTCAAACAAAT
GTACAAAACCCCAACTTTGAAATATTTTGGTGGTTTTAATTTTTCACAAATATTACCTGACCCTCTAAAGC
CAACTAAGAGGTCTTTTATTGAGGACTTGCTCTTTAATAAGGTGACACTCGCTGATGCTGGCTTCATGAAG
CAATATGGCGAATGCCTAGGTGATATTAATGCTAGAGATCTCATTTGTGCGCAGAAGTTCAATGGACTTAC
AGTGTTGCCACCTCTGCTCACTGATGATATGATTGCTGCCTACACTGCTGCTCTAGTTAGTGGTACTGCCA
CTGCTGGATGGACATTTGGTGCTGGCGCTGCTCTTCAAATACCTTTTGCTATGCAAATGGCATATAGGTTC
AATGGCATTGGAGTTACCCAAAATGTTCTCTATGAGAACCAAAAACAAATCGCCAACCAATTTAACAAGGC
GATTAGTCAAATTCAAGAATCACTTACAACAACATCAACTGCATTGGGCAAGCTGCAAGACGTTGTTAACC
```

FIGURE 3F

```
AGAATGCTCAAGCATTAAACACACTTGTTAAACAACTTAGCTCTAATTTTGGTGCAATTTCAAGTGTGCTA
AATGATATCCTTTCGCGACTTGATAAAGTCGAGGCGGAGGTACAAATTGACAGGTTAATTACAGGCAGACT
TCAAAGCCTTCAAACCTATGTAACACAACAACTAATCAGGGCTGCTGAAATCAGGGCTTCTGCTAATCTTG
CTGCTACTAAAATGTCTGAGTGTGTTCTTGGACAATCAAAAGAGTTGACTTTTGTGGAAAGGGCTACCAC
CTTATGTCCTTCCCACAAGCAGCCCCGCATGGTGTTGTCTTCCTACATGTCACGTATGTGCCATCCCAGGA
GAGGAACTTCACCACAGCGCCAGCAATTTGTCATGAAGGCAAAGCATACTTCCCTCGTGAAGGTGTTTTTG
TGTTTAATGGCACTTCTTGGTTTATTACACAGAGGAACTTCTTTTCTCCACAAATAATTACTACAGACAAT
ACATTTGTCTCAGGAAATTGTGATGTCGTTATTGGCATCATTAACAACACAGTTTATGATCCTCTGCAACC
TGAGCTTGACTCATTCAAAGAAGAGCTGGACAAGTACTTCAAAAATCATACATCACCAGATGTTGATCTTG
GCGACATTTCAGGCATTAACGCTTCTGTCGTCAACATTCAAAAAGAAATTGACCGCCTCAATGAGGTCGCT
AAAAATTTAAATGAATCACTCATTGACCTTCAAGAATGGGAAAATATGAGCAATATATTAAATGGCCTTG
GTATGTTTGGCTCGGCTTCATTGCTGGACTAATTGCCATCGTCATGGTTACAATCTTGCTTTGTTGCATGA
CTAGTTGTTGCAGTTGCCTCAAGGGTGCATGCTCTTGTGGTTCTTGCTGCAAGTTTGATGAGGATGACTCT
GAGCCAGTTCTCAAGGGTGTCAAATTACATTACACATAAACGAACTTATGGATTTGTTTATGAGATTTTTT
ACTCTTGGATCAATTACTGCACAGCCAGTAAAAATTGACAATGCTTCTCCTGCAAGTACTGTTCATGCTAC
AGCAACGATACCGCTACAAGCCTCACTCCCTTTCGGATGGCTTGTTATTGGCGTTGCATTTCTTGCTGTTT
TTCAGAGCGCTACCAAAATAATTGCGCTCAATAAAAGATGGCAGCTAGCCCTTTATAAGGGCTTCCAGTTC
ATTTGCAATTTACTGCTGCTATTTGTTACCATCTATTCACATCTTTTGCTTGTCGCTGCAGGTATGGAGGC
GCAATTTTTGTACCTCTATGCCTTGATATATTTCTACAATGCATCAACGCATGTAGAATTATTATGAGAT
GTTGGCTTTGTTGGAAGTGCAAATCCAAGAACCCATTACTTTATGATGCCAACTACTTTGTTTGCTGGCAC
ACACATAACTATGACTACTGTATACCATATAACAGTGTCACAGATACAATTGTCGTTACTGAAGGTGACGG
CATTTCAACACCAAAACTCAAAGAAGACTACCAAATTGGTGGTTATTCTGAGGATAGGCACTCAGGTGTTA
AAGACTATGTCGTTGTACATGGCTATTTCACCGAAGTTTACTACCAGCTTGAGTCTACACAAATTACTACA
GACACTGGTATTGAAAATGCTACATTCTTCATCTTTAACAAGCTTGTTAAAGACCCACCGAATGTGCAAAT
ACACACAATCGACGGCTCTTCAGGAGTTGCTAATCCAGCAATGGATCCAATTTATGATGAGCCGACGACGA
CTACTAGCGTGCCTTTGTAAGCACAAGAAAGTGAGTACGAACTTATGTACTCATTCGTTTCGGAAGAAACA
GGTACGTTAATAGTTAATAGCGTACTTCTTTTTCTTGCTTTCGTGGTATTCTTGCTAGTCACACTAGCCAT
CCTTACTGCGCTTCGATTGTGTGCGTACTGCTGCAATATTGTTAACGTGAGTTTAGTAAAACCAACGGTTT
ACGTCTACTCGCGTGTTAAAAATCTGAACTCTTCTGAAGGAGTTCCTGATCTTCTGGTCTAAACGAACTAA
CTATTATTATTATTCTGTTTGGAACTTTAACATTGCTTATCATGGCAGACAACGGTACTATTACCGTTGAG
GAGCTTAAACAACTCCTGGAACAATGGAACCTAGTAATAGGTTTCCTATTCCTAGCCTGGATTATGTTACT
ACAATTTGCCTATTCTAATCGGAACAGGTTTTTGTACATAATAAAGCTTGTTTTCCTCTGGCTCTTGTGGC
CAGTAACACTTGCTTGTTTTGTGCTTGCTGCTGTCTACAGAATTAATTGGGTGACTGGCGGGATTGCGATT
GCAATGGCTTGTATTGTAGGCTTGATGTGGCTTAGCTACTTCGTTGCTTCCTTCAGGCTGTTTGCTCGTAC
CCGCTCAATGTGGTCATTCAACCCAGAAACAAACATTCTTCTCAATGTGCCTCTCCGGGGGACAATTGTGA
CCAGACCGCTCATGGAAAGTGAACTTGTCATTGGTGCTGTGATCATTCGTGGTCACTTGCGAATGGCCGGA
CACTCCCTAGGGCGCTGTGACATTAAGGACCTGCCAAAAGAGATCACTGTGGCTACATCACGAACGCTTTC
TTATTACAAATTAGGAGCGTCGCAGCGTGTAGGCACTGATTCAGGTTTTGCTGCATACAACCGCTACCGTA
TTGGAAACTATAAATTAAATACAGACCACGCCGGTAGCAACGACAATATTGCTTTGCTAGTACAGTAAGTG
ACAACAGATGTTTCATCTTGTTGACTTCCAGGTTACAATAGCAGAGATATTGATTATCATTATGAGGACTT
TCAGGATTGCTATTTGGAATCTTGACGTTATAATAAGTTCAATAGTGAGACAATTATTTAAGCCTCTAACT
AAGAAGAATTATTCGGAGTTAGATGATGAAGAACCTATGGAGTTAGATTATCCATAAAACGAACATGAAAA
TTATTCTCTTCCTGACATTGATTGTATTTACATCTTGCGAGCTATATCACTATCAGGAGTGTGTTAGAGGT
ACGACTGTACTACTAAAAGAACCTTGCCCATCAGGAACATACGAGGGCAATTCACCATTTCACCCTCTTGC
TGACAATAAATTTGCACTAACTTGCACTAGCACACACTTTGCTTTTGCTTGTGCTGACGGTACTCGACATA
CCTATCAGCTGCGTGCAAGATCAGTTTCACCAAAACTTTTCATCAGACAAGAGGAGGTTCAACAAGAGCTC
TACTCGCCACTTTTTCTCATTGTTGCTGCTCTAGTATTTTAATACTTTGCTTCACCATTAAGAGAAAGAC
AGAATGAATGAGCTCACTTTAATTGACTTCTATTTGTGCTTTTTAGCCTTTCTGCTATTCCTTGTTTTAAT
AATGCTTATTATATTTTGGTTTTCACTCGAAATCCAGGATCTAGAAGAACCTTGTACCAAAGTCTAAACGA
ACATGAAACTTCTCATTGTTTTGACTTGTATTTCTCTATGCAGTTGCATATGCACTGTAGTACAGCGCTGT
GCATCTAATAAACCTCATGTGCTTGAAGATCCTTGTAAGGTACAACACTAGGGGTAATACTTATAGCACTG
CTTGGCTTTGTGCTCTAGGAAAGGTTTTACCTTTTCATAGATGGCACACTATGGTTCAAACATGCACACCT
AATGTTACTATCAACTGTCAAGATCCAGCTGGTGGTGCGCTTATAGCTAGGTGTTGGTACCTTCATGAAGG
TCACCAAACTGCTGCATTTAGAGACGTACTTGTTGTTTAAATAAACGAACAAATTAAAATGTCTGATAAT
GGACCCCAATCAAACCAACGTAGTGCCCCCCGCATTACATTTGGTGGACCCACAGATTCAACTGACAATAA
CCAGAATGGAGGACGCAATGGGGCAAGGCCAAAACAGCGCCGACCCCAAGGTTTACCCAATAATACTGCGT
CTTGGTTCACAGCTCTCACTCAGCATGGCAAGGAGGAACTTAGATTCCCTCGAGGCCAGGGCGTTCCAATC
```

FIGURE 3G

```
AACACCAATAGTGGTCCAGATGACCAAATTGGCTACTACCGAAGAGCTACCCGACGAGTTCGTGGTGGTGA
CGGCAAAATGAAAGAGCTCAGCCCCAGATGGTACTTCTATTACCTAGGAACTGGCCCAGAAGCTTCACTTC
CCTACGGCGCTAACAAAGAAGGCATCGTATGGGTTGCAACTGAGGGAGCCTTGAATACACCCAAAGACCAC
ATTGGCACCCGCAATCCTAATAACAATGCTGCCACCGTGCTACAACTTCCTCAAGGAACAACATTGCCAAA
AGGCTTCTACGCAGAGGGAAGCAGAGGCGGCAGTCAAGCCTCTTCTCGCTCCTCATCACGTAGTCGCGGTA
ATTCAAGAAATTCAACTCCTGGCAGCAGTAGGGGAAATTCTCCTGCTCGAATGGCTAGCGGAGGTGGTGAA
ACTGCCCTCGCGCTATTGCTGCTAGACAGATTGAACCAGCTTGAGAGCAAAGTTTCTGGTAAAGGCCAACA
ACAACAAGGCCAAACTGTCACTAAGAAATCTGCTGCTGAGGCATCTAAAAAGCCTCGCCAAAAACGTACTG
CCACAAAACAGTACAACGTCACTCAAGCATTTGGGAGACGTGGTCCAGAACAAACCCAAGGAAATTTCGGG
GACCAAGACCTAATCAGACAAGGAACTGATTACAAACATTGGCCGCAAATTGCACAATTTGCTCCAAGTGC
CTCTGCATTCTTTGGAATGTCACGCATTGGCATGGAAGTCACACCTTCGGGAACATGGCTGACTTATCATG
GAGCCATTAAATTGGATGACAAAGATCCACAATTCAAAGACAACGTCATACTGCTGAACAAGCACATTGAC
GCATACAAAACATTCCCACCAACAGAGCCTAAAAAGGACAAAAAGAAAAAGACTGATGAAGCTCAGCCTTT
GCCGCAGAGACAAAAGAAGCAGCCCACTGTGACTCTTCTTCCTGCGGCTGACATGGATGATTTCTCCAGAC
AACTTCAAAATTCCATGAGTGGAGCTTCTGCTGATTCAACTCAGGCATAAACACTCATGATGACCACACAA
GGCAGATGGGCTATGTAAACGTTTTCGCAATTCCGTTTACGATACATAGTCTACTCTTGTGCAGAATGAAT
TCTCGTAACTAAACAGCACAAGTAGGTTTAGTTAACTTTAATCTCACATAGCAATCTTTAATCAATGTGTA
ACATTAGGGAGGACTTGAAAGAGCCACCACATTTTCATCGAGGCCACGCGGAGTACGATCGAGGGTACAGT
GAATAATGCTAGGGAGAGCTGCCTATATGGAAGAGCCCTAATGTGTAAAATTAATTTTAGTAGTGCTATCC
CCATGTGATTTTAATAGCTTCTTAGGAGAATGACAAAAAAAAAAAAAAAAAAAAAA
```

GenBank Accession No. AY274119.1; SEQ ID NO: 1

FIGURE 3H

```
CTACCCAGGAAAAGCCAACCAACCTCGATCTCTTGTAGATCTGTTCTCTAAACGAACTTTAAAATCTGTGT
AGCTGTCGCTCGGCTGCATGCCTAGTGCACCTACGCAGTATAAACAATAATAAATTTTACTGTCGTTGACA
AGAAACGAGTAACTCGTCCCTCTTCTGCAGACTGCTTACGGTTTCGTCCGTGTTGCAGTCGATCATCAGCA
TACCTAGGTTTCGTCCGGGTGTGACCGAAAGGTAAGATGGAGAGCCTTGTTCTTGGTGTCAACGAGAAAAC
ACACGTCCAACTCAGTTTGCCTGTCCTTCAGGTTAGAGACGTGCTAGTGCGTGGCTTCGGGGACTCTGTGG
AAGAGGCCCTATCGGAGGCACGTGAACACCTCAAAAATGGCACTTGTGGTCTAGTAGAGCTGGAAAAAGGC
GTACTGCCCCAGCTTGAACAGCCCTATGTGTTCATTAAACGTTCTGATGCCTTAAGCACCAATCACGGCCA
CAAGGTCGTTGAGCTGGTTGCAGAAATGGACGGCATTCAGTACGGTCGTAGCGGTATAACACTGGGAGTAC
TCGTGCCACATGTGGGCGAAACCCCAATTGCATACCGCAATGTTCTTCTTCGTAAGAACGGTAATAAGGGA
GCCGGTGGTCATAGCTATGGCATCGATCTAAAGTCTTATGACTTAGGTGACGAGCTTGGCACTGATCCCAT
TGAAGATTATGAACAAAACTGGAACACTAAGCATGGCAGTGGTGCACTCCGTGAACTCACTCGTGAGCTCA
ATGGAGGTGCAGTCACTCGCTATGTCGACAACAATTTCTGTGGCCCAGATGGGTACCCTCTTGATTGCATC
AAAGATTTTCTCGCACGCGCGGGCAAGTCAATGTGCACTCTTTCCGAACAACTTGATTACATCGAGTCGAA
GAGAGGTGTCTACTGCTGCCGTGACCATGAGCATGAAATTGCCTGGTTCACTGAGCGCTCTGATAAGAGCT
ACGAGCACCAGACACCCTTCGAAATTAAGAGTGCCAAGAAATTTGACACTTTCAAAGGGGAATGCCCAAAG
TTTGTGTTTCCTCTTAACTCAAAAGTCAAAGTCATTCAACCACGTGTTGAAAAGAAAAAGACTGAGGGTTT
CATGGGGCGTATACGCTCTGTGTACCCTGTTGCATCTCCACAGGAGTGTAACAATATGCACTTGTCTACCT
TGATGAAATGTAATCATTGCGATGAAGTTTCATGGCAGACGTGCGACTTTCTGAAAGCCACTTGTGAACAT
TGTGGCACTGAAAATTTAGTTATTGAAGGACCTACTACATGTGGGTACCTACCTACTAATGCTGTAGTGAA
AATGCCATGTCCTGCCTGTCAAGACCCAGAGATTGGACCTGAGCATAGTGTTGCAGATTATCACAACCACT
CAAACATTGAAACTCGACTCCGCAAGGGAGGTAGGACTAGATGTTTTGGAGGCTGTGTGTTTGCCTATGTT
GGCTGCTATAATAAGCGTGCCTACTGGGTTCCTCGTGCTAGTGCTGATATTGGCTCAGGCCATACTGGCAT
TACTGGTGACAATGTGGAGACCTTGAATGAGGATCTCCTTGAGATACTGAGTCGTGAACGTGTTAACATTA
ACATTGTTGGCGATTTTCATTTGAATGAAGAGGTTGCCATCATTTTGGCATCTTTCTCTGCTTCTACAAGT
GCCTTTATTGACACTATAAAGAGTCTTGATTACAAGTCTTTCAAAACCATTGTTGAGTCCTGCGGTAACTA
TAAAGTTACCAAGGGAAAGCCCGTAAAAGGTGCTTGGAACATTGGACAACAGAGATCAGTTTTAACACCAC
TGTGTGGTTTTCCCTCACAGGCTGCTGGTGTTATCAGATCAATTTTTGCGCGCACACTTGATGCAGCAAAC
CACTCAATTCCTGATTTGCAAAGAGCAGCTGTCACCATACTTGATGGTATTTCTGAACAGTCATTACGTCT
TGTCGACGCCATGGTTTATACTTCAGACCTGCTCACCAACAGTGTCATTATTATGGCATATGTAACTGGTG
GTCTTGTACAACAGACTTCTCAGTGGTTGTCTAATCTTTTGGGCACTACTGTTGAAAAACTCAGGCCTATC
TTTGAATGGATTGAGGCGAAACTTAGTGCAGGAGTTGAATTTCTCAAGGATGCTTGGGAGATTCTCAAATT
TCTCATTACAGGTGTTTTTGACATCGTCAAGGGTCAAATACAGGTTGCTTCAGATAACATCAAGGATTGTG
TAAAATGCTTCATTGATGTTGTTAACAAGGCACTCGAAATGTGCATTGATCAAGTCACTATCGCTGGCGCA
AAGTTGCGATCACTCAACTTAGGTGAAGTCTTCATCGCTCAAAGCAAGGGACTTTACCGTCAGTGTATACG
TGGCAAGGAGCAGCTGCAACTACTCATGCCTCTTAAGGCACCAAAAGAAGTAACCTTTCTTGAAGGTGATT
CACATATGACACAGTACTTACCTCTGAGGAGGTTGTTCTCAAGAACGGTGAACTCGAAGCACTCGAGACGCCC
GTTGATAGCTTCACAAATGGAGCTATCGTTGGCACACCAGTCTGTGTAAATGGCCTCATGCTCTTAGAGAT
TAAGGACAAAGAACAATACTGCGCATTGTCTCCTGGTTTACTGGCTACAAACAATGTCTTTCGCTTAAAAG
GGGGTGCACCAATTAAAGGTGTAACCTTTGGAGAAGATACTGTTTGGGAAGTTCAAGGTTACAAGAATGTG
AGAATCACATTTGAGCTTGATGAACGTGTTGACAAAGTGCTTAATGAAAAGTGCTCTGTCTACACTGTTGA
ATCCGGTACCGAAGTTACTGAGTTTGCATGTGTTGTAGCAGAGGCTGTTGTGAAGACTTTACAACCAGTTT
CTGATCTCCTTACCAACATGGGTATTGATCTTGATGAGTGGAGTGTAGCTACATTCTACTTATTTGATGAT
GCTGGTGAAGAAAACTTTTCATCACGTATGTATTGTTCCTTTTACCCTCCAGATGAGGAAGAAGAGGACGA
TGCAGAGTGTGAGGAAGAAGAAATTGATGAAACCTGTGAACATGAGTACGGTACAGAGGATGATTATCAAG
GTCTCCCTCTGGAATTTGGTGCCTCAGCTGAAACAGTTCGAGTTGAGGAAGAAGAAGAGGAAGACTGGCTG
GATGATACTACTGAGCAATCAGAGATTGAGCCAGAACCAGAACCTACACCTGAAGAACCAGTTAATCAGTT
TACTGGTTATTTAAAACTTACTGACAATGTTGCCATTAAATGTGTTGACATCGTTAAGGAGGCACAAAGTG
CTAATCCTATGGTGATTGTAAATGCTGCTAACATACACCTGAAACATGGTGGTGGTGTAGCAGGTGCACTC
AACAAGGCAACCAATGGTGCCATGCAAAAGGAGAGTGATGATTACATTAAGCTAAATGGCCCTCTTACAGT
AGGAGGGTCTTGTTTGCTTTCTGGACATAATCTTGCTAAGAAGTGTCTGCATGTTGTTGGACCTAACCTAA
ATGCAGGTGAGGACATCCAGCTTCTTAAGGCAGCATATGAAAATTTCAATTCACAGGACATCTTACTTGCA
CCATTGTTGTCAGCAGGCATATTTGGTGCTAAACCACTTCAGTCTTTACAAGTGTGCGTGCAGACGGTTCG
TACACAGGTTTATATTGCAGTCAATGACAAAGCTCTTTATGAGCAGGTTGTCATGGATTATCTTGATAACC
TGAAGCCTAGAGTGGAAGCACCTAAACAAGAGGAGCCACCAAACACAGAAGATTCCAAAACTGAGGAGAAA
TCTGTCGTACAGAAGCCTGTCGATGTGAAGCCAAAAATTAAGGCCTGCATTGATGAGGTTACCACAACACT
GGAAGAAACTAAGTTTCTTACCAATAAGTTACTCTTGTTTGCTGATATCAATGGTAAGCTTTACCATGATT
CTCAGAACATGCTTAGAGGTGAAGATATGTCTTTCCTTGAGAAGGATGCACCTTACATGGTAGGTGATGTT
```

FIGURE 3I

```
ATCACTAGTGGTGATATCACTTGTGTTGTAATACCCTCCAAAAAGGCTGGTGGCACTACTGAGATGCTCTC
AAGAGCTTTGAAGAAAGTGCCAGTTGATGAGTATATAACCACGTACCCTGGACAAGGATGTGCTGGTTATA
CACTTGAGGAAGCTAAGACTGCTCTTAAGAAATGCAAATCTGCATTTTATGTACTACCTTCAGAAGCACCT
AATGCTAAGGAAGAGATTCTAGGAACTGTATCCTGGAATTTGAGAGAAATGCTTGCTCATGCTGAAGAGAC
AAGAAAATTAATGCCTATATGCATGGATGTTAGAGCCATAATGGCAACCATCCAACGTAAGTATAAAGGAA
TTAAAATTCAAGAGGGCATCGTTGACTATGGTGTCCGATTCTTCTTTTATACTAGTAAAGAGCCTGTAGCT
TCTATTATTACGAAGCTGAACTCTCTAAATGAGCCGCTTGTCACAATGCCAATTGGTTATGTGACACATGG
TTTTAATCTTGAAGAGGCTGCGCGCTGTATGCGTTCTCTTAAAGCTCCTGCCGTAGTGTCAGTATCATCAC
CAGATGCTGTTACTACATATAATGGATACCTCACTTCGTCATCAAAGACATCTGAGGAGCACTTTGTAGAA
ACAGTTTCTTTGGCTGGCTCTTACAGAGATTGGTCCTATTCAGGACAGCGTACAGAGTTAGGTGTTGAATT
TCTTAAGCGTGGTGACAAAATTGTGTACCACACTCTGGAGAGCCCCGTCGAGTTTCATCTTGACGGTGAGG
TTCTTTCACTTGACAAACTAAAGAGTCTCTTATCCCTGCGGGAGGTTAAGACTATAAAAGTGTTCACAACT
GTGGACAACACTAATCTCCACACACAGCTTGTGGATATGTCTATGACATATGGACAGCAGTTTGGTCCAAC
ATACTTGGATGGTGCTGATGTTACAAAAATTAAACCTCATGTAAATCATGAGGGTAAGACTTTCTTTGTAC
TACCTAGTGATGACACACTACGTAGTGAAGCTTTCGAGTACTACCATACTCTTGATGAGAGTTTTCTTGGT
AGGTACATGTCTGCTTTAAACCACACAAAGAAATGGAAATTTCCTCAAGTTGGTGGTTTAACTTCAATTAA
ATGGGCTGATAACAATTGTTATTTGTCTAGTGTTTTATTAGCACTTCAACAGCTTGAAGTCAAATTCAATG
CACCAGCACTTCAAGAGGCTTATTATAGAGCCCGTGCTGGTGATGCTGCTAACTTTTGTGCACTCATACTC
GCTTACAGTAATAAAACTGTTGGCGAGCTTGGTGATGTCAGAGAAACTATGACCCATCTTCTACAGCATGC
TAATTTGGAATCTGCAAAGCGAGTTCTTAATGTGGTGTGTAAACATTGTGGTCAGAAAACTACTACCTTAA
CGGGTGTAGAAGCTGTGATGTATATGGGTACTCTATCTTATGATAATCTTAAGACAGGTGTTTCCATTCCA
TGTGTGTGTGGTCGTGATGCTACACAATATCTAGTACAACAAGAGTCTTCTTTTGTTATGATGTCTGCACC
ACCTGCTGAGTATAAATTACAGCAAGGTACATTCTTATGTGCGAATGAGTACACTGGTAACTATCAGTGTG
GTCATTACACTCATATAACTGCTAAGGAGACCCTCTATCGTATTGACGGAGCTCACCTTACAAAGATGTCA
GAGTACAAAGGACCAGTGACTGATGTTTTCTACAAGGAAACATCTTACACTACAACCATCAAGCCTGTGTC
GTATAAACTCGATGGAGTTACTTACACAGAGATTGAACCAAAATTGGATGGGTATTATAAAAGGATAATG
CTTACTATACAGAGCAGCCTATAGACCTTGTACCAACTCAACCATTACCAAATGCGAGTTTTGATAATTTC
AAACTCACATGTTCTAACACAAAATTTGCTGATGATTTAAATCAAATGACAGGCTTCACAAAGCCAGCTTC
ACGAGAGCTATCTGTCACATTCTTCCCAGACTTGAATGGCGATGTAGTGGCTATTGACTATAGACACTATT
CAGCGAGTTTCAAGAAAGGTGCTAAATTACTGCATAAGCCAATTGTTTGGCACATTAACCAGGCTACAACC
AAGACAACGTTCAAACCAAACACTTGGTGTTTACGTTGTCTTTGGAGTACAAAGCCAGTAGATACTTCAAA
TTCATTTGAAGTTCTGGCAGTAGAAGACACACAAGGAATGGACAATCTTGCTTGTGAAAGTCAACAACCCA
CCTCTGAAGAAGTAGTGGAAAATCCTACCATACAGAAGGAAGTCATAGAGTGTGACGTGAAAACTACCGAA
GTTGTAGGCAATGTCATACTTAAACCATCAGATGAAGGTGTTAAAGTAACACAAGAGTTAGGTCATGAGGA
TCTTATGGCTGCTTATGTGGAAAACACAAGCATTACCATTAAGAAACCTAATGAGCTTTCACTAGCCTTAG
GTTTAAAAACAATTGCCACTCATGGTATTGCTGCAATTAATAGTGTTCCTTGGAGTAAAATTTTGGCTTAT
GTCAAACCATTCTTAGGACAAGCAGCAATTACAACATCAAATTGCGCTAAGAGATTAGCACAACGTGTGTT
TAACAATTATATGCCTTATGTGTTTACATTATTGTTCCAATTGTGTACTTTTACTAAAAGTACCAATTCTA
GAATTAGAGCTTCACTACCTACAACTATTGCTAAAAATAGTGTTAAGAGTGTTGCTAAATTATGTTTGGAT
GCCGGCATTAATTATGTGAAGTCACCCAAATTTTCTAAATTGTTCACAATCGCTATGTGGCTATTGTTGTT
AAGTATTTGCTTAGGTTCTCTAATCTGTGTAACTGCTGCTTTTGGTGTACTCTTATCTAATTTTGGTGCTC
CTTCTTATTGTAATGGCGTTAGAGAATTGTATCTTAATTCGTCTAACGTTACTACTATGGATTTCTGTGAA
GGTTCTTTTCCTTGCAGCATTTGTTTAAGTGGATTAGACTCCCTTGATTCTTATCCAGCTCTTGAAACCAT
TCAGGTGACGATTTCATCGTACAAGCTAGACTTGACAATTTTAGGTCTGGCCGCTGAGTGGGTTTTGGCAT
ATATGTTGTTCACAAAATTCTTTTATTTATTAGGTCTTTCAGCTATAATGCAGGTGTTCTTTGGCTATTTT
GCTAGTCATTTCATCAGCAATTCTTGGCTCATGTGGTTTATCATTAGTATTGTACAAATGGCACCCGTTTC
TGCAATGGTTAGGATGTACATCTTCTTTGCTTCTTTCTACTACATATGGAAGAGCTATGTTCATATCATGG
ATGGTTGCACCTCTTCGACTTGCATGATGTGCTATAAGCGCAATCGTGCCACACGCGTTGAGTGTACAACT
ATTGTTAATGGCATGAAGAGATCTTTCTATGTCTATGCAAATGGAGGCCGTGGCTTCTGCAAGACTCACAA
TTGGAATTGTCTCAATTGTGACACATTTTGCACTGGTAGTACATTCATTAGTGATGAAGTTGCTCGTGATT
TGTCACTCCAGTTTAAAAGACCAATCAACCCTACTGACCAGTCATCGTATATTGTTGATAGTGTTGCTGTG
AAAAATGGCGCGCTTCACCTCTACTTTGACAAGGCTGGTCAAAAGACCTATGAGAGACATCCGCTCTCCCA
TTTTGTCAATTTAGACAATTTGAGAGCTAACAACACTAAAGGTTCACTGCCTATTAATGTCATAGTTTTTG
ATGGCAAGTCCAAATGCGACGAGTCTCGTTCTTAAGTCTGCTTCTGTGTACTACAGTCAGCTGATGTGCCAA
CCTATTCTGTTGCTTGACCAAGCTCTTGTATCAGACGTTGGAGATAGTACTGAAGTTTCCGTTAAGATGTT
TGATGCTTATGTCGACACCTTTTCAGCAACTTTTAGTGTTCCTATGGAAAAACTTAAGGCACTTGTTGCTA
CAGCTCACAGCGAGTTAGCAAAGGGTGTAGCTTTAGATGGTGTCCTTTCTACATTCGTGTCAGCTGCCCGA
```

FIGURE 3J

```
CAAGGTGTTGTTGATACCGATGTTGACACAAAGGATGTTATTGAATGTCTCAAACTTTCACATCACTCTGA
CTTAGAAGTGACAGGTGACAGTTGTAACAATTTCATGCTCACCTATAATAAGGTTGAAAACATGACGCCCA
GAGATCTTGGCGCATGTATTGACTGTAATGCAAGGCATATCAATGCCCAAGTAGCAAAAAGTCACAATGTT
TCACTCATCTGGAATGTAAAAGACTACATGTCTTTATCTGAACAGCTGCGTAAACAAATTCGTAGTGCTGC
CAAGAAGAACAACATACCTTTTAGACTAACTTGTGCTACAACTAGACAGGTTGTCAATGTCATAACTACTA
AAATCTCACTCAAGGGTGGTAAGATTGTTAGTACTTGTTTTAAACTTATGCTTAAGGCCACATTATTGTGC
GTTCTTGCTGCATTGGTTTGTTATATCGTTATGCCAGTACATACATTGTCAATCCATGATGGTTACACAAA
TGAAATCATTGGTTACAAAGCCATTCAGGATGGTGTCACTCGTGACATCATTTCTACTGATGATTGTTTTG
CAAATAAACATGCTGGTTTTGACGCATGGTTTAGCCAGCGTGGTGGTTCATACAAAAATGACAAAAGCTGC
CCTGTAGTAGCTGCTATCATTACAAGAGAGATTGGTTTCATAGTGCCTGGCTTACCGGGTACTGTGCTGAG
AGCAATCAATGGTGACTTCTTGCATTTTCTACCTCGTGTTTTTAGTGCTGTTGGCAACATTTGCTACACAC
CTTCCAAACTCATTGAGTATAGTGATTTTGCTACCTCTGCTTGCGTTCTTGCTGCTGAGTGTACAATTTTT
AAGGATGCTATGGGCAAACCTGTGCCATATTGTTATGACACTAATTTGCTAGAGGGTTCTATTTCTTATAG
TGAGCTTCGTCCAGACACTCGTTATGTGCTTATGGATGGTTCCATCATACAGTTTCCTAACACTTACCTGG
AGGGTTCTGTTAGAGTAGTAACAACTTTTGATGCTGAGTACTGTAGACATGGTACATGCGAAAGGTCAGAA
GTAGGTATTTGCCTATCTACCAGTGGTAGATGGGTTCTTAATAATGAGCATTACAGAGCTCTATCAGGAGT
TTTCTGTGGTGTTGATGCGATGAATCTCATAGCTAACATCTTTACTCCTCTTGTGCAACCTGTGGGTGCTT
TAGATGTGTCTGCTTCAGTAGTGGCTGGTGGTATTATTGCCATATTGGTGACTTGTGCTGCCTACTACTTT
ATGAAATTCAGACGTGTTTTTGGTGAGTACAACCATGTTGTTGCTGCTAATGCACTTTTGTTTTGATGTC
TTTCACTATACTCTGTCTGGTACCAGCTTACAGCTTTCTGCCGGGAGTCTACTCAGTCTTTTACTTGTACT
TGACATTCTATTTCACCAATGATGTTTCATTCTTGGCTCACCTTCAATGGTTTGCCATGTTTTCTCCTATT
GTGCCTTTTTGGATAACAGCAATCTATGTATTCTGTATTTCTCTGAAGCACTGCCATTGGTTCTTTAACAA
CTATCTTAGGAAAAGAGTCATGTTTAATGGAGTTACATTTAGTACCTTCGAGGAGGCTGCTTTGTGTACCT
TTTTGCTCAACAAGGAAATGTACCTAAAATTGCGTAGCGAGACACTGTTGCCACTTACACAGTATAACAGG
TATCTTGCTCTATATAACAAGTACAAGTATTTCAGTGGAGCCTTAGATACTACCAGCTATCGTGAAGCAGC
TTGCTGCCACTTAGCAAAGGCTCTAAATGACTTTAGCAACTCAGGTGCTGATGTTCTCTACCAACCACCAC
AGACATCAATCACTTCTGCTGTTCTGCAGAGTGGTTTTAGGAAAATGGCATTCCCGTCAGGCAAAGTTGAA
GGGTGCATGGTACAAGTAACCTGTGGAACTACAACTCTTAATGGATTGTGGTTGGATGACACAGTATACTG
TCCAAGACATGTCATTTGCACAGCAGAAGACATGCTTAATCCTAACTATGAAGATCTGCTCATTCGCAAAT
CCAACCATAGCTTTCTTGTTCAGGCTGGCAATGTTCAACTTCGTGTTATTGGCCATTCTATGCAAAATTGT
CTGCTTAGGCTTAAAGTTGATACTTCTAACCCTAAGACACCCAAGTATAAATTTGTCCGTATCCAACCTGG
TCAAACATTTTCAGTTCTAGCATGCTACAATGGTTCACCATCTGGTGTTTATCAGTGTGCCATGAGACCTA
ATCATACCATTAAAGGTTCTTTCCTTAATGGATCATGTGGTAGTGTTGGTTTTAACATTGATTATGATTGC
GTGTCTTTCTGCTATATGCATCATATGGAGCTTCCAACAGGAGTACACGCTGGTACTGACTTAGAAGGTAA
ATTCTATGGTCCATTTGTTGACAGACAAACTGCACAGGCTGCAGGTACAGACACAACCATAACATTAAATG
TTTTGGCATGGCTGTATGCTGCTGTTATCAATGGTGATAGGTGGTTTCTTAATAGATTCACCACTACTTTG
AATGACTTTAACCTTGTGGCAATGAAGTACAACTATGAACCTTTGACACAAGATCATGTTGACATATTGGG
ACCTCTTTCTGCTCAAACAGGAATTGCCGTCTTAGATATGTGTGCTGCTTTGAAAGAGCTGCTGCAGAATG
GTATGAATGGTCGTACTATCCTTGGTAGCACTATTTTAGAAGATGAGTTTACACCATTTGATGTTGTTAGA
CAATGCTCTGGTGTTACCTTCCAAGGTAAGTTCAAGAAAATTGTTAAGGGCACTCATCATTGGATGCTTTT
AACTTTCTTGACATCACTATTGATTCTTGTTCAAAGTACACAGTGGTCACTGTTTTTCTTTGTTTACGAGA
ATGCTTTCTTGCCATTTACTCTTGGTATTATGGCAATTGCTGCATGTGCTATGCTGCTTGTTAAGCATAAG
CACGCATTCTTGTGCTTGTTTCTGTTACCTTCTCTTGCAACAGTTGCTTACTTTAATATGGTCTACATGCC
TGCTAGCTGGGTGATGCGTATCATGACATGGCTTGAATTGGCTGACACTAGCTTGTCTGGTTATAGGCTTA
AGGATTGTGTTATGTATGCTTCAGCTTTAGTTTTGCTTATTCTCATGACAGCTCGCACTGTTTATGATGAT
GCTGCTAGACGTGTTTGGACACTGATGAATGTCATTACACTTGTTTACAAAGTCTACTATGGTAATGCTTT
AGATCAAGCTATTTCCATGTGGGCCTTAGTTATTTCTGTAACCTCTAACTATTCTGGTGTCGTTACGACTA
TCATGTTTTTAGCTAGAGCTATAGTGTTTGTGTGTGTTGAGTATTACCCATTGTTATTTATTACTGGCAAC
ACCTTACAGTGTATCATGCTTGTTTATTGTTTCTTAGGCTATTGTTGCTGCTGCTACTTTGGCCTTTTCTG
TTTACTCAACCGTTACTTCAGGCTTACTCTTGGTGTTTATGACTACTTGGTCTCTACACAAGAATTTAGGT
ATATGAACTCCCAGGGGCTTTTGCCTCCTAAGAGTAGTATTGATGCTTTCAAGCTTAACATTAAGTTGTTG
GGTATTGGAGGTAAACCATGTATCAAGGTTGCTACTGTACAGTCTAAAATGTCTGACGTAAAGTGCACATC
TGTGGTACTGCTCTCGGTTCTTCAACAACTTAGAGTAGAGTCATCTTCTAAATTGTGGGCACAATGTGTAC
AACTCCACAATGATATTCTTCTTGCAAAAGACACAACTGAAGCTTTCGAAGAAGATGGTTTCTCTTTTGTCT
GTTTTGCTATCCATGCAGGGTGCTGTAGACATTAATAGGTTGTGCGAGGAAATGCTCGATAACCGTGCTAC
TCTTCAGGCTATTGCTTCAGAATTTAGTTCTTTACCATCATATGCCGCTTATGCCACTGCCCAGGAGGCCT
ATGAGCAGGCTGTAGCTAATGGTGATTCTGAAGTCGTTCTCAAAAAGTTAAAGAAATCTTTGAATGTGGCT
```

```
AAATCTGAGTTTGACCGTGATGCTGCCATGCAACGCAAGTTGGAAAAGATGGCAGATCAGGCTATGACCCA
AATGTACAAACAGGCAAGATCTGAGGACAAGAGGGCAAAAGTAACTAGTGCTATGCAAACAATGCTCTTCA
CTATGCTTAGGAAGCTTGATAATGATGCACTTAACAACATTATCAACAATGCGCGTGATGGTTGTGTTCCA
CTCAACATCATACCATTGACTACAGCAGCCAAACTCATGGTTGTTGTCCCTGATTATGGTACCTACAAGAA
CACTTGTGATGGTAACACCTTTACATATGCATCTGCACTCTGGGAAATCCAGCAAGTTGTTGATGCGGATA
GCAAGATTGTTCAACTTAGTGAAATTAACATGGACAATTCACCAAATTTGGCTTGGCCTCTTATTGTTACA
GCTCTAAGAGCCAACTCAGCTGTTAAACTACAGAATAATGAACTGAGTCCAGTAGCACTACGACAGATGTC
CTGTGCGGCTGGTACCACACAAACAGCTTGTACTGATGACAATGCACTTGCCTACTATAACAATTCGAAGG
GAGGTAGGTTTGTGCTGGCATTACTATCAGACCACCAAGATCTCAAATGGGCTAGATTCCCTAAGAGTGAT
GGTACAGGTACAATTTACACAGAACTGGAACCACCTTGTAGGTTTGTTACAGACACACCAAAAGGGCCTAA
AGTGAAATACTTGTACTTCATCAAAGGCTTAAACAACCTAAATAGAGGTATGGTGCTGGGCAGTTTAGCTG
CTACAGTACGTCTTCAGGCTGGAAATGCTACAGAAGTACCTGCCAATTCAACTGTGCTTTCCTTCTGTGCT
TTTGCAGTAGACCCTGCTAAAGCATATAAGGATTACCTAGCAAGTGGAGGACAACCAATCACCAACTGTGT
GAAGATGTTGTGTACACACACTGGTACAGGACAGGCAATTACTGTAACACCAGAAGCTAACATGGACCAAG
AGTCCTTTGGTGGTGCTTCATGTTGTCTGTATTGTAGATGCCACATTGACCATCCAAATCCTAAAGGATTC
TGTGACTTGAAAGGTAAGTACGTCCAAATACCTACCACTTGTGCTAATGACCCAGTGGGTTTTACACTTAG
AAACACAGTCTGTACCGTCTGCGGAATGTGGAAAGGTTATGGCTGTAGTTGTGACCAACTCCGCGAACCCT
TGATGCAGTCTGCGGATGCATCAACGTTTTTAAACGGGTTTGCGGTGTAAGTGCAGCCCGTCTTACACCGT
GCGGCACAGGCACTAGTACTGATGTCGTCTACAGGGCTTTTGATATTTACAACGAAAAAGTTGCTGGTTTT
GCAAAGTTCCTAAAAACTAATTGCTGTCGCTTCCAGGAGAAGGATGAGGAAGGCAATTTATTAGACTCTTA
CTTTGTAGTTAAGAGGCATACTATGTCTAACTACCAACATGAAGAGACTATTTATAACTTGGTTAAAGATT
GTCCAGCGGTTGCTGTCCATGACTTTTTCAAGTTTAGAGTAGATGGTGACATGGTACCACATATATCACGT
CAGCGTCTAACTAAATACACAATGGCTGATTTAGTCTATGCTCTACGTCATTTTGATGAGGGTAATTGTGA
TACATTAAAAGAAATACTCGTCACATACAATTGCTGTGATGATGATTATTTCAATAAGAAGGATTGGTATG
ACTTCGTAGAGAATCCTGACATCTTACGCGTATATGCTAACTTAGGTGAGCGTGTACGCCAATCATTATTA
AAGACTGTACAATTCTGCGATGCTATGCGTGATGCAGGCATTGTAGGCGTACTGACATTAGATAATCAGGA
TCTTAATGGGAACTGGTACGATTTCGGTGATTTCGTACAAGTAGCACCAGGCTGCGGAGTTCCTATTGTGG
ATTCATATTACTCATTGCTGATGCCCATCCTCACTTTGACTAGGGCATTGGCTGCTGAGTCCCATATGGAT
GCTGATCTCGCAAAACCACTTATTAAGTGGGATTTGCTGAAATATGATTTTACGGAAGAGAGACTTTGTCT
CTTCGACCGTTATTTTAAATATTGGGACCAGACATACCATCCCAATTGTATTAACTGTTTGGATGATAGGT
GTATCCTTCATTGTGCAAACTTTAATGTGTTATTTTCTACTGTGTTTCCACCTACAAGTTTTGGACCACTA
GTAAGAAAAATATTTGTAGATGGTGTTCCTTTTGTTGTTTCAACTGGATACCATTTTCGTGAGTTAGGAGT
CGTACATAATCAGGATGTAAACTTACATAGCTCGCGTCTCAGTTTCAAGGAACTTTTAGTGTATGCTGCTG
ATCCAGCTATGCATGCAGCTTCTGGCAATTTATTGCTAGATAAACGCACTACATGCTTTTCAGTAGCTGCA
CTAACAAACAATGTTGCTTTTCAAACTGTCAAACCCGGTAATTTTAATAAAGACTTTTATGACTTTGCTGT
GTCTAAAGGTTTCTTTAAGGAAGGAAGTTCTGTTGAACTAAAACACTTCTTCTTTGCTCAGGATGGCAACG
CTGCTATCAGTGATTATGACTATTATCGTTATAATCTGCCAACAATGTGTGATATCAGACAACTCCTATTC
GTAGTTGAAGTTGTTGATAAATACTTTGATTGTTACGATGGTGGCTGTATTAATGCCAACCAAGTAATCGT
TAACAATCTGGATAAATCAGCTGGTTTCCCATTTAATAAATGGGGTAAGGCTAGACTTTATTATGACTCAA
TGAGTTATGAGGATCAAGATGCACTTTTCGCGTATACTAAGCGTAATGTCATCCCTACTATAACTCAAATG
AATCTTAAGTATGCCATTAGTGCAAAGAATAGAGCTCGCACCGTAGCTGGTGTCTCTATCTGTAGTACTAT
GACAAATAGACAGTTTCATCAGAAATTATTGAAGTCAATAGCCGCCACTAGAGGAGCTACTGTGGTAATTG
GAACAAGCAAGTTTTACGGTGGCTGGCATAATATGTTAAAAACTGTTTACAGTGATGTAGAAACTCCACAC
CTTATGGGTTGGGATTATCCAAAATGTGACAGAGCCATGCCTAACATGCTTAGGATAATGGCCTCTCTTGT
TCTTGCTCGCAAACATAACACTTGCTGTAACTTATCACACCGTTTCTACAGGTTAGCTAACGAGTGTGCGC
AAGTATTAAGTGAGATGGTCATGTGTGGCGGCTCACTATATGTTAAACCAGGTGGAACATCATCCGGTGAT
GCTACAACTGCTTATGCTAATAGTGTCTTTAACATTTGTCAAGCTGTTACAGCCAATGTAAATGCACTTCT
TTCAACTGATGGTAATAAGATAGCTGACAAGTATGTCCGCAATCTACAACACAGGCTCTATGAGTGTCTCT
ATAGAAATAGGGATGTTGATCATGAATTCGTGGATGAGTTTTACGCTTACCTGCGTAAACATTTCTCCATG
ATGATTCTTTCTGATGATGCCGTTGTGTGCTATAACAGTAACTATGCGGCTCAAGGTTTAGTAGCTAGCAT
TAAGAACTTTAAGGCAGTTCTTTATTATCAAAATAATGTGTTCATGTCTGAGGCAAAATGTTGGACTGAGA
CTGACCTTACTAAAGGACCTCACGAATTTTGCTCACAGCATACAATGCTAGTTAAACAAGGAGATGATTAC
GTGTACCTGCCTTACCCAGATCCATCAAGAATATTAGGCGCAGGCTGTTTTGTCGATGATATTGTCAAAAC
AGATGGTACACTTATGATTGAAAGGTTCGTGTCACTGCTATTGATGCTTACCCACTTACAAAACATCCTA
ATCAGGAGTATGCTGATGTCTTTCACTTGTATTTACAATACATTAGAAAGTTACATGATGAGCTTACTGGC
CACATGTTGGACATGTATTCCGTAATGCTAACTAATGATAACACCCTCACGGTACTGGGAACCTGAGTTTTA
TGAGGCTATGTACACACCACATACAGTCTTGCAGGCTGTAGGTGCTTGTGTATTGTGCAATTCACAGACTT
```

FIGURE 3L

```
CACTTCGTTGCGGTGCCTGTATTAGGAGACCATTCCTATGTTGCAAGTGCTGCTATGACCATGTCATTTCA
ACATCACACAAATTAGTGTTGTCTGTTAATCCCTATGTTTGCAATGCCCCAGGTTGTGATGTCACTGATGT
GACACAACTGTATCTAGGAGGTATGAGCTATTATTGCAAGTCACATAAGCCTCCCATTAGTTTTCCATTAT
GTGCTAATGGTCAGGTTTTTGGTTTATACAAAAACACATGTGTAGGCAGTGACAATGTCACTGACTTCAAT
GCGATAGCAACATGTGATTGGACTAATGCTGGCGATTACATACTTGCCAACACTTGTACTGAGAGACTCAA
GCTTTTCGCAGCAGAAACGCTCAAAGCCACTGAGGAAACATTTAAGCTGTCATATGGTATTGCCACTGTAC
GCGAAGTACTCTCTGACAGAGAATTGCATCTTTCATGGGAGGTTGGAAAACCTAGACCACCATTGAACAGA
AACTATGTCTTTACTGGTTACCGTGTAACTAAAAATAGTAAAGTACAGATTGGAGAGTACACCTTTGAAAA
AGGTGACTATGGTGATGCTGTTGTGTACAGAGGTACTACGACATACAAGTTGAATGTTGGTGATTACTTTG
TGTTGACATCTCACACTGTAATGCCACTTAGTGCACCTACTCTAGTGCCACAAGAGCACTATGTGAGAATT
ACTGGCTTGTACCCAACACTCAACATCTCAGATGAGTTTTCTAGCAATGTTGCAAATTATCAAAAGGTCGG
CATGCAAAAGTACTCTACACTCCAAGGACCACCTGGTACTGGTAAGAGTCATTTTGCCATCGGACTTGCTC
TCTATTACCCATCTGCTCGCATAGTGTATACGGCATGCTCTCATGCAGCTGTTGATGCCCTATGTGAAAAG
GCATTAAAATATTTGCCCATAGATAAATGTAGTAGAATCATACCTGCGCGTGCGCGCGTAGAGTGTTTTGA
TAAATTCAAAGTGAATTCAACACTAGAACAGTATGTTTTCTGCACTGTAAATGCATTGCCAGAAACAACTG
CTGACATTGTAGTCTTTGATGAAATCTCTATGGCTACTAATTATGACTTGAGTGTTGTCAATGCTAGACTT
CGTGCAAAACACTACGTCTATATTGGCGATCCTGCTCAATTACCAGCCCCCGCACATTGCTGACTAAAGG
CACACTAGAACCAGAATATTTTAATTCAGTGTGCAGACTTATGAAAACAATAGGTCCAGACATGTTCCTTG
GAACTTGTCGCCGTTGTCCTGCTGAAATTGTTGACACTGTGAGTGCTTTAGTTTATGACAATAAGCTAAAA
GCACACAAGGATAAGTCAGCTCAATGCTTCAAAATGTTCTACAAAGGTGTTATTACACATGATGTTTCATC
TGCAATCAACAGACCTCAAATAGGCGTTGTAAGAGAATTTCTTACACGCAATCCTGCTTGGAGAAAAGCTG
TTTTTATCTCACCTTATAATTCACAGAACGCTGTAGCTTCAAAAATCTTAGGATTGCCTACGCAGACTGTT
GATTCATCACAGGGTTCTGAATATGACTATGTCATATTCACACAAACTACTGAAACAGCACACTCTTGTAA
TGTCAACCGCTTCAATGTGGCTATCACAAGGGCAAAAATTGGCATTTTGTGCATAATGTCTGATAGAGATC
TTTATGACAAACTGCAATTTACAAGTCTAGAAATACCACGTCGCAATGTGGCTACATTACAAGCAGAAAAT
GTAACTGGACTTTTTAAGGACTGTAGTAAGATCATTACTGGTCTTCATCCTACACAGGCACCTACACACCT
CAGCGTTGATATAAAGTTCAAGACTGAAGGATTATGTGTTGACATACCAGGCATACCAAAGGACATGACCT
ACCGTAGACTCATCTCTATGATGGGTTTCAAAATGAATTACCAAGTCAATGGTTACCCTAATATGTTTATC
ACCCGCGAAGAAGCTATTCGTCACGTTCGTGCGTGGATTGGCTTTGATGTAGAGGGCTGTCATGCAACTAG
AGATGCTGTGGGTACTAACCTACCTCTCCAGCTAGGATTTTCTACAGGTGTTAACTTAGTAGCTGTACCGA
CTGGTTATGTTGACACTGAAAATAACACAGAATTCACCAGAGTTAATGCAAAACCTCCACCAGGTGACCAG
TTTAAACATCTTATACCACTCATGTATAAAGGCTTGCCCTGGAATGTAGTGCGTATTAAGATAGTACAAAT
GCTCAGTGATACACTGAAAGGATTGTCAGACAGAGTCGTGTTCGTCCTTTGGGCGCATGGCTTTGAGCTTA
CATCAATGAAGTACTTTGTCAAGATTGGACCTGAAAGAACGTGTTGTCTGTGTGACAAACGTGCAACTTGC
TTTTCTACTTCATCAGATACTTATGCCTGCTGGAATCATTCTGTGGGTTTTGACTATGTCTATAACCCATT
TATGATTGATGTTCAGCAGTGGGGCTTTACGGGTAACCTTCAGAGTAACCATGACCAACATTGCCAGGTAC
ATGGAAATGCACATGTGGCTAGTTGTGATGCTATCATGACTAGATGTTTAGCAGTCCATGAGTGCTTTGTT
AAGCGCGTTGATTGGTCTGTTGAATACCCTATTATAGGAGATGAACTGAGGGTTAATTCTGCTTGCAGAAA
AGTACAACACATGGTTGTGAAGTCTGCATTGCTTGCTGATAAGTTTCCAGTTCTTCATGACATTGGAAATC
CAAAGGCTATCAAGTGTGTGCCTCAGGCTGAAGTAGAATGGAAGTTCTACGATGCTCAGCCATGTAGTGAC
AAAGCTTACAAAATAGAGGAACTCTTCTATTCTTATGCTACACATCACGATAAATTCACTGATGGTGTTTG
TTTGTTTTGGAATTGTAACGTTGATCGTTACCCAGCCAATGCAATTGTGTGTAGGTTTGACACAAGAGTCT
TGTCAAACTTGAACTTACCAGGCTGTGATGGTGGTAGTTTGTATGTGAATAAGCATGCATTCCACACTCCA
GCTTTCGATAAAAGTGCATTTACTAATTTAAAGCAATTGCCTTTCTTTTACTATTCTGATAGTCCTTGTGA
GTCTCATGGCAAACAAGTAGTGTCGGATATTGATTATGTTCCACTCAAATCTGCTACGTGTATTACACGAT
GCAATTTAGGTGTGCTGTTTGCAGACACCATGCAAATGAGTACCGACAGTACTTGGATGCTATATAATATG
ATGATTTCTGCTGGATTTAGCCCTATGGATTTACAAACAATTTGATACTTATAACCTGTGGAATACATTTAC
CAGGTTACAGAGTTTAGAAAATGTGGCTTATAATGTTGTTAATAAAGGACACTTTGATGGACACGCCGGCG
AAGCACCTGTTTCCATCATTAATAATGCTGTTTACACAAAGGTAGATGGTATTGATGTGGAGATCTTTGAA
AATAAGACAACACTTCCTGTTAATGTTGCATTTGAGCTTTGGGCTAAGCGTAACATTAAACCAGTGCCAGA
GATTAAGATACTCAATAATTTGGGTGTTGATATCGCTGCTAATACTGTAATCTGGGACTACAAAAGAGAAG
CCCCAGCACATGTATCTACAATAGGTGTCTGCACAATGACTGACATTGCCAAGAAACCTACTGAGAGTGCT
TGTTCTTCACTTACTGTCTTGTTTGATGGTAGAGTGGAAGGACAGGTAGACCTTTTTAGAAACGCCCGTAA
TGGTGTTTTAATAACAGAAGGTTCAGTCAAAGGTCTAACACCTTCAAAGGGACCAGCACAAGCTAGCGTCA
ATGGAGTCACATTAATTGGAGAATCAGTAAAAACACAGTTTAACTACTTTAAGAAAGTAGACGGCATTATT
CAACAGTTGCCTGAAACCTACTTTACTCAGAGCAGAGACTTAGAGGATTTTAAGCCCAGATCACAAATGGA
AACTGACTTTCTCGAGCTCGCTATGGATGAATTCATACAGCGATATAAGCTCGAGGGCTATGCCTTCGAAC
```

FIGURE 3M

```
ACATCGTTTATGGAGATTTCAGTCATGGACAACTTGGCGGTCTTCATTTAATGATAGGCTTAGCCAAGCGC
TCACAAGATTCACCACTTAAATTAGAGGATTTTATCCCTATGGACAGCACAGTGAAAAATTACTTCATAAC
AGATGCGCAAACAGGTTCATCAAAATGTGTGTGTTCTGTGATTGATCTTTTACTTGATGACTTTGTCGAGA
TAATAAAGTCACAAGATTTGTCAGTGATTTCAAAAGTGGTCAAGGTTACAATTGACTATGCTGAAATTTCA
TTCATGCTTTGGTGTAAGGATGGACATGTTGAAACCTTCTACCCAAAACTACAAGCAAGTCAAGCGTGGCA
ACCAGGTGTTGCGATGCCTAACTTGTACAAGATGCAAAGAATGCTTCTTGAAAAGTGTGACCTTCAGAATT
ATGGTGAAAATGCTGTTATACCAAAAGGAATAATGATGAATGTCGCAAAGTATACTCAACTGTGTCAATAC
TTAAATACACTTACTTTAGCTGTACCCTACAACATGAGAGTTATTCACTTTGGTGCTGGCTCTGATAAAGG
AGTTGCACCAGGTACAGCTGTGCTCAGACAATGGTTGCCAACTGGCACACTACTTGTCGATTCAGATCTTA
ATGACTTCGTCTCCGACGCAGATTCTACTTTAATTGGAGACTGTGCAACAGTACATACGGCTAATAAATGG
GACCTTATTATTAGCGATATGTATGACCCTAGGACCAAACATGTGACAAAAGAGAATGACTCTAAAGAAGG
GTTTTTCACTTATCTGTGTGGATTTATAAAGCAAAAACTAGCCCTGGGTGGTTCTATAGCTGTAAAGATAA
CAGAGCATTCTTGGAATGCTGACCTTTACAAGCTTATGGGCCATTTCTCATGGTGGACAGCTTTTGTTACA
AATGTAAATGCATCATCATCGGAAGCATTTTTAATTGGGGCTAACTATCTTGGCAAGCCGAAGGAACAAAT
TGATGGCTATACCATGCATGCTAACTACATTTTCTGGAGGAACACAAATCCTATCCAGTTGTCTTCCTATT
CACTCTTTGACATGAGCAAATTTCCTCTTAAATTAAGAGGAACTGCTGTAATGTCTCTTAAGGAGAATCAA
ATCAATGATATGATTTATTCTCTTCTGGAAAAAGGTAGGCTTATCATTAGAGAAAACAACAGAGTTGTGGT
TTCAAGTGATATTCTTGTTAACAACTAAACGAACATGTTTATTTTCTTATTATTTCTTACTCTCACTAGTG
GTAGTGACCTTGACCGGTGCACCACTTTTGATGATGTTCAAGCTCCTAATTACACTCAACATACTTCATCT
ATGAGGGGGGTTTACTATCCTGATGAAATTTTTAGATCAGACACTCTTTATTTAACTCAGGATTTATTTCT
TCCATTTTATTCTAATGTTACAGGGTTTCATACTATTAATCATACGTTTGGCAACCCTGTCATACCTTTTA
AGGATGGTATTTATTTTGCTGCCACAGAGAAATCAAATGTTGTCCGTGGTTGGGTTTTTGGTTCTACCATG
AACAACAAGTCACAGTCGGTGATTATTATTAACAATTCTACTAATGTTGTTATACGAGCATGTAACTTTGA
ATTGTGTGACAACCCTTTCTTTGCTGTTTCTAAACCCATGGGTACACAGACACATACTATGATATTCGATA
ATGCATTTAATTGCACTTTCGAGTACATATCTGATGCCTTTTCGCTTGATGTTTCAGAAAAGTCAGGTAAT
TTTAAACACTTACGAGAGTTTGTGTTTAAAAATAAAGATGGGTTTCTCTATGTTTATAAGGGCTATCAACC
TATAGATGTAGTTCGTGATCTACCTTCTGGTTTTAACACTTTGAAACCTATTTTTAAGTTGCCTCTTGGTA
TTAACATTACAAATTTTAGAGCCATTCTTACAGCCTTTTCACCTGCTCAAGACATTTGGGGCACGTCAGCT
GCAGCCTATTTTGTTGGCTATTTAAAGCCAACTACATTTATGCTCAAGTATGATGAAAATGGTACAATCAC
AGATGCTGTTGATTGTTCTCAAAATCCACTTGCTGAACTCAAATGCTCTGTTAAGAGCTTTGAGATTGACA
AAGGAATTTACCAGACCTCTAATTTCAGGGTTGTTCCCTCAGGAGATGTTGTGAGATTCCCTAATATTACA
AACTTGTGTCCTTTTGGAGAGGTTTTTAATGCTACTAAATTCCCTTCTGTCTATGCATGGGAGAGAAAAAA
AATTTCTAATTGTGTTGCTGATTACTCTGTGCTCTACAACTCAACATTTTTTTCAACCTTTAAGTGCTATG
GCGTTTCTGCCACTAAGTTGAATGATCTTTGCTTCTCCAATGTCTATGCAGATTCTTTTGTAGTCAAGGGA
GATGATGTAAGACAAATAGCGCCAGGACAAACTGGTGTTATTGCTGATTATAATTATAAATTGCCAGATGA
TTTCATGGGTTGTGTCCTTGCTTGGAATACTAGGAACATTGATGCTACTTCAACTGGTAATTATAATTATA
AATATAGGTATCTTAGACATGGCAAGCTTAGGCCCTTTGAGAGAGACATATCTAATGTGCCTTTCTCCCCT
GATGGCAAACCTTGCACCCCACCTGCTCTTAATTGTTATTGGCCATTAAATGATTATGGTTTTTACACCAC
TACTGGCATTGGCTACCAACCTTACAGAGTTGTAGTACTTTCTTTTGAACTTTTAAATGCACCGGCCACGG
TTTGTGGACCAAAATTATCCACTGACCTTATTAAGAACCAGTGTGTCAATTTTAATTTTAATGGACTCACT
GGTACTGGTGTGTTAACTCCTTCTTCAAAGAGATTTCAACCATTTCAACAATTTGGCCGTGATGTTTCTGA
TTTCACTGATTCCGTTCGAGATCCTAAAACATCTGAAATATTAGACATTTCACCTTGCGCTTTTGGGGTG
TAAGTGTAATTACACCTGGAACAAATGCTTCATCTGAAGTTGCTGTTCTATATCAAGATGTTAACTGCACT
GATGTTTCTACAGCAATTCATGCAGATCAACTCACACCAGCTTGGCGCATATATTCTACTGGAAACAATGT
ATTCCAGACTCAAGCAGGCTGTCTTATAGGAGCTGAGCATGTCGACACTTCTTATGAGTGCGACATTCCTA
TTGGAGCTGGCATTTGTGCTAGTTACCATACAGTTTCTTTATTACGTAGTACTAGCCAAAAATCTATTGTG
GCTTATACTATGTCTTTAGGTGCTGATAGTTCAATTGCTTACTCTAATAACACCATTGCTATACCTACTAA
CTTTTCAATTAGCATTACTACAGAAGTAATGCCTGTTTCTATGGCTAAAACCTCCGTAGATTGTAATATGT
ACATCTGCGGAGATTCTACTGAATGTGCTAATTTGCTTCTCCAATATGGTAGCTTTTGCACACAACTAAAT
CGTGCACTCTCAGGTATTGCTGCTGAACAGGATCGCAACACACGTGAAGTGTTCGCTCAAGTCAAACAAAT
GTACAAAACCCCAACTTTGAAATATTTTGGTGGTTTTAATTTTTCACAAATATTACCTGACCCTCTAAAGC
CAACTAAGAGGTCTTTTATTGAGGACTTGCTCTTTAATAAGGTGACACTCGCTGATGCTGGCTTCATGAAG
CAATATGGCGAATGCCTAGGTGATATTAATGCTAGAGATCTCATTTGTGCTCAGAAGTTCAATGGACTTAC
AGTGTTGCCACCTCTGCTCACTGATGATATGATTGCTGCCTACACTGCTGCTCTAGTTAGTGGTACTGCCA
CTGCTGGATGGACATTTGGTGCTGGCGCTGCTCTTCAAATACCTTTTGCTATGCAAATGGCATATAGGTTC
AATGGCATTGGAGTTACCCAAAATGTTCTCTATGAGAACCAAAAACAAATCGCCAACCAATTTAACAAGGC
GATTAGTCAAATTCAAGAATCACTTACAACAACATCAACTGCATTGGGCAAGCTGCAAGACGTTGTTAACC
```

```
AGAATGCTCAAGCATTAAACACACTTGTTAAACAACTTAGCTCTAATTTTGGTGCAATTTCAAGTGTGCTA
AATGATATCCTTTCGCGACTTGATAAAGTCGAGGCGGAGGTACAAATTGACAGGTTAATTACAGGCAGACT
TCAAAGCCTTCAAACCTATGTAACACAACAACTAATCAGGGCTGCTGAAATCAGGGCTTCTGCTAATCTTG
CTGCTACTAAAATGTCTGAGTGTGTTCTTGGACAATCAAAAAGAGTTGACTTTTGTGGAAAGGGCTACCAC
CTTATGTCCTTCCCACAAGCAGCCCCGCATGGTGTTGTCTTCCTACATGTCACGTATGTGCCATCCCAGGA
GAGGAACTTCACCACAGCGCCAGCAATTTGTCATGAAGGCAAAGCATACTTCCCTCGTGAAGGTGTTTTG
TGTTTAATGGCACTTCTTGGTTTATTACACAGAGGAACTTCTTTTCTCCACAAATAATTACTACAGACAAT
ACATTTGTCTCAGGAAATTGTGATGTCGTTATTGGCATCATTAACAACACAGTTTATGATCCTCTGCAACC
TGAGCTTGACTCATTCAAAGAAGAGCTGGACAAGTACTTCAAAAATCATACATCACCAGATGTTGATCTTG
GCGACATTTCAGGCATTAACGCTTCTGTCGTCAACATTCAAAAAGAAATTGACCGCCTCAATGAGGTCGCT
AAAAATTTAAATGAATCACTCATTGACCTTCAAGAATTGGGAAAATATGAGCAATATATTAAATGGCCTTG
GTATGTTTGGCTCGGCTTCATTGCTGGACTAATTGCCATCGTCATGGTTACAATCTTGCTTTGTTGCATGA
CTAGTTGTTGCAGTTGCCTCAAGGGTGCATGCTCTTGTGGTTCTTGCTGCAAGTTTGATGAGGATGACTCT
GAGCCAGTTCTCAAGGGTGTCAAATTACATTACACATAAACGAACTTATGGATTTGTTTATGAGATTTTTT
ACTCTTAGATCAATTACTGCACAGCCAGTAAAAATTGACAATGCTTCTCCTGCAAGTACTGTTCATGCTAC
AGCAACGATACCGCTACAAGCCTCACTCCCTTTCGGATGGCTTGTTATTGGCGTTGCATTTCTTGCTGTTT
TTCAGAGCGCTACCAAAATAATTGCGCTCAATAAAAGATGGCAGCTAGCCCTTTATAAGGGCTTCCAGTTC
ATTTGCAATTTACTGCTGCTATTTGTTACCATCTATTCACATCTTTTGCTTGTCGCTGCAGGTATGGAGGC
GCAATTTTTGTACCTCTATGCCTTGATATATTTTCTACAATGCATCAACGCATGTAGAATTATTATGAGAT
GTTGGCTTTGTTGGAAGTGCAAATCCAAGAACCCATTACTTTATGATGCCAACTACTTTGTTTGCTGGCAC
ACACATAACTATGACTACTGTATACCATATAACAGTGTCACAGATACAATTGTCGTTACTGAAGGTGACGG
CATTTCAACACCAAAACTCAAAGAAGACTACCAAATTGGTGGTTATTCTGAGGATAGGCACTCAGGTGTTA
AAGACTATGTCGTTGTACATGGCTATTTCACCGAAGTTTACTACCAGCTTGAGTCTACACAAATTACTACA
GACACTGGTATTGAAAATGCTACATTCTTCATCTTTAACAAGCTTGTTAAAGACCCACCGAATGTGCAAAT
ACACACAATCGACGGCTCTTCAGGAGTTGCTAATCCAGCAATGGATCCAATTTATGATGAGCCGACGACGA
CTACTAGCGTGCCTTTGTAAGCACAAGAAAGTGAGTACGAACTTATGTACTCATTCGTTTCGGAAGAAACA
GGTACGTTAATAGTTAATAGCGTACTTCTTTTTCTTGCTTTCGTGGTATTCTTGCTAGTCACACTAGCCAT
CCTTACTGCGCTTCGATTGTGTGCGTACTGCTGCAATATTGTTAACGTGAGTTTAGTAAAACCAACGGTTT
ACGTCTACTCGCGTGTTAAAAATCTGAACTCTTCTGAAGGAGTTCCTGATCTTCTGGTCTAAACGAACTAA
CTATTATTATTATTCTGTTTGGAACTTTAACATTGCTTATCATGGCAGACAACGGTACTATTACCGTTGAG
GAGCTTAAACAACTCCTGGAACAATGGAACCTAGTAATAGGTTTCCTATTCCTAGCCTGGATTATGTTACT
ACAATTTGCCTATTCTAATCGGAACAGGTTTTTGTACATAATAAAGCTTGTTTTCCTCTGGCTCTTGTGGC
CAGTAACACTTGCTTGTTTTGTGCTTGCTGCTGTCTACAGAATTAATTGGGTGACTGGCGGGATTGCGATT
GCAATGGCTTGTATTGTAGGCTTGATGTGGCTTAGCTACTTCGTTGCTTCCTTCAGGCTGTTTGCTCGTAC
CCGCTCAATGTGGTCATTCAACCCAGAAACAAACATTCTTCTCAATGTGCCTCTCCGGGGGACAATTGTGA
CCAGACCGCTCATGGAAAGTGAACTTGTCATTGGTGCTGTGATCATTCGTGGTCACTTGCGAATGGCCGGA
CACTCCCTAGGGCGCTGTGACATTAAGGACCTGCCAAAAGAGATCACTGTGGCTACATCACGAACGCTTTC
TTATTACAAATTAGGAGCGTCGCAGCGTGTAGGCACTGATTCAGGTTTTGCTGCATACAACCGCTACCGTA
TTGGAAACTATAAATTAAATACAGACCACGCCGGTAGCAACGACAATATTGCTTTGCTAGTACAGTAAGTG
ACAACAGATGTTTCATCTTGTTGACTTCCAGGTTACAATAGCAGAGATATTGATTATCATTATGAGGACTT
TCAGGATTGCTATTTGGAATCTTGACGTTATAATAAGTTCAATAGTGAGACAATTATTTAAGCCTCTAACT
AAGAAGAATTATTCGGAGTTAGATGATGAAGAACCTATGGAGTTAGATTATCCATAAAACGAACATGAAAA
TTATTCTCTTCCTGACATTGATTGTATTTACATCTTGCGAGCTATATCACTATCAGGAGTGTGTTAGAGGT
ACGACTGTACTACTAAAAGAACCTTGCCCATCAGGAACATACGAGGGCAATTCACCATTTCACCCTCTTGC
TGACAATAAATTTGCACTAACTTGCACTAGCACACACTTTGCTTTTGCTTGTGCTGACGGTACTCGACATA
CCTATCAGCTGCGTGCAAGATCAGTTTCACCAAAACTTTTCATCAGACAAGAGGAGGTTCAACAAGAGCTC
TACTCGCCACTTTTTCTCATTGTTGCTGCTCTAGTATTTTTAATACTTTGCTTCACCATTAAGAGAAAGAC
AGAATGAATGAGCTCACTTTAATTGACTTCTATTTGTGCTTTTTAGCCTTTCTGCTATTCCTTGTTTTAAT
AATGCTTATTATATTTTGGTTTTCACTCGAAATCCAGGATCTAGAAGAACCTTGTACCAAAGTCTAAACGA
ACATGAAACTTCTCATTGTTTTGACTTGTATTTCTCTATGCAGTTGCATATGCACTGTAGTACAGCGCTGT
GCATCTAATAAACCTCATGTGCTTGAAGATCCTTGTAAGGTACAACACTAGGGGTAATACTTATAGCACTG
CTTGGCTTTGTGCTCTAGGAAAGGTTTTACCTTTTCATAGATGGCACACTATGGTTCAAACATGCACACCT
AATGTTACTATCAACTGTCAAGATCCAGCTGGTGGTGCGCTTATAGCTAGGTGTTGGTACCTTCATGAAGG
TCACCAAACTGCTGCATTTAGAGACGTACTTGTTGTTTTAAATAAACGAACAAATTAAAATGTCTGATAAT
GGACCCCAATCAAACCAACGTAGTGCCCCCCGCATTACATTTGGTGGACCCACAGATTCAACTGACAATAA
CCAGAATGGAGGACGCAATGGGCAAGGCCAAAACAGCGCCGACCCCAAGGTTTACCCAATAATACTGCGT
CTTGGTTCACAGCTCTCACTCAGCATGGCAAGGAGGAACTTAGATTCCCTCGAGGCCAGGGCGTTCCAATC
```

FIGURE 30

```
AACACCAATAGTGGTCCAGATGACCAAATTGGCTACTACCGAAGAGCTACCCGACGAGTTCGTGGTGGTGA
CGGCAAAATGAAAGAGCTCAGCCCCAGATGGTACTTCTATTACCTAGGAACTGGCCCAGAAGCTTCACTTC
CCTACGGCGCTAACAAAGAAGGCATCGTATGGGTTGCAACTGAGGGAGCCTTGAATACACCCAAAGACCAC
ATTGGCACCCGCAATCCTAATAACAATGCTGCCACCGTGCTACAACTTCCTCAAGGAACAACATTGCCAAA
AGGCTTCTACGCAGAGGGAAGCAGAGGCGGCAGTCAAGCCTCTTCTCGCTCCTCATCACGTAGTCGCGGTA
ATTCAAGAAATTCAACTCCTGGCAGCAGTAGGGGAAATTCTCCTGCTCGAATGGCTAGCGGAGGTGGTGAA
ACTGCCCTCGCGCTATTGCTGCTAGACAGATTGAACCAGCTTGAGAGCAAAGTTTCTGGTAAAGGCCAACA
ACAACAAGGCCAAACTGTCACTAAGAAATCTGCTGCTGAGGCATCTAAAAAGCCTCGCCAAAAACGTACTG
CCACAAAACAGTACAACGTCACTCAAGCATTTGGGAGACGTGGTCCAGAACAAACCCAAGGAAATTTCGGG
GACCAAGACCTAATCAGACAAGGAACTGATTACAAACATTGGCCGCAAATTGCACAATTTGCTCCAAGTGC
CTCTGCATTCTTTGGAATGTCACGCATTGGCATGGAAGTCACACCTTCGGGAACATGGCTGACTTATCATG
GAGCCATTAAATTGGATGACAAAGATCCACAATTCAAAGACAACGTCATACTGCTGAACAAGCACATTGAC
GCATACAAAACATTCCCACCAACAGAGCCTAAAAAGGACAAAAAGAAAAAGACTGATGAAGCTCAGCCTTT
GCCGCAGAGACAAAAGAAGCAGCCCACTGTGACTCTTCTTCCTGCGGCTGACATGGATGATTTCTCCAGAC
AACTTCAAAATTCCATGAGTGGAGCTTCTGCTGATTCAACTCAGGCATAAACACTCATGATGACCACACAA
GGCAGATGGGCTATGTAAACGTTTTCGCAATTCCGTTTACGATACATAGTCTACTCTTGTGCAGAATGAAT
TCTCGTAACTAAACAGCACAAGTAGGTTTAGTTAACTTTAATCTCACATAGCAATCTTTAATCAATGTGTA
ACATTAGGGAGGACTTGAAAGAGCCACCACATTTTCATCGAGGCCACGCGGAGTACGATCGAGGGTACAGT
GAATAATGCTAGGGAGAGCTGCCTATATGGAAGAGCCCTAATGTGTAAAATTAATTTTAGTAGTGCTATCC
CCATGTGATTTTAATAGCTTCTTAGGAGAATGACAAAAAAAAAAAAAAAAAAAAAAAA

GenBank Accession No. AY274119.2.; SEQ ID NO: 2
```

FIGURE 3P

```
ERV-2    ------------------------------------------------------------
TOR2     ACACTCATGATGACCACACAAGGCAGATGGGCTATGTAAACGTTTTCGCAATTCCGTTTA
AIBV     ------------------------------------------------------------

ERV-2    ------------------------------------------------------------
TOR2     CGATACATAGTCTACTCTTGTGCAGAATGAATTCTCGTAACTAAACAGCACAAGTAGGTT
AIBV     ------------------------------------------------------------

ERV-2    --------------------------------ACCCGTTACCCTAAAATTCCCTCC
TOR2     TAGTTAACTTTAATCTCACATAGCAATCTTTAATCAATGTGTAACATTAGGGAGGACTTG
AIBV     ---------------------------------TAGTTTAGTTTAAGTTAGTTTAG
                                           * *   **          *

ERV-2    CCTTTCTCTTCAC------TCGCCGAGGCCACGCCGAGTAGGACCGAGGGTACAGC----
TOR2     AAAGAGCCACCACATTT--TCATCGAGGCCACGCGGAGTACGATCGAGGGTACAGT----
AIBV     AGTAGGTATAAAGATGCCAGTGCCGGGGCCACGCGGAGTACGATCGAGGGTACAGCACTA
                *          ** ******** ***** ** ************

ERV-2    -GAGTCTTT-TAGTTTAAGGTGT-TAGATGTAAGGTACGTGGGCTTTCT--TTTGGTTTA
TOR2     -GAATAATGCTAGGGAGAGCTGCCTATATGGAAGAGCCCTAATGTGTAAAATTAATTTTA
AIBV     GGACGCCCATTAGGGGAAGA-GCTAAATTTTAGTTTAAGTTAAGTTTAA---TTGGCTAA
          **       ***   **    *  *    *        *   *       *   *  *

ERV-2    CTTCTTC--------------------------------- GenBank: AF361253 (SEQ ID NO: 31)
TOR2     GTAGTGCTATCCCCATGTGATTTTAATAGCTTCTTAGGAGAATGAC (SEQ ID NO: 18)
AIBV     GTATAGTTAAAATTTATAGGCTAGTATAGAGTTAGAGCA------- GenBank: NC_001451 (SEQ ID NO: 32)
          *
```

Figure 4

MFIFLLFLTLTSGSDLDRCTTFDDVQAPNYTQHTSSMRGVYYPDEIFRSD
TLYLTQDLFLPFYSNVTGFHTINHTFGNPVIPFKDGIYFAATEKSNVVRG
WVFGSTMNNKSQSVIIINNSTNVVIRACNFELCDNPFFAVSKPMGTQTHT
MIFDNAFNCTFEYISDAFSLDVSEKSGNFKHLREFVFKNKDGFLYVYKGY
QPIDVVRDLPSGFNTLKPIFKLPLGINITNFRAILTAFSPAQDIWGTSAA
AYFVGYLKPTTFMLKYDENGTITDAVDCSQNPLAELKCSVKSFEIDKGIY
QTSNFRVVPSGDVVRFPNITNLCPFGEVFNATKFPSVYAWERKKISNCVA
DYSVLYNSTFFSTFKCYGVSATKLNDLCFSNVYADSFVVKGDDVRQIAPG
QTGVIADYNYKLPDDFMGCVLAWNTRNIDATSTGNYNYKYRYLRHGKLRP
FERDISNVPFSPDGKPCTPPALNCYWPLNDYGFYTTTGIGYQPYRVVVLS
FELLNAPATVCGPKLSTDLIKNQCVNFNFNGLTGTGVLTPSSKRFQPFQQ
FGRDVSDFTDSVRDPKTSEILDISPCAFGGVSVITPGTNASSEVAVLYQD
VNCTDVSTAIHADQLTPAWRIYSTGNNVFQTQAGCLIGAEHVDTSYECDI
PIGAGICASYHTVSLLRSTSQKSIVAYTMSLGADSSIAYSNNTIAIPTNF
SISITTEVMPVSMAKTSVDCNMYICGDSTECANLLLQYGSFCTQLNRALS
GIAAEQDRNTREVFAQVKQMYKTPTLKYFGGFNFSQILPDPLKPTKRSFI
EDLLFNKVTLADAGFMKQYGECLGDINARDLICAQKFNGLTVLPPLLTDD
MIAAYTAALVSGTATAGWTFGAGAALQIPFAMQMAYRFNGIGVTQNVLYE
NQKQIANQFNKAISQIQESLTTTSTALGKLQDVVNQNAQALNTLVKQLSS
NFGAISSVLNDILSRLDKVEAEVQIDRLITGRLQSLQTYVTQQLIRAAEI
RASANLAATKMSECVLGQSKRVDFCGKGYHLMSFPQAAPHGVVFLHVTYV
PSQERNFTTAPAICHEGKAYFPREGVFVFNGTSWFITQRNFFSPQIITTD
NTFVSGNCDVVIGIINNTVYDPLQPELDSFKEELDKYFKNHTSPDVDLGD
ISGINASVVNIQKEIDRLNEVAKNLNESLIDLQELGKYEQYIKWPWYVWL
GFIAGLIAIVMVTILLCCMTSCCSCLKGACSCGSCCKFDEDDSEPVLKGV
KLHYT    (SEQ ID NO: 33)

Figure 5

MADNGTITVEELKQLLEQWNLVIGFLFLAWIMLLQFAYSNRNRFLYIIKL
VFLWLLWPVTLACFVLAAVYRINWVTGGIAIAMACIVGLMWLSYFVASFR
LFARTRSMWSFNPETNILLNVPLRGTIVTRPLMESELVIGAVIIRGHLRM
AGHSLGRCDIKDLPKEITVATSRTLSYYKLGASQRVGTDSGFAAYNRYRI
GNYKLNTDHAGSNDNIALLV    (SEQ ID NO: 34)

Figure 6

MYSFVSEETGTLIVNSVLLFLAFVVFLLVTLAILTALRLCAYCCNIVNVS
LVKPTVYVYSRVKNLNSSEGVPDLLV (SEQ ID NO: 35)

Figure 7

MSDNGPQSNQRSAPRITFGGPTDSTDNNQNGGRNGARPKQRRPQGLPNNT
ASWFTALTQHGKEELRFPRGQGVPINTNSGPDDQIGYYRRATRRVRGGDG
KMKELSPRWYFYYLGTGPEASLPYGANKEGIVWVATEGALNTPKDHIGTR
NPNNNAATVLQLPQGTTLPKGFYAEGSRGGSQASSRSSSRSRGNSRNSTP
GSSRGNSPARMASGGGETALALLLLDRLNQLESKVSGKGQQQQGQTVTKK
SAAEASKKPRQKRTATKQYNVTQAFGRRGPEQTQGNFGDQDLIRQGTDYK
HWPQIAQFAPSASAFFGMSRIGMEVTPSGTWLTYHGAIKLDDKDPQFKDN
VILLNKHIDAYKTFPPTEPKKDKKKKTDEAQPLPQRQKKQPTVTLLPAAD
MDDFSRQLQNSMSGASADSTQA (SEQ ID NO: 36)

Figure 8

```
BoCov      ------------------------------MSSVTTPAP--VYTWTADEAIKFLKEWNFSL
OC43       ------------------------------MSSKTTPAP--VYIWTADEAIKFLKEWNFSL
PHEV       ------------------------------MSSPTTPVP--VISWTADEAIKFLKEWNFSL
FCV        MKILLILACAVACVYGEQIRYCAMQ-ETGLSCRNGTASDCESCFNGGDLIWHLANWNFSW
TGEV       MKILLILACVIACACGE--RYCAMKSDTDLSCRNSTASDCESCFNGGDLIWHLANWNFSW
TOR2_M     -----------------------------------MAD--NGTITVEELKQLLEQWNLVI
ORF5       -----------------------------------MAD--NGTITVEELKQLLEQWNLVI
AIBV2      ------------------------------MMEN---CTLNLEQATLLFKEYNLFI
AIBV       ------------------------------MSNGTEN---CTLSTQQAAELFKEYNLFI
                                                 .  :     :  ::*:

BoCov      GIILLFITVILQFGYTSRSMFVYVIKMVILWLMWPLTIILTIFNCV--YALNN-VYLGFS
OC43       GIIILFITIILQFGYTSRSMFVYVIKMIILWLMWPLTIILTIFNCV--YALNN-VYLGLS
PHEV       GIIVLFITIILQFGYTSRSMFVYVIKMVILWLMWPLTIILTIFNCV--YALNN-VYLGFS
FCV        SIILIVFITVLQYGRPQFSWFVYGIKMLIMWLLWPIVLALTIFNAYSEYEVSRYVMFGFS
TGEV       SIILIVFITVLQYGRPQFSWFVYGIKMLIMWLLWPVVLALTIFNAYSEYQVSRYVMFGFS
TOR2_M     GFLFLAWIMLLQFAYSNRNRFLYIIKLVFLWLLWPVTLACFVLAAV--YRINW-VTGGIA
ORF5       GFLFLAWIMLLQFAYSNRNRFLYIIKLVFLWLLWPVTLACFVLAAV--YRINW-VTGGIA
AIBV2      TAFLLFLTILLQYGYATRSRFIYILKMIVLWCFWPLNIAVGVISCI--YPPNT-GGLVAA
AIBV       TAFLLFLTILLQYGYATRSRFIYILKMIVLWCFWPLNIAVGIISCI--YPPNT-GGLVAA
           ::      :**:  .  *:*  :*::.:* :**:     ::  .      *.       :

BoCov      IVFTIVAIIMWIVYFVNSIRLFIRTGSWWSFNPETNNLMCIDMK-GRMYVRPIIEDYHTL
OC43       IVFTIVAIIMWIVYFVNSIRLFIRTGSFWSFNPETNNLMCIDMK-GTMYVRPIIEDYHTL
PHEV       IVFTIVAIIMWVVYFVNSIRLFIRTGSWWSFNPETNNLMCIDMK-GRMYVRPIIEDYHTL
FCV        VAGAVVTFALWMMYFVRSIQLYRRTKSWWSFNPETNAILCVNAL-GRSYVLPLDGTPTGV
TGEV       IAGAIVTPVLWIMYFVRSIQLYRRTKSWWSFNPETKAILCVSAL-GRSYVLPLEGVPTGV
TOR2_M     IAMACIVGLMWLSYFVASFRLFARTRSMWSFNPETNILLNVPLR-GTIVTRPLMESELVI
ORF5       IAMACIVGLMWLSYFVASFRLFARTRSMWSFNPETNILLNVPLR-GTIVTRPLMESELVI
AIBV2      IILTVFACLSFVGYWIQSCRLFKRCRSWWSFNPESNAVGSILLTNGQQCNFAIESVPMVL
AIBV       IILTVFACLSFVGYWIQSFRLFKRCRSWWSFNPESNAVGSILLTNGQQCNFAIESVPMVL
           :  :  ..     ::  *::  *  :*  *  * *****::  :       *    .:       :

BoCov      TVTIIRGHLYMQGIKLGTGYSLSDLPAYVTVAKVSHLLTYKR---GFLDKIGDTSGFAVY
OC43       TVTIIRGHLYIQGIKLGTGYSWADLPAYMTVAKVTHLCTYKR---GFLDRISDTSGFAVY
PHEV       TATIIRGHLYIQGIKLGTGYSLSDLPAYVTVAKVTHLCTYKR---GFLDRIGDTSGFAVY
FCV        TLTLLSGNLYAEGFKMAGGLTIEHLPKYVMIRTPNRTIVYTLV--GKQLKATTATGWAYY
TGEV       TLTLLSGNLYAEGFKIAGGMNIDNLPKYVMVALPSRTIVYTLV--GKKLKASSATGWAYY
TOR2_M     GAVIIRGHLRMAGHSLGR-CDIKDLPKEITVAT-SRTLSYYKL-GASQRVGTDSGFAAY
ORF5       GAVIIRGHLRMAGHSLGR-CDIKDLPKEITVAT-SRTLSYYKL-GASQRVGTDSGFAAY
AIBV2      APIIKNGVLYCEGQWLAK-CEPDHLPKDIFVCTPDRRNIYRMVQKYTGDQSGNKKRVATF
AIBV       SPIIKNGALYCEGQWLAK-CEPDHLPKDIFVCTPDRRNIYRMVQKYTGDQSGNKKRFATF
             :  *  *   *  :.     .**  : :        :    *               :   . * :

BoCov      VKSKVGNYRLPSTQKGSGLDTALLRNNI
OC43       VKSKVGNYRLPSTQKGSGMDTALLRNNI
PHEV       VKSKVGNYRLPSTHKGSGMDTALLRNNI
FCV        VKSKAGDYSTEARTDNLSEHEKLLHMV-
TGEV       VKSKAGDYSTEARTDNLSEQEKLLHMV-
TOR2_M     NRYRIGNYKLNTDHAGSNDNIALLVQ--
ORF5       NRYRIGNYKLNTDHAGSNDNIALLVQ--
AIBV2      VYAKQSVDTGELESVPTGGSSLYT----
AIBV       VYAKQSVDTGELGSVATGGSSLYT----
              :  .               :   .
```

| Key | Name | Genbank | %ID | |
|---|---|---|---|---|
| PHEV | Porcine hemagglutinating encephalomyelitis virus | AAL80035 | 40.4% | (SEQ ID NO: 37) |
| BoCov | matrix protein [Bovine coronavirus]. | NP_150082 | 40.0% | (SEQ ID NO: 38) |
| AIBV | membrane protein [Avian infectious bronchitis virus]. | AAF35863 | 31.3% | (SEQ ID NO: 39) |
| TGEV | membrane protein [Transmissible gastroenteritis virus]. | NP_058427 | 28.5% | (SEQ ID NO: 40) |
| FCV | membrane [feline coronavirus]. | BAC01160 | 27.7% | (SEQ ID NO: 41) |
| OC43 | membrane glycoprotein [Human coronavirus OC43]. | AAA45462 | 39.1% | (SEQ ID NO: 42) |
| AIBV2 | membrane protein [Avian infectious bronchitis virus]. | AAK83027 | 32.0% | (SEQ ID NO: 43) |
| TOR2_M/ORF 5 | Sars associated coronavirus M glycoprotein | (SEQ ID NO: 34) | | |

Figure 9

```
BoCov    MSFTPGKQSS-SRASSGNRSGNGILK---WADQSDQSRNVQTRGRRAQP--KQTATSQQP
OC43     MSFTPGKQSS-SRASSGNRSGNGILK---WADQSDQVRNVQTRGRRAQP--KQTATSQQP
PHEV     MSFTPGKQSS-SRASSGNRSGNGILK---WADQSDQSRNVQTRGRRVQS--KQTATSQQP
MHV      MSFVPGQENAGSRSSSVNRAGNGILKKTTWADQTERGPNNQNRGRRNQP--KQTATTQ-P
AIBV2    ----------------MASGKAAGK---TDAPAPVIK----LGGPKPP--KVGSSGN--
TCV      ----------------MASGKATGK---TDAPAPIIK----LGGPKPP--KVGSSGN--
AIBV     ----------------MASGKAAGK---TDAPAPVIK----LGGPKPP--KVGSSGN--
FCV      ----------------MATQGQRVN---WGDEPSKRR-----GRSNSR--GRKNNDIP-
PTGV     ----------------MANQGQRVS---WGDESTKTR-----GRSNSR--GRKNNNIP-
229E     --------------------MATVK---WADASEPQR-----GRQ-----GRIPYSL--
TOR2_N   ------------MSDNGPQSNQRSAPRITFGGPTDSTDNNQNGGRNGARPKQRRPQGLPN
                                 .                                 *

BoCov    SGGNVVPYYSWFSGITQFQKGKEFEFAEGQGVPIAPGVPATEAKGYWYRHNRRSFKTADG
OC43     SGGNVVPYYSWFSGITQFQKGKEFEFVEGQGPPIAPGVPATEAKGYWYRHNRGSFKTADG
PHEV     SGGTVVPYYSWFSGITQFQKGKEFQFAEGQGVPIAPGVPSTEAKGYWYRHNRRSFKTPDG
MHV      NSGSVVPHYSWFSGITQFQKGKEFQFAQGQGVPIANGIPASEQKGYWYRHNRRSFKTPDG
AIBV2    AS--------WFQAIKAKKLNTPPPKFEGSGVPDNENIKPSQQHGYWRRQAR--FKPGKG
TCV      AS--------WFQSIKAKKLNSPQPKFEGSGVPDNENIKTSQQHGYWRRQAR--FKPGKG
AIBV     AS--------WFQALKAKKLNAPAPKFEGSGVPDNENLKISQQHGYWRRQAR--YKPGKG
FCV      LS--------YFNPITLDQGSKFWNLCPRDFVPKGIGNK-DQQIGYWNRQAR--YRIVKG
PTGV     LS--------FFNPITLQQGSKFWNLCPRDFVPKGIGNR-DQQIGYWNRQTR--YRMVKG
229E     -Y---------SPLLVDS-EQPWKVIPRNLVPINKKDK-NKLIGYWNVQKR--FRTRKG
TOR2_N   NTAS------WFTALTQHG-KEELRFPRGQGVPINTNSGPDDQIGYYRRATRR-VRGGDG
                :        . *      . **:     *     :  . *

BoCov    NQRQLLPRWYFYYLGTGPHAKDQYGTDIDGVYWVASNQADVNTPADILDRDPSSDEAIPT
OC43     NQRQLLPRWYFYYLGTGPHAKDQYGTDIDGVYWVASNQADVNTPADIVDRDPSSDEAIPT
PHEV     NQRQLLPRWYFYYLGTGPHAKDQYGTDIDGVFWVASNQADINTPADIVDRDPSSDEAIPT
MHV      QQKQLLPRWYFYYLGTGPHAGAEYGDDIDGVWWVASQQADTKTTADIVERDPSSHEAIPT
AIBV2    GRKPVPDAWYFYYTGTGPAADLNWGDTQDGIVWVAAKGADTKSRSNQGTRDPDKFDQYPL
TCV      GRKPVPDAWYFYYTGTGPAADLNWGDTQDGIVWVAAKGADVKSRSNQGTRDPDKFDQYPL
AIBV     GRKPVPDAWYFYYTGTGPAADLNWGDSQDGIVWVAAKGADVKSRSNQGTRDPDKFDQYPL
FCV      QRVELPERWFFYFLGTGPHADAKFKAKIDGVFWVARDGAMN-KPTSLGTRG-TNNESKPL
PTGV     QRKELPERWFFYYLGTGPHADAKFKDKLDGVWWVAKDGAMN-KPTTLGSRG-ANNESKAL
229E     KRVDLSPKLHPYYYLGTGPHKDAKFRERVEGVVWWVAVDGAKT-EPTGYGVRR-KNSEPEIP
TOR2_N   KMKELSPRWYFYYLGTGPEASLPYGANKEGIVWVATEGALNTPKDHIGTRNPNNNAATVL
             :   .**: ****     :   :*: ***  .    *      *      .

BoCov    RFPPGTVLPQGYYIEGS-GRSAPNSRSTSRASSRASSA---GSRSRANSGNR---TPTSG
OC43     RFPPGTVLPQGYYIEGS-GRSAPNSRSTSRTSSRASSA---GSRSRANSGNR---TPTSG
PHEV     RFPPGTVLPQGYYIEGS-GRSAPNSRSTSRAPNRAPSA---GSRSRANSGNR---TSTPG
MHV      RFAPGTVLPQGFYVEGS-GRSAPASRSGSRSQSRGP-----NNRARSSSNQR---QPAST
AIBV2    RFSDG--GPDNFRWDF-IPLKNRGRSG-RSTAASSAA---ASRAPSSREGSR---GRRSD
TCV      RFSDG--GPDSNFRWDF-IPLH-RGRSG-RSTAASSAA---SSRAPSRDGSR---GRRSG
AIBV     RFSDG--GPDNFRWDF-IPLN-RGRSG-RSTAASSAA---SSRAPSREGSR---GRLNG
FCV      KFDGK-IPPQFQLEVNR-SRNNSRSGSQSRSVSRNRS----QSRGRQQSNNQ--NTNVED
PTGV     KFDGK-VPGEFQLEVNQ-QSRDNSRLRSQSRSRSRNRS---QSRGRQQSNNKK-DDSVEQ
229E     HFNQK--LPNGVTVVEE-PDSRAPSRSQSRSQSRGRGESKPQSRNPSSDRNHNSQDDIMK
TOR2_N   QLPQGTTLPKGFYAEGSRGGSQASSRSSSRSRGNSRNSTPGSSRGNSPARMAS-GGGETA
          ::       .           *  *:                      .*

BoCov    VTPDMADQIASLVLAKLGKDAAKP-----------------QQVTKQTAKEIRQK--IL
OC43     VTPDMADQIASLVLAKLGKDATKP-----------------QQVTKHTAKEVRQK--IL
PHEV     VTPDMADQIASLVLAKLGKDATKP-----------------QQVTKQTAKEVRQK--IL
MHV      VKPDMAEEIAALVLAKLGKDAGQP-----------------KQVTKQSAKEVRQK--IL
AIBV2    SGDDLIARAAKIIQDQQKKGS-----------------RITKAKADEMAHR--RY
TCV      SEDDLIARAAKIIQDQQKKGS-----------------RITKAKADEMAHR-RY
AIBV     AEDDLIARAAKIIQDQQKKGS-----------------RITKAKAEEMIHR--RY
FCV      TIVAVLQKLGVTDK---QRSRSKS-----------------KERSNSKIRDTTPK--NE
PTGV     AVLAALKKLGVYTEKQQQRSRSKS-----------------KERSNSKIRDTTPK--NE
229E     AVAAALKSLGFDKPQEKDKKSAKTGTPKPSRNQSPASSQTSAKSLARSQSSETKEQKHEM
TOR2_N   LALLLLDRLNQLESKVSGKGQQQQG----------------QTVTKKSAAEASKK--PR
              :                 :.      :   :
```

FIGURE 10A

```
BoCov      NKPRQKRSPNKQCT--VQQCFGKR---GPNQNFGGGEMLKLGTSDPQFPILAELAPTAGA
OC43       NKPRQKRSPNKQCT--VQQCFGKR---GPNQNFGGGEMLKLGTSDPQFPILAELAPTAGA
PHEV       NKPRQKRSPNKQCT--VQQCFGKR---GPNQNFGGGEMLKLGTSDPQFPILAELAPTAGA
MHV        NKPRQKRTPNKQCP--VQQCFGKR---GPNQNFGGSEMLKLGTSDPQFPILAELAPTPSA
AIBV2      CK----RTIPPNYR--VDQVFGPRT-KGKEGNFGDDKMNEEGIKDGRVTAMLNLVPSSHA
TCV        CK----RTVPPGYK--VDQVFGPRT-KGKEGNFGDDKMNEEGIKDGRVTAMLNLVPSSHA
AIBV       CK----RTVPPGVS--IDKVFGPRT-KGKEGNFGDDKMNEEGIKDGRVTAMLNLVPSSHA
FCV        NKHTWKKTAGKGD---VTNFYGAR---SSSANFGDSDLVANGNAAKCYPQIAECVPSVSS
PTGV       NKHTWKRTAGKGD---VTRFYGTR---SNSANFGDSDLVANGSSAKHYPQLAECVPSVSS
229E       QKPRWKRQPNDDVTSNVTQCFGPR---DLDHNFGSAGVVANGVKAKGYPQFAELVPSTAA
TOR2_N     QK----RTATKQYN--VTQAFGRRGPEQTQGNFGDQDLIRQGTDYKHWPQIAQFAPSASA
                  :         :.:*  *    . ***.  :     *    . : :.*:  :

BoCov      FFFGSRLELAKVQNLSGNLDEPQKDVYELRYNGAIR-----FDSTLSGFETIMKVLNENL
OC43       FFFGSRLELAKVQNLSGNPDEPQKDVYELRYNGAIR-----FDSTLSGFETIMKVLNENL
PHEV       FFFGSRLELAKVQNLSGNPDEPQKDVYELRYNGAIR-----FDSTLSGFETIMKVLNQNL
MHV        FFFGSKLELVKKN--SGGADDPTKDVYELQYSGAIR-----FDSTLPGFETIMKVLNENL
AIBV2      CLFGSRVTPKLQL--DGLHLRFEFTTVVPCDDPQFDNYVKICDQCVDGVGTRPKDDEPKP
TCV        CLFGSRVTPKLQP--DGLHLRFEFTTVVPRDDPQFDNYVTICDQCVDGIGTRPKDNEPRP
AIBV       CLFGSQVTPKLQP--DGLHLTFRFTTVVSRDDPQFDNYVKICDECVDGVGTRPKDEVVRP
FCV        ILFGSQWSAEEAG--DQVKVTLTHNYYLPKDDAKTS----------------QFLEQI
PTGV       ILFGSYWTSKEDG--DQIEVTFTHKYHLPKDDPKTG----------------QFLQQI
229E       MLFDSHIVSKESG--NTVVLTFTTRVTVPKDHPHLG----------------KFLEEL
TOR2_N     FFGMSRIGMEVTP--SGTWLTYHGAIKLDDKDPQFK------DN--------VILLNKHI
             :   *           :.           .

BoCov      NAYQQQ-DGTMNMSPKPQRQRG----QKNGQGENDNISVAAPKSRVQQNKIRELTAEDIS
OC43       NAYQQQ-DGMMNMSPKPQRQRG----HKNGQGENDNISVAVPKSRVQQNKSRELTAEDIS
PHEV       NAYQHQEDGMMNISPKPQRQRG----QKNGQVENDNVSVAAPKSRVQQNKSRELTAEDIS
MHV        DAYQDQAGGADVVSPKPQRKRGT--KQKALKGEVDNVSVAKPKSSVQRNVSRELTPEDRS
AIBV2      KSRSSSRPATRGNSPAPRQQRPK--KEKKLKKQDDEADKALTSDEERNNAQLEFYDEP-K
TCV        KSRPSSRPATRGNSPAPRQQRPK--KEKKPKKQDDEVDKALTSDEERNNAQLEFDDEP-K
AIBV       KSRSSSRPATRGTSPAPKQQRPK--KEKKPKKQDDEVDKALTSDEERNNAQLEFDDEP-K
FCV        DAYKRP-------SEVAKDQRQ----RKSRSKSADKKPEELS--VTLEAYTDVFDDTQVE
PTGV       NAYARP-------SEVAKEQRK----RKSRSKSAERSEQEVVPDALIENYTDVFDDTQVE
229E       NAPTRE----------MQQHP------LLNPSALEFNPSQTSPATAEPVRDEVSIET-D
TOR2_N     DAYKTFPP----TEPKKDKKKKTDEAQPLPQRQKKQPTVTLLPAADMDDFSRQLQNSMSG
              .:           ::             .  .

BoCov      LLKKMDEP-----FTEDTSEI
OC43       LLKKMDEP-----YTEDTSEI
PHEV       LLKKMDEP-----YTEDTSEI
MHV        LLAQILDDGVVPDGLEDDSNV
AIBV2      VINWGDAA-----LGENEL--
TCV        VINWGDSA-----LGENHL--
AIBV       VINWGDSA-----LGENEL--
FCV        MIDEVTN--------------
PTGV       MIDEVTN--------------
229E       IIDEVN---------------
TOR2_N     ASADSTQA-------------

Key
                                                                    Genbank    *%ID
MHV        NUCLEOCAPSID PROTEIN                                     P18446     34.3%   (SEQ ID NO: 44)
BoCov      nucleocapsid protein [Bovine coronavirus].               NP_150083  34.4%   (SEQ ID NO: 45)
AIBV       nucleocapsid protein [Avian infectious bronchitis virus]. AAK27162  28.3%   (SEQ ID NO: 46)
FCV        nucleocapsid [Feline coronavirus].                       CAA74230   29.4%   (SEQ ID NO: 47)
PTGV       nucleoprotein [porcine transmissible gastroenteritis virus]. AAM97563 28.0% (SEQ ID NO: 48)
229E       nucleocapsid protein [Human coronavirus 229E].           NP_073556  24.6%   (SEQ ID NO: 49)
OC43       NUCLEOCAPSID PROTEIN.                                    P33469     33.9%   (SEQ ID NO: 50)
PHEV       nucleocapsid protein [porcine hemagglutinating encephalomyelitis] AAL80036 33.3% (SEQ ID NO: 51)
TCV        nucleocapsid protein [turkey coronavirus].               AAP23873   28.2%   (SEQ ID NO: 52)
TOR_N      SARS associated virus nucleocapsid protein   (SEQ ID NO: 36)
```

FIGURE 10B

```
ATATTAGGTTTTTACCTACCCAGGAAAAGCCAACCAACCTCGATCTCTTG
TAGATCTGTTCTCTAAACGAACTTTAAAATCTGTGTAGCTGTCGCTCGGC
TGCATGCCTAGTGCACCTACGCAGTATAAACAATAATAAATTTTACTGTC
GTTGACAAGAAACGAGTAACTCGTCCCTCTTCTGCAGACTGCTTACGGTT
TCGTCCGTGTTGCAGTCGATCATCAGCATACCTAGGTTTCGTCCGGGTGT
GACCGAAAGGTAAGATGGAGAGCCTTGTTCTTGGTGTCAACGAGAAAACA
CACGTCCAACTCAGTTTGCCTGTCCTTCAGGTTAGAGACGTGCTAGTGCG
TGGCTTCGGGGACTCTGTGGAAGAGGCCCTATCGGAGGCACGTGAACACC
TCAAAAATGGCACTTGTGGTCTAGTAGAGCTGGAAAAAGGCGTACTGCCC
CAGCTTGAACAGCCCTATGTGTTCATTAAACGTTCTGATGCCTTAAGCAC
CAATCACGGCCACAAGGTCGTTGAGCTGGTTGCAGAAATGGACGGCATTC
AGTACGGTCGTAGCGGTATAACACTGGGAGTACTCGTGCCACATGTGGGC
GAAACCCCAATTGCATACCGCAATGTTCTTCTTCGTAAGAACGGTAATAA
GGGAGCCGGTGGTCATAGCTATGGCATCGATCTAAAGTCTTATGACTTAG
GTGACGAGCTTGGCACTGATCCCATTGAAGATTATGAACAAAACTGGAAC
ACTAAGCATGGCAGTGGTGCACTCCGTGAACTCACTCGTGAGCTCAATGG
AGGTGCAGTCACTCGCTATGTCGACAACAATTTCTGTGGCCCAGATGGGT
ACCCTCTTGATTGCATCAAAGATTTTCTCGCACGCGCGGGCAAGTCAATG
TGCACTCTTTCCGAACAACTTGATTACATCGAGTCGAAGAGAGGTGTCTA
CTGCTGCCGTGACCATGAGCATGAAATTGCCTGGTTCACTGAGCGCTCTG
ATAAGAGCTACGAGCACCAGACACCCTTCGAAATTAAGAGTGCCAAGAAA
TTTGACACTTTCAAAGGGGAATGCCCAAAGTTTGTGTTTCCTCTTAACTC
AAAAGTCAAAGTCATTCAACCACGTGTTGAAAAGAAAAAGACTGAGGGTT
TCATGGGCGTATACGCTCTGTGTACCCTGTTGCATCTCCACAGGAGTGT
AACAATATGCACTTGTCTACCTTGATGAAATGTAATCATTGCGATGAAGT
TTCATGGCAGACGTGCGACTTTCTGAAAGCCACTTGTGAACATTGTGGCA
CTGAAAATTTAGTTATTGAAGGACCTACTACATGTGGGTACCTACCTACT
AATGCTGTAGTGAAAATGCCATGTCCTGCCTGTCAAGACCCAGAGATTGG
ACCTGAGCATAGTGTTGCAGATTATCACAACCACTCAAACATTGAAACTC
GACTCCGCAAGGGAGGTAGGACTAGATGTTTTGGAGGCTGTGTGTTTGCC
TATGTTGGCTGCTATAATAAGCGTGCCTACTGGGTTCCTCGTGCTAGTGC
TGATATTGGCTCAGGCCATACTGGCATTACTGGTGACAATGTGGAGACCT
TGAATGAGGATCTCCTTGAGATACTGAGTCGTGAACGTGTTAACATTAAC
ATTGTTGGCGATTTTCATTTGAATGAAGAGGTTGCCATCATTTTGGCATC
TTTCTCTGCTTCTACAAGTGCCTTTATTGACACTATAAAGAGTCTTGATT
ACAAGTCTTTCAAAACCATTGTTGAGTCCTGCGGTAACTATAAAGTTACC
AAGGGAAAGCCCGTAAAAGGTGCTTGGAACATTGGACAACAGAGATCAGT
TTTAACACCACTGTGTGGTTTTCCCTCACAGGCTGCTGGTGTTATCAGAT
CAATTTTTGCGCGCACACTTGATGCAGCAAACCACTCAATTCCTGATTTG
CAAAGAGCAGCTGTCACCATACTTGATGGTATTTCTGAACAGTCATTACG
TCTTGTCGACGCCATGGTTTATACTTCAGACCTGCTCACCAACAGTGTCA
TTATTATGGCATATGTAACTGGTGGTCTTGTACAACAGACTTCTCAGTGG
TTGTCTAATCTTTTGGGCACTACTGTTGAAAAACTCAGGCCTATCTTTGA
ATGGATTGAGGCGAAACTTAGTGCAGGAGTTGAATTTCTCAAGGATGCTT
GGGAGATTCTCAAATTTCTCATTACAGGTGTTTTTGACATCGTCAAGGGT
CAAATACAGGTTGCTTCAGATAACATCAAGGATTGTGTAAAATGCTTCAT
TGATGTTGTTAACAAGGCACTCGAAATGTGCATTGATCAAGTCACTATCG
CTGGCGCAAAGTTGCGATCACTCAACTTAGGTGAAGTCTTCATCGCTCAA
AGCAAGGGACTTTACCGTCAGTGTATACGTGGCAAGGAGCAGCTGCAACT
ACTCATGCCTCTTAAGGCACCAAAAGAAGTAACCTTTCTTGAAGGTGATT
CACATGACACAGTACTTACCTCTGAGGAGGTTGTTCTCAAGAACGGTGAA
CTCGAAGCACTCGAGACGCCCGTTGATAGCTTCACAAATGGAGCTATCGT
TGGCACACCAGTCTGTGTAAATGGCCTCATGCTCTTAGAGATTAAGGACA
AAGAACAATACTGCGCATTGTCTCCTGGTTTACTGGCTACAAACAATGTC
TTTCGCTTAAAAGGGGTGCACCAATTAAAGGTGTAACCTTTGGAGAAGA
TACTGTTTGGGAAGTTCAAGGTTACAAGAATGTGAGAATCACATTTGAGC
TTGATGAACGTGTTGACAAAGTGCTTAATGAAAAGTGCTCTGTCTACACT
```

FIGURE 11A

```
GTTGAATCCGGTACCGAAGTTACTGAGTTTGCATGTGTTGTAGCAGAGGC
TGTTGTGAAGACTTTACAACCAGTTTCTGATCTCCTTACCAACATGGGTA
TTGATCTTGATGAGTGGAGTGTAGCTACATTCTACTTATTTGATGATGCT
GGTGAAGAAAACTTTTCATCACGTATGTATTGTTCCTTTTACCCTCCAGA
TGAGGAAGAAGAGGACGATGCAGAGTGTGAGGAAGAAGAAATTGATGAAA
CCTGTGAACATGAGTACGGTACAGAGGATGATTATCAAGGTCTCCCTCTG
GAATTTGGTGCCTCAGCTGAAACAGTTCGAGTTGAGGAAGAAGAAGAGGA
AGACTGGCTGGATGATACTACTGAGCAATCAGAGATTGAGCCAGAACCAG
AACCTACACCTGAAGAACCAGTTAATCAGTTTACTGGTTATTTAAAACTT
ACTGACAATGTTGCCATTAAATGTGTTGACATCGTTAAGGAGGCACAAAG
TGCTAATCCTATGGTGATTGTAAATGCTGCTAACATACACCTGAAACATG
GTGGTGGTGTAGCAGGTGCACTCAACAAGGCAACCAATGGTGCCATGCAA
AAGGAGAGTGATGATTACATTAAGCTAAATGGCCCTCTTACAGTAGGAGG
GTCTTGTTTGCTTTCTGGACATAATCTTGCTAAGAAGTGTCTGCATGTTG
TTGGACCTAACCTAAATGCAGGTGAGGACATCCAGCTTCTTAAGGCAGCA
TATGAAAATTTCAATTCACAGGACATCTTACTTGCACCATTGTTGTCAGC
AGGCATATTTGGTGCTAAACCACTTCAGTCTTTACAAGTGTGCGTGCAGA
CGGTTCGTACACAGGTTTATATTGCAGTCAATGACAAAGCTCTTTATGAG
CAGGTTGTCATGGATTATCTTGATAACCTGAAGCCTAGAGTGGAAGCACC
TAAACAAGAGGAGCCACCAAACACAGAAGATTCCAAAACTGAGGAGAAAT
CTGTCGTACAGAAGCCTGTCGATGTGAAGCCAAAAATTAAGGCCTGCATT
GATGAGGTTACCACAACACTGGAAGAAACTAAGTTTCTTACCAATAAGTT
ACTCTTGTTTGCTGATATCAATGGTAAGCTTTACCATGATTCTCAGAACA
TGCTTAGAGGTGAAGATATGTCTTTCCTTGAGAAGGATGCACCTTACATG
GTAGGTGATGTTATCACTAGTGGTGATATCACTTGTGTTGTAATACCCTC
CAAAAAGGCTGGTGGCACTACTGAGATGCTCTCAAGAGCTTTGAAGAAAG
TGCCAGTTGATGAGTATATAACCACGTACCCTGGACAAGGATGTGCTGGT
TATACACTTGAGGAAGCTAAGACTGCTCTTAAGAAATGCAAATCTGCATT
TTATGTACTACCTTCAGAAGCACCTAATGCTAAGGAAGAGATTCTAGGAA
CTGTATCCTGGAATTTGAGAGAAATGCTTGCTCATGCTGAAGAGACAAGA
AAATTAATGCCTATATGCATGGATGTTAGAGCCATAATGGCAACCATCCA
ACGTAAGTATAAAGGAATTAAAATTCAAGAGGGCATCGTTGACTATGGTG
TCCGATTCTTCTTTTATACTAGTAAAGAGCCTGTAGCTTCTATTATTACG
AAGCTGAACTCTCTAAATGAGCCGCTTGTCACAATGCCAATTGGTTATGT
GACACATGGTTTTAATCTTGAAGAGGCTGCGCGCTGTATGCGTTCTCTTA
AAGCTCCTGCCGTAGTGTCAGTATCATCACCAGATGCTGTTACTACATAT
AATGGATACCTCACTTCGTCATCAAAGACATCTGAGGAGCACTTTGTAGA
AACAGTTTCTTTGGCTGGCTCTTACAGAGATTGGTCCTATTCAGGACAGC
GTACAGAGTTAGGTGTTGAATTTCTTAAGCGTGGTGACAAAATTGTGTAC
CACACTCTGGAGAGCCCCGTCGAGTTTCATCTTGACGGTGAGGTTCTTTC
ACTTGACAAACTAAAGAGTCTCTTATCCCTGCGGGAGGTTAAGACTATAA
AAGTGTTCACAACTGTGGACAACACTAATCTCCACACACAGCTTGTGGAT
ATGTCTATGACATATGGACAGCAGTTTGGTCCAACATACTTGGATGGTGC
TGATGTTACAAAAATTAAACCTCATGTAAATCATGAGGGTAAGACTTTCT
TTGTACTACCTAGTGATGACACACTACGTAGTGAAGCTTTCGAGTACTAC
CATACTCTTGATGAGAGTTTTCTTGGTAGGTACATGTCTGCTTTAAACCA
CACAAAGAAATGGAAATTTCCTCAAGTTGGTGGTTTAACTTCAATTAAAT
GGGCTGATAACAATTGTTATTTGTCTAGTGTTTTATTAGCACTTCAACAG
CTTGAAGTCAAATTCAATGCACCAGCACTTCAAGAGGCTTATTATAGAGC
CCGTGCTGGTGATGCTGCTAACTTTTGTGCACTCATACTCGCTTACAGTA
ATAAAACTGTTGGCGAGCTTGGTGATGTCAGAGAAACTATGACCCATCTT
CTACAGCATGCTAATTTGGAATCTGCAAAGCGAGTTCTTAATGTGGTGTG
TAAACATTGTGGTCAGAAAACTACTACCTTAACGGGTGTAGAAGCTGTGA
TGTATATGGGTACTCTATCTTATGATAATCTTAAGACAGGTGTTTCCATT
CCATGTGTGTGTGGTCGTGATGCTACACAATATCTAGTACAACAAGAGTC
TTCTTTTGTTATGATGTCTGCACCACCTGCTGAGTATAAATTACAGCAAG
GTACATTCTTATGTGCGAATGAGTACACTGGTAACTATCAGTGTGGTCAT
```

FIGURE 11B

```
TACACTCATATAACTGCTAAGGAGACCCTCTATCGTATTGACGGAGCTCA
CCTTACAAAGATGTCAGAGTACAAAGGACCAGTGACTGATGTTTTCTACA
AGGAAACATCTTACACTACAACCATCAAGCCTGTGTCGTATAAACTCGAT
GGAGTTACTTACACAGAGATTGAACCAAAATTGGATGGGTATTATAAAA
GGATAATGCTTACTATACAGAGCAGCCTATAGACCTTGTACCAACTCAAC
CATTACCAAATGCGAGTTTTGATAATTTCAAACTCACATGTTCTAACACA
AAATTTGCTGATGATTTAAATCAAATGACAGGCTTCACAAAGCCAGCTTC
ACGAGAGCTATCTGTCACATTCTTCCCAGACTTGAATGGCGATGTAGTGG
CTATTGACTATAGACACTATTCAGCGAGTTTCAAGAAAGGTGCTAAATTA
CTGCATAAGCCAATTGTTTGGCACATTAACCAGGCTACAACCAAGACAAC
GTTCAAACCAAACACTTGGTGTTTACGTTGTCTTTGGAGTACAAAGCCAG
TAGATACTTCAAATTCATTTGAAGTTCTGGCAGTAGAAGACACACAAGGA
ATGGACAATCTTGCTTGTGAAAGTCAACAACCCACCTCTGAAGAAGTAGT
GGAAAATCCTACCATACAGAAGGAAGTCATAGAGTGTGACGTGAAAACTA
CCGAAGTTGTAGGCAATGTCATACTTAAACCATCAGATGAAGGTGTTAAA
GTAACACAAGAGTTAGGTCATGAGGATCTTATGGCTGCTTATGTGGAAAA
CACAAGCATTACCATTAAGAAACCTAATGAGCTTTCACTAGCCTTAGGTT
TAAAAACAATTGCCACTCATGGTATTGCTGCAATTAATAGTGTTCCTTGG
AGTAAAATTTTGGCTTATGTCAAACCATTCTTAGGACAAGCAGCAATTAC
AACATCAAATTGCGCTAAGAGATTAGCACAACGTGTGTTTAACAATTATA
TGCCTTATGTGTTTACATTATTGTTCCAATTGTGTACTTTTACTAAAAGT
ACCAATTCTAGAATTAGAGCTTCACTACCTACAACTATTGCTAAAAATAG
TGTTAAGAGTGTTGCTAAATTATGTTTGGATGCCGGCATTAATTATGTGA
AGTCACCCAAATTTTCTAAATTGTTCACAATCGCTATGTGGCTATTGTTG
TTAAGTATTTGCTTAGGTTCTCTAATCTGTGTAACTGCTGCTTTTGGTGT
ACTCTTATCTAATTTTGGTGCTCCTTCTTATTGTAATGGCGTTAGAGAAT
TGTATCTTAATTCGTCTAACGTTACTACTATGGATTTCTGTGAAGGTTCT
TTTCCTTGCAGCATTTGTTTAAGTGGATTAGACTCCCTTGATTCTTATCC
AGCTCTTGAAACCATTCAGGTGACGATTTCATCGTACAAGCTAGACTTGA
CAATTTTAGGTCTGGCCGCTGAGTGGGTTTTGGCATATATGTTGTTCACA
AAATTCTTTTATTTATTAGGTCTTTCAGCTATAATGCAGGTGTTCTTTGG
CTATTTTGCTAGTCATTTCATCAGCAATTCTTGGCTCATGTGGTTTATCA
TTAGTATTGTACAAATGGCACCCGTTTCTGCAATGGTTAGGATGTACATC
TTCTTTGCTTCTTTCTACTACATATGGAAGAGCTATGTTCATATCATGGA
TGGTTGCACCTCTTCGACTTGCATGATGTGCTATAAGCGCAATCGTGCCA
CACGCGTTGAGTGTACAACTATTGTTAATGGCATGAAGAGATCTTTCTAT
GTCTATGCAAATGGAGGCCGTGGCTTCTGCAAGACTCACAATTGGAATTG
TCTCAATTGTGACACATTTTGCACTGGTAGTACATTCATTAGTGATGAAG
TTGCTCGTGATTTGTCACTCCAGTTTAAAAGACCAATCAACCCTACTGAC
CAGTCATCGTATATTGTTGATAGTGTTGCTGTGAAAAATGGCGCGCTTCA
CCTCTACTTTGACAAGGCTGGTCAAAAGACCTATGAGAGACATCCGCTCT
CCCATTTTGTCAATTTAGACAATTTGAGAGCTAACAACACTAAAGGTTCA
CTGCCTATTAATGTCATAGTTTTTGATGGCAAGTCCAAATGCGACGAGTC
TGCTTCTAAGTCTGCTTCTGTGTACTACAGTCAGCTGATGTGCCAACCTA
TTCTGTTGCTTGACCAAGCTCTTGTATCAGACGTTGGAGATAGTACTGAA
GTTTCCGTTAAGATGTTTGATGCTTATGTCGACACCTTTTCAGCAACTTT
TAGTGTTCCTATGGAAAAACTTAAGGCACTTGTTGCTACAGCTCACAGCG
AGTTAGCAAAGGGTGTAGCTTTAGATGGTGTCCTTTCTACATTCGTGTCA
GCTGCCCGACAAGGTGTTGTTGATACCGATGTTGACACAAAGGATGTTAT
TGAATGTCTCAAACTTTCACATCACTCTGACTTAGAAGTGACAGGTGACA
GTTGTAACAATTTCATGCTCACCTATAATAAGGTTGAAAACATGACGCCC
AGAGATCTTGGCGCATGTATTGACTGTAATGCAAGGCATATCAATGCCCA
AGTAGCAAAAGTCACAATGTTTCACTCATCTGGAATGTAAAAGACTACA
TGTCTTTATCTGAACAGCTGCGTAAACAAATTCGTAGTGCTGCCAAGAAG
AACAACATACCTTTTAGACTAACTTGTGCTACAACTAGACAGGTTGTCAA
TGTCATAACTACTAAAATCTCACTCAAGGGTGGTAAGATTGTTAGTACTT
GTTTTAAACTTATGCTTAAGGCCACATTATTGTGCGTTCTTGCTGCATTG
```

FIGURE 11C

```
GTTTGTTATATCGTTATGCCAGTACATACATTGTCAATCCATGATGGTTA
CACAAATGAAATCATTGGTTACAAAGCCATTCAGGATGGTGTCACTCGTG
ACATCATTTCTACTGATGATTGTTTTGCAAATAAACATGCTGGTTTTGAC
GCATGGTTTAGCCAGCGTGGTGGTTCATACAAAAATGACAAAAGCTGCCC
TGTAGTAGCTGCTATCATTACAAGAGAGATTGGTTTCATAGTGCCTGGCT
TACCGGGTACTGTGCTGAGAGCAATCAATGGTGACTTCTTGCATTTTCTA
CCTCGTGTTTTTAGTGCTGTTGGCAACATTTGCTACACACCTTCCAAACT
CATTGAGTATAGTGATTTTGCTACCTCTGCTTGCGTTCTTGCTGCTGAGT
GTACAATTTTTAAGGATGCTATGGGCAAACCTGTGCCATATTGTTATGAC
ACTAATTTGCTAGAGGGTTCTATTTCTTATAGTGAGCTTCGTCCAGACAC
TCGTTATGTGCTTATGGATGGTTCCATCATACAGTTTCCTAACACTTACC
TGGAGGGTTCTGTTAGAGTAGTAACAACTTTTGATGCTGAGTACTGTAGA
CATGGTACATGCGAAAGGTCAGAAGTAGGTATTTGCCTATCTACCAGTGG
TAGATGGGTTCTTAATAATGAGCATTACAGAGCTCTATCAGGAGTTTTCT
GTGGTGTTGATGCGATGAATCTCATAGCTAACATCTTTACTCCTCTTGTG
CAACCTGTGGGTGCTTTAGATGTGTCTGCTTCAGTAGTGGCTGGTGGTAT
TATTGCCATATTGGTGACTTGTGCTGCCTACTACTTTATGAAATTCAGAC
GTGTTTTTGGTGAGTACAACCATGTTGTTGCTGCTAATGCACTTTTGTTT
TTGATGTCTTTCACTATACTCTGTCTGGTACCAGCTTACAGCTTTCTGCC
GGGAGTCTACTCAGTCTTTTACTTGTACTTGACATTCTATTTCACCAATG
ATGTTTCATTCTTGGCTCACCTTCAATGGTTTGCCATGTTTTCTCCTATT
GTGCCTTTTTGGATAACAGCAATCTATGTATTCTGTATTTCTCTGAAGCA
CTGCCATTGGTTCTTTAACAACTATCTTAGGAAAAGAGTCATGTTTAATG
GAGTTACATTTAGTACCTTCGAGGAGGCTGCTTTGTGTACCTTTTTGCTC
AACAAGGAAATGTACCTAAAATTGCGTAGCGAGACACTGTTGCCACTTAC
ACAGTATAACAGGTATCTTGCTCTATATAACAAGTACAAGTATTTCAGTG
GAGCCTTAGATACTACCAGCTATCGTGAAGCAGCTTGCTGCCACTTAGCA
AAGGCTCTAAATGACTTTAGCAACTCAGGTGCTGATGTTCTCTACCAACC
ACCACAGACATCAATCACTTCTGCTGTTCTGCAGAGTGGTTTTAGGAAAA
TGGCATTCCCGTCAGGCAAAGTTGAAGGGTGCATGGTACAAGTAACCTGT
GGAACTACAACTCTTAATGGATTGTGGTTGGATGACACAGTATACTGTCC
AAGACATGTCATTTGCACAGCAGAAGACATGCTTAATCCTAACTATGAAG
ATCTGCTCATTCGCAAATCCAACCATAGCTTTCTTGTTCAGGCTGGCAAT
GTTCAACTTCGTGTTATTGGCCATTCTATGCAAAATTGTCTGCTTAGGCT
TAAAGTTGATACTTCTAACCCTAAGACACCCAAGTATAAATTTGTCCGTA
TCCAACCTGGTCAAACATTTTCAGTTCTAGCATGCTACAATGGTTCACCA
TCTGGTGTTTATCAGTGTGCCATGAGACCTAATCATACCATTAAAGGTTC
TTTCCTTAATGGATCATGTGGTAGTGTTGGTTTTAACATTGATTATGATT
GCGTGTCTTTCTGCTATATGCATCATATGGAGCTTCCAACAGGAGTACAC
GCTGGTACTGACTTAGAAGGTAAATTCTATGGTCCATTTGTTGACAGACA
AACTGCACAGGCTGCAGGTACAGACACAACCATAACATTAAATGTTTTGG
CATGGCTGTATGCTGCTGTTATCAATGGTGATAGGTGGTTTCTTAATAGA
TTCACCACTACTTTGAATGACTTTAACCTTGTGGCAATGAAGTACAACTA
TGAACCTTTGACACAAGATCATGTTGACATATTGGGACCTCTTTCTGCTC
AAACAGGAATTGCCGTCTTAGATATGTGTGCTGCTTTGAAAGAGCTGCTG
CAGAATGGTATGAATGGTCGTACTATCCTTGGTAGCACTATTTTAGAAGA
TGAGTTTACACCATTTGATGTTGTTAGACAATGCTCTGGTGTTACCTTCC
AAGGTAAGTTCAAGAAAATTGTTAAGGGCACTCATCATTGGATGCTTTTA
ACTTTCTTGACATCACTATTGATTCTTGTTCAAAGTACACAGTGGTCACT
GTTTTCTTTGTTTACGAGAATGCTTTCTTGCCATTTACTCTTGGTATTA
TGGCAATTGCTGCATGTGCTATGCTGCTTGTTAAGCATAAGCACGCATTC
TTGTGCTTGTTTCTGTTACCTTCTCTTGCAACAGTTGCTTACTTTAATAT
GGTCTACATGCCTGCTAGCTGGGTGATGCGTATCATGACATGGCTTGAAT
TGGCTGACACTAGCTTGTCTGGTTATAGGCTTAAGGATTGTGTTATGTAT
GCTTCAGCTTTAGTTTTGCTTATTCTCATGACAGCTCGCACTGTTTATGA
TGATGCTGCTAGACGTGTTTGGACACTGATGAATGTCATTACACTTGTTT
ACAAAGTCTACTATGGTAATGCTTTAGATCAAGCTATTTCCATGTGGGCC
```

FIGURE 11D

```
TTAGTTATTTCTGTAACCTCTAACTATTCTGGTGTCGTTACGACTATCAT
GTTTTTAGCTAGAGCTATAGTGTTTGTGTGTGTTGAGTATTACCCATTGT
TATTTATTACTGGCAACACCTTACAGTGTATCATGCTTGTTTATTGTTTC
TTAGGCTATTGTTGCTGCTGCTACTTTGGCCTTTTCTGTTTACTCAACCG
TTACTTCAGGCTTACTCTTGGTGTTTATGACTACTTGGTCTCTACACAAG
AATTTAGGTATATGAACTCCCAGGGGCTTTTGCCTCCTAAGAGTAGTATT
GATGCTTTCAAGCTTAACATTAAGTTGTTGGGTATTGGAGGTAAACCATG
TATCAAGGTTGCTACTGTACAGTCTAAAATGTCTGACGTAAAGTGCACAT
CTGTGGTACTGCTCTCGGTTCTTCAACAACTTAGAGTAGAGTCATCTTCT
AAATTGTGGGCACAATGTGTACAACTCCACAATGATATTCTTCTTGCAAA
AGACACAACTGAAGCTTTCGAGAAGATGGTTTCTCTTTTGTCTGTTTTGC
TATCCATGCAGGGTGCTGTAGACATTAATAGGTTGTGCGAGGAAATGCTC
GATAACCGTGCTACTCTTCAGGCTATTGCTTCAGAATTTAGTTCTTTACC
ATCATATGCCGCTTATGCCACTGCCCAGGAGGCCTATGAGCAGGCTGTAG
CTAATGGTGATTCTGAAGTCGTTCTCAAAAAGTTAAAGAAATCTTTGAAT
GTGGCTAAATCTGAGTTTGACCGTGATGCTGCCATGCAACGCAAGTTGGA
AAAGATGGCAGATCAGGCTATGACCCAAATGTACAAACAGGCAAGATCTG
AGGACAAGAGGGCAAAAGTAACTAGTGCTATGCAAACAATGCTCTTCACT
ATGCTTAGGAAGCTTGATAATGATGCACTTAACAACATTATCAACAATGC
GCGTGATGGTTGTGTTCCACTCAACATCATACCATTGACTACAGCAGCCA
AACTCATGGTTGTTGTCCCTGATTATGGTACCTACAAGAACACTTGTGAT
GGTAACACCTTTACATATGCATCTGCACTCTGGGAAATCCAGCAAGTTGT
TGATGCGGATAGCAAGATTGTTCAACTTAGTGAAATTAACATGGACAATT
CACCAAATTTGGCTTGGCCTCTTATTGTTACAGCTCTAAGAGCCAACTCA
GCTGTTAAACTACAGAATAATGAACTGAGTCCAGTAGCACTACGACAGAT
GTCCTGTGCGGCTGGTACCACACAAACAGCTTGTACTGATGACAATGCAC
TTGCCTACTATAACAATTCGAAGGGAGGTAGGTTTGTGCTGGCATTACTA
TCAGACCACCAAGATCTCAAATGGGCTAGATTCCCTAAGAGTGATGGTAC
AGGTACAATTTACACAGAACTGGAACCACCTTGTAGGTTTGTTACAGACA
CACCAAAAGGGCCTAAAGTGAAATACTTGTACTTCATCAAAGGCTTAAAC
AACCTAAATAGAGGTATGGTGCTGGGCAGTTTAGCTGCTACAGTACGTCT
TCAGGCTGGAAATGCTACAGAAGTACCTGCCAATTCAACTGTGCTTTCCT
TCTGTGCTTTTGCAGTAGACCCTGCTAAAGCATATAAGGATTACCTAGCA
AGTGGAGGACAACCAATCACCAACTGTGTGAAGATGTTGTGTACACACAC
TGGTACAGGACAGGCAATTACTGTAACACCAGAAGCTAACATGGACCAAG
AGTCCTTTGGTGGTGCTTCATGTTGTCTGTATTGTAGATGCCACATTGAC
CATCCAAATCCTAAAGGATTCTGTGACTTGAAAGGTAAGTACGTCCAAAT
ACCTACCACTTGTGCTAATGACCCAGTGGGTTTTACACTTAGAAACACAG
TCTGTACCGTCTGCGGAATGTGGAAAGGTTATGGCTGTAGTTGTGACCAA
CTCCGCGAACCCTTGATGCAGTCTGCGGATGCATCAACGTTTTTAAACGG
GTTTGCGGTGTAAGTGCAGCCCGTCTTACACCGTGCGGCACAGGCACTAG
TACTGATGTCGTCTACAGGGCTTTTGATATTTACAACGAAAAAGTTGCTG
GTTTTGCAAAGTTCCTAAAAACTAATTGCTGTCGCTTCCAGGAGAAGGAT
GAGGAAGGCAATTTATTAGACTCTTACTTTGTAGTTAAGAGGCATACTAT
GTCTAACTACCAACATGAAGAGACTATTTATAACTTGGTTAAAGATTGTC
CAGCGGTTGCTGTCCATGACTTTTTCAAGTTTAGAGTAGATGGTGACATG
GTACCACATATATCACGTCAGCGTCTAACTAAATACACAATGGCTGATTT
AGTCTATGCTCTACGTCATTTTGATGAGGGTAATTGTGATACATTAAAAG
AAATACTCGTCACATACAATTGCTGTGATGATGATTATTTCAATAAGAAG
GATTGGTATGACTTCGTAGAGAATCCTGACATCTTACGCGTATATGCTAA
CTTAGGTGAGCGTGTACGCCAATCATTATTAAAGACTGTACAATTCTGCG
ATGCTATGCGTGATGCAGGCATTGTAGGCGTACTGACATTAGATAATCAG
GATCTTAATGGGAACTGGTACGATTTCGGTGATTTCGTACAAGTAGCACC
AGGCTGCGGAGTTCCTATTGTGGATTCATATTACTCATTGCTGATGCCCA
TCCTCACTTTGACTAGGGCATTGGCTGCTGAGTCCCATATGGATGCTGAT
CTCGCAAAACCACTTATTAAGTGGGATTTGCTGAAATATGATTTTACGGA
AGAGAGACTTTGTCTCTTCGACCGTTATTTTAAATATTGGGACCAGACAT
```

FIGURE 11E

```
ACCATCCCAATTGTATTAACTGTTTGGATGATAGGTGTATCCTTCATTGT
GCAAACTTTAATGTGTTATTTTCTACTGTGTTTCCACCTACAAGTTTTGG
ACCACTAGTAAGAAAAATATTTGTAGATGGTGTTCCTTTTGTTGTTTCAA
CTGGATACCATTTTCGTGAGTTAGGAGTCGTACATAATCAGGATGTAAAC
TTACATAGCTCGCGTCTCAGTTTCAAGGAACTTTTAGTGTATGCTGCTGA
TCCAGCTATGCATGCAGCTTCTGGCAATTTATTGCTAGATAAACGCACTA
CATGCTTTTCAGTAGCTGCACTAACAAACAATGTTGCTTTTCAAACTGTC
AAACCCGGTAATTTTAATAAAGACTTTTATGACTTTGCTGTGTCTAAAGG
TTTCTTTAAGGAAGGAAGTTCTGTTGAACTAAAACACTTCTTCTTTGCTC
AGGATGGCAACGCTGCTATCAGTGATTATGACTATTATCGTTATAATCTG
CCAACAATGTGTGATATCAGACAACTCCTATTCGTAGTTGAAGTTGTTGA
TAAATACTTTGATTGTTACGATGGTGGCTGTATTAATGCCAACCAAGTAA
TCGTTAACAATCTGGATAAATCAGCTGGTTTCCCATTTAATAAATGGGGT
AAGGCTAGACTTTATTATGACTCAATGAGTTATGAGGATCAAGATGCACT
TTTCGCGTATACTAAGCGTAATGTCATCCCTACTATAACTCAAATGAATC
TTAAGTATGCCATTAGTGCAAAGAATAGAGCTCGCACCGTAGCTGGTGTC
TCTATCTGTAGTACTATGACAAATAGACAGTTTCATCAGAAATTATTGAA
GTCAATAGCCGCCACTAGAGGAGCTACTGTGGTAATTGGAACAAGCAAGT
TTTACGGTGGCTGGCATAATATGTTAAAAACTGTTTACAGTGATGTAGAA
ACTCCACACCTTATGGGTTGGGATTATCCAAAATGTGACAGAGCCATGCC
TAACATGCTTAGGATAATGGCCTCTCTTGTTCTTGCTCGCAAACATAACA
CTTGCTGTAACTTATCACACCGTTTCTACAGGTTAGCTAACGAGTGTGCG
CAAGTATTAAGTGAGATGGTCATGTGTGGCGGCTCACTATATGTTAAACC
AGGTGGAACATCATCCGGTGATGCTACAACTGCTTATGCTAATAGTGTCT
TTAACATTTGTCAAGCTGTTACAGCCAATGTAAATGCACTTCTTTCAACT
GATGGTAATAAGATAGCTGACAAGTATGTCCGCAATCTACAACACAGGCT
CTATGAGTGTCTCTATAGAAATAGGGATGTTGATCATGAATTCGTGGATG
AGTTTTACGCTTACCTGCGTAAACATTTCTCCATGATGATTCTTTCTGAT
GATGCCGTTGTGTGCTATAACAGTAACTATGCGGCTCAAGGTTTAGTAGC
TAGCATTAAGAACTTTAAGGCAGTTCTTTATTATCAAAATAATGTGTTCA
TGTCTGAGGCAAAATGTTGGACTGAGACTGACCTTACTAAAGGACCTCAC
GAATTTTGCTCACAGCATACAATGCTAGTTAAACAAGGAGATGATTACGT
GTACCTGCCTTACCCAGATCCATCAAGAATATTAGGCGCAGGCTGTTTTG
TCGATGATATTGTCAAAACAGATGGTACACTTATGATTGAAAGGTTCGTG
TCACTGGCTATTGATGCTTACCCACTTACAAAACATCCTAATCAGGAGTA
TGCTGATGTCTTTCACTTGTATTTACAATACATTAGAAAGTTACATGATG
AGCTTACTGGCCACATGTTGGACATGTATTCCGTAATGCTAACTAATGAT
AACACCTCACGGTACTGGGAACCTGAGTTTTATGAGGCTATGTACACACC
ACATACAGTCTTGCAGGCTGTAGGTGCTTGTGTATTGTGCAATTCACAGA
CTTCACTTCGTTGCGGTGCCTGTATTAGGAGACCATTCCTATGTTGCAAG
TGCTGCTATGACCATGTCATTTCAACATCACACAAATTAGTGTTGTCTGT
TAATCCCTATGTTTGCAATGCCCCAGGTTGTGATGTCACTGATGTGACAC
AACTGTATCTAGGAGGTATGAGCTATTATTGCAAGTCACATAAGCCTCCC
ATTAGTTTTCCATTATGTGCTAATGGTCAGGTTTTTGGTTTATACAAAAA
CACATGTGTAGGCAGTGACAATGTCACTGACTTCAATGCGATAGCAACAT
GTGATTGGACTAATGCTGGCGATTACATACTTGCCAACACTTGTACTGAG
AGACTCAAGCTTTTCGCAGCAGAAACGCTCAAAGCCACTGAGGAAACATT
TAAGCTGTCATATGGTATTGCCACTGTACGCGAAGTACTCTCTGACAGAG
AATTGCATCTTTCATGGGAGGTTGGAAAACCTAGACCACCATTGAACAGA
AACTATGTCTTTACTGGTTACCGTGTAACTAAAAATAGTAAAGTACAGAT
TGGAGAGTACACCTTTGAAAAAGGTGACTATGGTGATGCTGTTGTGTACA
GAGGTACTACGACATACAAGTTGAATGTTGGTGATTACTTTGTGTTGACA
TCTCACACTGTAATGCCACTTAGTGCACCTACTCTAGTGCCACAAGAGCA
CTATGTGAGAATTACTGGCTTGTACCCAACACTCAACATCTCAGATGAGT
TTTCTAGCAATGTTGCAAATTATCAAAAGGTCGGCATGCAAAAGTACTCT
ACACTCCAAGGACCACCTGGTACTGGTAAGAGTCATTTTGCCATCGGACT
TGCTCTCTATTACCCATCTGCTCGCATAGTGTATACGGCATGCTCTCATG
```

FIGURE 11F

```
CAGCTGTTGATGCCCTATGTGAAAAGGCATTAAAATATTTGCCCATAGAT
AAATGTAGTAGAATCATACCTGCGCGTGCGCGCGTAGAGTGTTTTGATAA
ATTCAAAGTGAATTCAACACTAGAACAGTATGTTTTCTGCACTGTAAATG
CATTGCCAGAAACAACTGCTGACATTGTAGTCTTTGATGAAATCTCTATG
GCTACTAATTATGACTTGAGTGTTGTCAATGCTAGACTTCGTGCAAAACA
CTACGTCTATATTGGCGATCCTGCTCAATTACCAGCCCCCGCACATTGC
TGACTAAAGGCACACTAGAACCAGAATATTTTAATTCAGTGTGCAGACTT
ATGAAAACAATAGGTCCAGACATGTTCCTTGGAACTTGTCGCCGTTGTCC
TGCTGAAATTGTTGACACTGTGAGTGCTTTAGTTTATGACAATAAGCTAA
AAGCACACAAGGATAAGTCAGCTCAATGCTTCAAAATGTTCTACAAAGGT
GTTATTACACATGATGTTTCATCTGCAATCAACAGACCTCAAATAGGCGT
TGTAAGAGAATTTCTTACACGCAATCCTGCTTGGAGAAAAGCTGTTTTTA
TCTCACCTTATAATTCACAGAACGCTGTAGCTTCAAAAATCTTAGGATTG
CCTACGCAGACTGTTGATTCATCACAGGGTTCTGAATATGACTATGTCAT
ATTCACACAAACTACTGAAACAGCACACTCTTGTAATGTCAACCGCTTCA
ATGTGGCTATCACAAGGGCAAAAATTGGCATTTTGTGCATAATGTCTGAT
AGAGATCTTTATGACAAACTGCAATTTACAAGTCTAGAAATACCACGTCG
CAATGTGGCTACATTACAAGCAGAAAATGTAACTGGACTTTTTAAGGACT
GTAGTAAGATCATTACTGGTCTTCATCCTACACAGGCACCTACACACCTC
AGCGTTGATATAAAGTTCAAGACTGAAGGATTATGTGTTGACATACCAGG
CATACCAAAGGACATGACCTACCGTAGACTCATCTCTATGATGGGTTTCA
AAATGAATTACCAAGTCAATGGTTACCCTAATATGTTTATCACCCGCGAA
GAAGCTATTCGTCACGTTCGTGCGTGGATTGGCTTTGATGTAGAGGGCTG
TCATGCAACTAGAGATGCTGTGGGTACTAACCTACCTCTCCAGCTAGGAT
TTTCTACAGGTGTTAACTTAGTAGCTGTACCGACTGGTTATGTTGACACT
GAAAATAACACAGAATTCACCAGAGTTAATGCAAAACCTCCACCAGGTGA
CCAGTTTAAACATCTTATACCACTCATGTATAAAGGCTTGCCCTGGAATG
TAGTGCGTATTAAGATAGTACAAATGCTCAGTGATACACTGAAAGGATTG
TCAGACAGAGTCGTGTTCGTCCTTTGGGCGCATGGCTTTGAGCTTACATC
AATGAAGTACTTTGTCAAGATTGGACCTGAAAGAACGTGTTGTCTGTGTG
ACAAACGTGCAACTTGCTTTTCTACTTCATCAGATACTTATGCCTGCTGG
AATCATTCTGTGGGTTTTGACTATGTCTATAACCCATTTATGATTGATGT
TCAGCAGTGGGGCTTTACGGGTAACCTTCAGAGTAACCATGACCAACATT
GCCAGGTACATGGAAATGCACATGTGGCTAGTTGTGATGCTATCATGACT
AGATGTTTAGCAGTCCATGAGTGCTTTGTTAAGCGCGTTGATTGGTCTGT
TGAATACCCTATTATAGGAGATGAACTGAGGGTTAATTCTGCTTGCAGAA
AAGTACAACACATGGTTGTGAAGTCTGCATTGCTTGCTGATAAGTTTCCA
GTTCTTCATGACATTGGAAATCCAAAGGCTATCAAGTGTGTGCCTCAGGC
TGAAGTAGAATGGAAGTTCTACGATGCTCAGCCATGTAGTGACAAAGCTT
ACAAAATAGAGGAACTCTTCTATTCTTATGCTACACATCACGATAAATTC
ACTGATGGTGTTTGTTTGTTTTGGAATTGTAACGTTGATCGTTACCCAGC
CAATGCAATTGTGTGTAGGTTTGACACAAGAGTCTTGTCAAACTTGAACT
TACCAGGCTGTGATGGTGGTAGTTTGTATGTGAATAAGCATGCATTCCAC
ACTCCAGCTTTCGATAAAAGTGCATTTACTAATTTAAAGCAATTGCCTTT
CTTTTACTATTCTGATAGTCCTTGTGAGTCTCATGGCAAACAAGTAGTGT
CGGATATTGATTATGTTCCACTCAAATCTGCTACGTGTATTACACGATGC
AATTTAGGTGGTGCTGTTTGCAGACACCATGCAAATGAGTACCGACAGTA
CTTGGATGCATATAATATGATGATTTCTGCTGGATTTAGCCTATGGATTT
ACAAACAATTTGATACTTATAACCTGTGGAATACATTTACCAGGTTACAG
AGTTTAGAAAATGTGGCTTATAATGTTGTTAATAAAGGACACTTTGATGG
ACACGCCGGCGAAGCACCTGTTTCCATCATTAATAATGCTGTTTACACAA
AGGTAGATGGTATTGATGTGGAGATCTTTGAAAATAAGACAACACTTCCT
GTTAATGTTGCATTTGAGCTTTGGGCTAAGCGTAACATTAAACCAGTGCC
AGAGATTAAGATACTCAATAATTTGGGTGTTGATATCGCTGCTAATACTG
TAATCTGGGACTACAAAAGAGAAGCCCAGCACATGTATCTACAATAGGT
GTCTGCACAATGACTGACATTGCCAAGAAACCTACTGAGAGTGCTTGTTC
TTCACTTACTGTCTTGTTTGATGGTAGAGTGGAAGGACAGGTAGACCTTT
```

FIGURE 11G

```
TTAGAAACGCCCGTAATGGTGTTTTAATAACAGAAGGTTCAGTCAAAGGT
CTAACACCTTCAAAGGGACCAGCACAAGCTAGCGTCAATGGAGTCACATT
AATTGGAGAATCAGTAAAAACACAGTTTAACTACTTTAAGAAAGTAGACG
GCATTATTCAACAGTTGCCTGAAACCTACTTTACTCAGAGCAGAGACTTA
GAGGATTTTAAGCCCAGATCACAAATGGAAACTGACTTTCTCGAGCTCGC
TATGGATGAATTCATACAGCGATATAAGCTCGAGGGCTATGCCTTCGAAC
ACATCGTTTATGGAGATTTCAGTCATGGACAACTTGGCGGTCTTCATTTA
ATGATAGGCTTAGCCAAGCGCTCACAAGATTCACCACTTAAATTAGAGGA
TTTTATCCCTATGGACAGCACAGTGAAAAATTACTTCATAACAGATGCGC
AAACAGGTTCATCAAAATGTGTGTGTTCTGTGATTGATCTTTTACTTGAT
GACTTTGTCGAGATAATAAAGTCACAAGATTTGTCAGTGATTTCAAAAGT
GGTCAAGGTTACAATTGACTATGCTGAAATTTCATTCATGCTTTGGTGTA
AGGATGGACATGTTGAAACCTTCTACCCAAAACTACAAGCAAGTCAAGCG
TGGCAACCAGGTGTTGCGATGCCTAACTTGTACAAGATGCAAAGAATGCT
TCTTGAAAAGTGTGACCTTCAGAATTATGGTGAAAATGCTGTTATACCAA
AAGGAATAATGATGAATGTCGCAAAGTATACTCAACTGTGTCAATACTTA
AATACACTTACTTTAGCTGTACCCTACAACATGAGAGTTATTCACTTTGG
TGCTGGCTCTGATAAAGGAGTTGCACCAGGTACAGCTGTGCTCAGACAAT
GGTTGCCAACTGGCACACTACTTGTCGATTCAGATCTTAATGACTTCGTC
TCCGACGCAGATTCTACTTTAATTGGAGACTGTGCAACAGTACATACGGC
TAATAAATGGGACCTTATTATTAGCGATATGTATGACCCTAGGACCAAAC
ATGTGACAAAAGAGAATGACTCTAAAGAAGGGTTTTTCACTTATCTGTGT
GGATTTATAAAGCAAAAACTAGCCCTGGGTGGTTCTATAGCTGTAAAGAT
AACAGAGCATTCTTGGAATGCTGACCTTTACAAGCTTATGGGCCATTTCT
CATGGTGGACAGCTTTTGTTACAAATGTAAATGCATCATCATCGGAAGCA
TTTTTAATTGGGGCTAACTATCTTGGCAAGCCGAAGGAACAAATTGATGG
CTATACCATGCATGCTAACTACATTTTCTGGAGGAACACAAATCCTATCC
AGTTGTCTTCCTATTCACTCTTTGACATGAGCAAATTTCCTCTTAAATTA
AGAGGAACTGCTGTAATGTCTCTTAAGGAGAATCAAATCAATGATATGAT
TTATTCTCTTCTGGAAAAAGGTAGGCTTATCATTAGAGAAAACAACAGAG
TTGTGGTTTCAAGTGATATTCTTGTTAACAACTAAACGAACATGTTTATT
TTCTTATTATTTCTTACTCTCACTAGTGGTAGTGACCTTGACCGGTGCAC
CACTTTTGATGATGTTCAAGCTCCTAATTACACTCAACATACTTCATCTA
TGAGGGGGGTTTACTATCCTGATGAAATTTTTAGATCAGACACTCTTTAT
TTAACTCAGGATTTATTTCTTCCATTTTATTCTAATGTTACAGGGTTTCA
TACTATTAATCATACGTTTGGCAACCCTGTCATACCTTTTAAGGATGGTA
TTTATTTTGCTGCCACAGAGAAATCAAATGTTGTCCGTGGTTGGGTTTTT
GGTTCTACCATGAACAACAAGTCACAGTCGGTGATTATTATTAACAATTC
TACTAATGTTGTTATACGAGCATGTAACTTTGAATTGTGTGACAACCCTT
TCTTTGCTGTTTCTAAACCCATGGGTACACAGACACATACTATGATATTC
GATAATGCATTTAATTGCACTTTCGAGTACATATCTGATGCCTTTTCGCT
TGATGTTTCAGAAAAGTCAGGTAATTTTAAACACTTACGAGAGTTTGTGT
TTAAAAATAAAGATGGGTTTCTCTATGTTTATAAGGGCTATCAACCTATA
GATGTAGTTCGTGATCTACCTTCTGGTTTTAACACTTTGAAACCTATTTT
TAAGTTGCCTCTTGGTATTAACATTACAAATTTTAGAGCCATTCTTACAG
CCTTTTCACCTGCTCAAGACATTTGGGGCACGTCAGCTGCAGCCTATTTT
GTTGGCTATTTAAAGCCAACTACATTTATGCTCAAGTATGATGAAAATGG
TACAATCACAGATGCTGTTGATTGTTCTCAAAATCCACTTGCTGAACTCA
AATGCTCTGTTAAGAGCTTTGAGATTGACAAAGGAATTTACCAGACCTCT
AATTTCAGGGTTGTTCCCTCAGGAGATGTTGTGAGATTCCCTAATATTAC
AAACTTGTGTCCTTTTGGAGAGGTTTTTAATGCTACTAAATTCCCTTCTG
TCTATGCATGGGAGAGAAAAAAAATTTCTAATTGTGTTGCTGATTACTCT
GTGCTCTACAACTCAACATTTTTTTCAACCTTTAAGTGCTATGGCGTTTC
TGCCACTAAGTTGAATGATCTTTGCTTCTCCAATGTCTATGCAGATTCTT
TTGTAGTCAAGGGAGATGATGTAAGACAAATAGCGCCAGGACAAACTGGT
GTTATTGCTGATTATAATTATAAATTGCCAGATGATTTCATGGGTTGTGT
CCTTGCTTGGAATACTAGGAACATTGATGCTACTTCAACTGGTAATTATA
```

FIGURE 11H

```
ATTATAAATATAGGTATCTTAGACATGGCAAGCTTAGGCCCTTTGAGAGA
GACATATCTAATGTGCCTTTCTCCCCTGATGGCAAACCTTGCACCCCACC
TGCTCTTAATTGTTATTGGCCATTAAATGATTATGGTTTTTACACCACTA
CTGGCATTGGCTACCAACCTTACAGAGTTGTAGTACTTTCTTTTGAACTT
TTAAATGCACCGGCCACGGTTTGTGGACCAAAATTATCCACTGACCTTAT
TAAGAACCAGTGTGTCAATTTTAATTTTAATGGACTCACTGGTACTGGTG
TGTTAACTCCTTCTTCAAAGAGATTTCAACCATTTCAACAATTTGGCCGT
GATGTTTCTGATTTCACTGATTCCGTTCGAGATCCTAAAACATCTGAAAT
ATTAGACATTTCACCTTGCGCTTTTGGGGGTGTAAGTGTAATTACACCTG
GAACAAATGCTTCATCTGAAGTTGCTGTTCTATATCAAGATGTTAACTGC
ACTGATGTTTCTACAGCAATTCATGCAGATCAACTCACACCAGCTTGGCG
CATATATTCTACTGGAAACAATGTATTCCAGACTCAAGCAGGCTGTCTTA
TAGGAGCTGAGCATGTCGACACTTCTTATGAGTGCGACATTCCTATTGGA
GCTGGCATTTGTGCTAGTTACCATACAGTTTCTTTATTACGTAGTACTAG
CCAAAAATCTATTGTGGCTTATACTATGTCTTTAGGTGCTGATAGTTCAA
TTGCTTACTCTAATAACACCATTGCTATACCTACTAACTTTTCAATTAGC
ATTACTACAGAAGTAATGCCTGTTTCTATGGCTAAAACCTCCGTAGATTG
TAATATGTACATCTGCGGAGATTCTACTGAATGTGCTAATTTGCTTCTCC
AATATGGTAGCTTTTGCACACAACTAAATCGTGCACTCTCAGGTATTGCT
GCTGAACAGGATCGCAACACACGTGAAGTGTTCGCTCAAGTCAAACAAAT
GTACAAAACCCCAACTTTGAAATATTTTGGTGGTTTTAATTTTTCACAAA
TATTACCTGACCCTCTAAAGCCAACTAAGAGGTCTTTTATTGAGGACTTG
CTCTTTAATAAGGTGACACTCGCTGATGCTGGCTTCATGAAGCAATATGG
CGAATGCCTAGGTGATATTAATGCTAGAGATCTCATTTGTGCGCAGAAGT
TCAATGGACTTACAGTGTTGCCACCTCTGCTCACTGATGATATGATTGCT
GCCTACACTGCTGCTCTAGTTAGTGGTACTGCCACTGCTGGATGGACATT
TGGTGCTGGCGCTGCTCTTCAAATACCTTTTGCTATGCAAATGGCATATA
GGTTCAATGGCATTGGAGTTACCCAAAATGTTCTCTATGAGAACCAAAAA
CAAATCGCCAACCAATTTAACAAGGCGATTAGTCAAATTCAAGAATCACT
TACAACAACATCAACTGCATTGGGCAAGCTGCAAGACGTTGTTAACCAGA
ATGCTCAAGCATTAAACACACTTGTTAAACAACTTAGCTCTAATTTTGGT
GCAATTTCAAGTGTGCTAAATGATATCCTTTCGCGACTTGATAAAGTCGA
GGCGGAGGTACAAATTGACAGGTTAATTACAGGCAGACTTCAAAGCCTTC
AAACCTATGTAACACAACAACTAATCAGGGCTGCTGAAATCAGGGCTTCT
GCTAATCTTGCTGCTACTAAAATGTCTGAGTGTGTTCTTGGACAATCAAA
AAGAGTTGACTTTTGTGGAAAGGGCTACCACCTTATGTCCTTCCCACAAG
CAGCCCCGCATGGTGTTGTCTTCCTACATGTCACGTATGTGCCATCCCAG
GAGAGGAACTTCACCACAGCGCCAGCAATTTGTCATGAAGGCAAAGCATA
CTTCCCTCGTGAAGGTGTTTTTGTGTTTAATGGCACTTCTTGGTTTATTA
CACAGAGGAACTTCTTTTCTCCACAAATAATTACTACAGACAATACATTT
GTCTCAGGAAATTGTGATGTCGTTATTGGCATCATTAACAACACAGTTTA
TGATCCTCTGCAACCTGAGCTTGACTCATTCAAAGAAGAGCTGGACAAGT
ACTTCAAAAATCATACATCACCAGATGTTGATCTTGGCGACATTTCAGGC
ATTAACGCTTCTGTCGTCAACATTCAAAAAGAAATTGACCGCCTCAATGA
GGTCGCTAAAAATTTAAATGAATCACTCATTGACCTTCAAGAATTGGGAA
AATATGAGCAATATATTAAATGGCCTTGGTATGTTTGGCTCGGCTTCATT
GCTGGACTAATTGCCATCGTCATGGTTACAATCTTGCTTTGTTGCATGAC
TAGTTGTTGCAGTTGCCTCAAGGGTGCATGCTCTTGTGGTTCTTGCTGCA
AGTTTGATGAGGATGACTCTGAGCCAGTTCTCAAGGGTGTCAAATTACAT
TACACATAAACGAACTTATGGATTTGTTTATGAGATTTTTTACTCTTAGA
TCAATTACTGCACAGCCAGTAAAAATTGACAATGCTTCTCCTGCAAGTAC
TGTTCATGCTACAGCAACGATACCGCTACAAGCCTCACTCCCTTTCGGAT
GGCTTGTTATTGGCGTTGCATTTCTTGCTGTTTTTCAGAGCGCTACCAAA
ATAATTGCGCTCAATAAAAGATGGCAGCTAGCCCTTTATAAGGGCTTCCA
GTTCATTTGCAATTTACTGCTGCTATTTGTTACCATCTATTCACATCTTT
TGCTTGTCGCTGCAGGTATGGAGGCGCAATTTTTGTACCTCTATGCCTTG
ATATATTTTCTACAATGCATCAACGCATGTAGAATTATTATGAGATGTTG
```

FIGURE 11I

```
GCTTTGTTGGAAGTGCAAATCCAAGAACCCATTACTTTATGATGCCAACT
ACTTTGTTTGCTGGCACACACATAACTATGACTACTGTATACCATATAAC
AGTGTCACAGATACAATTGTCGTTACTGAAGGTGACGGCATTTCAACACC
AAAACTCAAAGAAGACTACCAAATTGGTGGTTATTCTGAGGATAGGCACT
CAGGTGTTAAAGACTATGTCGTTGTACATGGCTATTTCACCGAAGTTTAC
TACCAGCTTGAGTCTACACAAATTACTACAGACACTGGTATTGAAAATGC
TACATTCTTCATCTTTAACAAGCTTGTTAAAGACCCACCGAATGTGCAAA
TACACACAATCGACGGCTCTTCAGGAGTTGCTAATCCAGCAATGGATCCA
ATTTATGATGAGCCGACGACGACTACTAGCGTGCCTTTGTAAGCACAAGA
AAGTGAGTACGAACTTATGTACTCATTCGTTTCGGAAGAAACAGGTACGT
TAATAGTTAATAGCGTACTTCTTTTTCTTGCTTTCGTGGTATTCTTGCTA
GTCACACTAGCCATCCTTACTGCGCTTCGATTGTGTGCGTACTGCTGCAA
TATTGTTAACGTGAGTTTAGTAAAACCAACGGTTTACGTCTACTCGCGTG
TTAAAAATCTGAACTCTTCTGAAGGAGTTCCTGATCTTCTGGTCTAAACG
AACTAACTATTATTATTATTCTGTTTGGAACTTTAACATTGCTTATCATG
GCAGACAACGGTACTATTACCGTTGAGGAGCTTAAACAACTCCTGGAACA
ATGGAACCTAGTAATAGGTTTCCTATTCCTAGCCTGGATTATGTTACTAC
AATTTGCCTATTCTAATCGGAACAGGTTTTTGTACATAATAAAGCTTGTT
TTCCTCTGGCTCTTGTGGCCAGTAACACTTGCTTGTTTTGTGCTTGCTGC
TGTCTACAGAATTAATTGGGTGACTGGCGGGATTGCGATTGCAATGGCTT
GTATTGTAGGCTTGATGTGGCTTAGCTACTTCGTTGCTTCCTTCAGGCTG
TTTGCTCGTACCCGCTCAATGTGGTCATTCAACCCAGAAACAAACATTCT
TCTCAATGTGCCTCTCCGGGGACAATTGTGACCAGACCGCTCATGGAAA
GTGAACTTGTCATTGGTGCTGTGATCATTCGTGGTCACTTGCGAATGGCC
GGACACTCCCTAGGGCGCTGTGACATTAAGGACCTGCCAAAAGAGATCAC
TGTGGCTACATCACGAACGCTTTCTTATTACAAATTAGGAGCGTCGCAGC
GTGTAGGCACTGATTCAGGTTTTGCTGCATACAACCGCTACCGTATTGGA
AACTATAAATTAAATACAGACCACGCCGGTAGCAACGACAATATTGCTTT
GCTAGTACAGTAAGTGACAACAGATGTTTCATCTTGTTGACTTCCAGGTT
ACAATAGCAGAGATATTGATTATCATTATGAGGACTTTCAGGATTGCTAT
TTGGAATCTTGACGTTATAATAAGTTCAATAGTGAGACAATTATTTAAGC
CTCTAACTAAGAAGAATTATTCGGAGTTAGATGATGAAGAACCTATGGAG
TTAGATTATCCATAAAACGAACATGAAAATTATTCTCTTCCTGACATTGA
TTGTATTTACATCTTGCGAGCTATATCACTATCAGGAGTGTGTTAGAGGT
ACGACTGTACTACTAAAAGAACCTTGCCCATCAGGAACATACGAGGGCAA
TTCACCATTTCACCCTCTTGCTGACAATAAATTTGCACTAACTTGCACTA
GCACACACTTTGCTTTTGCTTGTGCTGACGGTACTCGACATACCTATCAG
CTGCGTGCAAGATCAGTTTCACCAAAACTTTTCATCAGACAAGAGGAGGT
TCAACAAGAGCTCTACTCGCCACTTTTTCTCATTGTTGCTGCTCTAGTAT
TTTTAATACTTTGCTTCACCATTAAGAGAAAGACAGAATGAATGAGCTCA
CTTTAATTGACTTCTATTTGTGCTTTTTAGCCTTTCTGCTATTCCTTGTT
TTAATAATGCTTATTATATTTTGGTTTTCACTCGAAATCCAGGATCTAGA
AGAACCTTGTACCAAAGTCTAAACGAACATGAAACTTCTCATTGTTTTGA
CTTGTATTTCTCTATGCAGTTGCATATGCACTGTAGTACAGCGCTGTGCA
TCTAATAAACCTCATGTGCTTGAAGATCCTTGTAAGGTACAACACTAGGG
GTAATACTTATAGCACTGCTTGGCTTTGTGCTCTAGGAAAGGTTTTACCT
TTTCATAGATGGCACACTATGGTTCAAACATGCACACCTAATGTTACTAT
CAACTGTCAAGATCCAGCTGGTGGTGCGCTTATAGCTAGGTGTTGGTACC
TTCATGAAGGTCACCAAACTGCTGCATTTAGAGACGTACTTGTTGTTTTA
AATAAACGAACAAATTAAAATGTCTGATAATGGACCCCAATCAAACCAAC
GTAGTGCCCCCCGCATTACATTTGGTGGACCCACAGATTCAACTGACAAT
AACCAGAATGGAGGACGCAATGGGGCAAGGCCAAAACAGCGCCGACCCCA
AGGTTTACCCAATAATACTGCGTCTTGGTTCACAGCTCTCACTCAGCATG
GCAAGGAGGAACTTAGATTCCCTCGAGGCCAGGGCGTTCCAATCAACACC
AATAGTGGTCCAGATGACCAAATTGGCTACTACCGAAGAGCTACCCGACG
AGTTCGTGGTGGTGACGGCAAAATGAAAGAGCTCAGCCCCAGATGGTACT
TCTATTACCTAGGAACTGGCCCAGAAGCTTCACTTCCCTACGGCGCTAAC
```

FIGURE 11J

```
AAAGAAGGCATCGTATGGGTTGCAACTGAGGGAGCCTTGAATACACCCAA
AGACCACATTGGCACCCGCAATCCTAATAACAATGCTGCCACCGTGCTAC
AACTTCCTCAAGGAACAACATTGCCAAAAGGCTTCTACGCAGAGGGAAGC
AGAGGCGGCAGTCAAGCCTCTTCTCGCTCCTCATCACGTAGTCGCGGTAA
TTCAAGAAATTCAACTCCTGGCAGCAGTAGGGGAAATTCTCCTGCTCGAA
TGGCTAGCGGAGGTGGTGAAACTGCCCTCGCGCTATTGCTGCTAGACAGA
TTGAACCAGCTTGAGAGCAAAGTTTCTGGTAAAGGCCAACAACAACAAGG
CCAAACTGTCACTAAGAAATCTGCTGCTGAGGCATCTAAAAAGCCTCGCC
AAAAACGTACTGCCACAAAACAGTACAACGTCACTCAAGCATTTGGGAGA
CGTGGTCCAGAACAAACCCAAGGAAATTTCGGGGACCAAGACCTAATCAG
ACAAGGAACTGATTACAAACATTGGCCGCAAATTGCACAATTTGCTCCAA
GTGCCTCTGCATTCTTTGGAATGTCACGCATTGGCATGGAAGTCACACCT
TCGGGAACATGGCTGACTTATCATGGAGCCATTAAATTGGATGACAAAGA
TCCACAATTCAAAGACAACGTCATACTGCTGAACAAGCACATTGACGCAT
ACAAAACATTCCCACCAACAGAGCCTAAAAAGGACAAAAAGAAAAAGACT
GATGAAGCTCAGCCTTTGCCGCAGAGACAAAAGAAGCAGCCCACTGTGAC
TCTTCTTCCTGCGGCTGACATGGATGATTTCTCCAGACAACTTCAAAATT
CCATGAGTGGAGCTTCTGCTGATTCAACTCAGGCATAAACACTCATGATG
ACCACACAAGGCAGATGGGCTATGTAAACGTTTTCGCAATTCCGTTTACG
ATACATAGTCTACTCTTGTGCAGAATGAATTCTCGTAACTAAACAGCACA
AGTAGGTTTAGTTAACTTTAATCTCACATAGCAATCTTTAATCAATGTGT
AACATTAGGGAGGACTTGAAAGAGCCACCACATTTTCATCGAGGCCACGC
GGAGTACGATCGAGGGTACAGTGAATAATGCTAGGGAGAGCTGCCTATAT
GGAAGAGCCCTAATGTGTAAAATTAATTTTAGTAGTGCTATCCCCATGTG
ATTTTAATAGCTTCTTAGGAGAATGACAAAAAAAAAAAAAAAAAAAAAA A
```

GenBank Accession No. AY274119.3, SEQ ID NO: 15

FIGURE 11K

Membrane Glycoprotein

Figure 13B

```
229E    ------MRSLIYFWLLLPVLPTLSLPQDVTRCQSTT---------NFRRFFSKFNVQAPA
PEDV    
CCov    MIVLILCLLLFSYNSVICTSNNDCVQGNVTQLPGNE---------NIIKDFLFHTFKEEP
PRC     
FICV    --------MIFIILTLLSVAKSEDAPHGVTLPQFNTSHNNERFELNFYNFLQTWDIPPNT
BoCov   
OC43    -----------------------------------------------MFLILLISLPMA
PHEV    -----------------------------------------------MFLILLISLPMA
MHV     -----------------------------------------------MFFILLISLPSA
TOR2_S  -----------------------------------------------MLFVFILLLPSC
AIBV

229E    
PEDV    VVVLGGYLP----------------SMNSSSWYCGTGIETASGVHGIFLSYIDSGQGFE
CCov    SVVVGGYYPTE-------------VWYNCSRSATTTAYKDFSNIHAFYFDMEAMENSTG
PRC     
FICV    ETILGGYLPYCGAGVNCGWYNFSQSVGQNGKYAYINTQNLNIPNVHGVYFDVREHNNDGE
BoCov   FAVIGDLKCT-----------------------TVSINDVDTGAPSISTDIVDVTNGLG
OC43    LAVIGDLKCT-----------------------TVAINDVDTGVPSTSTDIVDVTNGLG
PHEV    FAVIGDLKCT-----------------------TSLINDVDTGVPSISSEVVDVTNGLG
MHV     LGYIGDFRCIQ----------------------TVNYNGNNASAPSISTEAVDVSKGRG
TOR2_S  --------------------------MFIFLLFLTLTSGSDLDRCTTFDDVQAPNYTQ
AIBV

229E    
PEDV    IG-----ISQEPFDPSGYQLYLHKATNGNTNATARLR--ICQFPDNKTLGPTVNDVTTG-
CCov    NARGKPLLVHVHGDPVSIIIYISAYRDDVQPRPLLKHGLLCITKNKIIDYNTFTSAQWS-
PRC     
FICV    WDDDRDKVGLLIAIHGNSKYSLLMVLQDAVEANQPHVAVKICHWKPGNISSYHAFSVNLGD
BoCov   TY-----YVLDRVYLNTTLLLLNGYYPTSGSTYRNMALKGTLLLSRLWFKPPPFLSDFING-
OC43    TY-----YVLDRVYLNTTLLLLNGYYPTSGSTYRNMALKGTLLLSRLWFKPPPFLSDFING-
PHEV    TF-----YVLDRVYLNTTLLLLNGYYPISGATFRNMALKGTRLLSTLWFKPPPFLSPFNDG-
MHV     TY-----YVLDRVYLNATLLLTGYYPVDGSNYRNLALTGTNTLSLTWFKPPPFLSEFNDG-
TOR2_S  HT-----SSMRGVYYPDEIFRSDTLYLTQDLFLPFYSNVTGFHTINHTFGNPVIPFKDG-
AIBV

229E    
PEDV    -RNCLFNKAIP---AYMRDGKDIVVGITWDNDRVT-VFADKIYHFYLKNDWSR-------
CCov    -AICLGDDRKIPFSVIPTDNGTKIFGLEWNDDYVTAYISDRSHHLNINNNWFNNVTILYS
PRC     
FICV    GGQCVFNQRFS---LDTVLTTNDFYGFQWTDTYVDIYLGGTITKVWVDNDWSIVEAS---
BoCov   ----IFAKVKN-----TKVIKKGVMYSEFPAITIGSTFVNTSYSVVVQPHTTN-------
OC43    ----IFAKVKN-----TKVIKHGVMYSEFPAITIGSTFVNTSYSVVVQPHTTN-------
PHEV    ----IFAKVKN-----SRFSKDGVIYSEFPAITIGSTFVNTSYSIVVEPHTSL-------
MHV     ----IFAKVQN-----LKTNTPTGATSYFPTIVIGSLFGNTSYTVVLEPYNN--------
TOR2_S  ---IYFAATEK-----SNVVRGWVFGSTMNNKSQSVIIINNSTNVVIRACNFELCDN---
AIBV    -----------------MLGKSLFLVTILCALCSANLFDPANYVYYYQSAFRP-------

229E    ----------MFVLLVAYALLHIAGCQTTNGLN--TSYSVCNG---CVGYSENVFAVES
PEDV    --VATRCYNRRSCAMQYVYTPTYYMLNVTSAGEDG-IYYEPCTAN--CTGYAANVFATDS
CCov    RSSSATWQKSAAYVYQGVSNFTYYKLNNTNGLKS----YELCEDYEYCTGYATNVFAPTV
PRC     --------MKKLFVVLVVMPLIYGDKFPTSVVSN-------CTD--QCASYVANVFTTQP
FICV    -ISYHWNRINYGYYMQFVNRTTYYAYNNTGGANYTQLQLSECHTD-YCAGYAKNVFVP-I
BoCov   -LDNKLQGLLEISVCQYTMCEYPHTICHPKL-GNKRVELWHWDTGVVSCLYKRNFTYDVN
OC43    -LDNKLQGLLEISVCQYTMCEYPNTICHPNL-GNRRVELWHWDTGVVSCLYKRNFTYDVN
PHEV    -INGNLQGLLQISVCQYTMCEYPHTICHPNL-GNQRIELWHYDTDVVSCLYRRNFTYDVN
MHV     --------IIMASVCTYTICQLPYTPCKPNTNGNRVIGFWHTDVKPPICLLKRNFTFNVN
TOR2_S  ---PFFAVSKPMGTQTHTMIFDNAFNCTFEYISDAFSLDVSEKSGNFKHLREFVFKNKDG
AIBV    ----SNGWHLQGGAYAVVNSSNYANNAGSASECT---VGVIKDVYNQSAASIAMTAPLQG
```

FIGURE 14A

```
229E     GGYIPSDFAFNN--WFLLTNTSSVVDGVVRSFQPLLLNCLWSVSGLRFTTGFVYFNGTGR
PEDV     NGHIPEGFSFNN--WPLLSNDSTLLHGKVVSNQPLLVNCLLAIPKIYGLGQFFSFNHTMD
CCov     GGYIPHGFSFNN--WFMRTNSSTFVSGRFVTNQPLLVNCLWPVPSFGVAAQQFCFEGAQF
PRC      GGFIPSDFSFNN--WFLLTNSSTLVSGKLVTKQPLLVNCLWPVPSFEEAASTFCFEGADF
FICV     DGKIPEDFSFSN--WFLLSDKSTLVQGRVLSSQPVFVQCLRPVPSWSNNTAVVHFKN-D
BoCov    ADYLYFHFYQEGGTFYAYFTDTGVVTKFLFNVYLGTVLSHYYVLPLTCS----SAMTLEY
OC43     ADYLYFHFYQEGGIFYAYFTDTGVVTKFLFNVYLGTVLSYYYVMPLTCN----SAMTLEY
PHEV     ADYLYFHFYQEGGTFYAYFTDTGFVTKFLFKLYLGTVLSHYYVMPLTCN----SALSLEY
MHV      APWLYFHFYQQGGTFYAYYADKPSATTFLFSVYIGDILTQYFVLPFICTPTAGSTLAPLY
TOR2_S   FLYVYKGYQPIDVVRDLPSGFNTLKPIFKLPLGINITNFRAILTAFSPAQDIWGTSAAAY
AIBV     MAWSKSQFCSAHCDFSEITVFVTHCYSSGSGSCPITGMIARGHIRISAMKNGSLFYNLTV
                                                   :

229E     GDCKGFSSDVLSDVIRYNLN-FEENLRRGT-----ILFKTSYGV-VVFYCTNNT------
PEDV     GVCNGAAVDRAPEALRFNINDTSVILAEGS-----IVLHTALGTNLSFVCSNSSD-----
CCov     SQCNGVSLNNTVDVIRFNLN-FTALVQSGMGATV-FSLNTTGGVILEISCYNDTVS---S
PRC      DQCNGAVLNNTVDVIRFNLN-FTTNVQSGKGATV-FSLNTTGGVTLEISCYNDTVS---D
FICV     AFCP----NVTADVLRFNLNFSDTDVYTDSTNDEQLFFTFEDNTTASIACYSSANVTDFQ
BoCov    WVTPLTSKQYLLAFNQDGVIFNAVDCKSDFMS---EIKCKTLSIAPSTGVYELNG-----
OC43     WVTPLTSKQYLLAFNQDGVIFNAVDCKSDFMS---EIKCKTLSIAPSTGVYELNG-----
PHEV     WVTPLTTRQFLLAFDQDGVLYHAVDCASDFMS---EIMCKTSSITPPTGVYELNG-----
MHV      WVTPLLKRQYLFNFNEKGVITSAVDCASSYIS---EIKCKTQSLLPSTGVYDLSG-----
TOR2_S   FVGYLKPTTFMLKYDENGTITDAVDCSQNPLA---ELKCSVKSFEIDKGIYQTSN-----
AIBV     SVSKYPNFKSFQCVNNFTSVYLNGDLVFTSNKTTDVTSAGVYFKAGGPVNYSIMK-----
                                  .

229E     -LVSGDAHIPFGTVLGNFYCFVNTTIGTETTSAFVGALPKTVREFVISRTGHFYINGYRY
PEDV     -PHLAIFAIPLGATEVPYYCFLKVDTYNSTVYKFLAVLPSTVREIVITKYGDVYVNGFGY
CCov     SSFYSYGEISFGVTDGPRYCFA---LYNGTALKYLGTLPPSVKEIAISKWGHFYINGYNF
PRC      SSFSSYGEIPFGVTNGPRYCYV---LYNGTALKYLGTLPPSVKEIAISKWGHFYINGYNF
FICV     PANNSVSHIPFGKT--AHFCFAN-FSHSIVSRQFLGILPPTVREFAFGRDGSIFVNGYKY
BoCov    -YTVQPIADVYRRIPNLPDCNIEAWLNDKSVPSPLNWERKTFSNCNFNMSSLMSFIQADS
OC43     -YTVQPIADVYRRIPNLPDCNIEAWLNDKSVPSPLNWERKTFSNCNFNMSSLMSFIQADS
PHEV     -YTVQPVATVYRRIPDLPNCDIEAWLNSKTVSSPLNWERKIFSNCNFNMGRLMSFIQADS
MHV      -YTVQPVGVVYRRVPNLPDCKIEEWLTAKSVPSPLNWERRTFQNCNFNLSSLLRYVQAES
TOR2_S   -FRVVPSGDVVRFPNITNLCPFGEVFNATKFPSVYAWERKKISNCVADYSVLYNSTFFST
AIBV     -EFKVLAYFVNGTAQDVILCDNSPKGLLACQYNTGNFSDGFYPFTNSTLVREKFIVYRES
                         *

229E     FTLGNVEAVNFNVTTAETTD----FFTVALASYADVLVNVSQTSIANIIYCNSVINRLRC
PEDV     LHLGLLDAVTIYFTGHGTDDDVSGFWTIASTNFVDALIEVQGTSIQRILYCDDPVSQLKC
CCov     FSTFPIDCISFNLTTGDSGA----FWTIAYTSYTDALVQVENTAITNVTYCNSYVNNIKC
PRC      FSTFPIDCISFNLTTGDSDV----FWTIAYTSYTEALVQVENTAITNVTYCNSYVNNIKC
FICV     FSLPAIRSVNFSISSVEEYG----FWTIAYTNYTDVMVDVNGTAITRLFYCDSPLNRIKC
BoCov    FTCNNIDAAKIYGMCFSSIT----IDKFAIPNGRKVDLQLGNLGYLQSFNYRIDTTATSC
OC43     FTCNNIDAAKIYGMCFSSIT----IDKFAIPNGRKVDLQLGNLGYLQSFNYRIDTTATSC
PHEV     FGCNNIDASRLYGMCFGSIT----IDKFAIPNSRKVDLQVGKSGYLQSFNYKIDTAVSSC
MHV      LSCNNIDASKVYGMCFGSVS----VDKFAIPRSRQIDLQIGNSGFLQTANYKIDTAATSC
TOR2_S   FKCYGVSATKLNDLCFSNVY----ADSFVVKGDDVRQIAPGQTGVIADYNYKLPDDFMGC
AIBV     SVNTTLALTNFTFTNVSNAQ----PNSGGVHTFHLYQTQTAQSGYYNFNLSFLSQFVYKA
                :      .                 ,         .

229E     DQLSFYVPDGFYSTSP--IQSVELPVSIVSLP--------VYHKHMFIVLYVDFKPQ---
PEDV     SQVAFDLDDGFYPISSRNLLSHEQPISFVTLP--------SFNDHSFVNITVSAA-----
CCov     SQLTANLQNGFYPVAS--SEVGLVNKSVVLLP--------SFYSHTSVNITIDLGMKR--
PRC      SQLTANLNNGFYPVSS--SEVGSVNKSVVLLP--------SFLTHTIVNITIGLGMKR--
FICV     QQLKHELPDGFYSASM--LVKKDLPKTFVTMP--------QFYHWMNVTLHVVLNDTEKK
BoCov    -QLYYNLPAANVSVSRFNPSTWNRRFGFTEQFVFKPQPVGVFTHHDVVYAQHCFKAPKNF
OC43     -QLYYNLPAANVSVSRFNPSIWNRRFGFTEQSVFKPQPAGVFTDHDVVYAQHCFKAPTNF
PHEV     -QLYYSLPAANVSVTHYNPSSWNRRYGFNNQS------FGSRGLHDAVYSQQCFNTPNTY
MHV      -QLYYSLPKNNVTINNYNPSSWNRRYGFKVND----------------------------
TOR2_S   -VLAWNTRNIDATSTG----NYNYKYRYLRHG----------------------------
AIBV     SDYMYGSYHPICAFRP---ETINSGLWFNSLS----------------------------
                  .
```

FIGURE 14B

```
229E      ---SGGGKCFNCYPAGVNITLANFNETKG---PLCVDTSHFT---------TKYVAVYAN
PEDV      ---FGGLSSANLVAS--DTTINGFSS-------PCVDTRQFTI--------TLFYNVTNS
CCov      ---SGYGQPIASTLS--NITLPMQDNNTD---VYCIRSNRFSVYFHSTCKSSLWDDVFNS
PRC       ---SGYGQPIASTLS--NITLPMQDNNTD---VYCVRSDQFSVYVHSTCKSALWDNVFKR
FICV      YDIILAKAPELAALADVHFEIAQANGSVTNVTSLCVQARQLA---------LFYKYTSL
BoCov     --CPCKLDGSLCVGNGPGIDAGYKNSGIG----TCPAGTNYLT----CHNAA----QCDC
OC43      --CPCKLDGSLCVGNGPGIDAGYKNSGIG----TCPAGTNYLT----CHNAV----QCNC
PHEV      --CPCRT--SQCIG---G-------AGTG----TCPVGTTVRK----CFAAVTKATKCTC
MHV       ------------------------------------------------------------
TOR2_S    ------------------------------------------------------------
AIBV      ------------------------------------------------------------

229E      ----VGRWSASINTGNCPFSFGKVNNFVKFGSVCFSLKDIPGG-CAMPIVANWAYSKYYT
PEDV      ----YGYVSKSQDS-NCPFTLQSVNDYLSFSKFCVSTSLLAGA-CTIDLFGYPAFGSGVK
CCov      DCTDVLYATAVIKTGTCPFSFDKLNNYLTFNKFCLSLNPVGAN-CKFDVAARTRTNEQVV
PRC       NCTDVLDATAVIKTGTCPFSFDKLNNYLTFNKFCLSLSPVGAN-CKFDVAARTRTNEQVV
FICV      QGLYTYSNLVELQNYDCPFSPQQFNNYLQFETLCFDVNPAVAG-CKWSLVHDVQWRTQFA
BoCov     LCTPDPITSKSTGPYKCPQTKYLVGIGEHCSGLAIKSDYCGGNPCTCQPQAFLGWSVDSC
OC43      LCTPDPITSKSTGPYKCPQTKYLVGIGEHCSGLAIKSDYCGGNPCTCQPQAFLGWSVDSC
PHEV      WCQPDPSTYKGVNAWTCPQSKVSIQPGQHCPGLGLVEDDCSGNPCTCKPQAFIGWSSETC
MHV       ------------------------------------------------------------
TOR2_S    --------KLR------PFERDISN--VPFSPDGKPCTPPALN-CYWPLNDYGFYTTTGI
AIBV      ----------VSLTYGPLQGGYKQSVFSGKATCCYAYSYNGPRACKGVVYSGELSRDFECG

229E      IG----TLYVSWSDGDGITGVPQ-PVEGVSSFMNVTLDKCTKYNIYDVSGVGVIRVSNDT
PEDV      LT----SLYFQFTKGELITGTPK-PLEGITDVSFMTLDVCTKYTIYGFKGEGIITLTNSS
CCov      R-----SLYVIYEEGDNIVGVPS-DNSGLHDLSVLHLDSCTDYNIYGITGVGIIRQTNST
PRC       R-----SLYVIYEEGDSIVGVPS-DNSGLHDLSVLHLDSCTDYNIYGRTGVGIIRQTNRT
FICV      T------ITVSYKHGSMITTHAKGHSWGFQDTSVLVKDECTDYNIYGFQGTGIIRNTTSR
BoCov     LQGDRCNIFANFIPHDVNSGTTC-STDLQKSNTDIILGVCVNYDLYGITGQGIFVEVNAT
OC43      LQGDRCNIFANFILHDVNSGTTC-STDLQKSNTDIILGVCVNYDLYGITGQGIFVEVNAT
PHEV      LQNGRCNIFANFILNDVNSGTTC-STDLQQGNTIITTDVCVNYDLYGITGQGILIEVNAT
MHV       ----RCQIFANILLNGINSGTTC-STDLQLPNTEVATGVCVRYDLYGITGQGVFKEVKAD
TOR2_S    G----YQPYRVVVLSFELLNAPA-TVCGPKLSTDLIKNQCVNFNFNGLTGTGVLTPSSKR
AIBV      L-----LVYVTKSDGSRIQTRTEPLVLTQHNYNNITLDKCVAYNIYGRVGQGFITNVTDS
                            .     *.:  :.  * *.:        .

229E      FLN--------GITYTSTSGNLLGFKDVTKGTIYSITPCNP---PDQLVVYQQAVVGAM
PEDV      ILA--------GVYYTSDSGQLLAFKNVTSGAVYSVTPCSF---SEQAAYVNDDIVGVI
CCov      LLS--------GLYYTSLSGDLLGFKNVSDGVIYSVTPCDV---SAHAAVIDGAIVGAM
PRC       LLS--------GLYYTSLSGDLLGFKNVSDGVIYSVTPCDV---SAQAAVIDGTIVGAI
FICV      LVA--------GLYYTSISGDLLAFKNSTTGEIFTVVPCDL---TAQVAVINDEIVGAI
BoCov     YYNS-------WQNLLYDSNGNLYGFRDYLTNRTFMIRSCYSG--RVSAAFHANSSEPAL
OC43      YYNS-------WQNLLYDSNGNLYGFRDYLTNRTFMIRSCYSG--RVSAAFHANSSEPAL
PHEV      YYNS-------WQNLLYDSSGNLYGFRDYLSNRTFLIRSCYSG--RVSAVFHANSSEPAL
MHV       YYNS-------WQALLYDVNGNLNGPRDLTTNKTYTIRSCYSG--RVSAAYHKEAPEPAL
TOR2_S    FQP--------FQQFGRDVSDFTDSVRDPKTSEILDISPCAFGGVSVITPGTNASSEVAV
AIBV      VANFSYLADGGLAILDTSGAIDVFVVQGSYGLNYYKVNPCEDVN--QQFVVSGGNIVGIL
                         .:.       :  .*               :

229E      LSENFTSY---------------GFSNVVELPKFFYASNGTYN--------------
PEDV      SSLSNST----------------FNNTRELPGFFYHSNDGSN---------------
CCov      TSINSELL---------------GLTHWTTTPNFYYYSIYNYTNERTRGTAID--SND
PRC       TSINSELL---------------GLTHWTITPNFYYYSIYNYTNDKTRGTPID--SND
FICV      TAVNQTDLFEFVNNTQARRSRSSTPNFVTSYTMPQFYYITKWNNDTS-S--------
BoCov     LFRNIKCN---------------YVFNNTLSRQLQPINYFDSYLGCVVNADN------STS
OC43      LFRNIKCN---------------YVFNNTLSRQLQPINYFDSYLGCVVNADN------STA
PHEV      MFRNLKCS---------------HVFNNTILRQIQLVNYFDSYLGCVVNAYN------NTA
MHV       LYRNINCS---------------YVFTNNISREENPLNYFDSYLGCVVNADN------RTD
TOR2_S    LYQDVNCT---------------DVSTAIHADQLTPAWRIYSTGNNVFQTQAGCLIGAEHV
AIBV      TSRNETGS---------------E-QVENQFYVKLTNSSHRRRRS--------IG

229E      -CTDAVLTYSSFGVCADGSIIAVQ-----PRNVSYDSVSAIVTANLS----------
PEDV      -CTEPVLVYSNIGVCKSGSIGYV------PSQYGQVKIAPTVTGNIS----------
CCov      VDCEPIITYSNIGVCKNGALVFI------NVTHSDGDVQPISTGNVT----------
PRC       VGCEPVITYSNIGVCKNGALVFI------NVTHSDGDVQPISTGNVT----------
FICV      -NCTSAITYSSFAICNTGEIKYVNVTHVEIVDDSIGVIKPVSTGNIS----------
BoCov     SVVQTCDLTVGSGYCVDYSTKRRSR-RAITTGYRFTNFEPPFTVNSVNDSLEPVGGLYEIQ
```

FIGURE 14C

```
OC43      SAVQTCDLTVGSGYCVDYSTKRRSR-RAITTGYRPTNFEPFTVNSVNDSLEHVGGLYEIQ
PHEV      SAVSTCDLTVGSGYCVDYVTALRSR-RSFTTGYRFTNFEPFAANLVNDSIEPVGGLYEIQ
MHV       EALPNCNLRMGAGLCVDYSKSRRAR-RSVSTGYRLTTFEPYMPMLVNDSVQSVGGLYEMQ
TOR2_S    DTSYECDIPIGAGICASYHTVSLLRSTSQKSIVAYTMSLGADSSIAYSNN------TIA
AIBV      QNVTSCPYVSYGRFCIEPDGSLKMI----VPEELKQFVAPLLNITES----------VL
                                *

229E      IPSNWTISVQVEYLQITSTPIVVDCSTYVCNGNVRCVELLKQYTSACKTIEDALRNSARL
PEDV      IPTNFSMSIRTEYLQLYNTPVSVDCATYVCNGNSRCKQLLTQYTAACKTIESALQLSARL
CCov      IPTNFTISVQVEYIQVYTTPVSIDCSRYVCNGNPRCNKLLTQYVSACQTIEQALAMGARL
PRC       IPTNFTISVQVEYIQVYTTPVSIDCSRYVCNGNPRCNKLLTQYVSACQTIEQALAMGARL
FICV      IPKNFTVAVQAEYIQIQVKPVVVDCATYVCNGNTHCLKLLTQYTSACQTIENALNLGARL
BoCov     IPSEFTIGNMEEFIQTSSPKVTIDCSAFVCGDYAACKSQLVEYGSFCDNINAILTEVNEL
OC43      IPSEFTIGNMEEFIQTSSPKVTIDCSAFVCGDCAACKSQLVEYGSFCDNINAILTEVNEL
PHEV      IPSEFTIGNLEEFIQTRSPKVTIDCATFVCGDYAACRQQLAEYGSFCENINAILTEVNEL
MHV       IPTNFTIGHHEEFIQIRAPKVTIDCAAFVCGDNAACRQQLVEYGSFCDNVNAILNEVNNL
TOR2_S    IPTNFSISITTEVMPVSMAKTSVDCNMYICGDSTECANLLLQYGSFCTQLNRALSGIAAE
AIBV      IPNSFNLTVTDEYIQTRMDKVQINCLQYVCGNSLECRKLFQQYGPVCDNILSVVNSVSQK
          **..:.:     *  :        ::*  ::*..   *.  : :*  . *   :   :

229E      ESADVSEMLTFDKKAFTLANVSSF-GD-------YNLSSVIPS--------LPTSGSR--
PEDV      ESVEVNSMLTISEEALQLATISSFNGDG------YNFTNVLGASVY-----DPASGRV--
CCov      ENMEIDSMLFVSENALKLASVEAFNSTETLDPIYKEWPNIGGSWLGGLKDILPSHNSK--
PRC       ENMEVDSMLFVSENALKLASVEAFNSSETLDPIYTQWPNIGGFWLEGLKYILPSDNSK--
FICV      ESLMLNDMITVSDRGLELATVERFNATA------LGGEKLGGLYFDG---LSSLLPPK--
BoCov     LDTTQLQVANSLMNGVTLSTKLKDGVN-------FNVDDINFSPVLG---CLGSACNK--
OC43      LDTTQLQVANSLMNGVTLSTKLKDGVN-------FNVDDVNFSPVLG---CLGSECNK--
PHEV      LDTTQLQVANSLMNGVTLSTKIKDGIN-------FNVDDINFSPVLG---CLGSECNR--
MHV       LDNMQLQVASALMQGVTISSRLPDGIS-------GPIDDINFSPLLG---CIGSTCAEDG
TOR2_S    QDRNTREVFAQVKQMYKTPTLKYFGGF--------NFSQILPDPLKP-------------
AIBV      EDMELLSFYSSTKPKGYDTPVLSNVSTG-----EFNISLLLTPPSSP-------------
                .   ..                  .                :

229E      -----VAGRSAIEDILFSKIVTSGLGTVDADYKNCTKGLS--IADLACAQYYNGIMVLPG
PEDV      -----VQKRSVIEDLLFNKVVTNGLGTVDEDYKRCSNGRS--VADLVCAQYYSGVMVLPG
CCov      -----RKYRSAIEDLLFDKVVTSGLGTVDEDYKRCTGGYD--IADLVCAQYYNGIMVLPG
PRC       -----RKYRSAIEDLLFSKVVTSGLGTVDEDYKRCTGGYD--IADLVCAQYYNGIMVLPG
FICV      -----IGKRSAVEDLLFNKVVTSGLGTVDDDYKKCSSGTD--VADLVCAQYYNGIMVLPG
BoCov     -----VSSRSAIEDLLFSKVKLSDVG-FVEAYNNCTGGAE--IRDLICVQSYNGIKVLPP
OC43      -----VSSRSAIEDLLFSKVRLSDVG-FVEAYNNCTGGAG--IRDLICVQSYNGIKVLPP
PHEV      -----ASTRSAIEDLLFDKVKLSDVG-FVQAYNNCTGGAE--IRDLICVQSYNGIKVLPP
MHV       NGPSAIRGRSAIEDLLFDKVKLSDVG-FVEAYNNCTGGQE--VRDLLCVQSFNGIKVLPP
TOR2_S    ------TKRSFIEDLLFNKVTLADAG-FMKQYGECLGDIN--ARDLICAQKFNGLTVLPP
AIBV      ------SGRSPVEDLLFTSVETVGLP-TDAEYKKCTAGPLGTLKDLICAREYNGLLVLPP
                ** :**:**  .:          *  *             ** *.: :.*; ***

229E      VADAERMAMYTGSLIGGIALGGLT----SAVSIPFSLAIQARLNYVALQTDVLQENQKIL
PEDV      VVDAEKLHMYSASLIGGMALGGIT----AAAALPFSYAVQARLNYLALQTDVLQRNQQLL
CCov      VANDDKMAMYTASLAGGITLGSLGG---GAVSIPFAIAVQARLNYVALQTDVLNKNQQIL
PRC       VANADKMTMYTASLAGGITLGAFGG---GAVSIPFAVAVQARLNYVALQTDVLNKNQQIL
FICV      VVDGNKMSMYTASLIGGMALGSIT----SAVAVPFAMQVQARLNYVALQTDVLQENQKIL
BoCov     LLSVNQISGYTLAATSASLFPPLS----AAVGVPFYLNVQYRINGIGVTMDVLSQNQKLI
OC43      LLSDNQISGYTLAATSANLFPPWS----AAAGVPFYLNVQYRINGIGVTMDVLSQNQKLI
PHEV      LLSENQISGYTLAATAASLFPPWT----AAAGVPFYLNVQYRINGLGVTMDVLSQNQKLI
MHV       VLSESQISGYTAGATAAAMFPPWT----AAAGVPFSLNVQYRINGLGVTMNVLSENQKMI
TOR2_S    LLTDDMIAAYTAALVSGTATAGWTFGAGAALQIPFAMQMAYRFNGIGVTQNVLYENQKQI
AIBV      IITADMQTMYTASLVGAMAFGGIT----SAAAIPFATQIQARINHLGIAQSLMKNQEKI
          :    .    *:. ..            .*  :**      :  *:* :.:  ..:* .**: :

229E      AASFNKAMTNIVDAFTGVNDAITQTSQALQTVATALNKIQDVVNQQGNSLNHLTSQLRQN
PEDV      AESFNSAIGNITSAFESVKEAISQTSKGLNTVAHALTKVQEVVNSQGSALNQLTVQLQHN
CCov      ANAFNQAIGNITQAFGKVNDAIHQTSQGLATVAKVLAKVQDVVNTQGQALSHLTLQLQNN
PRC       ASAFNQAIGNITQSFGKVNDAIHQTSRGLTTVAKALAKVQDVVNTQGQALRHLTVQLQNN
FICV      ANAFNNAIGNITLALGKVSNAITTTSDGFNSMASALTKIQSVVNQQGEALSQLTSQLQKN
BoCov     ANAFNNALDAIQEGFDATN-----------S-ALVKIQAVVNANAEALNNLLQQLSNR
OC43      ANAFNNALDAIQEGFDATN-----------S-ALVKIQAVVNADAEALNNLLQQLSNR
PHEV      ASAFNNALDAIQEGFDATN-----------S-ALVKIQAVVNANAEALNNLLQQLSNR
MHV       ASAFNNALGAIQEGFDATN-----------S-ALGKIQSVVNANAEALNNLLNQLSNR
TOR2_S    ANQFNKAISQIQESLTTTS-----------TALGKLQDVVNQNAQALNTLVKQLSSN
AIBV      AASFNKAIGHMQEGFRSTS-----------LALQQVQDVVNKQSAILTETMNSLNKN
          *  **.*:   :  .:  ..          .* ::*  *** :.  *    .* .
```

FIGURE 14D

```
229E     FQAISSSIQAIYDRLDTIQADQQVDRLITGRLAALNVFVSHTLTKYTEVRASRQLAQQKV
PEDV     FQAISSSIDDIYSRLDILLADVQVDRLITGRLSALNAFVAQTLTKYTEVQASRKLAQQKV
CCov     FQAISSSISDIYNRLDELSADAQVDRLITGRLTALNAFVSQTLTRQAEVRASRQLAKDKV
PRC      FQAISSSISDIYNRLDELSADAQVDRLITGRLTALNAFVSQTLTRQAEVRASRQLAKDKV
FICV     FQAISSSIAEIYNRLEKVEADAQVDRLITGRLAALNAYVSQTLTQYAEVKASRQIALEKV
BoCov    FGAISSSLQEILSRLDALEAQAQIDRLINGRLTALNVYVSQQLSDSTLVKFSAAQAMEKV
OC43     FGAISSSLQEILSRLDALEAQAQIDRLINGRLTALDAYVSQQLSDSTLVKFSAAQAMEKV
PHEV     FGAISASLQEILSRLDALEAKAQIDRLINGRLTALNAYVSQQLSDSTLVKFSAAQAIEKV
MHV      FGAISASLQEILTRLDAVEAKAQIDRLINGRLTALNAYISKQLSDSTLIKFSAAQAIEKV
TOR2_S   FGAISSVLNDILSRLDKVEAEVQIDRLITGRLQSLQTYVTQQLIRAAEIRASANLAATKM
AIBV   >        FGAISSVIQDIYAQLDAIQADAQVDRLITGRLSSLSVLASAKQSEYIRVSQQRELATQKI
          * *** : * :*: : *. *:****.*** :*..  :     :  .  *  *:

229E     NECVKSQSKRYGFCG-NGTHIFSIVNAAPEGLVFLHTVLLPTQYKDVEAWSGLCV-DG--
PEDV     NECVKSQSQRYGFCGGDEHIFSLVQAAPQGLLFLHTVLVPGDFVNVLAIAGLCV-NG--
CCov     NECVRSQSQRFGFCG-NGTHLFSLANAAPNGMIFFHTVLLPTAYETVTAWSGICASDGDR
PRC      NECVRSQSQRFGFCG-NGTHLFSLANAAPNGMIFFHTVLLPTAYETVTAWSGICALDGDR
FICV     NECVKSQSNRYGFCG-NGTHLFSLVNSAPEGLLFFHTVLLPTEWEEVTAWSGICVNDT--
BoCov    NECVKSQSSRINFCG-NGNHIISLVQNAPYGLYFIHFSYVPTKYVTAKVSPGLCI-----
OC43     NECVKSQSSRINFCG-NGNHIISLVQNAPYGLYPIHFSYVPTKYVTAKVSPGLCI-----
PHEV     NECVKSQSSRINFCG-NGNHIISLVQNAPYGLYFIHFSYVPTKYVTAKVSPGLCI-----
MHV      NECVKSQTTRINFCG-NGNHILSLVQNAPYGLCFIHFSYVPTSFKTANVSPGLCI-----
TOR2_S   SECVLGQSKRVDFCG-KGYHLMSFPQAAPHGVVFLHVTYVPSQERNFTTAPAICH-----
AIBV   >        NECVKSQSNRYGFCG-SGRHVLSIPQNAPNGIVFIHFTYTPETFVNVTAIVGFCVNPLNA
          .*** .*: * .*** .* *::*: : ** *; *;*     *      .  ..:*

229E     TNGYVLRQPNLALYK------EGNYYRITSRIMFEPRIPTMADFVQIENCNVTFVNISRS
PEDV     EIALTLREPGLVLFTHELQTYTATEYFVSSRRMFEPRKPTVSDFVQIESCVVTYVNLTSD
CCov     TFGLVVKDVQLTLFRN-----LDDKFYLTPRTMYQPIVATSSDFVQIEGCDVLFVNATVI
PRC      TFGLVVKDVQLTLFRN-----LDDKFYLTPRTMYQPIVATSSDFVQIEGCDVLFVNTTVS
FICV     -YAYVLKDFDHSIFS------YNGTYMVTPRNMFQPRKPQMSDFVQITSCEVTFLNMTYT
BoCov    -AGDRGIAPKSGYFVN-----VNNTWMFTGSGYYYPEPITGNNVVVMSTCAVNYTKAPDV
OC43     -AGDRGIAPKSGYFVN-----VNNTWMFTGSRYYYPEPITGNNVVVMSTCAVNYTKAPDV
PHEV     -AGDIGISPKSGYFIN-----VNNSWMFTGSSYYYPEPITQNNVVVMSTCAVNYTKAPDL
MHV      -SGDRGLAPKAGYFVQ-----DNGEWKFTGSNYYYPEPITDKNSVAMISCAVNYTKAPEV
TOR2_S   -EGKAYFPREGVFVFN------GTSWFITQRNFFSPQIITTDNTFVSGNCDVVIGIINNT
AIBV   >        SQYAIVPANGRGIFIQ-----VNGTYYITSRDMYMPRDITAGDIVTLTSCQANYVNVNKT
                  : .:      :    *    :.      *  :

229E     ELQTIVP-EYIDVNKTLQELSYKL-PNYTVPDLV---VEQYNQTILNLTSEISTLENKSA
PEDV     QLPDVIP-DYIDVNKTLDEILASL-PNRTGPSLP---LDVFNATYLNLTGEIADLEQRSE
CCov     DLPSIIP-DYIDINQTVQDILENFRPNWTVPELP---LDIFNATYLNLTGEINDLEFRSE
PRC      DLPSIIP-DYIDINQTVQDILENFRPNWTVPELT---LDVFNATYLNLTGEIDDLEFRSE
FICV     TFQEIVI-DYIDINKTIADMLEQYNPNYTTPELNL-LLDIFNQTKLNLTAEIDQLEQRAD
BoCov    MLNISTP-NLHDFKEELDQWFKNQ--TSVAPDLSL-DY--INVTFLDLQDEMN-------
OC43     MLNISTP-NLPDFKEELDQWFKNQ--TLVAPDLSL-DY--INVTFLDLQDEMN-------
PHEV     MLNTSTP-NLPDFKEELYQWFKNQ--SSVAPDLSL-DY--INVTFLDLQDEMN-------
MHV      FLNNSIP-NLPDFKEELDKWFKNQ--TSIAPDLSL-DFEKLNVTFLDLTYEMN-------
TOR2_S   VYDPLQP-ELDSFKEELDKYFKNH----TSPDVDLGDISGINASVVNIQKEID-------
AIBV   >        VITTFVEDDDFNFDDELSKWWNDT--KGHLPDFD---DFNYTVPILNISGEID-------
          :   ....:. .      *..        ..:::  *:

229E     ELNYTVQKLQTLIDNINSTLVDLKWLNRVETYIKWPWWVWLCISVVLIFVVSMLLLCCCS
PEDV     SLRNTTEELRSLINNINNTLVDLEWLNRVETYIKWPWWVWLIIVIVLIFVVSLLVFCCIS
CCov     KLHNTTVELAILIDNINNTLVNLEWLNRIETYVKWPWYVWLLIGLVVIFCIPLLLFCCCS
PRC      KLHNTTVELAILIDNINNTLVNLEWLNRIETYVKWPWYVWLLIGLVVIFCIPLLLFCCCS
FICV     NLTTIAHELQQYIDNLNKTLVDLDWLNRIETYVKWPWYVWLLIGLVVVFCIPLLLFCCLS
BoCov    -------RLQEAIKVLNQSYINLKDIGTYEYYVKWPWYVWLLIGFAGVAMLVLLFFICCC
OC43     -------RLQEAIKVLNQSYINLKDIGTYEYYVKWPWYVWLLIGFAGVAMLVLLFFICCC
PHEV     -------RLQEAIKVLNQSYINLKDIGTYEYYVKWPWYVWLLIGLAGVAMLVLLFFICCC
MHV      -------RIQDAIKKLNESYINLKEVGTYEMYVKWPWYVWLLIGLAGVAVCVLLFFICCC
TOR2_S   -------RLNEVAKNLNESLIDLQELGKYEQYIKWPWYVWLGFIAGLIAIVMVTILLCCM
AIBV   >        -------NIQGVIQGLNDSLINLEELSIIKTYIKWPWYVWLAIGFAIIIFILILGWVFFM
                 .:      . :*.: ::*. :.  :  *:****:***  :      :    :
```

FIGURE 14E

```
229E       TGCCG-FFSCFASSIRGCCESTKL-PYYDVEKIHIQ---------
PEDV       TGCCG-CCGCCGACPSGCCRGPRLQPYEAFEKVHVQ---------
CCoV       TGCCG-CIGCLGSCCHSICSRRQFESYEPIEKVHVH---------
PRC        TGCCG-CIGCLGSCCHSIFSRRQFENYEPIEKVHVH---------
FICV       TGFCG-CFGCVGSCCHSLCSRRQFETYEPIEKVHIH---------
BoCoV      TGCGTSCFKICGGCCD-DYTGHQELVIK---TSHDD---------
OC43       TGCGTSCFKKCGGCCD-DYTGHQELVIK---TSHEG---------
PHEV       TGCGTSCFKKCGGCCD-DYTGHQEFVIK---TSHDD---------
MHV        TGCGSCCFRKCGSCCD-EYGGHQDSIVIHNISAHED---------
TOR2_S     TSCCSCLKGACSCGSCCKFDEDDSEPVLKGVKLHYT---------
AIBV   >       TGCCGCCCGCFGIIPLISKCGKKSSYYTTFDNDVVTEQYRPKKSV
               * .                .
```

| Key | Name | Genbank | % ID* | |
|---|---|---|---|---|
| 229E | spike glycoprotein [Human coronavirus 229E]. | AAK32191 | 28.6% | (SEQ ID NO: 53) |
| AIBV | spike glycoprotein [Avian infectious bronchitis virus]. | AAO34396 | 27.6% | (SEQ ID NO: 54) |
| BoCoV | E2 glycoprotein precursor (Spike glycoprotein) | P25193 | 30.5% | (SEQ ID NO: 55) |
| CCoV | spike protein - canine coronavirus | S41453 | 26.1% | (SEQ ID NO: 56) |
| FICV | peplomer protein [Feline infectious peritonitis virus]. | BAA06805 | 25.4% | (SEQ ID NO: 57) |
| MHV | E2 glycoprotein precursor (Spike glycoprotein) | P11225 | 31.9% | (SEQ ID NO: 58) |
| OC43 | surface protein - human coronavirus | S44241 | 30.7% | (SEQ ID NO: 59) |
| PEDV | spike protein [Porcine epidemic diarrhea virus]. | CAA80971 | 26.0% | (SEQ ID NO: 60) |
| PHEV | spike glycoprotein [porcine hemagglutinating encephalomyelitis virus] | AAL80031 | 30.5% | (SEQ ID NO: 61) |
| PRC | S protein [Porcine respiratory coronavirus]. | AAA46905 | 27.5% | (SEQ ID NO: 62) |
| TOR2_S | Sars associated virus S glycoprotein (SEQ ID NO: 33) | | | |

FIGURE 14F

```
         10        20        30        40        50
TOR2_E   MYSFVSEETGTLIVNSVLLFLAFVVFLLVTLAILTALRLCAYCCNIVNVSLVKPTV
         :  ...:  ...:  .. ::  ....:...:.: ..::  :::.  . .. :.
PGV      MTFPRALTVIDDNG-MVINIIFWFLLIIILILLSIALLNIIKLCMVCCNLGRTVIIVPAQ
            10        20        30        40        50

60        70
TOR2_E   YVYSRVKNLNSSEGVPDLLV      (SEQ ID NO: 35)
         ..:.   ::..
PGV      HAYDAYKNFMRIKAYNPDGALLA   (SEQ ID NO: 63)
            60        70        80
```

FIGURE 15

```
MESLVLGVNEKTHVQLSLPVLQVRDVLVRGFGDSVEEALSEAREHLKNGT
CGLVELEKGVLPQLEQPYVFIKRSDALSTNHGHKVVELVAEMDGIQYGRS
GITLGVLVPHVGETPIAYRNVLLRKNGNKGAGGHSYGIDLKSYDLGDELG
TDPIEDYEQNWNTKHGSGALRELTRELNGGAVTRYVDNNFCGPDGYPLDC
IKDFLARAGKSMCTLSEQLDYIESKRGVYCCRDHEHEIAWFTERSDKSYE
HQTPFEIKSAKKFDTFKGECPKFVFPLNSKVKVIQPRVEKKKTEGFMGRI
RSVYPVASPQECNNMHLSTLMKCNHCDEVSWQTCDFLKATCEHCGTENLV
IEGPTTCGYLPTNAVVKMPCPACQDPEIGPEHSVADYHNHSNIETRLRKG
GRTRCFGGCVFAYVGCYNKRAYWVPRASADIGSGHTGITGDNVETLNEDL
LEILSRERVNINIVGDFHLNEEVAIILASFSASTSAFIDTIKSLDYKSFK
TIVESCGNYKVTKGKPVKGAWNIGQQRSVLTPLCGFPSQAAGVIRSIFAR
TLDAANHSIPDLQRAAVTILDGISEQSLRLVDAMVYTSDLLTNSVIIMAY
VTGGLVQQTSQWLSNLLGTTVEKLRPIFEWIEAKLSAGVEPLKDAWEILK
FLITGVFDIVKGQIQVASDNIKDCVKCFIDVVNKALEMCIDQVTIAGAKL
RSLNLGEVFIAQSKGLYRQCIRGKEQLQLLMPLKAPKEVTFLEGDSHDTV
LTSEEVVLKNGELEALETPVDSFTNGAIVGTPVCVNGLMLLEIKDKEQYC
ALSPGLLATNNVFRLKGGAPIKGVTFGEDTVWEVQGYKNVRITFELDERV
DKVLNEKCSVYTVESGTEVTEFACVVAEAVVKTLQPVSDLLTNMGIDLDE
WSVATFYLFDDAGEENFSSRMYCSFYPPDEEEEDDAECEEEEIDETCEHE
YGTEDDYQGLPLEFGASAETVRVEEEBEEDWLDDTTEQSEIEPEPEPTPE
EPVNQFTGYLKLTDNVAIKCVDIVKEAQSANPMVIVNAANIHLKHGGGVA
GALNKATNGAMQKESDDYIKLNGPLTVGGSCLLSGHNLAKKCLHVVGPNL
NAGEDIQLLKAAYENFNSQDILLAPLLSAGIFGAKPLQSLQVCVQTVRTQ
VYIAVNDKALYEQVVMDYLDNLKPRVEAPKQEEPPNTEDSKTEEKSVVQK
PVDVKPKIKACIDEVTTTLEETKFLTNKLLLFADINGKLYHDSQNMLRGE
DMSFLEKDAPYMVGDVITSGDITCVVIPSKKAGGTTEMLSRALKKVPVDE
YITTYPGQGCAGYTLEEAKTALKKCKSAFYVLPSEAPNAKEEILGTVSWN
LREMLAHAEETRKLMPICMDVRAIMATIQRKYKGIKIQEGIVDYGVRFFF
YTSKEPVASIITKLNSLNEPLVTMPIGYVTHGFNLEEAARCMRSLKAPAV
VSVSSPDAVTTYNGYLTSSSKTSEEHFVETVSLAGSYRDWSYSGQRTELG
VEFLKRGDKIVYHTLESPVEFHLDGEVLSLDKLKSLLSLREVKTIKVFTT
VDNTNLHTQLVDMSMTYGQQFGPTYLDGADVTKIKPHVNHEGKTFFVLPS
DDTLRSEAFEYYHTLDESFLGRYMSALNHTKKWKFPQVGGLTSIKWADNN
CYLSSVLLALQQLEVKFNAPALQEAYYRARAGDAANFCALILAYSNKTVG
ELGDVRETMTHLLQHANLESAKRVLNVVCKHCGQKTTTLTGVEAVMYMGT
LSYDNLKTGVSIPCVCGRDATQYLVQQESSFVMMSAPPAEYKLQQGTFLC
ANEYTGNYQCGHYTHITAKETLYRIDGAHLTKMSEYKGPVTDVFYKETSY
TTTIKPVSYKLDGVTYTEIEPKLDGYYKKDNAYYTEQPIDLVPTQPLPNA
SFDNFKLTCSNTKFADDLNQMTGFTKPASRELSVTFFPDLNGDVVAIDYR
HYSASFKKGAKLLHKPIVWHINQATTKTTFKPNTWCLRCLWSTKPVDTSN
SFEVLAVEDTQGMDNLACESQQPTSEEVVENPTIQKEVIECDVKTTEVVG
NVILKPSDEGVKVTQELGHEDLMAAYVENTSITIKKPNELSLALGLKTIA
THGIAAINSVPWSKILAYVKPFLGQAAITTSNCAKRLAQRVFNNYMPYVF
TLLFQLCTFTKSTNSRIRASLPTTIAKNSVKSVAKLCLDAGINYVKSPKF
SKLFTIAMWLLLLSICLGSLICVTAAFGVLLSNFGAPSYCNGVRELYLNS
SNVTTMDFCEGSFPCSICLSGLDSLDSYPALETIQVTISSYKLDLTILGL
AAEWVLAYMLFTKFFYLLGLSAIMQVFFGYFASHFISNSWLMWFIISIVQ
MAPVSAMVRMYIFFASFYYIWKSYVHIMDGCTSSTCMMCYKRNRATRVEC
TTIVNGMKRSFVVYANGGRGFCKTHNWNCLNCDTFCTGSTFISDEVARDL
SLQFKRPINPTDQSSYIVDSVAVKNGALHLYFDKAGQKTYERHPLSHFVN
LDNLRANNTKGSLPINVIVPDGKSKCDESASKSASVYYSQLMCQPILLLD
QALVSDVGDSTEVSVKMFDAYVDTFSATPSVPMEKLKALVATAHSELAKG
VALDGVLSTFVSAARQGVVDTDVDTKDVIECLKLSHHSDLEVTGDSCNNF
MLTYNKVENMTPRDLGACIDCNARHINAQVAKSHNVSLIWNVKDYMSLSE
QLRKQIRSAAKKNNIPFRLTCATTRQVVNVITTKISLKGGKIVSTCFKLM
LKATLLCVLAALVCYIVMPVHTLSIHDGYTNEIIGYKAIQDGVTRDIIST
DDCFANKHAGFDAWFSQRGGSYKNDKSCPVVAAIITREIGFIVPGLPGTV
LRAINGDFLHFLPRVFSAVGNICYTPSKLIEYSDFATSACVLAAECTIFK
DAMGKPVPYCYDTNLLEGSISYSELRPDTRYVLMDGSIIQFPNTYLEGSV
RVVTTFDAEYCRHGTCERSEVGICLSTSGRWVLNNEHYRALSGVFCGVDA
MNLIANIFTPLVQPVGALDVSASVVAGGIIAILVTCAAYYFMKFRRVFGE
YNHVVAANALLFLMSFTILCLVPAYSFLPGVYSVFYLYLTFYFTNDVSFL
AHLQWFAMFSPIVPFWITAIYVFCISLKHCHWFFNNYLRKRVMFNGVTFS
TFEBAALCTFLLNKEMYLKLRSETLLPLTQYNRYLALYNKYKYFSGALDT
TSYREAACCHLAKALNDFSNSGADVLYQPPQTSITSAVLQSGFRKMAFPS
GKVEGCMVQVTCGTTTLNGLWLDDTVYCPRHVICTAEDMLNPNYEDLLIR
KSNHSFLVQAGNVQLRVIGHSMQNCLLRLKVDTSNPKTPKYKFVRIQPGQ
TFSVLACYNGSPSGVYQCAMRPNHTIKGSFLNGSCGSVGFNIDYDCVSFC
YMHHMELPTGVHAGTDLEGKFYGPFVDRQTAQAAGTDTTITLNVLAWLYA
AVINGDRWFLNRFTTTLNDFNLVAMKYNYEPLTQDHVDILGPLSAQTGIA
VLDMCAALKELLQNGMNGRTILGSTILEDEFTPFDVVRQCSGVTFQGKFK
```

FIGURE 16A

```
KIVKGTHHWMLLTFLTSLLILVQSTQWSLFFFVYENAFLPFTLGIMAIAA
CAMLLVKHKHAFLCLFLLPSLATVAYFNMVYMPASWVMRIMTWLELADTS
LSGYRLKDCVMYASALVLLILMTARTVYDDAARRVWTLMNVITLVYKVYY
GNALDQAISMWALVISVTSNYSGVVTTIMFLARAIVFVCVEYYPLLFITG
NTLQCIMLVYCFLGYCCCCYFGLFCLLNRYFRLTLGVYDYLVSTQEFRYM
NSQGLLPPKSSIDAFKLNIKLLGIGGKPCIKVATVQSKMSDVKCTSVVLL
SVLQQLRVESSSKLWAQCVQLHNDILLAKDTTEAFEKMVSLLSVLLSMQG
AVDINRLCEEMLDNRATLQAIASEFSSLPSYAAYATAQEAYEQAVANGDS
EVVLKKLKKSLNVAKSEFDRDAAMQRKLEKMADQAMTQMYKQARSEDKRA
KVTSAMQTMLFTMLRKLDNDALNNIINNARDGCVPLNIIPLTTAAKLMVV
VPDYGTYKNTCDGNTFTYASALWEIQQVVDADSKIVQLSEINMDNSPNLA
WPLIVTALRANSAVKLQNNELSPVALRQMSCAAGTTQTACTDDNALAYYN
NSKGGRFVLALLSDHQDLKWARFPKSDGTGTIYTELEPPCRFVTDTPKGP
KVKYLYFIKGLNNLNRGMVLGSLAATVRLQAGNATEVPANSTVLSFCAFA
VDPAKAYKDYLASGGQPITNCVKMLCTHTGTGQAITVTPEANMDQESFGG
ASCCLYCRCHIDHPNPKGFCDLKGKYVQIPTTCANDPVGFTLRNTVCTVC
GMWKGYGCSCDQLREPLMQSADASTF
```

(SEQ ID NO: 64)

FIGURE 16B

```
FKRVCG
VSAARLTPCGTGTSTDVVYRAFDIYNEKVAGFAKFLKTNCCRFQEKDEEG
NLLDSYFVVKRHTMSNYQHEETIYNLVKDCPAVAVHDFFKFRVDGDMVPH
ISRQRLTKYTMADLVYALRHFDEGNCDTLKEILVTYNCCDDDYFNKKDWY
DFVENPDILRVYANLGERVRQSLLKTVQFCDAMRDAGIVGVLTLDNQDLN
GNWYDFGDFVQVAPGCGVPIVDSYYSLLMPILTLTRALAAESHMDADLAK
PLIKWDLLKYDFTEERLCLFDRYFKYWDQTYHPNCINCLDDRCILHCANF
NVLFSTVFPPTSFGPLVRKIFVDGVPFVVSTGYHFRELGVVHNQDVNLHS
SRLSFKELLVYAADPAMHAASGNLLLDKRTTCFSVAALTNNVAFQTVKPG
NFNKDFYDFAVSKGFFKEGSSVELKHFPFAQDGNAAISDYDYYRYNLPTM
CDIRQLLFVVEVVDKYFDCYDGGCINANQVIVNNLDKSAGFPFNKWGKAR
LYYDSMSYEDQDALFAYTKRNVIPTITQMNLKYAISAKNRARTVAGVSIC
STMTNRQFHQKLLKSIAATRGATVVIGTSKFYGGWHNMLKTVYSDVETPH
LMGWDYPKCDRAMPNMLRIMASLVLARKHNTCCNLSHRFYRLANECAQVL
SEMVMCGGSLYVKPGGTSSGDATTAYANSVFNICQAVTANVNALLSTDGN
KIADKYVRNLQHRLYECLYRNRDVDHEFVDEFYAYLRKHFSMMILSDDAV
VCYNSNYAAQGLVASIKNFKAVLYYQNNVFMSEAKCWTETDLTKGPHEFC
SQHTMLVKQGDDYVYLPYPDPSRILGAGCFVDDIVKTDGTLMIERFVSLA
IDAYPLTKHPNQEYADVFHLYLQYIRKLHDELTGHMLDMYSVMLTNDNTS
RYWEPEFYEAMYTPHTVLQAVGACVLCNSQTSLRCGACIRRPFLCCKCCY
DHVISTSHKLVLSVNPYVCNAPGCDVTDVTQLYLGGMSYYCKSHKPPISF
PLCANGQVFGLYKNTCVGSDNVTDFNAIATCDWTNAGDYILANTCTERLK
LFAAETLKATEETFKLSYGIATVREVLSDRELHLSWEVGKPRPPLNRNYV
FTGYRVTKNSKVQIGEYTFEKGDYGDAVVYRGTTTYKLNVGDYFVLTSHT
VMPLSAPTLVPQEHYVRITGLYPTLNISDEFSSNVANYQKVGMQKYSTLQ
GPPGTGKSHFAIGLALYYPSARIVYTACSHAAVDALCEKALKYLPIDKCS
RIIPARARVECFDKFKVNSTLEQYVFCTVNALPETTADIVVFDEISMATN
YDLSVVNARLRAKHYVYIGDPAQLPAPRTLLTKGTLEPEYFNSVCRLMKT
IGPDMFLGTCRRCPAEIVDTVSALVYDNKLKAHKDKSAQCFKMFYKGVIT
HDVSSAINRPQIGVVREFLTRNPAWRKAVFISPYNSQNAVASKILGLPTQ
TVDSSQGSEYDYVIFTQTTETAHSCNVNRFNVAITRAKIGILCIMSDRDL
YDKLQFTSLEIPRRNVATLQAENVTGLFKDCSKIITGLHPTQAPTHLSVD
IKFKTEGLCVDIPGIPKDMTYRRLISMMGFKMNYQVNGYPNMFITREEAI
RHVRAWIGFDVEGCHATRDAVGTNLPLQLGFSTGVNLVAVPTGYVDTENN
TEFTRVNAKPPPGDQFKHLIPLMYKGLPWNVVRIKIVQMLSDTLKGLSDR
VVFVLWAHGFELTSMKYFVKIGPERTCCLCDKRATCFSTSSDTYACWNHS
VGFDYVYNPFMIDVQQWGFTGNLQSNHDQHCQVHGNAHVASCDAIMTRCL
AVHECFVKRVDWSVEYPIIGDELRVNSACRKVQHMVVKSALLADKFPVLH
DIGNPKAIKCVPQAEVEWKFYDAQPCSDKAYKIEELFYSYATHHDKFTDG
VCLFWNCNVDRYPANAIVCRFDTRVLSNLNLPGCDGGSLYVNKHAFHTPA
FDKSAFTNLKQLPFFYYSDSPCESHGKQVVSDIDYVPLKSATCITRCNLG
GAVCRHHANEYRQYLDAYNMMISAGFSLWIYKQFDTYNLWNTFTRLQSLE
NVAYNVVNKGHFDGHAGEAPVSIINNAVYTKVDGIDVEIFENKTTLPVNV
AFELWAKRNIKPVPEIKILNNLGVDIAANTVIWDYKREAPAHVSTIGVCT
MTDIAKKPTESACSSLTVLFDGRVEGQVDLFRNARNGVLITEGSVKGLTP
SKGPAQASVNGVTLIGESVKTQFNYFKKVDGIIQQLPETYFTQSRDLEDF
KPRSQMETDFLELAMDEFIQRYKLEGYAFEHIVYGDFSHGQLGGLHLMIG
LAKRSQDSPLKLEDFIPMDSTVKNYFITDAQTGSSKCVCSVIDLLLDDFV
EIIKSQDLSVISKVVKVTIDYAEISFMLWCKDGHVETFYPKLQASQAWQP
GVAMPNLYKMQRMLLEKCDLQNYGENAVIPKGIMMNVAKYTQLCQYLNTL
TLAVPYNMRVIHFGAGSDKGVAPGTAVLRQWLPTGTLLVDSDLNDFVSDA
DSTLIGDCATVHTANKWDLIISDMYDPRTKHVTKENDSKEGFFTYLCGFI
KQKLALGGSIAVKITEHSWNADLYKLMGHFSWWTAFVTNVNASSSEAFLI
GANYLGKPKEQIDGYTMHANYIFWRNTNPIQLSSYSLFDMSKFPLKLRGT
AVMSLKENQINDMIYSLLEKGRLIIRENNRVVVSSDILVNN (SEQ ID NO: 65)
```

FIGURE 17

MDLFMRFFTLRSITAQPVKIDNASPASTVHATATIPLQASLPFGWLVIGV
AFLAVFQSATKIIALNKRWQLALYKGFQFICNLLLLFVTIYSHLLLVAAG
MEAQFLYLYALIYFLQCINACRIIMRCWLCWKCKSKNPLLYDANYFVCWH
THNYDYCIPYNSVTDTIVVTEGDGISTPKLKEDYQIGGYSEDRHSGVKDY
VVVHGYFTEVYYQLESTQITTDTGIENATFFIFNKLVKDPPNVQIHTIDG
SSGVANPAMDPIYDEPTTTTSVPL    (SEQ ID NO: 66)

FIGURE 18

MMPTTLFAGTHITMTTVYHITVSQIQLSLLKVTAFQHQNSKKTTKLVVIL
RIGTQVLKTMSLYMAISPKFTTSLSLHKLLQTLVLKMLHSSSLTSLLKTH
RMCKYTQSTALQELLIQQWIQFMMSRRRLLACLCKHKKVSTNLCTHSFRK
KQVR    (SEQ ID NO: 67)

FIGURE 19

MFHLVDFQVTIAEILIIMRTFRIAIWNLDVIISSIVRQLFKPLTKKNYS
ELDDEEPMELDYP    (SEQ ID NO: 68)

FIGURE 20

MKIILFLTLIVFTSCELYHYQECVRGTTVLLKEPCPSGTYEGNSPFHPLA
DNKFALTCTSTHFAFACADGTRHTYQLRARSVSPKLFIRQEEVQQELYSP
LFLIVAALVFLILCFTIKRKTE    (SEQ ID NO: 69)

FIGURE 21

MNELTLIDFYLCFLAFLLFLVLIMLIIFWFSLEIQDLEEPCTKV (SEQ ID NO: 70)

FIGURE 22

MKLLIVLTCISLCSCICTVVQRCASNKPHVLEDPCKVQH (SEQ ID NO: 71)

FIGURE 23

MCLKILVRYNTRGNTYSTAWLCALGKVLPFHRWHTMVQTCTPNVTINCQD
PAGGALIARCWYLHEGHQTAAFRDVLVVLNKRTN    (SEQ ID NO: 72)

FIGURE 24

MDPNQTNVVPPALHLVDPQIQLTITRMEDAMGQGQNSADPKVYPIILRLG
SQLSLSMARRNLDSLEARAFQSTPIVVQMTKLATTEELPDEFVVVTAK (SEQ ID NO: 73)

FIGURE 25

MLPPCYNFLKEQHCQKASTQREAEAAVKPLLAPHHVVAVIQEIQLLAAVG
EILLLEWLAEVVKLPSRYCC  (SEQ ID NO: 74)

FIGURE 26

```
CIAVGQLCVFWNIGRPCCSGLCVFA--CTVKL        conotoxin
CISLCS-CICTVVQRCASNKPHVLEDPCKVQH        sars
**::.   *:    :  *  ...    *:   *.*:
```

FIGURE 27

SEQUENCE LISTING

```
<160> NUMBER OF SEQ ID NOS: 206

<210> SEQ ID NO 1
<211> LENGTH: 29736
<212> TYPE: DNA
<213> ORGANISM: Severe acute respiratory syndrome virus

<400> SEQUENCE: 1
ctacccagga aaagccaacc aacctcgatc tcttgtagat ctgttctcta aacgaacttt      60
aaaatctgtg tagctgtcgc tcggctgcat gcctagtgca cctacgcagt ataaacaata     120
ataaatttta ctgtcgttga caagaaacga gtaactcgtc cctcttctgc agactgctta     180
cggtttcgtc cgtgttgcag tcgatcatca gcatacctag gtttcgtccg ggtgtgaccg     240
aaaggtaaga tggagagcct tgttcttggt gtcaacgaga aaacacacgt ccaactcagt     300
ttgcctgtcc ttcaggttag agacgtgcta gtgcgtggct tcggggactc tgtggaagag     360
gccctatcgg aggcacgtga acacctcaaa aatggcactt gtggtctagt agagctggaa     420
```

-continued

```
aaaggcgtac tgccccagct tgaacagccc tatgtgttca ttaaacgttc tgatgcctta    480
agcaccaatc acggccacaa ggtcgttgag ctggttgcag aaatggacgg cattcagtac    540
ggtcgtagcg gtataacact gggagtactc gtgccacatg tgggcgaaac cccaattgca    600
taccgcaatg ttcttcttcg taagaacggt aataagggag ccggtggtca tagctatggc    660
atcgatctaa agtcttatga cttaggtgac gagcttggca ctgatcccat tgaagattat    720
gaacaaaact ggaacactaa gcatggcagt ggtgcactcc gtgaactcac tcgtgagctc    780
aatggaggtg cagtcactcg ctatgtcgac aacaatttct gtggcccaga tgggtaccct    840
cttgattgca tcaaagattt tctcgcacgc gcgggcaagt caatgtgcac tctttccgaa    900
caacttgatt acatcgagtc gaagagaggt gtctactgct gccgtgacca tgagcatgaa    960
attgcctggt tcactgagcg ctctgataag agctacgagc accagacacc cttcgaaatt   1020
aagagtgcca agaaatttga cactttcaaa ggggaatgcc caaagtttgt gtttcctctt   1080
aactcaaaag tcaaagtcat tcaaccacgt gttgaaaaga aaagactga gggtttcatg    1140 gggcgtatac gctctgtgta ccctgttgca ctcccacagg agtgtaacaa tatgcacttg   1200
tctaccttga tgaaatgtaa tcattgcgat gaagtttcat ggcagacgtg cgactttctg   1260
aaagccactt gtgaacattg tggcactgaa aatttagtta ttgaaggacc tactacatgt   1320
gggtacctac ctactaatgc tgtagtgaaa atgccatgtc ctgcctgtca agacccagag   1380
attggacctg agcatagtgt tgcagattat cacaaccact caaacattga aactcgactc   1440
cgcaagggag gtaggactag atgttttgga ggctgtgtgt ttgcctatgt tggctgctat   1500
aataagcgtg cctactgggt tcctcgtgct agtgctgata ttggctcagg ccatactggc   1560
attactggtg acaatgtgga gaccttgaat gaggatctcc ttgagatact gagtcgtgaa   1620
cgtgttaaca ttaacattgt tggcgatttt catttgaatg aagaggttgc catcatttg    1680 gcatctttct ctgcttctac aagtgccttt attgacacta taaagagtct tgattacaag   1740
tctttcaaaa ccattgttga gtcctgcggt aactataaag ttaccaaggg aaagcccgta   1800
aaaggtgctt ggaacattgg acaacagaga tcagttttaa caccactgtg tggttttccc   1860
tcacaggctg ctggtgttat cagatcaatt tttgcgcgca cacttgatgc agcaaaccac   1920
tcaattcctg atttgcaaag agcagctgtc accatacttg atggtatttc tgaacagtca   1980
ttacgtcttg tcgacgccat ggtttatact tcagacctgc tcaccaacag tgtcattatt   2040
atggcatatg taactggtgg tcttgtacaa cagacttctc agtggttgtc taatcttttg   2100
ggcactactg ttgaaaaact caggcctatc tttgaatgga ttgaggcgaa acttagtgca   2160
ggagttgaat ttctcaagga tgcttgggag attctcaaat ttctcattac aggtgttttt   2220
gacatcgtca agggtcaaat acaggttgct tcagataaca tcaaggattg tgtaaaatgc   2280
ttcattgatg ttgttaacaa ggcactcgaa atgtgcattg atcaagtcac tatcgctggc   2340
gcaaagttgc gatcactcaa cttaggtgaa gtcttcatcg ctcaaagcaa gggactttac   2400
cgtcagtgta tacgtggcaa ggagcagctg caactactca tgcctcttaa ggcaccaaaa   2460
gaagtaacct ttcttgaagg tgattcacat gacacagtac ttacctctga ggaggttgtt   2520
ctcaagaacg gtgaactcga agcactcgag acgcccgttg atagcttcac aaatggagct   2580
atcgtcggca caccagtctg tgtaaatggc ctcatgctct tagagattaa ggacaaagaa   2640
caatactgcg cattgtctcc tggttttact gctacaaaca atgtctttcg cttaaaaggg   2700
ggtgcaccaa ttaaaggtgt aaccttggga gaagatactg tttgggaagt tcaaggttac   2760
```

-continued

```
aagaatgtga gaatcacatt tgagcttgat gaacgtgttg acaaagtgct taatgaaaag    2820
tgctctgtct acactgttga atccggtacc gaagttactg agtttgcatg tgttgtagca    2880
gaggctgttg tgaagacttt acaaccagtt tctgatctcc ttaccaacat gggtattgat    2940
cttgatgagt ggagtgtagc tacattctac ttatttgatg atgctggtga agaaaacttt    3000
tcatcacgta tgtattgttc cttttaccct ccagatgagg aagaaggagg cgatgcagag    3060
tgtgaggaag aagaaattga tgaaacctgt gaacatgagt acggtacaga ggatgattat    3120
caaggtctcc ctctggaatt tggtgcctca gctgaaacag ttcgagttga gaagaagaa     3180 gaggaagact ggctggatga tactactgag caatcagaga ttgagccaga accagaacct    3240
acacctgaag aaccagttaa tcagtttact ggttatttaa aacttactga caatgttgcc    3300
attaaatgtg ttgacatcgt taaggaggca caaagtgcta atcctatggt gattgtaaat    3360
gctgctaaca tacacctgaa acatggtggt ggtgtagcag gtgcactcaa caaggcaacc    3420
aatggtgcca tgcaaaagga gagtgatgat tacattaagc taaatggccc tcttacagta    3480
ggagggtctt gtttgctttc tggacataat cttgctaaga agtgtctgca tgttgttgga    3540
cctaacctaa atgcaggtga ggacatccag cttcttaagg cagcatatga aaatttcaat    3600
tcacaggaca tcttacttgc accattgttg tcagcaggca tatttggtgc taaaccactt    3660
cagtctttac aagtgtgcgt gcagacggtt cgtacacagg tttatattgc agtcaatgac    3720
aaagctcttt atgagcaggt tgtcatggat tatcttgata acctgaagcc tagagtggaa    3780
gcacctaaac aagaggagcc accaaacaca gaagattcca aaactgagga gaaatctgtc    3840
gtacagaagc ctgtcgatgt gaagccaaaa attaaggcct gcattgatga ggttaccaca    3900
acactggaag aaactaagtt tcttaccaat aagttactct tgtttgctga tatcaatggt    3960
aagctttacc atgattctca gaacatgctt agaggtgaag atatgtcttt ccttgagaag    4020
gatgcacctt acatggtagg tgatgttatc actagtggtg atatcacttg tgttgtaata    4080
ccctccaaaa aggctggtgg cactactgag atgctctcaa gagctttgaa gaaagtgcca    4140
gttgatgagt atataaccac gtaccctgga caaggatgtg ctggttatac acttgaggaa    4200
gctaagactg ctcttaagaa atgcaaatct gcattttatg tactaccttc agaagcacct    4260
aatgctaagg aagagattct aggaactgta tcctggaatt tgagagaaat gcttgctcat    4320
gctgaagaga caagaaaatt aatgcctata tgcatggatg ttagagccat aatggcaacc    4380
atccaacgta agtataaagg aattaaaatt caagagggca tcgttgacta tggtgtccga    4440
ttcttctttt atactagtaa agagcctgta gcttctatta ttacgaagct gaactctcta    4500
aatgagccgc ttgtcacaat gccaattggt tatgtgacac atggttttaa tcttgaagag    4560
gctgcgcgct gtatgcgttc tcttaaagct cctgccgtag tgtcagtatc atcaccagat    4620
gctgttacta catataatgg ataccttcact tcgtcatcaa agacatctga ggagcacttt    4680
gtagaaacag tttctttggc tggctcttac agagattggt cctattcagg acagcgtaca    4740
gagttaggtg ttgaatttct taagcgtggt gacaaaattg tgtaccacac tctggagagc    4800
cccgtcgagt ttcatcttga cggtgaggtt ctttcacttg acaaactaaa gagtctctta    4860
tccctgcggg aggttaagac tataaaagtg ttcacaactg tggacaacac taatctccac    4920
acacagcttg tggatatgtc tatgacatat ggacagcagt ttggtccaac atacttggat    4980
ggtgctgatg ttacaaaaat taaacctcat gtaaatcatg agggtaagac tttctttgta    5040
ctacctagtg atgacacact acgtagtgaa gctttcgagt actaccatac tcttgatgag    5100
agttttcttg gtaggtacat gtctgcttta aaccacacaa agaaatggaa atttcctcaa    5160
```

```
gttggtggtt taacttcaat taaatgggct gataacaatt gttatttgtc tagtgtttta    5220
ttagcacttc aacagcttga agtcaaattc aatgcaccag cacttcaaga ggcttattat    5280
agagcccgtg ctggtgatgc tgctaacttt tgtgcactca tactcgctta cagtaataaa    5340
actgttggcg agcttggtga tgtcagagaa actatgaccc atcttctaca gcatgctaat    5400
ttggaatctg caaagcgagt tcttaatgtg gtgtgtaaac attgtggtca gaaaactact    5460
accttaacgg gtgtagaagc tgtgatgtat atgggtactc tatcttatga taatcttaag    5520
acaggtgttt ccattccatg tgtgtgtggt cgtgatgcta cacaatatct agtacaacaa    5580
gagtcttctt ttgttatgat gtctgcacca cctgctgagt ataaattaca gcaaggtaca    5640
ttcttatgtg cgaatgagta cactggtaac tatcagtgtg gtcattacac tcatataact    5700
gctaaggaga ccctctatcg tattgacgga gctcacctta caaagatgtc agagtacaaa    5760
ggaccagtga ctgatgtttt ctacaaggaa acatcttaca ctacaaccat caagcctgtg    5820
tcgtataaac tcgatggagt tacttacaca gagattgaac caaaattgga tgggtattat    5880
aaaaaggata atgcttacta tacagagcag cctatagacc ttgtaccaac tcaaccatta    5940
ccaaatgcga gttttgataa tttcaaactc acatgttcta acacaaaatt tgctgatgat    6000
ttaaatcaaa tgacaggctt cacaaagcca gcttcacgag agctatctgt cacattcttc    6060
ccagacttga atggcgatgt agtggctatt gactatagac actattcagc gagtttcaag    6120
aaaggtgcta aattactgca taagccaatt gtttggcaca ttaaccaggc tacaaccaag    6180
acaacgttca aaccaaacac ttggtgttta cgttgtcttt ggagtacaaa gccagtagat    6240
acttcaaatt catttgaagt tctggcagta gaagacacac aaggaatgga caatcttgct    6300
tgtgaaagtc aacaacccac ctctgaagaa gtagtggaaa atcctaccat acagaaggaa    6360
gtcatagagt gtgacgtgaa aactaccgaa gttgtaggca atgtcatact taaaccatca    6420
gatgaaggtg ttaaagtaac acaagagtta ggtcatgagg atcttatggc tgcttatgtg    6480
gaaaacacaa gcattaccat taagaaacct aatgagcttt cactagcctt aggtttaaaa    6540
acaattgcca ctcatggtat tgctgcaatt aatagtgttc cttggagtaa aattttggct    6600
tatgtcaaac cattcttagg acaagcagca attacaacat caaattgcgc taagagatta    6660
gcacaacgtg tgtttaacaa ttatatgcct tatgtgttta cattattgtt ccaattgtgt    6720 actttacta aaagtaccaa ttctagaatt agagcttcac tacctacaac tattgctaaa    6780
aatagtgtta agagtgttgc taaattatgt ttggatgccg gcattaatta tgtgaagtca    6840
cccaaatttt ctaaattgtt cacaatcgct atgtggctat tgttgttaag tatttgctta    6900
ggttctctaa tctgtgtaac tgctgctttt ggtgtactct tatctaattt tggtgctcct    6960
tcttattgta atggcgttag agaattgtat cttaattcgt ctaacgttac tactatggat    7020
ttctgtgaag ttcttttcc ttgcagcatt tgtttaagtg gattagactc ccttgattct    7080
tatccagctc ttgaaaccat tcaggtgacg atttcatcgt acaagctaga cttgacaatt    7140
ttaggtctgg ccgctgagtg ggttttggca tatatgttgt tcacaaaatt cttttattta    7200
ttaggtcttt cagctataat gcaggtgttc tttggctatt ttgctagtca tttcatcagc    7260
aattcttggc tcatgtggtt tatcattagt attgtacaaa tggcacccgt ttctgcaatg    7320
gttaggatgt acatcttctt tgcttctttc tactacatgg gaagagcta tgttcatatc    7380 atggatggtt gcacctcttc gacttgcatg atgtgctata gcgcaatcg tgccacacgc    7440 gttgagtgta caactattgt taatggcatg aagagatctt tctatgtcta tgcaaatgga    7500
```

```
ggccgtggct tctgcaagac tcacaattgg aattgtctca attgtgacac attttgcact   7560
ggtagtacat tcattagtga tgaagttgct cgtgatttgt cactccagtt taaaagacca   7620 atcaaccta ctgaccagtc atcgtatatt gttgatagtg ttgctgtgaa aaatggcgcg    7680
cttcacctct actttgacaa ggctggtcaa aagacctatg agagacatcc gctctcccat   7740
tttgtcaatt tagacaattt gagagctaac aacactaaag gttcactgcc tattaatgtc   7800
atagtttttg atggcaagtc caaatgcgac gagtctgctt ctaagtctgc ttctgtgtac   7860
tacagtcagc tgatgtgcca acctattctg ttgcttgacc aagctcttgt atcagacgtt   7920
ggagatagta ctgaagtttc cgttaagatg tttgatgctt atgtcgacac cttttcagca   7980
acttttagtg ttcctatgga aaacttaag gcacttgttg ctacagctca cagcgagtta    8040
gcaaagggtg tagctttaga tggtgtcctt tctacattcg tgtcagctgc ccgacaaggt   8100
gttgttgata ccgatgttga cacaaaggat gttattgaat gtctcaaact ttcacatcac   8160
tctgacttag aagtgacagg tgacagttgt aacaatttca tgctcaccta taataaggtt   8220
gaaaacatga cgcccagaga tcttggcgca tgtattgact gtaatgcaag gcatatcaat   8280
gcccaagtag caaaaagtca caatgtttca ctcatctgga atgtaaaaga ctacatgtct   8340
ttatctgaac agctgcgtaa acaaattcgt agtgctgcca agaagaacaa cataccttt    8400 agactaactt gtgctacaac tagacaggtt gtcaatgtca taactactaa aatctcactc   8460
aagggtggta agattgttag tacttgtttt aaacttatgc ttaaggccac attattgtgc   8520
gttcttgctg cattggtttg ttatatcgtt atgccagtac atacattgtc aatccatgat   8580
ggttacacaa atgaaatcat tggttacaaa gccattcagg atggtgtcac tcgtgacatc   8640
atttctactg atgattgttt tgcaaataaa catgctggtt ttgacgcatg gtttagccag   8700
cgtggtggtt catacaaaaa tgacaaaagc tgccctgtag tagctgctat cattacaaga   8760
gagattggtt tcatagtgcc tggcttaccg gtactgtgc tgagagcaat caatggtgac    8820
ttcttgcatt ttctacctcg tgtttttagt gctgttggca catttgcta cacaccttcc    8880 aaactcattg agtatagtga ttttgctacc tctgcttgcg ttcttgctgc tgagtgtaca   8940
atttttaagg atgctatggg caaacctgtg ccatattgtt atgacactaa tttgctagag   9000
ggttctattt cttatagtga gcttcgtcca gacactcgtt atgtgcttat ggatggttcc   9060
atcatacagt ttcctaacac ttacctggag ggttctgtta gagtagtaac aactttgat    9120 gctgagtact gtagacatgg tacatgcgaa aggtcagaag taggtatttg cctatctacc   9180
agtggtagat gggttcttaa taatgagcat acagagctc tatcaggagt tttctgtggt    9240
gttgatgcga tgaatctcat agctaacatc tttactcctc ttgtgcaacc tgtgggtgct   9300
ttagatgtgt ctgcttcagt agtggctggt ggtattattg ccatattggt gacttgtgct   9360
gcctactact ttatgaaatt cagacgtgtt tttggtgagt acaaccatgt tgttgctgct   9420
aatgcacttt tgttttgat gtctttcact atactctgtc tggtaccagc ttacagcttt    9480
ctgccgggag tctactcagt cttttacttg tacttgacat tctatttcac caatgatgtt   9540
tcattcttgg ctcaccttca atggtttgcc atgttttctc ctattgtgcc tttttggata   9600
acagcaatct atgtattctg tatttctctg aagcactgcc attggttctt taacaactat   9660
cttaggaaaa gagtcatgtt taatggagtt acatttagta ccttcgagga ggctgctttg   9720 tgtaccttt tgctcaacaa ggaaatgtac ctaaaattgc gtagcgagac actgttgcca    9780
cttacacagt ataacaggta tcttgctcta tataacaagt acaagtattt cagtggagcc   9840
ttagatacta ccagctatcg tgaagcagct tgctgccact agcaaaggc tctaaatgac    9900
```

```
tttagcaact caggtgctga tgttctctac caaccaccac agacatcaat cacttctgct    9960
gttctgcaga gtggttttag gaaaatggca ttcccgtcag gcaaagttga agggtgcatg   10020
gtacaagtaa cctgtggaac tacaactctt aatggattgt ggttggatga cacagtatac   10080
tgtccaagac atgtcatttg cacagcagaa gacatgctta atcctaacta tgaagatctg   10140
ctcattcgca aatccaacca tagctttctt gttcaggctg gcaatgttca acttcgtgtt   10200
attggccatt ctatgcaaaa ttgtctgctt aggcttaaag ttgatacttc taaccctaag   10260
acacccaagt ataaatttgt ccgtatccaa cctggtcaaa cattttcagt tctagcatgc   10320
tacaatggtt caccatctgg tgtttatcag tgtgccatga gacctaatca taccattaaa   10380
ggttctttcc ttaatggatc atgtggtagt gttggtttta acattgatta tgattgcgtg   10440
tctttctgct atatgcatca tatggagctt ccaacaggag tacacgctgg tactgactta   10500
gaaggtaaat tctatggtcc atttgttgac agacaaactg cacaggctgc aggtacagac   10560
acaaccataa cattaaatgt tttggcatgg ctgtatgctg ctgttatcaa tggtgatagg   10620
tggtttctta atagattcac cactactttg aatgacttta accttgtggc aatgaagtac   10680
aactatgaac ctttgacaca agatcatgtt gacatattgg gacctctttc tgctcaaaca   10740
ggaattgccg tcttagatat gtgtgctgct ttgaaagagc tgctgcagaa tggtatgaat   10800
ggtcgtacta tccttggtag cactatttta gaagatgagt ttacaccatt tgatgttgtt   10860
agacaatgct ctggtgttac cttccaaggt aagttcaaga aaattgttaa gggcactcat   10920
cattggatgc ttttaacttt cttgacatca ctattgattc ttgttcaaag tacacagtgg   10980
tcactgtttt tctttgttta cgagaatgct ttcttgccat ttactcttgg tattatggca   11040
attgctgcat gtgctatgct gcttgttaag cataagcacg cattcttgtg cttgtttctg   11100
ttaccttctc ttgcaacagt tgcttacttt aatatggtct acatgcctgc tagctgggtg   11160
atgcgtatca tgacatggct tgaattggct gacactagct tgtctggtta taggcttaag   11220
gattgtgtta tgtatgcttc agctttagtt ttgcttattc tcatgacagc tcgcactgtt   11280
tatgatgatg ctgctagacg tgtttggaca ctgatgaatg tcattacact tgtttacaaa   11340
gtctactatg gtaatgcttt agatcaagct atttccatgt gggcttagt tatttctgta   11400
acctctaact attctggtgt cgttacgact atcatgtttt tagctagagc tatagtgttt   11460
gtgtgtgttg agtattaccc attgttattt attactggca acaccttaca gtgtatcatg   11520
cttgtttatt gttcttagg ctattgttgc tgctgctact ttggcctttt ctgtttactc   11580
aaccgttact tcaggcttac tcttggtgtt tatgactact tggtctctac acaagaattt   11640
aggtatatga actcccaggg gcttttgcct cctaagagta gtattgatgc tttcaagctt   11700
aacattaagt tgttgggtat tggaggtaaa ccatgtatca aggttgctac tgtacagtct   11760
aaaatgtctg acgtaaagtg cacatctgtg gtactgctct cggttcttca acaacttaga   11820
gtagagtcat cttctaaatt gtgggcacaa tgtgtacaac tccacaatga tattcttctt   11880
gcaaaagaca caactgaagc tttcgagaag atggtttctc ttttgtctgt tttgctatcc   11940
atgcagggtg ctgtagacat taataggttg tgcgaggaaa tgctcgataa ccgtgctact   12000
cttcaggcta ttgcttcaga atttagttct ttaccatcat atgccgctta tgccactgcc   12060
caggaggcct atgagcaggc tgtagctaat ggtgattctg aagtcgttct caaaaagtta   12120
aagaaatctt tgaatgtggc taaatctgag tttgaccgtg atgctgccat gcaacgcaag   12180
ttggaaaaga tggcagatca ggctatgacc caaatgtaca aacaggcaag atctgaggac   12240
```

```
aagagggcaa aagtaactag tgctatgcaa acaatgctct tcactatgct taggaagctt   12300
gataatgatg cacttaacaa cattatcaac aatgcgcgtg atggttgtgt tccactcaac   12360
atcataccat tgactacagc agccaaactc atggttgttg tccctgatta tggtacctac   12420
aagaacactt gtgatggtaa caccttaca tatgcatctg cactctggga aatccagcaa    12480
gttgttgatg cggatagcaa gattgttcaa cttagtgaaa ttaacatgga caattcacca   12540
aatttggctt ggcctcttat tgttacagct ctaagagcca actcagctgt taaactacag   12600
aataatgaac tgagtccagt agcactacga cagatgtcct gtgcggctgg taccacacaa   12660
acagcttgta ctgatgacaa tgcacttgcc tactataaca attcgaaggg aggtaggttt   12720
gtgctggcat tactatcaga ccaccaagat ctcaaatggg ctagattccc taagagtgat   12780
ggtacaggta caatttacac agaactggaa ccaccttgta ggtttgttac agacacacca   12840
aaagggccta aagtgaaata cttgtacttc atcaaaggct taaacaacct aaatagaggt   12900
atggtgctgg gcagtttagc tgctacagta cgtcttcagg ctggaaatgc tacagaagta   12960
cctgccaatt caactgtgct ttccttctgt gcttttgcag tagaccctgc taaagcatat   13020
aaggattacc tagcaagtgg aggacaacca atcaccaact gtgtgaagat gttgtgtaca   13080
cacactggta caggacaggc aattactgta acaccagaag ctaacatgga ccaagagtcc   13140
tttggtggtc cttcatgttg tctgtattgt agatgccaca ttgaccatcc aaatcctaaa   13200
ggattctgtg acttgaaagg taagtacgtc caaatacta ccacttgtgc taatgaccca   13260
gtgggtttta cacttagaaa cacagtctgt accgtctgcg gaatgtggaa aggttatggc   13320
tgtagttgtg accaactccg cgaacccttg atgcagtctg cggatgcatc aacgttttta   13380
aacgggtttg cggtgtaagt gcagcccgtc ttacaccgtg cggcacaggc actagtactg   13440
atgtcgtcta cagggctttt gatatttaca acgaaaaagt tgctggtttt gcaaagttcc   13500
taaaaactaa ttgctgtcgc ttccaggaga aggatgagga aggcaattta ttagactctt   13560
actttgtagt taagaggcat actatgtcta actaccaaca tgaagagact atttataact   13620
tggttaaaga ttgtccagcg gttgctgtcc atgacttttt caagtttaga gtagatggtg   13680
acatggtacc acatatatca cgtcagcgtc taactaaata cacaatggct gatttagtct   13740
atgctctacg tcatttttgat gagggtaatt gtgatacatt aaaagaaata ctcgtcacat   13800
acaattgctg tgatgatgat tatttcaata agaaggattg gtatgacttc gtagagaatc   13860
ctgacatctt acgcgtatat gctaacttag gtgagcgtgt acgccaatca ttattaaaga   13920
ctgtacaatt ctgcgatgct atgcgtgatg caggcattgt aggcgtactg acattagata   13980
atcaggatct taatgggaac tggtacgatt tcggtgattt cgtacaagta gcaccaggct   14040
gcggagttcc tattgtggat tcatattact cattgctgat gcccatcctc actttgacta   14100
gggcattggc tgctgagtcc catatggatg ctgatctcgc aaaaccactt attaagtggg   14160
atttgctgaa atatgatttt acggaagaga gactttgtct cttcgaccgt tattttaaat   14220
attgggacca gacataccat cccaattgta ttaactgttt ggatgatagg tgtatccttc   14280
attgtgcaaa ctttaatgtg ttattttcta ctgtgtttcc acctacaagt tttgaccac    14340 tagtaagaaa atatttgta gatggtgttc cttttgttgt ttcaactgga taccatttc     14400 gtgagttagg agtcgtacat aatcaggatg taaacttaca tagctcgcgt ctcagtttca   14460
aggaactttt agtgtatgct gctgatccag ctatgcatgc agcttctggc aatttattgc   14520
tagataaacg cactacatgc ttttcagtag ctgcactaac aaacaatgtt gcttttcaaa   14580
ctgtcaaacc cggtaatttt aataaagact tttatgactt tgctgtgtct aaaggtttct   14640
```

```
ttaaggaagg aagttctgtt gaactaaaac acttcttctt tgctcaggat ggcaacgctg    14700
ctatcagtga ttatgactat tatcgttata atctgccaac aatgtgtgat atcagacaac    14760
tcctattcgt agttgaagtt gttgataaat actttgattg ttacgatggt ggctgtatta    14820
atgccaacca agtaatcgtt aacaatctgg ataaatcagc tggtttccca tttaataaat    14880
ggggtaaggc tagactttat tatgactcaa tgagttatga ggatcaagat gcacttttcg    14940
cgtatactaa gcgtaatgtc atccctacta taactcaaat gaatcttaag tatgccatta    15000
gtgcaaagaa tagagctcgc accgtagctg gtgtctctat ctgtagtact atgacaaata    15060
gacagtttca tcagaaatta ttgaagtcaa tagccgccac tagaggagct actgtggtaa    15120
ttggaacaag caagttttac ggtggctggc ataatatgtt aaaaactgtt tacagtgatg    15180
tagaaactcc acaccttatg ggttgggatt atccaaaatg tgacagagcc atgcctaaca    15240
tgcttaggat aatggcctct cttgttcttg ctcgcaaaca taacacttgc tgtaacttat    15300
cacaccgttt ctacaggtta gctaacgagt gtgcgcaagt attaagtgag atggtcatgt    15360
gtggcggctc actatatgtt aaaccaggtg gaacatcatc cggtgatgct acaactgctt    15420
atgctaatag tgtcttaac atttgtcaag ctgttacagc caatgtaaat gcacttcttt    15480
caactgatgg taataagata gctgacaagt atgtccgcaa tctacaacac aggctctatg    15540
agtgtctcta tagaaatagg gatgttgatc atgaattcgt ggatgagttt tacgcttacc    15600
tgcgtaaaca tttctccatg atgattcttt ctgatgatgc cgttgtgtgc tataacagta    15660
actatgcggc tcaaggttta gtagctagca ttaagaactt taaggcagtt ctttattatc    15720
aaaataatgt gttcatgtct gaggcaaaat gttggactga gactgacctt actaaaggac    15780
ctcacgaatt ttgctcacag catacaatgc tagttaaaca aggagatgat tacgtgtacc    15840
tgccttaccc agatccatca agaatattag gcgcaggctg ttttgtcgat gatattgtca    15900
aaacagatgg tacacttatg attgaaaggt tcgtgtcact ggctattgat gcttacccac    15960
ttacaaaaca tcctaatcag gagtatgctg atgtctttca cttgtattta caatacatta    16020
gaaagttaca tgatgagctt actggccaca tgttggacat gtattccgta atgctaacta    16080
atgataacac ctcacggtac tgggaacctg agttttatga ggctatgtac acaccacata    16140
cagtcttgca ggctgtaggt gcttgtgtat tgtgcaattc acagactca cttcgttgcg    16200 gtgcctgtat taggagacca ttcctatgtt gcaagtgctg ctatgaccat gtcatttcaa    16260
catcacacaa attagtgttg tctgttaatc cctatgtttg caatgcccca ggttgtgatg    16320
tcactgatgt gacacaactg tatctaggag gtatgagcta ttattgcaag tcacataagc    16380
ctcccattag ttttccatta tgtgctaatg gtcaggtttt tggtttatac aaaaacacat    16440
gtgtaggcag tgacaatgtc actgacttca atgcgatagc aacatgtgat tggactaatg    16500
ctggcgatta catacttgcc aacacttgta ctgagagact caagctttc gcagcagaaa    16560 cgctcaaagc cactgaggaa acatttaagc tgtcatatgg tattgccact gtacgcgaag    16620
tactctctga cagagaattg catctttcat gggaggttgg aaaacctaga ccaccattga    16680
acagaaacta tgtctttact ggttaccgtg taactaaaaa tagtaaagta cagattggag    16740
agtcaccttt tgaaaaggt gactatggtg atgctgttgt gtacagaggt actacgacat    16800
acaagttgaa tgttggtgat tactttgtgt tgacatctca cactgtaatg ccacttagtg    16860
cacctactct agtgccacaa gagcactatg tgagaattac tggcttgtac ccaacactca    16920
acatctcaga tgagttttct agcaatgttg caaattatca aaaggtcggc atgcaaaagt    16980
```

```
actctacact ccaaggacca cctggtactg gtaagagtca ttttgccatc ggacttgctc   17040
tctattaccc atctgctcgc atagtgtata cggcatgctc tcatgcagct gttgatgccc   17100
tatgtgaaaa ggcattaaaa tatttgccca tagataaatg tagtagaatc atacctgcgc   17160
gtgcgcgcgt agagtgtttt gataaattca aagtgaattc aacactagaa cagtatgttt   17220
tctgcactgt aaatgcattg ccagaaacaa ctgctgacat tgtagtcttt gatgaaatct   17280
ctatggctac taattatgac ttgagtgttg tcaatgctag acttcgtgca aaacactacg   17340
tctatattgg cgatcctgct caattaccag cccccgcac attgctgact aaaggcacac   17400
tagaaccaga atattttaat tcagtgtgca gacttatgaa acaataggt ccagacatgt   17460 tccttggaac ttgtcgccgt tgtcctgctg aaattgttga cactgtgagt gctttagttt   17520
atgcaaataa gctaaaagca cacaaggata agtcagctca atgcttcaaa atgttctaca   17580
aaggtgttat tacacatgat gtttcatctg caatcaacag acctcaaata ggcgttgtaa   17640
gagaatttct tacacgcaat cctgcttgga gaaaagctgt ttttatctca ccttataatt   17700
cacagaacgc tgtagcttca aaaatcttag gattgcctac gcagactgtt gattcatcac   17760
agggttctga atatgactat gtcatattca cacaaactac tgaaacagca cactcttgta   17820
atgtcaaccg cttcaatgtg gctatcacaa gggcaaaaat tggcattttg tgcataatgt   17880
ctgatagaga tctttatgac aaactgcaat ttacaagtct agaaatacca cgtcgcaatg   17940
tggctacatt acaagcagaa aatgtaactg gacttttaa ggactgtagt aagatcatta   18000
ctggtcttca tcctacacag gcacctacac acctcagcgt tgatataaag ttcaagactg   18060
aaggattatg tgttgacata ccaggcatac caaaggacat gacctaccgt agactcatct   18120
ctatgatggg ttcaaaatg aattaccaag tcaatggtta ccctaatatg tttatcaccc   18180
gcgaagaagc tattcgtcac gttcgtgcgt ggattggctt tgatgtagag ggctgtcatg   18240
caactagaga tgctgtgggt actaacctac ctctccagct aggattttct acaggtgtta   18300
acttagtagc tgtaccgact ggttatgttg acactgaaaa taacacagaa ttcaccagag   18360
ttaatgcaaa acctccacca ggtgaccagt ttaaacatct tataccactc atgtataaag   18420
gcttgccctg gaatgtagtg cgtattaaga gtacaaaat gctcagtgat acactgaaag   18480
gattgtcaga cagagtcgtg ttcgtccttt gggcgcatgg ctttgagctt acatcaatga   18540
agtactttgt caagattgga cctgaaagaa cgtgttgtct gtgtgacaaa cgtgcaactt   18600
gcttttctac ttcatcagat acttatgcct gctggaatca ttctgtgggt tttgactatg   18660
tctataaccc atttatgatt gatgttcagc agtggggctt tacgggtaac cttcagagta   18720
accatgacca acattgccag gtacatggaa atgcacatgt ggctagttgt gatgctatca   18780
tgactagatg tttagcagtc catgagtgct ttgttaagcg cgttgattgg tctgttgaat   18840
accctattat aggagatgaa ctgagggtta ttctgcttg cagaaaagta caacacatgg   18900
ttgtgaagtc tgcattgctt gctgataagt ttccagttct tcatgacatt ggaaatccaa   18960
aggctatcaa gtgtgtgcct caggctgaag tagaatggaa gttctacgat gctcagccat   19020
gtagtgacaa agcttacaaa atagaggaac tcttctattc ttatgctaca catcacgata   19080
aattcactga tggtgtttgt ttgttttgga attgtaacgt tgatcgttac ccagccaatg   19140
caattgtgtg taggtttgac acaagagtct tgtcaaactt gaacttacca ggctgtgatg   19200
gtggtagttt gtatgtgaat aagcatgcat tccacactcc agcttcgat aaaagtgcat   19260 ttactaattt aaagcaattg ccttttcttt actattctga tagtccttgt gagtctcatg   19320
gcaaacaagt agtgtcggat attgattatg ttccactcaa atctgctacg tgtattacac   19380
```

```
gatgcaattt aggtggtgct gtttgcagac accatgcaaa tgagtaccga cagtacttgg   19440
atgcatataa tatgatgatt tctgctggat ttagcctatg gatttacaaa caatttgata   19500
cttataacct gtggaataca tttaccaggt tacagagttt agaaaatgtg gcttataatg   19560
ttgttaataa aggacacttt gatggacacg ccggcgaagc acctgttttcc atcattaata   19620 atgctgttta cacaaaggta gatggtattg atgtggagat ctttgaaaat aagcaacac    19680 ttcctgttaa tgttgcattt gagctttggg ctaagcgtaa cattaaacca gtgccagaga   19740
ttaagatact caataatttg ggtgttgata tcgctgctaa tactgtaatc tgggactaca   19800
aaagagaagc cccagcacat gtatctacaa taggtgtctg cacaatgact gacattgcca   19860
agaaacctac tgagagtgct tgttcttcac ttactgtctt gtttgatggt agagtggaag   19920
gacaggtaga cctttttaga aacgcccgta atggtgtttt aataacagaa ggttcagtca   19980
aaggtctaac accttcaaag ggaccagcac aagctagcgt caatggagtc acattaattg   20040
gagaatcagt aaaaacacag tttaactact ttaagaaagt agacggcatt attcaacagt   20100
tgcctgaaac ctactttact cagagcagag acttagagga ttttaagccc agatcacaaa   20160
tggaaactga ctttctcgag ctcgctatgg atgaattcat acagcgatat aagctcgagg   20220
gctatgcctt cgaacacatc gtttatggag atttcagtca tggacaactt ggcggtcttc   20280
atttaatgat aggcttagcc aagcgctcac aagattcacc acttaaatta gaggatttta   20340
tccctatgga cagcacagtg aaaaattact tcataacaga tgcgcaaaca ggttcatcaa   20400
aatgtgtgtg ttctgtgatt gatcttttac ttgatgactt tgtcgagata ataaagtcac   20460
aagatttgtc agtgatttca aaagtggtca aggttacaat tgactatgct gaaatttcat   20520
tcatgctttg gtgtaaggat ggacatgttg aaaccttcta cccaaaacta caagcaagtc   20580
gagcgtggca accaggtgtt gcgatgccta acttgtacaa gatgcaaaga atgcttcttg   20640
aaaagtgtga ccttcagaat tatggtgaaa atgctgttat accaaaagga ataatgatga   20700
atgtcgcaaa gtatactcaa ctgtgtcaat acttaaatac acttactta gctgtaccct   20760 acaacatgag agttattcac tttggtgctg gctctgataa aggagttgca ccaggtacag   20820
ctgtgctcag acaatggttg ccaactggca cactacttgt cgattcagat cttaatgact   20880
tcgtctccga cgcatattct actttaattg gagactgtgc aacagtacat acggctaata   20940
aatgggacct tattattagc gatatgtatg accctaggac caaacatgtg acaaaagaga   21000
atgactctaa agaagggttt ttcacttatc tgtgtggatt tataaagcaa aaactagccc   21060
tgggtggttc tatagctgta aagataacag agcattcttg gaatgctgac ctttacaagc   21120
ttatgggcca tttctcatgg tggacagctt ttgttacaaa tgtaaatgca tcatcatcgg   21180
aagcattttt aattggggct aactatcttg gcaagccgaa ggaacaaatt gatggctata   21240
ccatgcatgc taactacatt ttctggagga acacaaatcc tatccagttg tcttcctatt   21300
cactctttga catgagcaaa tttcctctta aattaagagg aactgctgta atgtctctta   21360
aggagaatca aatcaatgat atgatttatt ctcttctgga aaaggtagg cttatcatta   21420 gagaaaacaa cagagttgtg gtttcaagtg atattcttgt taacaactaa acgaacatgt   21480
ttattttctt attatttctt actctcacta gtggtagtga ccttgaccgg tgcaccactt   21540
ttgatgatgt tcaagctcct aattacactc aacatacttc atctatgagg ggggtttact   21600
atcctgatga aattttagg tcagacactc tttatttaac tcaggattta ttcttccat    21660 tttattctaa tgttacaggg tttcatacta ttaatcatac gtttggcaac cctgtcatac   21720
```

```
cttttaagga tggtatttat tttgctgcca cagagaaatc aaatgttgtc cgtggttggg    21780 ttttttggttc taccatgaac aacaagtcac agtcggtgat tattattaac aattctacta   21840
atgttgttat acgagcatgt aactttgaat tgtgtgacaa ccctttcttt gctgtttcta    21900
aacccatggg tacacagaca catactatga tattcgataa tgcatttaat tgcactttcg    21960
agtacatatc tgatgccttt tcgcttgatg tttcagaaaa gtcaggtaat tttaaacact    22020
tacgagagtt tgtgtttaaa aataaagatg ggtttctcta tgtttataag ggctatcaac    22080
ctatagatgt agttcgtgat ctaccttctg gttttaacac tttgaaacct attttttaagt   22140 tgcctcttgg tattaacatt acaaatttta gagccattct tacagccttt tcacctgctc    22200
aagacatttg gggcacgtca gctgcagcct attttgttgg ctatttaaag ccaactacat    22260
ttatgctcaa gtatgatgaa aatggtacaa tcacagatgc tgttgattgt tctcaaaatc    22320
cacttgctga actcaaatgc tctgttaaga gctttgagat tgacaaagga atttaccaga    22380
cctctaattt caggggttgtt ccctcaggag atgttgtgag attccctaat attacaaact   22440
tgtgtccttt tggagaggtt tttaatgcta ctaaattccc ttctgtctat gcatgggaga    22500
gaaaaaaaat ttctaattgt gttgctgatt actctgtgct ctacaactca acatttttttt   22560 caaccttttaa gtgctatggc gtttctgcca ctaagttgaa tgatctttgc ttctccaatg    22620
tctatgcaga ttcttttgta gtcaagggag atgatgtaag acaaatagcg ccaggacaaa    22680
ctggtgttat tgctgattat aattataaat tgccagatga tttcatgggt tgtgtccttg    22740
cttggaatac taggaacatt gatgctactt caactggtaa ttataattat aaatataggt    22800
atcttagaca tggcaagctt aggccctttg agagagacat atctaatgtg cctttctccc    22860
ctgatggcaa accttgcacc ccacctgctc ttaattgtta ttggccatta aatgattatg    22920 gttttttacac cactactggc attggctacc aaccttacag agttgtagta cttttctttttg   22980 aacttttaaa tgcaccggcc acggtttgtg gaccaaaatt atccactgac cttattaaga    23040
accagtgtgt caattttaat tttaatggac tcactggtac tggtgtgtta actccttctt    23100
caaagagatt tcaaccattt caacaatttg gccgtgatgt ttctgatttc actgattccg    23160
ttcgagatcc taaaacatct gaaatattag acatttcacc ttgcgctttt ggggggtgtaa    23220 gtgtaattac acctgaaaca aatgcttcat ctgaagttgc tgttctatat caagatgtta    23280
actgcactga tgtttctaca gcaattcatg cagatcaact cacaccagct tggcgcatat    23340
attctactgg aaacaatgta ttccagactc aagcaggctg tcttatagga gctgagcatg    23400
tcgacacttc ttatgagtgc gacattccta ttggagctgg catttgtgct agttaccata    23460
cagtttcttt attacgtagt actagccaaa aatctattgt ggcttatact atgtctttag    23520
gtgctgatag ttcaattgct tactctaata acaccattgc tatacctact aacttttcaa    23580
ttagcattac tacagaagta atgcctgttt ctatggctaa aacctccgta gattgtaata    23640
tgtacatctg cggagattct actgaatgtg ctaatttgct tctccaatat ggtagctttt    23700
gcacacaact aaatcgtgca ctctcaggta ttgctgctga acaggatcgc aacacacgtg    23760
aagtgttcgc tcaagtcaaa caaatgtaca aaacccccaac tttgaaatat tttggtggtt    23820 ttaattttttc acaaatatta cctgaccctc taaagccaac taagaggtct tttattgagg    23880
acttgctctt taataaggtg acactcgctg atgctggctt catgaagcaa tatggcgaat    23940
gcctaggtga tattaatgct agagatctca tttgtgcgca gaagttcaat ggacttacag    24000
tgttgccacc tctgctcact gatgatatga ttgctgccta cactgctgct ctagttagtg    24060
gtactgccac tgctggatgg acatttggtg ctggcgctgc tcttcaaata cctttttgcta   24120
```

```
tgcaaatggc atataggttc aatggcattg gagttaccca aaatgttctc tatgagaacc   24180
aaaaacaaat cgccaaccaa tttaacaagg cgattagtca aattcaagaa tcacttacaa   24240
caacatcaac tgcattgggc aagctgcaag acgttgttaa ccagaatgct caagcattaa   24300
acacacttgt taaacaactt agctctaatt ttggtgcaat ttcaagtgtg ctaaatgata   24360
tcctttcgcg acttgataaa gtcgaggcgg aggtacaaat tgacaggtta attacaggca   24420
gacttcaaag ccttcaaacc tatgtaacac aacaactaat cagggctgct gaaatcaggg   24480
cttctgctaa tcttgctgct actaaaatgt ctgagtgtgt tcttggacaa tcaaaaagag   24540
ttgacttttg tggaaagggc taccaccta tgtccttccc acaagcagcc ccgcatggtg   24600
ttgtcttcct acatgtcacg tatgtgccat cccaggagag gaacttcacc acagcgccag   24660
caatttgtca tgaaggcaaa gcatacttcc ctcgtgaagg tgtttttgtg tttaatggca   24720
cttcttggtt tattacacag aggaacttct tttctccaca ataattact acagacaata   24780 catttgtctc aggaaattgt gatgtcgtta ttggcatcat taacaacaca gtttatgatc   24840
ctctgcaacc tgagcttgac tcattcaaag aagagctgga caagtacttc aaaaatcata   24900
catcaccaga tgttgatctt ggcgacattt caggcattaa cgcttctgtc gtcaacattc   24960
aaaaagaaat tgaccgcctc aatgaggtcg ctaaaaattt aaatgaatca ctcattgacc   25020
ttcaagaatt gggaaaatat gagcaatata ttaaatggcc ttggtatgtt tggctcggct   25080
tcattgctgg actaattgcc atcgtcatgg ttacaatctt gctttgttgc atgactagtt   25140
gttgcagttg cctcaagggt gcatgctctt gtggttcttg ctgcaagttt gatgaggatg   25200
actctgagcc agttctcaag ggtgtcaat tacattacac ataaacgaac ttatggattt   25260
gtttatgaga ttttttactc ttggatcaat tactgcacag ccagtaaaaa ttgacaatgc   25320
ttctcctgca gtactgttc atgctacagc aacgataccg ctacaagcct cactcccttt   25380
cggatggctt gttattggcg ttgcatttct tgctgttttt cagagcgcta ccaaaataat   25440
tgcgctcaat aaaagatggc agctagccct ttataagggc ttccagttca tttgcaattt   25500
actgctgcta tttgttacca tctattcaca tcttttgctt gtcgctgcag gtatggaggc   25560 gcaattttg tacctctatg ccttgatata ttttctacaa tgcatcaacg catgtagaat   25620
tattatgaga tgttggcttt gttggaagtg caaatccaag aacccattac tttatgatgc   25680
caactacttt gtttgctggc acacacataa ctatgactac tgtataccat ataacagtgt   25740
cacagataca attgtcgtta ctgaaggtga cggcatttca acaccaaaac tcaaagaaga   25800
ctaccaaatt ggtggttatt ctgaggatag gcactcaggt gttaaagact atgtcgttgt   25860
acatggctat ttcaccgaag tttactacca gcttgagtct acacaaatta ctacagacac   25920
tggtattgaa aatgctacat tcttcatctt taacaagctt gttaaagacc caccgaatgt   25980
gcaaatacac acaatcgacg gctcttcagg agttgctaat ccagcaatgg atccaattta   26040
tgatgagccg acgacgacta ctagcgtgcc tttgtaagca caagaaagtg agtacgaact   26100
tatgtactca ttcgtttcgg aagaaacagg tacgttaata gttaatagcg tacttctttt   26160
tcttgctttc gtggtattct tgctagtcac actagccatc cttactgcgc ttcgattgtg   26220
tgcgtactgc tgcaatattg ttaacgtgag tttagtaaaa ccaacggttt acgtctactc   26280
gcgtgttaaa aatctgaact cttctgaagg agttcctgat cttctggtct aaacgaacta   26340
actattatta ttattctgtt tggaacttta acattgctta tcatggcaga caacggtact   26400
attaccgttg aggagcttaa acaactcctg gaacaatgga acctagtaat aggtttccta   26460
```

```
ttcctagcct ggattatgtt actacaattt gcctattcta atcggaacag gtttttgtac   26520
ataataaagc ttgttttcct ctggctcttg tggccagtaa cacttgcttg ttttgtgctt   26580
gctgctgtct acagaattaa ttgggtgact ggcgggattg cgattgcaat ggcttgtatt   26640
gtaggcttga tgtggcttag ctacttcgtt gcttccttca ggctgtttgc tcgtacccgc   26700
tcaatgtggt cattcaaccc agaaacaaac attcttctca atgtgcctct ccggggaca   26760
attgtgacca gaccgctcat ggaaagtgaa cttgtcattg gtgctgtgat cattcgtggt   26820
cacttgcgaa tggccggaca ctccctaggg cgctgtgaca ttaaggacct gccaaaagag   26880
atcactgtgg ctacatcacg aacgctttct tattacaaat taggagcgtc gcagcgtgta   26940
ggcactgatt caggttttgc tgcatacaac cgctaccgta ttggaaacta taattaaat   27000
acagaccacg ccgtagcaa cgacaatatt gctttgctag tacagtaagt gacaacagat   27060
gtttcatctt gttgacttcc aggttacaat agcagagata ttgattatca ttatgaggac   27120
tttcaggatt gctatttgga atcttgacgt tataataagt tcaatagtga gacaattatt   27180
taagcctcta actaagaaga attattcgga gttagatgat gaagaaccta tggagttaga   27240
ttatccataa aacgaacatg aaaattattc tcttcctgac attgattgta tttacatctt   27300
gcgagctata tcactatcag gagtgtgtta gaggtacgac tgtactacta aaagaacctt   27360
gcccatcagg aacatacgag ggcaattcac catttcaccc tcttgctgac aataaatttg   27420
cactaacttg cactagcaca cactttgctt ttgcttgtgc tgacggtact cgacataacct   27480
atcagctgcg tgcaagatca gtttcaccaa aacttttcat cagacaagag gaggttcaac   27540
aagagctcta ctcgccactt tttctcattg ttgctgctct agtattttta atactttgct   27600
tcaccattaa gagaaagaca gaatgaatga gctcactta attgacttct atttgtgctt   27660
tttagccttt ctgctattcc ttgttttaat aatgcttatt atatttggt tttcactcga   27720
aatccaggat ctagaagaac cttgtaccaa agtctaaacg aacatgaaac ttctcattgt   27780
tttgacttgt atttctctat gcagttgcat atgcactgta gtacagcgct gtgcatctaa   27840
taaacctcat gtgcttgaag atccttgtaa ggtacaacac tagggtaat acttatagca   27900
ctgcttggct ttgtgctcta ggaaaggttt taccttttca tagatggcac actatggttc   27960
aaacatgcac acctaatgtt actatcaact gtcaagatcc agctggtggt gcgcttatag   28020
ctaggtgttg gtaccttcat gaaggtcacc aaactgctgc atttagagac gtacttgttg   28080
ttttaaataa cgaacaaat taaaatgtct gataatggac cccaatcaaa ccaacgtagt   28140
gcccccgca ttcatttgg tggacccaca gattcaactg acaataacca gaatggagga   28200
cgcaatgggg caaggccaaa acagcgccga ccccaaggtt tacccaataa tactgcgtct   28260
tggttcacag ctctcactca gcatggcaag gaggaactta gattccctcg aggccagggc   28320
gttccaatca acaccaatag tggtccagat gaccaaattg gctactaccg aagagctacc   28380
cgacgagttc gtggtggtga cggcaaaatg aaagagctca gccccagatg gtacttctat   28440
tacctaggaa ctggcccaga agcttcactt ccctacggcg ctaacaaaga aggcatcgta   28500
tgggttgcaa ctgagggagc cttgaataca cccaaagacc acattggcac cgcaatcct   28560
aataacaatg ctgccaccgt gctacaactt cctcaaggaa caacattgcc aaaaggcttc   28620
tacgcagagg gaagcagagg cggcagtcaa gcctcttctc gctcctcatc acgtagtcgc   28680
ggtaattcaa gaaattcaac tcctggcagc agtaggggaa attctcctgc tcgaatggct   28740
agcggaggtg tgtgaaactgc cctcgcgcta ttgctgctag acagattgaa ccagcttgag   28800
agcaaagttt ctggtaaagg ccaacaacaa caaggccaaa ctgtcactaa gaaatctgct   28860
```

-continued

```
gctgaggcat ctaaaaagcc tcgccaaaaa cgtactgcca caaaacagta caacgtcact   28920
caagcatttg ggagacgtgg tccagaacaa acccaaggaa atttcgggga ccaagaccta   28980
atcagacaag gaactgatta caaacattgg ccgcaaattg cacaatttgc tccaagtgcc   29040
tctgcattct ttggaatgtc acgcattggc atggaagtca ccttcgggaa catggctg    29100 acttatcatg gagccattaa attggatgac aaagatccac aattcaaaga caacgtcata   29160
ctgctgaaca agcacattga cgcatacaaa acattcccac caacagagcc taaaaaggac   29220
aaaaagaaaa agactgatga agctcagcct ttgccgcaga gacaaaagaa gcagcccact   29280
gtgactcttc ttcctgcggc tgacatggat gatttctcca gacaacttca aaattccatg   29340
agtggagctt ctgctgattc aactcaggca taaacactca tgatgaccac acaaggcaga   29400
tgggctatgt aaacgttttc gcaattccgt ttacgataca tagtctactc ttgtgcagaa   29460
tgaattctcg taactaaaca gcacaagtag gtttagttaa ctttaatctc acatagcaat   29520
ctttaatcaa tgtgtaacat tagggaggac ttgaaagagc caccacattt tcatcgaggc   29580
cacgcggagt acgatcgagg gtacagtgaa taatgctagg gagagctgcc tatatggaag   29640
agccctaatg tgtaaaatta attttagtag tgctatcccc atgtgatttt aatagcttct   29700
taggagaatg acaaaaaaaa aaaaaaaaaa aaaaaa                             29736
```

<210> SEQ ID NO 2
<211> LENGTH: 29736
<212> TYPE: DNA
<213> ORGANISM: Severe acute respiratory syndrome virus

<400> SEQUENCE: 2

```
ctacccagga aaagccaacc aacctcgatc tcttgtagat ctgttctcta aacgaacttt     60
aaaatctgtg tagctgtcgc tcggctgcat gcctagtgca cctacgcagt ataaacaata    120
ataattttta ctgtcgttga caagaaacga gtaactcgtc cctcttctgc agactgctta    180
cggtttcgtc cgtgttgcag tcgatcatca gcatacctag gtttcgtccg ggtgtgaccg    240
aaaggtaaga tggagagcct tgttcttggt gtcaacgaga aaacacacgt ccaactcagt    300
ttgcctgtcc ttcaggttag agacgtgcta gtgcgtggct cggggactc tgtggaagag     360 gccctatcgg aggcacgtga acacctcaaa aatggcactt gtggtctagt agagctggaa    420
aaaggcgtac tgccccagct tgaacagccc tatgtgttca ttaaacgttc tgatgcctta    480
agcaccaatc acggccacaa ggtcgttgag ctggttgcag aaatgacgg cattcagtac    540 ggtcgtagcg gtataacact gggagtactc gtgccacatg tgggcgaaac cccaattgca    600
taccgcaatg ttcttcttcg taagaacggt aataagggag ccgtggtca tagctatggc    660 atcgatctaa agtcttatga cttaggtgac gagcttggca ctgatcccat tgaagattat    720
gaacaaaact ggaacactaa gcatggcagt ggtgcactcc gtgaactcac tcgtgagctc    780
aatggaggtg cagtcactcg ctatgtcgac aacaatttct gtggcccaga tgggtaccct    840
cttgattgca tcaaagattt tctcgcacgc gcgggcaagt caatgtgcac tctttccgaa    900
caacttgatt acatcgagtc gaagagaggt gtctactgct gccgtgacca tgagcatgaa    960
attgcctggt tcactgagcg ctctgataag agctacgagc accagacacc cttcgaaatt   1020
aagagtgcca agaaatttga cacttccaaa ggggaatgcc caaagtttgt gtttcctctt   1080
aactcaaaag tcaagtcat tcaaccacgt gttgaaaaga aaagactga gggtttcatg    1140 gggcgtatac gctctgtgta ccctgttgca tctccacagg agtgtaacaa tatgcacttg   1200
```

```
tctaccttga tgaaatgtaa tcattgcgat gaagtttcat ggcagacgtg cgactttctg    1260
aaagccactt gtgaacattg tggcactgaa aatttagtta ttgaaggacc tactacatgt    1320
gggtacctac ctactaatgc tgtagtgaaa atgccatgtc ctgcctgtca agacccagag    1380
attggacctg agcatagtgt tgcagattat cacaaccact caaacattga aactcgactc    1440
cgcaagggag gtaggactag atgttttgga ggctgtgtgt ttgcctatgt tggctgctat    1500
aataagcgtg cctactgggt tcctcgtgct agtgctgata ttggctcagg ccatactggc    1560
attactggtg acaatgtgga gaccttgaat gaggatctcc ttgagatact gagtcgtgaa    1620
cgtgttaaca ttaacattgt tggcgatttt catttgaatg aagaggttgc catcattttg    1680
gcatctttct ctgcttctac aagtgccttt attgacacta taaagagtct tgattacaag    1740
tctttcaaaa ccattgttga gtcctgcggt aactataaag ttaccaaggg aaagcccgta    1800
aaaggtgctt ggaacattgg acaacagaga tcagttttaa caccactgtg tggttttccc    1860
tcacaggctg ctggtgttat cagatcaatt tttgcgcgca cacttgatgc agcaaaccac    1920
tcaattcctg atttgcaaag agcagctgtc accatacttg atggtatttc tgaacagtca    1980
ttacgtcttg tcgacgccat ggtttatact tcagacctgc tcaccaacag tgtcattatt    2040
atggcatatg taactggtgg tcttgtacaa cagacttctc agtggttgtc taatctttg    2100 ggcactactg ttgaaaaact caggcctatc tttgaatgga ttgaggcgaa acttagtgca    2160
ggagttgaat tctcaagga tgcttgggag attctcaaat ttctcattac aggtgttttt    2220
gacatcgtca agggtcaaat acaggttgct tcagataaca tcaaggattg tgtaaaatgc    2280
ttcattgatg ttgttaacaa ggcactcgaa atgtgcattg atcaagtcac tatcgctggc    2340
gcaaagttgc gatcactcaa cttaggtgaa gtcttcatcg ctcaaagcaa gggactttac    2400
cgtcagtgta tacgtggcaa ggagcagctg caactactca tgcctcttaa ggcaccaaaa    2460
gaagtaacct ttcttgaagg tgattccat gacacagtac ttacctctga ggaggttgtt    2520
ctcaagaacg gtgaactcga agcactcgag acgcccgttg atagcttcac aaatggagct    2580
atcgttggca caccagtctg tgtaaatggc ctcatgctct tagagattaa ggacaaagaa    2640
caatactgcg cattgtctcc tggtttactg gctacaaaca atgtctttcg cttaaaaggg    2700
ggtgcaccaa ttaaaggtgt aaccttgga gaagatactg tttgggaagt tcaaggttac    2760
aagaatgtga gaatcacatt tgagcttgat gaacgtgttg acaaagtgct taatgaaaag    2820
tgctctgtct acactgttga atccggtacc gaagttactg agtttgcatg tgttgtagca    2880
gaggctgttg tgaagacttt acaaccagtt tctgatctcc ttaccaacat gggtattgat    2940
cttgatgagt ggagtgtagc tacattctac ttatttgatg atgctggtga agaaaacttt    3000
tcatcacgta tgtattgttc cttttaccct ccagatgagg aagaagagga cgatgcagag    3060
tgtgaggaag aagaaattga tgaaacctgt gaacatgagt acggtacaga ggatgattat    3120
caaggtctcc ctctggaatt tggtgcctca gctgaaacag ttcgagttga ggaagaagaa    3180
gaggaagact ggctggatga tactactgag caatcagaga ttgagccaga accagaacct    3240
acacctgaag aaccagttaa tcagtttact ggttatttaa aacttactga caatgttgcc    3300
attaaatgtg ttgacatcgt taaggaggca caaagtgcta atcctatggt gattgtaaat    3360
gctgctaaca tacacctgaa acatggtggt ggtgtagcag gtgcactcaa caaggcaacc    3420
aatggtgcca tgcaaaagga gagtgatgat tacattaagc taaatggccc tcttacagta    3480
ggagggtctt gtttgctttc tggacataat cttgctaaga agtgtctgca tgttgttgga    3540
cctaacctaa atgcaggtga ggacatccag cttcttaagg cagcatatga aaatttcaat    3600
```

```
tcacaggaca tcttacttgc accattgttg tcagcaggca tatttggtgc taaaccactt    3660
cagtctttac aagtgtgcgt gcagacggtt cgtacacagg tttatattgc agtcaatgac    3720
aaagctcttt atgagcaggt tgtcatggat tatcttgata acctgaagcc tagagtggaa    3780
gcacctaaac aagaggagcc accaaacaca gaagattcca aaactgagga gaaatctgtc    3840
gtacagaagc ctgtcgatgt gaagccaaaa attaaggcct gcattgatga ggttaccaca    3900
acactggaag aaactaagtt tcttaccaat aagttactct tgtttgctga tatcaatggt    3960
aagctttacc atgattctca gaacatgctt agaggtgaag atatgtcttt ccttgagaag    4020
gatgcacctt acatggtagg tgatgttatc actagtggtg atatcacttg tgttgtaata    4080
ccctccaaaa aggctggtgg cactactgag atgctctcaa gagctttgaa gaaagtgcca    4140
gttgatgagt atataaccac gtaccctgga caaggatgtg ctggttatac acttgaggaa    4200
gctaagactg ctcttaagaa atgcaaatct gcattttatg tactaccttc agaagcacct    4260
aatgctaagg aagagattct aggaactgta tcctggaatt tgagagaaat gcttgctcat    4320
gctgaagaga caagaaaatt aatgcctata tgcatggatg ttagagccat aatggcaacc    4380
atccaacgta agtataaagg aattaaaatt caagagggca tcgttgacta tggtgtccga    4440
ttcttctttt atactagtaa agagcctgta gcttctatta ttacgaagct gaactctcta    4500
aatgagccgc ttgtcacaat gccaattggt tatgtgacac atggttttaa tcttgaagag    4560
gctgcgcgct gtatgcgttc tcttaaagct cctgccgtag tgtcagtatc atcaccagat    4620
gctgttacta catataatgg atacctcact tcgtcatcaa agacatctga ggagcacttt    4680
gtagaaacag tttctttggc tggctcttac agagattggt cctattcagg acagcgtaca    4740
gagttaggtg ttgaatttct taagcgtggt gacaaaattg tgtaccacac tctggagagc    4800
cccgtcgagt ttcatcttga cggtgaggtt ctttcacttg acaaactaaa gagtctctta    4860
tccctgcggg aggttaagac tataaaagtg ttcacaactg tggacaacac taatctccac    4920
acacagcttg tggatatgtc tatgacatat ggacagcagt ttggtccaac atacttggat    4980
ggtgctgatg ttacaaaaat taaacctcat gtaaatcatg agggtaagac tttctttgta    5040
ctacctagtg atgacacact acgtagtgaa gctttcgagt actaccatac tcttgatgag    5100
agttttcttg gtaggtacat gtctgcttta aaccacacaa agaaatggaa atttcctcaa    5160
gttggtggtt taacttcaat taaatgggct gataacaatt gttatttgtc tagtgtttta    5220
ttagcacttc aacagcttga agtcaaattc aatgcaccag cacttcaaga ggcttattat    5280
agagcccgtg ctggtgatgc tgctaacttt tgtgcactca tactcgctta cagtaataaa    5340
actgttggcg agcttggtga tgtcagagaa actatgaccc atcttctaca gcatgctaat    5400
ttggaatctg caaagcgagt tcttaatgtg tgtgtaaac attgtggtca gaaaactact    5460
accttaacgg tgtagaagc tgtgatgtat atgggtactc tatcttatga taatcttaag    5520
acaggtgttt ccattccatg tgtgtgtggt cgtgatgcta cacaatatct agtacaacaa    5580
gagtcttctt ttgttatgat gtctgcacca ccctgctgagt ataaattaca gcaaggtaca    5640
ttcttatgtg cgaatgagta cactggtaac tatcagtgtg gtcattacac tcatataact    5700
gctaaggaga ccctctatcg tattgacgga gctcacctta caaagatgtc agagtacaaa    5760
ggaccagtga ctgatgtttt ctacaaggaa acatcttaca ctacaaccat caagcctgtg    5820
tcgtataaac tcgatggagt tacttacaca gagattgaac caaaattgga tgggtattat    5880
aaaaaggata atgcttacta tacagagcag cctatagacc ttgtaccaac tcaaccatta    5940
```

```
ccaaatgcga gttttgataa tttcaaactc acatgttcta acacaaaatt tgctgatgat    6000
ttaaatcaaa tgacaggctt cacaaagcca gcttcacgag agctatctgt cacattcttc    6060
ccagacttga atggcgatgt agtggctatt gactatagac actattcagc gagtttcaag    6120
aaaggtgcta aattactgca taagccaatt gtttggcaca ttaaccaggc tacaaccaag    6180
acaacgttca aaccaaacac ttggtgttta cgttgtcttt ggagtacaaa gccagtagat    6240
acttcaaatt catttgaagt tctggcagta gaagacacac aaggaatgga caatcttgct    6300
tgtgaaagtc aacaacccac ctctgaagaa gtagtggaaa atcctaccat acagaaggaa    6360
gtcatagagt gtgacgtgaa aactaccgaa gttgtaggca atgtcatact aaaccatca     6420 gatgaaggtg ttaaagtaac acaagagtta ggtcatgagg atcttatggc tgcttatgtg    6480
gaaaacacaa gcattaccat taagaaacct aatgagcttt cactagcctt aggttttaaaa   6540 acaattgcca ctcatggtat tgctgcaatt aatagtgttc cttggagtaa aattttggct    6600
tatgtcaaac cattcttagg acaagcagca attacaacat caaattgcgc taagagatta    6660
gcacaacgtg tgtttaacaa ttatatgcct tatgtgttta cattattgtt ccaattgtgt    6720
acttttacta aaagtaccaa ttctagaatt agagcttcac tacctacaac tattgctaaa    6780
aatagtgtta agagtgttgc taaattatgt ttggatgccg gcattaatta tgtgaagtca    6840
cccaaatttt ctaaattgtt cacaatcgct atgtggctat tgttgttaag tatttgctta    6900
ggttctctaa tctgtgtaac tgctgctttt ggtgtactct tatctaattt tggtgctcct    6960
tcttattgta atggcgttag agaattgtat cttaattcgt ctaacgttac tactatggat    7020
ttctgtgaag gttcttttcc ttgcagcatt tgtttaagtg gattagactc ccttgattct    7080
tatccagctc ttgaaaccat tcaggtgacg atttcatcgt acaagctaga cttgacaatt    7140
ttaggtctgg ccgctgagtg ggtttttggca tatatgttgt tcacaaaatt cttttattta    7200 ttaggtctt cagctataat gcaggtgttc tttggctatt ttgctagtca tttcatcagc    7260
aattcttggc tcatgtggtt tatcattagt attgtacaaa tggcacccgt ttctgcaatg    7320
gttaggatgt acatcttctt tgcttctttc tactacatat ggaagagcta tgttcatatc    7380
atggatggtt gcacctcttc gacttgcatg atgtgctata agcgcaatcg tgccacacgc    7440
gttgagtgta caactattgt taatggcatg aagagatctt tctatgtcta tgcaaatgga    7500
ggccgtggct tctgcaagac tcacaattgg aattgtctca attgtgacac attttgcact    7560
ggtagtacat tcattagtga tgaagttgct cgtgatttgt cactccagtt taaaagacca    7620 atcaaccta ctgaccagtc atcgtatatt gttgatagtg ttgctgtgaa aaatggcgcg    7680
cttcacctct actttgacaa ggctggtcaa aagacctatg agagacatcc gctctcccat    7740
tttgtcaatt tagacaattt gagagctaac aacactaaag gttcactgcc tattaatgtc    7800 atagttttg atggcaagtc caaatgcgac gagtctgctt ctaagtctgc ttctgtgtac    7860
tacagtcagc tgatgtgcca acctattctg ttgcttgacc aagctcttgt atcagacgtt    7920
ggagatagta ctgaagtttc cgttaagatg ttcgatgctt atgtcgacac cttttcagca    7980 actttagtg ttcctatgga aaacttaag gcacttgttg ctacagctca cagcgagtta     8040
gcaaagggtg tagctttaga tggtgtcctt tctacattcg tgtcagctgc ccgacaaggt    8100
gttgttgata ccgatgttga cacaaaggat gttattgaat gtctcaaact ttcacatcac    8160
tctgacttag aagtgacagg tgacagttgt aacaatttca tgctcaccta taataaggtt    8220
gaaaacatga cgcccagaga tcttggcgca tgtattgact gtaatgcaag gcatatcaat    8280
gcccaagtag caaaaagtca caatgtttca ctcatctgga atgtaaaaga ctacatgtct    8340
```

```
ttatctgaac agctgcgtaa acaaattcgt agtgctgcca agaagaacaa catacctttt    8400
agactaactt gtgctacaac tagacaggtt gtcaatgtca taactactaa aatctcactc    8460
aagggtggta agattgttag tacttgtttt aaacttatgc ttaaggccac attattgtgc    8520
gttcttgctg cattggtttg ttatatcgtt atgccagtac atacattgtc aatccatgat    8580
ggttacacaa atgaaatcat tggttacaaa gccattcagg atggtgtcac tcgtgacatc    8640
atttctactg atgattgttt tgcaaataaa catgctggtt ttgacgcatg gtttagccag    8700
cgtggtggtt catacaaaaa tgacaaaagc tgccctgtag tagctgctat cattacaaga    8760
gagattggtt tcatagtgcc tggcttaccg ggtactgtgc tgagagcaat caatggtgac    8820
ttcttgcatt ttctacctcg tgtttttagt gctgttggca acatttgcta cacaccttcc    8880
aaactcattg agtatagtga ttttgctacc tctgcttgcg ttcttgctgc tgagtgtaca    8940
attttttaagg atgctatggg caaacctgtg ccatattgtt atgacactaa tttgctagag    9000
ggttctatttt cttatagtga gcttcgtcca gacactcgtt atgtgcttat ggatggttcc    9060
atcatacagt ttcctaacac ttacctggag ggttctgtta gagtagtaac aacttttgat    9120
gctgagtact gtagacatgg tacatgcgaa aggtcagaag taggtatttg cctatctacc    9180
agtggtagat gggttcttaa taatgagcat tacagagctc tatcaggagt tttctgtggt    9240
gttgatgcga tgaatctcat agctaacatc tttactcctc ttgtgcaacc tgtgggtgct    9300
ttagatgtgt ctgcttcagt agtggctggt ggtattattg ccatattggt gacttgtgct    9360
gcctactact ttatgaaatt cagacgtgtt tttggtgagt acaaccatgt tgttgctgct    9420
aatgcacttt tgttttttgat gtcttttcact atactctgtc tggtaccagc ttacagcttt    9480
ctgccgggag tctactcagt cttttacttg tacttgacat tctatttcac caatgatgtt    9540
tcattcttgg ctcaccttca atggtttgcc atgttttctc ctattgtgcc tttttggata    9600
acagcaatct atgtattctg tatttctctg aagcactgcc attggttctt taacaactat    9660
cttaggaaaa gagtcatgtt taatggagtt acatttagta ccttcgagga ggctgctttg    9720
tgtacctttt tgctcaacaa ggaaatgtac ctaaaattgc gtagcgagac actgttgcca    9780
cttacacagt ataacaggta tcttgctcta tataacaagt acaagtattt cagtggagcc    9840
ttagatacta ccagctatcg tgaagcagct tgctgccact tagcaaaggc tctaaatgac    9900
tttagcaact caggtgctga tgttctctac caaccaccac agacatcaat cacttctgct    9960
gttctgcaga gtggttttag gaaaatggca ttcccgtcag gcaaagttga agggtgcatg   10020
gtacaagtaa cctgtggaac tacaactctt aatggattgt ggttggatga cacagtatac   10080
tgtccaagac atgtcatttg cacagcagaa gacatgctta atcctaacta tgaagatctg   10140
ctcattcgca aatccaacca tagctttctt gttcaggctg gcaatgttca acttcgtgtt   10200
attggccatt ctatgcaaaa ttgtctgctt aggcttaaag ttgatacttc taaccctaag   10260
acacccaagt ataaatttgt ccgtatccaa cctggtcaaa cattttcagt tctagcatgc   10320
tacaatggtt caccatctgg tgtttatcag tgtgccatga gacctaatca taccattaaa   10380
ggttctttcc ttaatggatc atgtggtagt gttggtttta acattgatta tgattgcgtg   10440
tcttttctgct atatgcatca tatggagctt ccaacaggag tacacgctgg tactgactta   10500
gaaggtaaat tctatggtcc atttgttgac agacaaactg cacaggctgc aggtacagac   10560
acaaccataa cattaaatgt tttggcatgg ctgtatgctg ctgttatcaa tggtgatagg   10620
tggtttctta atagattcac cactactttg aatgacttta acttgtggc aatgaagtac   10680
```

```
aactatgaac ctttgacaca agatcatgtt gacctctttc tgctcaaaca  10740
ggaattgccg tcttagatat gtgtgctgct ttgaaagagc tgctgcagaa tggtatgaat  10800
ggtcgtacta tccttggtag cactatttta gaagatgagt ttacaccatt tgatgttgtt  10860
agacaatgct ctggtgttac cttccaaggt aagttcaaga aaattgttaa gggcactcat  10920
cattggatgc ttttaacttt cttgacatca ctattgattc ttgttcaaag tacacagtgg  10980
tcactgtttt tctttgttta cgagaatgct ttcttgccat ttactcttgg tattatggca  11040
attgctgcat gtgctatgct gcttgttaag cataagcacg cattcttgtg cttgtttctg  11100
ttaccttctc ttgcaacagt tgcttacttt aatatggtct acatgcctgc tagctgggtg  11160
atgcgtatca tgacatggct tgaattggct gacactagct tgtctggtta taggcttaag  11220
gattgtgtta tgtatgcttc agctttagtt ttgcttattc tcatgacagc tcgcactgtt  11280
tatgatgatg ctgctagacg tgtttggaca ctgatgaatg tcattacact tgtttacaaa  11340
gtctactatg gtaatgcttt agatcaagct atttccatgt gggccttagt tatttctgta  11400
acctctaact attctggtgt cgttacgact atcatgtttt tagctagagc tatagtgttt  11460
gtgtgtgttg agtattaccc attgttattt attactggca acaccttaca gtgtatcatg  11520
cttgtttatt gtttcttagg ctattgttgc tgctgctact ttggcttttt ctgtttactc  11580
aaccgttact tcaggcttac tcttggtgtt tatgactact tggtctctac acaagaattt  11640
aggtatatga actcccaggg gcttttgcct cctaagagta gtattgatgc tttcaagctt  11700
aacattaagt tgttgggtat tggaggtaaa ccatgtatca aggttgctac tgtacagtct  11760
aaaatgtctg acgtaaagtg cacatctgtg gtactgctct cggttcttca acaacttaga  11820
gtagagtcat cttctaaatt gtgggcacaa tgtgtacaac tccacaatga tattcttctt  11880
gcaaaagaca caactgaagc tttcgagaag atggtttctc ttttgtctgt tttgctatcc  11940
atgcagggtg ctgtagacat taataggttg tgcgaggaaa tgctcgataa ccgtgctact  12000
cttcaggcta ttgcttcaga atttagttct ttaccatcat atgccgctta tgccactgcc  12060
caggaggcct atgagcaggc tgtagctaat ggtgattctg aagtcgttct caaaaagtta  12120
aagaaatctt tgaatgtggc taaatctgag tttgaccgtg atgctgccat gcaacgcaag  12180
ttggaaaaga tggcagatca ggctatgacc caaatgtaca acaggcaag atctgaggac  12240
aagagggcaa aagtaactag tgctatgcaa acaatgctct tcactatgct taggaagctt  12300
gataatgatg cacttaacaa cattatcaac aatgcgcgtg atggttgtgt tccactcaac  12360
atcataccat tgactacagc agccaaactc atggttgttg tccctgatta tggtacctac  12420
aagaacactt gtgatggtaa caccttaca tatgcatctg cactctggga aatccagcaa  12480
gttgttgatg cggatagcaa gattgttcaa cttagtgaaa ttaacatgga caattccacca  12540
aatttggctt ggcctcttat tgttacagct ctaagagcca actcagctgt taaactacag  12600
aataatgaac tgagtccagt agcactacga cagatgtcct gtgcggctgg taccacacaa  12660
acagcttgta ctgatgacaa tgcacttgcc tactataaca attcgaaggg aggtaggttt  12720
gtgctggcat tactatcaga ccaccaagat ctcaaatggg ctagattccc taagagtgat  12780
ggtacaggta caatttacac agaactggaa ccaccttgta ggtttgttac agacacacca  12840
aaagggccta agtgaaaata cttgtacttc atcaaaggct aaacaacct aaatagaggt  12900
atggtgctgg gcagtttagc tgctacagta cgtcttcagg ctggaaatgc tacagaagta  12960
cctgccaatt caactgtgct ttccttctgt gcttttgcag tagaccctgc taaagcatat  13020
aaggattacc tagcaagtgg aggacaacca atcaccaact gtgtgaagat gttgtgtaca  13080
```

```
cacactggta caggacaggc aattactgta acaccagaag ctaacatgga ccaagagtcc   13140
tttggtggtg cttcatgttg tctgtattgt agatgccaca ttgaccatcc aaatcctaaa   13200
ggattctgtg acttgaaagg taagtacgtc caaataccta ccacttgtgc taatgaccca   13260
gtgggtttta cacttagaaa cacagtctgt accgtctgcg gaatgtggaa aggttatggc   13320
tgtagttgtg accaactccg cgaacccttg atgcagtctg cggatgcatc aacgttttta   13380
aacgggtttg cggtgtaagt gcagcccgtc ttacaccgtg cggcacaggc actagtactg   13440
atgtcgtcta cagggctttt gatatttaca acgaaaaagt tgctggtttt gcaaagttcc   13500
taaaaactaa ttgctgtcgc ttccaggaga aggatgagga aggcaattta ttagactctt   13560
actttgtagt taagaggcat actatgtcta actaccaaca tgaagagact atttataact   13620
tggttaaaga ttgtccagcg gttgctgtcc atgactttt caagtttaga gtagatggtg   13680
acatggtacc acatatatca cgtcagcgtc taactaaata cacaatggct gatttagtct   13740
atgctctacg tcattttgat gagggtaatt gtgatacatt aaaagaaata ctcgtcacat   13800
acaattgctg tgatgatgat tatttcaata agaaggattg gtatgacttc gtagagaatc   13860
ctgacatctt acgcgtatat gctaacttag gtgagcgtgt acgccaatca ttattaaaga   13920
ctgtacaatt ctgcgatgct atgcgtgatg caggcattgt aggcgtactg acattagata   13980
atcaggatct taatgggaac tggtacgatt tcggtgattt cgtacaagta gcaccaggct   14040
gcggagttcc tattgtggat tcatattact cattgctgat gcccatcctc actttgacta   14100
gggcattggc tgctgagtcc catatggatg ctgatctcgc aaaaccactt attaagtggg   14160
atttgctgaa atatgatttt acggaagaga gactttgtct cttcgaccgt tattttaaat   14220
attgggacca gacataccat cccaattgta ttaactgttt ggatgatagg tgtatccttc   14280
attgtgcaaa ctttaatgtg ttattttcta ctgtgtttcc acctacaagt tttggaccac   14340
tagtaagaaa atatttgta gatggtgttc cttttgttgt ttcaactgga taccattttc   14400
gtgagttagg agtcgtacat aatcaggatg taaacttaca tagctcgcgt ctcagtttca   14460
aggaactttt agtgtatgct gctgatccag ctatgcatgc agcttctggc aatttattgc   14520
tagataaacg cactacatgc ttttcagtag ctgcactaac aaacaatgtt gcttttcaaa   14580
ctgtcaaacc cggtaatttt aataaagact tttatgactt tgctgtgtct aaaggtttct   14640
ttaaggaagg aagttctgtt gaactaaaac acttcttctt tgctcaggat ggcaacgctg   14700
ctatcagtga ttatgactat tatcgttata atctgccaac aatgtgtgat atcagacaac   14760
tcctattcgt agttgaagtt gttgataaat actttgattg ttacgatggt ggctgtatta   14820
atgccaacca agtaatcgtt aacaatctgg ataaatcagc tggttcccca tttaataaat   14880
ggggtaaggc tagactttat tatgactcaa tgagttatga ggatcaagat gcacttttcg   14940
cgtatactaa gcgtaatgtc atccctacta taactcaaat gaatcttaag tatgccatta   15000
gtgcaaagaa tagagctcgc accgtagctg tgtctctat ctgtagtact atgacaaata   15060
gacagtttca tcagaaatta ttgaagtcaa tagccgccac tagaggagct actgtggtaa   15120
ttggaacaag caagttttac ggtggctggc ataatatgtt aaaaactgtt tacagtgatg   15180
tagaaactcc acaccttatg ggttgggatt atccaaaatg tgacagagcc atgcctaaca   15240
tgcttaggat aatggcctct cttgttcttg ctcgcaaaca taacacttgc tgtaacttat   15300
cacaccgttt ctacaggtta gctaacgagt gtgcgcaagt attaagtgag atggtcatgt   15360
gtggcggctc actatatgtt aaaccaggtg gaacatcatc cggtgatgct acaactgctt   15420
```

```
atgctaatag tgtctttaac atttgtcaag ctgttacagc caatgtaaat gcacttcttt   15480
caactgatgg taataagata gctgacaagt atgtccgcaa tctacaacac aggctctatg   15540
agtgtctcta tagaaatagg gatgttgatc atgaattcgt ggatgagttt tacgcttacc   15600
tgcgtaaaca tttctccatg atgattcttt ctgatgatgc cgttgtgtgc tataacagta   15660
actatgcggc tcaaggttta gtagctagca ttaagaactt taaggcagtt ctttattatc   15720
aaaataatgt gttcatgtct gaggcaaaat gttggactga gactgacctt actaaaggac   15780
ctcacgaatt ttgctcacag catacaatgc tagttaaaca aggagatgat tacgtgtacc   15840
tgccttaccc agatccatca agaatattag gcgcaggctg ttttgtcgat gatattgtca   15900
aaacagatgg tacacttatg attgaaaggt tcgtgtcact ggctattgat gcttacccac   15960
ttacaaaaca tcctaatcag gagtatgctg atgtctttca cttgtattta caatacatta   16020
gaaagttaca tgatgagctt actggccaca tgttggacat gtattccgta atgctaacta   16080
atgataacac ctcacggtac tgggaacctg agttttatga ggctatgtac acaccacata   16140
cagtcttgca ggctgtaggt gcttgtgtat tgtgcaattc acagacttca cttcgttgcg   16200
gtgcctgtat taggagacca ttcctatgtt gcaagtgctg ctatgaccat gtcatttcaa   16260
catcacacaa attagtgttg tctgttaatc cctatgtttg caatgcccca ggttgtgatg   16320
tcactgatgt gacacaactg tatcgaggag gtatgagcta ttattgcaag tcacataagc   16380
ctcccattag ttttccatta tgtgctaatg gtcaggtttt tggtttatac aaaaacacat   16440
gtgtaggcag tgacaatgtc actgacttca atgcgatagc aacatgtgat tggactaatg   16500
ctggcgatta catacttgcc aacacttgta ctgagagact caagcttttc gcagcagaaa   16560
cgctcaaagc cactgaggaa acatttaagc tgtcatatgg tattgccact gtacgcgaag   16620
tactctctga cagagaattg catctttcat gggaggttgg aaaacctaga ccaccattga   16680
acagaaacta tgtctttact ggttaccgtg taactaaaaa tagtaaagta cagattggag   16740
agtacacctt tgaaaaaggt gactatggtg atgctgttgt gtacagaggt actacgacat   16800
acaagttgaa tgttggtgat tactttgtgt tgacatctca cactgtaatg ccacttagtg   16860
cacctactct agtgccacaa gagcactatg tgagaattac tggcttgtac ccaacactca   16920
acatctcaga tgagttttct agcaatgttg caaattatca aaaggtcggc atgcaaaagt   16980
actctacact ccaaggacca cctggtactg gtaagagtca ttttgccatc ggacttgctc   17040
tctattaccc atctgctcgc atagtgtata cggcatgctc tcatgcagct gttgatgccc   17100
tatgtgaaaa ggcattaaaa tatttgccca tagataaatg tagtagaatc ataccctgcgc   17160 gtgcgcgcgt agagtgtttt gataaattca aagtgaattc aacactagaa cagtatgttt   17220
tctgcactgt aaatgcattg ccagaaacaa ctgctgacat tgtagtcttt gatgaaatct   17280
ctatggctac taattatgac ttgagtgttg tcaatgctag acttcgtgca aaacactacg   17340
tctatattgg cgatcctgct caattaccag ccccccgcac attgctgact aaaggcacac   17400
tagaaccaga atattttaat tcagtgtgca gacttatgaa aacaataggt ccagacatgt   17460
tccttggaac ttgtcgccgt tgtcctgctg aaattgttga cactgtgagt gctttagttt   17520
atgacaataa gctaaaagca cacaaggata agtcagctca atgcttcaaa atgttctaca   17580 aggtgttat tacacatgat gtttcatctg caatcaacag acctcaaata ggcgttgtaa   17640
gagaatttct tacacgcaat cctgcttgga gaaaagctgt ttttatctca ccttataatt   17700
cacagaacgc tgtagcttca aaaatcttag gattgcctac gcagactgtt gattcatcac   17760
agggttctga atatgactat gtcatattca cacaaactac tgaaacagca cactcttgta   17820
```

```
atgtcaaccg cttcaatgtg gctatcacaa gggcaaaaat tggcattttg tgcataatgt   17880
ctgatagaga tctttatgac aaactgcaat ttacaagtct agaaatacca cgtcgcaatg   17940
tggctacatt acaagcagaa aatgtaactg gactttttaa ggactgtagt aagatcatta   18000
ctggtcttca tcctacacag gcacctacac acctcagcgt tgatataaag ttcaagactg   18060
aaggattatg tgttgacata ccaggcatac caaaggacat gacctaccgt agactcatct   18120
ctatgatggg tttcaaaatg aattaccaag tcaatggtta ccctaatatg tttatcaccc   18180
gcgaagaagc tattcgtcac gttcgtgcgt ggattggctt tgatgtagag ggctgtcatg   18240
caactagaga tgctgtgggt actaacctac ctctccagct aggattttct acaggtgtta   18300
acttagtagc tgtaccgact ggttatgttg acactgaaaa taacacagaa ttcaccagag   18360
ttaatgcaaa acctccacca ggtgaccagt ttaaacatct tataccactc atgtataaag   18420
gcttgccctg gaatgtagtg cgtattaaga tagtacaaat gctcagtgat acactgaaag   18480
gattgtcaga cagagtcgtg ttcgtccttt gggcgcatgg ctttgagctt acatcaatga   18540
agtactttgt caagattgga cctgaaagaa cgtgttgtct gtgtgacaaa cgtgcaactt   18600
gcttttctac ttcatcagat acttatgcct gctggaatca ttctgtgggt tttgactatg   18660
tctataaccc atttatgatt gatgttcagc agtggggctt tacgggtaac cttcagagta   18720
accatgacca acattgccag gtacatgaaa atgcacatgt ggctagttgt gatgctatca   18780
tgactagatg tttagcagtc catgagtgct ttgttaagcg cgttgattgg tctgttgaat   18840
accctattat aggagatgaa ctgagggtta attctgcttg cagaaaagta caacacatgg   18900
ttgtgaagtc tgcattgctt gctgataagt ttccagttct tcatgacatt ggaaatccaa   18960
aggctatcaa gtgtgtgcct caggctgaag tagaatggaa gttctacgat gctcagccat   19020
gtagtgacaa agcttacaaa atagaggaac tcttctattc ttatgctaca catcacgata   19080
aattcactga tggtgtttgt ttgttttgga attgtaacgt tgatcgttac ccagccaatg   19140
caattgtgtg taggtttgac acaagagtct tgtcaaactt gaacttacca ggctgtgatg   19200
gtggtagttt gtatgtgaat aagcatgcat tccacactcc agcttttgat aaaagtgcat   19260
ttactaattt aaagcaattg cctttctttt actattctga tagtccttgt gagtctcatg   19320
gcaaacaagt agtgtcggat attgattatg ttccactcaa atctgctacg tgtattacac   19380
gatgcaattt aggtggtgct gtttgcagac accatgcaaa tgagtaccga cagtacttgg   19440
atgcatataa tatgatgatt tctgctggat ttagcctatg gatttacaaa caatttgata   19500
cttataacct gtggaataca tttaccaggt tacagagttt agaaaatgtg cttataatg   19560 ttgttaataa aggacacttt gatggacacg ccggcgaagc acctgtttcc atcattaata   19620
atgctgttta cacaaaggta gatggtattg atgtggagat ctttgaaaat aagacaacac   19680
ttcctgttaa tgttgcattt gagctttggg ctaagcgtaa cattaaacca gtgccagaga   19740
ttaagatact caataatttg ggtgttgata tcgctgctaa tactgtaatc tgggactaca   19800
aaagagaagc cccagcacat gtatctacaa taggtgtctg cacaatgact gacattgcca   19860
agaaacctac tgagagtgct tgttcttcac ttactgtctt gtttgatggt agagtggaag   19920
gacaggtaga ccttttttaga aacgcccgta atggtgtttt aataacagaa ggttcagtca   19980
aaggtctaac accttcaaag ggaccagcac aagctagcgt caatggagtc acattaattg   20040
gagaatcagt aaaaacacag tttaactact ttaagaaagt agacggcatt attcaacagt   20100
tgcctgaaac ctactttact cagagcagag acttagagga ttttaagccc agatcacaaa   20160
```

```
tggaaactga ctttctcgag ctcgctatgg atgaattcat acagcgatat aagctcgagg    20220
gctatgcctt cgaacacatc gtttatggag atttcagtca tggacaactt ggcggtcttc    20280
atttaatgat aggcttagcc aagcgctcac aagattcacc acttaaatta gaggatttta    20340
tccctatgga cagcacagtg aaaaattact tcataacaga tgcgcaaaca ggttcatcaa    20400
aatgtgtgtg ttctgtgatt gatcttttac ttgatgactt tgtcgagata ataaagtcac    20460
aagatttgtc agtgatttca aaagtggtca aggttacaat tgactatgct gaaatttcat    20520
tcatgctttg gtgtaaggat ggacatgttg aaaccttcta cccaaaacta caagcaagtc    20580
aagcgtggca accaggtgtt gcgatgccta acttgtacaa gatgcaaaga atgcttcttg    20640
aaaagtgtga ccttcagaat tatggtgaaa atgctgttat accaaaagga ataatgatga    20700
atgtcgcaaa gtatactcaa ctgtgtcaat acttaaatac acttacttta gctgtaccct    20760
acaacatgag agttattcac tttggtgctg ctctgataa aggagttgca ccaggtacag    20820
ctgtgctcag acaatggttg ccaactggca cactacttgt cgattcagat cttaatgact    20880
tcgtctccga cgcagattct actttaattg gagactgtgc aacagtacat acggctaata    20940
aatgggacct tattattagc gatatgtatg accctaggac caaacatgtg acaaaagaga    21000
atgactctaa agaagggttt ttcacttatc tgtgtggatt tataaagcaa aaactagccc    21060
tgggtggttc tatagctgta aagataacag agcattcttg gaatgctgac ctttacaagc    21120
ttatgggcca tttctcatgg tggacagctt ttgttacaaa tgtaaatgca tcatcatcgg    21180 aagcatttt aattggggct aactatcttg gcaagccgaa ggaacaaatt gatggctata    21240
ccatgcatgc taactacatt ttctggagga acacaaatcc tatccagttg tcttcctatt    21300
cactctttga catgagcaaa tttcctctta aattaagagg aactgctgta atgtctctta    21360
aggagaatca aatcaatgat atgatttatt ctcttctgga aaaaggtagg cttatcatta    21420
gagaaaacaa cagagttgtg gtttcaagtg atattcttgt taacaactaa acgaacatgt    21480
ttattttctt attatttctt actctcacta gtggtagtga ccttgaccgg tgcaccactt    21540
ttgatgatgt tcaagctcct aattacactc aacatacttc atctatgagg ggggtttact    21600
atcctgatga aattttagat tcagacactc tttatttaac tcaggattta tttcttccat    21660
tttattctaa tgttacaggg tttcatacta ttaatcatac gtttggcaac cctgtcatac    21720
cttttaagga tggtatttat tttgctgcca cagagaaatc aaatgttgtc cgtggttggg    21780 ttttttggttc taccatgaac aacaagtcac agtcggtgat tattattaac aattctacta    21840
atgttgttat acgagcatgt aactttgaat tgtgtgacaa cccctttctt gctgtttcta    21900
aacccatggg tacacagaca catactatga tattcgataa tgcatttaat tgcacttttcg    21960 agtacatatc tgatgccttt tcgcttgatg tttcagaaaa gtcaggtaat tttaaacact    22020
tacgagagtt tgtgtttaaa ataaagatg ggttctctta tgtttataag ggctatcaac    22080
ctatagatgt agttcgtgat ctaccttctg gtttaacac tttgaaacct atttttaagt    22140
tgcctcttgg tattaacatt acaaatttta gagccattct tacagccttt tcacctgctc    22200
aagacatttg gggcacgtca gctgcagcct attttgttgg ctatttaaag ccaactacat    22260
ttatgctcaa gtatgatgaa aatggtacaa tcacagatgc tgttgattgt tctcaaaatc    22320
cacttgctga actcaaatgc tctgttaaga gctttgagat tgacaaagga atttaccaga    22380
cctctaattt cagggttgtt ccctcaggag atgttgtgag attccctaat attacaaact    22440
tgtgtccttt tggagaggtt tttaatgcta ctaaattccc ttctgtctat gcatgggaga    22500
gaaaaaaaat ttctaattgt gttgctgatt actctgtgct ctacaactca acattttttt    22560
```

```
caacctttaa gtgctatggc gtttctgcca ctaagttgaa tgatctttgc ttctccaatg    22620
tctatgcaga ttcttttgta gtcaagggag atgatgtaag acaaatagcg ccaggacaaa    22680
ctggtgttat tgctgattat aattataaat tgccagatga tttcatgggt tgtgtccttg    22740
cttggaatac taggaacatt gatgctactt caactggtaa ttataattat aaatataggt    22800
atcttagaca tggcaagctt aggccctttg agagagacat atctaatgtg cctttctccc    22860
ctgatggcaa accttgcacc ccacctgctc ttaattgtta ttggccatta aatgattatg    22920
gttttttacac cactactggc attggctacc aaccttacag agttgtagta ctttcttttg    22980
aactttaaa tgcaccggcc acggtttgtg gaccaaaatt atccactgac cttattaaga    23040
accagtgtgt caattttaat tttaatggac tcactggtac tggtgtgtta actccttctt    23100
caaagagatt tcaaccattt caacaatttg gccgtgatgt ttctgatttc actgattccg    23160
ttcgagatcc taaaacatct gaaatattag acatttcacc ttgcgctttt ggggtgtaa    23220
gtgtaattac acctggaaca aatgcttcat ctgaagttgc tgttctatat caagatgtta    23280
actgcactga tgtttctaca gcaattcatg cagatcaact cacaccagct tggcgcatat    23340
attctactgg aaacaatgta ttccagactc aagcaggctg tcttatagga gctgagcatg    23400
tcgacacttc ttatgagtgc gacattccta ttggagctgg catttgtgct agttaccata    23460
cagtttcttt attacgtagt actagccaaa aatctattgt ggcttatact atgtctttag    23520
gtgctgatag ttcaattgct tactctaata caccattgc tatacctact aacttttcaa    23580
ttagcattac tacagaagta atgcctgttt ctatggctaa aacctccgta gattgtaata    23640
tgtacatctg cggagattct actgaatgtg ctaatttgct tctccaatat ggtagctttt    23700
gcacacaact aaatcgtgca ctctcaggta ttgctgctga acaggatcgc aacacacgtg    23760
aagtgttcgc tcaagtcaaa caaatgtaca aaaccccaac tttgaaatat tttggtggtt    23820
ttaattttc acaaatatta cctgacccctc taaagccaac taagaggtct tttattgagg    23880
acttgctctt taataaggtg acactcgctg atgctggctt catgaagcaa tatggcgaat    23940
gcctaggtga tattaatgct agagatctca tttgtgcgca gaagttcaat ggacttacag    24000
tgttgccacc tctgctcact gatgatatga ttgctgccta cactgctgct ctagttagtg    24060
gtactgccac tgctggatgg acatttggtg ctggcgctgc tcttcaaata cctttttgcta    24120
tgcaaatggc atataggttc aatggcattg gagttaccca aaatgttctc tatgagaacc    24180
aaaaacaaat cgccaaccaa tttaacaagg cgattagtca aattcaagaa tcacttacaa    24240
caacatcaac tgcattgggc aagctgcaag acgttgttaa ccagaatgct caagcattaa    24300
acacacttgt taaacaactt agctctaatt ttggtgcaat ttcaagtgtg ctaaatgata    24360
tcctttcgcg acttgataaa gtcgaggcgg aggtacaaat tgacaggtta attacaggca    24420
gacttcaaag ccttcaaacc tatgtaacac aacaactaat cagggctgct gaaatcaggg    24480
cttctgctaa tcttgctgct actaaaatgt ctgagtgtgt tcttggacaa tcaaaaagag    24540
ttgactttg tggaaagggc taccaccta tgtccttccc acaagcagcc ccgcatggtg    24600
ttgtcttcct acatgtcacg tatgtgccat cccaggagag gaacttcacc acagcgccag    24660
caatttgtca tgaaggcaaa gcatacttcc ctcgtgaagg tgtttttgtg tttaatggca    24720
cttcttggtt tattacacag aggaacttct tttctccaca aataaattact acagacaata    24780
catttgtctc aggaaattgt gatgtcgtta ttggcatcat taacaacaca gtttatgatc    24840
ctctgcaacc tgagcttgac tcattcaaag aagagctgga caagtacttc aaaaatcata    24900
```

```
catcaccaga tgttgatctt ggcgacattt caggcattaa cgcttctgtc gtcaacattc    24960
aaaaagaaat tgaccgcctc aatgaggtcg ctaaaaattt aaatgaatca ctcattgacc    25020
ttcaagaatt gggaaaatat gagcaatata ttaaatggcc ttggtatgtt tggctcggct    25080
tcattgctgg actaattgcc atcgtcatgg ttacaatctt gctttgttgc atgactagtt    25140
gttgcagttg cctcaagggt gcatgctctt gtggttcttg ctgcaagttt gatgaggatg    25200
actctgagcc agttctcaag ggtgtcaaat tacattacac ataaacgaac ttatggattt    25260
gtttatgaga ttttttactc ttagatcaat tactgcacag ccagtaaaaa ttgacaatgc    25320
ttctcctgca agtactgttc atgctacagc aacgataccg ctacaagcct cactcccttt    25380
cggatggctt gttattggcg ttgcatttct tgctgttttt cagagcgcta ccaaaataat    25440
tgcgctcaat aaaagatggc agctagccct ttataagggc ttccagttca tttgcaattt    25500
actgctgcta tttgttacca tctattcaca tcttttgctt gtcgctgcag gtatggaggc    25560
gcaattttg tacctctatg ccttgatata ttttctacaa tgcatcaacg catgtagaat    25620
tattatgaga tgttggcttt gttggaagtg caaatccaag aacccattac tttatgatgc    25680
caactacttt gtttgctggc acacacataa ctatgactac tgtataccat ataacagtgt    25740
cacagataca attgtcgtta ctgaaggtga cggcatttca acaccaaaac tcaaagaaga    25800
ctaccaaatt ggtggttatt ctgaggatag gcactcaggt gttaaagact atgtcgttgt    25860
acatggctat ttcaccgaag tttactacca gcttgagtct acacaaatta ctacagacac    25920
tggtattgaa aatgctacat tcttcatctt taacaagctt gttaaagacc caccgaatgt    25980
gcaaatacac acaatcgacg gctcttcagg agttgctaat ccagcaatgg atccaattta    26040
tgatgagccg acgacgacta ctagcgtgcc tttgtaagca caagaaagtg agtacgaact    26100
tatgtactca ttcgtttcgg aagaaacagg tacgttaata gttaatagcg tacttctttt    26160
tcttgctttc gtggtattct tgctagtcac actagccatc cttactgcgc ttcgattgtg    26220
tgcgtactgc tgcaatattg ttaacgtgag tttagtaaaa ccaacggttt acgtctactc    26280
gcgtgttaaa aatctgaact cttctgaagg agttcctgat cttctggtct aaacgaacta    26340
actattatta ttattctgtt tggaacttta acattgctta tcatggcaga caacggtact    26400
attaccgttg aggagcttaa acaactcctg gaacaatgga acctagtaat aggtttccta    26460
ttcctagcct ggattatgtt actacaattt gcctattcta atcggaacag gttttttgtac    26520
ataataaagc ttgttttcct ctggctcttg tggccagtaa cacttgcttg ttttgtgctt    26580
gctgctgtct acagaattaa ttgggtgact ggcgggattg cgattgcaat ggcttgtatt    26640
gtaggcttga tgtggcttag ctacttcgtt gcttccttca ggctgtttgc tcgtacccgc    26700
tcaatgtggt cattcaaccc agaaacaaac attcttctca atgtgcctct ccgggggaca    26760
attgtgacca gaccgctcat ggaaagtgaa cttgtcattg gtgctgtgat cattcgtggt    26820
cacttgcgaa tggccggaca ctccctaggg cgctgtgaca ttaaggacct gccaaaagag    26880
atcactgtgg ctacatcacg aacgctttct tattacaaat taggagcgtc gcagcgtgta    26940
ggcactgatt caggttttgc tgcatacaac cgctaccgta ttggaaacta taaattaaat    27000
acagaccacg ccggtagcaa cgacaatatt gctttgctag tacagtaagt gacaacagat    27060
gtttcatctt gttgacttcc aggttacaat agcagagata ttgattatca ttatgaggac    27120
tttcaggatt gctatttgga atcttgacgt tataataagt tcaatagtga gacaattatt    27180
taagcctcta actaagaaga attattcgga gttgatgatg aagaaccta tggagttaga    27240
ttatccataa aacgaacatg aaaattattc tcttcctgac attgattgta tttacatctt    27300
```

```
gcgagctata tcactatcag gagtgtgtta gaggtacgac tgtactacta aaagaacctt    27360
gcccatcagg aacatacgag ggcaattcac catttcaccc tcttgctgac aataaatttg    27420
cactaacttg cactagcaca cactttgctt ttgcttgtgc tgacggtact cgacataccT    27480
atcagctgcg tgcaagatca gtttcaccaa aacttttcat cagacaagag gaggttcaac    27540
aagagctcta ctcgccactt tttctcattg ttgctgctct agtattttta atactttgct    27600
tcaccattaa gagaaagaca gaatgaatga gctcacttta attgacttct atttgtgctt    27660
tttagccttt ctgctattcc ttgttttaat aatgcttatt atattttggt tttcactcga    27720
aatccaggat ctagaagaac cttgtaccaa agtctaaacg aacatgaaac ttctcattgt    27780
tttgacttgt atttctctat gcagttgcat atgcactgta gtacagcgct gtgcatctaa    27840
taaacctcat gtgcttgaag atccttgtaa ggtacaacac taggggtaat acttatagca    27900
ctgcttggct ttgtgctcta ggaaaggttt tacctttTca tagatggcac actatggttc    27960
aaacatgcac acctaatgtt actatcaact gtcaagatcc agctggtggt gcgcttatag    28020
ctaggtgttg gtaccttcat gaaggtcacc aaactgctgc atttagagac gtacttgttg    28080
ttttaaataa acgaacaaat taaaatgtct gataatggac cccaatcaaa ccaacgtagt    28140
gccccccgca ttacatttgg tggacccaca gattcaactg acaataacca gaatggagga    28200
cgcaatgggg caaggccaaa acagcgccga ccccaaggtt tacccaataa tactgcgtct    28260
tggttcacag ctctcactca gcatggcaag gaggaactta gattccctcg aggccagggc    28320
gttccaatca acaccaatag tggtccagat gaccaaattg gctactaccg aagagctacc    28380
cgacgagttc gtggtggtga cggcaaaatg aaagagctca gccccagatg gtacttctat    28440
tacctaggaa ctggcccaga agcttcactt ccctacggcg ctaacaaaga aggcatcgta    28500
tgggttgcaa ctgagggagc cttgaataca cccaaagacc acattggcac ccgcaatcct    28560
aataacaatg ctgccaccgt gctacaactt cctcaaggaa caacattgcc aaaaggcttc    28620
tacgcagagg gaagcagagg cggcagtcaa gcctcttctc gctcctcatc acgtagtcgc    28680
ggtaattcaa gaaattcaac tcctggcagc agtaggggaa attctcctgc tcgaatggct    28740
agcggaggtg gtgaaactgc cctcgcgcta ttgctgctag acagattgaa ccagcttgag    28800
agcaaagttt ctggtaaagg ccaacaacaa caaggccaaa ctgtcactaa gaaatctgct    28860
gctgaggcat ctaaaaagcc tcgccaaaaa cgtactgcca caaaacagta caacgtcact    28920
caagcatttg ggagacgtgg tccagaacaa acccaaggaa atttcggga ccaagaccta    28980 atcagacaag gaactgatta caaacattgg ccgcaaattg cacaatttgc tccaagtgcc    29040
tctgcattct ttgaatgtct acgcattggc atggaagtca caccttcggg aacatggctg    29100
acttatcatg gagccattaa attggatgac aaagatccac aattcaaaga caacgtcata    29160
ctgctgaaca gcacattga cgcatacaaa acattcccac caacagagcc taaaaaggac    29220
aaaaagaaaa agactgatga agctcagcct ttgccgcaga gacaaaagaa gcagcccact    29280
gtgactcttc ttcctgcggc tgacatggat gatttctcca gacaacttca aaattccatg    29340
agtggagctt ctgctgattc aactcaggca taaacactca tgatgaccac acaaggcaga    29400
tgggctatgt aaacgttttc gcaattccgt ttacgataca tagtctactc ttgtgcagaa    29460
tgaattctcg taactaaaca gcacaagtag gtttagttaa ctttaatctc acatagcaat    29520
ctttaatcaa tgtgtaacat tagggaggac ttgaaagagc caccacattt tcatcgaggc    29580
cacgcggagt acgatcgagg gtacagtgaa taatgctagg gagagctgcc tatatggaag    29640
```

```
agccctaatg tgtaaaatta attttagtag tgctatcccc atgtgatttt aatagcttct   29700
taggagaatg acaaaaaaaa aaaaaaaaaa aaaaa                              29736

<210> SEQ ID NO 3
<211> LENGTH: 26
<212> TYPE: DNA
<213> ORGANISM: Severe acute respiratory syndrome virus

<400> SEQUENCE: 3
tctctaaacg aactttaaaa tctgtg                                        26

<210> SEQ ID NO 4
<211> LENGTH: 16
<212> TYPE: DNA
<213> ORGANISM: Severe acute respiratory syndrome virus

<400> SEQUENCE: 4
caactaaacg aacatg                                                   16

<210> SEQ ID NO 5
<211> LENGTH: 18
<212> TYPE: DNA
<213> ORGANISM: Severe acute respiratory syndrome virus

<400> SEQUENCE: 5
cacataaacg aacttatg                                                 18

<210> SEQ ID NO 6
<211> LENGTH: 16
<212> TYPE: DNA
<213> ORGANISM: Severe acute respiratory syndrome virus

<400> SEQUENCE: 6
tgagtacgaa cttatg                                                   16

<210> SEQ ID NO 7
<211> LENGTH: 18
<212> TYPE: DNA
<213> ORGANISM: Severe acute respiratory syndrome virus

<400> SEQUENCE: 7
ggtctaaacg aactaact                                                 18

<210> SEQ ID NO 8
<211> LENGTH: 11
<212> TYPE: DNA
<213> ORGANISM: Severe acute respiratory syndrome virus

<400> SEQUENCE: 8
aactataaat t                                                        11

<210> SEQ ID NO 9
<211> LENGTH: 17
<212> TYPE: DNA
<213> ORGANISM: Severe acute respiratory syndrome virus

<400> SEQUENCE: 9
tccataaaac gaacatg                                                  17

<210> SEQ ID NO 10
<211> LENGTH: 24
<212> TYPE: DNA
<213> ORGANISM: Severe acute respiratory syndrome virus
```

```
<400> SEQUENCE: 10
tgctctagta tttttaatac tttg                                          24

<210> SEQ ID NO 11
<211> LENGTH: 16
<212> TYPE: DNA
<213> ORGANISM: Severe acute respiratory syndrome virus

<400> SEQUENCE: 11
agtctaaacg aacatg                                                   16

<210> SEQ ID NO 12
<211> LENGTH: 15
<212> TYPE: DNA
<213> ORGANISM: Severe acute respiratory syndrome virus

<400> SEQUENCE: 12
ctaataaacc tcatg                                                    15

<210> SEQ ID NO 13
<211> LENGTH: 24
<212> TYPE: DNA
<213> ORGANISM: Severe acute respiratory syndrome virus

<400> SEQUENCE: 13
taaataaacg aacaaattaa aatg                                          24

<210> SEQ ID NO 14
<211> LENGTH: 20
<212> TYPE: PRT
<213> ORGANISM: Severe acute respiratory syndrome virus

<400> SEQUENCE: 14

Lys Thr Phe Pro Pro Thr Glu Pro Lys Lys Asp Lys Lys Lys Lys Thr
1               5                   10                  15

Asp Glu Ala Gln
            20

<210> SEQ ID NO 15
<211> LENGTH: 29751
<212> TYPE: DNA
<213> ORGANISM: Severe acute respiratory syndrome virus

<400> SEQUENCE: 15
atattaggtt tttacctacc caggaaaagc caaccaacct cgatctcttg tagatctgtt    60
ctctaaacga actttaaaat ctgtgtagct gtcgctcggc tgcatgccta gtgcacctac   120
gcagtataaa caataataaa ttttactgtc gttgacaaga acgagtaac tcgtccctct    180 tctgcagact gcttacggtt tcgtccgtgt tgcagtcgat catcagcata cctaggtttc   240
gtccgggtgt gaccgaaagg taagatggag agccttgttc ttggtgtcaa cgagaaaaca   300
cacgtccaac tcagtttgcc tgtccttcag gttagacg tgctagtgcg tggcttcggg     360
gactctgtgg aagaggccct atcggaggca cgtgaacacc tcaaaaatgg cacttgtggt   420
ctagtagagc tggaaaaagg cgtactgccc cagcttgaac agccctatgt gttcattaaa   480
cgttctgatg ccttaagcac caatcacggc acaaggtcg ttgagctggt tgcagaaatg   540
gacggcattc agtacggtcg tagcggtata acactgggag tactcgtgcc acatgtgggc   600
gaaaccccaa ttgcataccg caatgttctt cttcgtaaga cggtaataa gggagccggt    660
```

-continued

```
ggtcatagct atggcatcga tctaaagtct tatgacttag gtgacgagct tggcactgat    720
cccattgaag attatgaaca aaactggaac actaagcatg gcagtggtgc actccgtgaa    780
ctcactcgtg agctcaatgg aggtgcagtc actcgctatg tcgacaacaa tttctgtggc    840
ccagatgggt accctcttga ttgcatcaaa gattttctcg cacgcgcggg caagtcaatg    900
tgcactcttt ccgaacaact tgattacatc gagtcgaaga gaggtgtcta ctgctgccgt    960
gaccatgagc atgaaattgc ctggttcact gagcgctctg ataagagcta cgagcaccag   1020
acacccttcg aaattaagag tgccaagaaa tttgacactt tcaaagggga atgcccaaag   1080
tttgtgtttc ctcttaactc aaaagtcaaa gtcattcaac cacgtgttga aaagaaaaag   1140
actgagggtt tcatggggcg tatacgctct gtgtaccctg ttgcatctcc acaggagtgt   1200
aacaatatgc acttgtctac cttgatgaaa tgtaatcatt gcgatgaagt ttcatggcag   1260
acgtgcgact ttctgaaagc cacttgtgaa cattgtggca ctgaaaattt agttattgaa   1320
ggacctacta catgtgggta cctacctact aatgctgtag tgaaaatgcc atgtcctgcc   1380
tgtcaagacc cagagattgg acctgagcat agtgttgcag attatcacaa ccactcaaac   1440
attgaaactc gactccgcaa gggaggtagg actagatgtt ttggaggctg tgtgtttgcc   1500
tatgttggct gctataataa gcgtgcctac tgggttcctc gtgctagtgc tgatattggc   1560
tcaggccata ctggcattac tggtgacaat gtggagacct gaatgagga tctccttgag   1620
atactgagtc gtgaacgtgt taacattaac attgttggcg attttcattt gaatgaagag   1680
gttgccatca ttttggcatc tttctctgct tctacaagtg cctttattga cactataaag   1740
agtcttgatt acaagtcttt caaaaccatt gttgagtcct gcggtaacta taagttacc    1800
aagggaaagc ccgtaaaagg tgcttggaac attggacaac agagatcagt tttaacacca   1860
ctgtgtggtt ttccctcaca ggctgctggt gttatcagat caattttttgc gcgcacactt   1920
gatgcagcaa accactcaat tcctgatttg caaagagcag ctgtcaccat acttgatggt   1980
atttctgaac agtcattacg tcttgtcgac gccatggttt atacttcaga cctgctcacc   2040
aacagtgtca ttattatggc atatgtaact ggtggtcttg tacaacagac ttctcagtgg   2100
ttgtctaatc ttttgggcac tactgttgaa aaactcaggc ctatctttga atggattgag   2160
gcgaaactta gtgcaggagt tgaatttctc aaggatgctt gggagattct caaatttctc   2220
attacaggtg ttttttgacat cgtcaagggt caaatacagg ttgcttcaga taacatcaag   2280
gattgtgtaa aatgcttcat tgatgttgtt aacaaggcac tcgaaatgtg cattgatcaa   2340
gtcactatcg ctggcgcaaa gttgcgatca ctcaacttag gtgaagtctt catcgctcaa   2400
agcaagggac tttaccgtca gtgtatacgt ggcaaggagc agctgcaact actcatgcct   2460
cttaaggcac caaaagaagt aacctttctt gaaggtgatt cacatgacac agtacttacc   2520
tctgaggagg ttgttctcaa gaacggtgaa ctcgaagcac tcgagacgcc cgttgatagc   2580
ttcacaaatg gagctatcgt tggcacacca gtctgtgtaa atggcctcat gctcttagag   2640
attaaggaca agaacaata ctgcgcattg tctcctggtt tactggctac aaacaatgtc   2700
tttcgcttaa aaggggggtgc accaattaaa ggtgtaacct tggagaaga tactgtttgg   2760
gaagttcaag gttacaagaa tgtgagaatc acatttgagc ttgatgaacg tgttgacaaa   2820
gtgcttaatg aaaagtgctc tgtctacact gttgaatccg gtaccgaagt tactgagttt   2880
gcatgtgttg tagcagaggc tgttgtgaag actttacaac cagtttctga tctccttacc   2940
aacatgggta ttgatcttga tgagtggagt gtagctacat ctacttatt tgatgatgct   3000
ggtgaagaaa acttttcatc acgtatgtat tgttcctttt accctccaga tgaggaagaa   3060
```

```
gaggacgatg cagagtgtga ggaagaagaa attgatgaaa cctgtgaaca tgagtacggt    3120
acagaggatg attatcaagg tctccctctg gaatttggtg cctcagctga aacagttcga    3180
gttgaggaag aagaagagga agactggctg atgatgatacta ctgagcaatc agagattgag    3240
ccagaaccag aacctacacc tgaagaacca gttaatcagt ttactggtta tttaaaactt    3300
actgacaatg ttgccattaa atgtgttgac atcgttaagg aggcacaaag tgctaatcct    3360
atggtgattg taaatgctgc taacatacac ctgaaacatg tggtggtgt agcaggtgca    3420 ctcaacaagg caaccaatgg tgccatgcaa aaggagagtg atgattacat taagctaaat    3480
ggccctctta cagtaggagg gtcttgtttg ctttctggac ataatcttgc taagaagtgt    3540
ctgcatgttt ttggacctaa cctaaatgca ggtgaggaca tccagcttct taaggcagca    3600
tatgaaaatt tcaattcaca ggacatctta cttgcaccat tgttgtcagc aggcatattt    3660
ggtgctaaac cacttcagtc tttacaagtg tgcgtgcaga cggttcgtac acaggtttat    3720
attgcagtca atgacaaagc tctttatgag caggttgtca tggattatct tgataacctg    3780
aagcctagag tggaagcacc taaacaagag gagccaccaa acacagaaga ttccaaaact    3840
gaggagaaat ctgtcgtaca aagcctgtc gatgtgaagc caaaaattaa ggcctgcatt    3900
gatgaggtta ccacaacact ggaagaaact aagtttctta ccaataagtt actcttgttt    3960
gctgatatca atggtaagct ttaccatgat tctcagaaca tgcttagagg tgaagatatg    4020 tcttccttg agaaggatgc accttacatg gtaggtgatg ttatcactag tggtgatatc    4080
acttgtgttg taatacccctc caaaaaggct ggtggcacta ctgagatgct ctcaagagct    4140
ttgaagaaag tgccagttga tgagtatata accacgtacc ctggacaagg atgtgctggt    4200
tatacacttg aggaagctaa gactgctctt aagaaatgca atctgcatt ttatgtacta    4260 ccttcagaag cacctaatgc taaggaagag attctaggaa ctgtatcctg gaatttgaga    4320
gaaatgcttg ctcatgctga agagacaaga aaattaatgc ctatatgcat ggatgttaga    4380
gccataatgg caaccatcca acgtaagtat aaaggaatta aaattcaaga gggcatcgtt    4440
gactatggtg tccgattctt cttttatact agtaaagagc ctgtagcttc tattattacg    4500
aagctgaact ctctaaatga gccgcttgtc acaatgccaa ttggttatgt gacacatggt    4560
tttaatcttg aagaggctgc gcgctgtatg cgttctctta agctcctgc cgtagtgtca    4620 gtatcatcac cagatgctgt tactacatat aatggatacc tcacttcgtc atcaaagaca    4680
tctgaggagc actttgtaga aacagtttct ttggctggct cttacagaga ttggtcctat    4740
tcaggacagc gtacagagtt aggtgttgaa tttcttaagc gtggtgacaa aattgtgtac    4800
cacactctgg agagccccgt cgagtttcat cttgacggtg aggttctttc acttgacaaa    4860
ctaaagagtc tcttatccct gcgggaggtt aagactataa aagtgttcac aactgtggac    4920
aacactaatc tccacacaca gcttgtggat atgtctatga catatggaca gcagtttggt    4980
ccaacatact tggatggtgc tgatgttaca aaaattaaac ctcatgtaaa tcatgagggt    5040
aagactttct ttgtactacc tagtgatgac acactacgta gtgaagcttt cgagtactac    5100
catactcttg atgagagttt tcttggtagg tacatgtctg cttttaaacca cacaaagaaa    5160 tggaaatttc ctcaagttgg tggtttaact tcaattaaat gggctgataa caattgttat    5220
ttgtctagtg ttttattagc acttcaacag cttgaagtca aattcaatgc accagcactt    5280
caagaggctt attatagagc ccgtgctggt gatgctgcta acttttgtgc actcatactc    5340
gcttacagta ataaaactgt tggcgagctt ggtgatgtca gagaaactat gacccatctt    5400
```

```
ctacagcatg ctaatttgga atctgcaaag cgagttctta atgtggtgtg taaacattgt   5460
ggtcagaaaa ctactacctt aacgggtgta gaagctgtga tgtatatggg tactctatct   5520
tatgataatc ttaagacagg tgtttccatt ccatgtgtgt gtggtcgtga tgctacacaa   5580
tatctagtac aacaagagtc ttcttttgtt atgatgtctg caccacctgc tgagtataaa   5640
ttacagcaag gtacattctt atgtgcgaat gagtacactg gtaactatca gtgtggtcat   5700
tacactcata taactgctaa ggagaccctc tatcgtattg acggagctca ccttacaaag   5760
atgtcagagt acaaaggacc agtgactgat gtttctaca aggaaacatc ttacactaca   5820
accatcaagc ctgtgtcgta taaactcgat ggagttactt acacagagat tgaaccaaaa   5880
ttggatgggt attataaaaa ggataatgct tactatacag agcagcctat agaccttgta   5940
ccaactcaac cattaccaaa tgcgagtttt gataatttca aactcacatg ttctaacaca   6000
aaatttgctg atgatttaaa tcaaatgaca ggcttcacaa agccagcttc acgagagcta   6060
tctgtcacat tcttcccaga cttgaatggc gatgtagtgg ctattgacta tagacactat   6120
tcagcgagtt tcaagaaagg tgctaaatta ctgcataagc caattgtttg gcacattaac   6180
caggctacaa ccaagacaac gttcaaacca aacacttggt gtttacgttg tctttggagt   6240
acaaagccag tagatacttc aaattcattt gaagttctgg cagtagaaga cacacaagga   6300
atggacaatc ttgcttgtga agtcaacaa cccacctctg aagaagtagt ggaaaatcct   6360
accatacaga aggaagtcat agagtgtgac gtgaaaacta ccgaagttgt aggcaatgtc   6420
atacttaaac catcgagatga aggtgttaaa gtaacacaag agttaggtca tgaggatctt   6480
atggctgctt atgtggaaaa cacaagcatt accattaaga aacctaatga gctttcacta   6540
gccttaggtt taaaaacaat tgccactcat ggtattgctg caattaatag tgttccttgg   6600
agtaaaattt tggcttatgt caaaccattc ttaggacaag cagcaattac aacatcaaat   6660
tgcgctaaga gattagcaca acgtgtgttt aacaattata tgccttatgt gtttacatta   6720
ttgttccaat tgtgtacttt tactaaaagt accaattcta gaattagagc ttcactacct   6780
acaactattg ctaaaaatag tgttaagagt gttgctaaat tatgtttgga tgccggcatt   6840
aattatgtga agtcacccaa attttctaaa ttgttcacaa tcgctatgtg gctattgttg   6900
ttaagtattt gcttaggttc tctaatctgt gtaactgctg cttttggtgt actcttatct   6960
aattttggtg ctccttctta ttgtaatggc gttagagaat tgtatcttaa ttcgtctaac   7020
gttactacta tggatttctg tgaaggttct tttcccttgca gcatttgttt aagtggatta   7080
gactcccttg attcttatcc agctcttgaa accattcagg tgacgatttc atcgtacaag   7140
ctagacttga caattttagg tctggccgct gagtgggttt tggcatatat gttgttcaca   7200
aaattctttt atttattagg tctttcagct ataatgcagg tgttctttgg ctattttgct   7260
agtcatttca tcagcaattc ttggctcatg tggtttatca ttagtattgt acaaatggca   7320
cccgtttctg caatggttag gatgtacatc ttctttgctt ctttctacta catatggaag   7380
agctatgttc atatcatgga tggttgcacc tcttcgactt gcatgatgtg ctataagcgc   7440
aatcgtgcca cacgcgttga gtgtacaact attgttaatg gcatgaagag atctttctat   7500
gtctatgcaa atggaggccg tggcttctgc aagactcaca attggaattg tctcaattgt   7560
gacacatttt gcactggtag tacattcatt agtgatgaag ttgctcgtga tttgtcactc   7620
cagtttaaaa gaccaatcaa ccctactgac cagtcatcgt atattgttga tagtgttgct   7680
gtgaaaaatg cgcgcttca cctctacttt gacaaggctg tcaaagac ctatgagaga   7740 catccgctct cccatttgt caatttagac aatttgagag ctaacaacac taaaggttca   7800
```

```
ctgcctatta atgtcatagt ttttgatggc aagtccaaat gcgacgagtc tgcttctaag    7860
tctgcttctg tgtactacag tcagctgatg tgccaaccta ttctgttgct tgaccaagct    7920
cttgtatcag acgttggaga tagtactgaa gtttccgtta agatgtttga tgcttatgtc    7980 gacaccttt cagcaacttt tagtgttcct atggaaaaac ttaaggcact tgttgctaca    8040
gctcacagcg agttagcaaa gggtgtagct ttagatggtg tcctttctac attcgtgtca    8100
gctgcccgac aaggtgttgt tgataccgat gttgacacaa aggatgttat tgaatgtctc    8160
aaactttcac atcactctga cttagaagtg acaggtgaca gttgtaacaa tttcatgctc    8220
acctataata aggttgaaaa catgacgccc agagatcttg gcgcatgtat tgactgtaat    8280
gcaaggcata tcaatgccca agtagcaaaa agtcacaatg tttcactcat ctggaatgta    8340
aaagactaca tgtctttatc tgaacagctg cgtaaacaaa ttcgtagtgc tgccaagaag    8400
aacaacatac ttttagact aacttgtgct acaactagac aggttgtcaa tgtcataact    8460
actaaaatct cactcaaggg tggtaagatt gttagtactt gttttaaact tatgcttaag    8520
gccacattat tgtgcgttct tgctgcattg gtttgttata tcgttatgcc agtacataca    8580
ttgtcaatcc atgatggtta cacaaatgaa atcattggtt acaaagccat tcaggatggt    8640
gtcactcgtg acatcatttc tactgatgat tgttttgcaa ataaacatgc tggttttgac    8700
gcatggttta gccagcgtgg tggttcatac aaaaatgaca aaagctgccc tgtagtagct    8760
gctatcatta caagagagat tggtttcata gtgcctggct tacccgggtac tgtgctgaga    8820 gcaatcaatg gtgacttctt gcatttttcta cctcgtgttt ttagtgctgt tggcaacatt    8880
tgctacacac cttccaaact cattgagtat agtgatttg ctacctctgc ttgcgttctt    8940
gctgctgagt gtacaatttt taaggatgct atgggcaaac ctgtgccata ttgttatgac    9000
actaatttgc tagagggttc tatttcttat agtgagcttc gtccagacac tcgttatgtg    9060
cttatggatg gttccatcat acagtttcct aacacttacc tggagggttc tgttagagta    9120
gtaacaactt tgatgctga gtactgtaga catggtacat gcgaaaggtc agaagtaggt    9180
atttgcctat ctaccagtgg tagatggggtt cttaataatg agcattacag agctctatca    9240 ggagtttttct gtggtgttga tgcgatgaat ctcatagcta acatctttac tcctcttgtg    9300
caacctgtgg gtgctttaga tgtgtctgct tcagtagtgg ctggtggtat tattgccata    9360
ttggtgactt gtgctgccta ctactttatg aaattcagac gtgttttttgg tgagtacaac    9420 catgttgttg ctgctaatgc acttttgttt ttgatgtctt tcactatact ctgtctggta    9480
ccagcttaca gctttctgcc gggagtctac tcagtctttt acttgtactt gacattctat    9540
ttcaccaatg atgtttcatt cttggctcac cttcaatggt ttgccatgtt ttctcctatt    9600
gtgccttttt ggataacagc aatctatgta ttctgtattt ctctgaagca ctgccattgg    9660
ttctttaaca actatcttag gaaaagagtc atgtttaatg gagttacatt tagtaccttc    9720
gaggaggctg ctttgtgtac cttttttgctc aacaaggaaa tgtacctaaa attgcgtagc    9780
gagacactgt tgccacttac acagtataac aggtatcttg ctctatataa caagtacaag    9840
tatttcagtg gagccttaga tactaccagc tatcgtgaag cagcttgctg ccactagca    9900 aaggctctaa atgactttag caactcaggt gctgatgttc tctaccaacc accacagaca    9960
tcaatcactt ctgctgttct gcagagtggt tttaggaaaa tggcattccc gtcaggcaaa    10020
gttgaagggt gcatggtaca agtaacctgt ggaactacaa ctcttaatgg attgtggttg    10080
gatgacacag tatactgtcc aagacatgtc atttgcacag cagaagacat gcttaatcct    10140
```

```
aactatgaag atctgctcat tcgcaaatcc aaccatagct ttcttgttca ggctggcaat   10200
gttcaacttc gtgttattgg ccattctatg caaaattgtc tgcttaggct taaagttgat   10260
acttctaacc ctaagacacc caagtataaa tttgtccgta tccaacctgg tcaaacattt   10320
tcagttctag catgctacaa tggttcacca tctggtgttt atcagtgtgc catgagacct   10380
aatcatacca ttaaaggttc tttccttaat ggatcatgtg gtagtgttgg ttttaacatt   10440
gattatgatt gcgtgtcttt ctgctatatg catcatatgg agcttccaac aggagtacac   10500
gctggtactg acttagaagg taaattctat ggtccatttg ttgacagaca aactgcacag   10560
gctgcaggta cagacacaac cataacatta atgttttggg catggctgta tgctgctgtt   10620
atcaatggtg ataggtggtt tcttaataga ttcaccacta ctttgaatga ctttaacctt   10680
gtggcaatga agtacaacta tgaacctttg acacaagatc atgttgacat attgggacct   10740 cttctgctc aaacaggaat tgccgtctta gatatgtgtg ctgctttgaa agagctgctg   10800
cagaatggta tgaatggtcg tactatcctt ggtagcacta ttttagaaga tgagtttaca   10860
ccatttgatg ttgttagaca atgctctggt gttaccttcc aaggtaagtt caagaaaatt   10920
gttaagggca ctcatcattg gatgcttta actttcttga catcactatt gattcttgtt   10980
caaagtacac agtggtcact gttttttctt gtttacgaga atgctttctt gccatttact   11040
cttggtatta tggcaattgc tgcatgtgct atgctgcttg ttaagcataa gcacgcattc   11100
ttgtgcttgt ttctgttacc ttctcttgca acagttgctt actttaatat ggtctacatg   11160
cctgctagct gggtgatgcg tatcatgaca tggcttgaat tggctgacac tagcttgtct   11220
ggttataggc ttaaggattg tgttatgtat gcttcagctt tagttttgct tattctcatg   11280
acagctcgca ctgtttatga tgatgctgct agacgtgttt ggacactgat gaatgtcatt   11340
acacttgttt acaaagtcta ctatggtaat gctttagatc aagctatttc catgtgggcc   11400
ttagttattt ctgtaacctc taactattct ggtgtcgtta cgactatcat gttttttagct   11460 agagctatag tgtttgtgtg tgttgagtat tacccattgt tatttattac tggcaacacc   11520
ttacagtgta tcatgcttgt ttattgtttc ttaggctatt gttgctgctg ctactttggc   11580
cttttctgtt tactcaaccg ttacttcagg cttactcttg gtgtttatga ctacttggtc   11640
tctacacaag aatttaggta tatgaactcc caggggcttt tgcctcctaa gagtagtatt   11700
gatgctttca agcttaacat taagttgttg ggtattggag gtaaaccatg tatcaaggtt   11760
gctactgtac agtctaaaat gtctgacgta aagtgcacat ctgtggtact gctctcggtt   11820
cttcaacaac ttagagtaga gtcatcttct aaattgtggg cacaatgtgt acaactccac   11880
aatgatattc ttcttgcaaa agacacaact gaagctttcg agaagatggt ttctcttttg   11940
tctgttttgc tatccatgca gggtgctgta gacattaata ggttgtgcga ggaaatgctc   12000
gataaccgtg ctactcttca ggctattgct tcagaattta gttctttacc atcatatgcc   12060
gcttatgcca ctgcccagga ggcctatgag caggctgtag ctaatggtga ttctgaagtc   12120
gttctcaaaa agttaaagaa atctttgaat gtggctaaat ctgagtttga ccgtgatgct   12180
gccatgcaac gcaagttgga aaagatggca gatcaggcta tgacccaaat gtacaaacag   12240
gcaagatctg aggacaagag ggcaaaagta actagtgcta tgcaaacaat gctcttcact   12300
atgcttagga agcttgataa tgatgcactt aacaacatta tcaacaatgc gcgtgatggt   12360
tgtgttccac tcaacatcat accattgact acagcagcca aactcatggt tgttgtccct   12420
gattatggta cctacaagaa cacttgtgat ggtaacacct ttacatatgc atctgcactc   12480
tgggaaatcc agcaagttgt tgatgcggat agcaagattg ttcaacttag tgaaattaac   12540
```

```
atggacaatt caccaaattt ggcttggcct cttattgtta cagctctaag agccaactca   12600
gctgttaaac tacagaataa tgaactgagt ccagtagcac tacgacagat gtcctgtgcg   12660
gctggtacca cacaaacagc ttgtactgat gacaatgcac ttgcctacta taacaattcg   12720
aagggaggta ggtttgtgct ggcattacta tcagaccacc aagatctcaa atgggctaga   12780
ttccctaaga gtgatggtac aggtacaatt tacacagaac tggaaccacc ttgtaggttt   12840
gttacagaca caccaaaagg gcctaaagtg aaatacttgt acttcatcaa aggcttaaac   12900
aacctaaata gaggtatggt gctgggcagt ttagctgcta cagtacgtct tcaggctgga   12960
aatgctacag aagtacctgc caattcaact gtgctttcct tctgtgcttt tgcagtagac   13020
cctgctaaag catataagga ttacctagca agtggaggac aaccaatcac caactgtgtg   13080
aagatgttgt gtacacacac tggtacagga caggcaatta ctgtaacacc agaagctaac   13140
atggaccaag agtcctttgg tggtgcttca tgttgtctgt attgtagatg ccacattgac   13200
catccaaatc ctaaaggatt ctgtgacttg aaaggtaagt acgtccaaat acctaccact   13260
tgtgctaatg acccagtggg ttttacactt agaaacacag tctgtaccgt ctgcggaatg   13320
tggaaaggtt atgctgtag ttgtgaccaa ctccgcgaac ccttgatgca gtctgcggat   13380
gcatcaacgt ttttaaacgg gtttgcggtg taagtgcagc ccgtcttaca ccgtgcggca   13440
caggcactag tactgatgtc gtctacaggg cttttgatat ttacaacgaa aaagttgctg   13500
gttttgcaaa gttcctaaaa actaattgct gtcgcttcca ggagaaggat gaggaaggca   13560
atttattaga ctcttacttt gtagttaaga ggcatactat gtctaactac caacatgaag   13620
agactattta aacttggtt aaagattgtc cagcggttgc tgtccatgac ttttcaagt    13680 ttagagtaga tggtgacatg gtaccacata tatcacgtca gcgtctaact aaatacacaa   13740
tggctgattt agtctatgct ctacgtcatt ttgatgaggg taattgtgat acattaaaag   13800
aaatactcgt cacatacaat tgctgtgatg atgattattt caataagaag gattggtatg   13860
acttcgtaga gaatcctgac atcttacgcg tatatgctaa cttaggtgag cgtgtacgcc   13920
aatcattatt aaagactgta caattctgcg atgctatgcg tgatgcaggc attgtaggcg   13980
tactgacatt agataatcag gatcttaatg ggaactggta cgatttcggt gatttcgtac   14040
aagtagcacc aggctgcgga gttcctattg tggattcata ttactcattg ctgatgccca   14100
tcctcacttt gactagggca ttggctgctg agtcccatat ggatgctgat ctcgcaaaac   14160
cacttattaa gtgggatttg ctgaaatatg attttacgga agagagactt tgtctcttcg   14220
accgttattt taaatattgg gaccagacat accatcccaa ttgtattaac tgtttggatg   14280
ataggtgtat ccttcattgt gcaaacttta atgtgttatt ttctactgtg tttccaccta   14340
caagttttgg accactagta agaaaaatat ttgtagatgg tgttccttt gttgtttcaa    14400 ctggatacca ttttcgtgag ttaggagtcg tacataatca ggatgtaaac ttacatagct   14460
cgcgtctcag tttcaaggaa cttttagtgt atgctgctga tccagctatg catgcagctt   14520
ctggcaattt attgctagat aaacgcacta catgctttc agtagctgca ctaacaaaca    14580
atgttgcttt tcaaactgtc aaacccggta attttaataa agactttat gactttgctg    14640 tgtctaaagg tttcttaag gaaggaagtt ctgttgaact aaaacacttc ttctttgctc    14700
aggatggcaa cgctgctatc agtgattatg actattatcg ttataatctg ccaacaatgt   14760
gtgatatcag acaactccta ttcgtagttg aagttgttga taaatacttt gattgttacg   14820
atggtggctg tattaatgcc aaccaagtaa tcgttaacaa tctggataaa tcagctggtt   14880
```

```
tcccatttaa taaatggggt aaggctagac tttattatga ctcaatgagt tatgaggatc    14940
aagatgcact tttcgcgtat actaagcgta atgtcatccc tactataact caaatgaatc    15000
ttaagtatgc cattagtgca aagaatagag ctcgcaccgt agctggtgtc tctatctgta    15060
gtactatgac aaatagacag tttcatcaga aattattgaa gtcaatagcc gccactagag    15120
gagctactgt ggtaattgga acaagcaagt tttacggtgg ctggcataat atgttaaaaa    15180
ctgtttacag tgatgtagaa actccacacc ttatgggttg ggattatcca aaatgtgaca    15240
gagccatgcc taacatgctt aggataatgg cctctcttgt tcttgctcgc aaacataaca    15300
cttgctgtaa cttatcacac cgtttctaca ggttagctaa cgagtgtgcg caagtattaa    15360
gtgagatggt catgtgtggc ggctcactat atgttaaacc aggtggaaca tcatccggtg    15420
atgctacaac tgcttatgct aatagtgtct ttaacatttg tcaagctgtt acagccaatg    15480
taaatgcact tctttcaact gatggtaata agatagctga caagtatgtc cgcaatctac    15540
aacacaggct ctatgagtgt ctctatagaa atagggatgt tgatcatgaa ttcgtggatg    15600
agttttacgc ttacctgcgt aaacatttct ccatgatgat tctttctgat gatgccgttg    15660
tgtgctataa cagtaactat gcggctcaag gtttagtagc tagcattaag aactttaagg    15720
cagttcttta ttatcaaaat aatgtgttca tgtctgaggc aaaatgttgg actgagactg    15780
accttactaa aggacctcac gaattttgct cacagcatac aatgctagtt aaacaaggag    15840
atgattacgt gtacctgcct tacccagatc catcaagaat attaggcgca ggctgttttg    15900
tcgatgatat tgtcaaaaca gatggtacac ttatgattga aaggttcgtg tcactggcta    15960
ttgatgctta cccacttaca aaacatccta atcaggagta tgctgatgtc tttcacttgt    16020
atttacaata cattagaaag ttacatgatg agcttactgg ccacatgttg gacatgtatt    16080
ccgtaatgct aactaatgat aacacctcac ggtactggga acctgagttt tatgaggcta    16140
tgtacacacc acatacagtc ttgcaggctg taggtgcttg tgtattgtgc aattcacaga    16200
cttcacttcg ttgcggtgcc tgtattagga gaccattcct atgttgcaag tgctgctatg    16260
accatgtcat ttcaacatca cacaaattag tgttgtctgt taatccctat gtttgcaatg    16320
ccccaggttg tgatgtcact gatgtgacac aactgtatct aggaggtatg agctattatt    16380
gcaagtcaca taagcctccc attagttttc cattatgtgc taatggtcag ttttttggtt    16440
tatacaaaaa cacatgtgta ggcagtgaca atgtcactga cttcaatgcg atagcaacat    16500
gtgattggac taatgctggc gattacatac ttgccaacac ttgtactgag agactcaagc    16560
ttttcgcagc agaaacgctc aaagccactg aggaaacatt taagctgtca tatggtattg    16620
ccactgtacg cgaagtactc tctgacagag aattgcatct ttcatgggag gttggaaaac    16680
ctagaccacc attgaacaga aactatgtct ttactggtta ccgtgtaact aaaaatagta    16740
aagtacagat tggagagtac acctttgaaa aggtgactag tggtgatgct gttgtgtaca    16800
gaggtactac gacatacaag ttgaatgttg gtgattactt tgtgttgaca tctcacactg    16860
taatgccact agtgcaccct actctagtgc acaagagca  ctatgtgaga attactggct    16920
tgtacccaac actcaacatc tcagatgagt tttctagcaa tgttgcaaat tatcaaaagg    16980
tcggcatgca aaagtactct acactccaag gaccacctgg tactggtaag agtcattttg    17040
ccatcggact tgctctctat taccccatctg ctcgcatagt gtatacggca tgctctcatg    17100
cagctgttga tgccctatgt gaaaaggcat taaaatattt gcccatagat aaatgtagta    17160
gaatcatacc tgcgcgtgcg cgcgtagagt gttttgataa attcaaagtg aattcaacac    17220
tagaacagta tgttttctgc actgtaaatg cattgccaga aacaactgct gacattgtag    17280
```

```
tctttgatga aatctctatg gctactaatt atgacttgag tgttgtcaat gctagacttc    17340
gtgcaaaaca ctacgtctat attggcgatc ctgctcaatt accagccccc cgcacattgc    17400
tgactaaagg cacactagaa ccagaatatt ttaattcagt gtgcagactt atgaaaacaa    17460
taggtccaga catgttcctt ggaacttgtc gccgttgtcc tgctgaaatt gttgacactg    17520
tgagtgcttt agtttatgac aataagctaa aagcacacaa ggataagtca gctcaatgct    17580
tcaaaatgtt ctacaaaggt gttattacac atgatgtttc atctgcaatc aacagacctc    17640
aaataggcgt tgtaagagaa tttcttacac gcaatcctgc ttggagaaaa gctgttttta    17700
tctcacctta taattcacag aacgctgtag cttcaaaaat cttaggattg cctacgcaga    17760
ctgttgattc atcacagggt tctgaatatg actatgtcat attcacacaa actactgaaa    17820
cagcacactc ttgtaatgtc aaccgcttca atgtggctat cacaagggca aaaattggca    17880
ttttgtgcat aatgtctgat agagatcttt atgacaaact gcaatttaca agtctagaaa    17940
taccacgtcg caatgtggct acattacaag cagaaaatgt aactggactt tttaaggact    18000
gtagtaagat cattactggt cttcatccta cacaggcacc tacacacctc agcgttgata    18060
taaagttcaa gactgaagga ttatgtgttg acataccagg cataccaaag gacatgacct    18120
accgtagact catctctatg atgggttttca aaatgaatta ccaagtcaat ggttacccta    18180
atatgtttat cacccgcgaa gaagctattc gtcacgttcg tgcgtggatt ggctttgatg    18240
tagagggctg tcatgcaact agagatgctg tgggtactaa cctacctctc agctaggat    18300 tttctacagg tgttaactta gtagctgtac cgactggtta tgttgacact gaaaataaca    18360
cagaattcac cagagttaat gcaaaacctc caccaggtga ccagtttaaa catcttatac    18420
cactcatgta taaaggcttg ccctggaatg tagtgcgtat taagatagta caaatgctca    18480
gtgatacact gaaaggattg tcagacagag tcgtgttcgt cctttgggcg catggctttg    18540
agcttacatc aatgaagtac tttgtcaaga ttggacctga aagaacgtgt tgtctgtgtg    18600
acaaacgtgc aacttgctTt tctacttcat cagatactta tgcctgctgg aatcattctg    18660
tgggttttga ctatgtctat aacccattta tgattgatgt tcagcagtgg ggctttacgg    18720
gtaaccttca gagtaaccat gaccaacatt gccaggtaca tggaaatgca catgtggcta    18780
gttgtgatgc tatcatgact agatgtttag cagtccatga gtgctttgtt aagcgcgttg    18840
attggtctgt tgaatacccc taatataggag atgaactgag ggttaattct gcttgcagaa    18900
aagtacaaca catggttgtg aagtctgcat tgcttgctga taagtttcca gttcttcatg    18960
acattggaaa tccaaaggct atcaagtgtg tgcctcaggc tgaagtagaa tggaagttct    19020
acgatgctca gccatgtagt gacaaagctt acaaaataga ggaactcttc tattcttatg    19080
ctacacatca cgataaattc actgatggtg tttgtttgtt ttggaattgt aacgttgatc    19140
gttacccagc caatgcaatt gtgtgtaggt ttgacacaag agtcttgtca aacttgaact    19200
taccaggctg tgatggtggt agtttgtatg tgaataagca tgcattccac actccagctt    19260
tcgataaaag tgcatttact aatttaaagc aattgccttt ctttTactat tctgatagtc    19320
cttgtgagtc tcatggcaaa caagtagtgt cggatattga ttatgttcca ctcaaatctg    19380
ctacgtgtat tacacgatgc aatttaggtg gtgctgtttg cagacaccat gcaaatgagt    19440
accgacagta cttggatgca tataatatga tgatttctgc tggatttagc ctatggattt    19500
acaaacaatt tgatacttat aacctgtgga atacatttac caggttacag agtttagaaa    19560
atgtggctta taatgttgtt aataaaggac actttgatgg acacgccggc gaagcacctg    19620
```

```
tttccatcat taataatgct gtttacacaa aggtagatgg tattgatgtg gagatctttg   19680
aaaataagac aacacttcct gttaatgttg catttgagct ttgggctaag cgtaacatta   19740
aaccagtgcc agagattaag atactcaata atttgggtgt tgatatcgct gctaatactg   19800
taatctggga ctacaaaaga gaagccccag cacatgtatc tacaataggt gtctgcacaa   19860
tgactgacat tgccaagaaa cctactgaga gtgcttgttc ttacttact gtcttgtttg    19920 atggtagagt ggaaggacag gtagacctt ttagaaacgc ccgtaatggt gttttaataa    19980
cagaaggttc agtcaaaggt ctaacacctt caaagggacc agcacaagct agcgtcaatg   20040
gagtcacatt aattggagaa tcagtaaaaa cacagtttaa ctactttaag aaagtagacg   20100
gcattattca acagttgcct gaaacctact ttactcagag cagagactta gaggatttta   20160
agcccagatc acaaatggaa actgactttc tcgagctcgc tatggatgaa ttcatacagc   20220
gatataagct cgagggctat gccttcgaac acatcgttta tggagatttc agtcatggac   20280
aacttggcgg tcttcattta atgataggct tagccaagcg ctcacaagat tcaccactta   20340
aattagagga ttttatccct atggacagca cagtgaaaaa ttacttcata acagatgcgc   20400
aaacaggttc atcaaaatgt gtgtgttctg tgattgatct tttacttgat gactttgtcg   20460
agataataaa gtcacaagat tgtcagtga tttcaaaagt ggtcaaggtt acaattgact    20520
atgctgaaat tcattcatg ctttggtgta aggatggaca tgttgaaacc ttctacccaa    20580
aactacaagc aagtcaagcg tggcaaccag gtgttgcgat gcctaacttg tacaagatgc   20640
aaagaatgct tcttgaaaag tgtgaccttc agaattatgg tgaaaatgct gttataccaa   20700
aaggaataat gatgaatgtc gcaaagtata ctcaactgtg tcaatactta aatacactta   20760
ctttagctgt accctacaac atgagagtta ttcactttgg tgctggctct gataaaggag   20820
ttgcaccagg tacagctgtg ctcagacaat ggttgccaac tggcacacta cttgtcgatt   20880
cagatcttaa tgacttcgtc tccgacgcag attctacttt aattggagac tgtgcaacag   20940
tacatacggc taataaatgg gaccttatta ttagcgatat gtatgaccct aggaccaaac   21000
atgtgacaaa agagaatgac tctaaagaag gttttttcac ttatctgtgt ggatttataa   21060
agcaaaaact agccctgggt ggttctatag ctgtaaagat aacagagcat tcttggaatg   21120 ctgacctta caagcttatg ggccattct catggtggac agcttttgtt acaaatgtaa     21180
atgcatcatc atcggaagca ttttaattg gggctaacta tcttggcaag ccgaaggaac    21240
aaattgatgg ctataccatg catgctaact acatttctg gaggaacaca atcctatcc     21300 agttgtcttc ctattcactc tttgacatga gcaaatttcc tcttaaatta agaggaactg   21360
ctgtaatgtc tcttaaggag aatcaaatca atgatatgat ttattctctt ctggaaaaag   21420
gtaggcttat cattagagaa aacaacagag ttgtggttc aagtgatatt cttgttaaca   21480
actaaacgaa catgtttatt ttcttattat ttcttactct cactagtggt agtgaccttg   21540
accggtgcac cactttgat gatgttcaag ctcctaatta cactcaacat acttcatcta    21600
tgaggggggt ttactatcct gatgaaattt ttagatcaga cactctttat ttaactcagg   21660
atttatttct tccattttat tctaatgtta cagggtttca tactattaat catacgtttg   21720
gcaaccctgt cataccttt aaggatggta tttatttgc tgccacagag aaatcaaatg     21780
ttgtccgtgg ttgggttttt ggttctacca tgaacaacaa gtcacagtcg gtgattatta   21840
ttaacaattc tactaatgtt gttatacgag catgtaactt tgaattgtgt gacaacccTT   21900
tctttgctgt ttctaaaccc atgggtacac agacacatac tatgatattc gataatgcat   21960
ttaattgcac tttcgagtac atatctgatg ccttttcgct tgatgtttca gaaaagtcag   22020
```

```
gtaattttaa acacttacga gagtttgtgt ttaaaaataa agatgggttt ctctatgttt    22080
ataagggcta tcaacctata gatgtagttc gtgatctacc ttctggtttt aacactttga    22140
aacctatttt taagttgcct cttggtatta acattacaaa ttttagagcc attcttacag    22200
ccttttcacc tgctcaagac atttggggca cgtcagctgc agcctatttt gttggctatt    22260
taaagccaac tacatttatg ctcaagtatg atgaaaatgg tacaatcaca gatgctgttg    22320
attgttctca aaatccactt gctgaactca aatgctctgt taagagcttt gagattgaca    22380
aaggaattta ccagacctct aatttcaggg ttgttccctc aggagatgtt gtgagattcc    22440
ctaatattac aaacttgtgt ccttttggag aggttttttaa tgctactaaa ttcccttctg    22500
tctatgcatg ggagagaaaa aaaatttcta attgtgttgc tgattactct gtgctctaca    22560
actcaacatt ttttttcaacc tttaagtgct atggcgtttc tgccactaag ttgaatgatc    22620
tttgcttctc caatgtctat gcagattctt ttgtagtcaa gggagatgat gtaagacaaa    22680
tagcgccagg acaaactggt gttattgctg attataatta taaattgcca gatgatttca    22740
tgggttgtgt ccttgcttgg aatactagga acattgatgc tacttcaact ggtaattata    22800
attataaata taggtatctt agacatggca agcttaggcc ctttgagaga gacatatcta    22860
atgtgccttt ctcccctgat ggcaaacctt gcaccccacc tgctcttaat tgttattggc    22920
cattaaatga ttatggtttt tacaccacta ctggcattgg ctaccaacct tacagagttg    22980
tagtactttc ttttgaactt ttaaatgcac cggccacggt ttgtggacca aaattatcca    23040
ctgaccttat taagaaccag tgtgtcaatt ttaattttaa tggactcact ggtactggtg    23100
tgttaactcc ttcttcaaag agatttcaac catttcaaca atttggccgt gatgtttctg    23160
atttcactga ttccgttcga gatcctaaaa catctgaaat attagacatt tcaccttgcg    23220 cttttgggg tgtaagtgta attacacctg gaacaaatgc ttcatctgaa gttgctgttc    23280
tatatcaaga tgttaactgc actgatgttt ctacagcaat tcatgcagat caactcacac    23340
cagcttggcg catatattct actggaaaca atgtattcca gactcaagca ggctgtctta    23400
taggagctga gcatgtcgac acttcttatg agtgcgacat tcctattgga gctggcattt    23460
gtgctagtta ccatacagtt tctttattac gtagtactag ccaaaaatct attgtggctt    23520
atactatgtc tttaggtgct gatagttcaa ttgcttactc taataacacc attgctatac    23580
ctactaactt ttcaattagc attactacag aagtaatgcc tgtttctatg gctaaaacct    23640
ccgtagatta taatatgtac atctgcggag attctactga atgtgctaat ttgcttctcc    23700
aatatggtag cttttgcaca caactaaatc gtgcactctc aggtattgct gctgaacagg    23760
atcgcaacac acgtgaagtg ttcgctcaag tcaaacaaat gtacaaaacc ccaactttga    23820
aatattttgg tggtttttaat ttttcacaaa tattacctga ccctctaaag ccaactaaga    23880
ggtcttttat tgaggacttg ctctttaata aggtgacact cgctgatgct ggcttcatga    23940
agcaatatgg cgaatgccta ggtgatatta atgctagaga tctcatttgt gcgcagaagt    24000
tcaatggact tacagtgttg ccacctctgc tcactgatga tatgattgct gcctacactg    24060
ctgctctagt tagtggtact gccactgctg gatggacatt tggtgctggc gctgctcttc    24120 aaatacctttt tgctatgcaa atggcatata ggttcaatgg cattggagtt acccaaaatg    24180
ttctctatga gaaccaaaaa caaatcgcca accaattaa caaggcgatt agtcaaattc    24240
aagaatcact tacaacaaca tcaactgcat tgggcaagct gcaagacgtt gttaaccaga    24300
atgctcaagc attaaacaca cttgttaaac aacttagctc taattttggt gcaatttcaa    24360
```

```
gtgtgctaaa tgatatcctt tcgcgacttg ataaagtcga ggcggaggta caaattgaca   24420
ggttaattac aggcagactt caaagccttc aaacctatgt aacacaacaa ctaatcaggg   24480
ctgctgaaat cagggcttct gctaatcttg ctgctactaa aatgtctgag tgtgttcttg   24540
gacaatcaaa aagagttgac ttttgtggaa agggctacca ccttatgtcc ttcccacaag   24600
cagccccgca tggtgttgtc ttcctacatg tcacgtatgt gccatcccag gagaggaact   24660
tcaccacagc gccagcaatt tgtcatgaag gcaaagcata cttccctcgt gaaggtgttt   24720
ttgtgtttaa tggcacttct tggtttatta cacagaggaa cttctttttct ccacaaataa   24780 ttactacaga caatacattt gtctcaggaa attgtgatgt cgttattggc atcattaaca   24840
acacagttta tgatcctctg caacctgagc ttgactcatt caaagaagag ctggacaagt   24900
acttcaaaaa tcatacatca ccagatgttg atcttggcga catttcaggc attaacgctt   24960
ctgtcgtcaa cattcaaaaa gaaattgacc gcctcaatga ggtcgctaaa aatttaaatg   25020
aatcactcat tgaccttcaa gaattgggaa aatatgagca atatattaaa tggccttggt   25080
atgtttggct cggcttcatt gctggactaa ttgccatcgt catggttaca atcttgcttt   25140
gttgcatgac tagttgttgc agttgcctca agggtgcatg ctcttgtggt tcttgctgca   25200
agtttgatga ggatgactct gagccagttc tcaagggtgt caaattacat tacacataaa   25260
cgaacttatg gatttgttta tgagattttt tactcttaga tcaattactg cacagccagt   25320
aaaaattgac aatgcttctc ctgcaagtac tgttcatgct acagcaacga taccgctaca   25380
agcctcactc cctttcggat ggcttgttat tggcgttgca tttcttgctg tttttcagag   25440
cgctaccaaa ataattgcgc tcaataaaag atggcagcta gccctttata agggcttcca   25500
gttcatttgc aatttactgc tgctatttgt taccatctat tcacatcttt tgcttgtcgc   25560
tgcaggtatg gaggcgcaat ttttgtacct ctatgccttg atatatttttc tacaatgcat   25620 caacgcatgt agaattatta tgagatgttg gctttgttgg aagtgcaaat ccaagaaccc   25680
attactttat gatgccaact actttgtttg ctggcacaca cataactatg actactgtat   25740
accatataac agtgtcacag atacaattgt cgttactgaa ggtgacggca tttcaacacc   25800
aaaactcaaa gaagactacc aaattggtgg ttattctgag gataggcact caggtgttaa   25860
agactatgtc gttgtacatg gctatttcac cgaagtttac taccagcttg agtctacaca   25920
aattactaca gacactggta ttgaaaatgc tacattcttc atctttaaca gcttgttaa   25980 agacccaccg aatgtgcaaa tacacacaat cgacggctct tcaggagttg ctaatccagc   26040
aatggatcca atttatgatg agccgacgac gactactagc gtgcctttgt aagcacaaga   26100
aagtgagtac gaacttatgt actcattcgt ttcggaagaa acaggtacgt taatagttaa   26160
tagcgtactt cttttttcttg ctttcgtggt attcttgcta gtcacactag ccatccttac   26220
tgcgcttcga ttgtgtgcgt actgctgcaa tattgttaac gtgagtttag taaaaccaac   26280
ggtttacgtc tactcgcgtg ttaaaaatct gaactcttct gaaggagttc ctgatcttct   26340
ggtctaaacg aactaactat tattattatt ctgtttggaa ctttaacatt gcttatcatg   26400
gcagacaacg gtactattac cgttgaggag cttaaacaac tcctggaaca atggaaccta   26460
gtaataggtt tcctattcct agcctggatt atgttactac aatttgccta ttctaatcgg   26520
aacaggtttt tgtacataat aaagcttgtt ttcctctggc tcttgtggcc agtaacactt   26580
gcttgttttg tgcttgctgc tgtctacaga attaattggg tgactggcgg gattgcgatt   26640
gcaatggctt gtattgtagg cttgatgtgg cttagctact tcgttgcttc cttcaggctg   26700
tttgctcgta cccgctcaat gtggtcattc aacccagaaa caaacattct tctcaatgtg   26760
```

```
cctctccggg ggacaattgt gaccagaccg ctcatggaaa gtgaacttgt cattggtgct    26820
gtgatcattc gtggtcactt gcgaatggcc ggacactccc tagggcgctg tgacattaag    26880
gacctgccaa aagagatcac tgtggctaca tcacgaacgc tttcttatta caaattagga    26940
gcgtcgcagc gtgtaggcac tgattcaggt tttgctgcat acaaccgcta ccgtattgga    27000
aactataaat taaatacaga ccacgccggt agcaacgaca atattgcttt gctagtacag    27060
taagtgacaa cagatgtttc atcttgttga cttccaggtt acaatagcag agatattgat    27120
tatcattatg aggactttca ggattgctat ttggaatctt gacgttataa taagttcaat    27180
agtgagacaa ttatttaagc ctctaactaa gaagaattat tcggagttag atgatgaaga    27240
acctatggag ttagattatc cataaaacga acatgaaaat tattctcttc ctgacattga    27300
ttgtatttac atcttgcgag ctatatcact atcaggagtg tgttagaggt acgactgtac    27360
tactaaaaga accttgccca tcaggaacat acgagggcaa ttcaccattt caccctcttg    27420
ctgacaataa atttgcacta acttgcacta gcacacactt tgcttttgct tgtgctgacg    27480
gtactcgaca tacctatcag ctgcgtgcaa gatcagtttc accaaaactt ttcatcagac    27540
aagaggaggt tcaacaagag ctctactcgc cactttttct cattgttgct gctctagtat    27600
ttttaatact ttgcttcacc attaagagaa agacagaatg aatgagctca ctttaattga    27660
cttctatttg tgctttttag cctttctgct attccttgtt taataatgc ttattatatt    27720 ttggttttca ctcgaaatcc aggatctaga agaaccttgt accaaagtct aaacgaacat    27780
gaaacttctc attgttttga cttgtatttc tctatgcagt tgcatatgca ctgtagtaca    27840
gcgctgtgca tctaataaac ctcatgtgct tgaagatcct tgtaaggtac aacactaggg    27900
gtaatactta tagcactgct tggctttgtg ctctaggaaa ggttttacct tttcatagat    27960
ggcacactat ggttcaaaca tgcacaccta atgttactat caactgtcaa gatccagctg    28020
gtggtgcgct tatagctagg tgttggtacc ttcatgaagg tcaccaaaact gctgcattta    28080 gagacgtact tgttgtttta aataaacgaa caaattaaaa tgtctgataa tggaccccaa    28140
tcaaaccaac gtagtgcccc ccgcattaca tttggtggac ccacagattc aactgacaat    28200
aaccagaatg gaggacgcaa tgggcaagg ccaaacagc gccgacccca aggtttaccc    28260
aataatactg cgtcttggtt cacagctctc actcagcatg gcaaggagga acttagattc    28320
cctcgaggcc agggcgttcc aatcaacacc aatagtggtc cagatgacca aattggctac    28380
taccgaagag ctacccgacg agttcgtggt ggtgacggca aaatgaaaga gctcagcccc    28440
agatggtact tctattacct aggaactggc ccagaagctt cacttcccta cggcgctaac    28500
aaagaaggca tcgtatgggt tgcaactgag ggagccttga atacacccaa agaccacatt    28560
ggcacccgca atcctaataa caatgctgcc accgtgctac aacttcctca aggaacaaca    28620
ttgccaaaag gcttctacgc agagggaagc agaggcggca gtcaagcctc ttctcgctcc    28680
tcatcacgta gtcgcggtaa ttcaagaaat tcaactcctg gcagcagtag gggaaattct    28740
cctgctcgaa tggctagcgg aggtggtgaa actgccctcg cgctattgct gctagacaga    28800
ttgaaccagc ttgagagcaa agtttctggt aaaggccaac aacaacaagg ccaaactgtc    28860
actaagaaat ctgctgctga ggcatctaaa aagcctcgcc aaaaacgtac tgccacaaaa    28920
cagtacaacg tcactcaagc atttgggaga cgtggtccag aacaaaccca aggaaatttc    28980
ggggaccaag acctaatcag acaaggaact gattacaaac attggccgca aattgcacaa    29040
tttgctccaa gtgcctctgc attctttgga atgtcacgca ttggcatgga agtcacacct    29100
```

```
tcgggaacat ggctgactta tcatggagcc attaaattgg atgacaaaga tccacaattc      29160
aaagacaacg tcatactgct gaacaagcac attgacgcat acaaaacatt cccaccaaca      29220
gagcctaaaa aggacaaaaa gaaaaagact gatgaagctc agcctttgcc gcagagacaa      29280
aagaagcagc ccactgtgac tcttcttcct gcggctgaca tggatgattt ctccagacaa      29340
cttcaaaatt ccatgagtgg agcttctgct gattcaactc aggcataaac actcatgatg      29400
accacacaag gcagatgggc tatgtaaacg ttttcgcaat tccgtttacg atacatagtc      29460
tactcttgtg cagaatgaat tctcgtaact aaacagcaca agtaggttta gttaacttta      29520
atctcacata gcaatcttta atcaatgtgt aacattaggg aggacttgaa agagccacca      29580
cattttcatc gaggccacgc ggagtacgat cgagggtaca gtgaataatg ctagggagag      29640
ctgcctatat ggaagagccc taatgtgtaa aattaatttt agtagtgcta tccccatgtg      29700
attttaatag cttcttagga gaatgacaaa aaaaaaaaa aaaaaaaaa a                 29751

<210> SEQ ID NO 16
<211> LENGTH: 47
<212> TYPE: DNA
<213> ORGANISM: Severe acute respiratory syndrome virus

<400> SEQUENCE: 16
acattttcat cgaggccacg cggagtacga tcgagggtac agtgaat                    47

<210> SEQ ID NO 17
<211> LENGTH: 32
<212> TYPE: DNA
<213> ORGANISM: Severe acute respiratory syndrome virus

<400> SEQUENCE: 17
cgaggccacg cggagtacga tcgagggtac ag                                    32

<210> SEQ ID NO 18
<211> LENGTH: 339
<212> TYPE: DNA
<213> ORGANISM: Severe acute respiratory syndrome virus

<400> SEQUENCE: 18
acactcatga tgaccacaca aggcagatgg gctatgtaaa cgttttcgca attccgttta      60
cgatacatag tctactcttg tgcagaatga attctcgtaa ctaaacagca caagtaggtt     120
tagttaactt taatctcaca tagcaatctt taatcaatgt gtaacattag ggaggacttg     180
aaagagccac cacattttca tcgaggccac gcggagtacg atcgagggta cagtgaataa     240
tgctagggag agctgcctat atggaagagc cctaatgtgt aaaattaatt ttagtagtgc     300
tatccccatg tgatttttaat agcttcttag gagaatgac                           339

<210> SEQ ID NO 19
<211> LENGTH: 35
<212> TYPE: DNA
<213> ORGANISM: Artificial Sequence
<220> FEATURE:
<223> OTHER INFORMATION: s2m motif
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 19
```

-continued

```
gccgnggcca cgcsgagtas gancgagggt acags                          35

<210> SEQ ID NO 20
<211> LENGTH: 26
<212> TYPE: RNA
<213> ORGANISM: Severe acute respiratory syndrome virus

<400> SEQUENCE: 20
ucucuaaacg aacuuuaaaa ucugug                                    26

<210> SEQ ID NO 21
<211> LENGTH: 16
<212> TYPE: RNA
<213> ORGANISM: Severe acute respiratory syndrome virus

<400> SEQUENCE: 21
caacuaaacg aacaug                                               16

<210> SEQ ID NO 22
<211> LENGTH: 18
<212> TYPE: RNA
<213> ORGANISM: Severe acute respiratory syndrome virus

<400> SEQUENCE: 22
cacauaaacg aacuuaug                                             18

<210> SEQ ID NO 23
<211> LENGTH: 16
<212> TYPE: RNA
<213> ORGANISM: Severe acute respiratory syndrome virus

<400> SEQUENCE: 23
ugaguacgaa cuuaug                                               16

<210> SEQ ID NO 24
<211> LENGTH: 18
<212> TYPE: RNA
<213> ORGANISM: Severe acute respiratory syndrome virus

<400> SEQUENCE: 24
ggucuaaacg aacuaacu                                             18

<210> SEQ ID NO 25
<211> LENGTH: 11
<212> TYPE: RNA
<213> ORGANISM: Severe acute respiratory syndrome virus

<400> SEQUENCE: 25
aacuauaaau u                                                    11

<210> SEQ ID NO 26
<211> LENGTH: 17
<212> TYPE: RNA
<213> ORGANISM: Severe acute respiratory syndrome virus

<400> SEQUENCE: 26
uccauaaaac gaacaug                                              17

<210> SEQ ID NO 27
<211> LENGTH: 24
<212> TYPE: RNA
<213> ORGANISM: Severe acute respiratory syndrome virus
```

-continued

<400> SEQUENCE: 27
ugcucuagua uuuuuaauac uuug                                              24

<210> SEQ ID NO 28
<211> LENGTH: 16
<212> TYPE: RNA
<213> ORGANISM: Severe acute respiratory syndrome virus

<400> SEQUENCE: 28
agucuaaacg aacaug                                                       16

<210> SEQ ID NO 29
<211> LENGTH: 15
<212> TYPE: RNA
<213> ORGANISM: Severe acute respiratory syndrome virus

<400> SEQUENCE: 29
cuaauaaacc ucaug                                                        15

<210> SEQ ID NO 30
<211> LENGTH: 24
<212> TYPE: RNA
<213> ORGANISM: Severe acute respiratory syndrome virus

<400> SEQUENCE: 30
uaaauaaacg aacaaauuaa aaug                                              24

<210> SEQ ID NO 31
<211> LENGTH: 136
<212> TYPE: DNA
<213> ORGANISM: Equine rhinovirus

<400> SEQUENCE: 31
acccgttacc ctaaaattcc ctcccctttc tcttcactcg ccgaggccac gccgagtagg        60
accgagggta cagcgagtct tttagtttaa ggtgttagat gtaaggtacg tgggctttct       120
tttggtttac ttcttc                                                      136

<210> SEQ ID NO 32
<211> LENGTH: 178
<212> TYPE: DNA
<213> ORGANISM: Avian infectious bronchitis

<400> SEQUENCE: 32
tagtttagtt taagttagtt tagagtaggt ataaagatgc cagtgccggg gccacgcgga        60
gtacgatcga gggtacagca ctaggacgcc cattagggga agagctaaat tttagtttaa       120
gttaagttta attggctaag tatagttaaa atttataggc tagtatagag ttagagca         178

<210> SEQ ID NO 33
<211> LENGTH: 1255
<212> TYPE: PRT
<213> ORGANISM: Severe acute respiratory syndrome virus

<400> SEQUENCE: 33

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

-continued

```
Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
```

```
                465                 470                 475                 480
Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
                500                 505                 510

Pro Lys Leu Ser Thr Asp Leu Ile Lys Asn Gln Cys Val Asn Phe Asn
                515                 520                 525

Phe Asn Gly Leu Thr Gly Thr Gly Val Leu Thr Pro Ser Ser Lys Arg
                530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
                580                 585                 590

Glu Val Ala Val Leu Tyr Gln Asp Val Asn Cys Thr Asp Val Ser Thr
                595                 600                 605

Ala Ile His Ala Asp Gln Leu Thr Pro Ala Trp Arg Ile Tyr Ser Thr
                610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
                660                 665                 670

Ser Ile Val Ala Tyr Thr Met Ser Leu Gly Ala Asp Ser Ser Ile Ala
                675                 680                 685

Tyr Ser Asn Asn Thr Ile Ala Ile Pro Thr Asn Phe Ser Ile Ser Ile
                690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
                755                 760                 765

Gln Met Tyr Lys Thr Pro Thr Leu Lys Tyr Phe Gly Gly Phe Asn Phe
                770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
                835                 840                 845

Asp Asp Met Ile Ala Ala Tyr Thr Ala Ala Leu Val Ser Gly Thr Ala
                850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895
```

-continued

```
Val Leu Tyr Glu Asn Gln Lys Gln Ile Ala Asn Gln Phe Asn Lys Ala
            900                 905                 910
Ile Ser Gln Ile Gln Glu Ser Leu Thr Thr Thr Ser Thr Ala Leu Gly
        915                 920                 925
Lys Leu Gln Asp Val Val Asn Gln Asn Ala Gln Ala Leu Asn Thr Leu
        930                 935                 940
Val Lys Gln Leu Ser Ser Asn Phe Gly Ala Ile Ser Ser Val Leu Asn
945                 950                 955                 960
Asp Ile Leu Ser Arg Leu Asp Lys Val Glu Ala Glu Val Gln Ile Asp
                965                 970                 975
Arg Leu Ile Thr Gly Arg Leu Gln Ser Leu Gln Thr Tyr Val Thr Gln
            980                 985                 990
Gln Leu Ile Arg Ala Ala Glu Ile  Arg Ala Ser Ala Asn  Leu Ala Ala
        995                 1000                1005
Thr Lys Met Ser Glu Cys Val  Leu Gly Gln Ser Lys  Arg Val Asp
    1010                1015                1020
Phe Cys Gly Lys Gly Tyr His  Leu Met Ser Phe Pro  Gln Ala Ala
    1025                1030                1035
Pro His Gly Val Val Phe Leu  His Val Thr Tyr Val  Pro Ser Gln
    1040                1045                1050
Glu Arg Asn Phe Thr Thr Ala  Pro Ala Ile Cys His  Glu Gly Lys
    1055                1060                1065
Ala Tyr Phe Pro Arg Glu Gly  Val Phe Val Phe Asn  Gly Thr Ser
    1070                1075                1080
Trp Phe Ile Thr Gln Arg Asn  Phe Phe Ser Pro Gln  Ile Ile Thr
    1085                1090                1095
Thr Asp Asn Thr Phe Val Ser  Gly Asn Cys Asp Val  Val Ile Gly
    1100                1105                1110
Ile Ile Asn Asn Thr Val Tyr  Asp Pro Leu Gln Pro  Glu Leu Asp
    1115                1120                1125
Ser Phe Lys Glu Glu Leu Asp  Lys Tyr Phe Lys Asn  His Thr Ser
    1130                1135                1140
Pro Asp Val Asp Leu Gly Asp  Ile Ser Gly Ile Asn  Ala Ser Val
    1145                1150                1155
Val Asn Ile Gln Lys Glu Ile  Asp Arg Leu Asn Glu  Val Ala Lys
    1160                1165                1170
Asn Leu Asn Glu Ser Leu Ile  Asp Leu Gln Glu Leu  Gly Lys Tyr
    1175                1180                1185
Glu Gln Tyr Ile Lys Trp Pro  Trp Tyr Val Trp Leu  Gly Phe Ile
    1190                1195                1200
Ala Gly Leu Ile Ala Ile Val  Met Val Thr Ile Leu  Leu Cys Cys
    1205                1210                1215
Met Thr Ser Cys Cys Ser Cys  Leu Lys Gly Ala Cys  Ser Cys Gly
    1220                1225                1230
Ser Cys Cys Lys Phe Asp Glu  Asp Asp Ser Glu Pro  Val Leu Lys
    1235                1240                1245
Gly Val Lys Leu His Tyr Thr
    1250                1255

<210> SEQ ID NO 34
<211> LENGTH: 220
<212> TYPE: PRT
<213> ORGANISM: Severe acute respiratory syndrome virus
```

-continued

```
<400> SEQUENCE: 34

Met Ala Asp Asn Gly Thr Ile Thr Val Glu Glu Leu Lys Gln Leu Leu
1               5                   10                  15

Glu Gln Trp Asn Leu Val Ile Gly Phe Leu Phe Leu Ala Trp Ile Met
            20                  25                  30

Leu Leu Gln Phe Ala Tyr Ser Asn Arg Asn Arg Phe Leu Tyr Ile Ile
        35                  40                  45

Lys Leu Val Phe Leu Trp Leu Leu Trp Pro Val Thr Leu Ala Cys Phe
    50                  55                  60

Val Leu Ala Ala Val Tyr Arg Ile Asn Trp Val Thr Gly Gly Ile Ala
65                  70                  75                  80

Ile Ala Met Ala Cys Ile Val Gly Leu Met Trp Leu Ser Tyr Phe Val
                85                  90                  95

Ala Ser Phe Arg Leu Phe Ala Arg Thr Arg Ser Met Trp Ser Phe Asn
            100                 105                 110

Pro Glu Thr Asn Ile Leu Leu Asn Val Pro Leu Arg Gly Thr Ile Val
        115                 120                 125

Thr Arg Pro Leu Met Glu Ser Glu Leu Val Ile Gly Ala Val Ile Ile
    130                 135                 140

Arg Gly His Leu Arg Met Ala Gly His Ser Leu Gly Arg Cys Asp Ile
145                 150                 155                 160

Lys Asp Leu Pro Lys Glu Ile Thr Val Ala Thr Ser Arg Thr Leu Ser
                165                 170                 175

Tyr Tyr Lys Leu Gly Ala Ser Gln Arg Val Gly Thr Asp Ser Gly Phe
            180                 185                 190

Ala Ala Tyr Asn Arg Tyr Arg Ile Gly Asn Tyr Lys Leu Asn Thr Asp
        195                 200                 205

His Ala Gly Ser Asn Asp Asn Ile Ala Leu Leu Val
    210                 215                 220

<210> SEQ ID NO 35
<211> LENGTH: 76
<212> TYPE: PRT
<213> ORGANISM: Severe acute respiratory syndrome virus

<400> SEQUENCE: 35

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60

Leu Asn Ser Ser Glu Gly Val Pro Asp Leu Leu Val
65                  70                  75

<210> SEQ ID NO 36
<211> LENGTH: 422
<212> TYPE: PRT
<213> ORGANISM: Severe acute respiratory syndrome virus

<400> SEQUENCE: 36

Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
```

```
                  20                  25                  30
Arg Asn Gly Ala Arg Pro Lys Gln Arg Pro Gln Gly Leu Pro Asn
                35                  40                  45
Asn Thr Ala Ser Trp Phe Thr Ala Leu Thr Gln His Gly Lys Glu Glu
 50                  55                  60
Leu Arg Phe Pro Arg Gly Gln Gly Val Pro Ile Asn Thr Asn Ser Gly
 65                  70                  75                  80
Pro Asp Asp Gln Ile Gly Tyr Tyr Arg Arg Ala Thr Arg Arg Val Arg
                 85                  90                  95
Gly Gly Asp Gly Lys Met Lys Glu Leu Ser Pro Arg Trp Tyr Phe Tyr
                100                 105                 110
Tyr Leu Gly Thr Gly Pro Glu Ala Ser Leu Pro Tyr Gly Ala Asn Lys
                115                 120                 125
Glu Gly Ile Val Trp Val Ala Thr Glu Gly Ala Leu Asn Thr Pro Lys
                130                 135                 140
Asp His Ile Gly Thr Arg Asn Pro Asn Asn Asn Ala Ala Thr Val Leu
145                 150                 155                 160
Gln Leu Pro Gln Gly Thr Thr Leu Pro Lys Gly Phe Tyr Ala Glu Gly
                165                 170                 175
Ser Arg Gly Gly Ser Gln Ala Ser Ser Arg Ser Ser Arg Ser Arg
                180                 185                 190
Gly Asn Ser Arg Asn Ser Thr Pro Gly Ser Ser Arg Gly Asn Ser Pro
                195                 200                 205
Ala Arg Met Ala Ser Gly Gly Gly Glu Thr Ala Leu Ala Leu Leu Leu
                210                 215                 220
Leu Asp Arg Leu Asn Gln Leu Glu Ser Lys Val Ser Gly Lys Gly Gln
225                 230                 235                 240
Gln Gln Gln Gly Gln Thr Val Thr Lys Lys Ser Ala Ala Glu Ala Ser
                245                 250                 255
Lys Lys Pro Arg Gln Lys Arg Thr Ala Thr Lys Gln Tyr Asn Val Thr
                260                 265                 270
Gln Ala Phe Gly Arg Arg Gly Pro Glu Gln Thr Gln Gly Asn Phe Gly
                275                 280                 285
Asp Gln Asp Leu Ile Arg Gln Gly Thr Asp Tyr Lys His Trp Pro Gln
                290                 295                 300
Ile Ala Gln Phe Ala Pro Ser Ala Ser Ala Phe Phe Gly Met Ser Arg
305                 310                 315                 320
Ile Gly Met Glu Val Thr Pro Ser Gly Thr Trp Leu Thr Tyr His Gly
                325                 330                 335
Ala Ile Lys Leu Asp Asp Lys Asp Pro Gln Phe Lys Asp Asn Val Ile
                340                 345                 350
Leu Leu Asn Lys His Ile Asp Ala Tyr Lys Thr Phe Pro Pro Thr Glu
                355                 360                 365
Pro Lys Lys Asp Lys Lys Lys Thr Asp Glu Ala Gln Pro Leu Pro
                370                 375                 380
Gln Arg Gln Lys Lys Gln Pro Thr Val Thr Leu Leu Pro Ala Ala Asp
385                 390                 395                 400
Met Asp Asp Phe Ser Arg Gln Leu Gln Asn Ser Met Ser Gly Ala Ser
                405                 410                 415
Ala Asp Ser Thr Gln Ala
                420

<210> SEQ ID NO 37
```

<211> LENGTH: 230
<212> TYPE: PRT
<213> ORGANISM: Bovine coronavirus

<400> SEQUENCE: 37

Met Ser Ser Val Thr Thr Pro Ala Pro Val Tyr Thr Trp Thr Ala Asp
1               5                   10                  15

Glu Ala Ile Lys Phe Leu Lys Glu Trp Asn Phe Ser Leu Gly Ile Ile
            20                  25                  30

Leu Leu Phe Ile Thr Val Ile Leu Gln Phe Gly Tyr Thr Ser Arg Ser
        35                  40                  45

Met Phe Val Tyr Val Ile Lys Met Val Ile Leu Trp Leu Met Trp Pro
50                  55                  60

Leu Thr Ile Ile Leu Thr Ile Phe Asn Cys Val Tyr Ala Leu Asn Asn
65                  70                  75                  80

Val Tyr Leu Gly Phe Ser Ile Val Phe Thr Ile Val Ala Ile Ile Met
                85                  90                  95

Trp Ile Val Tyr Phe Val Asn Ser Ile Arg Leu Phe Ile Arg Thr Gly
            100                 105                 110

Ser Trp Trp Ser Phe Asn Pro Glu Thr Asn Asn Leu Met Cys Ile Asp
        115                 120                 125

Met Lys Gly Arg Met Tyr Val Arg Pro Ile Ile Glu Asp Tyr His Thr
130                 135                 140

Leu Thr Val Thr Ile Ile Arg Gly His Leu Tyr Met Gln Gly Ile Lys
145                 150                 155                 160

Leu Gly Thr Gly Tyr Ser Leu Ser Asp Leu Pro Ala Tyr Val Thr Val
                165                 170                 175

Ala Lys Val Ser His Leu Leu Thr Tyr Lys Arg Gly Phe Leu Asp Lys
            180                 185                 190

Ile Gly Asp Thr Ser Gly Phe Ala Val Tyr Val Lys Ser Lys Val Gly
        195                 200                 205

Asn Tyr Arg Leu Pro Ser Thr Gln Lys Gly Ser Gly Leu Asp Thr Ala
210                 215                 220

Leu Leu Arg Asn Asn Ile
225                 230

<210> SEQ ID NO 38
<211> LENGTH: 226
<212> TYPE: PRT
<213> ORGANISM: Avian infectious bronchitis virus

<400> SEQUENCE: 38

Met Ser Asn Gly Thr Glu Asn Cys Thr Leu Ser Thr Gln Gln Ala Ala
1               5                   10                  15

Glu Leu Phe Lys Glu Tyr Asn Leu Phe Ile Thr Ala Phe Leu Leu Phe
            20                  25                  30

Leu Thr Ile Leu Leu Gln Tyr Gly Tyr Ala Thr Arg Ser Arg Phe Ile
        35                  40                  45

Tyr Ile Leu Lys Met Ile Val Leu Trp Cys Phe Trp Pro Leu Asn Ile
50                  55                  60

Ala Val Gly Ile Ile Ser Cys Ile Tyr Pro Pro Asn Thr Gly Gly Leu
65                  70                  75                  80

Val Ala Ala Ile Ile Leu Thr Val Phe Ala Cys Leu Ser Phe Val Gly
                85                  90                  95

Tyr Trp Ile Gln Ser Phe Arg Leu Phe Lys Arg Cys Arg Ser Trp Trp
            100                 105                 110

```
Ser Phe Asn Pro Glu Ser Asn Ala Val Gly Ser Ile Leu Leu Thr Asn
            115                 120                 125

Gly Gln Gln Cys Asn Phe Ala Ile Glu Ser Val Pro Met Val Leu Ser
        130                 135                 140

Pro Ile Ile Lys Asn Gly Ala Leu Tyr Cys Glu Gly Gln Trp Leu Ala
145                 150                 155                 160

Lys Cys Glu Pro Asp His Leu Pro Lys Asp Ile Phe Val Cys Thr Pro
                165                 170                 175

Asp Arg Arg Asn Ile Tyr Arg Met Val Gln Lys Tyr Thr Gly Asp Gln
            180                 185                 190

Ser Gly Asn Lys Lys Arg Phe Ala Thr Phe Val Tyr Ala Lys Gln Ser
        195                 200                 205

Val Asp Thr Gly Glu Leu Gly Ser Val Ala Thr Gly Gly Ser Ser Leu
210                 215                 220

Tyr Thr
225

<210> SEQ ID NO 39
<211> LENGTH: 262
<212> TYPE: PRT
<213> ORGANISM: Transmissible gastroenteritis virus

<400> SEQUENCE: 39

Met Lys Ile Leu Leu Ile Leu Ala Cys Val Ile Ala Cys Ala Cys Gly
1               5                   10                  15

Glu Arg Tyr Cys Ala Met Lys Ser Asp Thr Asp Leu Ser Cys Arg Asn
            20                  25                  30

Ser Thr Ala Ser Asp Cys Glu Ser Cys Phe Asn Gly Gly Asp Leu Ile
        35                  40                  45

Trp His Leu Ala Asn Trp Asn Phe Ser Trp Ser Ile Ile Leu Ile Val
    50                  55                  60

Phe Ile Thr Val Leu Gln Tyr Gly Arg Pro Gln Phe Ser Trp Phe Val
65                  70                  75                  80

Tyr Gly Ile Lys Met Leu Ile Met Trp Leu Leu Trp Pro Val Val Leu
                85                  90                  95

Ala Leu Thr Ile Phe Asn Ala Tyr Ser Glu Tyr Gln Val Ser Arg Tyr
            100                 105                 110

Val Met Phe Gly Phe Ser Ile Ala Gly Ala Ile Val Thr Phe Val Leu
        115                 120                 125

Trp Ile Met Tyr Phe Val Arg Ser Ile Gln Leu Tyr Arg Arg Thr Lys
    130                 135                 140

Ser Trp Trp Ser Phe Asn Pro Glu Thr Lys Ala Ile Leu Cys Val Ser
145                 150                 155                 160

Ala Leu Gly Arg Ser Tyr Val Leu Pro Leu Glu Gly Val Pro Thr Gly
                165                 170                 175

Val Thr Leu Thr Leu Leu Ser Gly Asn Leu Tyr Ala Glu Gly Phe Lys
            180                 185                 190

Ile Ala Gly Gly Met Asn Ile Asp Asn Leu Pro Lys Tyr Val Met Val
        195                 200                 205

Ala Leu Pro Ser Arg Thr Ile Val Tyr Thr Leu Val Gly Lys Lys Leu
210                 215                 220

Lys Ala Ser Ser Ala Thr Gly Trp Ala Tyr Tyr Val Lys Ser Lys Ala
225                 230                 235                 240

Gly Asp Tyr Ser Thr Glu Ala Arg Thr Asp Asn Leu Ser Glu Gln Glu
```

-continued

```
                    245                 250                 255
Lys Leu Leu His Met Val
            260

<210> SEQ ID NO 40
<211> LENGTH: 263
<212> TYPE: PRT
<213> ORGANISM: feline coronavirus

<400> SEQUENCE: 40

Met Lys Ile Leu Leu Ile Leu Ala Cys Ala Val Ala Cys Val Tyr Gly
1               5                   10                  15

Glu Gln Ile Arg Tyr Cys Ala Met Gln Glu Thr Gly Leu Ser Cys Arg
            20                  25                  30

Asn Gly Thr Ala Ser Asp Cys Glu Ser Cys Phe Asn Gly Gly Asp Leu
        35                  40                  45

Ile Trp His Leu Ala Asn Trp Asn Phe Ser Trp Ser Ile Ile Leu Ile
50                  55                  60

Val Phe Ile Thr Val Leu Gln Tyr Gly Arg Pro Gln Phe Ser Trp Phe
65                  70                  75                  80

Val Tyr Gly Ile Lys Met Leu Ile Met Trp Leu Leu Trp Pro Ile Val
                85                  90                  95

Leu Ala Leu Thr Ile Phe Asn Ala Tyr Ser Glu Tyr Glu Val Ser Arg
            100                 105                 110

Tyr Val Met Phe Gly Phe Ser Val Ala Gly Ala Val Val Thr Phe Ala
        115                 120                 125

Leu Trp Met Met Tyr Phe Val Arg Ser Ile Gln Leu Tyr Arg Arg Thr
130                 135                 140

Lys Ser Trp Trp Ser Phe Asn Pro Glu Thr Asn Ala Ile Leu Cys Val
145                 150                 155                 160

Asn Ala Leu Gly Arg Ser Tyr Val Leu Pro Leu Asp Gly Thr Pro Thr
                165                 170                 175

Gly Val Thr Leu Thr Leu Leu Ser Gly Asn Leu Tyr Ala Glu Gly Phe
            180                 185                 190

Lys Met Ala Gly Gly Leu Thr Ile Glu His Leu Pro Lys Tyr Val Met
        195                 200                 205

Ile Arg Thr Pro Asn Arg Thr Ile Val Tyr Thr Leu Val Gly Lys Gln
210                 215                 220

Leu Lys Ala Thr Thr Ala Thr Gly Trp Ala Tyr Tyr Val Lys Ser Lys
225                 230                 235                 240

Ala Gly Asp Tyr Ser Thr Glu Ala Arg Thr Asp Asn Leu Ser Glu His
                245                 250                 255

Glu Lys Leu Leu His Met Val
            260

<210> SEQ ID NO 41
<211> LENGTH: 231
<212> TYPE: PRT
<213> ORGANISM: Human coronavirus OC43
        MSSKTTPAPVYIWTADEAIKFLKEWNFSLGIILLFITIILQFGYTSRSMFVYVIKMIILWLMWPLT
        IILTIFNCVYALNNVYLGLSIVFTIVAIIMWIVYFVNSIRLFIRTGSFWSFNPETNNLMCIDMKGT
        MYVRPIIEDYHTLTVTIIRGHLYIQGIKLGTGYSWADLPAYMTVAKVTHLCTYKRGFLDRISDTSG
        FAVYVKSKVGNYRLPSTQKGSGMDTALLRNNI
                <SEQ ID NO:37;prt;Porcine hemagglutinating encephalomyelitis virus

<400> SEQUENCE: 41

Met Ser Ser Pro Thr Thr Pro Val Pro Val Ile Ser Trp Thr Ala Asp
1               5                   10                  15
```

-continued

```
Glu Ala Ile Lys Phe Leu Lys Glu Trp Asn Phe Ser Leu Gly Ile Ile
             20                  25                  30

Val Leu Phe Ile Thr Ile Ile Leu Gln Phe Gly Tyr Thr Ser Arg Ser
             35                  40                  45

Met Phe Val Tyr Val Ile Lys Met Val Ile Leu Trp Leu Met Trp Pro
 50                  55                  60

Leu Thr Ile Ile Leu Thr Ile Phe Asn Cys Val Tyr Ala Leu Asn Asn
65                  70                  75                  80

Val Tyr Leu Gly Phe Ser Ile Val Phe Thr Ile Val Ala Ile Ile Met
                 85                  90                  95

Trp Val Val Tyr Phe Val Asn Ser Ile Arg Leu Phe Ile Arg Thr Gly
             100                 105                 110

Ser Trp Trp Ser Phe Asn Pro Glu Thr Asn Asn Leu Met Cys Ile Asp
             115                 120                 125

Met Lys Gly Arg Met Tyr Val Arg Pro Ile Ile Glu Asp Tyr His Thr
         130                 135                 140

Leu Thr Ala Thr Ile Ile Arg Gly His Leu Tyr Ile Gln Gly Ile Lys
145                 150                 155                 160

Leu Gly Thr Gly Tyr Ser Leu Ser Asp Leu Pro Ala Tyr Val Thr Val
                 165                 170                 175

Ala Lys Val Thr His Leu Cys Thr Tyr Lys Arg Gly Phe Leu Asp Arg
             180                 185                 190

Ile Gly Asp Thr Ser Gly Phe Ala Val Tyr Val Lys Ser Lys Val Gly
             195                 200                 205

Asn Tyr Arg Leu Pro Ser Thr His Lys Gly Ser Gly Met Asp Thr Ala
         210                 215                 220

Leu Leu Arg Asn Asn Ile Met
225                 230

<210> SEQ ID NO 42
<211> LENGTH: 223
<212> TYPE: PRT
<213> ORGANISM: Avian infectious bronchitis virus

<400> SEQUENCE: 42

Met Met Glu Asn Cys Thr Leu Asn Leu Glu Gln Ala Thr Leu Leu Phe
 1               5                  10                  15

Lys Glu Tyr Asn Leu Phe Ile Thr Ala Phe Leu Leu Phe Leu Thr Ile
             20                  25                  30

Leu Leu Gln Tyr Gly Tyr Ala Thr Arg Ser Arg Phe Ile Tyr Ile Leu
             35                  40                  45

Lys Met Ile Val Leu Trp Cys Phe Trp Pro Leu Asn Ile Ala Val Gly
 50                  55                  60

Val Ile Ser Cys Ile Tyr Pro Pro Asn Thr Gly Gly Leu Val Ala Ala
65                  70                  75                  80

Ile Ile Leu Thr Val Phe Ala Cys Leu Ser Phe Val Gly Tyr Trp Ile
                 85                  90                  95

Gln Ser Cys Arg Leu Phe Lys Arg Cys Arg Ser Trp Trp Ser Phe Asn
             100                 105                 110

Pro Glu Ser Asn Ala Val Gly Ser Ile Leu Leu Thr Asn Gly Gln Gln
             115                 120                 125

Cys Asn Phe Ala Ile Glu Ser Val Pro Met Val Leu Ala Pro Ile Ile
         130                 135                 140

Lys Asn Gly Val Leu Tyr Cys Glu Gly Gln Trp Leu Ala Lys Cys Glu
```

-continued

```
145                 150                 155                 160

Pro Asp His Leu Pro Lys Asp Ile Phe Val Cys Thr Pro Asp Arg Arg
                165                 170                 175

Asn Ile Tyr Arg Met Val Gln Lys Tyr Thr Gly Asp Gln Ser Gly Asn
            180                 185                 190

Lys Lys Arg Val Ala Thr Phe Val Tyr Ala Lys Gln Ser Val Asp Thr
        195                 200                 205

Gly Glu Leu Glu Ser Val Pro Thr Gly Gly Ser Ser Leu Tyr Thr
    210                 215                 220

<210> SEQ ID NO 43
<211> LENGTH: 455
<212> TYPE: PRT
<213> ORGANISM: Mouse Hepatitis Virus

<400> SEQUENCE: 43

Met Ser Phe Val Pro Gly Gln Glu Asn Ala Gly Ser Arg Ser Ser Ser
1               5                   10                  15

Val Asn Arg Ala Gly Asn Gly Ile Leu Lys Lys Thr Thr Trp Ala Asp
            20                  25                  30

Gln Thr Glu Arg Gly Pro Asn Asn Gln Asn Arg Gly Arg Arg Asn Gln
        35                  40                  45

Pro Lys Gln Thr Ala Thr Thr Gln Pro Asn Ser Gly Ser Val Val Pro
    50                  55                  60

His Tyr Ser Trp Phe Ser Gly Ile Thr Gln Phe Gln Lys Gly Lys Glu
65                  70                  75                  80

Phe Gln Phe Ala Gln Gly Gln Gly Val Pro Ile Ala Asn Gly Ile Pro
                85                  90                  95

Ala Ser Glu Gln Lys Gly Tyr Trp Tyr Arg His Asn Arg Arg Ser Phe
            100                 105                 110

Lys Thr Pro Asp Gly Gln Gln Lys Gln Leu Leu Pro Arg Trp Tyr Phe
        115                 120                 125

Tyr Tyr Leu Gly Thr Gly Pro His Ala Gly Ala Glu Tyr Gly Asp Asp
    130                 135                 140

Ile Asp Gly Val Val Trp Val Ala Ser Gln Gln Ala Asp Thr Lys Thr
145                 150                 155                 160

Thr Ala Asp Ile Val Glu Arg Asp Pro Ser Ser His Glu Ala Ile Pro
                165                 170                 175

Thr Arg Phe Ala Pro Gly Thr Val Leu Pro Gln Gly Phe Tyr Val Glu
            180                 185                 190

Gly Ser Gly Arg Ser Ala Pro Ala Ser Arg Ser Gly Ser Arg Ser Gln
        195                 200                 205

Ser Arg Gly Pro Asn Asn Arg Ala Arg Ser Ser Ser Asn Gln Arg Gln
    210                 215                 220

Pro Ala Ser Thr Val Lys Pro Asp Met Ala Glu Glu Ile Ala Ala Leu
225                 230                 235                 240

Val Leu Ala Lys Leu Gly Lys Asp Ala Gly Gln Pro Lys Gln Val Thr
                245                 250                 255

Lys Gln Ser Ala Lys Glu Val Arg Gln Lys Ile Leu Asn Lys Pro Arg
            260                 265                 270

Gln Lys Arg Thr Pro Asn Lys Gln Cys Pro Val Gln Gln Cys Phe Gly
        275                 280                 285

Lys Arg Gly Pro Asn Gln Asn Phe Gly Gly Ser Glu Met Leu Lys Leu
    290                 295                 300
```

-continued

```
Gly Thr Ser Asp Pro Gln Phe Pro Ile Leu Ala Glu Leu Ala Pro Thr
305                 310                 315                 320

Pro Ser Ala Phe Phe Gly Ser Lys Leu Glu Leu Val Lys Lys Asn
            325                 330                 335

Ser Gly Gly Ala Asp Asp Pro Thr Lys Asp Val Tyr Glu Leu Gln Tyr
            340                 345                 350

Ser Gly Ala Ile Arg Phe Asp Ser Thr Leu Pro Gly Phe Glu Thr Ile
        355                 360                 365

Met Lys Val Leu Asn Glu Asn Leu Asp Ala Tyr Gln Asp Gln Ala Gly
    370                 375                 380

Gly Ala Asp Val Val Ser Pro Lys Pro Gln Arg Lys Arg Gly Thr Lys
385                 390                 395                 400

Gln Lys Ala Leu Lys Gly Glu Val Asp Asn Val Ser Val Ala Lys Pro
                405                 410                 415

Lys Ser Ser Val Gln Arg Asn Val Ser Arg Glu Leu Thr Pro Glu Asp
            420                 425                 430

Arg Ser Leu Leu Ala Gln Ile Leu Asp Asp Gly Val Val Pro Asp Gly
        435                 440                 445

Leu Glu Asp Asp Ser Asn Val
    450                 455

<210> SEQ ID NO 44
<211> LENGTH: 448
<212> TYPE: PRT
<213> ORGANISM: Bovine coronavirus

<400> SEQUENCE: 44

Met Ser Phe Thr Pro Gly Lys Gln Ser Ser Ser Arg Ala Ser Ser Gly
1               5                   10                  15

Asn Arg Ser Gly Asn Gly Ile Leu Lys Trp Ala Asp Gln Ser Asp Gln
            20                  25                  30

Ser Arg Asn Val Gln Thr Arg Gly Arg Arg Ala Gln Pro Lys Gln Thr
        35                  40                  45

Ala Thr Ser Gln Gln Pro Ser Gly Gly Asn Val Val Pro Tyr Tyr Ser
    50                  55                  60

Trp Phe Ser Gly Ile Thr Gln Phe Gln Lys Gly Lys Glu Phe Glu Phe
65                  70                  75                  80

Ala Glu Gly Gln Gly Val Pro Ile Ala Pro Gly Val Pro Ala Thr Glu
                85                  90                  95

Ala Lys Gly Tyr Trp Tyr Arg His Asn Arg Arg Ser Phe Lys Thr Ala
            100                 105                 110

Asp Gly Asn Gln Arg Gln Leu Leu Pro Arg Trp Tyr Phe Tyr Tyr Leu
        115                 120                 125

Gly Thr Gly Pro His Ala Lys Asp Gln Tyr Gly Thr Asp Ile Asp Gly
    130                 135                 140

Val Tyr Trp Val Ala Ser Asn Gln Ala Asp Val Asn Thr Pro Ala Asp
145                 150                 155                 160

Ile Leu Asp Arg Asp Pro Ser Asp Glu Ala Ile Pro Thr Arg Phe
                165                 170                 175

Pro Pro Gly Thr Val Leu Pro Gln Gly Tyr Tyr Ile Glu Gly Ser Gly
            180                 185                 190

Arg Ser Ala Pro Asn Ser Arg Ser Thr Ser Arg Ala Ser Ser Arg Ala
        195                 200                 205

Ser Ser Ala Gly Ser Arg Ser Arg Ala Asn Ser Gly Asn Arg Thr Pro
    210                 215                 220
```

```
Thr Ser Gly Val Thr Pro Asp Met Ala Asp Gln Ile Ala Ser Leu Val
225                 230                 235                 240

Leu Ala Lys Leu Gly Lys Asp Ala Ala Lys Pro Gln Gln Val Thr Lys
            245                 250                 255

Gln Thr Ala Lys Glu Ile Arg Gln Lys Ile Leu Asn Lys Pro Arg Gln
        260                 265                 270

Lys Arg Ser Pro Asn Lys Gln Cys Thr Val Gln Cys Phe Gly Lys
    275                 280                 285

Arg Gly Pro Asn Gln Asn Phe Gly Gly Glu Met Leu Lys Leu Gly
290                 295                 300

Thr Ser Asp Pro Gln Phe Pro Ile Leu Ala Glu Leu Ala Pro Thr Ala
305                 310                 315                 320

Gly Ala Phe Phe Phe Gly Ser Arg Leu Glu Leu Ala Lys Val Gln Asn
            325                 330                 335

Leu Ser Gly Asn Leu Asp Glu Pro Gln Lys Asp Val Tyr Glu Leu Arg
        340                 345                 350

Tyr Asn Gly Ala Ile Arg Phe Asp Ser Thr Leu Ser Gly Phe Glu Thr
    355                 360                 365

Ile Met Lys Val Leu Asn Glu Asn Leu Asn Ala Tyr Gln Gln Gln Asp
370                 375                 380

Gly Thr Met Asn Met Ser Pro Lys Pro Gln Arg Gln Arg Gly Gln Lys
385                 390                 395                 400

Asn Gly Gln Gly Glu Asn Asp Asn Ile Ser Val Ala Ala Pro Lys Ser
            405                 410                 415

Arg Val Gln Gln Asn Lys Ile Arg Glu Leu Thr Ala Glu Asp Ile Ser
        420                 425                 430

Leu Leu Lys Lys Met Asp Glu Pro Phe Thr Glu Asp Thr Ser Glu Ile
    435                 440                 445

<210> SEQ ID NO 45
<211> LENGTH: 409
<212> TYPE: PRT
<213> ORGANISM: Avian infectious bronchitis virus

<400> SEQUENCE: 45

Met Ala Ser Gly Lys Ala Ala Gly Lys Thr Asp Ala Pro Ala Pro Val
1               5                   10                  15

Ile Lys Leu Gly Gly Pro Lys Pro Pro Lys Val Gly Ser Ser Gly Asn
            20                  25                  30

Ala Ser Trp Phe Gln Ala Leu Lys Ala Lys Lys Leu Asn Ala Pro Ala
        35                  40                  45

Pro Lys Phe Glu Gly Ser Gly Val Pro Asp Asn Glu Asn Leu Lys Ile
    50                  55                  60

Ser Gln Gln His Gly Tyr Trp Arg Arg Gln Ala Arg Tyr Lys Pro Gly
65                  70                  75                  80

Lys Gly Gly Arg Lys Pro Val Pro Asp Ala Trp Tyr Phe Tyr Tyr Thr
            85                  90                  95

Gly Thr Gly Pro Ala Ala Asp Leu Asn Trp Gly Asp Ser Gln Asp Gly
        100                 105                 110

Ile Val Trp Val Ala Ala Lys Gly Ala Asp Val Lys Ser Arg Ser Asn
    115                 120                 125

Gln Gly Thr Arg Asp Pro Asp Lys Phe Asp Gln Tyr Pro Leu Arg Phe
130                 135                 140

Ser Asp Gly Gly Pro Asp Gly Asn Phe Arg Trp Asp Phe Ile Pro Leu
```

```
                145                 150                 155                 160
Asn Arg Gly Arg Ser Gly Arg Ser Thr Ala Ala Ser Ser Ala Ala Ser
                    165                 170                 175
Ser Arg Ala Pro Ser Arg Glu Gly Ser Arg Gly Arg Leu Asn Gly Ala
                180                 185                 190
Glu Asp Asp Leu Ile Ala Arg Ala Ala Lys Ile Ile Gln Asp Gln Gln
            195                 200                 205
Lys Lys Gly Ser Arg Ile Thr Lys Ala Lys Ala Glu Met Ile His
        210                 215                 220
Arg Arg Tyr Cys Lys Arg Thr Val Pro Pro Gly Val Ser Ile Asp Lys
225                 230                 235                 240
Val Phe Gly Pro Arg Thr Lys Gly Lys Glu Gly Asn Phe Gly Asp Asp
                    245                 250                 255
Lys Met Asn Glu Glu Gly Ile Lys Asp Gly Arg Val Thr Ala Met Leu
                260                 265                 270
Asn Leu Val Pro Ser Ser His Ala Cys Leu Phe Gly Ser Gln Val Thr
            275                 280                 285
Pro Lys Leu Gln Pro Asp Gly Leu His Leu Thr Phe Arg Phe Thr Thr
        290                 295                 300
Val Val Ser Arg Asp Asp Pro Gln Phe Asp Asn Tyr Val Lys Ile Cys
305                 310                 315                 320
Asp Glu Cys Val Asp Gly Val Gly Thr Arg Pro Lys Asp Glu Val Val
                    325                 330                 335
Arg Pro Lys Ser Arg Ser Ser Ser Arg Pro Ala Thr Arg Gly Thr Ser
                340                 345                 350
Pro Ala Pro Lys Gln Gln Arg Pro Lys Lys Glu Lys Lys Pro Lys Lys
            355                 360                 365
Gln Asp Asp Glu Val Asp Lys Ala Leu Thr Ser Asp Glu Glu Arg Asn
        370                 375                 380
Asn Ala Gln Leu Glu Phe Asp Asp Glu Pro Lys Val Ile Asn Trp Gly
385                 390                 395                 400
Asp Ser Ala Leu Gly Glu Asn Glu Leu
                    405

<210> SEQ ID NO 46
<211> LENGTH: 376
<212> TYPE: PRT
<213> ORGANISM: Feline coronavirus

<400> SEQUENCE: 46

Met Ala Thr Gln Gly Gln Arg Val Asn Trp Gly Asp Glu Pro Ser Lys
1               5                   10                  15
Arg Arg Gly Arg Ser Asn Ser Arg Gly Arg Lys Asn Asn Asp Ile Pro
                20                  25                  30
Leu Ser Tyr Phe Asn Pro Ile Thr Leu Asp Gln Gly Ser Lys Phe Trp
            35                  40                  45
Asn Leu Cys Pro Arg Asp Phe Val Pro Lys Gly Ile Gly Asn Lys Asp
        50                  55                  60
Gln Gln Ile Gly Tyr Trp Asn Arg Gln Ala Arg Tyr Arg Ile Val Lys
65                  70                  75                  80
Gly Gln Arg Val Glu Leu Pro Glu Arg Trp Phe Phe Tyr Phe Leu Gly
                85                  90                  95
Thr Gly Pro His Ala Asp Ala Lys Phe Lys Ala Lys Ile Asp Gly Val
            100                 105                 110
```

```
Phe Trp Val Ala Arg Asp Gly Ala Met Asn Lys Pro Thr Ser Leu Gly
            115                 120                 125

Thr Arg Gly Thr Asn Asn Glu Ser Lys Pro Leu Lys Phe Asp Gly Lys
        130                 135                 140

Ile Pro Pro Gln Phe Gln Leu Glu Val Asn Arg Ser Arg Asn Asn Ser
145                 150                 155                 160

Arg Ser Gly Ser Gln Ser Arg Ser Val Ser Arg Asn Arg Ser Gln Ser
                165                 170                 175

Arg Gly Arg Gln Gln Ser Asn Asn Gln Asn Thr Asn Val Glu Asp Thr
            180                 185                 190

Ile Val Ala Val Leu Gln Lys Leu Gly Val Thr Asp Lys Gln Arg Ser
            195                 200                 205

Arg Ser Lys Ser Gly Glu Arg Ser Gln Ser Lys Ser Arg Asp Thr Thr
        210                 215                 220

Pro Lys Asn Ala Asn Lys His Thr Trp Lys Lys Thr Ala Gly Lys Gly
225                 230                 235                 240

Asp Val Thr Asn Phe Tyr Gly Ala Arg Ser Ser Ala Asn Phe Gly
                245                 250                 255

Asp Ser Asp Leu Val Ala Asn Gly Asn Ala Ala Lys Cys Tyr Pro Gln
            260                 265                 270

Ile Ala Glu Cys Val Pro Ser Val Ser Ser Ile Leu Phe Gly Ser Gln
            275                 280                 285

Trp Ser Ala Glu Glu Ala Gly Asp Gln Val Lys Val Thr Leu Thr His
        290                 295                 300

Asn Tyr Tyr Leu Pro Lys Asp Asp Ala Lys Thr Ser Gln Phe Leu Glu
305                 310                 315                 320

Gln Ile Asp Ala Tyr Lys Arg Pro Ser Glu Val Ala Lys Asp Gln Arg
                325                 330                 335

Gln Arg Lys Ser Arg Ser Lys Ser Ala Asp Lys Lys Pro Glu Glu Leu
            340                 345                 350

Ser Val Thr Leu Glu Ala Tyr Thr Asp Val Phe Asp Asp Thr Gln Val
        355                 360                 365

Glu Met Ile Asp Glu Val Thr Asn
        370                 375

<210> SEQ ID NO 47
<211> LENGTH: 382
<212> TYPE: PRT
<213> ORGANISM: porcine transmissible gastroenteritis virus

<400> SEQUENCE: 47

Met Ala Asn Gln Gly Gln Arg Val Ser Trp Gly Asp Glu Ser Thr Lys
1               5                   10                  15

Thr Arg Gly Arg Ser Asn Ser Arg Gly Arg Lys Asn Asn Asn Ile Pro
            20                  25                  30

Leu Ser Phe Phe Asn Pro Ile Thr Leu Gln Gln Gly Ser Lys Phe Trp
        35                  40                  45

Asn Leu Cys Pro Arg Asp Phe Val Pro Lys Gly Ile Gly Asn Arg Asp
    50                  55                  60

Gln Gln Ile Gly Tyr Trp Asn Arg Gln Thr Arg Tyr Arg Met Val Lys
65                  70                  75                  80

Gly Gln Arg Lys Glu Leu Pro Glu Arg Trp Phe Phe Tyr Tyr Leu Gly
                85                  90                  95

Thr Gly Pro His Ala Asp Ala Lys Phe Lys Asp Lys Leu Asp Gly Val
            100                 105                 110
```

-continued

Val Trp Val Ala Lys Asp Gly Ala Met Asn Lys Pro Thr Thr Leu Gly
         115                 120                 125

Ser Arg Gly Ala Asn Asn Glu Ser Lys Ala Leu Lys Phe Asp Gly Lys
130                 135                 140

Val Pro Gly Glu Phe Gln Leu Glu Val Asn Gln Ser Arg Asp Asn Ser
145                 150                 155                 160

Arg Leu Arg Ser Gln Ser Arg Ser Arg Asn Arg Ser Gln Ser
                165                 170                 175

Arg Gly Arg Gln Gln Ser Asn Asn Lys Lys Asp Asp Ser Val Glu Gln
             180                 185                 190

Ala Val Leu Ala Ala Leu Lys Lys Leu Gly Val Tyr Thr Glu Lys Gln
         195                 200                 205

Gln Gln Arg Ser Arg Ser Lys Ser Glu Arg Ser Asn Ser Lys Ile
         210                 215                 220

Arg Asp Thr Thr Pro Lys Asn Glu Asn Lys His Thr Trp Lys Arg Thr
225                 230                 235                 240

Ala Gly Lys Gly Asp Val Thr Arg Phe Tyr Gly Thr Arg Ser Asn Ser
                245                 250                 255

Ala Asn Phe Gly Asp Ser Asp Leu Val Ala Asn Gly Ser Ser Ala Lys
             260                 265                 270

His Tyr Pro Gln Leu Ala Glu Cys Val Pro Ser Val Ser Ser Ile Leu
         275                 280                 285

Phe Gly Ser Tyr Trp Thr Ser Lys Glu Asp Gly Asp Gln Ile Glu Val
         290                 295                 300

Thr Phe Thr His Lys Tyr His Leu Pro Lys Asp Asp Pro Lys Thr Gly
305                 310                 315                 320

Gln Phe Leu Gln Gln Ile Asn Ala Tyr Ala Arg Pro Ser Glu Val Ala
                325                 330                 335

Lys Glu Gln Arg Lys Arg Lys Ser Arg Ser Lys Ser Ala Glu Arg Ser
             340                 345                 350

Glu Gln Glu Val Val Pro Asp Ala Leu Ile Glu Asn Tyr Thr Asp Val
         355                 360                 365

Phe Asp Asp Thr Gln Val Glu Met Ile Asp Glu Val Thr Asn
370                 375                 380

<210> SEQ ID NO 48
<211> LENGTH: 389
<212> TYPE: PRT
<213> ORGANISM: Human coronavirus 229E

<400> SEQUENCE: 48

Met Ala Thr Val Lys Trp Ala Asp Ala Ser Glu Pro Gln Arg Gly Arg
1               5                   10                  15

Gln Gly Arg Ile Pro Tyr Ser Leu Tyr Ser Pro Leu Leu Val Asp Ser
            20                  25                  30

Glu Gln Pro Trp Lys Val Ile Pro Arg Asn Leu Val Pro Ile Asn Lys
        35                  40                  45

Lys Asp Lys Asn Lys Leu Ile Gly Tyr Trp Asn Val Gln Lys Arg Phe
    50                  55                  60

Arg Thr Arg Lys Gly Lys Arg Val Asp Leu Ser Pro Lys Leu His Phe
65                  70                  75                  80

Tyr Tyr Leu Gly Thr Gly Pro His Lys Asp Ala Lys Phe Arg Glu Arg
                85                  90                  95

Val Glu Gly Val Val Trp Val Ala Val Asp Gly Ala Lys Thr Glu Pro

```
                100                 105                 110
Thr Gly Tyr Gly Val Arg Arg Lys Asn Ser Glu Pro Glu Ile Pro His
            115                 120                 125

Phe Asn Gln Lys Leu Pro Asn Gly Val Thr Val Val Glu Glu Pro Asp
        130                 135                 140

Ser Arg Ala Pro Ser Arg Ser Gln Ser Arg Ser Gln Ser Arg Gly Arg
145                 150                 155                 160

Gly Glu Ser Lys Pro Gln Ser Arg Asn Pro Ser Ser Asp Arg Asn His
                165                 170                 175

Asn Ser Gln Asp Asp Ile Met Lys Ala Val Ala Ala Ala Leu Lys Ser
            180                 185                 190

Leu Gly Phe Asp Lys Pro Gln Glu Lys Asp Lys Lys Ser Ala Lys Thr
        195                 200                 205

Gly Thr Pro Lys Pro Ser Arg Asn Gln Ser Pro Ala Ser Ser Gln Thr
    210                 215                 220

Ser Ala Lys Ser Leu Ala Arg Ser Gln Ser Ser Glu Thr Lys Glu Gln
225                 230                 235                 240

Lys His Glu Met Gln Lys Pro Arg Trp Lys Arg Gln Pro Asn Asp Asp
                245                 250                 255

Val Thr Ser Asn Val Thr Gln Cys Phe Gly Pro Arg Asp Leu Asp His
            260                 265                 270

Asn Phe Gly Ser Ala Gly Val Val Ala Asn Gly Val Lys Ala Lys Gly
        275                 280                 285

Tyr Pro Gln Phe Ala Glu Leu Val Pro Ser Thr Ala Ala Met Leu Phe
    290                 295                 300

Asp Ser His Ile Val Ser Lys Glu Ser Gly Asn Thr Val Val Leu Thr
305                 310                 315                 320

Phe Thr Thr Arg Val Thr Val Pro Lys Asp His Pro His Leu Gly Lys
                325                 330                 335

Phe Leu Glu Glu Leu Asn Ala Phe Thr Arg Glu Met Gln Gln His Pro
            340                 345                 350

Leu Leu Asn Pro Ser Ala Leu Glu Phe Asn Pro Ser Gln Thr Ser Pro
        355                 360                 365

Ala Thr Ala Glu Pro Val Arg Asp Glu Val Ser Ile Glu Thr Asp Ile
    370                 375                 380

Ile Asp Glu Val Asn
385

<210> SEQ ID NO 49
<211> LENGTH: 448
<212> TYPE: PRT
<213> ORGANISM: Human coronavirus

<400> SEQUENCE: 49

Met Ser Phe Thr Pro Gly Lys Gln Ser Ser Arg Ala Ser Ser Gly
1               5                   10                  15

Asn Arg Ser Gly Asn Gly Ile Leu Lys Trp Ala Asp Gln Ser Asp Gln
            20                  25                  30

Val Arg Asn Val Gln Thr Arg Gly Arg Arg Ala Gln Pro Lys Gln Thr
        35                  40                  45

Ala Thr Ser Gln Gln Pro Ser Gly Gly Asn Val Val Pro Tyr Tyr Ser
    50                  55                  60

Trp Phe Ser Gly Ile Thr Gln Phe Gln Lys Gly Lys Glu Phe Glu Phe
65                  70                  75                  80
```

```
Val Glu Gly Gln Gly Pro Pro Ile Ala Pro Gly Val Pro Ala Thr Glu
            85                  90                  95

Ala Lys Gly Tyr Trp Tyr Arg His Asn Arg Gly Ser Phe Lys Thr Ala
            100                 105                 110

Asp Gly Asn Gln Arg Gln Leu Leu Pro Arg Trp Tyr Phe Tyr Tyr Leu
            115                 120                 125

Gly Thr Gly Pro His Ala Lys Asp Gln Tyr Gly Thr Asp Ile Asp Gly
            130                 135                 140

Val Tyr Trp Val Ala Ser Asn Gln Ala Asp Val Asn Thr Pro Ala Asp
145                 150                 155                 160

Ile Val Asp Arg Asp Pro Ser Ser Asp Glu Ala Ile Pro Thr Arg Phe
                165                 170                 175

Pro Pro Gly Thr Val Leu Pro Gln Gly Tyr Tyr Ile Glu Gly Ser Gly
            180                 185                 190

Arg Ser Ala Pro Asn Ser Arg Ser Thr Ser Arg Thr Ser Ser Arg Ala
            195                 200                 205

Ser Ser Ala Gly Ser Arg Ser Arg Ala Asn Ser Gly Asn Arg Thr Pro
210                 215                 220

Thr Ser Gly Val Thr Pro Asp Met Ala Asp Gln Ile Ala Ser Leu Val
225                 230                 235                 240

Leu Ala Lys Leu Gly Lys Asp Ala Thr Lys Pro Gln Gln Val Thr Lys
            245                 250                 255

His Thr Ala Lys Glu Val Arg Gln Lys Ile Leu Asn Lys Pro Arg Gln
            260                 265                 270

Lys Arg Ser Pro Asn Lys Gln Cys Thr Val Gln Gln Cys Phe Gly Lys
            275                 280                 285

Arg Gly Pro Asn Gln Asn Phe Gly Gly Gly Glu Met Leu Lys Leu Gly
            290                 295                 300

Thr Ser Asp Pro Gln Phe Pro Ile Leu Ala Glu Leu Ala Pro Thr Ala
305                 310                 315                 320

Gly Ala Phe Phe Phe Gly Ser Arg Leu Glu Leu Ala Lys Val Gln Asn
            325                 330                 335

Leu Ser Gly Asn Pro Asp Glu Pro Gln Lys Asp Val Tyr Glu Leu Arg
            340                 345                 350

Tyr Asn Gly Ala Ile Arg Phe Asp Ser Thr Leu Ser Gly Phe Glu Thr
            355                 360                 365

Ile Met Lys Val Leu Asn Glu Asn Leu Asn Ala Tyr Gln Gln Gln Asp
370                 375                 380

Gly Met Met Asn Met Ser Pro Lys Pro Gln Arg Gln Arg Gly His Lys
385                 390                 395                 400

Asn Gly Gln Gly Glu Asn Asp Asn Ile Ser Val Ala Val Pro Lys Ser
            405                 410                 415

Arg Val Gln Gln Asn Lys Ser Arg Glu Leu Thr Ala Glu Asp Ile Ser
            420                 425                 430

Leu Leu Lys Lys Met Asp Glu Pro Tyr Thr Glu Asp Thr Ser Glu Ile
            435                 440                 445

<210> SEQ ID NO 50
<211> LENGTH: 449
<212> TYPE: PRT
<213> ORGANISM: porcine hemagglutinating encephalomyelitis

<400> SEQUENCE: 50

Met Ser Phe Thr Pro Gly Lys Gln Ser Ser Ser Arg Ala Ser Ser Gly
1               5                   10                  15
```

-continued

Asn Arg Ser Gly Asn Gly Ile Leu Lys Trp Ala Asp Gln Ser Asp Gln
            20                  25                  30

Ser Arg Asn Val Gln Thr Arg Gly Arg Val Gln Ser Lys Gln Thr
        35                  40                  45

Ala Thr Ser Gln Gln Pro Ser Gly Gly Thr Val Val Pro Tyr Tyr Ser
        50                  55                  60

Trp Phe Ser Gly Ile Thr Gln Phe Gln Lys Gly Lys Glu Phe Glu Phe
 65                  70                  75                  80

Ala Glu Gly Gln Gly Val Pro Ile Ala Pro Gly Val Pro Ser Thr Glu
                    85                  90                  95

Ala Lys Gly Tyr Trp Tyr Arg His Asn Arg Arg Ser Phe Lys Thr Ala
                100                 105                 110

Asp Gly Asn Gln Arg Gln Leu Leu Pro Arg Trp Tyr Phe Tyr Tyr Leu
                115                 120                 125

Gly Thr Gly Pro His Ala Lys Asp Gln Tyr Gly Thr Asp Ile Asp Gly
                130                 135                 140

Val Phe Trp Val Ala Ser Asn Gln Ala Asp Ile Asn Thr Pro Ala Asp
145                 150                 155                 160

Ile Val Asp Arg Asp Pro Ser Ser Asp Glu Ala Ile Pro Thr Arg Phe
                165                 170                 175

Pro Pro Gly Thr Val Leu Pro Gln Gly Tyr Tyr Ile Glu Gly Ser Gly
                180                 185                 190

Arg Ser Ala Pro Asn Ser Arg Ser Thr Ser Arg Ala Pro Asn Arg Ala
                195                 200                 205

Pro Ser Ala Gly Ser Arg Ser Arg Ala Asn Ser Gly Asn Arg Thr Ser
                210                 215                 220

Thr Pro Gly Val Thr Pro Asp Met Ala Asp Gln Ile Ala Ser Leu Val
225                 230                 235                 240

Leu Ala Lys Leu Gly Lys Asp Ala Thr Lys Pro Gln Gln Val Thr Lys
                245                 250                 255

Gln Thr Ala Lys Glu Val Arg Gln Lys Ile Leu Asn Lys Pro Arg Gln
                260                 265                 270

Lys Arg Ser Pro Asn Lys Gln Cys Thr Val Gln Gln Cys Phe Gly Lys
                275                 280                 285

Arg Gly Pro Asn Gln Asn Phe Gly Gly Gly Glu Met Leu Lys Leu Gly
                290                 295                 300

Thr Ser Asp Pro Gln Phe Pro Ile Leu Ala Glu Leu Ala Pro Thr Ala
305                 310                 315                 320

Gly Ala Phe Phe Phe Gly Ser Arg Leu Glu Leu Ala Lys Val Gln Asn
                325                 330                 335

Leu Ser Gly Asn Pro Asp Glu Pro Gln Lys Asp Val Tyr Glu Leu Arg
                340                 345                 350

Tyr Asn Gly Ala Ile Arg Phe Asp Ser Thr Leu Ser Gly Phe Glu Thr
                355                 360                 365

Ile Met Lys Val Leu Asn Gln Asn Leu Asn Ala Tyr Gln His Gln Glu
                370                 375                 380

Asp Gly Met Met Asn Ile Ser Pro Lys Pro Gln Arg Gln Arg Gly Gln
385                 390                 395                 400

Lys Asn Gly Gln Val Glu Asn Asp Asn Val Ser Val Ala Ala Pro Lys
                405                 410                 415

Ser Arg Val Gln Gln Asn Lys Ser Arg Glu Leu Thr Ala Glu Asp Ile
                420                 425                 430

-continued

```
Ser Leu Leu Lys Lys Met Asp Glu Pro Tyr Thr Glu Asp Thr Ser Glu
        435                 440                 445

Ile

<210> SEQ ID NO 51
<211> LENGTH: 409
<212> TYPE: PRT
<213> ORGANISM: turkey coronavirus

<400> SEQUENCE: 51

Met Ala Ser Gly Lys Ala Thr Gly Lys Thr Asp Ala Pro Ala Pro Ile
1               5                   10                  15

Ile Lys Leu Gly Gly Pro Lys Pro Pro Lys Val Gly Ser Ser Gly Asn
            20                  25                  30

Ala Ser Trp Phe Gln Ser Ile Lys Ala Lys Lys Leu Asn Ser Pro Gln
        35                  40                  45

Pro Lys Phe Glu Gly Ser Gly Val Pro Asp Asn Glu Asn Ile Lys Thr
    50                  55                  60

Ser Gln Gln His Gly Tyr Trp Arg Arg Gln Ala Arg Phe Lys Pro Gly
65                  70                  75                  80

Lys Gly Gly Arg Lys Pro Val Pro Asp Ala Trp Tyr Phe Tyr Tyr Thr
                85                  90                  95

Gly Thr Gly Pro Ala Ala Asp Leu Asn Trp Gly Asp Thr Gln Asp Gly
            100                 105                 110

Ile Val Trp Val Ala Ala Lys Gly Ala Asp Val Lys Ser Arg Ser Asn
        115                 120                 125

Gln Gly Thr Arg Asp Pro Asp Lys Phe Asp Gln Tyr Pro Leu Arg Phe
    130                 135                 140

Ser Asp Gly Gly Pro Asp Ser Asn Phe Arg Trp Asp Phe Ile Pro Leu
145                 150                 155                 160

His Arg Gly Arg Ser Gly Arg Ser Thr Ala Ala Ser Ser Ala Ala Ser
                165                 170                 175

Ser Arg Ala Pro Ser Arg Asp Gly Ser Arg Gly Arg Arg Ser Gly Ser
            180                 185                 190

Glu Asp Asp Leu Ile Ala Arg Ala Ala Lys Ile Ile Gln Asp Gln Gln
        195                 200                 205

Lys Lys Gly Ser Arg Ile Thr Lys Ala Lys Ala Asp Glu Met Ala His
    210                 215                 220

Arg Arg Tyr Cys Lys Arg Thr Val Pro Pro Gly Tyr Lys Val Asp Gln
225                 230                 235                 240

Val Phe Gly Pro Arg Thr Lys Gly Lys Glu Gly Asn Phe Gly Asp Asp
                245                 250                 255

Lys Met Asn Glu Glu Gly Ile Lys Asp Gly Arg Val Thr Ala Met Leu
            260                 265                 270

Asn Leu Val Pro Ser Ser His Ala Cys Leu Phe Gly Ser Arg Val Thr
        275                 280                 285

Pro Lys Leu Gln Pro Asp Gly Leu His Leu Arg Phe Glu Phe Thr Thr
    290                 295                 300

Val Val Pro Arg Asp Asp Pro Gln Phe Asp Asn Tyr Val Thr Ile Cys
305                 310                 315                 320

Asp Gln Cys Val Asp Gly Ile Gly Thr Arg Pro Lys Asp Asn Glu Pro
                325                 330                 335

Arg Pro Lys Ser Arg Pro Ser Ser Arg Pro Ala Thr Arg Gly Asn Ser
            340                 345                 350
```

Pro Ala Pro Arg Gln Gln Arg Pro Lys Lys Glu Lys Lys Pro Lys Lys
        355                 360                 365

Gln Asp Asp Glu Val Asp Lys Ala Leu Thr Ser Asp Glu Glu Arg Asn
370                 375                 380

Asn Ala Gln Leu Glu Phe Asp Asp Glu Pro Lys Val Ile Asn Trp Gly
385                 390                 395                 400

Asp Ser Ala Leu Gly Glu Asn His Leu
                405

<210> SEQ ID NO 52
<211> LENGTH: 1173
<212> TYPE: PRT
<213> ORGANISM: Human coronavirus 229E

<400> SEQUENCE: 52

Met Phe Val Leu Leu Val Ala Tyr Ala Leu Leu His Ile Ala Gly Cys
1               5                   10                  15

Gln Thr Thr Asn Gly Leu Asn Thr Ser Tyr Ser Val Cys Asn Gly Cys
            20                  25                  30

Val Gly Tyr Ser Glu Asn Val Phe Ala Val Glu Ser Gly Gly Tyr Ile
        35                  40                  45

Pro Ser Asp Phe Ala Phe Asn Asn Trp Phe Leu Leu Thr Asn Thr Ser
    50                  55                  60

Ser Val Val Asp Gly Val Val Arg Ser Phe Gln Pro Leu Leu Leu Asn
65                  70                  75                  80

Cys Leu Trp Ser Val Ser Gly Leu Arg Phe Thr Thr Gly Phe Val Tyr
                85                  90                  95

Phe Asn Gly Thr Gly Arg Gly Asp Cys Lys Gly Phe Ser Ser Asp Val
            100                 105                 110

Leu Ser Asp Val Ile Arg Tyr Asn Leu Asn Phe Glu Glu Asn Leu Arg
        115                 120                 125

Arg Gly Thr Ile Leu Phe Lys Thr Ser Tyr Gly Val Val Val Phe Tyr
    130                 135                 140

Cys Thr Asn Asn Thr Leu Val Ser Gly Asp Ala His Ile Pro Phe Gly
145                 150                 155                 160

Thr Val Leu Gly Asn Phe Tyr Cys Phe Val Asn Thr Thr Ile Gly Thr
                165                 170                 175

Glu Thr Thr Ser Ala Phe Val Gly Ala Leu Pro Lys Thr Val Arg Glu
            180                 185                 190

Phe Val Ile Ser Arg Thr Gly His Phe Tyr Ile Asn Gly Tyr Arg Tyr
        195                 200                 205

Phe Thr Leu Gly Asn Val Glu Ala Val Asn Phe Asn Val Thr Thr Ala
    210                 215                 220

Glu Thr Thr Asp Phe Phe Thr Val Ala Leu Ala Ser Tyr Ala Asp Val
225                 230                 235                 240

Leu Val Asn Val Ser Gln Thr Ser Ile Ala Asn Ile Ile Tyr Cys Asn
                245                 250                 255

Ser Val Ile Asn Arg Leu Arg Cys Asp Gln Leu Ser Phe Tyr Val Pro
            260                 265                 270

Asp Gly Phe Tyr Ser Thr Ser Pro Ile Gln Ser Val Glu Leu Pro Val
        275                 280                 285

Ser Ile Val Ser Leu Pro Val Tyr His Lys His Met Phe Ile Val Leu
    290                 295                 300

Tyr Val Asp Phe Lys Pro Gln Ser Gly Gly Gly Lys Cys Phe Asn Cys
305                 310                 315                 320

```
Tyr Pro Ala Gly Val Asn Ile Thr Leu Ala Asn Phe Asn Glu Thr Lys
                325                 330                 335

Gly Pro Leu Cys Val Asp Thr Ser His Phe Thr Thr Lys Tyr Val Ala
            340                 345                 350

Val Tyr Ala Asn Val Gly Arg Trp Ser Ala Ser Ile Asn Thr Gly Asn
            355                 360                 365

Cys Pro Phe Ser Phe Gly Lys Val Asn Asn Phe Val Lys Phe Gly Ser
            370                 375                 380

Val Cys Phe Ser Leu Lys Asp Ile Pro Gly Gly Cys Ala Met Pro Ile
385                 390                 395                 400

Val Ala Asn Trp Ala Tyr Ser Lys Tyr Tyr Thr Ile Gly Thr Leu Tyr
                405                 410                 415

Val Ser Trp Ser Asp Gly Asp Gly Ile Thr Gly Val Pro Gln Pro Val
                420                 425                 430

Glu Gly Val Ser Ser Phe Met Asn Val Thr Leu Asp Lys Cys Thr Lys
                435                 440                 445

Tyr Asn Ile Tyr Asp Val Ser Gly Val Gly Val Ile Arg Val Ser Asn
            450                 455                 460

Asp Thr Phe Leu Asn Gly Ile Thr Tyr Thr Ser Ser Gly Asn Leu
465                 470                 475                 480

Leu Gly Phe Lys Asp Val Thr Lys Gly Thr Ile Tyr Ser Ile Thr Pro
                485                 490                 495

Cys Asn Pro Pro Asp Gln Leu Val Val Tyr Gln Gln Ala Val Val Gly
            500                 505                 510

Ala Met Leu Ser Glu Asn Phe Thr Ser Tyr Gly Phe Ser Asn Val Val
            515                 520                 525

Glu Leu Pro Lys Phe Phe Tyr Ala Ser Asn Gly Thr Tyr Asn Cys Thr
            530                 535                 540

Asp Ala Val Leu Thr Tyr Ser Ser Phe Gly Val Cys Ala Asp Gly Ser
545                 550                 555                 560

Ile Ile Ala Val Gln Pro Arg Asn Val Ser Tyr Asp Ser Val Ser Ala
                565                 570                 575

Ile Val Thr Ala Asn Leu Ser Ile Pro Ser Asn Trp Thr Ile Ser Val
            580                 585                 590

Gln Val Glu Tyr Leu Gln Ile Thr Ser Thr Pro Ile Val Val Asp Cys
            595                 600                 605

Ser Thr Tyr Val Cys Asn Gly Asn Val Arg Cys Val Glu Leu Leu Lys
            610                 615                 620

Gln Tyr Thr Ser Ala Cys Lys Thr Ile Glu Asp Ala Leu Arg Asn Ser
625                 630                 635                 640

Ala Arg Leu Glu Ser Ala Asp Val Ser Glu Met Leu Thr Phe Asp Lys
                645                 650                 655

Lys Ala Phe Thr Leu Ala Asn Val Ser Ser Phe Gly Asp Tyr Asn Leu
                660                 665                 670

Ser Ser Val Ile Pro Ser Leu Pro Thr Ser Gly Ser Arg Val Ala Gly
            675                 680                 685

Arg Ser Ala Ile Glu Asp Ile Leu Phe Ser Lys Ile Val Thr Ser Gly
            690                 695                 700

Leu Gly Thr Val Asp Ala Asp Tyr Lys Asn Cys Thr Lys Gly Leu Ser
705                 710                 715                 720

Ile Ala Asp Leu Ala Cys Ala Gln Tyr Tyr Asn Gly Ile Met Val Leu
                725                 730                 735
```

```
Pro Gly Val Ala Asp Ala Glu Arg Met Ala Met Tyr Thr Gly Ser Leu
            740                 745                 750

Ile Gly Gly Ile Ala Leu Gly Gly Leu Thr Ser Ala Val Ser Ile Pro
        755                 760                 765

Phe Ser Leu Ala Ile Gln Ala Arg Leu Asn Tyr Val Ala Leu Gln Thr
    770                 775                 780

Asp Val Leu Gln Glu Asn Gln Lys Ile Leu Ala Ala Ser Phe Asn Lys
785                 790                 795                 800

Ala Met Thr Asn Ile Val Asp Ala Phe Thr Gly Val Asn Asp Ala Ile
                805                 810                 815

Thr Gln Thr Ser Gln Ala Leu Gln Thr Val Ala Thr Ala Leu Asn Lys
            820                 825                 830

Ile Gln Asp Val Val Asn Gln Gln Gly Asn Ser Leu Asn His Leu Thr
        835                 840                 845

Ser Gln Leu Arg Gln Asn Phe Gln Ala Ile Ser Ser Ser Ile Gln Ala
    850                 855                 860

Ile Tyr Asp Arg Leu Asp Thr Ile Gln Ala Asp Gln Gln Val Asp Arg
865                 870                 875                 880

Leu Ile Thr Gly Arg Leu Ala Ala Leu Asn Val Phe Val Ser His Thr
                885                 890                 895

Leu Thr Lys Tyr Thr Glu Val Arg Ala Ser Arg Gln Leu Ala Gln Gln
            900                 905                 910

Lys Val Asn Glu Cys Val Lys Ser Gln Ser Lys Arg Tyr Gly Phe Cys
        915                 920                 925

Gly Asn Gly Thr His Ile Phe Ser Ile Val Asn Ala Ala Pro Glu Gly
    930                 935                 940

Leu Val Phe Leu His Thr Val Leu Leu Pro Thr Gln Tyr Lys Asp Val
945                 950                 955                 960

Glu Ala Trp Ser Gly Leu Cys Val Asp Gly Thr Asn Gly Tyr Val Leu
                965                 970                 975

Arg Gln Pro Asn Leu Ala Leu Tyr Lys Glu Gly Asn Tyr Tyr Arg Ile
            980                 985                 990

Thr Ser Arg Ile Met Phe Glu Pro Arg Ile Pro Thr Met Ala Asp Phe
        995                 1000                1005

Val Gln Ile Glu Asn Cys Asn Val Thr Phe Val Asn Ile Ser Arg
    1010                1015                1020

Ser Glu Leu Gln Thr Ile Val Pro Glu Tyr Ile Asp Val Asn Lys
    1025                1030                1035

Thr Leu Gln Glu Leu Ser Tyr Lys Leu Pro Asn Tyr Thr Val Pro
    1040                1045                1050

Asp Leu Val Val Glu Gln Tyr Asn Gln Thr Ile Leu Asn Leu Thr
    1055                1060                1065

Ser Glu Ile Ser Thr Leu Glu Asn Lys Ser Ala Glu Leu Asn Tyr
    1070                1075                1080

Thr Val Gln Lys Leu Gln Thr Leu Ile Asp Asn Ile Asn Ser Thr
    1085                1090                1095

Leu Val Asp Leu Lys Trp Leu Asn Arg Val Glu Thr Tyr Ile Lys
    1100                1105                1110

Trp Pro Trp Trp Val Trp Leu Cys Ile Ser Val Val Leu Ile Phe
    1115                1120                1125

Val Val Ser Met Leu Leu Leu Cys Cys Cys Ser Thr Gly Cys Cys
    1130                1135                1140

Gly Phe Phe Ser Cys Phe Ala Ser Ser Ile Arg Gly Cys Cys Glu
```

Ser Thr Lys Leu Pro Tyr Tyr Asp Val Glu Lys Ile His Ile Gln
           1160                          1165                         1170

```
<210> SEQ ID NO 53
<211> LENGTH: 1164
<212> TYPE: PRT
<213> ORGANISM: Avian infectious bronchitis virus

<400> SEQUENCE: 53
```

Met Leu Gly Lys Ser Leu Phe Leu Val Thr Ile Leu Cys Ala Leu Cys
1               5                   10                  15

Ser Ala Asn Leu Phe Asp Pro Ala Asn Tyr Val Tyr Tyr Tyr Gln Ser
            20                  25                  30

Ala Phe Arg Pro Ser Asn Gly Trp His Leu Gln Gly Gly Ala Tyr Ala
        35                  40                  45

Val Val Asn Ser Ser Asn Tyr Ala Asn Asn Ala Gly Ser Ala Ser Glu
    50                  55                  60

Cys Thr Val Gly Val Ile Lys Asp Val Tyr Asn Gln Ser Ala Ala Ser
65                  70                  75                  80

Ile Ala Met Thr Ala Pro Leu Gln Gly Met Ala Trp Ser Lys Ser Gln
                85                  90                  95

Phe Cys Ser Ala His Cys Asp Phe Ser Glu Ile Thr Val Phe Val Thr
            100                 105                 110

His Cys Tyr Ser Ser Gly Ser Gly Ser Cys Pro Ile Thr Gly Met Ile
        115                 120                 125

Ala Arg Gly His Ile Arg Ile Ser Ala Met Lys Asn Gly Ser Leu Phe
    130                 135                 140

Tyr Asn Leu Thr Val Ser Val Ser Lys Tyr Pro Asn Phe Lys Ser Phe
145                 150                 155                 160

Gln Cys Val Asn Asn Phe Thr Ser Val Tyr Leu Asn Gly Asp Leu Val
                165                 170                 175

Phe Thr Ser Asn Lys Thr Thr Asp Val Thr Ser Ala Gly Val Tyr Phe
            180                 185                 190

Lys Ala Gly Gly Pro Val Asn Tyr Ser Ile Met Lys Glu Phe Lys Val
        195                 200                 205

Leu Ala Tyr Phe Val Asn Gly Thr Ala Gln Asp Val Ile Leu Cys Asp
    210                 215                 220

Asn Ser Pro Lys Gly Leu Leu Ala Cys Gln Tyr Asn Thr Gly Asn Phe
225                 230                 235                 240

Ser Asp Gly Phe Tyr Pro Phe Thr Asn Ser Thr Leu Val Arg Glu Lys
                245                 250                 255

Phe Ile Val Tyr Arg Glu Ser Ser Val Asn Thr Thr Leu Ala Leu Thr
            260                 265                 270

Asn Phe Thr Phe Thr Asn Val Ser Asn Ala Gln Pro Asn Ser Gly Gly
        275                 280                 285

Val His Thr Phe His Leu Tyr Gln Thr Gln Thr Ala Gln Ser Gly Tyr
    290                 295                 300

Tyr Asn Phe Asn Leu Ser Phe Leu Ser Gln Phe Val Tyr Lys Ala Ser
305                 310                 315                 320

Asp Tyr Met Tyr Gly Ser Tyr His Pro Ile Cys Ala Phe Arg Pro Glu
                325                 330                 335

Thr Ile Asn Ser Gly Leu Trp Phe Asn Ser Leu Ser Val Ser Leu Thr
            340                 345                 350

```
Tyr Gly Pro Leu Gln Gly Gly Tyr Lys Gln Ser Val Phe Ser Gly Lys
            355                 360                 365
Ala Thr Cys Cys Tyr Ala Tyr Ser Tyr Asn Gly Pro Arg Ala Cys Lys
        370                 375                 380
Gly Val Tyr Ser Gly Glu Leu Ser Arg Asp Phe Glu Cys Gly Leu Leu
385                 390                 395                 400
Val Tyr Val Thr Lys Ser Asp Gly Ser Arg Ile Gln Thr Arg Thr Glu
                405                 410                 415
Pro Leu Val Leu Thr Gln His Asn Tyr Asn Asn Ile Thr Leu Asp Lys
            420                 425                 430
Cys Val Ala Tyr Asn Ile Tyr Gly Arg Val Gly Gln Gly Phe Ile Thr
        435                 440                 445
Asn Val Thr Asp Ser Val Ala Asn Phe Ser Tyr Leu Ala Asp Gly Gly
    450                 455                 460
Leu Ala Ile Leu Asp Thr Ser Gly Ala Ile Asp Val Phe Val Val Gln
465                 470                 475                 480
Gly Ser Tyr Gly Leu Asn Tyr Tyr Lys Val Asn Pro Cys Glu Asp Val
                485                 490                 495
Asn Gln Gln Phe Val Val Ser Gly Asn Ile Val Gly Ile Leu Thr
            500                 505                 510
Ser Arg Asn Glu Thr Gly Ser Glu Gln Val Glu Asn Gln Phe Tyr Val
        515                 520                 525
Lys Leu Thr Asn Ser Ser His Arg Arg Arg Ser Ile Gly Gln Asn
    530                 535                 540
Val Thr Ser Cys Pro Tyr Val Ser Tyr Gly Arg Phe Cys Ile Glu Pro
545                 550                 555                 560
Asp Gly Ser Leu Lys Met Ile Val Pro Glu Glu Leu Lys Gln Phe Val
                565                 570                 575
Ala Pro Leu Leu Asn Ile Thr Glu Ser Val Leu Ile Pro Asn Ser Phe
            580                 585                 590
Asn Leu Thr Val Thr Asp Glu Tyr Ile Gln Thr Arg Met Asp Lys Val
        595                 600                 605
Gln Ile Asn Cys Leu Gln Tyr Val Cys Gly Asn Ser Leu Glu Cys Arg
    610                 615                 620
Lys Leu Phe Gln Gln Tyr Gly Pro Val Cys Asp Asn Ile Leu Ser Val
625                 630                 635                 640
Val Asn Ser Val Ser Gln Lys Glu Asp Met Glu Leu Leu Ser Phe Tyr
                645                 650                 655
Ser Ser Thr Lys Pro Lys Gly Tyr Asp Thr Pro Val Leu Ser Asn Val
            660                 665                 670
Ser Thr Gly Glu Phe Asn Ile Ser Leu Leu Leu Thr Pro Pro Ser Ser
        675                 680                 685
Pro Ser Gly Arg Ser Phe Val Glu Asp Leu Leu Phe Thr Ser Val Glu
    690                 695                 700
Thr Val Gly Leu Pro Thr Asp Ala Glu Tyr Lys Lys Cys Thr Ala Gly
705                 710                 715                 720
Pro Leu Gly Thr Leu Lys Asp Leu Ile Cys Ala Arg Glu Tyr Asn Gly
                725                 730                 735
Leu Leu Val Leu Pro Pro Ile Ile Thr Ala Asp Met Gln Thr Met Tyr
            740                 745                 750
Thr Ala Ser Leu Val Gly Ala Met Ala Phe Gly Gly Ile Thr Ser Ala
        755                 760                 765
Ala Ala Ile Pro Phe Ala Thr Gln Ile Gln Ala Arg Ile Asn His Leu
```

-continued

```
              770                 775                 780
Gly Ile Ala Gln Ser Leu Leu Met Lys Asn Gln Glu Lys Ile Ala Ala
785                 790                 795                 800

Ser Phe Asn Lys Ala Ile Gly His Met Gln Glu Gly Phe Arg Ser Thr
                805                 810                 815

Ser Leu Ala Leu Gln Gln Val Gln Asp Val Val Asn Lys Gln Ser Ala
                820                 825                 830

Ile Leu Thr Glu Thr Met Asn Ser Leu Asn Lys Asn Phe Gly Ala Ile
                835                 840                 845

Ser Ser Val Ile Gln Asp Ile Tyr Ala Gln Leu Asp Ala Ile Gln Ala
850                 855                 860

Asp Ala Gln Val Asp Arg Leu Ile Thr Gly Arg Leu Ser Ser Leu Ser
865                 870                 875                 880

Val Leu Ala Ser Ala Lys Gln Ser Glu Tyr Ile Arg Val Ser Gln Gln
                885                 890                 895

Arg Glu Leu Ala Thr Gln Lys Ile Asn Glu Cys Val Lys Ser Gln Ser
                900                 905                 910

Asn Arg Tyr Gly Phe Cys Gly Ser Gly Arg His Val Leu Ser Ile Pro
                915                 920                 925

Gln Asn Ala Pro Asn Gly Ile Val Phe Ile His Phe Thr Tyr Thr Pro
                930                 935                 940

Glu Thr Phe Val Asn Val Thr Ala Ile Val Gly Phe Cys Val Asn Pro
945                 950                 955                 960

Leu Asn Ala Ser Gln Tyr Ala Ile Val Pro Ala Asn Gly Arg Gly Ile
                965                 970                 975

Phe Ile Gln Val Asn Gly Thr Tyr Tyr Ile Thr Ser Arg Asp Met Tyr
                980                 985                 990

Met Pro Arg Asp Ile Thr Ala Gly Asp Ile Val Thr Leu Thr Ser Cys
                995                1000                1005

Gln Ala Asn Tyr Val Asn Val Asn Lys Thr Val Ile Thr Thr Phe
        1010                1015                1020

Val Glu Asp Asp Asp Phe Asn Phe Asp Asp Glu Leu Ser Lys Trp
        1025                1030                1035

Trp Asn Asp Thr Lys His Gly Leu Pro Asp Phe Asp Asp Phe Asn
        1040                1045                1050

Tyr Thr Val Pro Ile Leu Asn Ile Ser Gly Glu Ile Asp Asn Ile
        1055                1060                1065

Gln Gly Val Ile Gln Gly Leu Asn Asp Ser Leu Ile Asn Leu Glu
        1070                1075                1080

Glu Leu Ser Ile Ile Lys Thr Tyr Ile Lys Trp Pro Trp Tyr Val
        1085                1090                1095

Trp Leu Ala Ile Gly Phe Ala Ile Ile Ile Phe Ile Leu Ile Leu
        1100                1105                1110

Gly Trp Val Phe Phe Met Thr Gly Cys Cys Gly Cys Cys Cys Gly
        1115                1120                1125

Cys Phe Gly Ile Ile Pro Leu Ile Ser Leu Cys Gly Lys Lys Ser
        1130                1135                1140

Ser Tyr Tyr Thr Thr Phe Asp Asn Asp Val Val Thr Glu Gln Tyr
        1145                1150                1155

Arg Pro Lys Lys Ser Val
        1160
```

<210> SEQ ID NO 54

```
<211> LENGTH: 1363
<212> TYPE: PRT
<213> ORGANISM: Bovine coronoavirus

<400> SEQUENCE: 54
```

| | | | | | | | | | | | | | | | |
|---|---|---|---|---|---|---|---|---|---|---|---|---|---|---|---|
| Met | Phe | Leu | Ile | Leu | Ile | Ser | Leu | Pro | Met | Ala | Phe | Ala | Val | Ile |
| 1 | | | | 5 | | | | | 10 | | | | | 15 |
| Gly | Asp | Leu | Lys | Cys | Thr | Thr | Val | Ser | Ile | Asn | Asp | Val | Asp | Thr | Gly |
| | | | 20 | | | | | 25 | | | | | 30 | | |
| Ala | Pro | Ser | Ile | Ser | Thr | Asp | Ile | Val | Asp | Val | Thr | Asn | Gly | Leu | Gly |
| | | | 35 | | | | 40 | | | | | 45 | | | |
| Thr | Tyr | Tyr | Val | Leu | Asp | Arg | Val | Tyr | Leu | Asn | Thr | Thr | Leu | Leu | Leu |
| | 50 | | | | | 55 | | | | | 60 | | | | |
| Asn | Gly | Tyr | Tyr | Pro | Thr | Ser | Gly | Ser | Thr | Tyr | Arg | Asn | Met | Ala | Leu |
| 65 | | | | | 70 | | | | | 75 | | | | | 80 |
| Lys | Gly | Thr | Leu | Leu | Leu | Ser | Arg | Leu | Trp | Phe | Lys | Pro | Pro | Phe | Leu |
| | | | | 85 | | | | | 90 | | | | | 95 | |
| Ser | Asp | Phe | Ile | Asn | Gly | Ile | Phe | Ala | Lys | Val | Lys | Asn | Thr | Lys | Val |
| | | | 100 | | | | | 105 | | | | | 110 | | |
| Ile | Lys | Lys | Gly | Val | Met | Tyr | Ser | Glu | Phe | Pro | Ala | Ile | Thr | Ile | Gly |
| | | | 115 | | | | | 120 | | | | | 125 | | |
| Ser | Thr | Phe | Val | Asn | Thr | Ser | Tyr | Ser | Val | Val | Gln | Pro | His | Thr |
| | 130 | | | | | 135 | | | | | 140 | | | | |
| Thr | Asn | Leu | Asp | Asn | Lys | Leu | Gln | Gly | Leu | Leu | Glu | Ile | Ser | Val | Cys |
| 145 | | | | | 150 | | | | | 155 | | | | | 160 |
| Gln | Tyr | Thr | Met | Cys | Glu | Tyr | Pro | His | Thr | Ile | Cys | His | Pro | Lys | Leu |
| | | | | 165 | | | | | 170 | | | | | 175 | |
| Gly | Asn | Lys | Arg | Val | Glu | Leu | Trp | His | Trp | Asp | Thr | Gly | Val | Val | Ser |
| | | | 180 | | | | | 185 | | | | | 190 | | |
| Cys | Leu | Tyr | Lys | Arg | Asn | Phe | Thr | Tyr | Asp | Val | Asn | Ala | Asp | Tyr | Leu |
| | | | 195 | | | | | 200 | | | | | 205 | | |
| Tyr | Phe | His | Phe | Tyr | Gln | Glu | Gly | Gly | Thr | Phe | Tyr | Ala | Tyr | Phe | Thr |
| | 210 | | | | | 215 | | | | | 220 | | | | |
| Asp | Thr | Gly | Val | Val | Thr | Lys | Phe | Leu | Phe | Asn | Val | Tyr | Leu | Gly | Thr |
| 225 | | | | | 230 | | | | | 235 | | | | | 240 |
| Val | Leu | Ser | His | Tyr | Tyr | Val | Leu | Pro | Leu | Thr | Cys | Ser | Ser | Ala | Met |
| | | | | 245 | | | | | 250 | | | | | 255 | |
| Thr | Leu | Glu | Tyr | Trp | Val | Thr | Pro | Leu | Thr | Ser | Lys | Gln | Tyr | Leu | Leu |
| | | | 260 | | | | | 265 | | | | | 270 | | |
| Ala | Phe | Asn | Gln | Asp | Gly | Val | Ile | Phe | Asn | Ala | Val | Asp | Cys | Lys | Ser |
| | | 275 | | | | | 280 | | | | | 285 | | | |
| Asp | Phe | Met | Ser | Glu | Ile | Lys | Cys | Lys | Thr | Leu | Ser | Ile | Ala | Pro | Ser |
| | 290 | | | | | 295 | | | | | 300 | | | | |
| Thr | Gly | Val | Tyr | Glu | Leu | Asn | Gly | Tyr | Thr | Val | Gln | Pro | Ile | Ala | Asp |
| 305 | | | | | 310 | | | | | 315 | | | | | 320 |
| Val | Tyr | Arg | Arg | Ile | Pro | Asn | Leu | Pro | Asp | Cys | Asn | Ile | Glu | Ala | Trp |
| | | | | 325 | | | | | 330 | | | | | 335 | |
| Leu | Asn | Asp | Lys | Ser | Val | Pro | Ser | Pro | Leu | Asn | Trp | Glu | Arg | Lys | Thr |
| | | | 340 | | | | | 345 | | | | | 350 | | |
| Phe | Ser | Asn | Cys | Asn | Phe | Asn | Met | Ser | Ser | Leu | Met | Ser | Phe | Ile | Gln |
| | | | 355 | | | | | 360 | | | | | 365 | | |
| Ala | Asp | Ser | Phe | Thr | Cys | Asn | Asn | Ile | Asp | Ala | Ala | Lys | Ile | Tyr | Gly |
| | 370 | | | | | 375 | | | | | 380 | | | | |
| Met | Cys | Phe | Ser | Ser | Ile | Thr | Ile | Asp | Lys | Phe | Ala | Ile | Pro | Asn | Gly |

-continued

```
385                 390                 395                 400
Arg Lys Val Asp Leu Gln Leu Gly Asn Leu Gly Tyr Leu Gln Ser Phe
            405                 410                 415
Asn Tyr Arg Ile Asp Thr Thr Ala Thr Ser Cys Gln Leu Tyr Tyr Asn
            420                 425                 430
Leu Pro Ala Ala Asn Val Ser Val Ser Arg Phe Asn Pro Ser Thr Trp
            435                 440                 445
Asn Arg Arg Phe Gly Phe Thr Glu Gln Phe Val Phe Lys Pro Gln Pro
    450                 455                 460
Val Gly Val Phe Thr His His Asp Val Val Tyr Ala Gln His Cys Phe
465                 470                 475                 480
Lys Ala Pro Lys Asn Phe Cys Pro Cys Lys Leu Asp Gly Ser Leu Cys
            485                 490                 495
Val Gly Asn Gly Pro Gly Ile Asp Ala Gly Tyr Lys Asn Ser Gly Ile
            500                 505                 510
Gly Thr Cys Pro Ala Gly Thr Asn Tyr Leu Thr Cys His Asn Ala Ala
            515                 520                 525
Gln Cys Asp Cys Leu Cys Thr Pro Asp Pro Ile Thr Ser Lys Ser Thr
            530                 535                 540
Gly Pro Tyr Lys Cys Pro Gln Thr Lys Tyr Leu Val Gly Ile Gly Glu
545                 550                 555                 560
His Cys Ser Gly Leu Ala Ile Lys Ser Asp Tyr Cys Gly Gly Asn Pro
            565                 570                 575
Cys Thr Cys Gln Pro Gln Ala Phe Leu Gly Trp Ser Val Asp Ser Cys
            580                 585                 590
Leu Gln Gly Asp Arg Cys Asn Ile Phe Ala Asn Phe Ile Phe His Asp
            595                 600                 605
Val Asn Ser Gly Thr Thr Cys Ser Thr Asp Leu Gln Lys Ser Asn Thr
            610                 615                 620
Asp Ile Ile Leu Gly Val Cys Val Asn Tyr Asp Leu Tyr Gly Ile Thr
625                 630                 635                 640
Gly Gln Gly Ile Phe Val Glu Val Asn Ala Thr Tyr Tyr Asn Ser Trp
            645                 650                 655
Gln Asn Leu Leu Tyr Asp Ser Asn Gly Asn Leu Tyr Gly Phe Arg Asp
            660                 665                 670
Tyr Leu Thr Asn Arg Thr Phe Met Ile Arg Ser Cys Tyr Ser Gly Arg
            675                 680                 685
Val Ser Ala Ala Phe His Ala Asn Ser Ser Glu Pro Ala Leu Leu Phe
            690                 695                 700
Arg Asn Ile Lys Cys Asn Tyr Val Phe Asn Asn Thr Leu Ser Arg Gln
705                 710                 715                 720
Leu Gln Pro Ile Asn Tyr Phe Asp Ser Tyr Leu Gly Cys Val Val Asn
            725                 730                 735
Ala Asp Asn Ser Thr Ser Ser Val Val Gln Thr Cys Asp Leu Thr Val
            740                 745                 750
Gly Ser Gly Tyr Cys Val Asp Tyr Ser Thr Lys Arg Arg Ser Arg Arg
            755                 760                 765
Ala Ile Thr Thr Gly Tyr Arg Phe Thr Asn Phe Glu Pro Phe Thr Val
            770                 775                 780
Asn Ser Val Asn Asp Ser Leu Glu Pro Val Gly Gly Leu Tyr Glu Ile
785                 790                 795                 800
Gln Ile Pro Ser Glu Phe Thr Ile Gly Asn Met Glu Glu Phe Ile Gln
            805                 810                 815
```

```
Thr Ser Ser Pro Lys Val Thr Ile Asp Cys Ser Ala Phe Val Cys Gly
        820                 825                 830

Asp Tyr Ala Ala Cys Lys Ser Gln Leu Val Glu Tyr Gly Ser Phe Cys
        835                 840                 845

Asp Asn Ile Asn Ala Ile Leu Thr Glu Val Asn Glu Leu Leu Asp Thr
    850                 855                 860

Thr Gln Leu Gln Val Ala Asn Ser Leu Met Asn Gly Val Thr Leu Ser
865                 870                 875                 880

Thr Lys Leu Lys Asp Gly Val Asn Phe Asn Val Asp Asp Ile Asn Phe
                885                 890                 895

Ser Pro Val Leu Gly Cys Leu Gly Ser Ala Cys Asn Lys Val Ser Ser
            900                 905                 910

Arg Ser Ala Ile Glu Asp Leu Leu Phe Ser Lys Val Lys Leu Ser Asp
        915                 920                 925

Val Gly Phe Val Glu Ala Tyr Asn Asn Cys Thr Gly Gly Ala Glu Ile
    930                 935                 940

Arg Asp Leu Ile Cys Val Gln Ser Tyr Asn Gly Ile Lys Val Leu Pro
945                 950                 955                 960

Pro Leu Leu Ser Val Asn Gln Ile Ser Gly Tyr Thr Leu Ala Ala Thr
                965                 970                 975

Ser Ala Ser Leu Phe Pro Pro Leu Ser Ala Ala Val Gly Val Pro Phe
            980                 985                 990

Tyr Leu Asn Val Gln Tyr Arg Ile Asn Gly Ile Gly Val Thr Met Asp
        995                 1000                1005

Val Leu Ser Gln Asn Gln Lys Leu Ile Ala Asn Ala Phe Asn Asn
    1010                1015                1020

Ala Leu Asp Ala Ile Gln Glu Gly Phe Asp Ala Thr Asn Ser Ala
    1025                1030                1035

Leu Val Lys Ile Gln Ala Val Val Asn Ala Asn Ala Glu Ala Leu
    1040                1045                1050

Asn Asn Leu Leu Gln Gln Leu Ser Asn Arg Phe Gly Ala Ile Ser
    1055                1060                1065

Ser Ser Leu Gln Glu Ile Leu Ser Arg Leu Asp Ala Leu Glu Ala
    1070                1075                1080

Gln Ala Gln Ile Asp Arg Leu Ile Asn Gly Arg Leu Thr Ala Leu
    1085                1090                1095

Asn Val Tyr Val Ser Gln Gln Leu Ser Asp Ser Thr Leu Val Lys
    1100                1105                1110

Phe Ser Ala Ala Gln Ala Met Glu Lys Val Asn Glu Cys Val Lys
    1115                1120                1125

Ser Gln Ser Ser Arg Ile Asn Phe Cys Gly Asn Gly Asn His Ile
    1130                1135                1140

Ile Ser Leu Val Gln Asn Ala Pro Tyr Gly Leu Tyr Phe Ile His
    1145                1150                1155

Phe Ser Tyr Val Pro Thr Lys Tyr Val Thr Ala Lys Val Ser Pro
    1160                1165                1170

Gly Leu Cys Ile Ala Gly Asp Arg Gly Ile Ala Pro Lys Ser Gly
    1175                1180                1185

Tyr Phe Val Asn Val Asn Asn Thr Trp Met Phe Thr Gly Ser Gly
    1190                1195                1200

Tyr Tyr Tyr Pro Glu Pro Ile Thr Gly Asn Asn Val Val Val Met
    1205                1210                1215
```

```
Ser Thr Cys Ala Val Asn Tyr Thr Lys Ala Pro Asp Val Met Leu
    1220                1225                1230

Asn Ile Ser Thr Pro Asn Leu His Asp Phe Lys Glu Glu Leu Asp
    1235                1240                1245

Gln Trp Phe Lys Asn Gln Thr Ser Val Ala Pro Asp Leu Ser Leu
    1250                1255                1260

Asp Tyr Ile Asn Val Thr Phe Leu Asp Leu Gln Asp Glu Met Asn
    1265                1270                1275

Arg Leu Gln Glu Ala Ile Lys Val Leu Asn Gln Ser Tyr Ile Asn
    1280                1285                1290

Leu Lys Asp Ile Gly Thr Tyr Glu Tyr Tyr Val Lys Trp Pro Trp
    1295                1300                1305

Tyr Val Trp Leu Leu Ile Gly Phe Ala Gly Val Ala Met Leu Val
    1310                1315                1320

Leu Leu Phe Phe Ile Cys Cys Cys Thr Gly Cys Gly Thr Ser Cys
    1325                1330                1335

Phe Lys Ile Cys Gly Gly Cys Cys Asp Asp Tyr Thr Gly His Gln
    1340                1345                1350

Glu Leu Val Ile Lys Thr Ser His Asp Asp
    1355                1360

<210> SEQ ID NO 55
<211> LENGTH: 1453
<212> TYPE: PRT
<213> ORGANISM: canine coronavirus

<400> SEQUENCE: 55

Met Ile Val Leu Ile Leu Cys Leu Leu Leu Phe Ser Tyr Asn Ser Val
1               5                   10                  15

Ile Cys Thr Ser Asn Asn Asp Cys Val Gln Gly Asn Val Thr Gln Leu
            20                  25                  30

Pro Gly Asn Glu Asn Ile Ile Lys Asp Phe Leu Phe His Thr Phe Lys
        35                  40                  45

Glu Glu Pro Ser Val Val Gly Gly Tyr Tyr Pro Thr Glu Val Trp
    50                  55                  60

Tyr Asn Cys Ser Arg Ser Ala Thr Thr Thr Ala Tyr Lys Asp Phe Ser
65                  70                  75                  80

Asn Ile His Ala Phe Tyr Phe Asp Met Glu Ala Met Glu Asn Ser Thr
                85                  90                  95

Gly Asn Ala Arg Gly Lys Pro Leu Leu Val His Val His Gly Asp Pro
            100                 105                 110

Val Ser Ile Ile Ile Tyr Ile Ser Ala Tyr Arg Asp Asp Val Gln Pro
        115                 120                 125

Arg Pro Leu Leu Lys His Gly Leu Leu Cys Ile Thr Lys Asn Lys Ile
    130                 135                 140

Ile Asp Tyr Asn Thr Phe Thr Ser Ala Gln Trp Ser Ala Ile Cys Leu
145                 150                 155                 160

Gly Asp Asp Arg Lys Ile Pro Phe Ser Val Ile Pro Thr Asp Asn Gly
                165                 170                 175

Thr Lys Ile Phe Gly Leu Glu Trp Asn Asp Asp Tyr Val Thr Ala Tyr
            180                 185                 190

Ile Ser Asp Arg Ser His His Leu Asn Ile Asn Asn Asn Trp Phe Asn
        195                 200                 205

Asn Val Thr Ile Leu Tyr Ser Arg Ser Ser Ser Ala Thr Trp Gln Lys
    210                 215                 220
```

```
Ser Ala Ala Tyr Val Tyr Gln Gly Val Ser Asn Phe Thr Tyr Lys
225                 230                 235                 240

Leu Asn Asn Thr Asn Gly Leu Lys Ser Tyr Glu Leu Cys Glu Asp Tyr
            245                 250                 255

Glu Tyr Cys Thr Gly Tyr Ala Thr Asn Val Phe Ala Pro Thr Val Gly
            260                 265                 270

Gly Tyr Ile Pro His Gly Phe Ser Phe Asn Asn Trp Phe Met Arg Thr
            275                 280                 285

Asn Ser Ser Thr Phe Val Ser Gly Arg Phe Val Thr Asn Gln Pro Leu
            290                 295                 300

Leu Val Asn Cys Leu Trp Pro Val Pro Ser Phe Gly Val Ala Ala Gln
305                 310                 315                 320

Gln Phe Cys Phe Glu Gly Ala Gln Phe Ser Gln Cys Asn Gly Val Ser
                325                 330                 335

Leu Asn Asn Thr Val Asp Val Ile Arg Phe Asn Leu Asn Phe Thr Ala
                340                 345                 350

Leu Val Gln Ser Gly Met Gly Ala Thr Val Phe Ser Leu Asn Thr Thr
                355                 360                 365

Gly Gly Val Ile Leu Glu Ile Ser Cys Tyr Asn Asp Thr Val Ser Glu
370                 375                 380

Ser Ser Phe Tyr Ser Tyr Gly Glu Ile Ser Phe Gly Val Thr Asp Gly
385                 390                 395                 400

Pro Arg Tyr Cys Phe Ala Leu Tyr Asn Gly Thr Ala Leu Lys Tyr Leu
                405                 410                 415

Gly Thr Leu Pro Pro Ser Val Lys Glu Ile Ala Ile Ser Lys Trp Gly
                420                 425                 430

His Phe Tyr Ile Asn Gly Tyr Asn Phe Phe Ser Thr Phe Pro Ile Asp
            435                 440                 445

Cys Ile Ser Phe Asn Leu Thr Thr Gly Asp Ser Gly Ala Phe Trp Thr
450                 455                 460

Ile Ala Tyr Thr Ser Tyr Thr Asp Ala Leu Val Gln Val Glu Asn Thr
465                 470                 475                 480

Ala Ile Lys Lys Val Thr Tyr Cys Asn Ser His Ile Asn Asn Ile Lys
                485                 490                 495

Cys Ser Gln Leu Thr Ala Asn Leu Gln Asn Gly Phe Tyr Pro Val Ala
                500                 505                 510

Ser Ser Glu Val Gly Leu Val Asn Lys Ser Val Val Leu Leu Pro Ser
            515                 520                 525

Phe Tyr Ser His Thr Ser Val Asn Ile Thr Ile Asp Leu Gly Met Lys
            530                 535                 540

Arg Ser Gly Tyr Gly Gln Pro Ile Ala Ser Thr Leu Ser Asn Ile Thr
545                 550                 555                 560

Leu Pro Met Gln Asp Asn Asn Thr Asp Val Tyr Cys Ile Arg Ser Asn
                565                 570                 575

Arg Phe Ser Val Tyr Phe His Ser Thr Cys Lys Ser Ser Leu Trp Asp
                580                 585                 590

Asp Val Phe Asn Ser Asp Cys Thr Asp Val Leu Tyr Ala Thr Ala Val
            595                 600                 605

Ile Lys Thr Gly Thr Cys Pro Phe Ser Phe Asp Lys Leu Asn Asn Tyr
            610                 615                 620

Leu Thr Phe Asn Lys Phe Cys Leu Ser Leu Asn Pro Val Gly Ala Asn
625                 630                 635                 640
```

-continued

```
Cys Lys Phe Asp Val Ala Ala Arg Thr Arg Thr Asn Glu Gln Val Val
            645                 650                 655

Arg Ser Leu Tyr Val Ile Tyr Glu Glu Gly Asp Asn Ile Val Gly Val
            660                 665                 670

Pro Ser Asp Asn Ser Gly Leu His Asp Leu Ser Val Leu His Leu Asp
            675                 680                 685

Ser Cys Thr Asp Tyr Asn Ile Tyr Gly Ile Thr Gly Val Gly Ile Ile
        690                 695                 700

Arg Gln Thr Asn Ser Thr Leu Leu Ser Gly Leu Tyr Tyr Thr Ser Leu
705                 710                 715                 720

Ser Gly Asp Leu Leu Gly Phe Lys Asn Val Ser Asp Gly Val Ile Tyr
                725                 730                 735

Ser Val Thr Pro Cys Asp Val Ser Ala His Ala Val Ile Asp Gly
            740                 745                 750

Ala Ile Val Gly Ala Met Thr Ser Ile Asn Ser Glu Leu Leu Gly Leu
            755                 760                 765

Thr His Trp Thr Thr Thr Pro Asn Phe Tyr Tyr Ser Ile Tyr Asn
770                 775                 780

Tyr Thr Asn Glu Arg Thr Arg Gly Thr Ala Ile Asp Ser Asn Asp Val
785                 790                 795                 800

Asp Cys Glu Pro Ile Ile Thr Tyr Ser Asn Ile Gly Val Cys Lys Asn
                805                 810                 815

Gly Ala Leu Val Phe Ile Asn Val Thr His Ser Asp Gly Asp Val Gln
            820                 825                 830

Pro Ile Ser Thr Gly Asn Val Thr Ile Pro Thr Asn Phe Thr Ile Ser
            835                 840                 845

Val Gln Val Glu Tyr Ile Gln Val Tyr Thr Thr Pro Val Ser Ile Asp
    850                 855                 860

Cys Ser Arg Tyr Val Cys Asn Gly Asn Pro Arg Cys Asn Lys Leu Leu
865                 870                 875                 880

Thr Gln Tyr Val Ser Ala Cys Gln Thr Ile Glu Gln Ala Leu Ala Met
                885                 890                 895

Gly Ala Arg Leu Glu Asn Met Glu Ile Asp Ser Met Leu Phe Val Ser
            900                 905                 910

Glu Asn Ala Leu Lys Leu Ala Ser Val Glu Ala Phe Asn Ser Thr Glu
            915                 920                 925

Thr Leu Asp Pro Ile Tyr Lys Glu Trp Pro Asn Ile Gly Gly Ser Trp
    930                 935                 940

Leu Gly Gly Leu Lys Asp Ile Leu Pro Ser His Asn Ser Lys Arg Lys
945                 950                 955                 960

Tyr Arg Ser Ala Ile Glu Asp Leu Leu Phe Asp Lys Val Thr Ser
                965                 970                 975

Gly Leu Gly Thr Val Asp Glu Asp Tyr Lys Arg Cys Thr Gly Gly Tyr
            980                 985                 990

Asp Ile Ala Asp Leu Val Cys Ala Gln Tyr Tyr Asn Gly Ile Met Val
        995                 1000                1005

Leu Pro Gly Val Ala Asn Asp Asp Lys Met Ala Met Tyr Thr Ala
    1010                1015                1020

Ser Leu Ala Gly Gly Ile Thr Leu Gly Ser Leu Gly Gly Gly Ala
    1025                1030                1035

Val Ser Ile Pro Phe Ala Ile Ala Val Gln Ala Arg Leu Asn Tyr
    1040                1045                1050

Val Ala Leu Gln Thr Asp Val Leu Asn Lys Asn Gln Gln Ile Leu
```

-continued

```
            1055                1060                1065

Ala Asn Ala Phe Asn Gln Ala Ile Gly Asn Ile Thr Gln Ala Phe
            1070                1075                1080

Gly Lys Val Asn Asp Ala Ile His Gln Thr Ser Gln Gly Leu Ala
            1085                1090                1095

Thr Val Ala Lys Val Leu Ala Lys Val Gln Asp Val Val Asn Thr
            1100                1105                1110

Gln Gly Gln Ala Leu Ser His Leu Thr Leu Gln Leu Gln Asn Asn
            1115                1120                1125

Phe Gln Ala Ile Ser Ser Ser Ile Ser Asp Ile Tyr Asn Arg Leu
            1130                1135                1140

Asp Glu Leu Ser Ala Asp Ala Gln Val Asp Arg Leu Ile Thr Gly
            1145                1150                1155

Arg Leu Thr Ala Leu Asn Ala Phe Val Ser Gln Thr Leu Thr Arg
            1160                1165                1170

Gln Ala Glu Val Arg Ala Ser Arg Gln Leu Ala Lys Asp Lys Val
            1175                1180                1185

Asn Glu Cys Val Arg Ser Gln Ser Gln Arg Phe Gly Phe Cys Gly
            1190                1195                1200

Asn Gly Thr His Leu Phe Ser Leu Ala Asn Ala Ala Pro Asn Gly
            1205                1210                1215

Met Ile Phe Phe His Thr Val Leu Leu Pro Thr Ala Tyr Glu Thr
            1220                1225                1230

Val Thr Ala Trp Ser Gly Ile Cys Ala Ser Asp Gly Asp Arg Thr
            1235                1240                1245

Phe Gly Leu Val Val Lys Asp Val Gln Leu Thr Leu Phe Arg Asn
            1250                1255                1260

Leu Asp Asp Lys Phe Tyr Leu Thr Pro Arg Thr Met Tyr Gln Pro
            1265                1270                1275

Ile Val Ala Thr Ser Ser Asp Phe Val Gln Ile Glu Gly Cys Asp
            1280                1285                1290

Val Leu Phe Val Asn Ala Thr Val Ile Asp Leu Pro Ser Ile Ile
            1295                1300                1305

Pro Asp Tyr Ile Asp Ile Asn Gln Thr Val Gln Asp Ile Leu Glu
            1310                1315                1320

Asn Phe Arg Pro Asn Trp Thr Val Pro Glu Leu Pro Leu Asp Ile
            1325                1330                1335

Phe Asn Ala Thr Tyr Leu Asn Leu Thr Gly Glu Ile Asn Asp Leu
            1340                1345                1350

Glu Phe Arg Ser Glu Lys Leu His Asn Thr Thr Val Glu Leu Ala
            1355                1360                1365

Ile Leu Ile Asp Asn Ile Asn Asn Thr Leu Val Asn Leu Glu Trp
            1370                1375                1380

Leu Asn Arg Ile Glu Thr Tyr Val Lys Trp Pro Trp Tyr Val Trp
            1385                1390                1395

Leu Leu Ile Gly Leu Val Val Ile Phe Cys Ile Pro Ile Leu Leu
            1400                1405                1410

Phe Cys Cys Cys Ser Thr Gly Cys Cys Gly Cys Ile Gly Cys Leu
            1415                1420                1425

Gly Ser Cys Cys His Ser Ile Cys Ser Arg Arg Gln Phe Glu Ser
            1430                1435                1440

Tyr Glu Pro Ile Glu Lys Val His Val His
            1445                1450
```

<210> SEQ ID NO 56
<211> LENGTH: 1464
<212> TYPE: PRT
<213> ORGANISM: Feline infectious peritonitis virus

<400> SEQUENCE: 56

Met Ile Phe Ile Ile Leu Thr Leu Leu Ser Val Ala Lys Ser Glu Asp
1               5                   10                  15

Ala Pro His Gly Val Thr Leu Pro Gln Phe Asn Thr Ser His Asn Asn
            20                  25                  30

Glu Arg Phe Glu Leu Asn Phe Tyr Asn Phe Leu Gln Thr Trp Asp Ile
        35                  40                  45

Pro Pro Asn Thr Glu Thr Ile Leu Gly Gly Tyr Leu Pro Tyr Cys Gly
    50                  55                  60

Ala Gly Val Asn Cys Gly Trp Tyr Asn Phe Ser Gln Ser Val Gly Gln
65                  70                  75                  80

Asn Gly Lys Tyr Ala Tyr Ile Asn Thr Gln Asn Leu Asn Ile Pro Asn
                85                  90                  95

Val His Gly Val Tyr Phe Asp Val Arg Glu His Asn Asn Asp Gly Glu
            100                 105                 110

Trp Asp Asp Arg Asp Lys Val Gly Leu Leu Ile Ala Ile His Gly Asn
        115                 120                 125

Ser Lys Tyr Ser Leu Leu Met Val Leu Gln Asp Ala Val Glu Ala Asn
    130                 135                 140

Gln Pro His Val Ala Val Lys Ile Cys His Trp Lys Pro Gly Asn Ile
145                 150                 155                 160

Ser Ser Tyr His Ala Phe Ser Val Asn Leu Gly Asp Gly Gly Gln Cys
                165                 170                 175

Val Phe Asn Gln Arg Phe Ser Leu Asp Thr Val Leu Thr Thr Asn Asp
            180                 185                 190

Phe Tyr Gly Phe Gln Trp Thr Asp Thr Tyr Val Asp Ile Tyr Leu Gly
        195                 200                 205

Gly Thr Ile Thr Lys Val Trp Val Asp Asn Asp Trp Ser Ile Val Glu
    210                 215                 220

Ala Ser Ile Ser Tyr His Trp Asn Arg Ile Asn Tyr Gly Tyr Tyr Met
225                 230                 235                 240

Gln Phe Val Asn Arg Thr Thr Tyr Tyr Ala Tyr Asn Asn Thr Gly Gly
                245                 250                 255

Ala Asn Tyr Thr Gln Leu Gln Leu Ser Glu Cys His Thr Asp Tyr Cys
            260                 265                 270

Ala Gly Tyr Ala Lys Asn Val Phe Val Pro Ile Asp Gly Lys Ile Pro
        275                 280                 285

Glu Asp Phe Ser Phe Ser Asn Trp Phe Leu Leu Ser Asp Lys Ser Thr
    290                 295                 300

Leu Val Gln Gly Arg Val Leu Ser Ser Gln Pro Val Phe Val Gln Cys
305                 310                 315                 320

Leu Arg Pro Val Pro Ser Trp Ser Asn Asn Thr Ala Val Val His Phe
                325                 330                 335

Lys Asn Asp Ala Phe Cys Pro Asn Val Thr Ala Asp Val Leu Arg Phe
            340                 345                 350

Asn Leu Asn Phe Ser Asp Thr Asp Val Tyr Thr Asp Ser Thr Asn Asp
        355                 360                 365

Glu Gln Leu Phe Phe Thr Phe Glu Asp Asn Thr Thr Ala Ser Ile Ala

```
              370                 375                 380
Cys Tyr Ser Ser Ala Asn Val Thr Asp Phe Gln Pro Ala Asn Asn Ser
385                 390                 395                 400

Val Ser His Ile Pro Phe Gly Lys Thr Ala His Phe Cys Phe Ala Asn
            405                 410                 415

Phe Ser His Ser Ile Val Ser Arg Gln Phe Leu Gly Ile Leu Pro Pro
            420                 425                 430

Thr Val Arg Glu Phe Ala Phe Gly Arg Asp Gly Ser Ile Phe Val Asn
            435                 440                 445

Gly Tyr Lys Tyr Phe Ser Leu Pro Ala Ile Arg Ser Val Asn Phe Ser
        450                 455                 460

Ile Ser Ser Val Glu Glu Tyr Gly Phe Trp Thr Ile Ala Tyr Thr Asn
465                 470                 475                 480

Tyr Thr Asp Val Met Val Asp Val Asn Gly Thr Ala Ile Thr Arg Leu
                485                 490                 495

Phe Tyr Cys Asp Ser Pro Leu Asn Arg Ile Lys Cys Gln Gln Leu Lys
            500                 505                 510

His Glu Leu Pro Asp Gly Phe Tyr Ser Ala Ser Met Leu Val Lys Lys
        515                 520                 525

Asp Leu Pro Lys Thr Phe Val Thr Met Pro Gln Phe Tyr His Trp Met
    530                 535                 540

Asn Val Thr Leu His Val Val Leu Asn Asp Thr Glu Lys Lys Tyr Asp
545                 550                 555                 560

Ile Ile Leu Ala Lys Ala Pro Glu Leu Ala Ala Leu Ala Asp Val His
                565                 570                 575

Phe Glu Ile Ala Gln Ala Asn Gly Ser Val Thr Asn Val Thr Ser Leu
            580                 585                 590

Cys Val Gln Ala Arg Gln Leu Ala Leu Phe Tyr Lys Tyr Thr Ser Leu
            595                 600                 605

Gln Gly Leu Tyr Thr Tyr Ser Asn Leu Val Glu Leu Gln Asn Tyr Asp
        610                 615                 620

Cys Pro Phe Ser Pro Gln Gln Phe Asn Asn Tyr Leu Gln Phe Glu Thr
625                 630                 635                 640

Leu Cys Phe Asp Val Asn Pro Ala Val Ala Gly Cys Lys Trp Ser Leu
                645                 650                 655

Val His Asp Val Gln Trp Arg Thr Gln Phe Ala Thr Ile Thr Val Ser
            660                 665                 670

Tyr Lys His Gly Ser Met Ile Thr Thr His Ala Lys Gly His Ser Trp
        675                 680                 685

Gly Phe Gln Asp Thr Ser Val Leu Val Lys Asp Glu Cys Thr Asp Tyr
    690                 695                 700

Asn Ile Tyr Gly Phe Gln Gly Thr Gly Ile Ile Arg Asn Thr Thr Ser
705                 710                 715                 720

Arg Leu Val Ala Gly Leu Tyr Tyr Thr Ser Ile Ser Gly Asp Leu Leu
                725                 730                 735

Ala Phe Lys Asn Ser Thr Thr Gly Glu Ile Phe Thr Val Val Pro Cys
            740                 745                 750

Asp Leu Thr Ala Gln Val Ala Val Ile Asn Asp Glu Ile Val Gly Ala
        755                 760                 765

Ile Thr Ala Val Asn Gln Thr Asp Leu Phe Glu Phe Val Asn Asn Thr
    770                 775                 780

Gln Ala Arg Arg Ser Arg Ser Thr Pro Asn Phe Val Thr Ser Tyr
785                 790                 795                 800
```

-continued

```
Thr Met Pro Gln Phe Tyr Tyr Ile Thr Lys Trp Asn Asn Asp Thr Ser
            805                 810                 815

Ser Asn Cys Thr Ser Ala Ile Thr Tyr Ser Ser Phe Ala Ile Cys Asn
            820                 825                 830

Thr Gly Glu Ile Lys Tyr Val Asn Val Thr His Val Glu Ile Val Asp
            835                 840                 845

Asp Ser Ile Gly Val Ile Lys Pro Val Ser Thr Gly Asn Ile Ser Ile
            850                 855                 860

Pro Lys Asn Phe Thr Val Ala Val Gln Ala Glu Tyr Ile Gln Ile Gln
865                 870                 875                 880

Val Lys Pro Val Val Asp Cys Ala Thr Tyr Val Cys Asn Gly Asn
                885                 890                 895

Thr His Cys Leu Lys Leu Leu Thr Gln Tyr Thr Ser Ala Cys Gln Thr
            900                 905                 910

Ile Glu Asn Ala Leu Asn Leu Gly Ala Arg Leu Glu Ser Leu Met Leu
            915                 920                 925

Asn Asp Met Ile Thr Val Ser Asp Arg Gly Leu Glu Leu Ala Thr Val
930                 935                 940

Glu Arg Phe Asn Ala Thr Ala Leu Gly Gly Glu Lys Leu Gly Gly Leu
945                 950                 955                 960

Tyr Phe Asp Gly Leu Ser Ser Leu Leu Pro Pro Lys Ile Gly Lys Arg
            965                 970                 975

Ser Ala Val Glu Asp Leu Leu Phe Asn Lys Val Val Thr Ser Gly Leu
            980                 985                 990

Gly Thr Val Asp Asp Asp Tyr Lys  Lys Cys Ser Ser Gly  Thr Asp Val
            995                 1000                1005

Ala Asp  Leu Val Cys Ala Gln  Tyr Tyr Asn Gly Ile  Met Val Leu
    1010                1015                1020

Pro Gly  Val Val Asp Gly Asn  Lys Met Ser Met Tyr  Thr Ala Ser
    1025                1030                1035

Leu Ile  Gly Gly Met Ala Leu  Gly Ser Ile Thr Ser  Ala Val Ala
    1040                1045                1050

Val Pro  Phe Ala Met Gln Val  Gln Ala Arg Leu Asn  Tyr Val Ala
    1055                1060                1065

Leu Gln  Thr Asp Val Leu Gln  Glu Asn Gln Lys Ile  Leu Ala Asn
    1070                1075                1080

Ala Phe  Asn Asn Ala Ile Gly  Asn Ile Thr Leu Ala  Leu Gly Lys
    1085                1090                1095

Val Ser  Asn Ala Ile Thr Thr  Thr Ser Asp Gly Phe  Asn Ser Met
    1100                1105                1110

Ala Ser  Ala Leu Thr Lys Ile  Gln Ser Val Val Asn  Gln Gln Gly
    1115                1120                1125

Glu Ala  Leu Ser Gln Leu Thr  Ser Gln Leu Gln Lys  Asn Phe Gln
    1130                1135                1140

Ala Ile  Ser Ser Ser Ile Ala  Glu Ile Tyr Asn Arg  Leu Glu Lys
    1145                1150                1155

Val Glu  Ala Asp Ala Gln Val  Asp Arg Leu Ile Thr  Gly Arg Leu
    1160                1165                1170

Ala Ala  Leu Asn Ala Tyr Val  Ser Gln Thr Leu Thr  Gln Tyr Ala
    1175                1180                1185

Glu Val  Lys Ala Ser Arg Gln  Ile Ala Leu Glu Lys  Val Asn Glu
    1190                1195                1200
```

-continued

```
Cys Val Lys Ser Gln Ser Asn Arg Tyr Gly Phe Cys Gly Asn Gly
    1205                1210                1215

Thr His Leu Phe Ser Leu Val Asn Ser Ala Pro Glu Gly Leu Leu
    1220                1225                1230

Phe Phe His Thr Val Leu Leu Pro Thr Glu Trp Glu Val Thr
    1235                1240                1245

Ala Trp Ser Gly Ile Cys Val Asn Asp Thr Tyr Ala Tyr Val Leu
    1250                1255                1260

Lys Asp Phe Asp His Ser Ile Phe Ser Tyr Asn Gly Thr Tyr Met
    1265                1270                1275

Val Thr Pro Arg Asn Met Phe Gln Pro Arg Lys Pro Gln Met Ser
    1280                1285                1290

Asp Phe Val Gln Ile Thr Ser Cys Glu Val Thr Phe Leu Asn Met
    1295                1300                1305

Thr Tyr Thr Thr Phe Gln Glu Ile Val Ile Asp Tyr Ile Asp Ile
    1310                1315                1320

Asn Lys Thr Ile Ala Asp Met Leu Glu Gln Tyr Asn Pro Asn Tyr
    1325                1330                1335

Thr Thr Pro Glu Leu Asn Leu Leu Leu Asp Ile Phe Asn Gln Thr
    1340                1345                1350

Lys Leu Asn Leu Thr Ala Glu Ile Asp Gln Leu Glu Gln Arg Ala
    1355                1360                1365

Asp Asn Leu Thr Thr Ile Ala His Glu Leu Gln Gln Tyr Ile Asp
    1370                1375                1380

Asn Leu Asn Lys Thr Leu Val Asp Leu Asp Trp Leu Asn Arg Ile
    1385                1390                1395

Glu Thr Tyr Val Lys Trp Pro Trp Tyr Val Trp Leu Leu Ile Gly
    1400                1405                1410

Leu Val Val Val Phe Cys Ile Pro Leu Leu Leu Phe Cys Cys Leu
    1415                1420                1425

Ser Thr Gly Phe Cys Gly Cys Phe Gly Cys Val Gly Ser Cys Cys
    1430                1435                1440

His Ser Leu Cys Ser Arg Arg Gln Phe Glu Thr Tyr Glu Pro Ile
    1445                1450                1455

Glu Lys Val His Ile His
    1460

<210> SEQ ID NO 57
<211> LENGTH: 1235
<212> TYPE: PRT
<213> ORGANISM: Mouse hepatitis virus

<400> SEQUENCE: 57

Met Leu Phe Val Phe Ile Leu Leu Pro Ser Cys Leu Gly Tyr Ile
1               5                   10                  15

Gly Asp Phe Arg Cys Ile Gln Thr Val Asn Tyr Asn Gly Asn Asn Ala
                20                  25                  30

Ser Ala Pro Ser Ile Ser Thr Glu Ala Val Asp Val Ser Lys Gly Arg
            35                  40                  45

Gly Thr Tyr Tyr Val Leu Asp Arg Val Tyr Leu Asn Ala Thr Leu Leu
        50                  55                  60

Leu Thr Gly Tyr Tyr Pro Val Asp Gly Ser Asn Tyr Arg Asn Leu Ala
65                  70                  75                  80

Leu Thr Gly Thr Asn Thr Leu Ser Leu Thr Trp Phe Lys Pro Pro Phe
                85                  90                  95
```

```
Leu Ser Glu Phe Asn Asp Gly Ile Phe Ala Lys Val Gln Asn Leu Lys
            100                 105                 110

Thr Asn Thr Pro Thr Gly Ala Thr Ser Tyr Phe Pro Thr Ile Val Ile
        115                 120                 125

Gly Ser Leu Phe Gly Asn Thr Ser Tyr Thr Val Val Leu Glu Pro Tyr
    130                 135                 140

Asn Asn Ile Ile Met Ala Ser Val Cys Thr Tyr Thr Ile Cys Gln Leu
145                 150                 155                 160

Pro Tyr Thr Pro Cys Lys Pro Asn Thr Asn Gly Asn Arg Val Ile Gly
                165                 170                 175

Phe Trp His Thr Asp Val Lys Pro Pro Ile Cys Leu Leu Lys Arg Asn
            180                 185                 190

Phe Thr Phe Asn Val Asn Ala Pro Trp Leu Tyr Phe His Phe Tyr Gln
        195                 200                 205

Gln Gly Gly Thr Phe Tyr Ala Tyr Tyr Ala Asp Lys Pro Ser Ala Thr
    210                 215                 220

Thr Phe Leu Phe Ser Val Tyr Ile Gly Asp Ile Leu Thr Gln Tyr Phe
225                 230                 235                 240

Val Leu Pro Phe Ile Cys Thr Pro Thr Ala Gly Ser Thr Leu Ala Pro
                245                 250                 255

Leu Tyr Trp Val Thr Pro Leu Leu Lys Arg Gln Tyr Leu Phe Asn Phe
            260                 265                 270

Asn Glu Lys Gly Val Ile Thr Ser Ala Val Asp Cys Ala Ser Ser Tyr
        275                 280                 285

Ile Ser Glu Ile Lys Cys Lys Thr Gln Ser Leu Leu Pro Ser Thr Gly
    290                 295                 300

Val Tyr Asp Leu Ser Gly Tyr Thr Val Gln Pro Val Gly Val Val Tyr
305                 310                 315                 320

Arg Arg Val Pro Asn Leu Pro Asp Cys Lys Ile Glu Glu Trp Leu Thr
                325                 330                 335

Ala Lys Ser Val Pro Ser Pro Leu Asn Trp Glu Arg Arg Thr Phe Gln
            340                 345                 350

Asn Cys Asn Phe Asn Leu Ser Ser Leu Leu Arg Tyr Val Gln Ala Glu
        355                 360                 365

Ser Leu Ser Cys Asn Asn Ile Asp Ala Ser Lys Val Tyr Gly Met Cys
    370                 375                 380

Phe Gly Ser Val Ser Val Asp Lys Phe Ala Ile Pro Arg Ser Arg Gln
385                 390                 395                 400

Ile Asp Leu Gln Ile Gly Asn Ser Gly Phe Leu Gln Thr Ala Asn Tyr
                405                 410                 415

Lys Ile Asp Thr Ala Ala Thr Ser Cys Gln Leu Tyr Tyr Ser Leu Pro
            420                 425                 430

Lys Asn Asn Val Thr Ile Asn Asn Tyr Asn Pro Ser Ser Trp Asn Arg
        435                 440                 445

Arg Tyr Gly Phe Lys Val Asn Asp Arg Cys Gln Ile Phe Ala Asn Ile
    450                 455                 460

Leu Leu Asn Gly Ile Asn Ser Gly Thr Thr Cys Ser Thr Asp Leu Gln
465                 470                 475                 480

Leu Pro Asn Thr Glu Val Ala Thr Gly Val Cys Val Arg Tyr Asp Leu
                485                 490                 495

Tyr Gly Ile Thr Gly Gln Gly Val Phe Lys Glu Val Lys Ala Asp Tyr
            500                 505                 510
```

```
-continued

Tyr Asn Ser Trp Gln Ala Leu Leu Tyr Asp Val Asn Gly Asn Leu Asn
            515                 520                 525

Gly Phe Arg Asp Leu Thr Thr Asn Lys Thr Tyr Thr Ile Arg Ser Cys
            530                 535                 540

Tyr Ser Gly Arg Val Ser Ala Ala Tyr His Lys Glu Ala Pro Glu Pro
545                 550                 555                 560

Ala Leu Leu Tyr Arg Asn Ile Asn Cys Ser Tyr Val Phe Thr Asn Asn
                565                 570                 575

Ile Ser Arg Glu Glu Asn Pro Leu Asn Tyr Phe Asp Ser Tyr Leu Gly
            580                 585                 590

Cys Val Val Asn Ala Asp Asn Arg Thr Asp Glu Ala Leu Pro Asn Cys
            595                 600                 605

Asn Leu Arg Met Gly Ala Gly Leu Cys Val Asp Tyr Ser Lys Ser Arg
            610                 615                 620

Arg Ala Arg Arg Ser Val Ser Thr Gly Tyr Arg Leu Thr Thr Phe Glu
625                 630                 635                 640

Pro Tyr Met Pro Met Leu Val Asn Asp Ser Val Gln Ser Val Gly Gly
                645                 650                 655

Leu Tyr Glu Met Gln Ile Pro Thr Asn Phe Thr Ile Gly His His Glu
            660                 665                 670

Glu Phe Ile Gln Ile Arg Ala Pro Lys Val Thr Ile Asp Cys Ala Ala
            675                 680                 685

Phe Val Cys Gly Asp Asn Ala Ala Cys Arg Gln Gln Leu Val Glu Tyr
            690                 695                 700

Gly Ser Phe Cys Asp Asn Val Asn Ala Ile Leu Asn Glu Val Asn Asn
705                 710                 715                 720

Leu Leu Asp Asn Met Gln Leu Gln Val Ala Ser Ala Leu Met Gln Gly
                725                 730                 735

Val Thr Ile Ser Ser Arg Leu Pro Asp Gly Ile Ser Gly Pro Ile Asp
            740                 745                 750

Asp Ile Asn Phe Ser Pro Leu Leu Gly Cys Ile Gly Ser Thr Cys Ala
            755                 760                 765

Glu Asp Gly Asn Gly Pro Ser Ala Ile Arg Gly Arg Ser Ala Ile Glu
            770                 775                 780

Asp Leu Leu Phe Asp Lys Val Lys Leu Ser Asp Val Gly Phe Val Glu
785                 790                 795                 800

Ala Tyr Asn Asn Cys Thr Gly Gly Gln Glu Val Arg Asp Leu Leu Cys
                805                 810                 815

Val Gln Ser Phe Asn Gly Ile Lys Val Leu Pro Pro Val Leu Ser Glu
            820                 825                 830

Ser Gln Ile Ser Gly Tyr Thr Ala Gly Ala Thr Ala Ala Ala Met Phe
            835                 840                 845

Pro Pro Trp Thr Ala Ala Ala Gly Val Pro Phe Ser Leu Asn Val Gln
            850                 855                 860

Tyr Arg Ile Asn Gly Leu Gly Val Thr Met Asn Val Leu Ser Glu Asn
865                 870                 875                 880

Gln Lys Met Ile Ala Ser Ala Phe Asn Asn Ala Leu Gly Ala Ile Gln
                885                 890                 895

Glu Gly Phe Asp Ala Thr Asn Ser Ala Leu Gly Lys Ile Gln Ser Val
            900                 905                 910

Val Asn Ala Asn Ala Glu Ala Leu Asn Leu Leu Asn Gln Leu Ser
            915                 920                 925

Asn Arg Phe Gly Ala Ile Ser Ala Ser Leu Gln Glu Ile Leu Thr Arg
```

-continued 930 935 940

Leu Asp Ala Val Glu Ala Lys Ala Gln Ile Asp Arg Leu Ile Asn Gly
945 950 955 960

Arg Leu Thr Ala Leu Asn Ala Tyr Ile Ser Lys Gln Leu Ser Asp Ser
965 970 975

Thr Leu Ile Lys Phe Ser Ala Ala Gln Ala Ile Glu Lys Val Asn Glu
980 985 990

Cys Val Lys Ser Gln Thr Thr Arg Ile Asn Phe Cys Gly Asn Gly Asn
995 1000 1005

His Ile Leu Ser Leu Val Gln Asn Ala Pro Tyr Gly Leu Cys Phe
1010 1015 1020

Ile His Phe Ser Tyr Val Pro Thr Ser Phe Lys Thr Ala Asn Val
1025 1030 1035

Ser Pro Gly Leu Cys Ile Ser Gly Asp Arg Gly Leu Ala Pro Lys
1040 1045 1050

Ala Gly Tyr Phe Val Gln Asp Asn Gly Glu Trp Lys Phe Thr Gly
1055 1060 1065

Ser Asn Tyr Tyr Tyr Pro Glu Pro Ile Thr Asp Lys Asn Ser Val
1070 1075 1080

Ala Met Ile Ser Cys Ala Val Asn Tyr Thr Lys Ala Pro Glu Val
1085 1090 1095

Phe Leu Asn Asn Ser Ile Pro Asn Leu Pro Asp Phe Lys Glu Glu
1100 1105 1110

Leu Asp Lys Trp Phe Lys Asn Gln Thr Ser Ile Ala Pro Asp Leu
1115 1120 1125

Ser Leu Asp Phe Glu Lys Leu Asn Val Thr Phe Leu Asp Leu Thr
1130 1135 1140

Tyr Glu Met Asn Arg Ile Gln Asp Ala Ile Lys Lys Leu Asn Glu
1145 1150 1155

Ser Tyr Ile Asn Leu Lys Glu Val Gly Thr Tyr Glu Met Tyr Val
1160 1165 1170

Lys Trp Pro Trp Tyr Val Trp Leu Leu Ile Gly Leu Ala Gly Val
1175 1180 1185

Ala Val Cys Val Leu Leu Phe Phe Ile Cys Cys Cys Thr Gly Cys
1190 1195 1200

Gly Ser Cys Cys Phe Arg Lys Cys Gly Ser Cys Cys Asp Glu Tyr
1205 1210 1215

Gly Gly His Gln Asp Ser Ile Val Ile His Asn Ile Ser Ala His
1220 1225 1230

Glu Asp
1235

<210> SEQ ID NO 58
<211> LENGTH: 1363
<212> TYPE: PRT
<213> ORGANISM: human coronavirus

<400> SEQUENCE: 58

Met Phe Leu Ile Leu Leu Ile Ser Leu Pro Met Ala Leu Ala Val Ile
1 5 10 15

Gly Asp Leu Lys Cys Thr Thr Val Ala Ile Asn Asp Val Asp Thr Gly
20 25 30

Val Pro Ser Thr Ser Thr Asp Ile Val Asp Val Thr Asn Gly Leu Gly
35 40 45

```
Thr Tyr Tyr Val Leu Asp Arg Val Tyr Leu Asn Thr Leu Leu Leu
    50                  55                  60

Asn Gly Tyr Tyr Pro Thr Ser Gly Ser Thr Tyr Arg Asn Met Ala Leu
65                  70                  75                  80

Lys Gly Thr Leu Leu Leu Ser Arg Leu Trp Phe Lys Pro Pro Phe Leu
                85                  90                  95

Ser Asp Phe Ile Asn Gly Ile Phe Ala Lys Val Lys Asn Thr Lys Val
            100                 105                 110

Ile Lys His Gly Val Met Tyr Ser Glu Phe Pro Ala Ile Thr Ile Gly
        115                 120                 125

Ser Thr Phe Val Asn Thr Ser Tyr Ser Val Val Gln Pro His Thr
130                 135                 140

Thr Asn Leu Asp Asn Lys Leu Gln Gly Leu Leu Glu Ile Ser Val Cys
145                 150                 155                 160

Gln Tyr Thr Met Cys Glu Tyr Pro Asn Thr Ile Cys His Pro Asn Leu
                165                 170                 175

Gly Asn Arg Arg Val Glu Leu Trp His Trp Asp Thr Gly Val Val Ser
                180                 185                 190

Cys Leu Tyr Lys Arg Asn Phe Thr Tyr Asp Val Asn Ala Asp Tyr Leu
            195                 200                 205

Tyr Phe His Phe Tyr Gln Glu Gly Gly Ile Phe Tyr Ala Tyr Phe Thr
        210                 215                 220

Asp Thr Gly Val Val Thr Lys Phe Leu Phe Asn Val Tyr Leu Gly Thr
225                 230                 235                 240

Val Leu Ser Tyr Tyr Tyr Val Met Pro Leu Thr Cys Asn Ser Ala Met
                245                 250                 255

Thr Leu Glu Tyr Trp Val Thr Pro Leu Thr Ser Lys Gln Tyr Leu Leu
            260                 265                 270

Ala Phe Asn Gln Asp Gly Val Ile Phe Asn Ala Val Asp Cys Lys Ser
        275                 280                 285

Asp Phe Met Ser Glu Ile Lys Cys Lys Thr Leu Ser Ile Ala Pro Ser
290                 295                 300

Thr Gly Val Tyr Glu Leu Asn Gly Tyr Thr Val Gln Pro Ile Ala Asp
305                 310                 315                 320

Val Tyr Arg Arg Ile Pro Asn Leu Pro Asp Cys Asn Ile Glu Ala Trp
                325                 330                 335

Leu Asn Asp Lys Ser Val Pro Ser Pro Leu Asn Trp Glu Arg Lys Thr
            340                 345                 350

Phe Ser Asn Cys Asn Phe Asn Met Ser Ser Leu Met Ser Phe Ile Gln
        355                 360                 365

Ala Asp Ser Phe Thr Cys Asn Asn Ile Asp Ala Ala Lys Ile Tyr Gly
370                 375                 380

Met Cys Phe Ser Ser Ile Thr Ile Asp Lys Phe Ala Ile Pro Asn Gly
385                 390                 395                 400

Arg Lys Val Asp Leu Gln Leu Gly Asn Leu Gly Tyr Leu Gln Ser Phe
                405                 410                 415

Asn Tyr Arg Ile Asp Thr Thr Ala Thr Ser Cys Gln Leu Tyr Tyr Asn
            420                 425                 430

Leu Pro Ala Ala Asn Val Ser Val Ser Arg Phe Asn Pro Ser Ile Trp
        435                 440                 445

Asn Arg Arg Phe Gly Phe Thr Glu Gln Ser Val Phe Lys Pro Gln Pro
450                 455                 460

Ala Gly Val Phe Thr Asp His Asp Val Val Tyr Ala Gln His Cys Phe
```

-continued

```
            465                 470                 475                 480
Lys Ala Pro Thr Asn Phe Cys Pro Cys Lys Leu Asp Gly Ser Leu Cys
                485                 490                 495
Val Gly Asn Gly Pro Gly Ile Asp Ala Gly Tyr Lys Asn Ser Gly Ile
                500                 505                 510
Gly Thr Cys Pro Ala Gly Thr Asn Tyr Leu Thr Cys His Asn Ala Val
                515                 520                 525
Gln Cys Asn Cys Leu Cys Thr Pro Asp Pro Ile Thr Ser Lys Ser Thr
                530                 535                 540
Gly Pro Tyr Lys Cys Pro Gln Thr Lys Tyr Leu Val Gly Ile Gly Glu
545                 550                 555                 560
His Cys Ser Gly Leu Ala Ile Lys Ser Asp Tyr Cys Gly Gly Asn Pro
                565                 570                 575
Cys Thr Cys Gln Pro Gln Ala Phe Leu Gly Trp Ser Val Asp Ser Cys
                580                 585                 590
Leu Gln Gly Asp Arg Cys Asn Ile Phe Ala Asn Phe Ile Leu His Asp
                595                 600                 605
Val Asn Ser Gly Thr Thr Cys Ser Thr Asp Leu Gln Lys Ser Asn Thr
                610                 615                 620
Asp Ile Ile Leu Gly Val Cys Val Asn Tyr Asp Leu Tyr Gly Ile Thr
625                 630                 635                 640
Gly Gln Gly Ile Phe Val Glu Val Asn Ala Pro Tyr Tyr Asn Ser Trp
                645                 650                 655
Gln Asn Leu Leu Tyr Asp Ser Asn Gly Asn Leu Tyr Gly Phe Arg Asp
                660                 665                 670
Tyr Leu Thr Asn Arg Thr Phe Met Ile Arg Ser Cys Tyr Ser Gly Arg
                675                 680                 685
Val Ser Ala Ala Phe His Ala Asn Ser Ser Glu Pro Ala Leu Leu Phe
690                 695                 700
Arg Asn Ile Lys Cys Asn Tyr Val Phe Asn Asn Thr Leu Ser Arg Gln
705                 710                 715                 720
Leu Gln Pro Ile Asn Tyr Phe Asp Ser Tyr Leu Gly Cys Val Val Asn
                725                 730                 735
Ala Asp Asn Ser Thr Ala Ser Ala Val Gln Thr Cys Asp Leu Thr Val
                740                 745                 750
Gly Ser Gly Tyr Cys Val Asp Tyr Ser Thr Lys Arg Arg Ser Arg Arg
                755                 760                 765
Ala Ile Thr Thr Gly Tyr Arg Phe Thr Asn Phe Glu Pro Phe Thr Val
                770                 775                 780
Asn Ser Val Asn Asp Ser Leu Glu His Val Gly Gly Leu Tyr Glu Ile
785                 790                 795                 800
Gln Ile Pro Ser Glu Phe Thr Ile Gly Asn Met Glu Glu Phe Ile Gln
                805                 810                 815
Thr Ser Ser Pro Lys Val Thr Ile Asp Cys Ser Ala Phe Val Cys Gly
                820                 825                 830
Asp Cys Ala Ala Cys Lys Ser Gln Leu Val Glu Tyr Gly Ser Phe Cys
                835                 840                 845
Asp Asn Ile Asn Ala Ile Leu Thr Glu Val Asn Glu Leu Leu Asp Thr
                850                 855                 860
Thr Gln Leu Gln Val Ala Asn Ser Leu Met Asn Gly Val Thr Leu Ser
865                 870                 875                 880
Thr Lys Leu Lys Asp Gly Val Asn Phe Asn Val Asp Asp Val Asn Phe
                885                 890                 895
```

-continued

```
Ser Pro Val Leu Gly Cys Leu Gly Ser Glu Cys Asn Lys Val Ser Ser
        900                 905                 910

Arg Ser Ala Ile Glu Asp Leu Leu Phe Ser Lys Val Arg Leu Ser Asp
        915                 920                 925

Val Gly Phe Val Glu Ala Tyr Asn Asn Cys Thr Gly Gly Ala Gly Ile
        930                 935                 940

Arg Asp Leu Ile Cys Val Gln Ser Tyr Asn Gly Ile Lys Val Leu Pro
945                 950                 955                 960

Pro Leu Leu Ser Asp Asn Gln Ile Ser Gly Tyr Thr Leu Ala Ala Thr
                965                 970                 975

Ser Ala Asn Leu Phe Pro Pro Trp Ser Ala Ala Gly Val Pro Phe
                980                 985                 990

Tyr Leu Asn Val Gln Tyr Arg Ile Asn Gly Ile Gly Val Thr Met Asp
                995                 1000                1005

Val Leu Ser Gln Asn Gln Lys Leu Ile Ala Asn Ala Phe Asn Asn
        1010                1015                1020

Ala Leu Asp Ala Ile Gln Glu Gly Phe Asp Ala Thr Asn Ser Ala
        1025                1030                1035

Leu Val Lys Ile Gln Ala Val Val Asn Ala Asp Ala Glu Ala Leu
        1040                1045                1050

Asn Asn Leu Leu Gln Gln Leu Ser Asn Arg Phe Gly Ala Ile Ser
        1055                1060                1065

Ser Ser Leu Gln Glu Ile Leu Ser Arg Leu Asp Ala Leu Glu Ala
        1070                1075                1080

Gln Ala Gln Ile Asp Arg Leu Ile Asn Gly Arg Leu Thr Ala Leu
        1085                1090                1095

Asp Ala Tyr Val Ser Gln Gln Leu Ser Asp Ser Thr Leu Val Lys
        1100                1105                1110

Phe Ser Ala Ala Gln Ala Met Glu Lys Val Asn Glu Cys Val Lys
        1115                1120                1125

Ser Gln Ser Ser Arg Ile Asn Phe Cys Gly Asn Gly Asn His Ile
        1130                1135                1140

Ile Ser Leu Val Gln Asn Ala Pro Tyr Gly Leu Tyr Phe Ile His
        1145                1150                1155

Phe Ser Tyr Val Pro Thr Lys Tyr Val Thr Ala Lys Val Ser Pro
        1160                1165                1170

Gly Leu Cys Ile Ala Gly Asp Arg Gly Ile Ala Pro Lys Ser Gly
        1175                1180                1185

Tyr Phe Val Asn Val Asn Asn Thr Trp Met Phe Thr Gly Ser Arg
        1190                1195                1200

Tyr Tyr Tyr Pro Glu Pro Ile Thr Gly Asn Asn Val Val Val Met
        1205                1210                1215

Ser Thr Cys Ala Val Asn Tyr Thr Lys Ala Pro Asp Val Met Leu
        1220                1225                1230

Asn Ile Ser Thr Pro Asn Leu Pro Asp Phe Lys Glu Glu Leu Asp
        1235                1240                1245

Gln Trp Phe Lys Asn Gln Thr Leu Val Ala Pro Asp Leu Ser Leu
        1250                1255                1260

Asp Tyr Ile Asn Val Thr Phe Leu Asp Leu Gln Asp Glu Met Asn
        1265                1270                1275

Arg Leu Gln Glu Ala Ile Lys Val Leu Asn Gln Ser Tyr Ile Asn
        1280                1285                1290
```

```
Leu Lys Asp Ile Gly Thr Tyr Glu Tyr Tyr Val Lys Trp Pro Trp
    1295                1300                1305

Tyr Val Trp Leu Leu Ile Gly Phe Ala Gly Val Ala Met Leu Val
    1310                1315                1320

Leu Leu Phe Phe Ile Cys Cys Cys Thr Gly Cys Gly Thr Ser Cys
    1325                1330                1335

Phe Lys Lys Cys Gly Gly Cys Cys Asp Asp Tyr Thr Gly His Gln
    1340                1345                1350

Glu Leu Val Ile Lys Thr Ser His Glu Gly
    1355                1360

<210> SEQ ID NO 59
<211> LENGTH: 1383
<212> TYPE: PRT
<213> ORGANISM: Porcine epidemic diarrhea virus

<400> SEQUENCE: 59

Met Arg Ser Leu Ile Tyr Phe Trp Leu Leu Leu Pro Val Leu Pro Thr
1               5                   10                  15

Leu Ser Leu Pro Gln Asp Val Thr Arg Cys Gln Ser Thr Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ser Met Asn Ser Ser Trp Tyr Cys Gly
    50                  55                  60

Thr Gly Ile Glu Thr Ala Ser Gly Val His Gly Ile Phe Leu Ser Tyr
65              70                  75                  80

Ile Asp Ser Gly Gln Gly Phe Glu Ile Gly Ile Ser Gln Glu Pro Phe
                85                  90                  95

Asp Pro Ser Gly Tyr Gln Leu Tyr Leu His Lys Ala Thr Asn Gly Asn
            100                 105                 110

Thr Asn Ala Thr Ala Arg Leu Arg Ile Cys Gln Phe Pro Asp Asn Lys
        115                 120                 125

Thr Leu Gly Pro Thr Val Asn Asp Val Thr Thr Gly Arg Asn Cys Leu
    130                 135                 140

Phe Asn Lys Ala Ile Pro Ala Tyr Met Arg Asp Gly Lys Asp Ile Val
145                 150                 155                 160

Val Gly Ile Thr Trp Asp Asn Asp Arg Val Thr Val Phe Ala Asp Lys
                165                 170                 175

Ile Tyr His Phe Tyr Leu Lys Asn Asp Trp Ser Arg Val Ala Thr Arg
            180                 185                 190

Cys Tyr Asn Arg Arg Ser Cys Ala Met Gln Tyr Val Tyr Thr Pro Thr
        195                 200                 205

Tyr Tyr Met Leu Asn Val Thr Ser Ala Gly Glu Asp Gly Ile Tyr Tyr
    210                 215                 220

Glu Pro Cys Thr Ala Asn Cys Thr Gly Tyr Ala Ala Asn Val Phe Ala
225                 230                 235                 240

Thr Asp Ser Asn Gly His Ile Pro Glu Gly Phe Ser Phe Asn Asn Trp
                245                 250                 255

Phe Leu Leu Ser Asn Asp Ser Thr Leu Leu His Gly Lys Val Val Ser
            260                 265                 270

Asn Gln Pro Leu Leu Val Asn Cys Leu Leu Ala Ile Pro Lys Ile Tyr
        275                 280                 285

Gly Leu Gly Gln Phe Phe Ser Phe Asn His Thr Met Asp Gly Val Cys
    290                 295                 300
```

-continued

```
Asn Gly Ala Ala Val Asp Arg Ala Pro Glu Ala Leu Arg Phe Asn Ile
305                 310                 315                 320

Asn Asp Thr Ser Val Ile Leu Ala Glu Gly Ser Ile Val Leu His Thr
                325                 330                 335

Ala Leu Gly Thr Asn Leu Ser Phe Val Cys Ser Asn Ser Ser Asp Pro
            340                 345                 350

His Leu Ala Ile Phe Ala Ile Pro Leu Gly Ala Thr Glu Val Pro Tyr
            355                 360                 365

Tyr Cys Phe Leu Lys Val Asp Thr Tyr Asn Ser Thr Val Tyr Lys Phe
    370                 375                 380

Leu Ala Val Leu Pro Ser Thr Val Arg Glu Ile Val Ile Thr Lys Tyr
385                 390                 395                 400

Gly Asp Val Tyr Val Asn Gly Phe Gly Tyr Leu His Leu Gly Leu Leu
                405                 410                 415

Asp Ala Val Thr Ile Tyr Phe Thr Gly His Gly Thr Asp Asp Asp Val
            420                 425                 430

Ser Gly Phe Trp Thr Ile Ala Ser Thr Asn Phe Val Asp Ala Leu Ile
            435                 440                 445

Glu Val Gln Gly Thr Ser Ile Gln Arg Ile Leu Tyr Cys Asp Asp Pro
450                 455                 460

Val Ser Gln Leu Lys Cys Ser Gln Val Ala Phe Asp Leu Asp Asp Gly
465                 470                 475                 480

Phe Tyr Pro Ile Ser Ser Arg Asn Leu Leu Ser His Glu Gln Pro Ile
                485                 490                 495

Ser Phe Val Thr Leu Pro Ser Phe Asn Asp His Ser Phe Val Asn Ile
            500                 505                 510

Thr Val Ser Ala Ala Phe Gly Gly Leu Ser Ser Ala Asn Leu Val Ala
            515                 520                 525

Ser Asp Thr Thr Ile Asn Gly Phe Ser Ser Phe Cys Val Asp Thr Arg
            530                 535                 540

Gln Phe Thr Ile Thr Leu Phe Tyr Asn Val Thr Asn Ser Tyr Gly Tyr
545                 550                 555                 560

Val Ser Lys Ser Gln Asp Ser Asn Cys Pro Phe Thr Leu Gln Ser Val
                565                 570                 575

Asn Asp Tyr Leu Ser Phe Ser Lys Phe Cys Val Ser Thr Ser Leu Leu
            580                 585                 590

Ala Gly Ala Cys Thr Ile Asp Leu Phe Gly Tyr Pro Ala Phe Gly Ser
            595                 600                 605

Gly Val Lys Leu Thr Ser Leu Tyr Phe Gln Phe Thr Lys Gly Glu Leu
            610                 615                 620

Ile Thr Gly Thr Pro Lys Pro Leu Glu Gly Ile Thr Asp Val Ser Phe
625                 630                 635                 640

Met Thr Leu Asp Val Cys Thr Lys Tyr Thr Ile Tyr Gly Phe Lys Gly
                645                 650                 655

Glu Gly Ile Ile Thr Leu Thr Asn Ser Ser Ile Leu Ala Gly Val Tyr
            660                 665                 670

Tyr Thr Ser Asp Ser Gly Gln Leu Leu Ala Phe Lys Asn Val Thr Ser
            675                 680                 685

Gly Ala Val Tyr Ser Val Thr Pro Cys Ser Phe Ser Glu Gln Ala Ala
            690                 695                 700

Tyr Val Asn Asp Asp Ile Val Gly Val Ile Ser Ser Leu Ser Asn Ser
705                 710                 715                 720
```

-continued

```
Thr Phe Asn Asn Thr Arg Glu Leu Pro Gly Phe Phe Tyr His Ser Asn
            725                 730                 735

Asp Gly Ser Asn Cys Thr Glu Pro Val Leu Val Tyr Ser Asn Ile Gly
            740                 745                 750

Val Cys Lys Ser Gly Ser Ile Gly Tyr Val Pro Ser Gln Tyr Gly Gln
            755                 760                 765

Val Lys Ile Ala Pro Thr Val Thr Gly Asn Ile Ser Ile Pro Thr Asn
            770                 775                 780

Phe Ser Met Ser Ile Arg Thr Glu Tyr Leu Gln Leu Tyr Asn Thr Pro
785                 790                 795                 800

Val Ser Val Asp Cys Ala Thr Tyr Val Cys Asn Gly Asn Ser Arg Cys
            805                 810                 815

Lys Gln Leu Leu Thr Gln Tyr Thr Ala Ala Cys Lys Thr Ile Glu Ser
            820                 825                 830

Ala Leu Gln Leu Ser Ala Arg Leu Glu Ser Val Glu Val Asn Ser Met
            835                 840                 845

Leu Thr Ile Ser Glu Glu Ala Leu Gln Leu Ala Thr Ile Ser Ser Phe
850                 855                 860

Asn Gly Asp Gly Tyr Asn Phe Thr Asn Val Leu Gly Ala Ser Val Tyr
865                 870                 875                 880

Asp Pro Ala Ser Gly Arg Val Val Gln Lys Arg Ser Val Ile Glu Asp
            885                 890                 895

Leu Leu Phe Asn Lys Val Val Thr Asn Gly Leu Gly Thr Val Asp Glu
            900                 905                 910

Asp Tyr Lys Arg Cys Ser Asn Gly Arg Ser Val Ala Asp Leu Val Cys
            915                 920                 925

Ala Gln Tyr Tyr Ser Gly Val Met Val Leu Pro Gly Val Val Asp Ala
            930                 935                 940

Glu Lys Leu His Met Tyr Ser Ala Ser Leu Ile Gly Gly Met Ala Leu
945                 950                 955                 960

Gly Gly Ile Thr Ala Ala Ala Ala Leu Pro Phe Ser Tyr Ala Val Gln
            965                 970                 975

Ala Arg Leu Asn Tyr Leu Ala Leu Gln Thr Asp Val Leu Gln Arg Asn
            980                 985                 990

Gln Gln Leu Leu Ala Glu Ser Phe Asn Ser Ala Ile Gly Asn Ile Thr
            995                1000                1005

Ser Ala Phe Glu Ser Val Lys Glu Ala Ile Ser Gln Thr Ser Lys
            1010               1015               1020

Gly Leu Asn Thr Val Ala His Ala Leu Thr Lys Val Gln Glu Val
            1025               1030               1035

Val Asn Ser Gln Gly Ser Ala Leu Asn Gln Leu Thr Val Gln Leu
            1040               1045               1050

Gln His Asn Phe Gln Ala Ile Ser Ser Ser Ile Asp Asp Ile Tyr
            1055               1060               1065

Ser Arg Leu Asp Ile Leu Leu Ala Asp Val Gln Val Asp Arg Leu
            1070               1075               1080

Ile Thr Gly Arg Leu Ser Ala Leu Asn Ala Phe Val Ala Gln Thr
            1085               1090               1095

Leu Thr Lys Tyr Thr Glu Val Gln Ala Ser Arg Lys Leu Ala Gln
            1100               1105               1110

Gln Lys Val Asn Glu Cys Val Lys Ser Gln Ser Gln Arg Tyr Gly
            1115               1120               1125

Phe Cys Gly Gly Asp Gly Glu His Ile Phe Ser Leu Val Gln Ala
```

-continued

```
           1130                1135                1140
Ala Pro Gln Gly Leu Leu Phe Leu His Thr Val Leu Val Pro Gly
    1145                1150                1155

Asp Phe Val Asn Val Leu Ala Ile Ala Gly Leu Cys Val Asn Gly
    1160                1165                1170

Glu Ile Ala Leu Thr Leu Arg Glu Pro Gly Leu Val Leu Phe Thr
    1175                1180                1185

His Glu Leu Gln Thr Tyr Thr Ala Thr Glu Tyr Phe Val Ser Ser
    1190                1195                1200

Arg Arg Met Phe Glu Pro Arg Lys Pro Thr Val Ser Asp Phe Val
    1205                1210                1215

Gln Ile Glu Ser Cys Val Val Thr Tyr Val Asn Leu Thr Ser Asp
    1220                1225                1230

Gln Leu Pro Asp Val Ile Pro Asp Tyr Ile Asp Val Asn Lys Thr
    1235                1240                1245

Leu Asp Glu Ile Leu Ala Ser Leu Pro Asn Arg Thr Gly Pro Ser
    1250                1255                1260

Leu Pro Leu Asp Val Phe Asn Ala Thr Tyr Leu Asn Leu Thr Gly
    1265                1270                1275

Glu Ile Ala Asp Leu Glu Gln Arg Ser Glu Ser Leu Arg Asn Thr
    1280                1285                1290

Thr Glu Glu Leu Arg Ser Leu Ile Asn Asn Ile Asn Asn Thr Leu
    1295                1300                1305

Val Asp Leu Glu Trp Leu Asn Arg Val Glu Thr Tyr Ile Lys Trp
    1310                1315                1320

Pro Trp Trp Val Trp Leu Ile Ile Val Ile Val Leu Ile Phe Val
    1325                1330                1335

Val Ser Leu Leu Val Phe Cys Cys Ile Ser Thr Gly Cys Cys Gly
    1340                1345                1350

Cys Cys Gly Cys Cys Gly Ala Cys Phe Ser Gly Cys Cys Arg Gly
    1355                1360                1365

Pro Arg Leu Gln Pro Tyr Glu Ala Phe Glu Lys Val His Val Gln
    1370                1375                1380
```

<210> SEQ ID NO 60
<211> LENGTH: 1349
<212> TYPE: PRT
<213> ORGANISM: porcine hemagglutinating encephalomyelitis virus

<400> SEQUENCE: 60

```
Met Phe Phe Ile Leu Leu Ile Ser Leu Pro Ser Ala Phe Ala Val Ile
1               5                   10                  15

Gly Asp Leu Lys Cys Thr Thr Ser Leu Ile Asn Asp Val Asp Thr Gly
                20                  25                  30

Val Pro Ser Ile Ser Ser Glu Val Val Asp Val Thr Asn Gly Leu Gly
            35                  40                  45

Thr Phe Tyr Val Leu Asp Arg Val Tyr Leu Asn Thr Thr Leu Leu Leu
    50                  55                  60

Asn Gly Tyr Tyr Pro Ile Ser Gly Ala Thr Phe Arg Asn Met Ala Leu
65                  70                  75                  80

Lys Gly Thr Arg Leu Leu Ser Thr Leu Trp Phe Lys Pro Pro Phe Leu
                85                  90                  95

Ser Pro Phe Asn Asp Gly Ile Phe Ala Lys Val Lys Asn Ser Arg Phe
                100                 105                 110
```

```
Ser Lys Asp Gly Val Ile Tyr Ser Glu Phe Pro Ala Ile Thr Ile Gly
        115                 120                 125

Ser Thr Phe Val Asn Thr Ser Tyr Ser Ile Val Val Glu Pro His Thr
        130                 135                 140

Ser Leu Ile Asn Gly Asn Leu Gln Gly Leu Leu Gln Ile Ser Val Cys
145                 150                 155                 160

Gln Tyr Thr Met Cys Glu Tyr Pro His Thr Ile Cys His Pro Asn Leu
                165                 170                 175

Gly Asn Gln Arg Ile Glu Leu Trp His Tyr Asp Thr Asp Val Val Ser
            180                 185                 190

Cys Leu Tyr Arg Arg Asn Phe Thr Tyr Asp Val Asn Ala Asp Tyr Leu
        195                 200                 205

Tyr Phe His Phe Tyr Gln Glu Gly Gly Thr Phe Tyr Ala Tyr Phe Thr
        210                 215                 220

Asp Thr Gly Phe Val Thr Lys Phe Leu Phe Lys Leu Tyr Leu Gly Thr
225                 230                 235                 240

Val Leu Ser His Tyr Tyr Val Met Pro Leu Thr Cys Asn Ser Ala Leu
                245                 250                 255

Ser Leu Glu Tyr Trp Val Thr Pro Leu Thr Thr Arg Gln Phe Leu Leu
            260                 265                 270

Ala Phe Asp Gln Asp Gly Val Leu Tyr His Ala Val Asp Cys Ala Ser
        275                 280                 285

Asp Phe Met Ser Glu Ile Met Cys Lys Thr Ser Ser Ile Thr Pro Pro
        290                 295                 300

Thr Gly Val Tyr Glu Leu Asn Gly Tyr Thr Val Gln Pro Val Ala Thr
305                 310                 315                 320

Val Tyr Arg Arg Ile Pro Asp Leu Pro Asn Cys Asp Ile Glu Ala Trp
                325                 330                 335

Leu Asn Ser Lys Thr Val Ser Ser Pro Leu Asn Trp Glu Arg Lys Ile
            340                 345                 350

Phe Ser Asn Cys Asn Phe Asn Met Gly Arg Leu Met Ser Phe Ile Gln
        355                 360                 365

Ala Asp Ser Phe Gly Cys Asn Ile Asp Ala Ser Arg Leu Tyr Gly
        370                 375                 380

Met Cys Phe Gly Ser Ile Thr Ile Asp Lys Phe Ala Ile Pro Asn Ser
385                 390                 395                 400

Arg Lys Val Asp Leu Gln Val Gly Lys Ser Gly Tyr Leu Gln Ser Phe
                405                 410                 415

Asn Tyr Lys Ile Asp Thr Ala Val Ser Ser Cys Gln Leu Tyr Tyr Ser
            420                 425                 430

Leu Pro Ala Ala Asn Val Ser Val Thr His Tyr Asn Pro Ser Ser Trp
        435                 440                 445

Asn Arg Arg Tyr Gly Phe Asn Asn Gln Ser Phe Gly Ser Arg Gly Leu
450                 455                 460

His Asp Ala Val Tyr Ser Gln Gln Cys Phe Asn Thr Pro Asn Thr Tyr
465                 470                 475                 480

Cys Pro Cys Arg Thr Ser Gln Cys Ile Gly Gly Ala Gly Thr Gly Thr
                485                 490                 495

Cys Pro Val Gly Thr Thr Val Arg Lys Cys Phe Ala Ala Val Thr Lys
            500                 505                 510

Ala Thr Lys Cys Thr Cys Trp Cys Gln Pro Asp Pro Ser Thr Tyr Lys
        515                 520                 525

Gly Val Asn Ala Trp Thr Cys Pro Gln Ser Lys Val Ser Ile Gln Pro
```

-continued

```
            530                 535                 540
Gly Gln His Cys Pro Gly Leu Gly Leu Val Glu Asp Asp Cys Ser Gly
545                 550                 555                 560

Asn Pro Cys Thr Cys Lys Pro Gln Ala Phe Ile Gly Trp Ser Ser Glu
                565                 570                 575

Thr Cys Leu Gln Asn Gly Arg Cys Asn Ile Phe Ala Asn Phe Ile Leu
                580                 585                 590

Asn Asp Val Asn Ser Gly Thr Thr Cys Ser Thr Asp Leu Gln Gln Gly
                595                 600                 605

Asn Thr Ile Ile Thr Thr Asp Val Cys Val Asn Tyr Asp Leu Tyr Gly
610                 615                 620

Ile Thr Gly Gln Gly Ile Leu Ile Glu Val Asn Ala Thr Tyr Tyr Asn
625                 630                 635                 640

Ser Trp Gln Asn Leu Leu Tyr Asp Ser Ser Gly Asn Leu Tyr Gly Phe
                645                 650                 655

Arg Asp Tyr Leu Ser Asn Arg Thr Phe Leu Ile Arg Ser Cys Tyr Ser
                660                 665                 670

Gly Arg Val Ser Ala Val Phe His Ala Asn Ser Ser Glu Pro Ala Leu
                675                 680                 685

Met Phe Arg Asn Leu Lys Cys Ser His Val Phe Asn Asn Thr Ile Leu
                690                 695                 700

Arg Gln Ile Gln Leu Val Asn Tyr Phe Asp Ser Tyr Leu Gly Cys Val
705                 710                 715                 720

Val Asn Ala Tyr Asn Asn Thr Ala Ser Ala Val Ser Thr Cys Asp Leu
                725                 730                 735

Thr Val Gly Ser Gly Tyr Cys Val Asp Tyr Val Thr Ala Leu Arg Ser
                740                 745                 750

Arg Arg Ser Phe Thr Thr Gly Tyr Arg Phe Thr Asn Phe Glu Pro Phe
                755                 760                 765

Ala Ala Asn Leu Val Asn Asp Ser Ile Glu Pro Val Gly Gly Leu Tyr
                770                 775                 780

Glu Ile Gln Ile Pro Ser Glu Phe Thr Ile Gly Asn Leu Glu Glu Phe
785                 790                 795                 800

Ile Gln Thr Arg Ser Pro Lys Val Thr Ile Asp Cys Ala Thr Phe Val
                805                 810                 815

Cys Gly Asp Tyr Ala Ala Cys Arg Gln Gln Leu Ala Glu Tyr Gly Ser
                820                 825                 830

Phe Cys Glu Asn Ile Asn Ala Ile Leu Thr Glu Val Asn Glu Leu Leu
                835                 840                 845

Asp Thr Thr Gln Leu Gln Val Ala Asn Ser Leu Met Asn Gly Val Thr
                850                 855                 860

Leu Ser Thr Lys Ile Lys Asp Gly Ile Asn Phe Asn Val Asp Asp Ile
865                 870                 875                 880

Asn Phe Ser Pro Val Leu Gly Cys Leu Gly Ser Glu Cys Asn Arg Ala
                885                 890                 895

Ser Thr Arg Ser Ala Ile Glu Asp Leu Leu Phe Asp Lys Val Lys Leu
                900                 905                 910

Ser Asp Val Gly Phe Val Gln Ala Tyr Asn Asn Cys Thr Gly Gly Ala
                915                 920                 925

Glu Ile Arg Asp Leu Ile Cys Val Gln Ser Tyr Asn Gly Ile Lys Val
                930                 935                 940

Leu Pro Pro Leu Leu Ser Glu Asn Gln Ile Ser Gly Tyr Thr Leu Ala
945                 950                 955                 960
```

-continued

```
Ala Thr Ala Ala Ser Leu Phe Pro Pro Trp Thr Ala Ala Ala Gly Val
            965                 970                 975

Pro Phe Tyr Leu Asn Val Gln Tyr Arg Ile Asn Gly Leu Gly Val Thr
            980                 985                 990

Met Asp Val Leu Ser Gln Asn Gln Lys Leu Ile Ala Ser Ala Phe Asn
            995                1000                1005

Asn Ala Leu Asp Ala Ile Gln Glu Gly Phe Asp Ala Thr Asn Ser
        1010                1015                1020

Ala Leu Val Lys Ile Gln Ala Val Val Asn Ala Asn Ala Glu Ala
        1025                1030                1035

Leu Asn Asn Leu Leu Gln Gln Leu Ser Asn Arg Phe Gly Ala Ile
        1040                1045                1050

Ser Ala Ser Leu Gln Glu Ile Leu Ser Arg Leu Asp Ala Leu Glu
        1055                1060                1065

Ala Lys Ala Gln Ile Asp Arg Leu Ile Asn Gly Arg Leu Thr Ala
        1070                1075                1080

Leu Asn Ala Tyr Val Ser Gln Gln Leu Ser Asp Ser Thr Leu Val
        1085                1090                1095

Lys Phe Ser Ala Ala Gln Ala Ile Glu Lys Val Asn Glu Cys Val
        1100                1105                1110

Lys Ser Gln Ser Ser Arg Ile Asn Phe Cys Gly Asn Gly Asn His
        1115                1120                1125

Ile Ile Ser Leu Val Gln Asn Ala Pro Tyr Gly Leu Tyr Phe Ile
        1130                1135                1140

His Phe Ser Tyr Val Pro Thr Lys Tyr Val Thr Ala Lys Val Ser
        1145                1150                1155

Pro Gly Leu Cys Ile Ala Gly Asp Ile Gly Ile Ser Pro Lys Ser
        1160                1165                1170

Gly Tyr Phe Ile Asn Val Asn Asn Ser Trp Met Phe Thr Gly Ser
        1175                1180                1185

Ser Tyr Tyr Tyr Pro Glu Pro Ile Thr Gln Asn Asn Val Val Val
        1190                1195                1200

Met Ser Thr Cys Ala Val Asn Tyr Thr Lys Ala Pro Asp Leu Met
        1205                1210                1215

Leu Asn Thr Ser Thr Pro Asn Leu Pro Asp Phe Lys Glu Glu Leu
        1220                1225                1230

Tyr Gln Trp Phe Lys Asn Gln Ser Ser Val Ala Pro Asp Leu Ser
        1235                1240                1245

Leu Asp Tyr Ile Asn Val Thr Phe Leu Asp Leu Gln Asp Glu Met
        1250                1255                1260

Asn Arg Leu Gln Glu Ala Ile Lys Val Leu Asn Gln Ser Tyr Ile
        1265                1270                1275

Asn Leu Lys Asp Ile Gly Thr Tyr Glu Tyr Tyr Val Lys Trp Pro
        1280                1285                1290

Trp Tyr Val Trp Leu Leu Ile Gly Leu Ala Gly Val Ala Met Leu
        1295                1300                1305

Val Leu Leu Phe Phe Ile Cys Cys Cys Thr Gly Cys Gly Thr Ser
        1310                1315                1320

Cys Phe Lys Lys Cys Gly Gly Cys Cys Asp Asp Tyr Thr Gly His
        1325                1330                1335

Gln Glu Phe Val Ile Lys Thr Ser His Asp Asp
        1340                1345
```

<210> SEQ ID NO 61
<211> LENGTH: 1225
<212> TYPE: PRT
<213> ORGANISM: Porcine respiratory coronavirus

<400> SEQUENCE: 61

```
Met Lys Lys Leu Phe Val Val Leu Val Val Met Pro Leu Ile Tyr Gly
1               5                   10                  15

Asp Lys Phe Pro Thr Ser Val Val Ser Asn Cys Thr Asp Gln Cys Ala
            20                  25                  30

Ser Tyr Val Ala Asn Val Phe Thr Thr Gln Pro Gly Gly Phe Ile Pro
        35                  40                  45

Ser Asp Phe Ser Phe Asn Asn Trp Phe Leu Leu Thr Asn Ser Ser Thr
    50                  55                  60

Leu Val Ser Gly Lys Leu Val Thr Lys Gln Pro Leu Leu Val Asn Cys
65                  70                  75                  80

Leu Trp Pro Val Pro Ser Phe Glu Glu Ala Ala Ser Thr Phe Cys Phe
                85                  90                  95

Glu Gly Ala Asp Phe Asp Gln Cys Asn Gly Ala Val Leu Asn Asn Thr
            100                 105                 110

Val Asp Val Ile Arg Phe Asn Leu Asn Phe Thr Thr Asn Val Gln Ser
        115                 120                 125

Gly Lys Gly Ala Thr Val Phe Ser Leu Asn Thr Thr Gly Gly Val Thr
    130                 135                 140

Leu Glu Ile Ser Cys Tyr Asn Asp Thr Val Ser Asp Ser Ser Phe Ser
145                 150                 155                 160

Ser Tyr Gly Glu Ile Pro Phe Gly Val Thr Asn Gly Pro Arg Tyr Cys
                165                 170                 175

Tyr Val Leu Tyr Asn Gly Thr Ala Leu Lys Tyr Leu Gly Thr Leu Pro
            180                 185                 190

Pro Ser Val Lys Glu Ile Ala Ile Ser Lys Trp Gly His Phe Tyr Ile
        195                 200                 205

Asn Gly Tyr Asn Phe Phe Ser Thr Phe Pro Ile Asp Cys Ile Ser Phe
    210                 215                 220

Asn Leu Thr Thr Gly Asp Ser Asp Val Phe Trp Thr Ile Ala Tyr Thr
225                 230                 235                 240

Ser Tyr Thr Glu Ala Leu Val Gln Val Glu Asn Thr Ala Ile Thr Asn
                245                 250                 255

Val Thr Tyr Cys Asn Ser Tyr Val Asn Asn Ile Lys Cys Ser Gln Leu
            260                 265                 270

Thr Ala Asn Leu Asn Asn Gly Phe Tyr Pro Val Ser Ser Ser Glu Val
        275                 280                 285

Gly Ser Val Asn Lys Ser Val Val Leu Leu Pro Ser Phe Leu Thr His
    290                 295                 300

Thr Ile Val Asn Ile Thr Ile Gly Leu Gly Met Lys Arg Ser Gly Tyr
305                 310                 315                 320

Gly Gln Pro Ile Ala Ser Thr Leu Ser Asn Ile Thr Leu Pro Met Gln
                325                 330                 335

Asp Asn Asn Thr Asp Val Tyr Cys Val Arg Ser Asp Gln Phe Ser Val
            340                 345                 350

Tyr Val His Ser Thr Cys Lys Ser Ala Leu Trp Asp Asn Val Phe Lys
        355                 360                 365

Arg Asn Cys Thr Asp Val Leu Asp Ala Thr Ala Val Ile Lys Thr Gly
    370                 375                 380
```

```
Thr Cys Pro Phe Ser Phe Asp Lys Leu Asn Asn Tyr Leu Thr Phe Asn
385                 390                 395                 400

Lys Phe Cys Leu Ser Leu Ser Pro Val Gly Ala Asn Cys Lys Phe Asp
            405                 410                 415

Val Ala Ala Arg Thr Arg Thr Asn Glu Gln Val Val Arg Ser Leu Tyr
                420                 425                 430

Val Ile Tyr Glu Glu Gly Asp Ser Ile Val Gly Val Pro Ser Asp Asn
            435                 440                 445

Ser Gly Leu His Asp Leu Ser Val Leu His Leu Asp Ser Cys Thr Asp
        450                 455                 460

Tyr Asn Ile Tyr Gly Arg Thr Gly Val Gly Ile Ile Arg Gln Thr Asn
465                 470                 475                 480

Arg Thr Leu Leu Ser Gly Leu Tyr Tyr Thr Ser Leu Ser Gly Asp Leu
                485                 490                 495

Leu Gly Phe Lys Asn Val Ser Asp Gly Val Ile Tyr Ser Val Thr Pro
            500                 505                 510

Cys Asp Val Ser Ala Gln Ala Ala Val Ile Asp Gly Thr Ile Val Gly
                515                 520                 525

Ala Ile Thr Ser Ile Asn Ser Glu Leu Leu Gly Leu Thr His Trp Thr
        530                 535                 540

Ile Thr Pro Asn Phe Tyr Tyr Tyr Ser Ile Tyr Asn Tyr Thr Asn Asp
545                 550                 555                 560

Lys Thr Arg Gly Thr Pro Ile Asp Ser Asn Asp Val Gly Cys Glu Pro
                565                 570                 575

Val Ile Thr Tyr Ser Asn Ile Gly Val Cys Lys Asn Gly Ala Leu Val
            580                 585                 590

Phe Ile Asn Val Thr His Ser Asp Gly Asp Val Gln Pro Ile Ser Thr
                595                 600                 605

Gly Asn Val Thr Ile Pro Thr Asn Phe Thr Ile Ser Val Gln Val Glu
        610                 615                 620

Tyr Ile Gln Val Tyr Thr Thr Pro Val Ser Ile Asp Cys Ser Arg Tyr
625                 630                 635                 640

Val Cys Asn Gly Asn Pro Arg Cys Asn Lys Leu Leu Thr Gln Tyr Val
                645                 650                 655

Ser Ala Cys Gln Thr Ile Glu Gln Ala Leu Ala Met Gly Ala Arg Leu
            660                 665                 670

Glu Asn Met Glu Val Asp Ser Met Leu Phe Val Ser Glu Asn Ala Leu
                675                 680                 685

Lys Leu Ala Ser Val Glu Ala Phe Asn Ser Ser Glu Thr Leu Asp Pro
        690                 695                 700

Ile Tyr Thr Gln Trp Pro Asn Ile Gly Gly Phe Trp Leu Glu Gly Leu
705                 710                 715                 720

Lys Tyr Ile Leu Pro Ser Asp Asn Ser Lys Arg Lys Tyr Arg Ser Ala
                725                 730                 735

Ile Glu Asp Leu Leu Phe Ser Lys Val Val Thr Ser Gly Leu Gly Thr
            740                 745                 750

Val Asp Glu Asp Tyr Lys Arg Cys Thr Gly Gly Tyr Asp Ile Ala Asp
                755                 760                 765

Leu Val Cys Ala Gln Tyr Tyr Asn Gly Ile Met Val Leu Pro Gly Val
        770                 775                 780

Ala Asn Ala Asp Lys Met Thr Met Tyr Thr Ala Ser Leu Ala Gly Gly
785                 790                 795                 800
```

-continued

```
Ile Thr Leu Gly Ala Phe Gly Gly Ala Val Ser Ile Pro Phe Ala
            805                 810                 815

Val Ala Val Gln Ala Arg Leu Asn Tyr Val Ala Leu Gln Thr Asp Val
                820                 825                 830

Leu Asn Lys Asn Gln Gln Ile Leu Ala Ser Ala Phe Asn Gln Ala Ile
            835                 840                 845

Gly Asn Ile Thr Gln Ser Phe Gly Lys Val Asn Asp Ala Ile His Gln
            850                 855                 860

Thr Ser Arg Gly Leu Thr Thr Val Ala Lys Ala Leu Ala Lys Val Gln
865                 870                 875                 880

Asp Val Val Asn Thr Gln Gly Gln Ala Leu Arg His Leu Thr Val Gln
                885                 890                 895

Leu Gln Asn Asn Phe Gln Ala Ile Ser Ser Ser Ile Ser Asp Ile Tyr
            900                 905                 910

Asn Arg Leu Asp Glu Leu Ser Ala Asp Ala Gln Val Asp Arg Leu Ile
            915                 920                 925

Thr Gly Arg Leu Thr Ala Leu Asn Ala Phe Val Ser Gln Thr Leu Thr
930                 935                 940

Arg Gln Ala Glu Val Arg Ala Ser Arg Gln Leu Ala Lys Asp Lys Val
945                 950                 955                 960

Asn Glu Cys Val Arg Ser Gln Ser Gln Arg Phe Gly Phe Cys Gly Asn
                965                 970                 975

Gly Thr His Leu Phe Ser Leu Ala Asn Ala Ala Pro Asn Gly Met Ile
            980                 985                 990

Phe Phe His Thr Val Leu Leu Pro Thr Ala Tyr Glu Thr Val Thr Ala
            995                 1000                1005

Trp Ser Gly Ile Cys Ala Leu Asp Gly Asp Arg Thr Phe Gly Leu
            1010                1015                1020

Val Val Lys Asp Val Gln Leu Thr Leu Phe Arg Asn Leu Asp Asp
            1025                1030                1035

Lys Phe Tyr Leu Thr Pro Arg Thr Met Tyr Gln Pro Arg Val Ala
            1040                1045                1050

Thr Ser Ser Asp Phe Val Gln Ile Glu Gly Cys Asp Val Leu Phe
            1055                1060                1065

Val Asn Thr Thr Val Ser Asp Leu Pro Ser Ile Ile Pro Asp Tyr
            1070                1075                1080

Ile Asp Ile Asn Gln Thr Val Gln Asp Ile Leu Glu Asn Phe Arg
            1085                1090                1095

Pro Asn Trp Thr Val Pro Glu Leu Thr Leu Asp Val Phe Asn Ala
            1100                1105                1110

Thr Tyr Leu Asn Leu Thr Gly Glu Ile Asp Asp Leu Glu Phe Arg
            1115                1120                1125

Ser Glu Lys Leu His Asn Thr Thr Val Glu Leu Ala Ile Leu Ile
            1130                1135                1140

Asp Asn Ile Asn Asn Thr Leu Val Asn Leu Glu Trp Leu Asn Arg
            1145                1150                1155

Ile Glu Thr Tyr Val Lys Trp Pro Trp Tyr Val Trp Leu Leu Ile
            1160                1165                1170

Gly Leu Val Val Ile Phe Cys Ile Pro Leu Leu Leu Phe Cys Cys
            1175                1180                1185

Cys Ser Thr Gly Cys Cys Gly Cys Ile Gly Cys Leu Gly Ser Cys
            1190                1195                1200

Cys His Ser Ile Phe Ser Arg Arg Gln Phe Glu Asn Tyr Glu Pro
```

```
        1205                1210                1215
Ile Glu Lys Val His Val His
    1220                1225

<210> SEQ ID NO 62
<211> LENGTH: 82
<212> TYPE: PRT
<213> ORGANISM: Porcine transmissible gastroenteritis coronoavirus

<400> SEQUENCE: 62

Met Thr Phe Pro Arg Ala Leu Thr Val Ile Asp Asp Asn Gly Met Val
1               5                   10                  15

Ile Asn Ile Ile Phe Trp Phe Leu Leu Ile Ile Ile Leu Ile Leu Leu
            20                  25                  30

Ser Ile Ala Leu Leu Asn Ile Lys Leu Cys Met Val Cys Cys Asn
        35                  40                  45

Leu Gly Arg Thr Val Ile Ile Val Pro Ala Gln His Ala Tyr Asp Ala
    50                  55                  60

Tyr Lys Asn Phe Met Arg Ile Lys Ala Tyr Asn Pro Asp Gly Ala Leu
65                  70                  75                  80

Leu Ala

<210> SEQ ID NO 63
<211> LENGTH: 4376
<212> TYPE: PRT
<213> ORGANISM: Severe acute respiratory syndrome virus

<400> SEQUENCE: 63

Met Glu Ser Leu Val Leu Gly Val Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Ala Leu Ser Glu Ala Arg Glu His Leu Lys Asn
        35                  40                  45

Gly Thr Cys Gly Leu Val Glu Leu Glu Lys Gly Val Leu Pro Gln Leu
    50                  55                  60

Glu Gln Pro Tyr Val Phe Ile Lys Arg Ser Asp Ala Leu Ser Thr Asn
65                  70                  75                  80

His Gly His Lys Val Val Glu Leu Val Ala Glu Met Asp Gly Ile Gln
            85                  90                  95

Tyr Gly Arg Ser Gly Ile Thr Leu Gly Val Leu Val Pro His Val Gly
            100                 105                 110

Glu Thr Pro Ile Ala Tyr Arg Asn Val Leu Leu Arg Lys Asn Gly Asn
        115                 120                 125

Lys Gly Ala Gly Gly His Ser Tyr Gly Ile Asp Leu Lys Ser Tyr Asp
    130                 135                 140

Leu Gly Asp Glu Leu Gly Thr Asp Pro Ile Glu Asp Tyr Glu Gln Asn
145                 150                 155                 160

Trp Asn Thr Lys His Gly Ser Gly Ala Leu Arg Glu Leu Thr Arg Glu
                165                 170                 175

Leu Asn Gly Gly Ala Val Thr Arg Tyr Val Asp Asn Asn Phe Cys Gly
            180                 185                 190

Pro Asp Gly Tyr Pro Leu Asp Cys Ile Lys Asp Phe Leu Ala Arg Ala
        195                 200                 205

Gly Lys Ser Met Cys Thr Leu Ser Glu Gln Leu Asp Tyr Ile Glu Ser
    210                 215                 220
```

-continued

```
Lys Arg Gly Val Tyr Cys Cys Arg Asp His Glu His Glu Ile Ala Trp
225                 230                 235                 240

Phe Thr Glu Arg Ser Asp Lys Ser Tyr Glu His Gln Thr Pro Phe Glu
            245                 250                 255

Ile Lys Ser Ala Lys Lys Phe Asp Thr Phe Lys Gly Glu Cys Pro Lys
        260                 265                 270

Phe Val Phe Pro Leu Asn Ser Lys Val Lys Val Ile Gln Pro Arg Val
    275                 280                 285

Glu Lys Lys Lys Thr Glu Gly Phe Met Gly Arg Ile Arg Ser Val Tyr
290                 295                 300

Pro Val Ala Ser Pro Gln Glu Cys Asn Asn Met His Leu Ser Thr Leu
305                 310                 315                 320

Met Lys Cys Asn His Cys Asp Glu Val Ser Trp Gln Thr Cys Asp Phe
            325                 330                 335

Leu Lys Ala Thr Cys Glu His Cys Gly Thr Glu Asn Leu Val Ile Glu
        340                 345                 350

Gly Pro Thr Thr Cys Gly Tyr Leu Pro Thr Asn Ala Val Val Lys Met
    355                 360                 365

Pro Cys Pro Ala Cys Gln Asp Pro Glu Ile Gly Pro Glu His Ser Val
370                 375                 380

Ala Asp Tyr His Asn His Ser Asn Ile Glu Thr Arg Leu Arg Lys Gly
385                 390                 395                 400

Gly Arg Thr Arg Cys Phe Gly Cys Val Phe Ala Tyr Val Gly Cys
            405                 410                 415

Tyr Asn Lys Arg Ala Tyr Trp Val Pro Arg Ala Ser Ala Asp Ile Gly
        420                 425                 430

Ser Gly His Thr Gly Ile Thr Gly Asp Asn Val Glu Thr Leu Asn Glu
    435                 440                 445

Asp Leu Leu Glu Ile Leu Ser Arg Glu Arg Val Asn Ile Asn Ile Val
450                 455                 460

Gly Asp Phe His Leu Asn Glu Glu Val Ala Ile Ile Leu Ala Ser Phe
465                 470                 475                 480

Ser Ala Ser Thr Ser Ala Phe Ile Asp Thr Ile Lys Ser Leu Asp Tyr
            485                 490                 495

Lys Ser Phe Lys Thr Ile Val Glu Ser Cys Gly Asn Tyr Lys Val Thr
        500                 505                 510

Lys Gly Lys Pro Val Lys Gly Ala Trp Asn Ile Gly Gln Gln Arg Ser
    515                 520                 525

Val Leu Thr Pro Leu Cys Gly Phe Pro Ser Gln Ala Ala Gly Val Ile
530                 535                 540

Arg Ser Ile Phe Ala Arg Thr Leu Asp Ala Ala Asn His Ser Ile Pro
545                 550                 555                 560

Asp Leu Gln Arg Ala Ala Val Thr Ile Leu Asp Gly Ile Ser Glu Gln
            565                 570                 575

Ser Leu Arg Leu Val Asp Ala Met Val Tyr Thr Ser Asp Leu Leu Thr
        580                 585                 590

Asn Ser Val Ile Ile Met Ala Tyr Val Thr Gly Gly Leu Val Gln Gln
    595                 600                 605

Thr Ser Gln Trp Leu Ser Asn Leu Leu Gly Thr Thr Val Glu Lys Leu
610                 615                 620

Arg Pro Ile Phe Glu Trp Ile Glu Ala Lys Leu Ser Ala Gly Val Glu
625                 630                 635                 640
```

-continued

```
Phe Leu Lys Asp Ala Trp Glu Ile Leu Lys Phe Leu Ile Thr Gly Val
                645                 650                 655
Phe Asp Ile Val Lys Gly Gln Ile Gln Val Ala Ser Asp Asn Ile Lys
                660                 665                 670
Asp Cys Val Lys Cys Phe Ile Asp Val Val Asn Lys Ala Leu Glu Met
                675                 680                 685
Cys Ile Asp Gln Val Thr Ile Ala Gly Ala Lys Leu Arg Ser Leu Asn
            690                 695                 700
Leu Gly Glu Val Phe Ile Ala Gln Ser Lys Gly Leu Tyr Arg Gln Cys
705                 710                 715                 720
Ile Arg Gly Lys Glu Gln Leu Gln Leu Leu Met Pro Leu Lys Ala Pro
                725                 730                 735
Lys Glu Val Thr Phe Leu Glu Gly Asp Ser His Asp Thr Val Leu Thr
                740                 745                 750
Ser Glu Glu Val Val Leu Lys Asn Gly Glu Leu Glu Ala Leu Glu Thr
            755                 760                 765
Pro Val Asp Ser Phe Thr Asn Gly Ala Ile Val Gly Thr Pro Val Cys
            770                 775                 780
Val Asn Gly Leu Met Leu Leu Glu Ile Lys Asp Lys Glu Gln Tyr Cys
785                 790                 795                 800
Ala Leu Ser Pro Gly Leu Leu Ala Thr Asn Asn Val Phe Arg Leu Lys
                805                 810                 815
Gly Gly Ala Pro Ile Lys Gly Val Thr Phe Gly Glu Asp Thr Val Trp
                820                 825                 830
Glu Val Gln Gly Tyr Lys Asn Val Arg Ile Thr Phe Glu Leu Asp Glu
            835                 840                 845
Arg Val Asp Lys Val Leu Asn Glu Lys Cys Ser Val Tyr Thr Val Glu
        850                 855                 860
Ser Gly Thr Glu Val Thr Glu Phe Ala Cys Val Val Ala Glu Ala Val
865                 870                 875                 880
Val Lys Thr Leu Gln Pro Val Ser Asp Leu Leu Thr Asn Met Gly Ile
                885                 890                 895
Asp Leu Asp Glu Trp Ser Val Ala Thr Phe Tyr Leu Phe Asp Asp Ala
                900                 905                 910
Gly Glu Glu Asn Phe Ser Ser Arg Met Tyr Cys Ser Phe Tyr Pro Pro
            915                 920                 925
Asp Glu Glu Glu Glu Asp Asp Ala Glu Cys Glu Glu Glu Glu Ile Asp
        930                 935                 940
Glu Thr Cys Glu His Glu Tyr Gly Thr Glu Asp Asp Tyr Gln Gly Leu
945                 950                 955                 960
Pro Leu Glu Phe Gly Ala Ser Ala Glu Thr Val Arg Val Glu Glu Glu
                965                 970                 975
Glu Glu Glu Asp Trp Leu Asp Asp Thr Thr Glu Gln Ser Glu Ile Glu
                980                 985                 990
Pro Glu Pro Glu Pro Thr Pro Glu  Glu Pro Val Asn Gln  Phe Thr Gly
            995                 1000                1005
Tyr Leu  Lys Leu Thr Asp Asn  Val Ala Ile Lys Cys  Val Asp Ile
        1010                1015                1020
Val Lys  Glu Ala Gln Ser Ala  Asn Pro Met Val Ile  Val Asn Ala
        1025                1030                1035
Ala Asn  Ile His Leu Lys His  Gly Gly Gly Val Ala  Gly Ala Leu
        1040                1045                1050
Asn Lys  Ala Thr Asn Gly Ala  Met Gln Lys Glu Ser  Asp Asp Tyr
```

```
                1055                1060                1065
Ile Lys Leu Asn Gly Pro Leu Thr Val Gly Gly Ser Cys Leu Leu
    1070                1075                1080

Ser Gly His Asn Leu Ala Lys Lys Cys Leu His Val Val Gly Pro
    1085                1090                1095

Asn Leu Asn Ala Gly Glu Asp Ile Gln Leu Leu Lys Ala Ala Tyr
    1100                1105                1110

Glu Asn Phe Asn Ser Gln Asp Ile Leu Leu Ala Pro Leu Leu Ser
    1115                1120                1125

Ala Gly Ile Phe Gly Ala Lys Pro Leu Gln Ser Leu Gln Val Cys
    1130                1135                1140

Val Gln Thr Val Arg Thr Gln Val Tyr Ile Ala Val Asn Asp Lys
    1145                1150                1155

Ala Leu Tyr Glu Gln Val Val Met Asp Tyr Leu Asp Asn Leu Lys
    1160                1165                1170

Pro Arg Val Glu Ala Pro Lys Gln Glu Pro Pro Asn Thr Glu
    1175                1180                1185

Asp Ser Lys Thr Glu Glu Lys Ser Val Val Gln Lys Pro Val Asp
    1190                1195                1200

Val Lys Pro Lys Ile Lys Ala Cys Ile Asp Glu Val Thr Thr Thr
    1205                1210                1215

Leu Glu Glu Thr Lys Phe Leu Thr Asn Lys Leu Leu Leu Phe Ala
    1220                1225                1230

Asp Ile Asn Gly Lys Leu Tyr His Asp Ser Gln Asn Met Leu Arg
    1235                1240                1245

Gly Glu Asp Met Ser Phe Leu Glu Lys Asp Ala Pro Tyr Met Val
    1250                1255                1260

Gly Asp Val Ile Thr Ser Gly Asp Ile Thr Cys Val Val Ile Pro
    1265                1270                1275

Ser Lys Lys Ala Gly Gly Thr Thr Glu Met Leu Ser Arg Ala Leu
    1280                1285                1290

Lys Lys Val Pro Val Asp Glu Tyr Ile Thr Thr Tyr Pro Gly Gln
    1295                1300                1305

Gly Cys Ala Gly Tyr Thr Leu Glu Glu Ala Lys Thr Ala Leu Lys
    1310                1315                1320

Lys Cys Lys Ser Ala Phe Tyr Val Leu Pro Ser Glu Ala Pro Asn
    1325                1330                1335

Ala Lys Glu Glu Ile Leu Gly Thr Val Ser Trp Asn Leu Arg Glu
    1340                1345                1350

Met Leu Ala His Ala Glu Glu Thr Arg Lys Leu Met Pro Ile Cys
    1355                1360                1365

Met Asp Val Arg Ala Ile Met Ala Thr Ile Gln Arg Lys Tyr Lys
    1370                1375                1380

Gly Ile Lys Ile Gln Glu Gly Ile Val Asp Tyr Gly Val Arg Phe
    1385                1390                1395

Phe Phe Tyr Thr Ser Lys Glu Pro Val Ala Ser Ile Ile Thr Lys
    1400                1405                1410

Leu Asn Ser Leu Asn Glu Pro Leu Val Thr Met Pro Ile Gly Tyr
    1415                1420                1425

Val Thr His Gly Phe Asn Leu Glu Glu Ala Ala Arg Cys Met Arg
    1430                1435                1440

Ser Leu Lys Ala Pro Ala Val Val Ser Val Ser Ser Pro Asp Ala
    1445                1450                1455
```

-continued

```
Val Thr Thr Tyr Asn Gly Tyr Leu Thr Ser Ser Ser Lys Thr Ser
    1460             1465             1470

Glu Glu His Phe Val Glu Thr Val Ser Leu Ala Gly Ser Tyr Arg
    1475             1480             1485

Asp Trp Ser Tyr Ser Gly Gln Arg Thr Glu Leu Gly Val Glu Phe
    1490             1495             1500

Leu Lys Arg Gly Asp Lys Ile Val Tyr His Thr Leu Glu Ser Pro
    1505             1510             1515

Val Glu Phe His Leu Asp Gly Glu Val Leu Ser Leu Asp Lys Leu
    1520             1525             1530

Lys Ser Leu Leu Ser Leu Arg Glu Val Lys Thr Ile Lys Val Phe
    1535             1540             1545

Thr Thr Val Asp Asn Thr Asn Leu His Thr Gln Leu Val Asp Met
    1550             1555             1560

Ser Met Thr Tyr Gly Gln Gln Phe Gly Pro Thr Tyr Leu Asp Gly
    1565             1570             1575

Ala Asp Val Thr Lys Ile Lys Pro His Val Asn His Glu Gly Lys
    1580             1585             1590

Thr Phe Phe Val Leu Pro Ser Asp Asp Thr Leu Arg Ser Glu Ala
    1595             1600             1605

Phe Glu Tyr Tyr His Thr Leu Asp Glu Ser Phe Leu Gly Arg Tyr
    1610             1615             1620

Met Ser Ala Leu Asn His Thr Lys Lys Trp Lys Phe Pro Gln Val
    1625             1630             1635

Gly Gly Leu Thr Ser Ile Lys Trp Ala Asp Asn Asn Cys Tyr Leu
    1640             1645             1650

Ser Ser Val Leu Leu Ala Leu Gln Gln Leu Glu Val Lys Phe Asn
    1655             1660             1665

Ala Pro Ala Leu Gln Glu Ala Tyr Tyr Arg Ala Arg Ala Gly Asp
    1670             1675             1680

Ala Ala Asn Phe Cys Ala Leu Ile Leu Ala Tyr Ser Asn Lys Thr
    1685             1690             1695

Val Gly Glu Leu Gly Asp Val Arg Glu Thr Met Thr His Leu Leu
    1700             1705             1710

Gln His Ala Asn Leu Glu Ser Ala Lys Arg Val Leu Asn Val Val
    1715             1720             1725

Cys Lys His Cys Gly Gln Lys Thr Thr Thr Leu Thr Gly Val Glu
    1730             1735             1740

Ala Val Met Tyr Met Gly Thr Leu Ser Tyr Asp Asn Leu Lys Thr
    1745             1750             1755

Gly Val Ser Ile Pro Cys Val Cys Gly Arg Asp Ala Thr Gln Tyr
    1760             1765             1770

Leu Val Gln Gln Glu Ser Ser Phe Val Met Met Ser Ala Pro Pro
    1775             1780             1785

Ala Glu Tyr Lys Leu Gln Gln Gly Thr Phe Leu Cys Ala Asn Glu
    1790             1795             1800

Tyr Thr Gly Asn Tyr Gln Cys Gly His Tyr Thr His Ile Thr Ala
    1805             1810             1815

Lys Glu Thr Leu Tyr Arg Ile Asp Gly Ala His Leu Thr Lys Met
    1820             1825             1830

Ser Glu Tyr Lys Gly Pro Val Thr Asp Val Phe Tyr Lys Glu Thr
    1835             1840             1845
```

```
Ser Tyr Thr Thr Thr Ile Lys Pro Val Ser Tyr Lys Leu Asp Gly
    1850                1855                1860

Val Thr Tyr Thr Glu Ile Glu Pro Lys Leu Asp Gly Tyr Tyr Lys
    1865                1870                1875

Lys Asp Asn Ala Tyr Tyr Thr Glu Gln Pro Ile Asp Leu Val Pro
    1880                1885                1890

Thr Gln Pro Leu Pro Asn Ala Ser Phe Asp Asn Phe Lys Leu Thr
    1895                1900                1905

Cys Ser Asn Thr Lys Phe Ala Asp Asp Leu Asn Gln Met Thr Gly
    1910                1915                1920

Phe Thr Lys Pro Ala Ser Arg Glu Leu Ser Val Thr Phe Phe Pro
    1925                1930                1935

Asp Leu Asn Gly Asp Val Val Ala Ile Asp Tyr Arg His Tyr Ser
    1940                1945                1950

Ala Ser Phe Lys Lys Gly Ala Lys Leu Leu His Lys Pro Ile Val
    1955                1960                1965

Trp His Ile Asn Gln Ala Thr Thr Lys Thr Thr Phe Lys Pro Asn
    1970                1975                1980

Thr Trp Cys Leu Arg Cys Leu Trp Ser Thr Lys Pro Val Asp Thr
    1985                1990                1995

Ser Asn Ser Phe Glu Val Leu Ala Val Glu Asp Thr Gln Gly Met
    2000                2005                2010

Asp Asn Leu Ala Cys Glu Ser Gln Gln Pro Thr Ser Glu Glu Val
    2015                2020                2025

Val Glu Asn Pro Thr Ile Gln Lys Glu Val Ile Glu Cys Asp Val
    2030                2035                2040

Lys Thr Thr Glu Val Val Gly Asn Val Ile Leu Lys Pro Ser Asp
    2045                2050                2055

Glu Gly Val Lys Val Thr Gln Glu Leu Gly His Glu Asp Leu Met
    2060                2065                2070

Ala Ala Tyr Val Glu Asn Thr Ser Ile Thr Ile Lys Lys Pro Asn
    2075                2080                2085

Glu Leu Ser Leu Ala Leu Gly Leu Lys Thr Ile Ala Thr His Gly
    2090                2095                2100

Ile Ala Ala Ile Asn Ser Val Pro Trp Ser Lys Ile Leu Ala Tyr
    2105                2110                2115

Val Lys Pro Phe Leu Gly Gln Ala Ala Ile Thr Thr Ser Asn Cys
    2120                2125                2130

Ala Lys Arg Leu Ala Gln Arg Val Phe Asn Asn Tyr Met Pro Tyr
    2135                2140                2145

Val Phe Thr Leu Leu Phe Gln Leu Cys Thr Phe Thr Lys Ser Thr
    2150                2155                2160

Asn Ser Arg Ile Arg Ala Ser Leu Pro Thr Thr Ile Ala Lys Asn
    2165                2170                2175

Ser Val Lys Ser Val Ala Lys Leu Cys Leu Asp Ala Gly Ile Asn
    2180                2185                2190

Tyr Val Lys Ser Pro Lys Phe Ser Lys Leu Phe Thr Ile Ala Met
    2195                2200                2205

Trp Leu Leu Leu Leu Ser Ile Cys Leu Gly Ser Leu Ile Cys Val
    2210                2215                2220

Thr Ala Ala Phe Gly Val Leu Leu Ser Asn Phe Gly Ala Pro Ser
    2225                2230                2235

Tyr Cys Asn Gly Val Arg Glu Leu Tyr Leu Asn Ser Ser Asn Val
```

-continued

```
            2240                2245                2250

Thr Thr Met Asp Phe Cys Glu Gly Ser Phe Pro Cys Ser Ile Cys
    2255                2260                2265

Leu Ser Gly Leu Asp Ser Leu Asp Ser Tyr Pro Ala Leu Glu Thr
    2270                2275                2280

Ile Gln Val Thr Ile Ser Ser Tyr Lys Leu Asp Leu Thr Ile Leu
    2285                2290                2295

Gly Leu Ala Ala Glu Trp Val Leu Ala Tyr Met Leu Phe Thr Lys
    2300                2305                2310

Phe Phe Tyr Leu Leu Gly Leu Ser Ala Ile Met Gln Val Phe Phe
    2315                2320                2325

Gly Tyr Phe Ala Ser His Phe Ile Ser Asn Ser Trp Leu Met Trp
    2330                2335                2340

Phe Ile Ile Ser Ile Val Gln Met Ala Pro Val Ser Ala Met Val
    2345                2350                2355

Arg Met Tyr Ile Phe Phe Ala Ser Phe Tyr Tyr Ile Trp Lys Ser
    2360                2365                2370

Tyr Val His Ile Met Asp Gly Cys Thr Ser Ser Thr Cys Met Met
    2375                2380                2385

Cys Tyr Lys Arg Asn Arg Ala Thr Arg Val Glu Cys Thr Thr Ile
    2390                2395                2400

Val Asn Gly Met Lys Arg Ser Phe Tyr Val Tyr Ala Asn Gly Gly
    2405                2410                2415

Arg Gly Phe Cys Lys Thr His Asn Trp Asn Cys Leu Asn Cys Asp
    2420                2425                2430

Thr Phe Cys Thr Gly Ser Thr Phe Ile Ser Asp Glu Val Ala Arg
    2435                2440                2445

Asp Leu Ser Leu Gln Phe Lys Arg Pro Ile Asn Pro Thr Asp Gln
    2450                2455                2460

Ser Ser Tyr Ile Val Asp Ser Val Ala Val Lys Asn Gly Ala Leu
    2465                2470                2475

His Leu Tyr Phe Asp Lys Ala Gly Gln Lys Thr Tyr Glu Arg His
    2480                2485                2490

Pro Leu Ser His Phe Val Asn Leu Asp Asn Leu Arg Ala Asn Asn
    2495                2500                2505

Thr Lys Gly Ser Leu Pro Ile Asn Val Ile Val Phe Asp Gly Lys
    2510                2515                2520

Ser Lys Cys Asp Glu Ser Ala Ser Lys Ser Ala Ser Val Tyr Tyr
    2525                2530                2535

Ser Gln Leu Met Cys Gln Pro Ile Leu Leu Leu Asp Gln Ala Leu
    2540                2545                2550

Val Ser Asp Val Gly Asp Ser Thr Glu Val Ser Val Lys Met Phe
    2555                2560                2565

Asp Ala Tyr Val Asp Thr Phe Ser Ala Thr Phe Ser Val Pro Met
    2570                2575                2580

Glu Lys Leu Lys Ala Leu Val Ala Thr Ala His Ser Glu Leu Ala
    2585                2590                2595

Lys Gly Val Ala Leu Asp Gly Val Leu Ser Thr Phe Val Ser Ala
    2600                2605                2610

Ala Arg Gln Gly Val Val Asp Thr Asp Val Asp Thr Lys Asp Val
    2615                2620                2625

Ile Glu Cys Leu Lys Leu Ser His His Ser Asp Leu Glu Val Thr
    2630                2635                2640
```

-continued

```
Gly Asp Ser Cys Asn Asn Phe Met Leu Thr Tyr Asn Lys Val Glu
    2645                2650                2655
Asn Met Thr Pro Arg Asp Leu Gly Ala Cys Ile Asp Cys Asn Ala
    2660                2665                2670
Arg His Ile Asn Ala Gln Val Ala Lys Ser His Asn Val Ser Leu
    2675                2680                2685
Ile Trp Asn Val Lys Asp Tyr Met Ser Leu Ser Glu Gln Leu Arg
    2690                2695                2700
Lys Gln Ile Arg Ser Ala Ala Lys Lys Asn Asn Ile Pro Phe Arg
    2705                2710                2715
Leu Thr Cys Ala Thr Thr Arg Gln Val Val Asn Val Ile Thr Thr
    2720                2725                2730
Lys Ile Ser Leu Lys Gly Gly Lys Ile Val Ser Thr Cys Phe Lys
    2735                2740                2745
Leu Met Leu Lys Ala Thr Leu Leu Cys Val Leu Ala Ala Leu Val
    2750                2755                2760
Cys Tyr Ile Val Met Pro Val His Thr Leu Ser Ile His Asp Gly
    2765                2770                2775
Tyr Thr Asn Glu Ile Ile Gly Tyr Lys Ala Ile Gln Asp Gly Val
    2780                2785                2790
Thr Arg Asp Ile Ile Ser Thr Asp Asp Cys Phe Ala Asn Lys His
    2795                2800                2805
Ala Gly Phe Asp Ala Trp Phe Ser Gln Arg Gly Gly Ser Tyr Lys
    2810                2815                2820
Asn Asp Lys Ser Cys Pro Val Val Ala Ala Ile Ile Thr Arg Glu
    2825                2830                2835
Ile Gly Phe Ile Val Pro Gly Leu Pro Gly Thr Val Leu Arg Ala
    2840                2845                2850
Ile Asn Gly Asp Phe Leu His Phe Leu Pro Arg Val Phe Ser Ala
    2855                2860                2865
Val Gly Asn Ile Cys Tyr Thr Pro Ser Lys Leu Ile Glu Tyr Ser
    2870                2875                2880
Asp Phe Ala Thr Ser Ala Cys Val Leu Ala Ala Glu Cys Thr Ile
    2885                2890                2895
Phe Lys Asp Ala Met Gly Lys Pro Val Pro Tyr Cys Tyr Asp Thr
    2900                2905                2910
Asn Leu Leu Glu Gly Ser Ile Ser Tyr Ser Glu Leu Arg Pro Asp
    2915                2920                2925
Thr Arg Tyr Val Leu Met Asp Gly Ser Ile Ile Gln Phe Pro Asn
    2930                2935                2940
Thr Tyr Leu Glu Gly Ser Val Arg Val Val Thr Thr Phe Asp Ala
    2945                2950                2955
Glu Tyr Cys Arg His Gly Thr Cys Glu Arg Ser Glu Val Gly Ile
    2960                2965                2970
Cys Leu Ser Thr Ser Gly Arg Trp Val Leu Asn Asn Glu His Tyr
    2975                2980                2985
Arg Ala Leu Ser Gly Val Phe Cys Gly Val Asp Ala Met Asn Leu
    2990                2995                3000
Ile Ala Asn Ile Phe Thr Pro Leu Val Gln Pro Val Gly Ala Leu
    3005                3010                3015
Asp Val Ser Ala Ser Val Val Ala Gly Gly Ile Ile Ala Ile Leu
    3020                3025                3030
```

-continued

```
Val Thr Cys Ala Ala Tyr Tyr Phe Met Lys Phe Arg Arg Val Phe
3035                3040                3045

Gly Glu Tyr Asn His Val Val Ala Ala Asn Ala Leu Leu Phe Leu
3050                3055                3060

Met Ser Phe Thr Ile Leu Cys Leu Val Pro Ala Tyr Ser Phe Leu
3065                3070                3075

Pro Gly Val Tyr Ser Val Phe Tyr Leu Tyr Leu Thr Phe Tyr Phe
3080                3085                3090

Thr Asn Asp Val Ser Phe Leu Ala His Leu Gln Trp Phe Ala Met
3095                3100                3105

Phe Ser Pro Ile Val Pro Phe Trp Ile Thr Ala Ile Tyr Val Phe
3110                3115                3120

Cys Ile Ser Leu Lys His Cys His Trp Phe Phe Asn Asn Tyr Leu
3125                3130                3135

Arg Lys Arg Val Met Phe Asn Gly Val Thr Phe Ser Thr Phe Glu
3140                3145                3150

Glu Ala Ala Leu Cys Thr Phe Leu Leu Asn Lys Glu Met Tyr Leu
3155                3160                3165

Lys Leu Arg Ser Glu Thr Leu Leu Pro Leu Thr Gln Tyr Asn Arg
3170                3175                3180

Tyr Leu Ala Leu Tyr Asn Lys Tyr Lys Tyr Phe Ser Gly Ala Leu
3185                3190                3195

Asp Thr Thr Ser Tyr Arg Glu Ala Ala Cys Cys His Leu Ala Lys
3200                3205                3210

Ala Leu Asn Asp Phe Ser Asn Ser Gly Ala Asp Val Leu Tyr Gln
3215                3220                3225

Pro Pro Gln Thr Ser Ile Thr Ser Ala Val Leu Gln Ser Gly Phe
3230                3235                3240

Arg Lys Met Ala Phe Pro Ser Gly Lys Val Glu Gly Cys Met Val
3245                3250                3255

Gln Val Thr Cys Gly Thr Thr Thr Leu Asn Gly Leu Trp Leu Asp
3260                3265                3270

Asp Thr Val Tyr Cys Pro Arg His Val Ile Cys Thr Ala Glu Asp
3275                3280                3285

Met Leu Asn Pro Asn Tyr Glu Asp Leu Leu Ile Arg Lys Ser Asn
3290                3295                3300

His Ser Phe Leu Val Gln Ala Gly Asn Val Gln Leu Arg Val Ile
3305                3310                3315

Gly His Ser Met Gln Asn Cys Leu Leu Arg Leu Lys Val Asp Thr
3320                3325                3330

Ser Asn Pro Lys Thr Pro Lys Tyr Lys Phe Val Arg Ile Gln Pro
3335                3340                3345

Gly Gln Thr Phe Ser Val Leu Ala Cys Tyr Asn Gly Ser Pro Ser
3350                3355                3360

Gly Val Tyr Gln Cys Ala Met Arg Pro Asn His Thr Ile Lys Gly
3365                3370                3375

Ser Phe Leu Asn Gly Ser Cys Gly Ser Val Gly Phe Asn Ile Asp
3380                3385                3390

Tyr Asp Cys Val Ser Phe Cys Tyr Met His His Met Glu Leu Pro
3395                3400                3405

Thr Gly Val His Ala Gly Thr Asp Leu Glu Gly Lys Phe Tyr Gly
3410                3415                3420

Pro Phe Val Asp Arg Gln Thr Ala Gln Ala Ala Gly Thr Asp Thr
```

```
                3425                3430                3435

Thr Ile Thr Leu Asn Val Leu Ala Trp Leu Tyr Ala Ala Val Ile
        3440                3445                3450

Asn Gly Asp Arg Trp Phe Leu Asn Arg Phe Thr Thr Thr Leu Asn
        3455                3460                3465

Asp Phe Asn Leu Val Ala Met Lys Tyr Asn Tyr Glu Pro Leu Thr
        3470                3475                3480

Gln Asp His Val Asp Ile Leu Gly Pro Leu Ser Ala Gln Thr Gly
        3485                3490                3495

Ile Ala Val Leu Asp Met Cys Ala Ala Leu Lys Glu Leu Leu Gln
        3500                3505                3510

Asn Gly Met Asn Gly Arg Thr Ile Leu Gly Ser Thr Ile Leu Glu
        3515                3520                3525

Asp Glu Phe Thr Pro Phe Asp Val Val Arg Gln Cys Ser Gly Val
        3530                3535                3540

Thr Phe Gln Gly Lys Phe Lys Lys Ile Val Lys Gly Thr His His
        3545                3550                3555

Trp Met Leu Leu Thr Phe Leu Thr Ser Leu Leu Ile Leu Val Gln
        3560                3565                3570

Ser Thr Gln Trp Ser Leu Phe Phe Phe Val Tyr Glu Asn Ala Phe
        3575                3580                3585

Leu Pro Phe Thr Leu Gly Ile Met Ala Ile Ala Ala Cys Ala Met
        3590                3595                3600

Leu Leu Val Lys His Lys His Ala Phe Leu Cys Leu Phe Leu Leu
        3605                3610                3615

Pro Ser Leu Ala Thr Val Ala Tyr Phe Asn Met Val Tyr Met Pro
        3620                3625                3630

Ala Ser Trp Val Met Arg Ile Met Thr Trp Leu Glu Leu Ala Asp
        3635                3640                3645

Thr Ser Leu Ser Gly Tyr Arg Leu Lys Asp Cys Val Met Tyr Ala
        3650                3655                3660

Ser Ala Leu Val Leu Leu Ile Leu Met Thr Ala Arg Thr Val Tyr
        3665                3670                3675

Asp Asp Ala Ala Arg Arg Val Trp Thr Leu Met Asn Val Ile Thr
        3680                3685                3690

Leu Val Tyr Lys Val Tyr Tyr Gly Asn Ala Leu Asp Gln Ala Ile
        3695                3700                3705

Ser Met Trp Ala Leu Val Ile Ser Val Thr Ser Asn Tyr Ser Gly
        3710                3715                3720

Val Val Thr Thr Ile Met Phe Leu Ala Arg Ala Ile Val Phe Val
        3725                3730                3735

Cys Val Glu Tyr Tyr Pro Leu Leu Phe Ile Thr Gly Asn Thr Leu
        3740                3745                3750

Gln Cys Ile Met Leu Val Tyr Cys Phe Leu Gly Tyr Cys Cys Cys
        3755                3760                3765

Cys Tyr Phe Gly Leu Phe Cys Leu Leu Asn Arg Tyr Phe Arg Leu
        3770                3775                3780

Thr Leu Gly Val Tyr Asp Tyr Leu Val Ser Thr Gln Glu Phe Arg
        3785                3790                3795

Tyr Met Asn Ser Gln Gly Leu Leu Pro Pro Lys Ser Ser Ile Asp
        3800                3805                3810

Ala Phe Lys Leu Asn Ile Lys Leu Leu Gly Ile Gly Gly Lys Pro
        3815                3820                3825
```

-continued

```
Cys Ile Lys Val Ala Thr Val Gln Ser Lys Met Ser Asp Val Lys
    3830                3835                3840

Cys Thr Ser Val Val Leu Leu Ser Val Leu Gln Gln Leu Arg Val
    3845                3850                3855

Glu Ser Ser Ser Lys Leu Trp Ala Gln Cys Val Gln Leu His Asn
    3860                3865                3870

Asp Ile Leu Leu Ala Lys Asp Thr Thr Glu Ala Phe Glu Lys Met
    3875                3880                3885

Val Ser Leu Leu Ser Val Leu Leu Ser Met Gln Gly Ala Val Asp
    3890                3895                3900

Ile Asn Arg Leu Cys Glu Glu Met Leu Asp Asn Arg Ala Thr Leu
    3905                3910                3915

Gln Ala Ile Ala Ser Glu Phe Ser Ser Leu Pro Ser Tyr Ala Ala
    3920                3925                3930

Tyr Ala Thr Ala Gln Glu Ala Tyr Glu Gln Ala Val Ala Asn Gly
    3935                3940                3945

Asp Ser Glu Val Val Leu Lys Lys Leu Lys Lys Ser Leu Asn Val
    3950                3955                3960

Ala Lys Ser Glu Phe Asp Arg Asp Ala Ala Met Gln Arg Lys Leu
    3965                3970                3975

Glu Lys Met Ala Asp Gln Ala Met Thr Gln Met Tyr Lys Gln Ala
    3980                3985                3990

Arg Ser Glu Asp Lys Arg Ala Lys Val Thr Ser Ala Met Gln Thr
    3995                4000                4005

Met Leu Phe Thr Met Leu Arg Lys Leu Asp Asn Asp Ala Leu Asn
    4010                4015                4020

Asn Ile Ile Asn Asn Ala Arg Asp Gly Cys Val Pro Leu Asn Ile
    4025                4030                4035

Ile Pro Leu Thr Thr Ala Ala Lys Leu Met Val Val Val Pro Asp
    4040                4045                4050

Tyr Gly Thr Tyr Lys Asn Thr Cys Asp Gly Asn Thr Phe Thr Tyr
    4055                4060                4065

Ala Ser Ala Leu Trp Glu Ile Gln Gln Val Val Asp Ala Asp Ser
    4070                4075                4080

Lys Ile Val Gln Leu Ser Glu Ile Asn Met Asp Asn Ser Pro Asn
    4085                4090                4095

Leu Ala Trp Pro Leu Ile Val Thr Ala Leu Arg Ala Asn Ser Ala
    4100                4105                4110

Val Lys Leu Gln Asn Asn Glu Leu Ser Pro Val Ala Leu Arg Gln
    4115                4120                4125

Met Ser Cys Ala Ala Gly Thr Thr Gln Thr Ala Cys Thr Asp Asp
    4130                4135                4140

Asn Ala Leu Ala Tyr Tyr Asn Asn Ser Lys Gly Gly Arg Phe Val
    4145                4150                4155

Leu Ala Leu Leu Ser Asp His Gln Asp Leu Lys Trp Ala Arg Phe
    4160                4165                4170

Pro Lys Ser Asp Gly Thr Gly Thr Ile Tyr Thr Glu Leu Glu Pro
    4175                4180                4185

Pro Cys Arg Phe Val Thr Asp Thr Pro Lys Gly Pro Lys Val Lys
    4190                4195                4200

Tyr Leu Tyr Phe Ile Lys Gly Leu Asn Asn Leu Asn Arg Gly Met
    4205                4210                4215
```

-continued

Val Leu Gly Ser Leu Ala Ala Thr Val Arg Leu Gln Ala Gly Asn
    4220                4225                4230

Ala Thr Glu Val Pro Ala Asn Ser Thr Val Leu Ser Phe Cys Ala
    4235                4240                4245

Phe Ala Val Asp Pro Ala Lys Ala Tyr Lys Asp Tyr Leu Ala Ser
    4250                4255                4260

Gly Gly Gln Pro Ile Thr Asn Cys Val Lys Met Leu Cys Thr His
    4265                4270                4275

Thr Gly Thr Gly Gln Ala Ile Thr Val Thr Pro Glu Ala Asn Met
    4280                4285                4290

Asp Gln Glu Ser Phe Gly Gly Ala Ser Cys Cys Leu Tyr Cys Arg
    4295                4300                4305

Cys His Ile Asp His Pro Asn Pro Lys Gly Phe Cys Asp Leu Lys
    4310                4315                4320

Gly Lys Tyr Val Gln Ile Pro Thr Thr Cys Ala Asn Asp Pro Val
    4325                4330                4335

Gly Phe Thr Leu Arg Asn Thr Val Cys Thr Val Cys Gly Met Trp
    4340                4345                4350

Lys Gly Tyr Gly Cys Ser Cys Asp Gln Leu Arg Glu Pro Leu Met
    4355                4360                4365

Gln Ser Ala Asp Ala Ser Thr Phe
    4370                4375

<210> SEQ ID NO 64
<211> LENGTH: 2697
<212> TYPE: PRT
<213> ORGANISM: Severe acute respiratory syndrome virus

<400> SEQUENCE: 64

Phe Lys Arg Val Cys Gly Val Ser Ala Ala Arg Leu Thr Pro Cys Gly
1               5                   10                  15

Thr Gly Thr Ser Thr Asp Val Val Tyr Arg Ala Phe Asp Ile Tyr Asn
                20                  25                  30

Glu Lys Val Ala Gly Phe Ala Lys Phe Leu Lys Thr Asn Cys Cys Arg
            35                  40                  45

Phe Gln Glu Lys Asp Glu Glu Gly Asn Leu Leu Asp Ser Tyr Phe Val
        50                  55                  60

Val Lys Arg His Thr Met Ser Asn Tyr Gln His Glu Glu Thr Ile Tyr
65                  70                  75                  80

Asn Leu Val Lys Asp Cys Pro Ala Val Ala Val His Asp Phe Phe Lys
                85                  90                  95

Phe Arg Val Asp Gly Asp Met Val Pro His Ile Ser Arg Gln Arg Leu
            100                 105                 110

Thr Lys Tyr Thr Met Ala Asp Leu Val Tyr Ala Leu Arg His Phe Asp
        115                 120                 125

Glu Gly Asn Cys Asp Thr Leu Lys Glu Ile Leu Val Thr Tyr Asn Cys
    130                 135                 140

Cys Asp Asp Asp Tyr Phe Asn Lys Lys Asp Trp Tyr Asp Phe Val Glu
145                 150                 155                 160

Asn Pro Asp Ile Leu Arg Val Tyr Ala Asn Leu Gly Glu Arg Val Arg
                165                 170                 175

Gln Ser Leu Leu Lys Thr Val Gln Phe Cys Asp Ala Met Arg Asp Ala
            180                 185                 190

Gly Ile Val Gly Val Leu Thr Leu Asp Asn Gln Asp Leu Asn Gly Asn
        195                 200                 205

```
Trp Tyr Asp Phe Gly Asp Phe Val Gln Val Ala Pro Gly Cys Gly Val
210                 215                 220

Pro Ile Val Asp Ser Tyr Tyr Ser Leu Leu Met Pro Ile Leu Thr Leu
225                 230                 235                 240

Thr Arg Ala Leu Ala Ala Glu Ser His Met Asp Ala Asp Leu Ala Lys
            245                 250                 255

Pro Leu Ile Lys Trp Asp Leu Leu Lys Tyr Asp Phe Thr Glu Glu Arg
            260                 265                 270

Leu Cys Leu Phe Asp Arg Tyr Phe Lys Tyr Trp Asp Gln Thr Tyr His
            275                 280                 285

Pro Asn Cys Ile Asn Cys Leu Asp Asp Arg Cys Ile Leu His Cys Ala
290                 295                 300

Asn Phe Asn Val Leu Phe Ser Thr Val Phe Pro Thr Ser Phe Gly
305                 310                 315                 320

Pro Leu Val Arg Lys Ile Phe Val Asp Gly Val Pro Phe Val Val Ser
            325                 330                 335

Thr Gly Tyr His Phe Arg Glu Leu Gly Val Val His Asn Gln Asp Val
            340                 345                 350

Asn Leu His Ser Ser Arg Leu Ser Phe Lys Glu Leu Leu Val Tyr Ala
            355                 360                 365

Ala Asp Pro Ala Met His Ala Ala Ser Gly Asn Leu Leu Leu Asp Lys
370                 375                 380

Arg Thr Thr Cys Phe Ser Val Ala Ala Leu Thr Asn Asn Val Ala Phe
385                 390                 395                 400

Gln Thr Val Lys Pro Gly Asn Phe Asn Lys Asp Phe Tyr Asp Phe Ala
            405                 410                 415

Val Ser Lys Gly Phe Phe Lys Glu Gly Ser Ser Val Glu Leu Lys His
            420                 425                 430

Phe Phe Phe Ala Gln Asp Gly Asn Ala Ala Ile Ser Asp Tyr Asp Tyr
            435                 440                 445

Tyr Arg Tyr Asn Leu Pro Thr Met Cys Asp Ile Arg Gln Leu Leu Phe
450                 455                 460

Val Val Glu Val Val Asp Lys Tyr Phe Asp Cys Tyr Asp Gly Gly Cys
465                 470                 475                 480

Ile Asn Ala Asn Gln Val Ile Val Asn Asn Leu Asp Lys Ser Ala Gly
            485                 490                 495

Phe Pro Phe Asn Lys Trp Gly Lys Ala Arg Leu Tyr Tyr Asp Ser Met
            500                 505                 510

Ser Tyr Glu Asp Gln Asp Ala Leu Phe Ala Tyr Thr Lys Arg Asn Val
            515                 520                 525

Ile Pro Thr Ile Thr Gln Met Asn Leu Lys Tyr Ala Ile Ser Ala Lys
            530                 535                 540

Asn Arg Ala Arg Thr Val Ala Gly Val Ser Ile Cys Ser Thr Met Thr
545                 550                 555                 560

Asn Arg Gln Phe His Gln Lys Leu Leu Lys Ser Ile Ala Ala Thr Arg
            565                 570                 575

Gly Ala Thr Val Val Ile Gly Thr Ser Lys Phe Tyr Gly Gly Trp His
            580                 585                 590

Asn Met Leu Lys Thr Val Tyr Ser Asp Val Glu Thr Pro His Leu Met
            595                 600                 605

Gly Trp Asp Tyr Pro Lys Cys Asp Arg Ala Met Pro Asn Met Leu Arg
610                 615                 620
```

-continued

```
Ile Met Ala Ser Leu Val Leu Ala Arg Lys His Asn Thr Cys Cys Asn
625                 630                 635                 640

Leu Ser His Arg Phe Tyr Arg Leu Ala Asn Glu Cys Ala Gln Val Leu
                645                 650                 655

Ser Glu Met Val Met Cys Gly Gly Ser Leu Tyr Val Lys Pro Gly Gly
            660                 665                 670

Thr Ser Ser Gly Asp Ala Thr Thr Ala Tyr Ala Asn Ser Val Phe Asn
        675                 680                 685

Ile Cys Gln Ala Val Thr Ala Asn Val Asn Ala Leu Leu Ser Thr Asp
    690                 695                 700

Gly Asn Lys Ile Ala Asp Lys Tyr Val Arg Asn Leu Gln His Arg Leu
705                 710                 715                 720

Tyr Glu Cys Leu Tyr Arg Asn Arg Asp Val Asp His Glu Phe Val Asp
                725                 730                 735

Glu Phe Tyr Ala Tyr Leu Arg Lys His Phe Ser Met Met Ile Leu Ser
            740                 745                 750

Asp Asp Ala Val Val Cys Tyr Asn Ser Asn Tyr Ala Ala Gln Gly Leu
        755                 760                 765

Val Ala Ser Ile Lys Asn Phe Lys Ala Val Leu Tyr Tyr Gln Asn Asn
    770                 775                 780

Val Phe Met Ser Glu Ala Lys Cys Trp Thr Glu Thr Asp Leu Thr Lys
785                 790                 795                 800

Gly Pro His Glu Phe Cys Ser Gln His Thr Met Leu Val Lys Gln Gly
                805                 810                 815

Asp Asp Tyr Val Tyr Leu Pro Tyr Pro Asp Pro Ser Arg Ile Leu Gly
            820                 825                 830

Ala Gly Cys Phe Val Asp Asp Ile Val Lys Thr Asp Gly Thr Leu Met
        835                 840                 845

Ile Glu Arg Phe Val Ser Leu Ala Ile Asp Ala Tyr Pro Leu Thr Lys
    850                 855                 860

His Pro Asn Gln Glu Tyr Ala Asp Val Phe His Leu Tyr Leu Gln Tyr
865                 870                 875                 880

Ile Arg Lys Leu His Asp Glu Leu Thr Gly His Met Leu Asp Met Tyr
                885                 890                 895

Ser Val Met Leu Thr Asn Asp Asn Thr Ser Arg Tyr Trp Glu Pro Glu
            900                 905                 910

Phe Tyr Glu Ala Met Tyr Thr Pro His Thr Val Leu Gln Ala Val Gly
        915                 920                 925

Ala Cys Val Leu Cys Asn Ser Gln Thr Ser Leu Arg Cys Gly Ala Cys
    930                 935                 940

Ile Arg Arg Pro Phe Leu Cys Cys Lys Cys Cys Tyr Asp His Val Ile
945                 950                 955                 960

Ser Thr Ser His Lys Leu Val Leu Ser Val Asn Pro Tyr Val Cys Asn
                965                 970                 975

Ala Pro Gly Cys Asp Val Thr Asp Val Thr Gln Leu Tyr Leu Gly Gly
            980                 985                 990

Met Ser Tyr Tyr Cys Lys Ser His Lys Pro Pro Ile Ser Phe Pro Leu
        995                 1000                1005

Cys Ala Asn Gly Gln Val Phe Gly Leu Tyr Lys Asn Thr Cys Val
        1010                1015                1020

Gly Ser Asp Asn Val Thr Asp Phe Asn Ala Ile Ala Thr Cys Asp
        1025                1030                1035

Trp Thr Asn Ala Gly Asp Tyr Ile Leu Ala Asn Thr Cys Thr Glu
```

-continued

```
             1040                1045                1050
    Arg  Leu  Lys  Leu  Phe  Ala  Ala  Glu  Thr  Leu  Lys  Ala  Thr  Glu  Glu
             1055                1060                1065

Thr  Phe  Lys  Leu  Ser  Tyr  Gly  Ile  Ala  Thr  Val  Arg  Glu  Val  Leu
             1070                1075                1080

Ser  Asp  Arg  Glu  Leu  His  Leu  Ser  Trp  Glu  Val  Gly  Lys  Pro  Arg
             1085                1090                1095

Pro  Pro  Leu  Asn  Arg  Asn  Tyr  Val  Phe  Thr  Gly  Tyr  Arg  Val  Thr
             1100                1105                1110

Lys  Asn  Ser  Lys  Val  Gln  Ile  Gly  Glu  Tyr  Thr  Phe  Glu  Lys  Gly
             1115                1120                1125

Asp  Tyr  Gly  Asp  Ala  Val  Val  Tyr  Arg  Gly  Thr  Thr  Thr  Tyr  Lys
             1130                1135                1140

Leu  Asn  Val  Gly  Asp  Tyr  Phe  Val  Leu  Thr  Ser  His  Thr  Val  Met
             1145                1150                1155

Pro  Leu  Ser  Ala  Pro  Thr  Leu  Val  Pro  Gln  Glu  His  Tyr  Val  Arg
             1160                1165                1170

Ile  Thr  Gly  Leu  Tyr  Pro  Thr  Leu  Asn  Ile  Ser  Asp  Glu  Phe  Ser
             1175                1180                1185

Ser  Asn  Val  Ala  Asn  Tyr  Gln  Lys  Val  Gly  Met  Gln  Lys  Tyr  Ser
             1190                1195                1200

Thr  Leu  Gln  Gly  Pro  Pro  Gly  Thr  Gly  Lys  Ser  His  Phe  Ala  Ile
             1205                1210                1215

Gly  Leu  Ala  Leu  Tyr  Tyr  Pro  Ser  Ala  Arg  Ile  Val  Tyr  Thr  Ala
             1220                1225                1230

Cys  Ser  His  Ala  Ala  Val  Asp  Ala  Leu  Cys  Glu  Lys  Ala  Leu  Lys
             1235                1240                1245

Tyr  Leu  Pro  Ile  Asp  Lys  Cys  Ser  Arg  Ile  Ile  Pro  Ala  Arg  Ala
             1250                1255                1260

Arg  Val  Glu  Cys  Phe  Asp  Lys  Phe  Lys  Val  Asn  Ser  Thr  Leu  Glu
             1265                1270                1275

Gln  Tyr  Val  Phe  Cys  Thr  Val  Asn  Ala  Leu  Pro  Glu  Thr  Thr  Ala
             1280                1285                1290

Asp  Ile  Val  Val  Phe  Asp  Glu  Ile  Ser  Met  Ala  Thr  Asn  Tyr  Asp
             1295                1300                1305

Leu  Ser  Val  Val  Asn  Ala  Arg  Leu  Arg  Ala  Lys  His  Tyr  Val  Tyr
             1310                1315                1320

Ile  Gly  Asp  Pro  Ala  Gln  Leu  Pro  Ala  Pro  Arg  Thr  Leu  Leu  Thr
             1325                1330                1335

Lys  Gly  Thr  Leu  Glu  Pro  Glu  Tyr  Phe  Asn  Ser  Val  Cys  Arg  Leu
             1340                1345                1350

Met  Lys  Thr  Ile  Gly  Pro  Asp  Met  Phe  Leu  Gly  Thr  Cys  Arg  Arg
             1355                1360                1365

Cys  Pro  Ala  Glu  Ile  Val  Asp  Thr  Val  Ser  Ala  Leu  Val  Tyr  Asp
             1370                1375                1380

Asn  Lys  Leu  Lys  Ala  His  Lys  Asp  Lys  Ser  Ala  Gln  Cys  Phe  Lys
             1385                1390                1395

Met  Phe  Tyr  Lys  Gly  Val  Ile  Thr  His  Asp  Val  Ser  Ser  Ala  Ile
             1400                1405                1410

Asn  Arg  Pro  Gln  Ile  Gly  Val  Val  Arg  Glu  Phe  Leu  Thr  Arg  Asn
             1415                1420                1425

Pro  Ala  Trp  Arg  Lys  Ala  Val  Phe  Ile  Ser  Pro  Tyr  Asn  Ser  Gln
             1430                1435                1440
```

-continued

```
Asn Ala Val Ala Ser Lys Ile Leu Gly Leu Pro Thr Gln Thr Val
    1445                1450                1455
Asp Ser Ser Gln Gly Ser Glu Tyr Asp Tyr Val Ile Phe Thr Gln
    1460                1465                1470
Thr Thr Glu Thr Ala His Ser Cys Asn Val Asn Arg Phe Asn Val
    1475                1480                1485
Ala Ile Thr Arg Ala Lys Ile Gly Ile Leu Cys Ile Met Ser Asp
    1490                1495                1500
Arg Asp Leu Tyr Asp Lys Leu Gln Phe Thr Ser Leu Glu Ile Pro
    1505                1510                1515
Arg Arg Asn Val Ala Thr Leu Gln Ala Glu Asn Val Thr Gly Leu
    1520                1525                1530
Phe Lys Asp Cys Ser Lys Ile Ile Thr Gly Leu His Pro Thr Gln
    1535                1540                1545
Ala Pro Thr His Leu Ser Val Asp Ile Lys Phe Lys Thr Glu Gly
    1550                1555                1560
Leu Cys Val Asp Ile Pro Gly Ile Pro Lys Asp Met Thr Tyr Arg
    1565                1570                1575
Arg Leu Ile Ser Met Met Gly Phe Lys Met Asn Tyr Gln Val Asn
    1580                1585                1590
Gly Tyr Pro Asn Met Phe Ile Thr Arg Glu Glu Ala Ile Arg His
    1595                1600                1605
Val Arg Ala Trp Ile Gly Phe Asp Val Glu Gly Cys His Ala Thr
    1610                1615                1620
Arg Asp Ala Val Gly Thr Asn Leu Pro Leu Gln Leu Gly Phe Ser
    1625                1630                1635
Thr Gly Val Asn Leu Val Ala Val Pro Thr Gly Tyr Val Asp Thr
    1640                1645                1650
Glu Asn Asn Thr Glu Phe Thr Arg Val Asn Ala Lys Pro Pro Pro
    1655                1660                1665
Gly Asp Gln Phe Lys His Leu Ile Pro Leu Met Tyr Lys Gly Leu
    1670                1675                1680
Pro Trp Asn Val Val Arg Ile Lys Ile Val Gln Met Leu Ser Asp
    1685                1690                1695
Thr Leu Lys Gly Leu Ser Asp Arg Val Val Phe Val Leu Trp Ala
    1700                1705                1710
His Gly Phe Glu Leu Thr Ser Met Lys Tyr Phe Val Lys Ile Gly
    1715                1720                1725
Pro Glu Arg Thr Cys Cys Leu Cys Asp Lys Arg Ala Thr Cys Phe
    1730                1735                1740
Ser Thr Ser Ser Asp Thr Tyr Ala Cys Trp Asn His Ser Val Gly
    1745                1750                1755
Phe Asp Tyr Val Tyr Asn Pro Phe Met Ile Asp Val Gln Gln Trp
    1760                1765                1770
Gly Phe Thr Gly Asn Leu Gln Ser Asn His Asp Gln His Cys Gln
    1775                1780                1785
Val His Gly Asn Ala His Val Ala Ser Cys Asp Ala Ile Met Thr
    1790                1795                1800
Arg Cys Leu Ala Val His Glu Cys Phe Val Lys Arg Val Asp Trp
    1805                1810                1815
Ser Val Glu Tyr Pro Ile Ile Gly Asp Glu Leu Arg Val Asn Ser
    1820                1825                1830
```

-continued

```
Ala Cys Arg Lys Val Gln His Met Val Val Lys Ser Ala Leu Leu
1835                1840                1845

Ala Asp Lys Phe Pro Val Leu His Asp Ile Gly Asn Pro Lys Ala
1850                1855                1860

Ile Lys Cys Val Pro Gln Ala Glu Val Glu Trp Lys Phe Tyr Asp
1865                1870                1875

Ala Gln Pro Cys Ser Asp Lys Ala Tyr Lys Ile Glu Glu Leu Phe
1880                1885                1890

Tyr Ser Tyr Ala Thr His His Asp Lys Phe Thr Asp Gly Val Cys
1895                1900                1905

Leu Phe Trp Asn Cys Asn Val Asp Arg Tyr Pro Ala Asn Ala Ile
1910                1915                1920

Val Cys Arg Phe Asp Thr Arg Val Leu Ser Asn Leu Asn Leu Pro
1925                1930                1935

Gly Cys Asp Gly Gly Ser Leu Tyr Val Asn Lys His Ala Phe His
1940                1945                1950

Thr Pro Ala Phe Asp Lys Ser Ala Phe Thr Asn Leu Lys Gln Leu
1955                1960                1965

Pro Phe Phe Tyr Tyr Ser Asp Ser Pro Cys Glu Ser His Gly Lys
1970                1975                1980

Gln Val Val Ser Asp Ile Asp Tyr Val Pro Leu Lys Ser Ala Thr
1985                1990                1995

Cys Ile Thr Arg Cys Asn Leu Gly Gly Ala Val Cys Arg His His
2000                2005                2010

Ala Asn Glu Tyr Arg Gln Tyr Leu Asp Ala Tyr Asn Met Met Ile
2015                2020                2025

Ser Ala Gly Phe Ser Leu Trp Ile Tyr Lys Gln Phe Asp Thr Tyr
2030                2035                2040

Asn Leu Trp Asn Thr Phe Thr Arg Leu Gln Ser Leu Glu Asn Val
2045                2050                2055

Ala Tyr Asn Val Val Asn Lys Gly His Phe Asp Gly His Ala Gly
2060                2065                2070

Glu Ala Pro Val Ser Ile Ile Asn Asn Ala Val Tyr Thr Lys Val
2075                2080                2085

Asp Gly Ile Asp Val Glu Ile Phe Glu Asn Lys Thr Thr Leu Pro
2090                2095                2100

Val Asn Val Ala Phe Glu Leu Trp Ala Lys Arg Asn Ile Lys Pro
2105                2110                2115

Val Pro Glu Ile Lys Ile Leu Asn Asn Leu Gly Val Asp Ile Ala
2120                2125                2130

Ala Asn Thr Val Ile Trp Asp Tyr Lys Arg Glu Ala Pro Ala His
2135                2140                2145

Val Ser Thr Ile Gly Val Cys Thr Met Thr Asp Ile Ala Lys Lys
2150                2155                2160

Pro Thr Glu Ser Ala Cys Ser Ser Leu Thr Val Leu Phe Asp Gly
2165                2170                2175

Arg Val Glu Gly Gln Val Asp Leu Phe Arg Asn Ala Arg Asn Gly
2180                2185                2190

Val Leu Ile Thr Glu Gly Ser Val Lys Gly Leu Thr Pro Ser Lys
2195                2200                2205

Gly Pro Ala Gln Ala Ser Val Asn Gly Val Thr Leu Ile Gly Glu
2210                2215                2220

Ser Val Lys Thr Gln Phe Asn Tyr Phe Lys Lys Val Asp Gly Ile
```

-continued

```
           2225                2230                2235

Ile Gln Gln Leu Pro Glu Thr Tyr Phe Thr Gln Ser Arg Asp Leu
       2240                2245                2250

Glu Asp Phe Lys Pro Arg Ser Gln Met Glu Thr Asp Phe Leu Glu
       2255                2260                2265

Leu Ala Met Asp Glu Phe Ile Gln Arg Tyr Lys Leu Glu Gly Tyr
       2270                2275                2280

Ala Phe Glu His Ile Val Tyr Gly Asp Phe Ser His Gly Gln Leu
       2285                2290                2295

Gly Gly Leu His Leu Met Ile Gly Leu Ala Lys Arg Ser Gln Asp
       2300                2305                2310

Ser Pro Leu Lys Leu Glu Asp Phe Ile Pro Met Asp Ser Thr Val
       2315                2320                2325

Lys Asn Tyr Phe Ile Thr Asp Ala Gln Thr Gly Ser Ser Lys Cys
       2330                2335                2340

Val Cys Ser Val Ile Asp Leu Leu Leu Asp Asp Phe Val Glu Ile
       2345                2350                2355

Ile Lys Ser Gln Asp Leu Ser Val Ile Ser Lys Val Val Lys Val
       2360                2365                2370

Thr Ile Asp Tyr Ala Glu Ile Ser Phe Met Leu Trp Cys Lys Asp
       2375                2380                2385

Gly His Val Glu Thr Phe Tyr Pro Lys Leu Gln Ala Ser Gln Ala
       2390                2395                2400

Trp Gln Pro Gly Val Ala Met Pro Asn Leu Tyr Lys Met Gln Arg
       2405                2410                2415

Met Leu Leu Glu Lys Cys Asp Leu Gln Asn Tyr Gly Glu Asn Ala
       2420                2425                2430

Val Ile Pro Lys Gly Ile Met Met Asn Val Ala Lys Tyr Thr Gln
       2435                2440                2445

Leu Cys Gln Tyr Leu Asn Thr Leu Thr Leu Ala Val Pro Tyr Asn
       2450                2455                2460

Met Arg Val Ile His Phe Gly Ala Gly Ser Asp Lys Gly Val Ala
       2465                2470                2475

Pro Gly Thr Ala Val Leu Arg Gln Trp Leu Pro Thr Gly Thr Leu
       2480                2485                2490

Leu Val Asp Ser Asp Leu Asn Asp Phe Val Ser Asp Ala Asp Ser
       2495                2500                2505

Thr Leu Ile Gly Asp Cys Ala Thr Val His Thr Ala Asn Lys Trp
       2510                2515                2520

Asp Leu Ile Ile Ser Asp Met Tyr Asp Pro Arg Thr Lys His Val
       2525                2530                2535

Thr Lys Glu Asn Asp Ser Lys Glu Gly Phe Phe Thr Tyr Leu Cys
       2540                2545                2550

Gly Phe Ile Lys Gln Lys Leu Ala Leu Gly Gly Ser Ile Ala Val
       2555                2560                2565

Lys Ile Thr Glu His Ser Trp Asn Ala Asp Leu Tyr Lys Leu Met
       2570                2575                2580

Gly His Phe Ser Trp Trp Thr Ala Phe Val Thr Asn Val Asn Ala
       2585                2590                2595

Ser Ser Ser Glu Ala Phe Leu Ile Gly Ala Asn Tyr Leu Gly Lys
       2600                2605                2610

Pro Lys Glu Gln Ile Asp Gly Tyr Thr Met His Ala Asn Tyr Ile
       2615                2620                2625
```

```
Phe Trp Arg Asn Thr Asn Pro Ile Gln Leu Ser Ser Tyr Ser Leu
        2630                2635                2640

Phe Asp Met Ser Lys Phe Pro Leu Lys Leu Arg Gly Thr Ala Val
    2645                2650                2655

Met Ser Leu Lys Glu Asn Gln Ile Asn Asp Met Ile Tyr Ser Leu
    2660                2665                2670

Leu Glu Lys Gly Arg Leu Ile Ile Arg Glu Asn Asn Arg Val Val
    2675                2680                2685

Val Ser Ser Asp Ile Leu Val Asn Asn
    2690                2695

<210> SEQ ID NO 65
<211> LENGTH: 274
<212> TYPE: PRT
<213> ORGANISM: Severe acute respiratory syndrome virus

<400> SEQUENCE: 65

Met Asp Leu Phe Met Arg Phe Phe Thr Leu Arg Ser Ile Thr Ala Gln
1               5                   10                  15

Pro Val Lys Ile Asp Asn Ala Ser Pro Ala Ser Thr Val His Ala Thr
            20                  25                  30

Ala Thr Ile Pro Leu Gln Ala Ser Leu Pro Phe Gly Trp Leu Val Ile
        35                  40                  45

Gly Val Ala Phe Leu Ala Val Phe Gln Ser Ala Thr Lys Ile Ile Ala
    50                  55                  60

Leu Asn Lys Arg Trp Gln Leu Ala Leu Tyr Lys Gly Phe Gln Phe Ile
65                  70                  75                  80

Cys Asn Leu Leu Leu Leu Phe Val Thr Ile Tyr Ser His Leu Leu Leu
                85                  90                  95

Val Ala Ala Gly Met Glu Ala Gln Phe Leu Tyr Leu Tyr Ala Leu Ile
            100                 105                 110

Tyr Phe Leu Gln Cys Ile Asn Ala Cys Arg Ile Ile Met Arg Cys Trp
        115                 120                 125

Leu Cys Trp Lys Cys Lys Ser Lys Asn Pro Leu Leu Tyr Asp Ala Asn
    130                 135                 140

Tyr Phe Val Cys Trp His Thr His Asn Tyr Asp Tyr Cys Ile Pro Tyr
145                 150                 155                 160

Asn Ser Val Thr Asp Thr Ile Val Val Thr Glu Gly Asp Gly Ile Ser
                165                 170                 175

Thr Pro Lys Leu Lys Glu Asp Tyr Gln Ile Gly Gly Tyr Ser Glu Asp
            180                 185                 190

Arg His Ser Gly Val Lys Asp Tyr Val Val Val His Gly Tyr Phe Thr
        195                 200                 205

Glu Val Tyr Tyr Gln Leu Glu Ser Thr Gln Ile Thr Thr Asp Thr Gly
    210                 215                 220

Ile Glu Asn Ala Thr Phe Phe Ile Phe Asn Lys Leu Val Lys Asp Pro
225                 230                 235                 240

Pro Asn Val Gln Ile His Thr Ile Asp Gly Ser Ser Gly Val Ala Asn
                245                 250                 255

Pro Ala Met Asp Pro Ile Tyr Asp Glu Pro Thr Thr Thr Thr Ser Val
            260                 265                 270

Pro Leu

<210> SEQ ID NO 66
```

```
<211> LENGTH: 154
<212> TYPE: PRT
<213> ORGANISM: Severe acute respiratory syndrome virus

<400> SEQUENCE: 66

Met Met Pro Thr Thr Leu Phe Ala Gly Thr His Ile Thr Met Thr Thr
1               5                   10                  15

Val Tyr His Ile Thr Val Ser Gln Ile Gln Leu Ser Leu Leu Lys Val
            20                  25                  30

Thr Ala Phe Gln His Gln Asn Ser Lys Lys Thr Thr Lys Leu Val Val
        35                  40                  45

Ile Leu Arg Ile Gly Thr Gln Val Leu Lys Thr Met Ser Leu Tyr Met
50                  55                  60

Ala Ile Ser Pro Lys Phe Thr Thr Ser Leu Ser Leu His Lys Leu Leu
65                  70                  75                  80

Gln Thr Leu Val Leu Lys Met Leu His Ser Ser Ser Leu Thr Ser Leu
                85                  90                  95

Leu Lys Thr His Arg Met Cys Lys Tyr Thr Gln Ser Thr Ala Leu Gln
            100                 105                 110

Glu Leu Leu Ile Gln Gln Trp Ile Gln Phe Met Met Ser Arg Arg Arg
        115                 120                 125

Leu Leu Ala Cys Leu Cys Lys His Lys Lys Val Ser Thr Asn Leu Cys
130                 135                 140

Thr His Ser Phe Arg Lys Lys Gln Val Arg
145                 150

<210> SEQ ID NO 67
<211> LENGTH: 63
<212> TYPE: PRT
<213> ORGANISM: Severe acute respiratory syndrome virus

<400> SEQUENCE: 67

Met Phe His Leu Val Asp Phe Gln Val Thr Ile Ala Glu Ile Leu Ile
1               5                   10                  15

Ile Ile Met Arg Thr Phe Arg Ile Ala Ile Trp Asn Leu Asp Val Ile
            20                  25                  30

Ile Ser Ser Ile Val Arg Gln Leu Phe Lys Pro Leu Thr Lys Lys Asn
        35                  40                  45

Tyr Ser Glu Leu Asp Asp Glu Glu Pro Met Glu Leu Asp Tyr Pro
    50                  55                  60

<210> SEQ ID NO 68
<211> LENGTH: 122
<212> TYPE: PRT
<213> ORGANISM: Severe acute respiratory syndrome virus

<400> SEQUENCE: 68

Met Lys Ile Ile Leu Phe Leu Thr Leu Ile Val Phe Thr Ser Cys Glu
1               5                   10                  15

Leu Tyr His Tyr Gln Glu Cys Val Arg Gly Thr Thr Val Leu Leu Lys
            20                  25                  30

Glu Pro Cys Pro Ser Gly Thr Tyr Glu Gly Asn Ser Pro Phe His Pro
        35                  40                  45

Leu Ala Asp Asn Lys Phe Ala Leu Thr Cys Thr Ser Thr His Phe Ala
    50                  55                  60

Phe Ala Cys Ala Asp Gly Thr Arg His Thr Tyr Gln Leu Arg Ala Arg
65                  70                  75                  80
```

```
Ser Val Ser Pro Lys Leu Phe Ile Arg Gln Glu Val Gln Gln Glu
            85                  90                  95

Leu Tyr Ser Pro Leu Phe Leu Ile Val Ala Ala Leu Val Phe Leu Ile
            100                 105                 110

Leu Cys Phe Thr Ile Lys Arg Lys Thr Glu
            115                 120

<210> SEQ ID NO 69
<211> LENGTH: 44
<212> TYPE: PRT
<213> ORGANISM: Severe acute respiratory syndrome virus

<400> SEQUENCE: 69

Met Asn Glu Leu Thr Leu Ile Asp Phe Tyr Leu Cys Phe Leu Ala Phe
1               5                   10                  15

Leu Leu Phe Leu Val Leu Ile Met Leu Ile Ile Phe Trp Phe Ser Leu
            20                  25                  30

Glu Ile Gln Asp Leu Glu Glu Pro Cys Thr Lys Val
            35                  40

<210> SEQ ID NO 70
<211> LENGTH: 39
<212> TYPE: PRT
<213> ORGANISM: Severe acute respiratory syndrome virus

<400> SEQUENCE: 70

Met Lys Leu Leu Ile Val Leu Thr Cys Ile Ser Leu Cys Ser Cys Ile
1               5                   10                  15

Cys Thr Val Val Gln Arg Cys Ala Ser Asn Lys Pro His Val Leu Glu
            20                  25                  30

Asp Pro Cys Lys Val Gln His
            35

<210> SEQ ID NO 71
<211> LENGTH: 84
<212> TYPE: PRT
<213> ORGANISM: Severe acute respiratory syndrome virus

<400> SEQUENCE: 71

Met Cys Leu Lys Ile Leu Val Arg Tyr Asn Thr Arg Gly Asn Thr Tyr
1               5                   10                  15

Ser Thr Ala Trp Leu Cys Ala Leu Gly Lys Val Leu Pro Phe His Arg
            20                  25                  30

Trp His Thr Met Val Gln Thr Cys Thr Pro Asn Val Thr Ile Asn Cys
            35                  40                  45

Gln Asp Pro Ala Gly Gly Ala Leu Ile Ala Arg Cys Trp Tyr Leu His
        50                  55                  60

Glu Gly His Gln Thr Ala Ala Phe Arg Asp Val Leu Val Val Leu Asn
65                  70                  75                  80

Lys Arg Thr Asn

<210> SEQ ID NO 72
<211> LENGTH: 98
<212> TYPE: PRT
<213> ORGANISM: Severe acute respiratory syndrome virus

<400> SEQUENCE: 72

Met Asp Pro Asn Gln Thr Asn Val Val Pro Pro Ala Leu His Leu Val
1               5                   10                  15
```

-continued

```
Asp Pro Gln Ile Gln Leu Thr Ile Thr Arg Met Glu Asp Ala Met Gly
            20                  25                  30

Gln Gly Gln Asn Ser Ala Asp Pro Lys Val Tyr Pro Ile Ile Leu Arg
        35                  40                  45

Leu Gly Ser Gln Leu Ser Leu Ser Met Ala Arg Arg Asn Leu Asp Ser
    50                  55                  60

Leu Glu Ala Arg Ala Phe Gln Ser Thr Pro Ile Val Val Gln Met Thr
65                  70                  75                  80

Lys Leu Ala Thr Thr Glu Glu Leu Pro Asp Glu Phe Val Val Val Thr
                85                  90                  95

Ala Lys

<210> SEQ ID NO 73
<211> LENGTH: 70
<212> TYPE: PRT
<213> ORGANISM: Severe acute respiratory syndrome virus

<400> SEQUENCE: 73

Met Leu Pro Pro Cys Tyr Asn Phe Leu Lys Glu Gln His Cys Gln Lys
1               5                   10                  15

Ala Ser Thr Gln Arg Glu Ala Glu Ala Val Lys Pro Leu Leu Ala
            20                  25                  30

Pro His His Val Val Ala Val Ile Gln Glu Ile Gln Leu Leu Ala Ala
        35                  40                  45

Val Gly Glu Ile Leu Leu Leu Glu Trp Leu Ala Glu Val Val Lys Leu
    50                  55                  60

Pro Ser Arg Tyr Cys Cys
65                  70

<210> SEQ ID NO 74
<211> LENGTH: 6
<212> TYPE: RNA
<213> ORGANISM: Coronavirus

<400> SEQUENCE: 74 cuaaac                                                                       6

<210> SEQ ID NO 75
<211> LENGTH: 13
<212> TYPE: PRT
<213> ORGANISM: Severe acute respiratory syndrome virus

<400> SEQUENCE: 75

Met Phe Ile Phe Leu Leu Phe Leu Thr Leu Thr Ser Gly
1               5                   10

<210> SEQ ID NO 76
<211> LENGTH: 23
<212> TYPE: PRT
<213> ORGANISM: Severe acute respiratory syndrome virus

<400> SEQUENCE: 76

Thr Ile Pro Leu Gln Ala Ser Leu Pro Phe Gly Trp Leu Val Ile Gly
1               5                   10                  15

Val Ala Phe Leu Ala Val Phe
            20

<210> SEQ ID NO 77
<211> LENGTH: 23
<212> TYPE: PRT
```

```
<213> ORGANISM: Severe acute respiratory syndrome virus

<400> SEQUENCE: 77

Phe Gln Phe Ile Cys Asn Leu Leu Leu Phe Val Thr Ile Tyr Ser
1               5                   10                  15
His Leu Leu Leu Val Ala Ala
            20

<210> SEQ ID NO 78
<211> LENGTH: 23
<212> TYPE: PRT
<213> ORGANISM: Severe acute respiratory syndrome virus

<400> SEQUENCE: 78

Ala Gln Phe Leu Tyr Leu Tyr Ala Leu Ile Tyr Phe Leu Gln Cys Ile
1               5                   10                  15
Asn Ala Cys Arg Ile Ile Met
            20

<210> SEQ ID NO 79
<211> LENGTH: 18
<212> TYPE: PRT
<213> ORGANISM: Severe acute respiratory syndrome virus

<400> SEQUENCE: 79

Val Leu Leu Phe Leu Ala Phe Val Val Phe Leu Leu Val Thr Leu Ala
1               5                   10                  15
Ile Leu

<210> SEQ ID NO 80
<211> LENGTH: 23
<212> TYPE: PRT
<213> ORGANISM: Severe acute respiratory syndrome virus

<400> SEQUENCE: 80

Leu Leu Glu Gln Trp Asn Leu Val Ile Gly Phe Leu Phe Leu Ala Trp
1               5                   10                  15
Ile Met Leu Leu Gln Phe Ala
            20

<210> SEQ ID NO 81
<211> LENGTH: 23
<212> TYPE: PRT
<213> ORGANISM: Severe acute respiratory syndrome virus

<400> SEQUENCE: 81

Leu Val Phe Leu Trp Leu Leu Trp Pro Val Thr Leu Ala Cys Phe Val
1               5                   10                  15
Leu Ala Ala Val Tyr Arg Ile
            20

<210> SEQ ID NO 82
<211> LENGTH: 23
<212> TYPE: PRT
<213> ORGANISM: Severe acute respiratory syndrome virus

<400> SEQUENCE: 82

Gly Gly Ile Ala Ile Ala Met Ala Cys Ile Val Gly Leu Met Trp Leu
1               5                   10                  15
Ser Tyr Phe Val Ala Ser Phe
            20
```

```
<210> SEQ ID NO 83
<211> LENGTH: 20
<212> TYPE: PRT
<213> ORGANISM: Severe acute respiratory syndrome virus

<400> SEQUENCE: 83

His Leu Val Asp Phe Gln Val Thr Ile Ala Glu Ile Leu Ile Ile Ile
1               5                   10                  15

Met Arg Thr Phe
            20

<210> SEQ ID NO 84
<211> LENGTH: 15
<212> TYPE: PRT
<213> ORGANISM: Severe acute respiratory syndrome virus

<400> SEQUENCE: 84

Met Lys Ile Ile Leu Phe Leu Thr Leu Ile Val Phe Thr Ser Cys
1               5                   10                  15

<210> SEQ ID NO 85
<211> LENGTH: 19
<212> TYPE: PRT
<213> ORGANISM: Severe acute respiratory syndrome virus

<400> SEQUENCE: 85

Ser Pro Leu Phe Leu Ile Val Ala Ala Leu Val Phe Leu Ile Leu Cys
1               5                   10                  15

Phe Thr Ile

<210> SEQ ID NO 86
<211> LENGTH: 83
<212> TYPE: PRT
<213> ORGANISM: Severe acute respiratory syndrome virus

<400> SEQUENCE: 86

Glu Leu Tyr His Tyr Gln Glu Cys Val Arg Gly Thr Thr Val Leu Leu
1               5                   10                  15

Lys Glu Pro Cys Pro Ser Gly Thr Tyr Glu Gly Asn Ser Pro Phe His
            20                  25                  30

Pro Leu Ala Asp Asn Lys Phe Ala Leu Thr Cys Thr Ser Thr His Phe
        35                  40                  45

Ala Phe Ala Cys Ala Asp Gly Thr Arg His Thr Tyr Gln Leu Arg Ala
    50                  55                  60

Arg Ser Val Ser Pro Lys Leu Phe Ile Arg Gln Glu Glu Val Gln Gln
65                  70                  75                  80

Glu Leu Tyr

<210> SEQ ID NO 87
<211> LENGTH: 37
<212> TYPE: DNA
<213> ORGANISM: Artificial Sequence
<220> FEATURE:
<223> OTHER INFORMATION: Primer

<400> SEQUENCE: 87
caggaaacag ctatgacacc aagaacaagg ctctcca                       37

<210> SEQ ID NO 88
<211> LENGTH: 37
<212> TYPE: DNA
```

<210> SEQ ID NO 89
<211> LENGTH: 496
<212> TYPE: DNA
<213> ORGANISM: Severe acute respiratory syndrome virus
<220> FEATURE:
<221> NAME/KEY: misc_feature
<222> LOCATION: (11)..(11)
<223> OTHER INFORMATION: n is a, c, g, or t

<400> SEQUENCE: 89

```
acctacccag ngaaaagcca accaacctcg atctcttgta gatctgttct ctaaacgaac      60
tttaaaatct gtgtagctgt cgctcggctg catgcctagt gcacctacgc agtataaaca     120
ataataaatt ttactgtcgt tgacaagaaa cgagtaactc gtccctcttc tgcagactgc     180
ttacggtttc gtccgtgttg cagtcgatca tcagcatacc taggtttcgt ccgggtgtga     240
ccgaaaggta agatggagag ccttgttctt ggtgtcaacg agaaaacaca cgtccaactc     300
agtttgcctg tccttcaggt tagagacgtg ctagtgcgtg gcttcgggga ctctgtggaa     360
gaggccctat cggaggcacg tgaacacctc aaaaatggca cttgtggtct agtagagctg     420
gaaaaaggcg tactgcccca gcttgaacag ccctatgtgt tcattaaacg ttctgatgcc     480
ttaagcacca atcacg                                                    496
```

<210> SEQ ID NO 90
<211> LENGTH: 523
<212> TYPE: DNA
<213> ORGANISM: Severe acute respiratory syndrome virus

<400> SEQUENCE: 90

```
gtcgacaaca atttctgtgg cccagatggg taccctcttg attgcatcaa agattttctc      60
gcacgcgcgg gcaagtcaat gtgcactctt tccgaacaac ttgattacat cgagtcgaag     120
agaggtgtct actgctgccg tgaccatgag catgaaattg cctggttcac tgagcgctct     180
gataagagct acgagcacca gacacccttc gaaattaaga gtgccaagaa atttgacact     240
ttcaaagggg aatgcccaaa gtttgtgttt cctcttaact caaaagtcaa agtcattcaa     300
ccacgtgttg aaaagaaaaa gactgagggt tcatggggc gtatacgctc tgtgtaccct     360
gttgcatctc cacaggagtg taacaatatg cacttgtcta ccttgatgaa atgtaatcat     420
tgcgatgaag tttcatggca gacgtgcgac tttctgaaag ccacttgtga acattgtggc     480
actgaaaatt tagttattga aggacctact acatgtgggt acc                      523
```

<210> SEQ ID NO 91
<211> LENGTH: 324
<212> TYPE: DNA
<213> ORGANISM: Severe acute respiratory syndrome virus

<400> SEQUENCE: 91

```
cttaggtgac gagcttggca ctgatcccat tgaagattat gaacaaaact ggaacactaa      60
gcatggcagt ggtgcactcc gtgaactcac tcgtgagctc aatggaggtg cagtcactcg     120
ctatgtcgac aacaatttct gtggcccaga tgggtaccct cttgattgca tcaaagattt     180
tctcgcacgc gcgggcaagt caatgtgcac tctttccgaa caacttgatt acatcgagtc     240
```

<400> SEQUENCE: 88
caggaaacag ctatgacgat agggcctctt ccacaga      37

```
gaagagaggt gtctactgct gccgtgacca tgagcatgaa attgcctggt tcactgagcg    300
ctcctgataa gagctacgag cacc                                           324
```

```
<210> SEQ ID NO 92
<211> LENGTH: 495
<212> TYPE: DNA
<213> ORGANISM: Severe acute respiratory syndrome virus

<400> SEQUENCE: 92
tgctataata agcgtgccta ctgggttcct cgtgctagtg ctgatattgg gctcaggcca     60
tactggcatt actggtgaca atgtggagac cttgaatgag atctccttg agatactgag    120 tcgtgaacgt gttaacatta acattgttgg cgatttcat ttgaatgaag aggttgccat    180
cattttggca tctttctctg cttctacaag tgcctttatt gacactataa agagtcttga   240
ttacaagtct ttcaaaacca tgttgagtc ctgcggtaac tataaagtta ccaagggaaa    300
gcccgtaaaa ggtgcttgga acattggaca acagagatca gttttaacac cactgtgtgg   360 ttttcccctca caggctgctg tgttatcag atcaattttt gcgcgcacac ttgatgcagc    420
aaaccactca attcctgatt tgcaaagagc agctgtcacc atacttgatg gtatttctga   480
acagtcatta cgtct                                                     495
```

```
<210> SEQ ID NO 93
<211> LENGTH: 486
<212> TYPE: DNA
<213> ORGANISM: Severe acute respiratory syndrome virus

<400> SEQUENCE: 93
gccactcaaa cattgaaact cgactccgca agggaggtag gactagatgt tttggaggct     60
gtgtgtttgc ctatgttggc tgctataata agcgtgccta ctgggttcct cgtgctagtg    120
ctgatattgg ctcaggccat actggcatta ctggtgacaa tgtggagacc ttgaatgagg    180
atctccttga gatactgagt cgtgaacgtg ttaacattaa cattgttggc gattttcatt    240
tgaatgaaga ggttgccatc attttggcat ctttctctgc ttctacaagt gcctttattg    300
acactataaa gagtcttgat tacaagtctt tcaaaaccat gttgagtcc tgcggtaact    360 ataaagttac caagggaaag cccgtaaaag gtgcttggaa cattggacaa cagagatcag   420
ttttaacacc actgtgtggt tttcccctcac aggctgctgg tgttatcaga tcaattttg    480 cgcgca                                                               486
```

```
<210> SEQ ID NO 94
<211> LENGTH: 567
<212> TYPE: DNA
<213> ORGANISM: Severe acute respiratory syndrome virus

<400> SEQUENCE: 94
cactactgtg gaaaaactca ggcctatctt tgaatggatt gaggcgaaac ttagtgcagg     60
agttgaattt ctcaaggatg cttgggagat tctcaaattt ctcattacag gtgttttga    120 catcgtcaag ggtcaaatac aggttgcttc agataacatc aaggattgtg taaaatgctt   180
cattgatgtt gttaacaagg cactcgaaat gtgcattgat caagtcacta tcgctggcgc   240
aaagttgcga tcactcaact taggtgaagt cttcatcgct caaagcaagg actttaccg    300 tcagtgtata cgtggcaagg agcagctgca actactcatg cctcttaagg caccaaaaga   360
agtaaccttt cttgaaggtg attcacatga cacagtactt acctctgagg aggttgttct   420
```

```
caagaacggt gaactcgaag cactcgagac gcccgttgat agcttcacaa atggagctat    480
cgttggcaca ccagtctgtg taaatggcct catgctctta gagattaagg acaaagaaca    540
atactgcgca ttgtctcctg gtttact                                       567
```

<210> SEQ ID NO 95
<211> LENGTH: 516
<212> TYPE: DNA
<213> ORGANISM: Severe acute respiratory syndrome virus

<400> SEQUENCE: 95

```
gggagattct caaatttctc attacaggtg tttttgacat cgtcaagggt caaatacagg     60
ttgcttcaga taacatcaag gattgtgtaa aatgcttcat tgatgttgtt aacaaggcac    120
tcgaaatgtg cattgatcaa gtcactatcg ctggcgcaaa gttgcgatca ctcaacttag    180
gtgaagtctt catcgctcaa agcaagggac tttaccgtca gtgtatacgt ggcaaggagc    240
agctgcaact actcatgcct cttaaggcac caaaagaagt aacctttctt gaaggtgatt    300
cacatgacac agtacttacc tctgaggagg ttgttctcaa gaacggtgaa ctcgaagcac    360
tcgagacgcc cgttgatagc ttcacaaatg gagctatcgt tggcacacca gtctgtgtaa    420
atggcctcat gctcttagag attaaggaca agaacaata ctgcgcattg tctcctggtt    480
tactggctac aaacaatgtc tttcgcttaa aagggg                              516
```

<210> SEQ ID NO 96
<211> LENGTH: 448
<212> TYPE: DNA
<213> ORGANISM: Severe acute respiratory syndrome virus

<400> SEQUENCE: 96

```
agttcgagtt gaggaagaag aagaggaaga ctggctggat gatactactg agcaatcaga     60
gattgagcca gaaccagaac ctacacctga agaaccagtt aatcagttta ctggttattt    120
aaaacttact gacaatgttg ccattaaatg tgttgacatc gttaaggagg cacaaagtgc    180
taatcctatg gtgattgtaa atgctgctaa catacacctg aaacatggtg gtggtgtagc    240
aggtgcactc aacaaggcaa ccaatggtgc catgcaaaag gagagtgatg attacattaa    300
gctaaatggc cctcttacag taggagggtc ttgtttgctt tctggacata atcttgctaa    360
gaagtgtctg catgttgttg gacctaacct aaatgcaggt gaggacatcc agcttcttaa    420
ggcagcatat gaaaatttca attcacag                                       448
```

<210> SEQ ID NO 97
<211> LENGTH: 333
<212> TYPE: DNA
<213> ORGANISM: Severe acute respiratory syndrome virus

<400> SEQUENCE: 97

```
agaggatgat tatcaaggtc tccctctgga atttggtgcc tcagctgaaa cagttcgagt     60
tgaggaagaa gaagaggaag actggctgga tgatactact gagcaatcag agattgagcc    120
agaaccagaa cctacacctg aagaaccagt taatcagttt actggttatt taaaacttac    180
tgacaatgtt gccattaaat gtgttgacat cgttaaggag gcacaaagtg ctaatcctat    240
ggtgattgta aatgctgcta acatacacct gaaacatggt ggtggtgtag caggtgcact    300
caacaaggca accaatggtg ccatgcaaaa gga                                 333
```

<210> SEQ ID NO 98
<211> LENGTH: 399

```
<212> TYPE: DNA
<213> ORGANISM: Severe acute respiratory syndrome virus

<400> SEQUENCE: 98
gagatgctct caagagcttt gaagaaagtg ccagttgatg agtatataac cacgtaccct      60
ggacaaggat gtgctggtta tacacttgag gaagctaaga ctgctcttaa gaaatgcaaa     120
tctgcatttt atgtactacc ttcagaagca cctaatgcta aggaagagat tctaggaact     180
gtatcctgga atttgagaga atgcttgct catgctgaag agacaagaaa attaatgcct      240
atatgcatgg atgttagagc cataatggca accatccaac gtaagtataa aggaattaaa     300
attcaagagg gcatcgttga ctatggtgtc cgattcttct tttatactag taaagagcct     360
gtagcttcta ttattacgaa gctgaactct ctaaatgag                            399

<210> SEQ ID NO 99
<211> LENGTH: 437
<212> TYPE: DNA
<213> ORGANISM: Severe acute respiratory syndrome virus

<400> SEQUENCE: 99
agaaatctgt cgtacagaag cctgtcgatg tgaagccaaa aattaaggcc tgcattgatg      60
aggttaccac aacactggaa gaaactaagt ttcttaccaa taagttactc ttgtttgctg     120
atatcaatgg taagctttac catgattctc agaacatgct tagaggtgaa gatatgtctt     180
tccttgagaa ggatgcacct acatggtag gtgatgttat cactagtggt gatatcactt      240
gtgttgtaat accctccaaa aaggctggtg gcactactga gatgctctca agagctttga     300
agaaagtgcc agttgatgag tatataacca cgtaccctgg acaaggatgt gctggttata     360
cacttgagga agctaagact gctcttaaga aatgcaaatc tgcattttat gtactacctt     420
cagaagcacc taatgct                                                    437

<210> SEQ ID NO 100
<211> LENGTH: 569
<212> TYPE: DNA
<213> ORGANISM: Severe acute respiratory syndrome virus

<400> SEQUENCE: 100
cctctatcgt attgacggag ctcaccttac aaagatgtca gagtacaaag gaccagtgac      60
tgatgttttc tacaaggaaa catcttacac tacaaccatc aagcctgtgt cgtataaact     120
cgatggagtt acttacacag agattgaacc aaaattggat gggtattata aaaaggataa     180
tgcttactat acagagcagc ctatagacct tgtaccaact caaccattac caatgcgag      240
ttttgataat ttcaaactca catgttctaa cacaaaattt gctgatgatt taatcaaat      300
gacaggcttc acaaagccag cttcacgaga gctatctgtc acattcttcc cagacttgaa     360
tggcgatgta gtggctattg actatagaca ctattcagcg agtttcaaga aggtgctaa      420
attactgcat aagccaattg tttggcacat taaccaggct acaaccaaga caacgttcaa     480
accaaacact tggtgtttac gttgtctttg gagtacaaag ccagtagata cttcaaattc     540
atttgaagtt ctggcagtag aagacacat                                       569

<210> SEQ ID NO 101
<211> LENGTH: 187
<212> TYPE: DNA
<213> ORGANISM: Severe acute respiratory syndrome virus

<400> SEQUENCE: 101
```

```
tcagcagata cttcaaattc atttgaagtt ctggcagtag aagacacaca aggaatggac      60
aatcttgctt gtgaaagtca acaacccacc tctgaagaag tagtggaaaa tcctaccata     120
cagaaggaag tcatagagcg tgacgtgaaa actaccgaag ttgtaggcaa tgtcatactt     180
aaaccat                                                              187

<210> SEQ ID NO 102
<211> LENGTH: 271
<212> TYPE: DNA
<213> ORGANISM: Severe acute respiratory syndrome virus

<400> SEQUENCE: 102
aaatgcgacg agtctgcttc taagtctgct tctgtgtact acagtcagct gatgtgccaa      60
cctattctgt tgcttgacca agctcttgta tcagacgttg agatagtac tgaagtttcc     120 gttaagatgt ttgatgctta tgtcgacacc ttttcagcaa cttttagtgt tcctatggaa     180
aaacttaagg cacttgttgc tacagctcac agcgagttag caaagggtgt agctttagat     240
ggtgtccttt ctacattcgt gtcagctgcc c                                    271

<210> SEQ ID NO 103
<211> LENGTH: 363
<212> TYPE: DNA
<213> ORGANISM: Severe acute respiratory syndrome virus

<400> SEQUENCE: 103
catttcatca gcaattcttg gctcatgtgg tttatcatta gtattgtaca aatggcaccc      60
gtttctgcaa tggttaggat gtacatcttc tttgcttctt tctactacat atggaagagc     120
tatgttcata tcatggatgg ttgcacctct tcgacttgca tgatgtgcta taagcgcaat     180
cgtgccacac gcgttgagtg tacaactatt gttaatggca tgaagagatc tttctatgtc     240
tatgcaaatg gaggccgtgg cttctgcaag actcacaatt ggaattgtct caattgtgac     300
acattttgca ctggtagtac attcattagt gatgaagttg ctcgagattt gtcactccag     360
ttt                                                                   363

<210> SEQ ID NO 104
<211> LENGTH: 500
<212> TYPE: DNA
<213> ORGANISM: Severe acute respiratory syndrome virus

<400> SEQUENCE: 104
agagatcttg gcgcatgtat tgactgtaat gcaaggcata tcaatgccca aggtagcaaa      60
aagtcacaat gtttcactca tctggaatgt aaaagactac atgtctttat ctgaacagct     120
gcgtaaacaa attcgtagtg ctgccaagaa gaacaacata ccttttagac taacttgtgc     180
tacaactaga caggttgtca atgtcataac tactaaaatc tcactcaagg gtggtaagat     240
tgttagtact tgttttaaac ttatgcttaa ggccacatta ttgtgcgttc ttgctgcatt     300
ggtttgttat atcgttatgc cagtacatac attgtcaatc catgatggtt acacaaatga     360
aatcattggt tacaaagcca ttcaggatgg tgtcactcgt gacatcattt ctactgatga     420
ttgttttgca aataaacatg ctggttttga cgcatggttt agccagcgtg gtggttcata     480
caaaaatgac aaaagctgcc                                                 500

<210> SEQ ID NO 105
<211> LENGTH: 537
<212> TYPE: DNA
<213> ORGANISM: Severe acute respiratory syndrome virus
```

<400> SEQUENCE: 105

```
cattgtcaat ccatgatggt tacacaaatg aaatcattgg ttacaaagcc attcaggatg    60
gtgtcactcg tgacatcatt tctactgatg attgttttgc aaataaacat gctggttttg   120
acgcatggtt tagccagcgt ggtggttcat acaaaaatga caaaagctgc cctgtagtag   180
ctgctatcat tacaagagag attggtttca tagtgcctgg cttaccgggt actgtgctga   240
gagcaatcaa tggtgacttc ttgcattttc tacctcgtgt ttttagtgct gttggcaaca   300
tttgctacac accttccaaa ctcattgagt atagtgattt tgctacctct gcttgcgttc   360
ttgctgctga gtgtacaatt ttaaggatg ctatgggcaa acctgtgcca tattgttatg    420
acactaattt gctagagggt tctatttctt atagtgagct tcgtccagac actcgttatg   480
tgcttatgga tggttccatc atacagtttc ctaacactta cctggagggg tctgtta      537
```

<210> SEQ ID NO 106
<211> LENGTH: 427
<212> TYPE: DNA
<213> ORGANISM: Severe acute respiratory syndrome virus

<400> SEQUENCE: 106

```
cacttttgtt tttgatgtct ttcactatac tctgtctggt accagcttac agctttctgc    60
cgggagtcta ctcagtcttt tacttgtact tgacattcta tttcaccaat gatgtttcat   120
tcttggctca ccttcaatgg tttgccatgt tttctcctat tgtgccttt tggataacag    180
caatctatgt attctgtatt tctctgaagc actgccattg ttctttaac aactatctta    240
ggaaaagagt catgtttaat ggagttacat ttagtacctt cgaggaggct gctttgtgta   300
cctttttgct caacaaggaa atgtacctaa aattgcgtag cgagacactg ttgccactta   360
cacagtataa caggtatctt gctctatata caagtacaa gtatttcagt ggagccttag    420
atactac                                                             427
```

<210> SEQ ID NO 107
<211> LENGTH: 537
<212> TYPE: DNA
<213> ORGANISM: Severe acute respiratory syndrome virus

<400> SEQUENCE: 107

```
agtaacaact tttgatgctg agtactgtag acatggtaca tgcgaaaggt cagaagtagg    60
tatttgccta tctaccagtg gtagatgggt tcttaataat gagcattaca gagctctatc   120
aggagttttc tgtggtgttg atgcgatgaa tctcatagct aacatcttta ctcctcttgt   180
gcaacctgtg ggtgctttag atgtgtctgc ttcagtagtg gctggtggta ttattgccat   240
attggtgact tgtgctgcct actactttat gaaattcaga cgtgtttttg gtgagtacaa   300
ccatgttgtt gctgctaatg cacttttgtt tttgatgtct ttcactatac tctgtctggt   360
accagcttac agctttctgc cgggagtcta ctcagtcttt tacttgtact tgacattcta   420
tttcaccaat gatgtttcat tcttggctca ccttcaatgg tttgccatgt tttctcctat   480
tgtgccttt tggataacag caatctatgt attctgtatt tctctgaagc actgcca       537
```

<210> SEQ ID NO 108
<211> LENGTH: 551
<212> TYPE: DNA
<213> ORGANISM: Severe acute respiratory syndrome virus

<400> SEQUENCE: 108

```
agtatactgt ccaagacatg tcatttgcac agcagaagac atgcttaatc ctaactatga    60
agatctgctc attcgcaaat ccaaccatag ctttcttgtt caggctggca atgttcaact   120 t

<400> SEQUENCE: 111

```
taggcttaag gattgtgtta tgtatgcttc agctttagtt ttgcttattc tcatgacagc    60
tcgcactgtt tatgatgatg ctgctagacg tgtttggaca ctgatgaatg tcattacact   120
tgtttacaaa gtctactatg gtaatgcttt agatcaagct atttccatgt gggccttagt   180
tatttctgta acctctaact attctggtgt cgttacgact atcatgtttt tagctagagc   240
tatagtgttt gtgtgtgttg agtattaccc attgttattt attacctggc aacaccctt    298
```

<210> SEQ ID NO 112
<211> LENGTH: 530
<212> TYPE: DNA
<213> ORGANISM: Severe acute respiratory syndrome virus

<400> SEQUENCE: 112

```
aaacaggcaa gatctgagga caagagggca aaagtaacta gtgctatgca acaatgctc    60
ttcactatgc ttaggaagct tgataatgat gcacttaaca acattatcaa caatgcgcgt  120
gatggttgtg ttccactcaa catcatacca ttgactacag cagccaaact catggttgtt  180
gtccctgatt atgtaaccta caagaacact tgtgatggta cacctttac atatgcatct   240
gcactctggg aaatccagca agttgttgat gcggatagca agattgttca acttagtgaa  300
attaacatgg acaattcacc aaatttggct tggcctctta ttgttacagc tctaagagcc  360
aactcagctg ttaaactaca gaataatgaa ctgagtccag tagcactacg acagatgtcc  420
tgtgcggctg gtaccacaca acagcttgt actgatgaca atgcacttgc ctactataac  480
aattcgaagg gaggtaggtt tgtgctggca ttactatcag accaccaagc              530
```

<210> SEQ ID NO 113
<211> LENGTH: 605
<212> TYPE: DNA
<213> ORGANISM: Severe acute respiratory syndrome virus

<400> SEQUENCE: 113

```
gaagtcgttc tcaaaaagtt aaagaaatct ttgaatgtgg ctaaatctga gtttgaccgt    60
gatgctgcca tgcaacgcaa gttggaaaag atggcagatc aggctatgac ccaaatgtac  120
aaacaggcaa gatctgagga caagagggca aaagtaacta gtgctatgca acaatgctc   180
ttcactatgc ttaggaagct tgataatgat gcacttaaca acattatcaa caatgcgcgt  240
gatggttgtg ttccactcaa catcatacca ttgactacag cagccaaact catggttgtt  300
gtccctgatt atgtaaccta caagaacact tgtgatggta cacctttac atatgcatct   360
gcactctggg aaatccagca agttgttgat gcggatagca agattgttca acttagtgaa  420
attaacatgg acaattcacc aaatttggct tggcctctta ttgttacagc tctaagagcc  480
aactcagctg ttaaactaca gaataatgaa ctgagtccag tagcactacg acagatgtcc  540
tgtgcggctg gtaccacaca acagcttgt actgatgaca atgcacttgc ctactataac   600
aattc                                                                605
```

<210> SEQ ID NO 114
<211> LENGTH: 176
<212> TYPE: DNA
<213> ORGANISM: Severe acute respiratory syndrome virus

<400> SEQUENCE: 114

```
acactggtac aggacaggca attactgtaa caccagaagc taacatggac caagagtcct    60
```

```
ttggtggtgc ttcatgttgt ctgtattgta gatgccacat tgaccatcca aatcctaaag    120
gattctgtga cttgaaaggt aagtacgtcc aaataccctac cacttgtgct aatgat       176
```

<210> SEQ ID NO 115
<211> LENGTH: 516
<212> TYPE: DNA
<213> ORGANISM: Severe acute respiratory syndrome virus

<400> SEQUENCE: 115

```
actgtaacac cagaagctaa catggaccaa gagtcctttg gtggtgcttc atgttgtctg     60
tattgtagat gccacattga ccatccaaat cctaaaggat tctgtgactt gaaaggtaag    120
tacgtccaaa tacctaccac ttgtgctaat gacccagtgg ttttacact tagaaacaca     180 gtctgtaccg tctgcggaat gtggaaaggt tatggctgta gttgtgacca actccgcgaa    240
cccttgatgc agtctgcgga tgcatcaacg tttttaaacg ggtttgcggt gtaagtgcag    300
cccgtcttac accgtgcggc acaggcacta gtactgatgt cgtctacagg gcttttgata    360
tttacaacga aaaagttgct ggttttgcaa agttcctaaa aactaattgc tgtcgcttcc    420
aggagaagga tgaggaaggc aatttattag actcttactt tgtagttaag aggcatacta    480
tgtctaccta ccaacatgaa gagactattt ataact                              516
```

<210> SEQ ID NO 116
<211> LENGTH: 366
<212> TYPE: DNA
<213> ORGANISM: Severe acute respiratory syndrome virus

<400> SEQUENCE: 116

```
accacttatt aagtgggatt tgctgaaata tgattttacg gaagagagac tttgtctctt     60
cgaccgttat tttaaatatt gggaccagac ataccatccc aattgtatta actgtttgga    120
tgataggtgt atccttcatt gtgcaaactg taatgtgtta ttttctgctg tgtttccacg    180
tacaagtttt ggaccactag taagaaaaat atttgtagat ggtgttcctt tgttgtttc     240 aactggatac cattttcgtg agttaggagt cgtacataat caggatgtaa acttacatag    300
ctcgcgtctc agtttcaagg aacttttagt gtatgctgct gatccagcta tgcatgcagc    360
ttctgg                                                                366
```

<210> SEQ ID NO 117
<211> LENGTH: 291
<212> TYPE: DNA
<213> ORGANISM: Severe acute respiratory syndrome virus

<400> SEQUENCE: 117

```
tgaaaaagtt gctggttttg caaagttcct aaaaactaat tgctgtcgct tccaggagaa     60
ggatgaggaa ggcaatttat tagactctta ctttgtagtt aagaggcata ctatgtctaa    120
ctaccaacat gaagagacta tttataactt ggttaaagat tgtccagcgg ttgctgtcca    180 tgacttttc aagtttagag tagatggtga catggtacca catatatcac gtcagcgtct    240
aactaaatac acaatggctg atttagtcta tgctctacgt cattttgatg a             291
```

<210> SEQ ID NO 118
<211> LENGTH: 480
<212> TYPE: DNA
<213> ORGANISM: Severe acute respiratory syndrome virus

<400> SEQUENCE: 118

```
gagtcccata tggatgctga tctcgcaaaa ccacttatta gtgggatttg ctgaaatat      60
```

```
gattttacgg aagagagact ttgtctcttc gaccgttatt ttaaatattg ggaccagaca      120
taccatccca attgtattaa ctgtttggat gataggtgta tccttcattg tgcaaacttt      180
aatgtgttat tttctactgt gtttccacct acaagttttg gaccactagt aagaaaaata      240
tttgtagatg gtgttccttt tgttgtttca actggatacc attttcgtga gttaggagtc      300
gtacataatc aggatgtaaa cttacatagc tcgcgtctca gtttcaagga acttttagtg      360
tatgctgctg atccagctat gcatgcagct tctggcaatt tattgctaga taaacgcact      420
acatgctttt cagtagctgc actaacaaac aatgttgctt ttcaaactgt caacccggt       480
```

<210> SEQ ID NO 119
<211> LENGTH: 405
<212> TYPE: DNA
<213> ORGANISM: Severe acute respiratory syndrome virus

<400> SEQUENCE: 119

```
aatgggaact ggtacgattt cggtgatttc gtacaagtag caccaggctg cggagttcct      60
attgtggatt catattactc attgctgatg cccatcctca ctttgactag ggcattggct      120
gctgagtccc atatggatgc tgatctcgca aaaccactta ttaagtgaga tttgctgaaa      180
tatgatttta cggaagagag acttgtctct tcgaccgtt attttaaata ttgggaccag       240
acataccatc ccaattgtat taactgtttg gatgataggt gtatccttca ttgtgcaaac      300
tttaatgtgt tatttttctac tgtgtttcca cctacaagct tggaccact agtaagaaaa      360 atatttgtag atggtgttcc ttttgttgtt tcaactggat accat                      405
```

<210> SEQ ID NO 120
<211> LENGTH: 562
<212> TYPE: DNA
<213> ORGANISM: Severe acute respiratory syndrome virus
<220> FEATURE:
<221> NAME/KEY: misc_feature
<222> LOCATION: (67)..(67)
<223> OTHER INFORMATION: n is a, c, g, or t

<400> SEQUENCE: 120

```
ctattgatgc ttacccactt acaaaacatc ctaatcagga gtatgctgat gtctttcact      60
tgtattnaca atacattaga agttacatg atgagcttac tggccacatg ttggacatgt       120
attccgtaat gctaactaat gataacacct cacggtactg ggaacctgag ttttatgagg      180
ctatgtacac accacataca gtcttgcagg ctgtaggtgc ttgtgtattg tgcaattcac      240
agacttcact tcgttgcggt gcctgtatta ggagaccatt cctatgttgc aagtgctgct      300
atgaccatgt catttcaaca tcacacaaat tagtgttgtc tgttaatccc tatgtttgca     360
atgccccagg ttgtgatgtc actgatgtga cacaactgta tctaggaggt atgagctatt      420
attgcaagtc acataagcct cccattagtt ttccattatg tgctaatggt caggtttttg      480
gtttatacaa aaacacatgt gtaggcagtg acaatgtcac tgacttcaat gcgatagcaa      540
catgtgattg gactaatgct gg                                               562
```

<210> SEQ ID NO 121
<211> LENGTH: 580
<212> TYPE: DNA
<213> ORGANISM: Severe acute respiratory syndrome virus

<400> SEQUENCE: 121

```
gctatgtaca caccacatac agtcttgcag gctgtaggtg cttgtgtatt gtgcaattca      60
```

```
cagacttcac ttcgttgcgg tgcctgtatt aggagaccat tcctatgttg caagtgctgc    120
tatgaccatg tcatttcaac atcacacaaa ttagtgttgt ctgttaatcc ctatgtttgc    180
aatgccccag gttgtgatgt cactgatgtg acacaactgt atctaggagg tatgagctat    240
tattgcaagt cacataagcc tcccattagt tttccattat gtgctaatgg tcaggttttt    300
ggtttataca aaacacatg tgtaggcagt gacaatgtca ctgacttcaa tgcgatagca     360
acatgtgatt ggactaatgc tggcgattac atacttgcca cacttgtac tgagagactc     420 aagcttttcg cagcagaaac gctcaaagcc actgaggaaa catttaagct gtcatatggt    480
attgccactg tacgcgaagt actctctgac agagaattgc atctttcatg ggaggttgga    540
aaacctagac caccattgaa cagaaactat gtctttactg                          580

<210> SEQ ID NO 122
<211> LENGTH: 610
<212> TYPE: DNA
<213> ORGANISM: Severe acute respiratory syndrome virus

<400> SEQUENCE: 122
tggtgatgct gttgtgtaca gaggtactac gacatacaag ttgaatgttg gtgattactt     60
tgtgttgaca tctcacactg taatgccact tagtgcacct actctagtgc cacaagagca    120
ctatgtgaga attactggct tgtacccaac actcaacatc tcagatgagt tttctagcaa    180
tgttgcaaat tatcaaaagg tcggcatgca aaagtactct cactccaag gaccacctgg     240 tactggtaag agtcattttg ccatcggact tgctctctat tacccatctg ctcgcatagt    300
gtatacggca tgctctcatg cagctgttga tgccctatgt gaaaaggcat taaaatattt    360
gcccatagat aaatgtagta gaatcatacc tgcgcgtgcg cgcgtagagt gttttgataa    420
attcaaagtg aattcaacac tagaacagta tgttttctgc actgtaaatg cattgccaga    480
aacaactgct gacattgtag tctttgatga aatctctatg ctactaatt atgacttgag     540 tgttgtcaat gctagacttc gtgcaaaaca ctacgtctat attggcgatc ctgctcaatt    600
accagcccct                                                            610

<210> SEQ ID NO 123
<211> LENGTH: 429
<212> TYPE: DNA
<213> ORGANISM: Severe acute respiratory syndrome virus

<400> SEQUENCE: 123
ccaacactca acatctcaga tgagtttct agcaatgttg caaattatca aaaggtcggc      60
atgcaaaagt actctacact ccaaggacca cctggtactg gtaagagtca ttttgccatc    120
ggacttgctc tctattaccc atctgctcgc atagtgtata cggcatgctc tcatgcagct    180
gttgatgccc tatgtgaaaa ggcattaaaa tatttgccca tagataaatg tagtagaatc    240
atacctgcgc gtgcgcgcgt agagtgtttt gataaattca agtgaattc aacactagaa     300 cagtatgttt tctgcactgt aaatgcattg ccagaaacaa ctgctgacat tgtagtcttt    360
gatgaaatct ctatggctac taattatgac ttgagtgttg tcaatgctag acttcgtgca    420
aaacactac                                                            429

<210> SEQ ID NO 124
<211> LENGTH: 486
<212> TYPE: DNA
<213> ORGANISM: Severe acute respiratory syndrome virus

<400> SEQUENCE: 124
```

-continued

```
caatgtggct atcacaaggg caaaaattgg cattttgtgc ataatgtctg atagagatct      60
ttatgacaaa ctgcaattta caagtctaga ataccacgt cgcaatgtgg ctacattaca     120
agcagaaaat gtaactggac tttttaagga ctgtagtaag atcattactg gtcttcatcc    180
tacacaggca cctacacacc tcagcgttga tataaagttc aagactgaag gattatgtgt    240
tgacatacca ggcataccaa aggacatgac ctaccgtaga ctcatctcta tgatgggttt    300
caaaatgaat taccaagtca atggttaccc taatatgttt atcacccgcg aagaagctat    360
tcgtcacgtt cgtgcgtgga ttggctttga tgtagagggc tgtcatgcaa ctagagatgc    420
tgtgggtact aacctacctc tccagctagg attttctaca ggtgttaact agtagctgt     480 accgac                                                               486
```

<210> SEQ ID NO 125
<211> LENGTH: 427
<212> TYPE: DNA
<213> ORGANISM: Severe acute respiratory syndrome virus

<400> SEQUENCE: 125

```
aaaggacatg acctaccgta gactcatctc tatgatgggt ttcaaaatga attaccaagt     60
caatggttac cctaatatgt ttatcacccg cgaagaagct attcgtcacg ttcgtgcgtg    120
gattggcttt gatgtagagg gctgtcatgc aactagagat gctgtgggta ctaacctacc    180
tctccagcta ggattttcta caggtgttaa cttagtagct gtaccgactg gttatgttga    240
cactgaaaat aacacagaat tcaccagagt taatgcaaaa cctccaccag gtgaccagtt    300
taaacatctt ataccactca tgtataaagg cttgccctgg aatgtagtgc gtattaagat    360
agtacaaatg ctcagtgata cactgaaagg attgtcagac agagtcgtgt tcgtcctttg    420
ggcgcat                                                              427
```

<210> SEQ ID NO 126
<211> LENGTH: 392
<212> TYPE: DNA
<213> ORGANISM: Severe acute respiratory syndrome virus

<400> SEQUENCE: 126

```
atggaaatgc acatgtggct agttgtgatg ctatcatgac tagatgttta gcagtccatg     60
agtgctttgt taagcgcgtt gattggtctg ttgaataccc tattataggg gatgaactga    120
gggttaattc tgcttgcaga aaagtacaac acatggttgt gaagtctgca ttgcttgctg    180
ataagtttcc agttcttcat gacattggaa atccaaaggc tatcaagtgt gtgcctcagg    240
ctgaagtaga atggaagttc tacgatgctc agccatgtag tgacaaagct acaaaaatag    300
aggaactctt ctattcttat gctacacatc acgataaatt cactgatggt gtttgtttgt    360
tttggaattg taacgttgat cgttacccag cc                                  392
```

<210> SEQ ID NO 127
<211> LENGTH: 483
<212> TYPE: DNA
<213> ORGANISM: Severe acute respiratory syndrome virus

<400> SEQUENCE: 127

```
gcttcatcag atacttatgc ctgctggaat cattctgtgg ttttgactta tgtctataac     60
ccatttatga ttgatgttca gcagtggggc tttacgggta accttcagag taaccatgac    120
caacattgcc aggtacatgg aaatgcacat gtggctagtt gtgatgctat catgactaga    180
```

```
tgtttagcag tccatgagtg ctttgttaag cgcgttgatt ggtctgttga atacctatt     240 ataggagatg aactgagggt taattctgct tgcagaaaag tacaacacat ggttgtgaag    300
tctgcattgc ttgctgataa gtttccagtt cttcatgaca ttggaaatcc aaaggctatc   360
aagtgtgtgc ctcaggctga agtagaatgg aagttctacg atgctcagcc atgtagtgac   420
aaagcttaca aaatagagga actcttctat tcttatgcta cacatcacga taaattcact   480
gat                                                                  483

<210> SEQ ID NO 128
<211> LENGTH: 326
<212> TYPE: DNA
<213> ORGANISM: Severe acute respiratory syndrome virus

<400> SEQUENCE: 128
tcaaagggac cagcacaagc tagcgtcaat ggagtcacat taattggaga atcagtaaaa    60
acacagttta actactttaa gaaagtagac ggcattattc aacagttgcc tgaaacctac   120
tttactcaga gcagagactt agaggatttt aagcccagat cacaaatgga aactgacttt   180
ctcgagctcg ctatggatga attcatacag cgatataagc tcgagggcta tgccttcgaa   240
cacatcgttt atggagattt cagtcatgga caacttggcg tcttcatttt aatgataggc   300
ttagccaagc gctcacaaga ttcact                                         326

<210> SEQ ID NO 129
<211> LENGTH: 457
<212> TYPE: DNA
<213> ORGANISM: Severe acute respiratory syndrome virus

<400> SEQUENCE: 129
acaccttcaa agggaccagc acaagctagc gtcaatggag tcacattaat tggagaatca    60
gtaaaaacac agtttaacta ctttaagaaa gtagacggca ttattcaaca gttgcctgaa   120
acctacttta ctcagagcag agacttagag gattttaagc ccagatcaca aatggaaact   180
gactttctcg agctcgctat ggatgaattc atacagcgat ataagctcga gggctatgcc   240
ttcgaacaca tcgtttatgg agatttcagt catggacaac ttggcggtct tcatttaatg   300
ataggcttag ccaagcgctc acaagattca ccacttaaat tagaggattt tatccctatg   360
gacagcacag tgaaaaatta cttcataaca gatgcgcaaa caggttcatc aaaatgtgtg   420
tgttctgtga ttgatctttt acttgatgac tttgtcg                             457

<210> SEQ ID NO 130
<211> LENGTH: 493
<212> TYPE: DNA
<213> ORGANISM: Severe acute respiratory syndrome virus

<400> SEQUENCE: 130
cgcaaagtat actcaactgt gtcaatactt aaatacactt actttagctg taccctacaa    60
catgagagtt attcactttg gtgctggctc tgataaagga gttgcaccag gtacagctgt   120
gctcagacaa tggttgccaa ctggcacact acttgtcgat tcagatctta atgacttcgt   180
ctccgacgca gattctactt taattggaga ctgtgcaaca gtacatacgg ctaataaatg   240
ggaccttatt attagcgata tgtatgaccc taggaccaaa catgtgacaa agagaatga   300 ctctaaagaa gggttttttca cttatctgtg tggatttata aagcaaaaac tagccctggg   360
tggttctata gctgtaaaga taacagcagca ttccttggaat gctgaccttt acaagcttat   420
gggccatttc tcatggtgga cagcttttgt tacaaatgta aatgcatcat catcggaagc   480
```
atttttaatt ggg                                                        493

<210> SEQ ID NO 131
<211> LENGTH: 490
<212> TYPE: DNA
<213> ORGANISM: Severe acute respiratory syndrome virus

<400> SEQUENCE: 131
acttaaatac acttacttta gctgtaccct acaacatgag agttattcac tttggtgctg    60
gctctgataa aggagttgca ccaggtacag ctgtgctcag acaatggttg ccaactggca   120
cactacttgt cgattcagat cttaatgact tcgtctccga cgcagattct actttaattg   180
gagactgtgc aacagtacat acggctaata aatgggacct tattattagc gatatgtatg   240
accctaggac caaacatgtg acaaaagaga atgactctaa agaagggttt ttcacttatc   300
tgtgtggatt tataaagcaa aaactagccc tgggtggttc tatagctgta aagataacag   360
agcattcttg gaatgctgac ctttacaagc ttatgggcca tttctcatgg tggacagctt   420
ttgttacaaa tgtaaatgca tcatcatcgg aagcattttt aattggggct aactatcttg   480
gcaagccgaa                                                           490

<210> SEQ ID NO 132
<211> LENGTH: 550
<212> TYPE: DNA
<213> ORGANISM: Severe acute respiratory syndrome virus

<400> SEQUENCE: 132
taaggagaat caaatcaatg atatgattta ttctcttctg gaaaaaggta ggcttatcat    60
tagagaaaac aacagagttg tggtttcaag tgatattctt gttaacaact aaacgaacat   120
gtttattttc ttattatttc ttactctcac tagtggtagt gaccttgacc ggtgcaccac   180
ttttgatgat gttcaagctc ctaattacac tcaacatact tcatctatga gggggggttta   240
ctatcctgat gaaattttta gatcagacac tctttattta actcaggatt tatttcttcc   300
attttattct aatgttacag ggtttcatac tattaatcat cgtttggcaa cccgtgtcat   360
acctttttaag gatggtattt attttgctgc cacagagaaa tcaaatgttg tccgtggttg   420
ggttttggt tctaccatga acaacaagtc acagtcggtg attattatta acaattctac   480
taatgttgtt atacgagcat gtaactttga attgtgtgac aaccctttct tgctgtttc   540
taaacccata                                                          550

<210> SEQ ID NO 133
<211> LENGTH: 490
<212> TYPE: DNA
<213> ORGANISM: Severe acute respiratory syndrome virus

<400> SEQUENCE: 133
acttaaatac acttacttta gctgtaccct acaacatgag agttattcac tttggtgctg    60
gctctgataa aggagttgca ccaggtacag ctgtgctcag acaatggttg ccaactggca   120
cactacttgt cgattcagat cttaatgact tcgtctccga cgcagattct actttaattg   180
gagactgtgc aacagtacat acggctaata aatgggacct tattattagc gatatgtatg   240
accctaggac caaacatgtg acaaaagaga atgactctaa agaagggttt ttcacttatc   300
tgtgtggatt tataaagcaa aaactagccc tgggtggttc tatagctgta aagataacag   360
agcattcttg gaatgctgac ctttacaagc ttatgggcca tttctcatgg tggacagctt   420

| | |
|---|---|
| ttgttacaaa tgtaaatgca tcatcatcgg aagcattttt aattggggct aactatcttg | 480 |
| gcaagccgaa | 490 |

<210> SEQ ID NO 134
<211> LENGTH: 550
<212> TYPE: DNA
<213> ORGANISM: Severe acute respiratory syndrome virus

<400> SEQUENCE: 134

| | |
|---|---|
| taaggagaat caaatcaatg atatgattta ttctcttctg gaaaaaggta ggcttatcat | 60 |
| tagagaaaac aacagagttg tggtttcaag tgatattctt gttaacaact aaacgaacat | 120 |
| gtttattttc ttattatttc ttactctcac tagtggtagt gaccttgacc ggtgcaccac | 180 |
| ttttgatgat gttcaagctc ctaattacac tcaacatact tcatctatga gggggggttta | 240 |
| ctatcctgat gaaattttta gatcagacac tctttattta actcaggatt tatttcttcc | 300 |
| attttattct aatgttacag ggtttcatac tattaatcat cgtttggca accctgtcat | 360 |
| acctttaag gatggtattt attttgctgc cacagagaaa tcaaatgttg tccgtggttg | 420 |
| ggttttggt tctaccatga acaacaagtc acagtcggtg attattatta acaattctac | 480 |
| taatgttgtt atacgagcat gtaactttga attgtgtgac aaccctttct tgctgtttc | 540 |
| taaacccata | 550 |

<210> SEQ ID NO 135
<211> LENGTH: 400
<212> TYPE: DNA
<213> ORGANISM: Severe acute respiratory syndrome virus

<400> SEQUENCE: 135

| | |
|---|---|
| atcaatgata tgatttattc tcttctggaa aaggtaggc ttatcattag agaaaacaac | 60 |
| agagttgtgg tttcaagtga tattcttgtt aacaactaaa cgaacatgtt tattttctta | 120 |
| ttatttctta ctctcactag tggtagtgac cttgaccggt gcaccacttt tgatgatgtt | 180 |
| caagctccta attacactca acatacttca tctatgaggg gggtttacta tcctgatgaa | 240 |
| atttttagat cagacactct ttatttaact caggattat tcttccatt ttattctaat | 300 |
| gttacagggt tcatactat taatcatcg tttggcaacc ctgtcatacc ttttaaggat | 360 |
| ggtatttatt ttgctgccac agagaaatca atgttgtcc | 400 |

<210> SEQ ID NO 136
<211> LENGTH: 288
<212> TYPE: DNA
<213> ORGANISM: Severe acute respiratory syndrome virus

<400> SEQUENCE: 136

| | |
|---|---|
| tgatctttgc ttctccaatg tctatgcaga ttctttggta gtcaagggag atgatgtaag | 60 |
| acaaatagcg ccaggacaaa ctggtgttat tgctgattat aattataaat tgccagatga | 120 |
| tttcatgggt tgtgtccttg cttggaatac taggaacatt gatgctactt caactggtaa | 180 |
| ttataattat aaatataggt atcttagaca tggcaagctt aggcccttg agagagacat | 240 |
| atctaatgtg cctttctcca cctgatggca aaccttgcac cccacctg | 288 |

<210> SEQ ID NO 137
<211> LENGTH: 411
<212> TYPE: DNA
<213> ORGANISM: Severe acute respiratory syndrome virus

<400> SEQUENCE: 137

```
ctttgagaga gacatatcta atgtgccttt ctcccctgat ggcaaacctt gcaccccacc      60
tgctcttaat tgttattggc cattaaatga ttatggtttt tacaccacta ctggcattgg     120
ctaccaacct tacagagttg tagtactttc ttttgaactt ttaaatgcac cggccacggt     180
ttgtggacca aaattatcca ctgaccttat taagaaccag tgtgtcaatt ttaattttaa     240
tggactcact ggtactggtg tgttaactcc ttcttcaaag agatttcaac catttcaaca     300
aattttgccg tgatgtttct gatttcactg attccgttcg agatcctaaa acatctgaaa     360
tattagacat ttcaccctgc gcttttgggg gtgtaagtgt aattacacct g              411

<210> SEQ ID NO 138
<211> LENGTH: 357
<212> TYPE: DNA
<213> ORGANISM: Severe acute respiratory syndrome virus

<400> SEQUENCE: 138
tggaaatatt ttggtggttt taattttca caaatattac ctgaccctct aaagccaact       60
aagaggtctt ttattgagga cttgctcttt aataaggtga cactcgctga tgctggcttc     120
atgaagcaat atggcgaatg cctaggtgat attaatgcta gagatctcat tgtgcgcag     180 aagttcaatg gacttacagt gttgccacct ctgctcactg atgatatgat tgctgcctac     240
actgctgctc tagttagtgg tactgccact gctggatgga catttggtgc tggcgctgct     300
cttcaaatac ctttgctat gcaaatggca tataggttca atggcattgg agttact        357

<210> SEQ ID NO 139
<211> LENGTH: 434
<212> TYPE: DNA
<213> ORGANISM: Severe acute respiratory syndrome virus

<400> SEQUENCE: 139
caatatggcg aatgcctagg tgatattaat gctagagatc tcatttgtgc gcagaagttc       60
aatggactta cagtgttgcc acctctgctc actgatgata tgattgctgc ctacactgct     120
gctctagtta gtggtactgc cactgctgga tggacatttg gtgctggcgc tgctcttcaa     180
ataccttttg ctatgcaaat ggcatatagg ttcaatggca ttggagttac ccaaaatgtt     240
ctctatgaga accaaaaaca atcgccaac caatttaaca aggcgattag tcaaattcaa     300
gaatcactta caacaacatc aactgcattg gcaagctgc aagacgttgt taaccagaat     360
gctcaagcat taaacacact tgttaaacaa cttagctcta ttttggtgc aatttcaagt     420 gtgctaaatg atat                                                        434

<210> SEQ ID NO 140
<211> LENGTH: 557
<212> TYPE: DNA
<213> ORGANISM: Severe acute respiratory syndrome virus

<400> SEQUENCE: 140
acagacaata catttgtctc aggaaattgt gatgtcgtta ttggcatcat taacaacaca       60
gtttatgatc ctctgcaacc tgagcttgac tcattcaaag aagagctgga caagtacttc     120
aaaaatcata catcaccaga tgttgatctt ggcgacattt caggcattaa cgcttctgtc     180
gtcaacattc aaaaagaaat tgaccgcctc aatgaggtcg ctaaaaattt aaatgaatca     240
ctcattgacc ttcaagaatt gggaaaatat gagcaatata ttaaatgcc ttggtatgtt     300 tggctcggct tcattgctgg actaattgcc atcgtcatgg ttacaatctt gctttgttgc     360
```

```
atgactagtt gttgcagttg cctcaagggt gcatgctctt gtggttcttg ctgcaagttt      420
gatgaggatg actctgagcc agttctcaag ggtgtcaaat tacattacac ataaacgaac      480
ttatggattt gtttatgaga ttttttactc ttagatcaat tactgcacag ccagtaaaaa      540
ttgacaatgc ttctcct                                                    557

<210> SEQ ID NO 141
<211> LENGTH: 530
<212> TYPE: DNA
<213> ORGANISM: Severe acute respiratory syndrome virus

<400> SEQUENCE: 141
atgtttggct cggcttcatt gctggactaa ttgccatcgt catggttaca atcttgcttt       60
gttgcatgac tagttgttgc agttgcctca agggtgcatg ctcttgtggt tcttgctgca      120
agtttgatga ggatgactct gagccagttc tcaagggtgt caaattacat tacacataaa      180
cgaacttatg gatttgttta tgagattttt tactcttaga tcaattactg cacagccagt      240
aaaaattgac aatgcttctc ctgcaagtac tgttcatgct acagcaacga taccgctaca      300
agcctcactc cctttcggat ggcttgttat tggcgttgca tttcttgctg tttttcagag      360
cgctaccaaa ataattgcgc tcaataaaag atggcagcta gccctttata agggcttcca      420
gttcatttgc aatttactgc tgctatttgt taccatctat tcacatcttt tgcttgtcgc      480
tgcaggtatg gaggcgcaat ttttgtacct ctatgccttg atatattttc                 530

<210> SEQ ID NO 142
<211> LENGTH: 320
<212> TYPE: DNA
<213> ORGANISM: Severe acute respiratory syndrome virus

<400> SEQUENCE: 142
ttgctcgtac ccgctcaatg tggtcattca acccagaaac aaacattctt ctcaatgtgc       60
ctctccgggg acaattgtg accagaccgc tcatggaaag tgaacttgtc attggtgctg      120
tgatcattcg tggtcacttg cgaatggccg acactccct agggcgctgt gacattaagg      180
acctgccaaa agagatcact gtggctacat cacgaacgct ttcttattac aaattaggag      240
cgtcgcagcg tgtaggcact gattcaggtt ttgctgcata caaccgctac cgtattggaa      300
actataaatt aaatacagac                                                 320

<210> SEQ ID NO 143
<211> LENGTH: 417
<212> TYPE: DNA
<213> ORGANISM: Severe acute respiratory syndrome virus

<400> SEQUENCE: 143
cgaacttatg tactcattcg tttcggaaga aacaggtacg ttaatagtta atagcgtact       60 tcttttctt gctttcgtgg tattcttgct agtcacacta gccatcctta ctgcgcttcg      120
attgtgtgcg tactgctgca atattgttaa cgtgagttta gtaaaaccaa cggtttacgt      180
ctactcgcgt gttaaaaatc tgaactcttc tgaaggagtt cctgatcttc tggtctaaac      240
gaactaacta ttattattat tctgtttgga actttaacat tgcttatcat ggcagacaac      300
ggtactatta ccgttgagga gcttaaacaa ctcctggaac aatggaacct agtaataggt      360
ttcctattcc tagcctggat tatgttacta caatttgcct attctaatcg gaacagg        417

<210> SEQ ID NO 144
<211> LENGTH: 516
```

<210> SEQ ID NO 144
<211> LENGTH: (not shown)
<212> TYPE: DNA
<213> ORGANISM: Severe acute respiratory syndrome virus

<400> SEQUENCE: 144

```
cttgtcattg gtgctgtgat cattcgtggt cacttgcgaa tggccggaca ctccctaggg    60
cgctgtgaca ttaaggacct gccaaaagag atcactgtgg ctacatcacg aacgctttct   120
tattacaaat taggagcgtc gcagcgtgta ggcactgatt caggttttgc tgcatacaac   180
cgctaccgta ttggaaacta taattaaat acagaccacg ccggtagcaa cgacaatatt    240
gctttgctag tacagtaagt gacaacagat gtttcatctt gttgacttcc aggttacaat   300
agcagagata ttgattatca ttatgaggac tttcaggatt gctatttgga atcttgacgt   360
tataataagt tcaatagtga gacaattatt taagcctcta actaagaaga attattcgga   420
gttagatgat gaagaaccta tggagttaga ttatccataa aacgaacatg aaaattattc   480
tcttcctgac attgatttta tttacatctt gcgagc                              516
```

<210> SEQ ID NO 145
<211> LENGTH: 310
<212> TYPE: DNA
<213> ORGANISM: Severe acute respiratory syndrome virus

<400> SEQUENCE: 145

```
cgatgtttca tcttgttgac ttccaggtta caatagcaga gatattgatt atcattatga    60
ggactttcag gattgctatt tggaatcttg acgttataat aagttcaata gtgagacaat   120
tatttaagcc tctaactaag aagaattatt cggagttaga tgatgaagaa cctatggagt   180
tagattatcc ataaaacgaa catgaaaatt attctcttcc tgacattgat tgtatttaca   240
tcttgcgagc tatatcacta tcaggagtgt gttagaggta cgactgtact actaaaagaa   300
ccttgcccat                                                           310
```

<210> SEQ ID NO 146
<211> LENGTH: 556
<212> TYPE: DNA
<213> ORGANISM: Severe acute respiratory syndrome virus

<400> SEQUENCE: 146

```
agaaagacag aatgaatgag ctcactttaa ttgacttcta tttgtgcttt ttagcctttc    60
tgctattcct tgtttaata atgcttatta tattttggtt ttcactcgaa atccaggatc   120
tagaagaacc ttgtaccaaa gtctaaacga acatgaaact tctcattgtt ttgacttgta   180
tttctctatg cagttgcata tgcactgtag tacagcgctg tgcatctaat aaacctcatg   240
tgcttgaaga tccttgtaag gtacaacact aggggtaata cttatagcac tgcttggctt   300
tgtgctctag gaaaggtttt acctttttcat agatggcaca ctatggttca acatgcaca   360
cctaatgtta ctatcaactg tcaagatcca gctggtggtg cgcttatagc taggtgttgg   420
taccttcatg aaggtcacca aactgctgca tttagagacg tacttgttgt tttaaataaa   480
cgaacaaatt aaaatgtctg ataatggacc ccaatcaaac caacgtagtg ccccccgcat   540
tacatttggt ggaccc                                                    556
```

<210> SEQ ID NO 147
<211> LENGTH: 110
<212> TYPE: DNA
<213> ORGANISM: Severe acute respiratory syndrome virus

<400> SEQUENCE: 147

```
acgaacatga aaattattct cttcctgaca ttgattgtat ttacatcttg cgagctatat      60
cactatcagg agtgtgttag aggtacgact gtactactaa agaaccttg                 110

<210> SEQ ID NO 148
<211> LENGTH: 363
<212> TYPE: DNA
<213> ORGANISM: Severe acute respiratory syndrome virus

<400> SEQUENCE: 148
gcatttagag acgtacttgt tgttttaaat aaacgaacaa attaaaatgt ctgataatgg      60
acctcaatca agccaacgta gtgccccccg cattacattt ggtggaccca cagattcaac    120
tgacaataac cagaatggag gacgcaatgg ggcaaggcca aacagcgcc gaccccaagg    180 tttacccaat aatactgcgt cttggttcac agctctcact cagcatggca aggaggaact    240
tagattccct cgaggccagg gcgttccaat caacaccaat agtggtccag atgaccaaat    300
tggctactac cgaagagcta cccgacgagt tcgtggtggt gacggcaaaa tgaaagagct    360
cag                                                                  363

<210> SEQ ID NO 149
<211> LENGTH: 294
<212> TYPE: DNA
<213> ORGANISM: Severe acute respiratory syndrome virus

<400> SEQUENCE: 149
ctatcagctg cgtgcaagat cagtttcacc aaaactttc atcagacaag aggaggttca      60
acaagagctc tactcgccac tttttctcat tgttgctgct ctagtatttt taatactttg    120
cttcaccatt aagagaaaga cagaatgaat gagctcactt taattgactt ctatttgtgc    180 ttttagcct ttctgctatt ccttgtttta ataatgctta ttatattttg gttttcactc    240
gaaatccagg atctagaaaa accttgtacc aaaggctaaa cgaacatgaa actt          294

<210> SEQ ID NO 150
<211> LENGTH: 504
<212> TYPE: DNA
<213> ORGANISM: Severe acute respiratory syndrome virus

<400> SEQUENCE: 150
caaactgctg catttagaga cgtacttgtt gtttaaataa acgaacaaat taaaatgtct      60
gataatggac cccaatcaaa ccaacgtagt gccccccgca ttacatttgg tggacccaca    120
gattcaactg acaataacca gaatggagga cgcaatgggg caaggccaaa acagcgccga    180
ccccaaggtt tacccaataa tactgcgtct tggttcacag ctctcactca gcatggcaag    240
gaggaactta gattccctcg aggccagggc gttccaatca acaccaatag tggtccagat    300
gaccaaattg ctactaccg aagagctacc cgacgagttc gtggtggtga cggcaaaatg    360
aaagagctca gccccagatg gtacttctat tacctaggaa ctgggcccaga agcttcactt    420 ccctacggcg ctaacaaaga aggcatcgta tgggttgcaa ctgagggagc cttgaataca    480
cccaaagacc acattggcac ccgt                                           504

<210> SEQ ID NO 151
<211> LENGTH: 474
<212> TYPE: DNA
<213> ORGANISM: Severe acute respiratory syndrome virus

<400> SEQUENCE: 151
ctcgccactt tttctcattg ttgctgctct agtattttta atactttgct tcaccattaa      60
```

```
gagaaagaca gaatgaatga gctcacttta atttgacttct atttgtgctt tttagccttt    120
ctgctattcc ttgttttaat aatgcttatt atattttggt tttcactcga aatccaggat    180
ctagaagaac cttgtaccaa agtctaaacg aacatgaaac ttctcattgt tttgacttgt    240
atttctctat gcagttgcat atgcactgta gtacagcgct gtgcatctaa taaacctcat    300
gtgcttgaag atccttgtaa ggtacaacac tagggggtaat acttatagca ctgcttggct    360
ttgtgctcta ggaaaggttt tacctttca tagatggcac actatggttc aaacatgcac    420
acctaatgtt actatcaact gtcaagatcc agctggtggt gcgcttatag ctag          474

<210> SEQ ID NO 152
<211> LENGTH: 516
<212> TYPE: DNA
<213> ORGANISM: Severe acute respiratory syndrome virus

<400> SEQUENCE: 152
cattaagaga aagacagaat gaatgagctc actttaattg acttctattt gtgcttttta    60
gcctttctgc tattccttgt tttaataatg cttattatat tttggttttc actcgaaatc    120
caggatctag aagaaccttg taccaaagtc taaacgaaca tgaaacttct cattgttttg    180
acttgtattt ctctatgcag ttgcatatgc actgtagtac agcgctgtgc atctaataaa    240
cctcatgtgc ttgaagatcc ttgtaaggta caacactagg gtaatactt atagcactgc    300 ttggctttgt gctctaggaa aggttttacc ttttcataga tggcacacta tggttcaaac    360
atgcacacct aatgttacta tcaactgtca agatccagct ggtggtgcgc ttatagctag    420
gtgttggtac cttcatgaag gtcaccaaac tgctgcattt agagacgtac ttgttgtttt    480
aaataaacga acaaattaaa atgtctgata atggac                              516

<210> SEQ ID NO 153
<211> LENGTH: 451
<212> TYPE: DNA
<213> ORGANISM: Severe acute respiratory syndrome virus

<400> SEQUENCE: 153
ccaaggttta cccaataata ctgcgtcttg gttcacagct ctcactcagc atggcaagga    60
ggaacttaga ttccctcgag gccagggcgt tccaatcaac accaatagtg gtccagatga    120
ccaaattggc tactaccgaa gagctacccg acgagttcgt ggtggtgacg gcaaaatgaa    180
agagctcagc cccagatggt acttctatta cctaggaact ggcccagaag cttcacttcc    240
ctacggcgct aacaaagaag gcatcgtatg ggttgcaact gagggagcct tgaatacacc    300
caaagaccac attggcaccc gcaatcctaa taacatgct gccaccgtgc tacaacttcc    360
tcaaggaaca acattgccaa aaggcttcta cgcagaggga agcagaggcg cagtcaagc    420 ctcttctcgc tcctcatcac gtagtcgcgg t                                    451

<210> SEQ ID NO 154
<211> LENGTH: 495
<212> TYPE: DNA
<213> ORGANISM: Severe acute respiratory syndrome virus

<400> SEQUENCE: 154
gatgaagctc agcctttgcc gcagagacaa aagaagcagc ccactgtgac tcttcttcct    60
gcggctgaca tggatgattt ctccagacaa cttcaaaatt ccatgagtgg agcttctgct    120
gattcaactc aggcataaac actcatgatg accacacaag gcagatgggc tatgtaaacg    180
```

```
ttttcgcaat tccgtttacg atacatagtc tactcttgtg cagaatgaat tctcgtaact    240
aaacagcaca agtaggttta gttaacttta atctcacata gcaatcttta atcaatgtgt    300
aacattaggg aggacttgaa agagccacca cattttcatc gaggccacgc ggagtacgat    360
cgagggtaca gtgaataatg ctagggagag ctgcctatat ggaagagccc taatgtgtaa    420
aattaatttt agtagtgcta tccccatgtg attttaatag cttcttagga gaatgacaaa    480
aaaaaaaaaa aaaaa                                                     495

<210> SEQ ID NO 155
<211> LENGTH: 512
<212> TYPE: DNA
<213> ORGANISM: Severe acute respiratory syndrome virus

<400> SEQUENCE: 155
acaaggccaa actgtcacta gaaatctgc tgctgaggca tctaaaaagc ctcgccaaaa     60
acgtactgcc acaaaacagt acaacgtcac tcaagcattt gggagacgtg gtccagaaca    120
aacccaagga aatttcgggg accaagacct aatcagacaa ggaactgatt acaaacattg    180
gccgcaaatt gcacaatttg ctccaagtgc ctctgcattc tttggaatgt cacgcattgg    240
catggaagtc acaccttcgg gaacatggct gacttatcat ggagccatta aattggatga    300
caaagatcca caattcaaag acaacgtcat actgctgaac aagcacattg acgcatacaa    360
aacattccca ccaacagagc ctaaaaagga caaaaagaaa aagactgatg aagctcagcc    420
tttgccgcag agacaaaaga agcagcccac tgtgactctt cttcctgcgg ctgatatgga    480
tgatttctcc agacaacttc aaaattccat ga                                  512

<210> SEQ ID NO 156
<211> LENGTH: 442
<212> TYPE: DNA
<213> ORGANISM: Severe acute respiratory syndrome virus

<400> SEQUENCE: 156
tgtgactctt cttcctgcgg ctgatatgga tgtttctcca gacaacttca aaattccatg     60
agtggagctt ctgctgattc aactcaggca taaacactca tgatgaccac acaaggcaga    120
tgggctatgt aaacgttttc gcaattccgt ttacgataca tagtctactc ttgtgcagaa    180
tgaattctcg taactaaaca gcacaagtag gtttagttaa cttaatctc acatagcaat    240 ctttaatcaa tgtgtaacat tagggaggac ttgaaagagc caccacattt tcatcgaggc    300
cacgcggagt acgatcgagg gtacagtgaa taatgctagg gagagctgcc tatatggaag    360
agccctaatg tgtaaaatta attttagtag tgctatcccc atgtgatttt aatagcttct    420
taggagaatg acaaaaaaaa aa                                             442

<210> SEQ ID NO 157
<211> LENGTH: 24
<212> TYPE: DNA
<213> ORGANISM: Artificial Sequence
<220> FEATURE:
<223> OTHER INFORMATION: Primer

<400> SEQUENCE: 157
atgaattacc aagtcaatgg ttac                                            24

<210> SEQ ID NO 158
<211> LENGTH: 20
<212> TYPE: DNA
<213> ORGANISM: Artificial Sequence
```

```
<220> FEATURE:
<223> OTHER INFORMATION: Primer

<400> SEQUENCE: 158
gaagctattc gtcacgttcg                                              20

<210> SEQ ID NO 159
<211> LENGTH: 22
<212> TYPE: DNA
<213> ORGANISM: Artificial Sequence
<220> FEATURE:
<223> OTHER INFORMATION: Primer

<400> SEQUENCE: 159
ctgtagaaaa tcctagctgg ag                                           22

<210> SEQ ID NO 160
<211> LENGTH: 21
<212> TYPE: DNA
<213> ORGANISM: Artificial Sequence
<220> FEATURE:
<223> OTHER INFORMATION: Primer

<400> SEQUENCE: 160
cataaccagt cggtacagct a                                            21

<210> SEQ ID NO 161
<211> LENGTH: 20
<212> TYPE: DNA
<213> ORGANISM: Artificial Sequence
<220> FEATURE:
<223> OTHER INFORMATION: Primer

<400> SEQUENCE: 161
ttatcacccg cgaagaagct                                              20

<210> SEQ ID NO 162
<211> LENGTH: 22
<212> TYPE: DNA
<213> ORGANISM: Artificial Sequence
<220> FEATURE:
<223> OTHER INFORMATION: Primer

<400> SEQUENCE: 162
ctctagttgc atgacagccc tc                                           22

<210> SEQ ID NO 163
<211> LENGTH: 24
<212> TYPE: DNA
<213> ORGANISM: Artificial Sequence
<220> FEATURE:
<223> OTHER INFORMATION: Primer

<400> SEQUENCE: 163
tcgtgcgtgg attggctttg atgt                                         24

<210> SEQ ID NO 164
<211> LENGTH: 24
<212> TYPE: DNA
<213> ORGANISM: Artificial Sequence
<220> FEATURE:
<223> OTHER INFORMATION: Primer

<400> SEQUENCE: 164
gggttgggac tatcctaagt gtga                                         24
```

```
<210> SEQ ID NO 165
<211> LENGTH: 22
<212> TYPE: DNA
<213> ORGANISM: Artificial Sequence
<220> FEATURE:
<223> OTHER INFORMATION: Primer

<400> SEQUENCE: 165
taacacacaa acaccatcat ca                                              22

<210> SEQ ID NO 166
<211> LENGTH: 23
<212> TYPE: DNA
<213> ORGANISM: Artificial Sequence
<220> FEATURE:
<223> OTHER INFORMATION: Primer

<400> SEQUENCE: 166
ggttgggact atcctaagtg tga                                             23

<210> SEQ ID NO 167
<211> LENGTH: 24
<212> TYPE: DNA
<213> ORGANISM: Artificial Sequence
<220> FEATURE:
<223> OTHER INFORMATION: Primer

<400> SEQUENCE: 167
ccatcatcag atagaatcat cata                                            24

<210> SEQ ID NO 168
<211> LENGTH: 21
<212> TYPE: DNA
<213> ORGANISM: Artificial Sequence
<220> FEATURE:
<223> OTHER INFORMATION: Primer

<400> SEQUENCE: 168
cctctcttgt tcttgctcgc a                                               21

<210> SEQ ID NO 169
<211> LENGTH: 21
<212> TYPE: DNA
<213> ORGANISM: Artificial Sequence
<220> FEATURE:
<223> OTHER INFORMATION: Primer

<400> SEQUENCE: 169
tatagtgagc cgccacacat g                                               21

<210> SEQ ID NO 170
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(12)
<223> OTHER INFORMATION: n is a, c, g, or t

<400> SEQUENCE: 170
taacacacaa cnccatcatc a                                               21

<210> SEQ ID NO 171
<211> LENGTH: 21
```

```
<212> TYPE: DNA
<213> ORGANISM: Artificial Sequence
<220> FEATURE:
<223> OTHER INFORMATION: Primer

<400> SEQUENCE: 171
ctaacatgct taggataatg g                                              21

<210> SEQ ID NO 172
<211> LENGTH: 21
<212> TYPE: DNA
<213> ORGANISM: Artificial Sequence
<220> FEATURE:
<223> OTHER INFORMATION: Primer

<400> SEQUENCE: 172
gcctctcttg ttcttgctcg c                                              21

<210> SEQ ID NO 173
<211> LENGTH: 21
<212> TYPE: DNA
<213> ORGANISM: Artificial Sequence
<220> FEATURE:
<223> OTHER INFORMATION: Primer

<400> SEQUENCE: 173
caggtaagcg taaaactcat c                                              21

<210> SEQ ID NO 174
<211> LENGTH: 17
<212> TYPE: DNA
<213> ORGANISM: Artificial Sequence
<220> FEATURE:
<223> OTHER INFORMATION: Primer

<400> SEQUENCE: 174
tacacacctc agcgttg                                                   17

<210> SEQ ID NO 175
<211> LENGTH: 16
<212> TYPE: DNA
<213> ORGANISM: Artificial Sequence
<220> FEATURE:
<223> OTHER INFORMATION: Primer

<400> SEQUENCE: 175
cacgaacgtg acgaat                                                    16

<210> SEQ ID NO 176
<211> LENGTH: 20
<212> TYPE: DNA
<213> ORGANISM: Artificial Sequence
<220> FEATURE:
<223> OTHER INFORMATION: Primer

<400> SEQUENCE: 176
gccggagctc tgcagaattc                                                20

<210> SEQ ID NO 177
<211> LENGTH: 47
<212> TYPE: DNA
<213> ORGANISM: Artificial Sequence
<220> FEATURE:
<223> OTHER INFORMATION: Primer

<400> SEQUENCE: 177
```
caggaaacag ctatgacttg catcaccact agttgtgcca ccaggtt                47

<210> SEQ ID NO 178
<211> LENGTH: 46
<212> TYPE: DNA
<213> ORGANISM: Artificial Sequence
<220> FEATURE:
<223> OTHER INFORMATION: Primer

<400> SEQUENCE: 178
tgtaaaacga cggccagttg atgggatggg actatcctaa gtgtga                46

<210> SEQ ID NO 179
<211> LENGTH: 20
<212> TYPE: DNA
<213> ORGANISM: Artificial Sequence
<220> FEATURE:
<223> OTHER INFORMATION: Primer

<400> SEQUENCE: 179
gcataggcag tagttgcatc                                              20

<210> SEQ ID NO 180
<211> LENGTH: 8
<212> TYPE: PRT
<213> ORGANISM: Artificial Sequence
<220> FEATURE:
<223> OTHER INFORMATION: ATP Binding Domain
<220> FEATURE:
<221> NAME/KEY: MISC_FEATURE
<222> LOCATION: (1)..(1)
<223> OTHER INFORMATION: Xaa = A or G
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa = S or T

<400> SEQUENCE: 180

Xaa Xaa Xaa Xaa Xaa Gly Lys Xaa
1               5

<210> SEQ ID NO 181
<211> LENGTH: 23
<212> TYPE: PRT
<213> ORGANISM: Severe acute respiratory syndrome virus

<400> SEQUENCE: 181

Trp Tyr Val Trp Leu Gly Phe Ile Ala Gly Leu Ile Ala Ile Val Met
1               5                   10                  15

Val Thr Ile Leu Leu Cys Cys
            20

<210> SEQ ID NO 182
<211> LENGTH: 16
<212> TYPE: PRT
<213> ORGANISM: Severe acute respiratory syndrome virus

<400> SEQUENCE: 182

Met Asp Leu Phe Met Arg Phe Phe Thr Leu Arg Ser Ile Thr Ala Gln
1               5                   10                  15

<210> SEQ ID NO 183
<211> LENGTH: 150

```
-continued

<212> TYPE: PRT
<213> ORGANISM: Severe acute respiratory syndrome virus

<400> SEQUENCE: 183

Met Arg Cys Trp Leu Cys Trp Lys Cys Lys Ser Lys Asn Pro Leu Leu
1               5                   10                  15

Tyr Asp Ala Asn Tyr Phe Val Cys Trp His Thr His Asn Tyr Asp Tyr
            20                  25                  30

Cys Ile Pro Tyr Asn Ser Val Thr Asp Thr Ile Val Val Thr Glu Gly
        35                  40                  45

Asp Gly Ile Ser Thr Pro Lys Leu Lys Glu Asp Tyr Gln Ile Gly Gly
    50                  55                  60

Tyr Ser Glu Asp Arg His Ser Gly Val Lys Asp Tyr Val Val Val His
65                  70                  75                  80

Gly Tyr Phe Thr Glu Val Tyr Tyr Gln Leu Glu Ser Thr Gln Ile Thr
                85                  90                  95

Thr Asp Thr Gly Ile Glu Asn Ala Thr Phe Phe Ile Phe Asn Lys Leu
            100                 105                 110

Val Lys Asp Pro Pro Asn Val Gln Ile His Thr Ile Asp Gly Ser Ser
        115                 120                 125

Gly Val Ala Asn Pro Ala Met Asp Pro Ile Tyr Asp Glu Pro Thr Thr
    130                 135                 140

Thr Thr Ser Val Pro Leu
145                 150

<210> SEQ ID NO 184
<211> LENGTH: 20
<212> TYPE: PRT
<213> ORGANISM: Severe acute respiratory syndrome virus

<400> SEQUENCE: 184

Met Met Pro Thr Thr Leu Phe Ala Gly Thr His Ile Thr Met Thr Thr
1               5                   10                  15

Val Tyr His Ile
            20

<210> SEQ ID NO 185
<211> LENGTH: 42
<212> TYPE: PRT
<213> ORGANISM: Severe acute respiratory syndrome virus

<400> SEQUENCE: 185

Thr Ala Leu Arg Leu Cys Ala Tyr Cys Cys Asn Ile Val Asn Val Ser
1               5                   10                  15

Leu Val Lys Pro Thr Val Tyr Val Tyr Ser Arg Val Lys Asn Leu Asn
            20                  25                  30

Ser Ser Glu Gly Val Pro Asp Leu Leu Val
        35                  40

<210> SEQ ID NO 186
<211> LENGTH: 39
<212> TYPE: PRT
<213> ORGANISM: Severe acute respiratory syndrome virus

<400> SEQUENCE: 186

Met Ala Asp Asn Gly Thr Ile Thr Val Glu Glu Leu Lys Gln Leu Leu
1               5                   10                  15

Glu Gln Trp Asn Leu Val Ile Gly Phe Leu Phe Leu Ala Trp Ile Met
            20                  25                  30
```

```
Leu Leu Gln Phe Ala Tyr Ser
        35

<210> SEQ ID NO 187
<211> LENGTH: 100
<212> TYPE: PRT
<213> ORGANISM: Severe acute respiratory syndrome virus

<400> SEQUENCE: 187

Pro Leu Arg Gly Thr Ile Val Thr Arg Pro Leu Met Glu Ser Glu Leu
1               5                   10                  15

Val Ile Gly Ala Val Ile Ile Arg Gly His Leu Arg Met Ala Gly His
            20                  25                  30

Ser Leu Gly Arg Cys Asp Ile Lys Asp Leu Pro Lys Glu Ile Thr Val
        35                  40                  45

Ala Thr Ser Arg Thr Leu Ser Tyr Tyr Lys Leu Gly Ala Ser Gln Arg
    50                  55                  60

Val Gly Thr Asp Ser Gly Phe Ala Ala Tyr Asn Arg Tyr Arg Ile Gly
65                  70                  75                  80

Asn Tyr Lys Leu Asn Thr Asp His Ala Gly Ser Asn Asp Asn Ile Ala
                85                  90                  95

Leu Leu Val Gln
            100

<210> SEQ ID NO 188
<211> LENGTH: 23
<212> TYPE: PRT
<213> ORGANISM: Severe acute respiratory syndrome virus

<400> SEQUENCE: 188

Phe Tyr Leu Cys Phe Leu Ala Phe Leu Leu Phe Leu Val Leu Ile Met
1               5                   10                  15

Leu Ile Ile Phe Trp Phe Ser
            20

<210> SEQ ID NO 189
<211> LENGTH: 19
<212> TYPE: PRT
<213> ORGANISM: Severe acute respiratory syndrome virus

<400> SEQUENCE: 189

Leu Leu Ile Val Leu Thr Cys Ile Ser Leu Cys Ser Cys Ile Cys Thr
1               5                   10                  15

Val Val Gln

<210> SEQ ID NO 190
<211> LENGTH: 24
<212> TYPE: PRT
<213> ORGANISM: Severe acute respiratory syndrome virus

<400> SEQUENCE: 190

Ile Cys Thr Val Val Gln Arg Cys Ala Ser Asn Lys Pro His Val Leu
1               5                   10                  15

Glu Asp Pro Cys Lys Val Gln His
            20

<210> SEQ ID NO 191
<211> LENGTH: 22
<212> TYPE: PRT
<213> ORGANISM: Severe acute respiratory syndrome virus
```

<400> SEQUENCE: 191

Cys Ile Cys Thr Val Val Gln Arg Cys Ala Ser Asn Lys Pro His Val
1               5                   10                  15

Leu Glu Asp Pro Cys Lys
            20

<210> SEQ ID NO 192
<211> LENGTH: 22
<212> TYPE: PRT
<213> ORGANISM: Severe acute respiratory syndrome virus

<400> SEQUENCE: 192

Val Val Ala Val Ile Gln Glu Ile Gln Leu Leu Ala Ala Val Gly Glu
1               5                   10                  15

Ile Leu Leu Leu Glu Trp
            20

<210> SEQ ID NO 193
<211> LENGTH: 19
<212> TYPE: DNA
<213> ORGANISM: Artificial Sequence
<220> FEATURE:
<223> OTHER INFORMATION: Linker

<400> SEQUENCE: 193
aattcgcggc cgcgtcgac                                              19

<210> SEQ ID NO 194
<211> LENGTH: 15
<212> TYPE: DNA
<213> ORGANISM: Artificial Sequence
<220> FEATURE:
<223> OTHER INFORMATION: Linker

<400> SEQUENCE: 194
gtcgacgcgg ccgcg                                                  15

<210> SEQ ID NO 195
<211> LENGTH: 19
<212> TYPE: DNA
<213> ORGANISM: Artificial Sequence
<220> FEATURE:
<223> OTHER INFORMATION: Primer

<400> SEQUENCE: 195
aattcgcggc cgcgtcgac                                              19

<210> SEQ ID NO 196
<211> LENGTH: 19
<212> TYPE: DNA
<213> ORGANISM: Artificial Sequence
<220> FEATURE:
<223> OTHER INFORMATION: Primer

<400> SEQUENCE: 196
ggcctcttcg ctattacgc                                              19

<210> SEQ ID NO 197
<211> LENGTH: 21
<212> TYPE: DNA
<213> ORGANISM: Artificial Sequence
<220> FEATURE:
<223> OTHER INFORMATION: Primer -continued

<400> SEQUENCE: 197
tgcaggtcga ctctagagga t								21

<210> SEQ ID NO 198
<211> LENGTH: 410
<212> TYPE: PRT
<213> ORGANISM: Avian infectious bronchitis virus

<400> SEQUENCE: 198

```
Met Ala Ser Gly Lys Ala Ala Gly Lys Thr Asp Ala Pro Ala Pro Val
1               5                   10                  15

Ile Lys Leu Gly Gly Pro Lys Pro Lys Val Gly Ser Ser Gly Asn
            20                  25                  30

Ala Ser Trp Phe Gln Ala Ile Lys Ala Lys Leu Asn Thr Pro Pro
        35                  40                  45

Pro Lys Phe Glu Gly Ser Gly Val Pro Asp Asn Glu Asn Ile Lys Pro
    50                  55                  60

Ser Gln Gln His Gly Tyr Trp Arg Arg Gln Ala Arg Phe Lys Pro Gly
65                  70                  75                  80

Lys Gly Gly Arg Lys Pro Val Pro Asp Ala Trp Tyr Phe Tyr Tyr Thr
                85                  90                  95

Gly Thr Gly Pro Ala Ala Asp Leu Asn Trp Gly Asp Thr Gln Asp Gly
            100                 105                 110

Ile Val Trp Val Ala Ala Lys Gly Ala Asp Thr Lys Ser Arg Ser Asn
        115                 120                 125

Gln Gly Thr Arg Asp Pro Asp Lys Phe Asp Gln Tyr Pro Leu Arg Phe
    130                 135                 140

Ser Asp Gly Gly Pro Asp Gly Asn Phe Arg Trp Asp Phe Ile Pro Leu
145                 150                 155                 160

Lys Asn Arg Gly Arg Ser Gly Arg Ser Thr Ala Ala Ser Ser Ala Ala
                165                 170                 175

Ala Ser Arg Ala Pro Ser Arg Glu Gly Ser Arg Gly Arg Arg Ser Asp
            180                 185                 190

Ser Gly Asp Asp Leu Ile Ala Arg Ala Ala Lys Ile Ile Gln Asp Gln
        195                 200                 205

Gln Lys Lys Gly Ser Arg Ile Thr Lys Ala Lys Ala Asp Glu Met Ala
    210                 215                 220

His Arg Arg Tyr Cys Lys Arg Thr Ile Pro Pro Asn Tyr Arg Val Asp
225                 230                 235                 240

Gln Val Phe Gly Pro Arg Thr Lys Gly Lys Glu Gly Asn Phe Gly Asp
                245                 250                 255

Asp Lys Met Asn Glu Glu Gly Ile Lys Asp Gly Arg Val Thr Ala Met
            260                 265                 270

Leu Asn Leu Val Pro Ser Ser His Ala Cys Leu Phe Gly Ser Arg Val
        275                 280                 285

Thr Pro Lys Leu Gln Leu Asp Gly Leu His Leu Arg Phe Glu Phe Thr
    290                 295                 300

Thr Val Val Pro Cys Asp Asp Pro Gln Phe Asp Asn Tyr Val Lys Ile
305                 310                 315                 320

Cys Asp Gln Cys Val Asp Gly Val Gly Thr Arg Pro Lys Asp Glu
                325                 330                 335

Pro Lys Pro Lys Ser Arg Ser Ser Arg Pro Ala Thr Arg Gly Asn
            340                 345                 350

Ser Pro Ala Pro Arg Gln Gln Arg Pro Lys Lys Glu Lys Lys Leu Lys
```

```
                355                 360                 365
Lys Gln Asp Asp Glu Ala Asp Lys Ala Leu Thr Ser Asp Glu Glu Arg
        370                 375                 380

Asn Asn Ala Gln Leu Glu Phe Tyr Asp Glu Pro Lys Val Ile Asn Trp
385                 390                 395                 400

Gly Asp Ala Ala Leu Gly Glu Asn Glu Leu
                405                 410

<210> SEQ ID NO 199
<211> LENGTH: 30
<212> TYPE: PRT
<213> ORGANISM: conotoxin

<400> SEQUENCE: 199

Cys Ile Ala Val Gly Gln Leu Cys Val Phe Trp Asn Ile Gly Arg Pro
1               5                   10                  15

Cys Cys Ser Gly Leu Cys Val Phe Ala Cys Thr Val Lys Leu
            20                  25                  30

<210> SEQ ID NO 200
<211> LENGTH: 31
<212> TYPE: PRT
<213> ORGANISM: Severe acute respiratory syndrome virus

<400> SEQUENCE: 200

Cys Ile Ser Leu Cys Ser Cys Ile Cys Thr Val Val Gln Arg Cys Ala
1               5                   10                  15

Ser Asn Lys Pro His Val Leu Glu Asp Pro Cys Lys Val Gln His
            20                  25                  30

<210> SEQ ID NO 201
<211> LENGTH: 310
<212> TYPE: DNA
<213> ORGANISM: Severe acute respiratory syndrome virus

<400> SEQUENCE: 201
cgatgtttca tcttgttgac ttccaggtta caatagcaga gatattgatt atcattatga     60
ggactttcag gattgctatt tggaatcttg acgttataat aagttcaata gtgagacaat    120
tatttaagcc tctaactaag aagaattatt cggagttaga tgatgaagaa cctatgggagt    180 tagattatcc ataaaacgaa catgaaaatt attctcttcc tgacattgat gtatttaca    240 tcttgcgagc tatatcacta tcaggagtgt gttagaggta cgactgtact actaaaagaa    300
ccttgcccat                                                          310

<210> SEQ ID NO 202
<211> LENGTH: 556
<212> TYPE: DNA
<213> ORGANISM: Severe acute respiratory syndrome virus

<400> SEQUENCE: 202
agaaagacag aatgaatgag ctcactttaa ttgacttcta tttgtgcttt ttagcctttc     60
tgctattcct tgttttaata atgcttatta tattttggtt tcactcgaa atccaggatc    120 tagaagaacc ttgtaccaaa gtctaaacga acatgaaact tctcattgtt ttgacttgta    180
tttctctatg cagttgcata tgcactgtag tacagcgctg tgcatctaat aaacctcatg    240
tgcttgaaga tccttgtaag gtacaacact aggggtaata cttatagcac tgcttggctt    300
tgtgctctag gaaaggtttt accttttcat agatggcaca ctatggttca acatgcaca    360
```

```
cctaatgtta ctatcaactg tcaagatcca gctggtggtg cgcttatagc taggtgttgg    420
taccttcatg aaggtcacca aactgctgca tttagagacg tacttgttgt tttaaataaa    480
cgaacaaatt aaaatgtctg ataatggacc ccaatcaaac caacgtagtg ccccccgcat    540
tacatttggt ggaccc                                                   556
```

<210> SEQ ID NO 203
<211> LENGTH: 1255
<212> TYPE: PRT
<213> ORGANISM: Severe acute respiratory syndrome virus

<400> SEQUENCE: 203

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335
```

-continued

```
Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
            355                 360                 365

Val Ser Ala Thr Lys Leu Asn Asp Leu Cys Phe Ser Asn Val Tyr Ala
            370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
            435                 440                 445

Arg Pro Phe Glu Arg Asp Ile Ser Asn Val Pro Phe Ser Pro Asp Gly
450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
            530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
            595                 600                 605

Ala Ile His Ala Asp Gln Leu Thr Pro Ala Trp Arg Ile Tyr Ser Thr
            610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
```

-continued

```
            755                 760                 765
Gln Met Tyr Lys Thr Pro Thr Leu Lys Tyr Phe Gly Gly Phe Asn Phe
770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
                835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
                900                 905                 910

Ile Ser Gln Ile Gln Glu Ser Leu Thr Thr Thr Ser Thr Ala Leu Gly
                915                 920                 925

Lys Leu Gln Asp Val Val Asn Gln Asn Ala Gln Ala Leu Asn Thr Leu
                930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
                980                 985                 990

Gln Leu Ile Arg Ala Ala Glu Ile  Arg Ala Ser Ala Asn  Leu Ala Ala
                995                 1000                1005

Thr Lys Met Ser Glu Cys Val  Leu Gly Gln Ser Lys  Arg Val Asp
    1010                1015                1020

Phe Cys Gly Lys Gly Tyr His  Leu Met Ser Phe Pro  Gln Ala Ala
    1025                1030                1035

Pro His Gly Val Val Phe Leu  His Val Thr Tyr Val  Pro Ser Gln
    1040                1045                1050

Glu Arg Asn Phe Thr Thr Ala  Pro Ala Ile Cys His  Glu Gly Lys
    1055                1060                1065

Ala Tyr Phe Pro Arg Glu Gly  Val Phe Val Phe Asn  Gly Thr Ser
    1070                1075                1080

Trp Phe Ile Thr Gln Arg Asn  Phe Phe Ser Pro Gln  Ile Ile Thr
    1085                1090                1095

Thr Asp Asn Thr Phe Val Ser  Gly Asn Cys Asp Val  Val Ile Gly
    1100                1105                1110

Ile Ile Asn Asn Thr Val Tyr  Asp Pro Leu Gln Pro  Glu Leu Asp
    1115                1120                1125

Ser Phe Lys Glu Glu Leu Asp  Lys Tyr Phe Lys Asn  His Thr Ser
    1130                1135                1140

Pro Asp Val Asp Leu Gly Asp  Ile Ser Gly Ile Asn  Ala Ser Val
    1145                1150                1155

Val Asn Ile Gln Lys Glu Ile  Asp Arg Leu Asn Glu  Val Ala Lys
    1160                1165                1170
```

-continued

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255

<210> SEQ ID NO 204
<211> LENGTH: 422
<212> TYPE: PRT
<213> ORGANISM: Severe acute respiratory syndrome virus

<400> SEQUENCE: 204

Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45

Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
    130                 135                 140

Asp His Ile Gly Thr Arg Asn Pro Asn Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Gly Glu Thr Ala Leu Ala Leu Leu Leu
    210                 215                 220

Leu Asp Arg Leu Asn Gln Leu Glu Ser Lys Val Ser Gly Lys Gly Gln
225                 230                 235                 240

Gln Gln Gln Gly Gln Thr Val Thr Lys Lys Ser Ala Ala Glu Ala Ser
                245                 250                 255

Lys Lys Pro Arg Gln Lys Arg Thr Ala Thr Lys Gln Tyr Asn Val Thr
            260                 265                 270

Gln Ala Phe Gly Arg Arg Gly Pro Glu Gln Thr Gln Gly Asn Phe Gly

```
                  275                 280                 285
Asp Gln Asp Leu Ile Arg Gln Gly Thr Asp Tyr Lys His Trp Pro Gln
    290                 295                 300

Ile Ala Gln Phe Ala Pro Ser Ala Ser Ala Phe Phe Gly Met Ser Arg
305                 310                 315                 320

Ile Gly Met Glu Val Thr Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
        355                 360                 365

Pro Lys Lys Asp Lys Lys Lys Thr Asp Glu Ala Gln Pro Leu Pro
    370                 375                 380

Gln Arg Gln Lys Lys Gln Pro Thr Val Thr Leu Leu Pro Ala Ala Asp
385                 390                 395                 400

Met Asp Asp Phe Ser Arg Gln Leu Gln Asn Ser Met Ser Gly Ala Ser
                405                 410                 415

Ala Asp Ser Thr Gln Ala
            420

<210> SEQ ID NO 205
<211> LENGTH: 221
<212> TYPE: PRT
<213> ORGANISM: Sars associated coronavirus

<400> SEQUENCE: 205

Met Ala Asp Asn Gly Thr Ile Thr Val Glu Glu Leu Lys Gln Leu Leu
1               5                   10                  15

Glu Gln Trp Asn Leu Val Ile Gly Phe Leu Phe Leu Ala Trp Ile Met
            20                  25                  30

Leu Leu Gln Phe Ala Tyr Ser Asn Arg Asn Arg Phe Leu Tyr Ile Ile
        35                  40                  45

Lys Leu Val Phe Leu Trp Leu Leu Trp Pro Val Thr Leu Ala Cys Phe
    50                  55                  60

Val Leu Ala Ala Val Tyr Arg Ile Asn Trp Val Thr Gly Gly Ile Ala
65                  70                  75                  80

Ile Ala Met Ala Cys Ile Val Gly Leu Met Trp Leu Ser Tyr Phe Val
                85                  90                  95

Ala Ser Phe Arg Leu Phe Ala Arg Thr Arg Ser Met Trp Ser Phe Asn
            100                 105                 110

Pro Glu Thr Asn Ile Leu Leu Asn Val Pro Leu Arg Gly Thr Ile Val
        115                 120                 125

Thr Arg Pro Leu Met Glu Ser Glu Leu Val Ile Gly Ala Val Ile Ile
    130                 135                 140

Arg Gly His Leu Arg Met Ala Gly His Ser Leu Gly Arg Cys Asp Ile
145                 150                 155                 160

Lys Asp Leu Pro Lys Glu Ile Thr Val Ala Thr Ser Arg Thr Leu Ser
                165                 170                 175

Tyr Tyr Lys Leu Gly Ala Ser Gln Arg Val Gly Thr Asp Ser Gly Phe
            180                 185                 190

Ala Ala Tyr Asn Arg Tyr Arg Ile Gly Asn Tyr Lys Leu Asn Thr Asp
        195                 200                 205

His Ala Gly Ser Asn Asp Asn Ile Ala Leu Leu Val Gln
    210                 215                 220
```

```
<210> SEQ ID NO 206
<211> LENGTH: 76
<212> TYPE: PRT
<213> ORGANISM: Severe acute respiratory syndrome virus

<400> SEQUENCE: 206

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60

Leu Asn Ser Ser Glu Gly Val Pro Asp Leu Leu Val
65                  70                  75
```

SARS VIRUS NUCLEOTIDE AND AMINO ACID SEQUENCES AND USES THEREOF

Sequence Listing

The instant application contains a Sequence Listing which has been submitted in ASCII format via EFS-Web and is hereby incorporated by reference in its entirety. Said ASCII copy, created on Jan. 18, 2010, is named 308410US.txt and is 462,420 bytes in size.

FIELD OF THE INVENTION

The invention is in the field of virology. More specifically, the invention is in the field of coronaviruses.

BACKGROUND OF THE INVENTION

Severe acute respiratory syndrome (SARS), a worldwide outbreak of atypical pneumonia with an overall mortality rate of about 3 to 6%, has been attributed to a coronavirus following tests of causation according to Koch's postulates, including monkey inoculation (R. Munch, *Microbes Infect* 5, 69-74, January 2003). The coronaviruses are members of a family of enveloped viruses that replicate in the cytoplasm of animal host cells (B. N. Fields et al., *Fields virology*, Lippincott Williams & Wilkins, Philadelphia, 4$^{th}$ ed., 2001). They are distinguished by the presence of a single-stranded plus sense RNA genome, approximately 30 kb in length, that has a 5' cap structure and 3' polyA tract. Hence the genome is essentially a very large mRNA. Upon infection of an appropriate host cell, the 5'-most open reading frame (ORF) of the viral genome is translated into a large polyprotein that is cleaved by viral-encoded proteases to release several nonstructural proteins including an RNA-dependent RNA polymerase (Pol) and an ATPase helicase (Hel). These proteins in turn are responsible for replicating the viral genome as well as generating nested transcripts that are used in the synthesis of the viral proteins. The mechanism by which these subgenomic mRNAs are made is not fully understood, however transcription regulating sequences (TRSs) at the 5'end of each gene may represent signals that regulate the discontinuous transcription of subgenomic mRNAs (sgmRNAs). The TRSs include a partially conserved core sequence (CS) that in some coronaviruses is 5'-CUAAAC-3'. Two major models have been proposed to explain the discontinuous transcription in coronaviruses and arterioviruses (M. M. C. Lai, D. Cavanagh, Adv Virus Res. 48, 1 (1997); S. G. Sawicki, D. L. Sawicki, Adv. Exp. Med Biol. 440, 215 (1998)). The discovery of transcriptionally active, subgenomic-size minus strands containing the antileader sequence and transcription intermediates active in the synthesis of mRNAs (D. L. Sawicki et al., J. Gen Virol 82, 386 (2001); S. G. Sawicki, D. L. Sawicki, J. Virol. 64, 1050 (1990); M. Schaad, R. S. J. Baric, J. Virol. 68, 8169 (1994); P. B. Sethna et al., Proc. Natl. Acad. Sci. U.S.A. 86, 5626 (1989)) favors the model of discontinuous transcription during the minus strand synthesis (S. G. Sawicki, D. L. Sawicki, Adv. Exp. Med Biol. 440, 215 (1998)).

The coronaviral membrane proteins, including the major proteins S (Spike) and M (Membrane), are inserted into the endoplasmic reticulum Golgi intermediate compartment (ERGIC) while full length replicated RNA (+ strands) assemble with the N (nucleocapsid) protein. This RNA-protein complex then associates with the M protein embedded in the membranes of the ER and virus particles form as the nucleocapsid complex buds into the ER. The virus then migrates through the Golgi complex and eventually exits the cell, likely by exocytosis (B. N. Fields et al., *Fields virology*, Lippincott Williams & Wilkins, Philadelphia, 4$^{th}$ ed., 2001). The site of viral attachment to the host cell resides within the S protein.

The coronaviruses include a large number of viruses that infect different animal species. The predominant diseases associated with these viruses are respiratory and enteric infections, although hepatic and neurological diseases also occur with some viruses. Coronaviruses are divided into three serotypes, Types I, II and III. Phylogenetic analysis of coronavirus sequences also identifies three main classes of these viruses, corresponding to each of the three serotypes. Type II coronaviruses contain a hemagglutinin esterase (HE) gene homologous to that of Influenza C virus. It is presumed that the precursor of the Type II coronaviruses acquired HE as a result of a recombination event within a doubly infected host cell.

In view of the rapid worldwide dissemination of SARS, which has the potential of creating a pandemic, along with its alarming morbidity and mortality rates, it would be useful to have a better understanding of this coronavirus agent at the molecular level to provide diagnostics, vaccines, and therapeutics, and to support public health control measures.

SUMMARY OF THE INVENTION

In general, the invention provides the genomic sequence of a novel coronavirus, the SARS virus, and provides novel nucleic acid molecules encoding novel proteins that may be used, for example, for the diagnosis or therapy of a variety of SARS virus-related disorders.

In one aspect, the invention provides a substantially pure SARS virus nucleic acid molecule or fragment thereof, for example, a genomic RNA or DNA, cDNA, synthetic DNA, or mRNA molecule. In some embodiments, the nucleic acid molecule includes a sequence substantially identical to any of the sequences of SEQ ID NOs: 1-13, 15-18, 20-30, 90-159, 208, 209. In some embodiments, the nucleic acid molecule includes a sequence from SEQ ID NO: 1, SEQ ID NO:2, or SEQ ID NO: 15 or a fragment of these sequences. In alternative embodiments, the nucleic acid molecule may include a sequence substantially identical to SEQ ID NO: 1, SEQ ID NO:2, or SEQ ID NO: 15, or a fragment thereof In alternative embodiments, the nucleic acid molecule may include a s2m motif (for example, a s2m sequence substantially identical to any of the sequence of SEQ ID NOs: 16, 17, and 18), a leader sequence (for example, a sequence substantially identical to the sequence of SEQ ID NO: 3), or a transcriptional regulatory sequence (for example, a sequence substantially identical to any of the sequence of SEQ ID NOs: 4-13 and 20-30). In alternative embodiments, the nucleic acid molecule includes a sequence substantially identical to any of the sequences of nucleotides 265-13,398; 13,398-21,485; 21,492-25,259; 25,268-26,092; 25,689-26,153; 26,117-26,347; 26,398-27,063; 27,074-27,265; 27,273-27,641; 27,638-27,772; 27,779-27,898; 27,864-28,118; 28,120-29,388; 28,130-28,426; 28,583-28,795; and 29,590-29,621 of SEQ ID NO: 15. In alternative embodiments, the nucleic acid molecule may encode a polyprotein or a polypeptide. In alternative embodiments, the invention provides a nucleic acid molecule including a sequence complementary to a SARS virus nucleotide sequence.

In an alternative aspect, the invention provides a substantially pure SARS virus polypeptide or fragment thereof, for example, a polyprotein, glycoprotein (for example, a matrix glycoprotein that may include a sequence substantially identical to the sequence of SEQ ID NO: 34), a transmembrane protein (for example, a multitransmembrane protein, a type I transmembrane protein, or a type II transmembrane protein), a RNA binding protein, or a viral envelope protein. In alternative embodiments, the invention provides a replicase 1a protein, replicase 1b protein, a spike glycoprotein, a small envelope protein, a matrix glycoprotein, or a nucleocapsid protein. In alternative embodiments, the invention provides a nucleic acid molecule encoding a SARS virus polypeptide. In alternative embodiments, the SARS virus polypeptide includes an identifiable signal sequence (for example, a signal sequence substantially identical to the sequence of SEQ ID NOs: 76 or 85), a transmembrane domain (for example, a transmembrane domain substantially identical to any of the sequences of SEQ ID NOs: 77-86), a transmembrane anchor, a transmembrane helix, an ATP-binding domain, a nuclear localization signal, a hydrophilic domain, (for example, a hydrophilic domain substantially identical to the sequence of SEQ ID NOs: 87), or a lysine-rich sequence (for example, a sequence substantially identical to the sequence of SEQ ID NO: 14). In alternative embodiments, the SARS virus polypeptide may include a sequence substantially identical to any of the sequences of SEQ ID NOs: 14, 33-36, 64-74, and 76-87.

In alternative embodiments, the invention provides a vector (for example, a gene therapy vector or a cloning vector) including a SARS virus nucleic acid molecule (for example, a molecule including a sequence substantially identical to any of the sequences of SEQ ID NOs: 1-13, 15-18, 20-30, 90-159, 208, 209), or a host cell (for example, a mammalian cell, a yeast, a bacterium, or a nematode cell) including the vector.

In alternative embodiments, the invention provides a nucleic acid molecule having substantial nucleotide sequence identity (for example, 30%, 40%, 50%, 60%, 70%, 80%, 90% or 100% complementarity) to a sequence encoding a SARS virus polypeptide or fragment thereof, for example where the fragment includes at least six amino acids, and where the nucleic acid molecule hybridizes under high stringency conditions to at least a portion of a SARS virus nucleic acid molecule.

In alternative embodiments, the invention provides a nucleic acid molecule having substantial nucleotide sequence identity (for example, 30%, 40%, 50%, 60%, 70%, 80%, 90% or 100% complementarity) to a SARS virus nucleotide sequence, for example where the nucleic acid molecule includes at least ten nucleotides, and where the nucleic acid molecule hybridizes under high stringency conditions to at least a portion of a SARS virus nucleic acid molecule.

In alternative embodiments, the invention provides a nucleic acid molecule comprising a sequence that is antisense to a SARS virus nucleic acid molecule, or an antibody (for example, a neutralizing antibody) that specifically binds to a SARS virus polypeptide.

In alternative embodiments, the invention provides a method for detecting a SARS epitope, such as a virion or polypeptide in a sample, by contacting the sample with an antibody that specifically binds a SARS epitope, such as a virus polypeptide, and determining whether the antibody specifically binds to the polypeptide. In alternative embodiments, the invention provides a method for detecting a SARS virus genome, gene, or homolog or fragment thereof in a sample by contacting a SARS virus nucleic acid molecule, for example where the nucleic acid molecule includes at least ten nucleotides, with a preparation of genomic DNA from the sample, under hybridization conditions providing detection of DNA sequences having nucleotide sequence identity to a SARS virus nucleic acid molecule. In alternative embodiments, the invention provides a method of targeting a protein for secretion from a cell, by attaching a signal sequence from a SARS virus polypeptide to the protein, such that the protein is secreted from the cell.

In alternative aspects, the invention provides a method for eliciting an immune response in an animal, by identifying an animal infected with or at risk for infection with a SARS virus and administering a SARS virus polypeptide or fragment thereof or fragment thereof, or administering a SARS virus nucleic acid molecule encoding a SARS virus polypeptide or fragment thereof to the animal. In alternative embodiments, the administering results in the production of an antibody in the mammal, or results in the generation of cytotoxic or helper T-lymphocytes in the mammal.

In alternative embodiments, the invention provides a kit for detecting the presence of a SARS virus nucleic acid molecule or polypeptide in a sample, where the kit includes a SARS virus nucleic acid molecule, or an antibody that specifically binds a SARS virus polypeptide.

In alternative aspects the invention provides a method for treating or preventing a SARS virus infection by identifying an animal (e.g., a human) infected with or at risk for infection with a SARS virus, and administering a SARS virus nucleic acid molecule or polypeptide, or administering a compound that inhibits pathogenicity or replication of a SARS virus, to the animal. In alternative embodiments, the invention provides the use of a SARS virus nucleic acid molecule or polypeptide for treating or preventing a SARS virus infection.

In alternative aspects the invention provides a method of identifying a compound for treating or preventing a SARS virus infection, by contacting sample including a SARS virus nucleic acid molecule or contacting a SARS virus polypeptide with the compound, where an increase or decrease in the expression or activity of the nucleic acid molecule or the polypeptide identifies a compound for treating or preventing a SARS virus infection.

In alternative aspects the invention provides a vaccine (e.g., a DNA vaccine) including a SARS virus nucleic acid molecule or polypeptide.

In alternative aspects the invention provides a microarray including a plurality of elements, wherein each element includes one or more distinct nucleic acid or amino acid sequences, and where the sequences are selected from a SARS virus nucleic acid molecule or polypeptide, or a antibody that specifically binds a SARS virus nucleic acid molecule or polypeptide.

In alternative aspects the invention provides a computer readable record (e.g., a database) including distinct SARS virus nucleic acid or amino acid sequences.

A "SARS virus" is a virus putatively belonging to the coronavirus family and identified as the causative agent for sudden acute respiratory syndrome (SARS). A SARS virus nucleic acid molecule may include a sequence substantially identical to the nucleotide sequences described herein or fragments thereof. A SARS virus polypeptide may include a sequence substantially identical to a sequence encoded by a SARS virus nucleic acid molecule, or may include a sequence substantially identical to the polypeptide sequences described herein, or fragments thereof.

A compound is "substantially pure" when it is separated from the components that naturally accompany it. Typically, a compound is substantially pure when it is at least 60%, more generally 75% or over 90%, by weight, of the total material in a sample. Thus, for example, a polypeptide that is chemically synthesized or produced by recombinant technology will be generally be substantially free from its naturally associated components. A nucleic acid molecule may be substantially pure when it is not immediately contiguous with (i.e., covalently linked to) the coding sequences with which it is normally contiguous in the naturally occurring genome of the organism from which the DNA of the invention is derived. A nucleic acid molecule may also be substantially pure when it is isolated from the organism in which it is normally found. A substantially pure compound can be obtained, for example, by extraction from a natural source; by expression of a recombinant nucleic acid molecule encoding a polypeptide compound; or by chemical synthesis. Purity can be measured using any appropriate method such as column chromatography, gel electrophoresis, HPLC, etc.

A "substantially identical" sequence is an amino acid or nucleotide sequence that differs from a reference sequence only by one or more conservative substitutions, as discussed herein, or by one or more non-conservative substitutions, deletions, or insertions located at positions of the sequence that do not destroy the biological function of the amino acid or nucleic acid molecule. Such a sequence can be at least 10%, 20%, 30%, 40%, 50%, 52.5%, 55% or 60% or 75%, or more generally at least 80%, 85%, 90%, or 95%, or as much as 99% or 100% identical at the amino acid or nucleotide level to the sequence used for comparison using, for example, the Align Program (Myers and Miller, CABIOS, 1989, 4:11-17) or FASTA. For polypeptides, the length of comparison sequences maybe at least 4, 5, 10, or 15 amino acids, or at least 20, 25, or 30 amino acids. In alternate embodiments, the length of comparison sequences may be at least 35, 40, or 50 amino acids, or over 60, 80, or 100 amino acids. For nucleic acid molecules, the length of comparison sequences may be at least 15, 20, or 25 nucleotides, or at least 30, 40, or 50 nucleotides. In alternate embodiments, the length of comparison sequences may be at least 60, 70, 80, or 90 nucleotides, or over 100, 200, or 500 nucleotides. Sequence identity can be readily measured using publicly available sequence analysis software (e.g., Sequence Analysis Software Package of the Genetics Computer Group, University of Wisconsin Biotechnology Center, 1710 University Avenue, Madison, Wis. 53705, or BLAST software available from the National Library of Medicine, or as described herein). Examples of useful software include the programs Pile-up and PrettyBox. Such software matches similar sequences by assigning degrees of homology to various substitutions, deletions, insertions, and other modifications.

Alternatively, or additionally, two nucleic acid sequences may be "substantially identical" if they hybridize under high stringency conditions. In some embodiments, high stringency conditions are, for example, conditions that allow hybridization comparable with the hybridization that occurs using a DNA probe of at least 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1× Denhardt's solution, 10% dextran sulfate, and 0.1% SDS, at a temperature of 42° C. (These are typical conditions for high stringency northern or Southern hybridizations.) Hybridizations may be carried out over a period of about 20 to 30 minutes, or about 2 to 6 hours, or about 10 to 15 hours, or over 24 hours or more. High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually about 16 nucleotides or longer for PCR or sequencing and about 40 nucleotides or longer for in situ hybridization). The high stringency conditions used in these techniques are well known to those skilled in the art of molecular biology, and examples of them can be found, for example, in Ausubel et al., Current Protocols in Molecular Biology, John Wiley & Sons, New York, N.Y., 1998, which is hereby incorporated by reference.

The terms "nucleic acid" or "nucleic acid molecule" encompass both RNA (plus and minus strands) and DNA, including cDNA, genomic DNA, and synthetic (e.g., chemically synthesized) DNA. The nucleic acid may be double-stranded or single-stranded. Where single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. By "RNA" is meant a sequence of two or more covalently bonded, naturally occurring or modified ribonucleotides. One example of a modified RNA included within this term is phosphorothioate RNA. By "DNA" is meant a sequence of two or more covalently bonded, naturally occurring or modified deoxyribonucleotides. By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

An "isolated nucleic acid" is a nucleic acid molecule that is free of the nucleic acid molecules that normally flank it in the genome or that is free of the organism in which it is normally found. Therefore, an "isolated" gene or nucleic acid molecule is in some cases intended to mean a gene or nucleic acid molecule which is not flanked by nucleic acid molecules which normally (in nature) flank the gene or nucleic acid molecule (such as in genomic sequences) and/or has been completely or partially purified from other transcribed sequences (as in a cDNA or RNA library). In some cases, an isolated nucleic acid molecule is intended to mean the genome of an organism such as a virus. An isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstances, the material may be purified to essential homogeneity, for example as determined by PAGE or column chromatography such as HPLC. The term therefore includes, e.g., a genome; a recombinant nucleic acid incorporated into a vector, such as an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant nucleic acid which is part of a hybrid gene encoding additional polypeptide sequences. Preferably, an isolated nucleic acid comprises at least about 50, 80 or 90 percent (on a molar basis) of all macromolecular species present. Thus, an isolated gene or nucleic acid molecule can include a gene or nucleic acid molecule which is synthesized chemically or by recombinant means. Recombinant DNA contained in a vector are included in the definition of "isolated" as used herein. Also, isolated nucleic acid molecules include recombinant DNA molecules in heterologous host cells, as well as partially or substantially purified DNA molecules in solution. In vivo and in vitro RNA transcripts of the DNA molecules of the present invention are also encompassed by "isolated" nucleic acid molecules. Such isolated nucleic acid molecules are useful in the manufacture of the encoded polypeptide, as probes for isolating homologous sequences (e.g., from other species), for gene mapping (e.g., by in situ hybridization with chromosomes), or for detecting expression of the nucleic acid molecule in tissue (e.g., human tissue, such as peripheral blood), such as by Northern blot analysis.

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

As used herein, "heterologous" in reference to a nucleic acid or protein is a molecule that has been manipulated by human intervention so that it is located in a place other than the place in which it is naturally found. For example, a nucleic acid sequence from one species may be introduced into the genome of another species, or a nucleic acid sequence from one genomic locus may be moved to another genomic or extrachromasomal locus in the same species. A heterologous protein includes, for example, a protein expressed from a heterologous coding sequence or a protein expressed from a recombinant gene in a cell that would not naturally express the protein.

By "antisense," as used herein in reference to nucleic acids, is meant a nucleic acid sequence that is complementary to one strand of a nucleic acid molecule. In some embodiments, an antisense sequence is complementary to the coding strand of a gene, preferably, a SARS virus gene. The preferred antisense nucleic acid molecule is one which is capable of lowering the level of polypeptide encoded by the complementary gene when both are expressed in a cell. In some embodiments, the polypeptide level is lowered by at least 10%, or at least 25%, or at least 50%, as compared to the polypeptide level in a cell expressing only the gene, and not the complementary antisense nucleic acid molecule.

A "probe" or "primer" is a single-stranded DNA or RNA molecule of defined sequence that can base pair to a second DNA or RNA molecule that contains a complementary sequence (the target). The stability of the resulting hybrid molecule depends upon the extent of the base pairing that occurs, and is affected by parameters such as the degree of complementarity between the probe and target molecule, and the degree of stringency of the hybridization conditions. The degree of hybridization stringency is affected by parameters such as the temperature, salt concentration, and concentration of organic molecules, such as formamide, and is determined by methods that are known to those skilled in the art. Probes or primers specific for SARS virus nucleic acid sequences or molecules may vary in length from at least 8 nucleotides to over 500 nucleotides, including any value in between, depending on the purpose for which, and conditions under which, the probe or primer is used. For example, a probe or primer may be 8, 10, 15, 20, or 25 nucleotides in length, or may be at least 30, 40, 50, or 60 nucleotides in length, or maybe over 100, 200, 500, or 1000 nucleotides in length. Probes or primers specific for SARS virus nucleic acid molecules may have greater than 20-30% sequence identity, or at least 55-75% sequence identity, or at least 75-85% sequence identity, or at least 85-99% sequence identity, or 100% sequence identity to the nucleic acid sequences described herein. In various embodiments of the invention, probes having the sequences: 5'-ATg AAT TAC CAA gTC AAT ggT TAC-3', SEQ ID NO: 160; 5'-gAA gCT ATT CgT CAC gTT Cg-3', SEQ ID NO: 161; 5'-CTg TAg AAA ATC CTA gCT ggA g-3', SEQ ID NO: 162; 5'-CAT AAC CAg TCg gTA CAg CTA-3', SEQ ID NO: 163; 5'-TTA TCA CCC gCgAAg AAg CT-3', SEQ ID NO: 164; 5'-CTC TAg TTg CATGAC AgC CCT C-3', SEQ ID NO: 165; 5'-TCg TgC gTg gAT TggCTT TgA TgT-3', SEQ ID NO: 166; 5'-ggg TTg ggA CTA TCC TAA gTg TgA-3', SEQ ID NO: 167; 5'-TAA CAC ACA AAC ACC ATC ATC A-3', SEQ ID NO: 168; 5'-ggT Tgg gAC TAT CCT AAg TgT gA-3', SEQ ID NO: 169; 5'-CCA TCA TCA gAT AgA ATC ATC ATA-3', SEQ ID NO: 170; 5'-CCT CTC TTg TTC TTg CTC gCA-3', SEQ ID NO: 171; 5'-TAT AgT gAg CCg CCA CAC Atg-3', SEQ ID NO: 172; 5'-TAACA-CACAACICCATCATCA-3', SEQ ID NO: 173; 5'-CTAA-CATGCTTAGGATAATGG-3', SEQ ID NO: 174; 5'-GC-CTCTCTTGTTCTTGCTCGC-3', SEQ ID NO: 175; 5'-CAGGTAAGCGTAAAACTCATC-3', SEQ ID NO: 176; 5'-TACACACCTCAGCGTTG-3', SEQ ID NO: 177; 5'-CACGAACGTGACGAAT-3', SEQ ID NO: 178; 5'-GC-CGGAGCTCTGCAGAATTC-3', SEQ ID NO: 179; 5'-CAG-GAAACAGCTATGAC TTGCATCACCACTAGTTGTGC-CACCAGGTT-3', SEQ ID NO: 180; 5'-TGTAAAACGACGGCCAGTTGATGG-GATGGGACTATCCTAAGTGTGA-3', SEQ ID NO: 181; 5'-GCATAGGCAGTAGTTGCATC-3', SEQ ID NO: 182, as well as sequences amplified by specific combinations of these probes, may be excluded from specific uses according to the invention. Probes can be detectably-labeled, either radioactively or non-radioactively, by methods that are known to those skilled in the art. Probes can be used for methods involving nucleic acid hybridization, such as nucleic acid sequencing, nucleic acid amplification by the polymerase chain reaction, single stranded conformational polymorphism (SSCP) analysis, restriction fragment polymorphism (RFLP) analysis, Southern hybridization, northern hybridization, in situ hybridization, electrophoretic mobility shift assay (EMSA), and other methods that are known to those skilled in the art.

By "complementary" is meant that two nucleic acid molecules, e.g., DNA or RNA, contain a sufficient number of nucleotides that are capable of forming Watson-Crick base pairs to produce a region of double-strandedness between the two nucleic acids. Thus, adenine in one strand of DNA or RNA pairs with thymine in an opposing complementary DNA strand or with uracil in an opposing complementary RNA strand. It will be understood that each nucleotide in a nucleic acid molecule need not form a matched Watson-Crick base pair with a nucleotide in an opposing complementary strand to form a duplex.

By "vector" is meant a DNA molecule derived, e.g., from a plasmid, bacteriophage, or mammalian or insect virus, or artificial chromosome, that may be used to introduce a polypeptide, for example a SARS virus polypeptide, into a host cell by means of replication or expression of an operably linked heterologous nucleic acid molecule. By "operably linked" is meant that a nucleic acid molecule such as a gene and one or more regulatory sequences (e.g., promoters, ribosomal binding sites, terminators in prokaryotes; promoters, terminators, enhancers in eukaryotes; leader sequences, etc.) are connected in such a way as to permit the desired function e.g. gene expression when the appropriate molecules (e.g., transcriptional activator proteins) are bound to the regulatory sequences. A vector may contain one or more unique restriction sites and may be capable of autonomous replication in a defined host or vehicle organism such that the cloned sequence is reproducible. By "DNA expression vector" is meant any autonomous element capable of directing the synthesis of a recombinant peptide. Such DNA expression vectors include bacterial plasmids and phages and mammalian and insect plasmids and viruses. A "shuttle vector" is understood as meaning a vector which can be propagated in at least two different cell types, or organisms, for example vectors which are first propagated or replicated in prokaryotes in order for, for example, subsequent transfection into eukaryotic cells. A "replicon" is a unit that is capable of autonomous replication in a cell and may includes plasmids, chromosomes (e.g., mini-chromosomes), cosmids, viruses, etc. A replicon may be a vector.

A "host cell" is any cell, including a prokaryotic or eukaryotic cell, into which a replicon, such as a vector, has been introduced by for example transformation, transfection, or infection.

An "open reading frame" or "ORF" is a nucleic acid sequence that encodes a polypeptide. An ORF may include a coding sequence having i.e., a sequence that is capable of being transcribed into mRNA and/or translated into a protein when combined with the appropriate regulatory sequences. In general, a coding sequence includes a 5' translation start codon and a 3' translation stop codon.

A "leader sequence" is a relatively short nucleotide sequence located at the 5' end of an RNA molecule that acts as a primer for transcription.

A "transcriptional regulatory sequence" "TRS" or "intergenic sequence" is a nucleotide sequence that lies upstream of an open reading frame (ORF) and serves as a template for the reassociation of a nascent RNA strand-polymerase complex.

A "frameshift mutation" is caused by a shift in a open reading frame, generally due to a deletion or addition of at least one nucleotide, such that an alternative polypeptide is ultimately translated.

By "detectably labeled" is meant any means for marking and identifying the presence of a molecule, e.g., an oligonucleotide probe or primer, a gene or fragment thereof, a cDNA molecule, a polypeptide, or an antibody. Methods for detectably-labeling a molecule are well known in the art and include, without limitation, radioactive labeling (e.g., with an isotope such as $^{32}P$ or $^{35}S$) and nonradioactive labeling such as, enzymatic labeling (for example, using horseradish peroxidase or alkaline phosphatase), chemiluminescent labeling, fluorescent labeling (for example, using fluorescein), bioluminescent labeling, antibody detection of a ligand attached to the probe, or detection of double-stranded nucleic acid. Also included in this definition is a molecule that is detectably labeled by an indirect means, for example, a molecule that is bound with a first moiety (such as biotin) that is, in turn, bound to a second moiety that may be observed or assayed (such as fluorescein-labeled streptavidin). Labels also include digoxigenin, luciferases, and aequorin.

A "peptide," "protein," "polyprotein" or "polypeptide" is any chain of two or more amino acids, including naturally occurring or non-naturally occurring amino acids or amino acid analogues, regardless of post-translational modification (e.g., glycosylation or phosphorylation). An "polyprotein", "polypeptide", "peptide" or "protein" of the invention may include peptides or proteins that have abnormal linkages, cross links and end caps, non-peptidyl bonds or alternative modifying groups. Such modified peptides are also within the scope of the invention. The term "modifying group" is intended to include structures that are directly attached to the peptidic structure (e.g., by covalent coupling), as well as those that are indirectly attached to the peptidic structure (e.g., by a stable non-covalent association or by covalent coupling to additional amino acid residues, or mimetics, analogues or derivatives thereof, which may flank the core peptidic structure). For example, the modifying group can be coupled to the amino-terminus or carboxy-terminus of a peptidic structure, or to a peptidic or peptidomimetic region flanling the core domain. Alternatively, the modifying group can be coupled to a side chain of at least one amino acid residue of a peptidic structure, or to a peptidic or peptidomimetic region flanking the core domain (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Modifying groups covalently coupled to the peptidic structure can be attached by means and using methods well known in the art for linking chemical structures, including, for example, amide, alkylamino, carbamate or urea bonds.

A "polyprotein" is the polypeptide that is initially translated from the genome of a plus-stranded RNA virus, for example, a SARS virus. Accordingly, a polyprotein has not been subjected to post-translational processing by proteolytic cleavage into its processed protein products, and therefore, retains its cleavage sites. In some embodiments of the invention, the protease cleavage sites of a polyprotein may be modified, for example, by amino acid substitution, to result in a polyprotein that is incapable of being cleaved into its processed protein products.

An antibody "specifically binds" or "selectively binds" an antigen when it recognizes and binds the antigen, but does not substantially recognize and bind other molecules in a sample, having for example an affinity for the antigen which is 10, 100, 1000 or 10000 times greater than the affinity of the antibody for another reference molecule in a sample. A "neutralizing antibody" is an antibody that selectively interferes with any of the biological activities of a SARS virus polypeptide or polyprotein, for example, replication of the SARS virus, or infection of host cells. A neutralizing antibody may reduce the ability of a SARS virus polypeptide to carry out its specific biological activity by about 50%, or by about 70%, or by about 90% or more, or may completely abolish the ability of a SARS virus polypeptide to carry out its specific biological activity. Any standard assay for the biological activity of any SARS virus polypeptide, for example, assays determining expression levels, ability to infect host cells, or ability to replicate DNA, including those assays described herein or known to those of skill in the art, may be used to assess potentially neutralizing antibodies that are specific for SARS virus polypeptides.

A "signal sequence" is a sequence of amino acids that may be identified, for example by homology or biological activity to a peptide sequence with the known function of targeting a polypeptide to a particular region of the cell. A signal sequence or signal peptide may be a peptide of any length, that is capable of targeting a polypeptide to a particular region of the cell. In some embodiments, the signal sequence may direct the polypeptide to the cellular membrane so that the polypeptide may be secreted. In alternate embodiments, the signal sequence may direct the polypeptide to an intracellular compartment or organelle, such as the Golgi apparatus, or to the surface of a virus, such as the SARS virus. In alternate embodiments, a signal sequence may range from about 13 or 15 amino acids in length to about 60 amino acids in length.

A "transmembrane protein" is an amphipathic protein having a hydrophobic region ("transmembrane domain") that spans the lipid bilayer of the cell membrane from the cytoplasm to the cell surface, or spans the viral envelope, interspersed between hydrophilic regions on both sides of the membrane. The number of hydrophobic regions in an amphipathic protein is often proportional to the number of times that proteins spans the lipid bilayer. Thus, a single transmembrane protein spans the lipid bilayer once, and has a single transmembrane domain, while a multi-transmembrane protein spans the lipid bilayer multiple times. Multi-transmembrane proteins may enable virus entry into a host cell, or act to initiate transduction of a signal from the cell surface to the interior of the cell, for example, by a conformational change upon ligand binding. A "transmembrane anchor" is a transmembrane domain that maintains a polypeptide in its position in the cell membrane or viral envelope and is generally hydrophobic. A transmembrane anchor may generally be in the structure of an alpha helix, i.e., a "transmembrane helix". Multi-transmembrane proteins may have multiple transmembrane alpha-helices.

A "nuclear localization signal" is an amino acid sequence that permits the entry of a polypeptide into the nucleus of a cell through nuclear pores. A nuclear localization signal generally has a cluster of positively charged residues, for example, lysines. A "lysine-rich sequence" is a sequence having at least two contiguous lysine residues, or at least three contiguous lysine residues. In some embodiments, a lysine-rich sequence may be a nuclear localization signal.

An "ATP binding domain" is a consensus domain that is found in many ATP or GTP-binding proteins, and that forms a flexible loop (P-loop) between alpha-helical and beta pleated sheet domains. The general consensus for an ATP binding domain may be (A or G)-XXXXGK-(S or T).

A "RNA binding protein" is a protein that is capable of binding to a RNA molecule (see, for example, "RNA Binding Proteins: New Concepts in Gene Regulation" 1st ed, eds. K. Sandberg and S. E. Mulroney, Kluwers Academic Publishers, 2001). RNA binding proteins may contain common structural features such as arginine-rich tracts, for example, arginines alternating with aspartates, serines, or glycines, or zinc finger regions. RNA binding proteins may also have a common ribonucleotide sequence domain. RNA binding proteins are believed to play diverse roles in modulating post-transcriptional gene expression.

An "immune response" includes, but is not limited to, one or more of the following responses in a mammal: induction of antibodies, B cells, T cells (including helper T cells, suppressor T cells, cytotoxic T cells, γδ T cells) directed specifically to the antigen(s) in a composition or vaccine, following administration of the composition or vaccine. An immune response to a composition or vaccine thus generally includes the development in the host mammal of a cellular and/or antibody-mediated response to the composition or vaccine of interest. In general, the immune response will result in prevention or reduction of infection by a SARS virus.

An "immunogenic fragment" of a polypeptide or nucleic acid molecule refers to an amino acid or nucleotide sequence that elicits an immune response. Thus, an immunogenic fragment may include, without limitation, any portion of any of the SARS virus sequences described herein, or a sequence substantially identical thereto, that includes one or more epitopes (the antigenic determinant i.e., site recognized by a specific immune system cell, such as a T cell or a B cell). An "epitope" may include amino acids in a spatial orientation that they are non-contiguous in the amino acid sequence but are near each other due to the three dimensional conformation of the polypeptide. A epitope may include at least 3, 5, 8, or 10 or more amino acids. Immunogenic fragments or epitopes may be identified using standard methods known to those of skill in the art, such as epitope mapping techniques or antigenicity or hydropathy plots using, for example, the Omiga version 1.0 program from Oxford Molecular Group (see, for example, U.S. Pat. No. 4,708,871). Immunogenic fragments or epitopes may also be identified using methods for determining three dimensional molecule structure such as X-ray crystallography or nuclear magnetic resonance.

A "sample" may be a tissue biopsy, amniotic fluid, cell, blood, serum, plasma, urine, stool, sputum, conjunctiva, or any other specimen, or any extract thereof, obtained from a patient (human or animal), test subject, or experimental animal. A "sample" may also be a cell or cell line created under experimental conditions, and constituents thereof (such as cell culture supernatants, cell fractions, infected cells, etc.). The sample may be analyzed to detect the presence of a SARS virus gene, genome, polypeptide, nucleic acid molecule or virion, or to detect a mutation in a SARS virus gene, expression levels of a SARS virus gene or polypeptide, or the biological function of a SARS virus polypeptide, using methods that are known in the art. For example, methods such as sequencing, single-strand conformational polymorphism (SSCP) analysis, or restriction fragment length polymorphism (RFLP) analysis of PCR products derived from a sample can be used to detect a mutation in a SARS virus gene; ELISA or western blotting can be used to measure levels of SARS virus polypeptide or antibody affinity; northern blotting can be used to measure SARS mRNA levels, or PCR can be used to measure the level of a SARS virus nucleic acid molecule.

Other features and advantages of the invention will be apparent from the following description of the drawings and the invention, and from the claims.

BRIEF DESCRIPTION OF THE DRAWINGS

FIGS. 1A-D show phylogenetic analyses of SARS proteins. Unrooted phylogenetic trees were generated by clustalw (Thompson, J. D. et al., *Nucleic Acids Res* 22, 4673-80, Nov. 11, 1994) bootstrap analysis using 1000 iterations. Genbank accessions for protein sequences are as follows: FIG. 1A: Replicase 1A: BoCov (Bovine Coronavirus): AAL40396, 229E (Human Coronavirus): NP_07355, MHV (Mouse Hepatitis Virus): NP_045298, AIBV (Avian Infectious bronchitis virus): CAC39113, TGEV (Transmissible Gastroenteritis Virus): NP_058423. FIG. 1B: Matrix Glycoprotein: PHEV (Porcine hemagglutinating encephalomyelitis virus): AAL80035, BoCov (Bovine Coronavirus):

NP_150082, AIBV & AIBV2 (Avian infectious bronchitis virus): AAF35863 & AAK83027, MHV (Mouse hepatitis virus): AAF36439, TGEV (Transmissible gastroenteritis virus): NP_058427, 229E & OC43 (Human Coronavirus): NP_073555 & AAA45462, FCV (Feline coronavirus): BAC01160. FIG. 1C: Nucleocapsid: MHV (Mouse hepatitis virus): P18446, BoCov (Bovine coronavirus): NP_150083, AIBV (Avian infectious bronchitis virus): AAK27162, FCV (Feline coronavirus): CAA74230, PTGV (Porcine transmissible gastroenteritis virus): AAM97563, 229E & OC43 (Human coronavirus): NP_073556 & P33469, PHEV (porcine hemagglutinating encephalomyelitis virus): AAL80036, TCV (Turkey coronavirus): AAF23873. FIG. 1D: S (Spike) Protein: BoCov (Bovine coronavirus): AAL40400, MHV (Mouse hepatitis virus): P11225, OC43 & 229E (Human coronavirus): S44241 & AAK32191, PHEV (Porcine hemagglutinating encephalomyelitis virus): AAL80031, PRC (Porcine respiratory coronavirus): AAA46905, PEDV (Porcine epidemic diarrhea virus): CAA80971, CCov (Canine coronavirus): S41453, FICV (Feline infectious peritonitis virus): BAA06805, AIBV (Avian infectious bronchitis virus): AAO34396.

FIGS. 3A-P show nucleotide sequences of the 29,736-base genome of the SARS virus (SEQ ID NOs: 1 and 2).

FIG. 4 shows an alignment of the s2m regions from Avian infectious bronchitis virus (AIBV; SEQ ID NO: 32) and equine rhinovirus serotype 2 (ERV-2; SEQ ID NO: 31) with the 3' untranslated region (UTR; SEQ ID NO: 18) of the SARS virus (TOR2). The conserved areas in the s2m region are indicated by asterisks.

FIG. 5 shows the amino acid sequence of the SARS virus S (Spike) Glycoprotein (SEQ ID NO: 33).

FIG. 6 shows the amino acid sequence of the SARS virus M (Matrix) Glycoprotein (residues 1-220 of SEQ ID NO: 34).

FIG. 7 shows the amino acid sequence of the SARS virus E (Small envelope) protein (SEQ ID NO: 35).

FIG. 8 shows the amino acid sequence of the SARS virus N (Nucleocapsid) Protein (SEQ ID NO: 36).

FIG. 9 shows an alignment of the matrix glycoprotein M from the SARS virus (Tor2_M or ORF5; SEQ ID NO: 34) and various other matrix glycoproteins (SEQ ID NOs: 37-43). Asterisks (*) indicate percentage identity to the SARS matrix protein as calculated by Align (Myers and Miller, CABIOS (1989) 4:11-17).

FIGS. 10A-B show an alignment of the nucleocapsid protein N from tehj SARS virus (Tor2_N; SEQ ID NO: 36) and various other nucleocapsid proteins (SEQ ID NOs: 44-52; and SEQ ID NO: 199 of AIBV2 nucleocapsid protein [Avian infectious bronchitis virus 2]). Asterisks (*) indicate percentage identity to the SARS nucleocapsid protein calculated by Align (Myers and Miller, CABIOS (1989) 4:11-17).

FIGS. 11A-K show the nucleotide sequence of the 29,751-base genome of the SARS virus (SEQ ID NO: 15).

FIGS. 13A-D show phylogenetic analyses of SARS proteins. Unrooted phylogenetic trees were generated by clustalw 1.74 (J. D. Thompson, D. G. Higgins, T. J. Gibson, Nucleic Acids Res 22, 4673-80 (Nov. 11, 1994) using the BLOSUM comparison matrix and a bootstrap analysis of 1000 iterations. Numbers indicate bootstrap replicates supporting each node. Phylogenetic trees were drawn with the Phylip Drawtree program 3.6a3 (Felsenstein, J. 1993. PHYLIP (Phylogeny Inference Package) version 3.5c. Distributed by the author. Department of Genetics, University of Washington, Seattle). Branch lengths indicate the number of substitutions per residue. Genbank accessions for protein sequences: A: Replicase 1A: BoCoV (Bovine Coronavirus): AAL40396, HCoV-229E (Human Coronavirus):NP_07355, MHV (Mouse Hepatitis Virus): NP_045298, IBV (Avian Infectious bronchitis virus): CAC39113, TGEV (Transmissible Gastroenteritis Virus): NP_058423. B: Membrane Glycoprotein: PHEV (Porcine hemagglutinating encephalomyelitis virus): AAL80035, BoCoV (Bovine Coronavirus):NP_150082, IBV & IBV2 (Avian infectious bronchitis virus): AAF35863 & AAK83027, MHV (Mouse hepatitis virus): AAF36439, TGEV (Transmissible gastroenteritis virus): NP_058427, HCoV-229E & HCoV-OC43 (Human Coronavirus): NP_073555 & AAA45462, FCoV (Feline coronavirus): BAC01160. C: Nucleocapsid: MHV (Mouse hepatitis virus): P18446, BoCoV (Bovine coronavirus): NP_150083, IBV 1 & 2 (Avian infectious bronchitis virus): AAK27162 & NP_040838, FCoV (Feline coronavirus): CAA74230, PTGV (Porcine transmissible gastroenteritis virus): AAM97563, HCoV-229E & HCoV-OC43 (Human coronavirus): NP_073556 & P33469, PHEV (porcine hemagglutinating encephalomyelitis virus): AAL80036, TCV (Turkey coronavirus): AAF23873. D: S (Spike) Protein: BoCoV (Bovine coronavirus): AAL40400, MHV (Mouse hepatitis virus): P11225, HCoV-OC43 & HCoV-229E (Human coronavirus): S44241 & AAK32191, PHEV (Porcine hemagglutinating encephalomyelitis virus): AAL80031, PRCOV (Porcine respiratory coronavirus): AAA46905, PEDV (Porcine epidemic diarrhea virus): CAA80971, CCoV (Canine coronavirus): S41453, FIPV (Feline infectious peritonitis virus): BAA06805, IBV (Avian infectious bronchitis virus): AAO34396.

FIGS. 14A-F show an alignment of the spike glycoprotein S from the SARS virus (Tor2_S; SEQ ID NO: 33) and various other spike glycoproteins (SEQ ID NOs: 53-62). Asterisks (*) indicate percentage identity to the SARS spike protein as calculated by Align (Myers and Miller, CABIOS (1989) 4:11-17).

FIG. 15 shows an alignment between the SARS virus Small envelope protein E (TOR2_E; SEQ ID NO: 35) and the Envelope protein (Protein 4) (X1 protein) (ORF 3) from Porcine transmissible gastroenteritis coronavirus (strain Purdue). Swissprot accession number P09048 (PGV; SEQ ID NO: 63), as calculated by FASTA (world wide web at ebi "dot" ac "dot" uk "forward slash" fasta33).

FIGS. 16A-B show the amino acid sequence of the SARS virus Replicase 1A protein (SEQ ID NO: 64).

FIG. 17 shows the amino acid sequence of the SARS virus Replicase 1B protein (SEQ ID NO: 65).

FIG. 18 shows the amino acid sequence of ORF3 of SARS virus (SEQ ID NO: 66).

FIG. 19 shows the amino acid sequence of ORF4 of SARS virus (SEQ ID NO: 67).

FIG. 20 shows the amino acid sequence (SEQ ID NO: 68) of ORF6 (nucleotides 27059-27247 of the 29,736-base genome sequence) or ORF 7 (nucleotides 27,074-27,265 of the 29,751-base genome sequence) of SARS virus.

FIG. 21 shows the amino acid sequence (SEQ ID NO: 69) of ORF7 (nucleotides 27258-27623 of the 29,736-base genome sequence) or ORF 8 (nucleotides 27,273-27,641 of the 29,751-base genome sequence), of SARS virus.

FIG. 22 shows the amino acid sequence (SEQ ID NO: 70) of ORF8 (nucleotides 27623-27754 of the 29,736-base genome sequence) or ORF9 8 (nucleotides 27,638-27,772 of the 29,751-base genome sequence) of SARS virus.

FIG. 23 shows the amino acid sequence (SEQ ID NO: 71) of ORF9 (nucleotides 27764-27880 of the 29,736-base genome sequence) or ORF10 (nucleotides 27,779-27,898 of the 29,751-base genome sequence) of SARS virus.

FIG. 24 shows the amino acid sequence (SEQ ID NO: 72) of ORF10 (nucleotides 27849-28100 of the 29,736-base genome sequence) or ORF11 (nucleotides 27,864-28118 of the 29,751-base genome sequence) of SARS virus.

FIG. 25 shows the amino acid sequence of ORF13 of SARS virus (SEQ ID NO: 73).

FIG. 26 shows the amino acid sequence of ORF14 of SARS virus (SEQ ID NO: 74).

FIG. 27 shows an alignment of the secreted region of the SARS virus ORF 10 (SEQ ID NO: 201) of the 29,751-base genome sequence (sars) with the conotoxin from *Conus ventricosus* (conotoxin) (SEQ ID NO: 200). Sequence identity is indicated by asterisks and sequence homology is indicated by dots.

DETAILED DESCRIPTION OF THE INVENTION

In general, the invention provides nucleic acid molecules, polypeptides, and other reagents derived from a SARS virus, as well as methods of using such nucleic acid molecules, polypeptides, and other reagents.

The genome sequence (FIGS. 3A-P, 11A-K, SEQ ID NOs: 1, 2, and 15) reveals that the SARS coronavirus is only moderately related to other known coronaviruses, including two human coronaviruses, OC43 and 229E. Thus, the SARS virus is a previously unknown virus. The 5' end of the SARS genome contains a 5' leader sequence (Table 1; SEQ ID NO: 3) with sequence similarity to the highly conserved coronavirus core leader sequence, 5'-CUAAAC-3 (SEQ ID NO: 75; Sawicki, S. G., et al., *Adv Exp Med Biol* 440, 215-9, 1998; Lai, M. M. and D. Cavanagh, *Adv Virus Res* 48, 1-100, 1997). Transcriptional regulatory sequences (TRSs) were identified upstream of all open reading frames (ORFs) (Tables 1 and 2; SEQ ID NOs: 3-13 and 20-30). ORF9 and ORF10 of the 29,736-base SARS genome (ORF 10 and ORF 11 of the 29,751 base genome) overlap by 12 amino acids, and have matches to the TRS consensus in close proximity to their respective initiating methionine codons.

The 3 ' UTR sequence (SEQ ID NO: 18) of SARS virus contains a s2m region having the sequence ACATTTTCATCGAGGCCACGCGGAGTACGAT CGAGGGTACAGTGAAT; SEQ ID NO: 16) that includes a conserved, discontinuous 32 base-pair s2m motif. The conserved 32 base-pair motif is a universal feature of astroviruses that has also been identified in avian coronavirus (AIBV) and the ERV-2 equine rhinovirus. This motif has been identified by Jonassen C. M. et al. (J Gen Virol 1998 April; 79 (Pt 4):715-8) as GCCGNGGCCACGC(G/C)GAGTA(C/G)GANCGAGGGTACAG(G/C) (SEQ ID NO: 19), where N is generally not part of the conserved motif, and can be any nucleotide. The region corresponding to the 32 base-pair motif in SARS virus includes the sequence: CGAGGCCACGCGGAGTACGATCGAGGGTACAG (SEQ ID NO: 17), and spans positions 29590-29621 of the 29,751 base genome. FIG. 4 shows an alignment of the s2m regions from Avian infectious bronchitis virus (AIBV; SEQ ID NO: 32) and equine rhinovirus serotype 2 (ERV-2; SEQ ID NO: 31), as defined in Jonassen C. M. et al. (J Gen Virol 1998 April; 79 (Pt 4):715-8), with the entire 3' untranslated region (UTR) of the SARS virus (TOR2) (SEQ ID NO: 18).

TABLE 1

Listing of the transcription regulatory sequences of the 29,736-base SARS genome, showing the nucleotide position (base) and associated open-reading frames (ORF). An asterisk (*) indicates consensus sequence.

| Base | ORF | TRS Sequence | |
|---|---|---|---|
| 45 | Leader | TCTCTAAACGAAACTTTAAAATCTGTG | (SEQ ID NO: 3) |
| 21464 | S | CAACTAAACGAACATG | (SEQ ID NO: 4) |
| 25238 | ORF3 | CACATAAACGAACTTATG | (SEQ ID NO: 5) |
| 26089 | E | TGAGTACGAACTTATG | (SEQ ID NO: 6) |
| 26326 | M | GGTCTAAACGAACTAACT 40 ATG | (SEQ ID NO: 7) |
| 26986 | ORF6 | AACTATAAATT 62 ATG | (SEQ ID NO: 8) |
| 27244 | ORF7 | TCCATAAAACGAACATG | (SEQ ID NO: 9) |
| 27575 | ORF8 | TGCTCTA---GTATTTTTTAACTTTG 24 ATG | (SEQ ID NO: 10) |
| 27751 | ORF9 | AGTCTAAACGAACATG | (SEQ ID NO: 11) |
| 27837 | ORF10 | CTAATAAACCTCATG | (SEQ ID NO: 12) |
| 28084 | N | TAAAATAAACGAACAAATTAAAATG | (SEQ ID NO: 13) |
| | | ******** | |

TABLE 2

Listing of the transcription regulatory sequences of the 29,751-base SARS genome, showing the nucleotide position (base), associated open-reading frames (ORF), and identified transcription regulatory sequences. Numbers in parentheses within the alignment indicate distance to the putative initiating codon. The conserved core sequence is indicated in bold in the putative leader sequence. Contigous sequences identical to region of the leader sequence containing the core sequence are shaded. No putative TRSs were detected for ORFs 4, 13 and 14, although ORF 13 may share the TRS associated with the N protein.

| Base | ORF | TRS Sequence | | |
|------|-----|--------------|---|---|
| 60 | Leader | UCUCUAAACGAACUUUAAAAUCUGUG | (SEQ ID NO: 20) | |
| 21479 | S (Spike) | CAACUAAACGAACAUG | (SEQ ID NO: 21) | |
| 25252 | ORF3 | CACAUAAACGAACUUAUG | (SEQ ID NO: 22) | |
| 26104 | Envelope | UGAGUACGAACUUAUG | (SEQ ID NO: 23) | |
| 26341 | M | GGUCUAAACGAACUAACU (40)AUG | (SEQ ID NO: 24) | |
| 27001 | ORF7 | AACUAUAAAUU (62)AUG | (SEQ ID NO: 25) | |
| 27259 | ORF8 | UCCAUAAAACGAACAUG | (SEQ ID NO: 26) | |
| 27590 | ORF9 | UGCUCUA---GUAUUUUUAAUACUUUG (24)AUG | (SEQ ID NO: 27) | |
| 27766 | ORF10 | AGUCUAAACGAACAUG | (SEQ ID NO: 28) | |
| 27852 | ORF11 | CUAAUAAACCUCAUG | (SEQ ID NO: 29) | |
| 28099 | NUCLEOCAPSID | UAAAUAAACGAACAAAUUAAAAUG | (SEQ ID NO: 30) | |

Figure 1A:
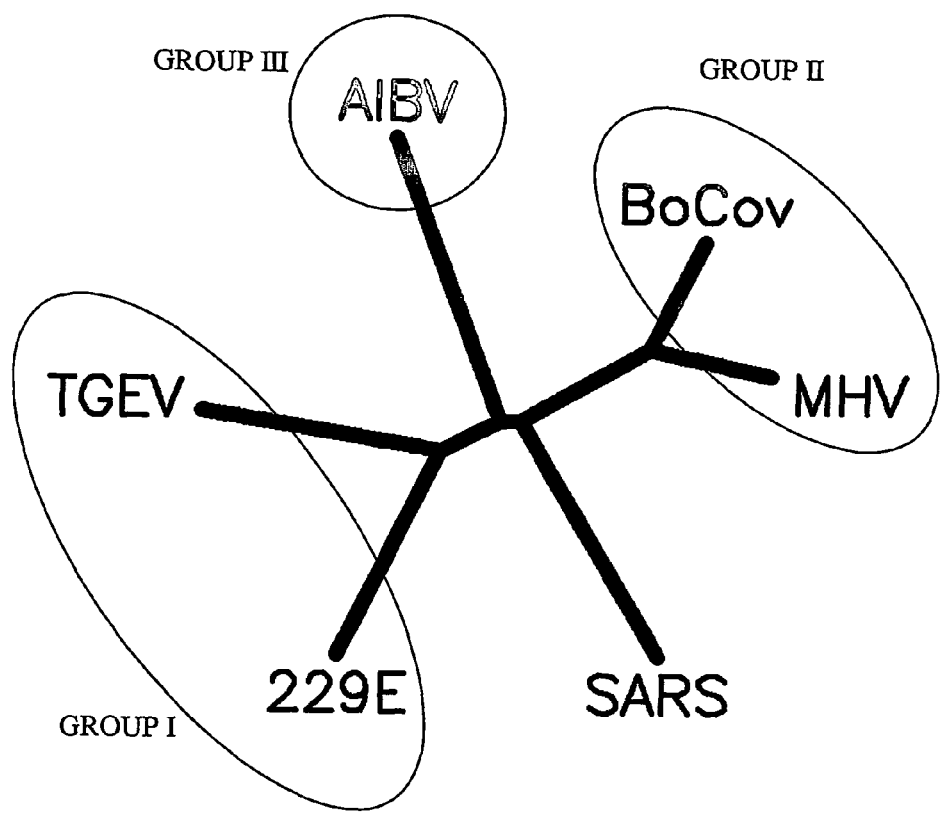
Figure 1C:
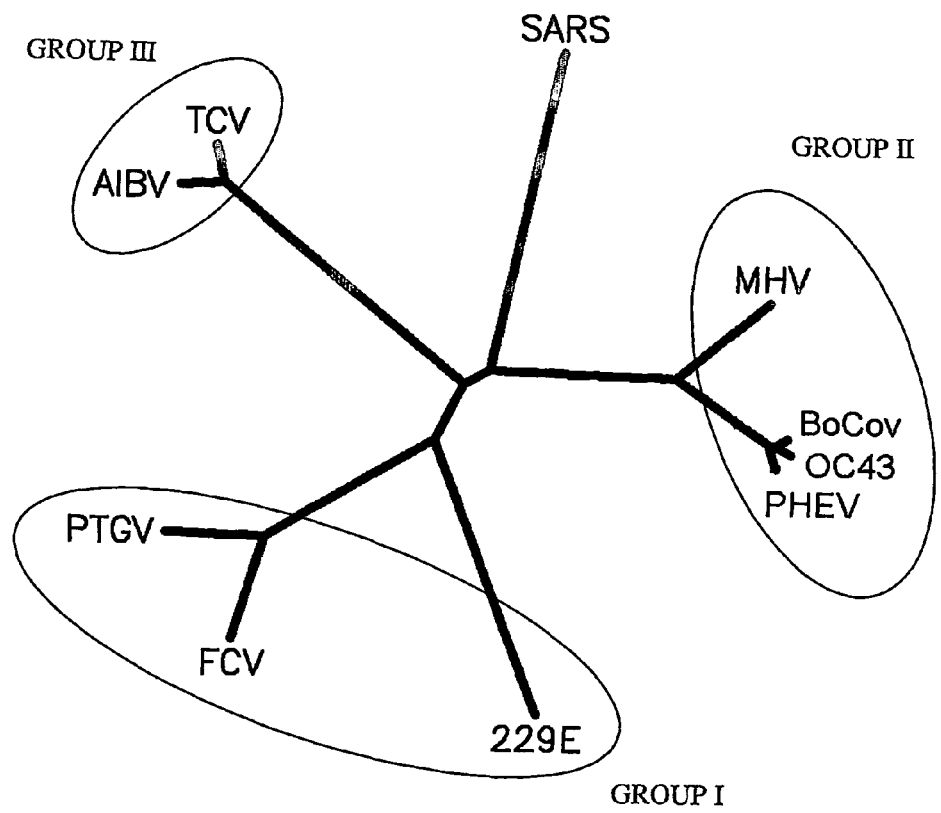
Figure 2:
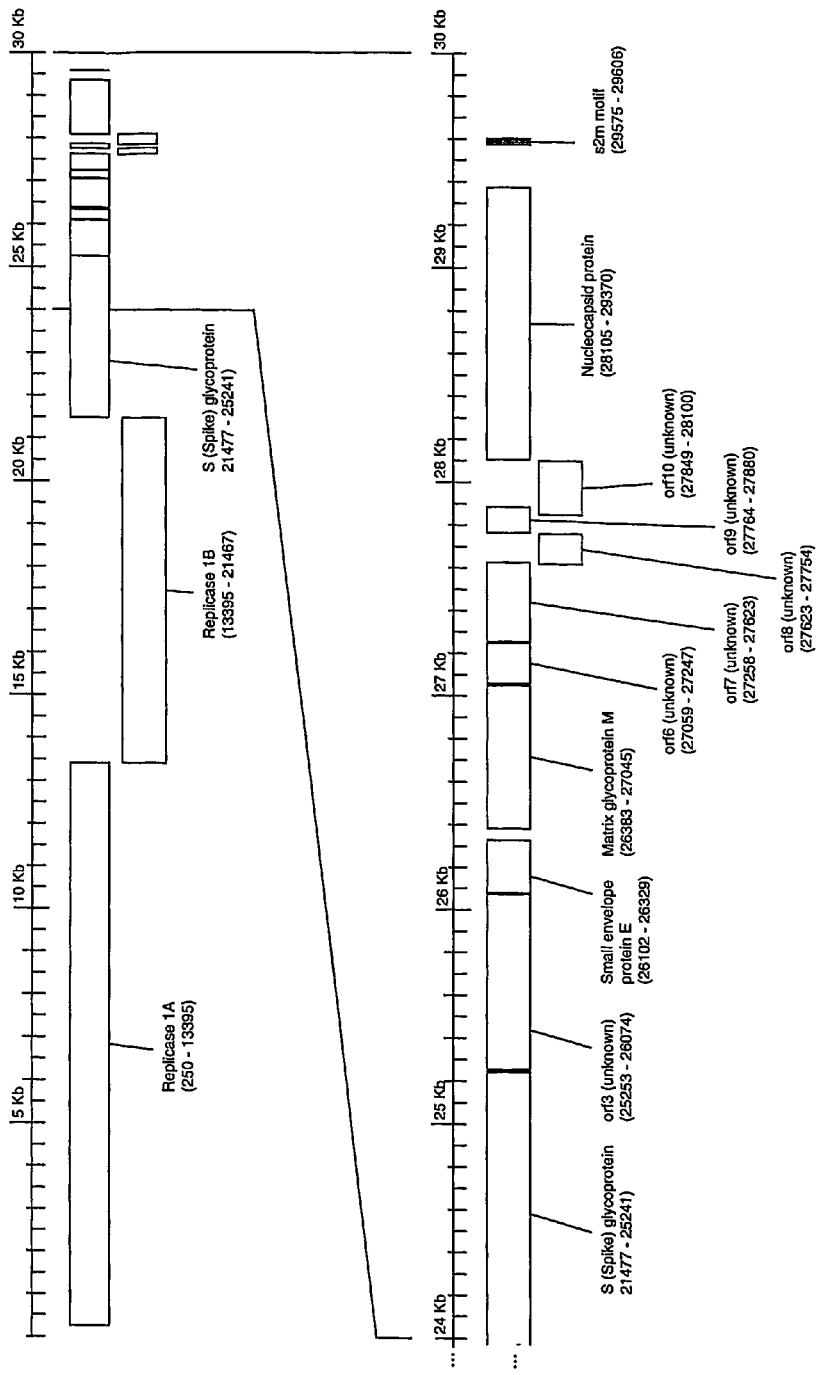
FIG. 2 shows a schematic representation of the ORFs and s2m motif in the 29,736-base SARS virus genome.
Figure 12:
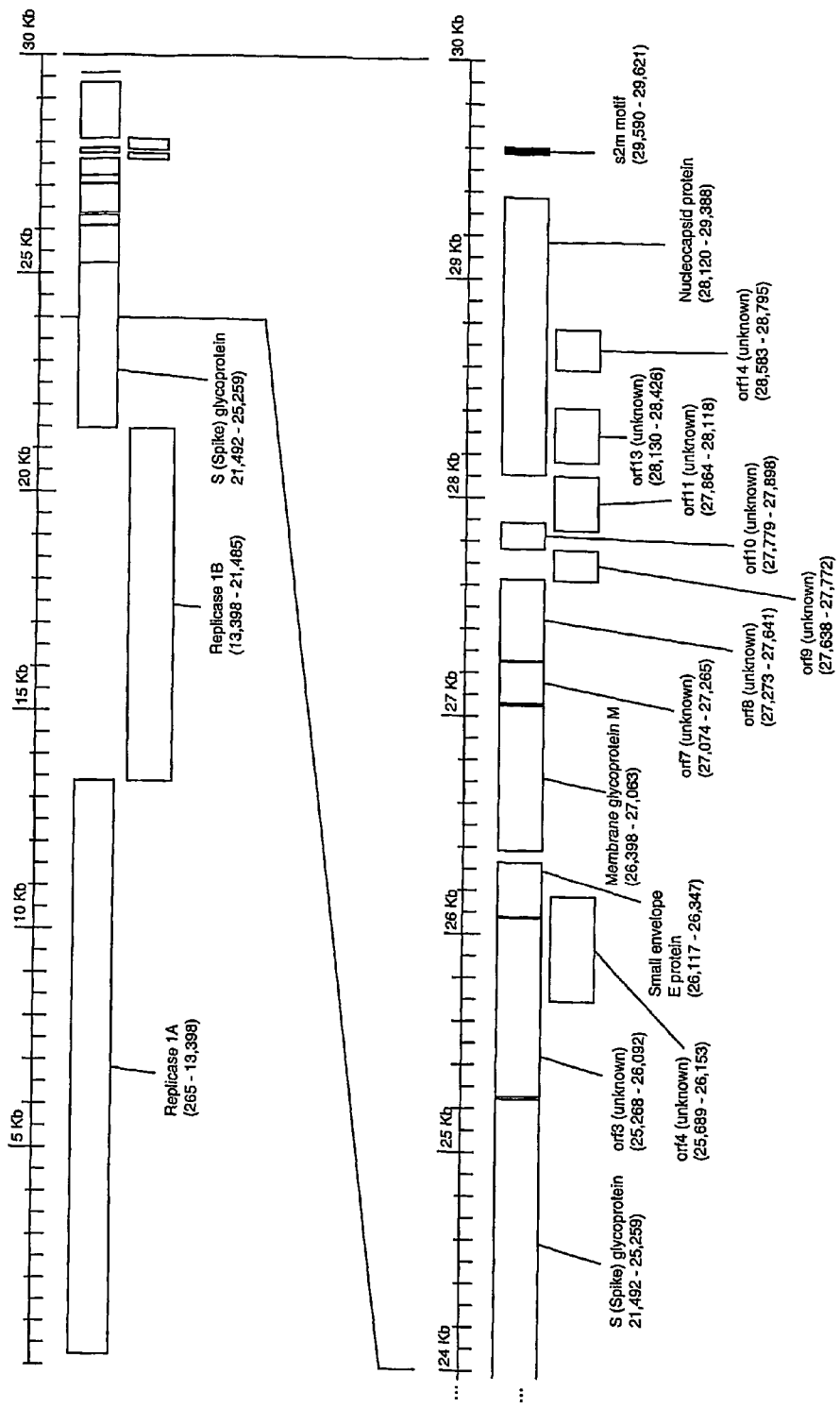
FIG. 12 shows a schematic representation of the ORFs and s2m motif in the 29,751-base SARS virus genome.
Figure 13A:
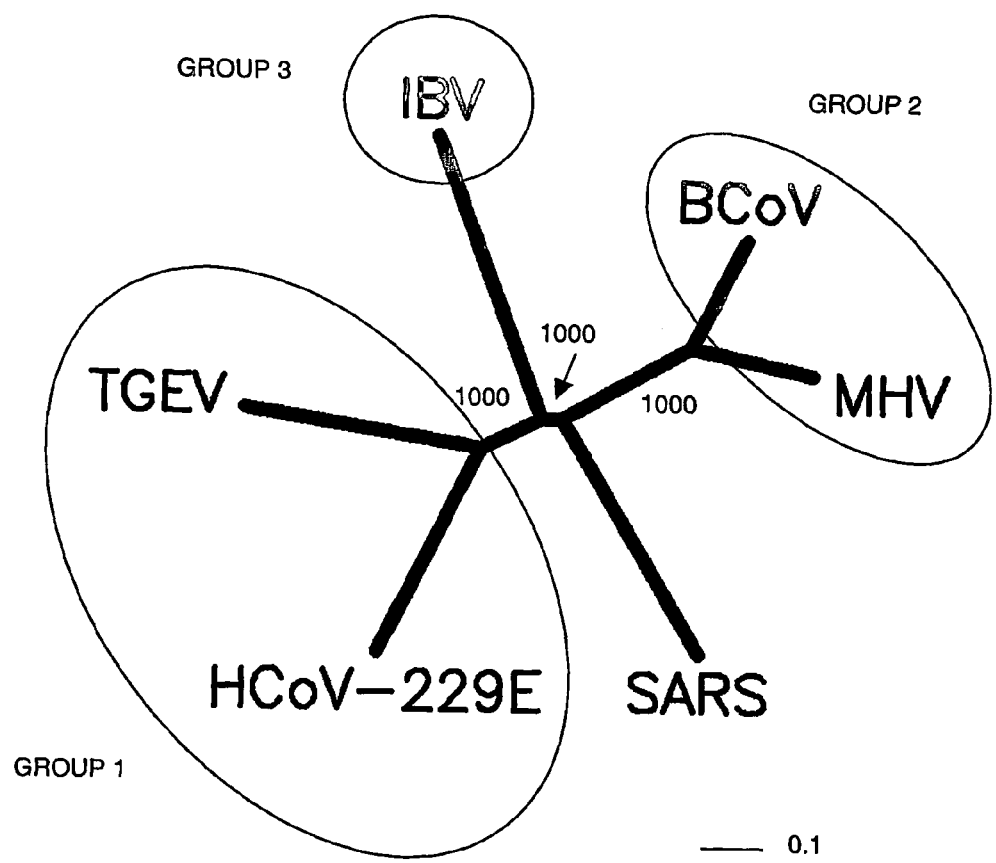
Figure 13C:
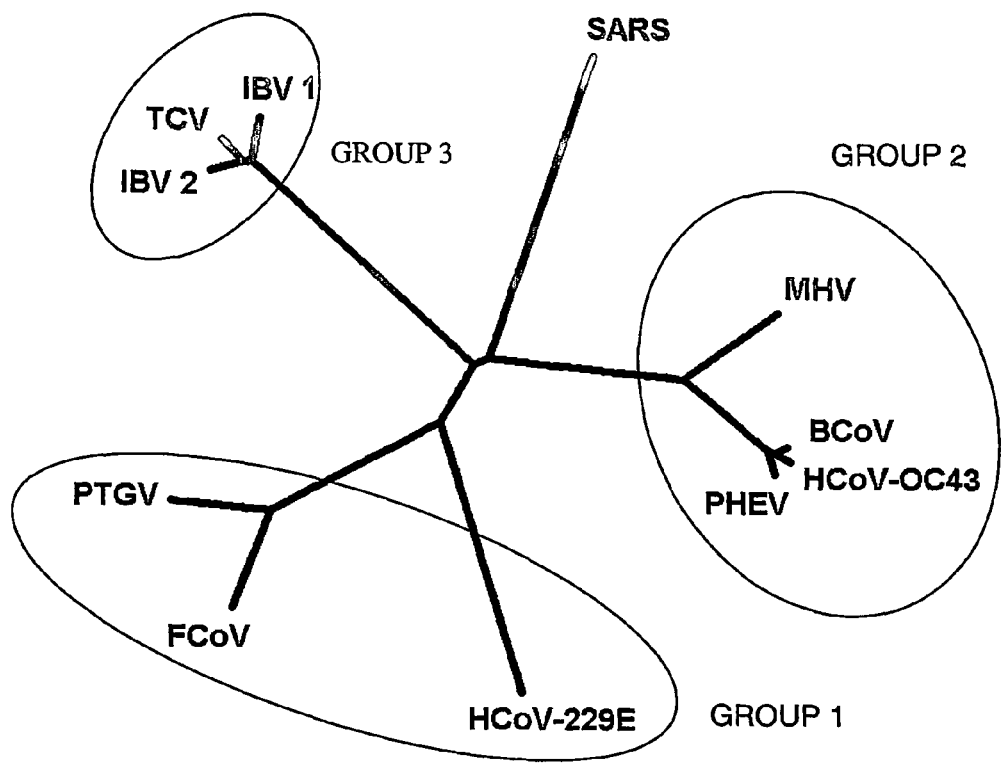
Figure 13D:
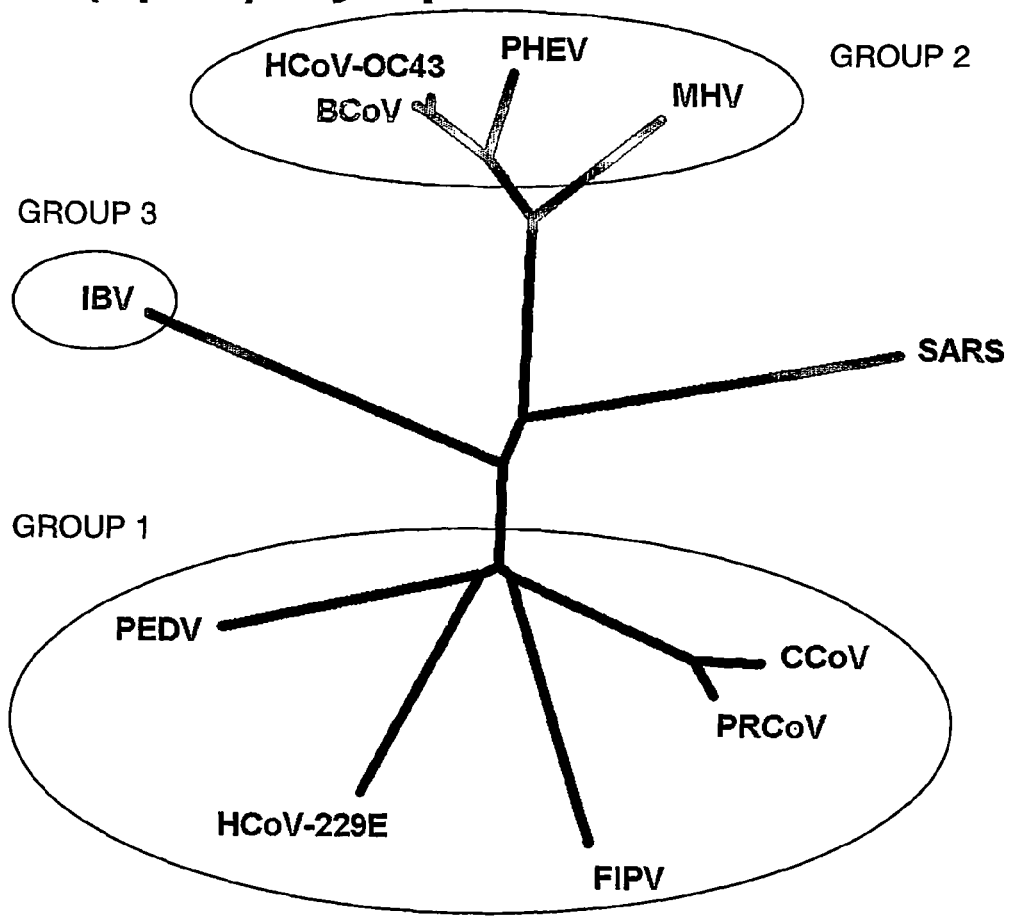

The coding potentials of the 29,736-base and 29,751-base genomes are depicted in FIGS. 2 and 12, respectively. Open reading frames (ORFs) include the Replicase 1a and 1b translation products, the Spike glycoprotein, the small Envelope protein, the Membrane and the Nucleocapsid protein. Construction of unrooted phylogenetic trees using this set of known proteins from representatives of the three known coronaviral groups reveals that the proteins encoded by the SARS virus do not readily cluster more closely with any known group than with any other (FIGS. 1A-D and 13A-D). In addition, nine novel ORFs have been analyzed.

The Replicase 1a ORF located at nucleotides 250-13395 of the 29,736-base genome, and nucleotides 265-13,398 of the 29,751-base genome, and replicase 1b ORF located at nucleotides 13395-21467 of the 29,736-base genome, and nucleotides 13,398-21,485 of the 29,751-base genome, occupy 21.2 kb of the SARS virus genome (FIGS. 2 and 12). These genes encode a number of proteins that are produced by proteolytic cleavage of a large polyprotein (Ziebuhr, J. et al., *J Gen Virol* 81, 853-79, April, 2000). A frame shift mutation interrupts the protein-coding region, separating the 1a and 1b open-reading frames. The proteins encoded by the Replicase 1a and 1b ORFs are depicted in FIGS. 16A-B and 17, SEQ ID NOs: 64 and 65).

The Spike glycoprotein (S) (E2 glycoprotein gene; FIGS. 2 and 12; nucleotides 21477 to 25241 of the 29,736-base genome, and nucleotides 21,492 to 25,259 of the 29,751-base genome) encodes a surface projection glycoprotein precursor of about 1,255 amino acids in length (FIG. 5; SEQ ID NO: 33), which may be significant in the virulence of the SARS virus. Mutations in this gene are correlated with altered pathogenesis and virulence in other coronaviruses (B. N. Fields et al., *Fields virology* (Lippincott Williams & Wilkins, Philadelphia, ed. 4th, 2001). In other coronaviruses, the mature spike protein is inserted in the viral envelope with the majority of the protein exposed on the surface of the particles. Three molecules of the Spike protein form the characteristic peplomers or corona-like structures of this virus family. Analysis of the spike glycoprotein with SignalP (Nielson, H. et al., *Prot Engineer.* 10:1-6 (1997) indicates a signal peptide (MFIFLLFLTLTSG; SEQ ID NO: 76)(probability 0.996) with cleavage between residues 13 and 14. TMHMM (Sonnhammer, E. L. et al., *Proc Int Conf Intell Syst Mol Biol* 6, 175-82 (1998)) indicates a transmembrane domain near the C-terminal end (WYVWLGFIAGLIAIVMVTILLCC; SEQ ID NO: 183). Together these data indicate a type I membrane protein with N-terminus and the majority of the protein (residues 14-1195) on the outside of the cell-surface or virus particle, which may be responsible for binding to a cellular receptor. The SARS virus Spike glycoprotein has limited sequence identity to other, known Spike glycoproteins (FIGS. 14A-F).

ORF 3 (FIGS. 2 and 12; nucleotides 25253-26074 of the 29,736-base genome and nucleotides 25,268-26,092 of the 29,751-base genome) encodes a protein of 274 amino acids (FIG. 18; SEQ ID NO: 66) that lacks significant similarities to any known protein when analyzed with BLAST (Altschul, S. F. et al., *Nucleic Acids Res* 25, 3389-402, Sep. 1, 1997), FASTA (Pearson, W. R. and D. J. Lipman, *Proc Natl Acad Sci USA* 85, 2444-8, April, 1988) or PFAM (Bateman, A. et al., *Nucleic Acids Res* 30, 276-80, Jan. 1, 2002). Analysis of the N-terminal 70 amino acids with SignalP indicates the existence of a signal peptide (MDLFMRFFTLRSITAQ; SEQ ID NO: 184) and a cleavage site (probability 0.540). Both TMpred (Hofinan, K. and W. Stoffel, *Biol. Chem. Hoope-Seyler* 374, 166 (1993) and TMHMM indicate three transmembrane regions spanning approximately residues 34-56 (TIPLQASLPFGWLVIGVAFLAVF, SEQ ID NO: 77), 77-99 (FQFICNLLLLFVTIYSHLLLVAA, SEQ ID NO: 78), and 103-125 (AQFLYLYALIYFLQCINACRIIM, SEQ ID NO: 79). Both TMpred and TMHMM indicate that the C-terminus and a large 149 amino acid domain is located inside the viral or cellular membrane. The C-terminal (interior) region of the protein, corresponding to about amino acids 124-274 (MRCWLCWKCKSKNPLLYDANYFVCWHTH-NYDYCIPYNSVTDTIVVTEGDGI STPKLKEDYQIGGY-SEDRHSGVKDYVVVHGYFTEVYYQLEST-QITTDTGIENAT FFIFNKLVKDPPNVQIHTIDGSSGVAN-PAMDPIYDEPTTTTSVPL; SEQ ID NO: 185) may encode a protein domain with ATP-binding properties (PD037277).

ORF 4 (FIG. 12; nucleotides 25,689-26,153 of the 29,751-base genome) encodes a predicted protein of 154 amino acids (FIG. 19; SEQ ID NO: 67). This ORF overlaps entirely with ORF 3 and the E protein. ORF4 may be expressed from the ORF mRNA using an internal ribosomal entry site. BLAST analyses failed to identify matching sequences. Analysis with TMPred predicts a single transmembrane helix, amino acids 1-20 MMPTTLFAGTHITMTTVYHI, SEQ ID NO: 186.

The small envelope protein E (FIGS. 2 and 12; nucleotides 26102-26329 of the 29,736-base genome and nucleotides 26,117-26,347, ORF 5, of the 29,751-genome) encodes a protein of 76 amino acids (FIG. 7; SEQ ID NO: 35). BLAST and FASTA comparisons indicate that the protein, while novel, is homologous to multiple envelope proteins (alternatively known as small membrane proteins) from several coronaviruses. An alignment of the SARS virus E protein with the envelope protein of Porcine transmissible gastroenteritis coronavirus indicates approximately 28% sequence identity between the two proteins over a 61 amino acid overlap, as calculated by FASTA (FIG. 15). PFAM analysis of the protein indicates that the small envelope protein E is a member of the NS3_EnvE protein family. InterProScan (R. Apweiler et al., *Nucleic Acids Res* 29, 37-40, Jan. 1, 2001; Zdobnov, E. M. and R. Apweiler, *Bioinformatics* 17, 847-8, September, 2001) analysis indicates that the protein is a component of the viral envelope, and homologs of it are found in other viruses, including gastroenteritis virus and murine hepatitis virus. SignalP analysis indicates the presence of a transmembrane anchor (probability 0.939). TMpred analysis indicates a similar transmembrane anchor at positions 17-34 (VLLFLAFV-VFLLVTLAIL, SEQ ID NO: 80), which is consistent with the known association of homologous proteins with the viral envelope. TMHMM indicates a type II membrane protein with the majority of the 46 residue C terminus hydrophilic domain (TALRLCAYCCNIVNVSLVKPTVYVYS-RVKNLNSSEGVPDLLV; SEQ ID NO: 187) located on the surface of the viral particle. The E protein may be important for viral replication.

The Matrix glycoprotein M (FIGS. 2 and 12; nucleotides 26383-27045 of the 29,736-base genome and nucleotides 26,398-27,063, ORF 6, of the 29,751-genome) encodes a protein of 221 amino acids (FIG. 6; SEQ ID NO: 34). BLAST and FASTA analysis of the protein, while novel, reveals homologies to coronaviral matrix glycoproteins (FIG. 9). The association of the spike glycoprotein (S) with the matrix glycoprotein (M) may be an essential step in the formation of the viral envelope and in the accumulation of both proteins at the site of virus assembly. Analysis of the amino acid sequence with SignalP indicates a signal sequence (probability 0.932), located at approximately residues 1-39 (MAD-NGTITVEELKQLLEQWNLVIGFLFLAWIMLLQFAYS; SEQ ID NO: 188) that is unlikely to be cleaved. TMHMM and TMpred analysis both indicate the presence of three trans-membrane helices, located at approximately residues 15-37 (LLEQWNLVIGFLFLAWIMLLQFA; SEQ ID NO: 81), 50-72 (LVFLWLLWPVTLACFVLAAVYRI; SEQ ID NO: 82) and 77-99 (GGIAIAMACIVGLMWLSYFVASF; SEQ ID NO: 83), with the 121 amino acid hydrophilic domain on the inside of the virus particle, where it may interact with nucleocapsid. The hydrophilic domain may run from approximately amino acids PLRGTIVTRPLMESELVI-GAVIIRGHLRMAGHSLGRCDIKDLPKEITVATSRTLS YYKLGASQRVGTDSGFAAYN-RYRIGNYKLNTDHAGSNDNIALLVQ (SEQ ID NO: 189) i.e. approximately amino acids 95 or 99 to 221 of SEQ ID NO: 34. PFAM analysis reveals a match to PFAM domain PF01635, and alignments to 85 other sequences in the PFAM database bearing this domain, which is indicative of the coronavirus matrix glycoprotein.

ORF6 (FIG. 2; nucleotides 27059-27247 of the 29,736-base genome sequence) or ORF 7 (FIG. 12; nucleotides 27,074-27,265 of the 29,751-base genome sequence) encodes a protein of 63 amino acids (FIG. 20; SEQ ID NO: 68). TMpred analysis indicates a trans-membrane helix located between residues 3 or 4 and 22 (HLVDFQVTI-AEILIIIMRTF; SEQ ID NO: 84), with the N-terminus located outside the viral particle.

Similarly, the gene encoding ORF7 (FIG. 2; nucleotides 27258-27623 of the 29,736-base genome sequence) or ORF 8 (FIG. 12; nucleotides 27,273-27,641 of the 29,751-base genome sequence), encoding a protein of 122 amino acids (FIG. 21; SEQ ID NO: 69), has no significant BLAST or FASTA matches to known proteins. Analysis of this sequence with SignalP indicates a cleaved signal sequence (MKIIL-FLTLIVFTSC; SEQ ID NO: 85) (probability 0.995), with the cleavage site located between residues 15 and 16. TMpred and TMHMM analysis also indicates a trans-membrane helix located approximately at residues 99-117 (SPLFLIVAALV-FLILCFTI; SEQ ID NO: 86). Together these data indicate that this protein is a type I membrane protein with the major hydrophilic domain of the protein (residues 16-98; ELY-HYQECVRGTTVLLKEPCP SGTYEGNSPFHPLADNK-FALTCTSTHFAFACADGTRHTYQLRARSVSPKLFIRQ EEVQQELY; SEQ ID NO: 87) and the amino-terminus is oriented inside the lumen of the ER/Golgi, or on the surface of the cell membrane or virus particle,depending on the membrane localization of the protein.

ORF8 (FIG. 2; nucleotides 27623-27754 of the 29,736-base genome sequence) or ORF9 (FIG. 12; nucleotides 27,638-27,772 of the 29,751-base genome sequence), encodes a protein of 44 amino acids (FIG. 22; SEQ ID NO: 70). FASTA analysis of this sequence revealed some weak similarities (37% identity over a 35 amino acid overlap) to Swiss-Prot accession Q9M883, annotated as a putative sterol-C5 desaturase. A similarly weak match to a hypothetical *Clostridium perfringens* protein (Swiss-Prot accession CPE2366) was also detected. TMpred indicated a single strong trans-membrane helix FYLCFLAFLLFLVLIMLIIF-WFS, SEQ ID NO: 190, with little preference for alternate models in which the N-terminus was located inside or outside the particle.

Similarly ORF9 (FIG. 2; nucleotides 27764-27880 of the 29,736-base genome sequence) or ORF10 (FIG. 12; nucleotides 27,779-27,898 of the 29,751-base genome sequence) encoding a protein of 39 amino acids (FIG. 23; SEQ ID NO: 71), exhibited no significant matches in BLAST and FASTA searches but encodes a trans-membrane helix LLIVLTCIS-LCSCICTVVQ (SEQ ID NO: 191) by TMPred, with the N-terminus located within the viral particle. The region immediately upstream of this protein exhibits a strong match to the TRS consensus (Table 2), indicating that a transcript initiates from this site. The large number of cysteine residues (6) may result in cross linking of the amino acids. Amino acids ICTVVQRCASNKPHVLEDPCKVQH (SEQ ID NO: 192) of this protein may be secreted. The secreted amino acids exhibit homology to toxin proteins, for example, to the cono-toxin of *Conus ventricosus* (FIG. 27). Antigenic peptides from the hydrophilic (secreted) region, for example, CICTV-VQRCASNKPHVLEDPCK (SEQ ID NO: 193), were used to generate monoclonal antibodies using standard techniques. Furthermore, the C terminal amino acids form a sequence that shares homology to farnesylation sites (CKQH), which generally require C terminal location to be functional. This protein may act as a virulence factor and/or may facilitate transmission to humans.

ORF10 (FIG. 2; nucleotides 27849-28100 of the 29,736-base genome sequence) or ORF11 (FIG. 12; nucleotides 27,864-28118 of the 29,751-base genome sequence) encoding a protein of 84 amino acids (FIG. 24; SEQ ID NO: 72) exhibited only very short (9-10 residues) matches to a region of the human coronavirus E2 glycoprotein precursor (starting at residue 801). Analysis by SignalP and TMHMM predict a soluble protein. A detectable alignment to the TRS consensus sequence was also found (Table 2).

The protein (422 amino acids; FIG. 8; SEQ ID NO: 36) encoded by the Nucleocapsid gene (FIG. 2; nucleotides 28105-29370 of the 29,736-base genome sequence; FIG. 12, nucleotides 28,120-29,388 of the 29,751-base genome sequence) aligns well with nucleocapsid proteins from other representative coronaviruses (FIGS. 10A-B), although a short lysine rich region (KTFPPTEPKKDKKKKTDEAQ; SEQ ID NO: 14) is unique to SARS. This region is suggestive of a nuclear localization signal Since some coronaviruses are able to replicate in enucleated cells, the SARS virus nucleocapsid protein may have evolved a novel nuclear function, which may play a role in pathogenesis. In addition, the basic nature of this peptide suggests it may assist in RNA binding. The SARS nucleocapsid protein is also a good candidate for diagnostic tests.

ORF13 (FIG. 12; nucleotides 28,130-28,426 of the 29,751-base genome sequence) encodes a novel protein of 98 amino acids (FIG. 25; SEQ ID NO: 73). ORF 14 (FIG. 12; nucleotides 28,583-28,795 of the 29,751-base genome sequence) encodes a novel protein of 70 amino acids (FIG. 26; SEQ ID NO: 74). TMPred predicts a single transmembrane helix VVAVIQEIQLLAAVGEILLLEW (SEQ ID NO: 194).

Various features of the SARS virus genome are summarised in Table 3. While Table 3 refers to the 29,751-base genome sequence, the features are also applicable to the 29,736-base genome sequence (SEQ ID NOs: 1 and 2).

TABLE 3

Features of the SARS virus 29,751-base genome sequence.

| Feature | Start-End[1] | No. amino acids | No. bases | Frame | TRS |
|---|---|---|---|---|---|
| Orf 1a | 265-13,398 | 4,382 | 13,149 | +1 | N/A |
| Orf 1b | 13,398-21,485 | 2,628 | 7,887 | +3 | N/A |
| S protein | 21,492-25,259 | 1,255 | 3,768 | +3 | Strong |
| Orf 3 | 25,268-26,092 | 274 | 825 | +2 | Strong |
| Orf 4 | 25,689-26,153 | 154 | 465 | +3 | Absent[2] |
| E protein | 26,117-26,347 | 76 | 231 | +2 | Weak |
| M protein | 26,398-27,063 | 221 | 666 | +1 | Strong |
| Orf 7 | 27,074-27,265 | 63 | 192 | +2 | Weak |
| Orf 8 | 27,273-27,641 | 122 | 369 | +3 | Strong |
| Orf 9 | 27,638-27,772 | 44 | 135 | +2 | Weak |
| Orf 10 | 27,779-27,898 | 39 | 120 | +2 | Strong |
| Orf 11 | 27,864-28,118 | 84 | 255 | +3 | Weak |
| N protein | 28,120-29,388 | 422 | 1,269 | +1 | Strong |
| Orf 13[3] | 28,130-28,426 | 98 | 297 | +2 | Absent[2] |
| Orf 14[3] | 28,583-28,795 | 70 | 213 | +2 | Absent |
| s2m motif | 29,590-29,621 | N/A | 30 | N/A | N/A |

[1]End coordinates include the stop codon, except for ORF 1a and s2m.
[2]These ORFs overlap substantially or completely with other and may share TRSs.
N/A indicates not applicable.

Various polymorphisms may exist in the SARS virus. In the SARS 29,736-base genome sequences (SEQ ID NO: 1 or 2), for example, nucleotides 7904, 16607, 19168, 24857, or 26842 may be C or T; or nucleotides 19049, 23205, or 25283 may be G or A, and in the SARS 29,751-base genome sequence (SEQ ID NO: 15), for example, nucleotides 7919, 16622, 19183, 24872, or 26857 may be C or T; or nucleotides 19064, 23220, or 25298 may be G or A. In some embodiments, the nucleotide changes may result in no change in the encoded amino acid, or in a conservative or non-conservative change in the encoded amino acid. In some embodiments, a nucleotide change, as described herein, at position 7904 or 7919, may result in a A to V amino acid substitution, in the Replicase 1A protein coding region; a change at position 19168 or 19183 may result in a V to A amino acid substitution, in the Replicase IB protein coding region; a change at position 23205 or 23220 may result in a A to S amino acid substitution (non-conservative change), affecting the Spike glycoprotein coding region; a change at position 25283 or 25298 may result in a R to G amino acid substitution (non-conservadve change), affecting ORF3; or a change at position 26842 or 26857 may result in a S to P amino acid substitution (non-conservative change), affecting the Nucleocapsid protein coding region, in the SARS 29,736-base (SEQ ID NO: 1 or 2) and 29,751-base genome (SEQ ID NO: 15) sequences, respectively. In various embodiments, a nucleotide or amino acid sequence including a particular polymorphism may be selected, for example, for use in the methods of the invention, or may be excluded, for example, from a particular use according to the invention.

Various alternative embodiments of the invention are described below. These embodiments include, without limitation, identification and use of SARS virus nucleic acid and amino acid sequences for diagnostic or therapeutic uses.

Diagnosis of SARS Virus-Related Disorders

A SARS virus-related disorder is any disorder that is mediated by the SARS virus, or by a nucleic acid molecule or polypeptide derived from the SARS virus. Accordingly, SARS virus nucleic acid molecules and polypeptides may be used to diagnose and identify a SARS virus-related disorder in a mammal, for example, a human or a domestic, farm, wild, or experimental animal. In some embodiments, SARS virus nucleic acid molecules and polypeptides may be used to screen such animals, e.g., civet cats, for the presence of SARS virus. A SARS virus-related disorder may be a hepatic, enteric, respiratory, or neurological disorder, and may be accompanied by one or more symptoms or indications including, but not limited to, fever, cough, shortness of breath, headache, low blood oxygen concentration, liver damage, or reduced lymphocyte numbers. Accordingly, samples for diagnosis may be obtained from cells, blood, serum, plasma, urine, stool, conjunctiva, sputum, asopharyngeal or oropharyngeal swabs, tracheal aspirates, bronchalveolar lavage, pleural fluid, amniotic fluid, or any other specimen, or any extract thereof, or by tissue biopsy of for example lungs or major organs, obtained from a patient (human or animal), test subject, or experimental animal.

A SARS virus-related disorder may be diagnosed by amplifying a SARS nucleic acid molecule or fragment thereof from a sample. Probes or primers for use in amplification may be prepared using standard techniques. In some embodiments, probes or primers are selected from regions of a SARS virus genome as described herein that show limited sequence homology or identity (e.g., less than 10%, 20%, 30%, 40%, 50%, 60%, 70%, 80%, 90%, or 100% identity) to other viruses or pathogens, or to host sequences.

Nucleic acid sequences can be amplified as needed by methods known in the art. For example, this can be accomplished by e.g., polymerase chain reaction "PCR" of DNA or of RNA by reverse transcriptase-PCR or "RT-PCR" (See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202 issued Jul. 28, 1987 to Mullis) Variations of standard PCR techniques, such as for example real time RT-PCR using internal as well as amplification primers, resulting in increased sensitivity and speed, and reduction of risk of sample contamination (see for example Higuchi, R., et al., "Kinetic PCR Analysis: Real-time Monitoring of DNA Amplification Reactions," Bio/Technology, vol. 11, pp. 1026-1030 (1993); Heid et al, "Real Time Quantitative PCT", Genome Research, 1996, pp. 986-994; Gibson U E et al., "A novel method for real time quantitative RT-PCR," Genome Res. 1996 October; 6(10):995-1001), or the "Tacman" approach to PCR, described by for example Holland et al, Proc. Natl. Acad. Sci., 88: 7276-7280 (1991), may be performed.

Other suitable amplification and analytical methods include the single base primer extension (see for example U.S. Pat. No. 6,004,744), mini-sequencing, ligase chain reaction (LCR) (see for example Wu and Wallace, Genomics 4, 560 (1989), Landegren et al., Science 241, 1077 (1988), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

A SARS virus-related disorder may also be diagnosed using an antibody directed against a SARS virus nucleic acid or amino acid sequence that specifically binds a nucleic acid molecule or polypeptide. In an alternative embodiment, the antibody may be directed against a SARS polypeptide, for example, the S polypeptide or fragment thereof that is located on the surface of the SARS virion. Methods for preparation of antibodies or for assaying antibody binding are well known in the art.

Serological diagnosis may included detection of antibodies against a SARS virus polypeptide or nucleic acid molecule, e.g., the Nucleocapsid protein, produced in response to infection using techniques such as indirect fluorescent antibody testing or enzyme-linked immunosorbent assays (ELISA). A SARS virus-related disorder may also be diagnosed by for example performing in situ probe hybridization studies on tissue specimens.

In some aspects, diagnostic tests as described herein or known to those of skill in the art may be performed for SARS virus variants that exhibit increased pathogenicity, such as strains having redundant sequences.

In some embodiments, reagents for diagnosis (e.g, probes, primers, antibodies, etc.) may be provided in kits which may optionally include instructions for using the reagent or may include other reagents for performing the appropriate assay e.g., controls, standards, buffers, etc.

Therapy or Prophylaxis for SARS Virus-Related Disorders

Compounds according to the invention may also be used to provide therapeutics or prophylactics for SARS virus-related disorders. Accordingly, such compounds may be used to treat a mammal, for example, a human or a domestic, farm, wild, or experimental animal that has or is at risk for a SARS virus-related disorder. Such compounds may include, without limitation, compounds that interfere with SARS virus replication, expression of SARS virus proteins, or the ability of the SARS virus to infect a host cell. Accordingly, in some embodiments, compounds that act as antagonists to SARS virus polypeptides may be used as therapeutics or prophylactics for SARS virus related disorders. In some embodiments, purified SARS virus polypeptides may be used as for example competitive inhibitors to disrupt viral function. For example, a Spike protein lacking a functional domain, or having some other modification that maintains binding but reduces or eliminates pathogenicity, may be used to disrupt viral function. In some embodiments, antibodies that bind SARS virus polypeptides or nucleic acid molecules, for example, humanized antibodies, may be used as therapeutics or prophylactics.

In some embodiments, the SARS-virus compounds may be used as vaccines, or may be used to develop vaccines. For example, peptides derived from portions of SARS-virus proteins or polypeptides located on the outside of the virion or cell surface may be useful for vaccines or for generation of therapeutic or prophylactic antibodies.

A "vaccine" is a composition that includes materials that elicit a desired immune response. A vaccine may select, activate or expand memory B and T cells of the immune system to, for example, enable the elimination of infectious agents, such as a SARS virus, or a component thereof. In some embodiments, a vaccine includes a suitable carrier, such as an adjuvant, which is an agent that acts in a non-specific manner to increase the immune response to a specific antigen, or to a group of antigens, enabling the reduction of the quantity of antigen in any given vaccine dose, or the reduction of the frequency of dosage required to generate the desired immune response.

Vaccines according to the invention may include SARS virus polypeptides and nucleic acid molecules described herein, or immunogenic fragments thereof. In some embodiments, a SARS virus Spike polypeptide, Envelope polypeptide, or membrane glycoprotein or fragments thereof may be suitable for vaccine applications. In some embodiments, the vaccines may be multivalent and include one or more epitopes from a SARS virus polypeptide or fragment thereof.

In some embodiments of the invention, a vaccine may include a live or killed microorganism e.g., a SARS virus or a component thereof. If a live SARS virus is used, which may be administered in the form of an oral vaccine, is may contain non-revertible genetic alterations (for example, large deletions or insertions in the genomic sequence) that reduce or eliminate the virulence of the virus ("attenuated virus"), but not its induction of an immune response. In some embodiments, a live vaccine may include an attenuated non-SARS microorganism (e.g, bacteria or virus such as vaccinia virus) that is capable of expressing a SARS virus polypeptide or immunogenic fragment thereof as described herein. In some embodiments, a vaccine may include SARS virus polypeptides or nucleic acid molecules having modifications that facilitate ease of administration. For example, an indigestible SARS virus polypeptide or nucleic acid molecule may be used for oral administration, and a modification that is suitable for inhalation may be used for administration to the lung.

A "nucleic acid vaccine" or "DNA vaccine" as used herein, is a nucleic acid construct comprising a polynucleotide encoding a polypeptide antigen, particularly an antigenic amino acid subsequence identified by methods described herein or known in the art. The nucleic acid construct can also include transcriptional promoter elements, enhancer elements, splicing signals, termination and polyadenylation signals, and other nucleic acid sequences. Thus, a nucleic acid vaccine is generally introduced into a subject animal using for example one or more DNA plasmids including one or more antigen-coding sequences (for example, a SARS virus Envelope polypeptide or membrane glycoprotein sequence) that are capable of transfecting cells in vivo and inducing an immune response (see for example Whalen RG et al. DNA-mediated immunization and the energetic immune response to hepatitis B surface antigen. Clin Immunol Immunopathol 1995; 75:1-12; Wolff J A et al. Direct gene transfer into mouse muscle in vivo. Science 1990; 247:1465-8; Fynan E F et al. DNA vaccines: protective immunizations by parental, mucosal, and genegun inoculations. Proc Natl Acad Sci USA 1993; 90:11478-82). In some embodiments, a library of nucleic acid fragments may be prepared by cloning SARS virus genomic DNA into a plasmid expression vector using known techniques and the library then used as a nucleic acid vaccine (see for example Barry M A, et al. Protection against mycoplasma infection using expression-library immunization. Nature 1995; 377:632-5).

The subject is administered the nucleic acid vaccine using standard methods. The vertebrate can be administered parenterally, subcutaneously, intravenously, intraperitoneally, intradermally, intramuscularly, topically, orally, rectally, nasally, buccally, vaginally, by inhalation spray, or via an implanted reservoir in dosage formulations containing conventional non-toxic, physiologically acceptable carriers or vehicles. Alternatively, the subject is administered the nucleic acid vaccine through the use of a particle acceleration or bombardment instrument (a "gene gun"). The form in which it is administered (e.g., capsule, tablet, solution, emulsion) will depend in part on the route by which it is administered. For example, for mucosal administration, nose drops, inhalants or suppositories can be used. The nucleic acid vaccine can be administered in conjunction with known adjuvants. The adjuvant is administered in a sufficient amount, which is that amount that is sufficient to generate an enhanced immune response to the nucleic acid vaccine. The adjuvant can be administered prior to (e.g., 1 or more days before) inoculation with the nucleic acid vaccine; concurrently with (e.g., within 24 hours of) inoculation with the nucleic acid vaccine; contemporaneously (simultaneously) with the nucleic acid vaccine (e.g., the adjuvant is mixed with the nucleic acid vaccine, and the mixture is administered to the vertebrate); or after (e.g., 1 or more days after) inoculation with the nucleic acid vaccine. The adjuvant can also be administered at more than one time (e.g., prior to inoculation with the nucleic acid vaccine and also after inoculation with the nucleic acid vaccine). As used herein, the term "in conjunction with" encompasses any time period, including those specifically described herein and combinations of the time periods specifically described herein, during which the adjuvant can be administered so as to generate an enhanced immune response to the nucleic acid vaccine (e.g., an increased antibody titer to the antigen encoded by the nucleic acid vaccine, or an increased antibody titer to the pathogenic agent). The adjuvant and the nucleic acid vaccine can be administered at approximately the same location on the vertebrate; for example, both the adjuvant and the nucleic acid vaccine are administered at a marked site on a limb of the subject.

In some embodiments, expression of a SARS virus gene or coding or non-coding region of interest may be inhibited or prevented using RNA interference (RNAi) technology, a type of post-transcriptional gene silencing. RNAi may be used to create a functional "knockout", i.e. a system in which the expression of a gene or coding or non-coding region of interest is reduced, resulting in an overall reduction of the encoded product. As such, RNAi may be performed to target a nucleic acid of interest or fragment or variant thereof, to in turn reduce its expression and the level of activity of the product which it encodes. Such a system may be used for therapy or prophylaxis, as well as for functional studies. RNAi is described in for example published US patent applications 20020173478 (Gewirtz; published Nov. 21, 2002) and 20020132788 (Lewis et al.; published Nov. 7, 2002). Reagents and kits for performing RNAi are available commercially from for example Ambion Inc. (Austin, Tex., USA) and New England Biolabs Inc. (Beverly, Mass., USA).

The initial agent for RNAi in some systems is thought to be dsRNA molecule corresponding to a target nucleic acid. The dsRNA is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the Rnase III family of dsRNA-specific ribonucleases. Alternatively, RNAi may be effected via directly introducing into the cell, or generating within the cell by introducing into the cell a suitable precursor (e.g. vector, etc.) of such an siRNA or siRNA-like molecule. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

RNAi may be effected by the introduction of suitable in vitro synthesized siRNA or siRNA-like molecules into cells. RNAi may for example be performed using chemically-synthesized RNA, for which suitable RNA molecules may chemically synthesized using known methods. Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using *E. coli* RNase III) in vitro to a size conducive to RNAi. The sense and antisense transcripts combined to form an RNA duplex which is introduced into a target cell of interest. Other vectors may be used, which express small hairpin RNAs (shRNAs) which can be processed into siRNA-like molecules. Various vector-based methods are known in the art. Various methods for introducing such vectors into cells, either in vitro or in vivo (e.g. gene therapy) are known in the art.

Accordingly, in an embodiment, expression of a polypeptide including an amino acid sequence substantially identical to a SARS virus sequence may be inhibited by introducing into or generating within a cell an siRNA or siRNA-like molecule corresponding to a nucleic acid molecule encoding the polypeptide or fragment thereof, or to an nucleic acid homologous thereto. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecules are about 21-23 nucleotides in length. In an embodiment, siRNA or siRNA-like molecules comprise and 19-21 bp duplex portion, each strand having a 2 nucleotide 3' overhang. In embodiments, the siRNA or siRNA-like molecule is substantially identical to a nucleic acid encoding the polypeptide or a fragment or variant (or a fragment of a variant) thereof. Such a variant is capable of encoding a protein having the activity of a SARS virus polypeptide. In embodiments, the sense strand of the siRNA or siRNA-like molecule is substantially identical to a SARS virus nucleic acid molecule or a fragment thereof (RNA having U in place of T residues of the DNA sequence).

SARS Virus Protein Expression

In general, SARS virus polypeptides according to the invention, may be produced by transformation of a suitable host cell with all or part of a SARS virus polypeptide-encoding genomic or cDNA molecule or fragment thereof (e.g., the genomic DNA or cDNAs described herein) in a suitable expression vehicle. Those skilled in the field of molecular biology will understand that any of a wide variety of expression systems may be used to provide the recombinant protein. The precise host cell used is not critical to the invention. The SARS virus polypeptide may be produced in a prokaryotic host (e.g., $E.$ $coli$ or a virus, for example, a coronovirus such as human OC43 or 229E, a bovine coronavirus, or a virus used for gene therapy, such as an adenovirus) or in a eukaryotic host (e.g., $Saccharomyces$ $cerevisiae$, insect cells, e.g., Sf21 cells, or mammalian cells, e.g., COS 1, NIH 3T3, VeroE6, or HeLa cells). Such cells are available from a wide range of sources (e.g., the American Type Culture Collection, Rockland, Md.; also, see, e.g., Ausubel et al., Current Protocols in Molecular Biology, John Wiley & Sons, New York, 1994). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual, P. H. Pouwels et al, 1985, Supp. 1987), or from commercially available sources. Suitable animal models, e.g. a ferret animal model, or any other animal model suitable for analysis of SARS virus infection or expression of SARS virus nucleic acid molecules may be used.

In an alternative embodiment, the baculovirus expression system (using, for example, the vector pBacPAK9) available from Clontech (Pal Alto, Calif.) may be used. If desired, this system may be used in conjunction with other protein expression techniques, for example, the myc tag approach described by Evan et al. (Mol. Cell Biol. 5:3610-3616, 1985). In an alternative embodiment, a SARS virus polypeptide may be produced by a stably-transfected mammalian cell line. A number of vectors suitable for stable transfection of mammalian cells are available to the public, e.g., see Pouwels et al (supra); methods for constructing such cell lines are also publicly available, e.g., in Ausubel et al. (supra). In one example, cDNA encoding the SARS virus polypeptide is cloned into an expression vector which includes the dihydrofolate reductase (DHFR) gene. Integration of the plasmid and, therefore, the SARS virus polypeptide-encoding gene into the host cell chromosome is selected for by inclusion of 0.01-300 µM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR.sup.—cells, ATCC Accession No. CRL 9096) are among the host cells preferred for DHFR selection of a stably-transfected cell line or DHFR-mediated gene amplification.

Once the recombinant SARS virus polypeptide is expressed, it is isolated, e.g., using affinity chromatography. In one example, an anti-SARS virus polypeptide antibody (e.g., produced as described herein) may be attached to a column and used to isolate the SARS virus polypeptide. Lysis and fractionation of SARS virus polypetde-harboring cells prior to affinity chromatography may be performed by standard methods (see, e.g., Ausubel et al., supra). In another example, SARS virus polypeptides may be purified or substantially purified from a mixture of compounds such as an extract or supernatant obtained from cells (Ausubel et al., supra). Standard purification techniques can be used to progressively eliminate undesirable compounds from the mixture until a single compound or minimal number of effective compounds has been isolated.

Once isolated, the recombinant protein can, if desired, be further purified, e.g., by high performance liquid chromatography (see, e.g., Fisher, Laboratory Techniques In Biochemistry And Molecular Biology, eds., Work and Burdon, Elsevier, 1980).

Polypeptides of the invention, particularly short SARS virus peptide fragments, can also be produced by chemical synthesis (e.g., by the methods described in Solid Phase Peptide Synthesis, 2nd ed., 1984 The Pierce Chemical Co., Rockford, Ill.).

These general techniques of polypeptide expression and purification can also be used to produce and isolate useful SARS virus protein fragments or analogs (described herein).

In certain alternative embodiments, the SARS polypeptide might have attached any one of a variety of tags. Tags can be amino acid tags or chemical tags and can be added for the purpose of purification (for example a 6-histidine tag for purification over a nickel column). In other preferred embodiments, various labels can be used as means for detecting binding of a SARS polypeptide to another polypeptide, for example to a cell surface receptor. Alternatively, SARS DNA or RNA may be labeled for detection, for example in a hybridization assay. SARS virus nucleic acids or proteins, or derivatives thereof, may be directly or indirectly labeled, for example, with a radioscope, a fluorescent compound, a bioluminescent compound, a chemiluminescent compound, a metal chelator or an enzyme. Those of ordinary skill in the art will know of other suitable labels or will be able to ascertain such, using routine experimentation. In yet another embodiment of the invention, the polypeptides disclosed herein, or derivatives thereof, are linked to toxins.

Isolation and Identification of Additional SARS Virus Molecules

Based on the SARS virus sequences described herein, the isolation and identification of additional SARS virus-related sequences such as SARS virus genes and of additional SARS virus strains or isolates is made possible using standard techniques. In addition, the SARS virus sequences provided herein also provide the basis for identification of homologous sequences from other species and genera from both prokaryotes and eukaryotes such as viruses, bacteria, fungi, parasites, yeast, and/or mammals. In some embodiments, the nucleic acid sequences described herein may be used to design probes or primers, including degenerate oligonucleotide probes or primers, based upon the sequence of either DNA strand. The probes or primers may then be used to screen genomic or cDNA libraries for sequences from for example naturally occurring variants or isolates of SARS viruses, using standard amplification or hybridization techniques.

In some embodiments, binding partners may be identified by tagging the polypeptides of the invention (e.g., those substantially identical to SARS virus polypeptides described herein) with an epitope sequence (e.g., FLAG or 2HA), and delivering it into host cells, either by transfection with a suitable vector containing a nucleic acid sequence encoding a polypeptide of the invention, followed by immunoprecipitation and identification of the binding partner. Cells may be infected with strains expressing the FLAG or 2HA fusions, followed by lysis and immunoprecipitation with anti-FLAG or anti-2HA antibodies. Binding partners may be identified by mass spectroscopy. If the polypeptide of the invention is not produced in sufficient quantities, such a method may not deliver enough tagged protein to identify its partner. As part of a complementary approach, each polypeptide of the invention may be cloned into a mammalian transfection vector fused to, for example, 2HA, GFP and/or FLAG. Following transfection, HeLa cells may be lysed and the tagged polypeptide immunoprecipitated. The binding partner may be identified by SDS PAGE followed by mass spectroscopy.

In some embodiments, polypeptides or antibodies of the invention may be tagged, produced, and used for example on affinity columns and/or in immunological assays to identify and/or confirm identified target compounds. FLAG, HA, and/or His tagged proteins can be used for such affinity columns to pull out host cell factors from cell extracts, and any hits may be validated by standard binding assays, saturation curves, and other methods as described herein or known to those of skill in the art.

In some embodiments, a two hybrid system may be used to study protein-protein interactions. The nucleic acid sequences described herein, or sequences substantially identical thereto, can be cloned into the pBT bait plasmid of the two hybrid system, and a commercially available murine spleen library of 5×10⁶ independent clones, may be used as the target library for the baits. Potential hits may be further characterized by recovering the plasmids and retransforming to reduce false positives resulting from clonal bait variants and library target clones which activate the reporter genes independent of the cloned bait. Reproducible hits may be studied further as described herein.

Virulence may be assayed as described herein or as known to those of skill in the art. Once coding sequences have been identified, they may be isolated using standard cloning techniques, and inserted into any suitable vector or replicon for, for example, production of polypeptides. Such vectors and replicons include, without limitation, bacteriophage λ (*E. coli*), pBR322 (*E. coli*), pACYC177 (*E. coli*), pKT230 (gram-negative bacteria), pGV1 106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) or bovine papilloma virus (mammalian cells). In general, the polypeptides of the invention may be produced in any suitable host cell transformed or transfected with a suitable vector. The method of transformation or transfection and the choice of expression vehicle will depend on the host system selected. A wide variety of expression systems may be used, and the precise host cell used is not critical to the invention. For example, a polypeptide according to the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or COS cells). Such cells are available from a wide range of sources (e.g., the American Type Culture Collection, Manassus, Va.). Bacterial expression systems for polypeptide production include the *E. coli* pET expression system (Novagen, Inc., Madison, Wis.), and the pGEX expression system (Pharmacia).

Compounds

In one aspect, compounds according to the invention include SARS virus nucleic acid molecules and polypeptides, such as the sequences disclosed in the Figures and Tables herein, and throughout the specification, and fragments thereof. In alternative embodiments, compounds according to the invention may be nucleic acid molecules that are at least 10 nucleotides in length, and that are derived from the sequences described herein. In alternative embodiments, compounds according to the invention may be peptides that are at least 5 amino acids in length, and that are derived from the sequences described herein.

In alternative embodiments, a compound according to the invention can be a non-peptide molecule as well as a peptide or peptide analogue. A peptide or peptide analogue will generally be as small as feasible while retaining full biological activity. A non-peptide molecule can be any molecule that exhibits biological activity as described herein or known in the art. Biological activity can, for example, be measured in terms of ability to elicit a cytotoxic response, to mediate DNA replication, or any other function of a SARS virus molecule.

Compounds can be prepared by, for example, replacing, deleting, or inserting an amino acid residue of SARS peptide or peptide analogue, as described herein, with other conservative amino acid residues, i.e., residues having similar physical, biological, or chemical properties, and screening for biological function.

It is well known in the art that some modifications and changes can be made in the structure of a polypeptide without substantially altering the biological function of that peptide, to obtain a biologically equivalent polypeptide. Such modifications may be made for the purpose of modifying function, or for facilitating administration or enhancing stability or inhibiting breakdown for, for example, therapeutic uses. For example, an indigestible SARS virus compound according to the invention may be used for oral administration; a modification that is suitable for inhalation may be used for administration to the lung; or addition of a leader sequence may increase protein expression levels.

In one aspect of the invention, SARS virus-derived peptides or epitopes may include peptides that differ from a portion of a native leader, protein or SARS virus sequence by conservative amino acid substitutions. The peptides and epitopes of the present invention also extend to biologically equivalent peptides that differ from a portion of the sequence of novel peptides of the present invention by conservative amino acid substitutions. As used herein, the term "conserved amino acid substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

In some embodiments, conserved amino acid substitutions may be made where an amino acid residue is substituted for another having a similar hydrophilicity value (e.g., within a value of plus or minus 2.0), where the following may-be an amino acid having a hydropathic index of about −1.6 such as Tyr (−1.3) or Pro (−1.6)s are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et aL (J. Mol. Bio. 179:125-142, 184). Genetically encoded hydrophobic amino acids include Gly, Ala, Phe, Val, Leu, Ile, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, —$NO_2$, —NO, —$NH_2$, —NHR, —NRR, —C(O)R, —C(O)OH, —C(O)OR, —C(O)$NH_2$, —C(O)NHR, —C(O)NRR, etc., where R is independently ($C_1$-$C_6$) alkyl, substituted ($C_1$-$C_6$) alkyl, ($C_1$-$C_6$) alkenyl, substituted ($C_1$-$C_6$) alkenyl, ($C_1$-$C_6$) alkynyl, substituted ($C_1$-$C_6$) alkynyl, ($C_5$-$C_{20}$) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Tryp, while non-genetically encoded aromatic amino acids include phenylglycine, 2-napthylalanine, beta-2-thienylalanine, 1,2,3,4-tetrahydro-isoquinoline-3-carboxylic acid, 4-chlorophenylalanine, 2-fluorobenylalanine3-fluorophenylalanine, and 4-fluorophenylalanine.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met, while non-genetically encoded apolar amino acids include cyclohexylalanine. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile, while non-genetically encoded aliphatic amino acids include norleucine.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln, while non-genetically encoded polar amino acids include citrulline, N-acetyl lysine, and methionine sulfoxide.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His, while non-genetically encoded basic amino acids include the non-cyclic amino acids ornithine, 2,3,-diaminopropionic acid, 2,4-diaminobutyric acid, and homoarginine.

It will be appreciated by one skilled in the art that the above classifications are not absolute and that an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid. Thus, these substitutions can include compounds whose free amino groups have been derivatised to amine hydrochlorides, p-toluene sulfonyl groups, carbobenzoxy groups, t-butyloxycarbonyl groups, chloroacetyl groups or formyl groups. Similarly, free carboxyl groups can be derivatized to form salts, methyl and ethyl esters or other types of esters or hydrazides, and side chains can be derivatized to form O-acyl or O-alkyl derivatives for free hydroxyl groups or N-im-benzylhistidine for the imidazole nitrogen of histidine. Peptide analogues also include amino acids that have been chemically altered, for example, by methylation, by amidation of the C-terminal amino acid by an alkylamine such as ethylamine, ethanolamine, or ethylene diamine, or acylation or methylation of an amino acid side chain (such as acylation of the epsilon amino group of lysine). Peptide analogues can also include replacement of the amide linkage in the peptide with a substituted amide (for example, groups of the formula —C(O)—NR, where R is ($C_1$-$C_6$) alkyl, ($C_1$-$C_6$) alkenyl, ($C_1$-$C_6$) alkynyl, substituted ($C_1$-$C_6$) alkyl, substituted ($C_1$-$C_6$) alkenyl, or substituted ($C_1$-$C_6$) alkynyl) or isostere of an amide linkage (for example, —$CH_2$NH—, —$CH_2$S, —$CH_2CH_2$—, —CH=CH— (cis and trans), —C(O)$CH_2$—, —CH(OH)$CH_2$—, or —$CH_2$SO—).

The compound can be covalently linked, for example, by polymerisation or conjugation, to form homopolymers or heteropolymers. Spacers and linkers, typically composed of small neutral molecules, such as amino acids that are uncharged under physiological conditions, can be used. Linkages can be achieved in a number of ways. For example, cysteine residues can be added at the peptide termini, and multiple peptides can be covalently bonded by controlled oxidation. Alternatively, heterobifunctional agents, such as disulfide/amide forming agents or thioether/amide forming agents can be used. The compound can also be constrained, for example, by having cyclic portions.

In some embodiments, three dimensional molecular modeling techniques may be used to identify or generate compounds that may be useful as therapeutics or diagnostics. Standard molecular modeling tools may be used, for example, those described in L-H Hung and R. Samudrala, PROTINFO: secondary and tertiary protein structure prediction, Nucleic Acids Research, 2003, Vol. 31, No. 13 3296-3299; A. Yamaguchi, et al., Enlarged FAMSBASE: protein 3D structure models of genome sequences for 41 species, Nucleic Acids Research, 2003, Vol. 31, No. 1 463-468; J. Chen, et al., MMDB: Entrez's 3D-structure database, Nucleic Acids Research, 2003, Vol. 31, No. 1 474-477; R. A. Chiang, et al., The Structure Superposition Database, Nucleic Acids Research, 2003, Vol. 31, No. 1 505-510.

Peptides or peptide analogues can be synthesized by standard chemical techniques, for example, by automated synthesis using solution or solid phase synthesis methodology. Automated peptide synthesizers are commercially available and use techniques well known in the art. Peptides and peptide analogues can also be prepared using recombinant DNA technology using standard methods such as those described in, for example, Sambrook, et aL (Molecular Cloning: A Laboratory Manual. 2.sup.nd, ed., Cold Spring Harbor Laboratory, Cold Spring Harbor Laboratory Press, Cold Spring Harbor, N.Y., 1989) or Ausubel et al. (Current Protocols in Molecular Biology, John Wiley & Sons, 1994).

Compounds, such as peptides (or analogues thereof) can be identified by routine experimentation by, for example, modifying residues within SARS peptides; introducing single or multiple amino acid substitutions, deletions, or insertions, and identifying those compounds that retain biological activity, e.g., those compounds that have cytotoxic ability.

In general, candidate compounds for prevention or treatment of SARS virus-mediated disorders are identified from large libraries of both natural product or synthetic (or semi-synthetic) extracts or chemical libraries according to methods known in the art. Candidate or test compounds may include, without limitation, peptides, polypeptides, synthesised organic molecules, naturally occurring organic molecules, and nucleic acid molecules. In some embodiments, such compounds screen for the ability to inhibit SARS virus replication or pathogenicity, while maintaining the infected cell's ability to grow or survive.

Those skilled in the field of drug discovery and development will understand that the precise source of test extracts or compounds is not critical to the method(s) of the invention. Accordingly, virtually any number of chemical extracts or compounds can be screened using the exemplary methods described herein or using standard methods. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla.), and PharmaMar, U.S.A. (Cambridge, Mass.). In addition, natural and synthetically produced libraries of, for example, SARS virus polypeptides containing leader sequences, are produced, if desired, according to methods known in the art, e.g., by standard extraction and fractionation methods. Furthermore, if desired, any library or compound is readily modified using standard chemical, physical, or biochemical methods.

When a crude extract is found to modulate cytotoxicity or viral infection, further fractionation of the positive lead extract is necessary to isolate chemical constituents responsible for the observed effect. Thus, the goal of the extraction, fractionation, and purification process is the careful characterization and identification of a chemical entity within the crude extract having, for example, anti-cytotoxicity or anti-viral properties. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic, prophylactic, diagnostic, or other value in for example cell culture systems, such as a Vero E6 culture system, may be subsequently analyzed using a ferret animal model, or any other animal model suitable for analysis of SARS.

Antibodies

The compounds of the invention can be used to prepare antibodies to SARS virus peptides, protein, polyproteins, or analogs thereof, or to SARS virus nucleic acid molecules or analogs thereof using standard techniques of preparation as, for example, described in Harlow and Lane (Antibodies; A Laboratory Manual, Cold Spring Harbor Laboratory, Cold Spring Harbor, N.Y., 1988), or known to those skilled in the art. Antibodies may include polyclonal antibodies, monoclonal antibodies, hybrid antibodies (e.g., divalent antibodies having different pairs of heavy and light chains), chimeric antibodies (e.g., antibodies having constant and variable domains from different species and/or class), modified antibodies (e.g, antibodies in which the naturally occurring sequence has been altered by for example recombinant techniques), Fab antibodies, anti-idiotype antibodies, etc. Antibodies can be tailored to minimise adverse host immune response by, for example, using chimeric antibodies containing an antigen binding domain from one species and the Fc portion from another species, or by using antibodies made from hybridomas of the appropriate species. For example, "humanized" antibodies may be used for administration to humans.

To generate SARS virus polypeptide-specific antibodies, a SARS virus polypeptide coding sequence may be expressed, for example, as a C-terminal fusion with glutathione S-transferase (GST) (Smith et al., Gene 67:31-40, 1988). The fusion polypeptide may then be purified on glutathione-Sepharose beads, eluted with glutathione cleaved with thrombin (at the engineered cleavage site), and purified to the degree necessary for immunization of rabbits. Primary immunizations are carried out with Freud's complete adjuvant and subsequent immunizations with Freud's incomplete adjuvant. Antibody titres are monitored by Western blot and immunoprecipitation analyzes using the thrombin-cleaved SARS virus polypeptide fragment of the GST-SARS virus fusion polypeptide. Immune sera are affinity purified using CNBr-Sepharose-coupled SARS virus polypeptide. Antiserum specificity is determined using a panel of unrelated GST polypeptides.

As an alternate or adjunct immunogen to GST fusion polypeptides, peptides corresponding to relatively unique hydrophilic SARS virus polypeptides may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using SARS virus polypeptide expressed as a GST fusion polypeptide.

Alternatively, monoclonal antibodies may be prepared using the SARS virus polypeptides described above and standard hybridoma technology (see, e.g., Kohler et al., Nature, 256:495, 1975; Kohler et al., Eur. J Immunol. 6:511, 1976; Kohler et al., Eur. J. Immunol. 6:292, 1976; Hammerling et al., In Monoclonal Antibodies and T Cell Hybridomas, Elsevier, NY, 1981; Ausubel et al., supra). Once produced, monoclonal antibodies are also tested for specific SARS virus polypeptide recognition by Western blot or immunoprecipitation analysis (by the methods described in Ausubel et al., supra). Antibodies which specifically recognize SARS virus polypeptides are considered to be useful in the invention; such antibodies may be used, e.g., in an immunoassay to monitor the level of SARS virus polypeptides produced by a mammal (for example, to determine the amount or location of a SARS virus polypeptide).

In an alternative embodiment, antibodies of the invention are not only produced using the whole SARS virus polypeptide, but using fragments of the SARS virus polypeptide which are unique or which lie outside highly conserved regions and appear likely to be antigenic, by criteria such as high frequency of charged residues may also be used. In one specific example, such fragments are generated by standard techniques of PCR and cloned into the pGEX expression vector (Ausubel et al., supra). Fusion polypeptides are expressed in *E. coli* and purified using a glutathione agarose affinity matrix as described in Ausubel et al. (supra). To attempt to minimize the potential problems of low affinity or specificity of antisera, two or three such fusions are generated for each polypeptide, and each fusion is injected into at least two rabbits. Antisera are raised by injections in a series, preferably including at least three booster injections. SARS virus antibodies may also be prepared against SARS virus nucleic acid molecules.

Antibodies may be used as diagnostics, therapeutics, or prophylactics for SARS virus-related disorders. Antibodies may also be used to isolate SARS virus and compounds by for example affinity chromatography, or to identify SARS virus compounds isolated or generated by other techniques.

Arrays and Libraries

In some aspects, biological assays, such as diagnostic or other assays, using high density nucleic acid, polypeptide, or antibody arrays, for example high density miniaturized arrays or "microarrays," of SARS virus nucleic acid molecules or polypeptides, or antibodies capable of specifically binding such nucleic acid molecules or polypeptides, may be performed. Macroarrays, performed for example by manual spotting techniques, may also be used. Arrays generally require a solid support (for example, nylon, glass, ceramic, plastic, silicon, nitrocellulose or PVDF membranes, microwells, microbeads, e.g., magnetic microbeads, etc.) to which the nucleic acid molecules or polypeptides or antibodies are attached in a specified two-dimensional arrangement, such that the pattern of hybridization is easily determinable. Suspension arrays (particles in suspension) that are coded to facilitate identification may also be used. SARS virus nucleic acid molecules or polypeptide probes or targets may be compounds as described herein.

In some embodiments, high density nucleic acid arrays may for example be used to monitor the presence or level of expression of a large number of SARS virus nucleic acid molecules or genes or for detecting or identifying SARS virus nucleic acid sequence variations, mutations or polymorphisms. For the purpose of such arrays, "nucleic acids" may include any polymer or oligomer of nucleosides or nucleotides (polynucleotides or oligonucleotides), which include pyrimidine and purine bases, preferably cytosine, thymine, and uracil, and adenine and guanine, respectively, or may include peptide nucleic acids (PNA). In an alternative aspect, the invention provides nucleic acid microarrays including a number of distinct nucleic acid sequence arrays of the invention, thus providing specific "sets" of sequences. The number of distinct sequences may for example be any integer between 2 and $1 \times 10^5$, such as at least $10^2$, $10^3$, $10^4$, or $10^5$.

The invention also provides gene knockout and expression libraries. Thus, nucleic acid molecules encoding SARS virus polypeptides or proteins (e.g., PCR products of ORF's or total mRNA) may for example be attached to a solid support, hybridized with single stranded detectably-labeled cDNAs (corresponding to an "antisense" orientation), and quantified using an appropriate method such that a signal is detected at each location at which hybridization has taken place. The intensity of the signal would then reflect the level of gene expression. Comparison of results from viruses, for example, of different strains or from different samples or subjects, would elucidate differing levels of expression of specified genes. Using similar techniques, homologous nucleic acids may be identified from different viruses if SARS virus nucleic acids are used in the microarray, and probed with nucleic acid molecules from different viruses or subjects. In some embodiments, this approach may involve constructing his-tagged ORP expression libraries of viral genomes in a bacterial host, similar to an expression library in yeast (Martzen M. R. et al., 1999. Science, 286:1153). ORF-encoded protein activities may for example be detected in purified his-tagged protein pools in cases where activities cannot be detected in extracts or cells. In one aspect of the invention, arrayed libraries may be constructed of viral strains each of which bears a plasmid expressing a different SARS virus ORF under control of an inducible promoter. ORFs are amplified using PCR and cloned into a vector that enables their expression as N-terminal his-tagged polypeptides. These amplicons are also used to construct hybridization microarrays and enable targeted gene disruption, reducing expenses. A suitable expression host is selected, and genes encoding particular biochemical activities are identified by screening arrayed pools of his-tagged proteins as described previously (Martzen M. R., McCraith S. M., Spinelli S. L., Torres F. M., Fields S., Grayhack E. J., and Phizicky E. M., 1999. Science, 286: 1153).

In some embodiments, protein arrays (including antibody or antigen arrays) may be used for the analysis and identification of SARS virus polypeptides or host responses to such polypeptides. Thus, protein arrays may be used to detect SARS virus polypeptides in a patient; distinguish a SARS virus polypeptide from a host polypeptide; detect interactions between SARS virus polypeptides and for example host proteins; determine the efficacy of potential therapeutics, such as small molecules or ligands that may bind SARS virus polypeptides; determine protein-antibody interactions; and/ or detect the interaction of enzyme-substrate interactions. Protein arrays may also be used to detect SARS virus antigens and antibodies in samples; to profile expression of SARS virus polypeptides; to identify suitable antibodies or map epitopes; or for a variety of protein function analyses.

A variety of methods are known for making and using microarrays, as for example disclosed in Cheung V. G., et al., 1999. Nature Genetics Supplement, 21:15-19; Lipshutz R. J., et al., 1999. Nature Genetics Supplement, 21:20-24; Bowtell D. D. L., 1999. Nature Genetics Supplement, 21:25-32; Singh-Gasson S., et al., 1999. Nature Biotechnol., 17:974-978; and Schweitzer B., et al., 2002. Nature Biotechnol., 20:359-365. Thus, for example, microarrays may be designed by synthesizing oligonucleotides with sequence variations based on a reference sequences, such as any SARS virus sequences described herein. Methods for storing, querying and analyzing microarray data have for example been disclosed in, for example, U.S. Pat. No. 6,484,183; U.S. Pat. No. 6,188,783; and Holloway A. J., et al., 2002. Nature Genetics Supplement, 32:481-489. Protein arrays may be constructed, detected, and analysed using methods known in the art for example mass spectrometric techniques, immunoassays such as ELISA and western (dot) blotting combined with for example fluorescence detection techniques, and adapted for high throughput analysis, as described in for example Mac-Beath, G. and Schreiber, S. L. Science 2000, 289, 1760-1763; Levit-Binnun N, et al. (2003) Quantitative detection of protein arrays. Anal Chem 75:1436-41; Kukar T, et al. (2002) Protein microarrays to detect protein-protein interactions using red and green fluorescent proteins. Anal Biochem 306: 50-4; Borrebaeck C A, et al. (2001) Protein chips based on -recombinant antibody fragments: a highly sensitive approach as detected by mass spectrometry. Biotechniques 30:1126-1132; Huang R P (2001) Detection of multiple proteins in an antibody-based protein microarray system. J Immunol Methods 255:1-13; Emili A Q and Cagney G (2000) Large-scale functional analysis using peptide or protein arrays. Nature Biotechnol 18:393-397; Zhu H, et al. (2000) Analysis of yeast protein kinases using protein chips. Nature Genet 26:283-9; Lueking A, et al. (1999) Protein Microarrays for Gene Expression and Antibody Screening. Anal. Biochem. 270:103-111; or Templin M F, et al. (2002) Protein microarray technology. Drug Discov Today 7:815-822. Tools for microarray techniques are available commercially from for example Affymetrix, Santa Clara, Calif.; Nanogen, San Diego, Calif.; or Sequenom, San Diego, Calif.

Computer Readable Records

Nucleic acid and polypeptide sequences, as described herein, or a fragment thereof, may be provided in a variety of media to facilitate access to these sequences and enable the use thereof. According, SARS virus nucleic acid and polypeptide sequences of the invention may be recorded or stored on computer readable media, using any technique and format that is appropriate for the particular medium.

In alternative embodiments, the invention provides computer readable media encoded with a number of distinct nucleic acid or amino acid data sequences of the invention. The number of distinct sequences may for example be any integer between 2 and $1 \times 10^5$, such as at least $10^2$, $10^3$, $10^4$ or $10^5$. In one embodiment, the invention features a computer medium having a plurality of digitally encoded data records. Each data record may include a value representing a nucleic acid or amino acid sequence of the invention. In some embodiments, the data record may further include values representing the level of expression, level or activity of a nucleic acid or amino acid sequence of the invention. The data record can be structured as a table, for example, a table that is part of a database such as a relational database (for example, a SQL database of the Oracle or Sybase database environments). The invention also includes a method of communicating information about a sample, for example by transmitting information, for example transmitting a computer readable record as described herein, for example over a computer network. The polypeptide and nucleic acid sequences of the invention, and sequence information pertaining thereto, may be routinely accessed by one of ordinary skill in the art for a variety of purposes, including for the purposes of comparing substantially identical sequences, etc. Such access may be facilitated using publicly available software as described herein. By "computer readable media" is meant any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

Pharmaceutical and Veterinary Compositions, Dosages, and Administration

Compounds of the invention can be provided alone or in combination with other compounds (for example, small molecules, peptides, or peptide analogues), in the presence of a liposome, an adjuvant, or any pharmaceutically acceptable carrier, in a form suitable for administration to humans or to animals.

Conventional pharmaceutical practice may be employed to provide suitable formulations or compositions to administer the compounds to patients suffering from or presymptomatic for SARS. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. In some embodiments, compounds are delivered directly to the lung, by for example, formulations suitable for inhalation. In some embodiments, gene therapy techniques may be used for administration of SARS virus nucleic acid molecules, for example, as DNA vaccines.Formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences" (18th edition), ed. A. Gennaro, 1990, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a compound according to the invention may be combined with more traditional therapies for the disease.

For therapeutic or prophylactic compositions, the compounds are administered to an individual in an amount sufficient to stop or slow the replication of the SARS virus, or to confer protective immunity against future SARS virus infection. Amounts considered sufficient will vary according to the specific compound used, the mode of administration, the stage and severity of the disease, the age, sex, and health of the individual being treated, and concurrent treatments. As a general rule, however, dosages can range from about 1 µg to about 100 mg per kg body weight of a patient for an initial dosage, with subsequent adjustments depending on the patient's response, which can be measured, for example by determining the presence of SARS nucleic acid molecules, polypeptides, or virions in the patient's peripheral blood.

In the case of vaccine formulations, an inmunogenically effective amount of a compound of the invention can be provided, alone or in combination with other compounds, with an adjuvant, for example, Freund's incomplete adjuvant or aluminum hydroxide. The compound may also be linked with a carrier molecule, such as bovine serum albumin or keyhole limpet hemocyanin to enhance immunogenicity. In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

Virus Isolation

Virus isolation was performed on a bronchoaveolar lavage specimen of a fatal SARS case belonging to the original case cluster from Toronto, Canada. All work with the infectious agent was performed in a biosafety level 3 (BSL3) laboratory using a N100 mask for personal protection. Samples were removed from BSL3 after addition of the RNA extraction buffer. The virus isolate, named the "Tor2 isolate" was grown in African Green Monkey Kidney (Vero E6) cells, the viral particles were purified, and the genetic material (RNA) was extracted from the Tor2 isolate (Poutanen, S. M. et al., N Engl J Med, Apr. 10, 2003). More specifically, one hundred microlitre specimens were used to inoculate Vero E6 cells (ATCC CRL 1586) on Dulbecco's Modified Eagle Medium supplemented with penicillin/streptomycin, glutamine and 2% fetal calf serum. The culture was incubated at 37° C. Cytopathogenic effect was observed 5 days post inoculation. The virus was passaged into newly seeded Vero E6 cells which showed a cytopathogenic effect as early as 2 days post infection (multiplicity of infection $10^{-2}$). A virus stock was prepared from passage 2 of these cells and preserved in liquid nitrogen. The titer of the virus stock was determined to be $1 \times 10^7$ plaque forming units (p.f.u.) by plaque assay and $5 \times 10^6$ by tissue culture infectious dose (TCID) 50.

For virus propagation, 10×T-162 flasks of Vero E6 cells were infected with a multiplicity of infection of $10^{-2}$. When infected cells showed a cytopathognic effect of '4+' (48 hours post infection), the cultures were then frozen and thawed to lyse the cells, and the supernatants were clarified from cell debris by centrifugation at 10,000 rpm in a Beckman high-speed centrifuge. The supernatants were treated with DNAse and RNAse for 3 hours at 37° C. to remove any cellular genomic nucleic acids and subsequently extracted with an equal volume of 1,1,2-trichloro-trifluoroethane. The top fraction was ultra-centrifuged through a 5%/40% glycerol step gradient at 151,000×g for 1 hour at 4° C. The virus pellet was resuspended in PBS. RNA was isolated using a commercial kit from QIAGEN and stored at −80° C. for further use.

cDNA Library Construction

The RNA and subsequent products were handled under biosafety level 2 (BSL2) conditions. The RNA sample was converted to a cDNA library, using a combined random-priming and oligo-dT priming strategy, and resultant subgenomic clones were processed under level 1 biosafety conditions. More specifically, purified viral RNA (55 ng) was used in the construction of a random primed and oligo-dT primed cDNA library, using the SuperScript Choice System for cDNA synthesis (Invitrogen). Linkers 5'-AATTCGCGGC-CGCGTCGAC-3', SEQ ID NO: 195, and 5'-pGTC-GACGCGGCCGCG-3', SEQ ID NO: 196, were ligated following cDNA synthesis. The cDNA synthesis products were visualized on agarose gels, revealing the anticipated low-yield smear. To produce sufficient cDNA for cloning, the cDNA product was size fractionated on a low-melting point preparative agarose gel, followed by PCR amplification using a single PCR primer 5'AATTCGCGGCCGCGTCGAC-3', SEQ ID NO: 197, specific to the linkers. This yielded sufficient material for cloning.

Size-selected cDNA products were cloned and single sequence reads were generated from each end of the insert from randomly picked clones. A list of the SARS virus clones is provided in the accompanying sequence listing, which is incorporated by reference herein (SEQ ID NOs: 92-159, 208 and 209).

More specifically, size-selected cDNAs were ligated into the pCR4-TOPO TA cloning vector (Invitrogen, CA), or after digestion with the restriction nuclease Not I into the pBR194c vector (The Institute for Genomic Research, Rockville, Md., USA). Ligated clones were then transformed by electroporation into DH10B T1 cells (Invitrogen), plated on 22 cm agar plates with the appropriate antibiotic and grown for 16 hours at 37° C. Colonies were picked into 384-well Axygen culture blocks containing 2×YT media and grown in a shaking incubator for 18 hours at 37° C. Cells were lysed and DNA purified using standard laboratory procedures. Sequencing primers for the 194c clones were 5'-GGCCTCTTCGCTAT- TACGC-3' (forward primer) (SEQ ID NO: 159) and 5' TGCAGGTCGACTCTAGAGGAT-3' (reverse primer) (SEQ ID NO: 198).

DNA Sequencing and Assembly of Reads

Sequences were assembled and the assembly edited to produce the genomic sequence of the SARS virus. More specifically, DNA sequencing of both ends of the plasmid templates was achieved using Applied Biosystems BigDye terminator reagent (version 3), with electrophoresis and data collection on AB 3700 and 3730 XL instruments DNA sequence reads were screened for non-viral contaminating sequences, trimmed for quality using PHRED (Ewing, B, and P. Green, *Genome Res* 8, 186-94, March, 1998) and assembled using PHRAP (Gordon, D. et al. *Genome Res* 8, 195-202, March, 1998). Simultaneously, sequences were used in BLAST searches of viral nucleotide and non-redundant protein datasets (NCBI, National Library of Medicine) to search for similarities. Sequence assemblies were visualized using CONSED (Gordon, D. et al. *Genome Res* 8, 195-202, March, 1998). Sequence mis-assemblies and contig joins were identified using Miropeats (Parsons, J. D., *Comput Appl Biosci* 11, 615-9 (December, 1995). As sequence data accrued, the additional sequences were assembled until it became apparent that the additional depth of sampling was increasing depth of coverage but not extending the length of the contig. At this point, 3,080 sequencing reads were generated, 2,634 of which were assembled into a single large contig.

The sequence information was imported into an ACEDB database (Durbin, J. Thierry-Mieg. 1991. A C. elegans Database. Documentation, code and data available from anonymous FTP servers at lirmm "dot" lirmm "dot" fr; cele "dot" mrc-1mb "dot" cam "dot" ac "dot" uk; and ncbi "dot" n1m "dot" nih "dot" gov) and subjected to biological analysis including the identification of open reading frames, detection of similar sequences by BLAST and searching for apparent frameshifts. When frameshifts were identified by this analysis, the sequence assembly was consulted for evidence of sequencing errors and if found, they were corrected. The sequences were also searched for any that could extend the 5' end of the sequence and these were incorporated when found. High quality sequence discrepancies between different sequence reads were identified and resolved. Sequence reads classified as deleted or chimeric were identified through manual inspection and removed from the assembly. The resulting sequence has an average PHRED consensus quality score of 89.96. The lowest quality bases in the assembly are in the immediate vicinity of the 5' and 3' ends of the viral genome, with the lowest quality base having a PHRED score of 35. Most (29,694 of the 29,736 (99.86%)) of the bases have a consensus score of 90. Almost all regions of the genome are represented by reads derived from both strands of the plasmid sequencing templates, the exceptions being 50 bases at the 5' end represented by a single sequencing read, and 5 bases at the 3' end represented by a single read. The average base in the assembly is represented by 30 reads in the forward direction and 30 reads in the reverse direction, as determined by PHRED. RT-PCR products predicted from the sequence and spanning the entire genome yield PCR products of the anticipated size on agarose gels. To confirm the 5' end of the viral genome RACE was performed using the RLM-RACE kit from Ambion, and primers 5'-CAGGAAACAGCTATGA-CACCAAGAACAAGGCTCTCCA-3' (SEQ ID NO: 90) and 5'-CAGGAAACAGCTATGACGATAGGGC-CTCTTCCACAGA-3' (SEQ ID NO: 91). Fourteen clones were recovered and sequenced. Analysis of these sequences confirmed the 5' end of the coronavirus genome. The SARS genomic sequences have been deposited into Genbank (Accession Nos. AY274119.1, AY274119.2, and AY274119.3).

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains, and may be applied to the essential features set forth herein and in the scope of the appended claims.

All patents, patent applications, and publications referred to herein are hereby incorporated by reference in their entirety to the same extent as if each individual patent, patent application, or publication was specifically and individually indicated to be incorporated by reference in its entirety.

What is claimed is:

1. An isolated SARS virus nucleic acid molecule comprising a nucleic acid sequence selected from the group consisting of SEQ ID NOs: 1, 2 and 15.

2. The molecule of claim 1, wherein said molecule is selected from the group consisting of genomic RNA, DNA, cDNA, synthetic DNA and mRNA.

3. The molecule of claim 1, wherein said molecule comprises a s2m motif.

4. The molecule of claim 1, wherein said molecule comprises a leader sequence.

5. The molecule of claim 1, wherein said molecule comprises a transcriptional regulatory sequence.

6. The molecule of claim 1, wherein said molecule encodes a polyprotein.

7. The molecule of claim 1, wherein said molecule encodes a polypeptide.

8. A vector comprising the nucleic acid molecule of claim 1.

9. An isolated host cell comprising the vector of claim 8.

10. The host cell of claim 9, wherein said cell is selected from the group consisting of a mammalian cell, a yeast, a bacterium, and a nematode cell.

11. An isolated nucleic acid molecule comprising a sequence complementary to the entire sequence of SEQ ID NOs: 1, 2 or 15.

12. A kit for detecting the presence of a SARS virus in a sample, wherein said kit comprises the isolated SARS virus nucleic acid molecule of claim 1 or 11.

13. A microarray comprising a plurality of elements, wherein the microarray comprises the nucleic acid of claim 1 or 11.

14. A composition comprising the nucleic acid of claim 1 or 11.

* * * * *